US012624355B2

(12) United States Patent
Zhang et al.

(10) Patent No.: US 12,624,355 B2
(45) Date of Patent: *May 12, 2026

(54) DOUBLE-STRANDED OLIGONUCLEOTIDE, COMPOSITION AND CONJUGATE COMPRISING DOUBLE-STRANDED OLIGONUCLEOTIDE, PREPARATION METHOD THEREOF AND USE THEREOF

(71) Applicant: SUZHOU RIBO LIFE SCIENCE CO., LTD., Kunshan (CN)

(72) Inventors: Hongyan Zhang, Kunshan (CN); Shan Gao, Kunshan (CN); Daiwu Kang, Kunshan (CN)

(73) Assignee: SUZHOU RIBO LIFE SCIENCE CO., LTD., Jiangsu (CN)

( * ) Notice: Subject to any disclaimer, the term of this patent is extended or adjusted under 35 U.S.C. 154(b) by 784 days.

This patent is subject to a terminal disclaimer.

(21) Appl. No.: 17/937,639

(22) Filed: Oct. 3, 2022

(65) Prior Publication Data

US 2023/0132756 A1 May 4, 2023

Related U.S. Application Data

(63) Continuation of application No. 16/758,720, filed as application No. PCT/CN2018/118212 on Nov. 29, 2018, now Pat. No. 11,492,620.

(30) Foreign Application Priority Data

| | | |
|---|---|---|
| Dec. 1, 2017 | (CN) | 201711249333.8 |
| Dec. 1, 2017 | (CN) | 201711249345.0 |
| Dec. 1, 2017 | (CN) | 201711249356.9 |
| Dec. 29, 2017 | (CN) | 201711479058.9 |
| Aug. 21, 2018 | (CN) | 201810951752.4 |
| Sep. 30, 2018 | (CN) | 201811165363.5 |

(51) Int. Cl.
*C12N 15/113* (2010.01)
*A61P 3/06* (2006.01)

(52) U.S. Cl.
CPC .............. *C12N 15/113* (2013.01); *A61P 3/06* (2018.01); *C12N 2310/14* (2013.01); *C12N 2310/312* (2013.01); *C12N 2310/315* (2013.01); *C12N 2310/321* (2013.01); *C12N 2310/322* (2013.01); *C12N 2310/343* (2013.01); *C12N 2310/344* (2013.01); *C12N 2310/346* (2013.01)

(58) Field of Classification Search
None
See application file for complete search history.

(56) References Cited

U.S. PATENT DOCUMENTS 8,030,474 B2 10/2011 Khvorova et al.
8,106,022 B2 1/2012 Manoharan et al.
8,334,372 B2 12/2012 Freier et al.
8,344,125 B2 1/2013 Manoharan et al.
9,428,751 B2 8/2016 Macdonald et al.
9,670,492 B2 6/2017 Freier et al.
10,130,651 B2 11/2018 Wooddell et al.
10,246,708 B2 4/2019 Kasperkovitz et al.
10,294,477 B2 5/2019 Swayze
10,370,453 B2 8/2019 Sexton et al.
10,934,544 B2 3/2021 Akinc et al.
11,084,884 B2 8/2021 Sexton et al.
11,414,661 B2 8/2022 Zhang et al.
11,414,665 B2 8/2022 Zhang et al.
11,492,620 B2 11/2022 Zhang et al.
11,633,482 B2 * 4/2023 Zhang .................... A61P 1/16 514/25
11,660,347 B2 * 5/2023 Zhang .................... A61P 3/06 536/1.11
11,896,674 B2 * 2/2024 Zhang .................. A61K 47/555
11,918,600 B2 3/2024 Zhang et al.
12,083,142 B2 * 9/2024 Zhang .................. A61P 31/20
12,084,661 B2 * 9/2024 Zhang ................ C12N 15/1131
12,274,752 B2 * 4/2025 Zhang .................... A61P 3/06
2003/0206887 A1 11/2003 Morrissey et al.
(Continued)

FOREIGN PATENT DOCUMENTS

AU 2014208251 A1 8/2014
CA 2930393 A1 6/2009
(Continued)

OTHER PUBLICATIONS

Kliuchnikov et al. Molecular Therapy Nucleic Acids vol. 36, pp. 1-14 (Year: 2025).*
Prakash , et al., "Comprehensive Structure-Activity Relationship of Triantennary N-Acetylgalactosamine Conjugated Antisense Oligonucleotides for Targeted Delivery to Hepatocytes", Journal of Medicinal Chemistry, vol. 59, No. 6, Feb. 25, 2016, pp. 2718-2733.
Rajeev , et al., "Hepatocyte-Specific Delivery of siRNAs Conjugated to Novel Non-nucleosidic Trivalent N-Acetylgalactosamine Elicits Robust Gene Silencing in Vivo", ChemBioChem, vol. 16, Issue 6, Apr. 13, 2015, pp. 903-908.
Ren , et al., "Gene Expression Profile of Transgenic Mouse Kidney Reveals Pathogenesis of Hepatitis B Virus Associated Nephropathy†", Journal of Medical Virology, vol. 78, Issue 5, May 2006, pp. 551-560.
(Continued)

*Primary Examiner* — Brian Whiteman
(74) *Attorney, Agent, or Firm* — Panitch Schwarze Belisario & Nadel LLP

(57) ABSTRACT

Provided is a modified double-stranded oligonucleotide, in which the sense strand comprises a nucleotide sequence 1, the anti-sense strand comprises a nucleotide sequence 2, the nucleotide sequences 1 and 2 are both 19 nucleotides in length, and in the direction from 5' end to 3' end, nucleotides at positions 7, 8 and 9 of the nucleotide sequence 1 and nucleotides at positions 2, 6, 14 and 16 of the nucleotide sequence 2 are all fluoro-modified nucleotides, and each nucleotide at other positions is independently one of non-fluoro-modified nucleotides. Further provided are a pharmaceutical composition and a conjugate comprising the oligonucleotide, and pharmaceutical use thereof.

25 Claims, 42 Drawing Sheets

Specification includes a Sequence Listing.

(56) References Cited

U.S. PATENT DOCUMENTS

| | | | |
|---|---|---|---|
| 2004/0266707 | A1 | 12/2004 | Leake et al. |
| 2005/0245475 | A1 | 11/2005 | Khvorova et al. |
| 2005/0246794 | A1 | 11/2005 | Khvorova et al. |
| 2005/0255487 | A1 | 11/2005 | Khvorova et al. |
| 2008/0113351 | A1 | 5/2008 | Naito et al. |
| 2008/0146788 | A1 | 6/2008 | Bhat et al. |
| 2010/0063132 | A1 | 3/2010 | Kim et al. |
| 2010/0137414 | A1 | 6/2010 | Freier et al. |
| 2011/0015252 | A1 | 1/2011 | Fitzgerald et al. |
| 2011/0039914 | A1 | 2/2011 | Pavco et al. |
| 2011/0054005 | A1 | 3/2011 | Naito et al. |
| 2012/0052487 | A9 | 3/2012 | Khvorova et al. |
| 2012/0108803 | A1 | 5/2012 | Han et al. |
| 2012/0172412 | A1 | 7/2012 | Rozema et al. |
| 2012/0184595 | A1 | 7/2012 | Macdonald et al. |
| 2012/0201756 | A1 | 8/2012 | Sexton |
| 2012/0227119 | A1 | 9/2012 | Doran et al. |
| 2013/0005793 | A1 | 1/2013 | Chin et al. |
| 2013/0023579 | A1 | 1/2013 | Crooke et al. |
| 2013/0041133 | A1 | 2/2013 | Aaronson et al. |
| 2013/0096288 | A1 | 4/2013 | Han et al. |
| 2013/0123482 | A1 | 5/2013 | Xi et al. |
| 2013/0158021 | A1 | 6/2013 | Dong et al. |
| 2013/0190484 | A1 | 7/2013 | Rozema et al. |
| 2014/0099666 | A1 | 4/2014 | Rossomando et al. |
| 2014/0128453 | A1 | 5/2014 | Mullick et al. |
| 2014/0179768 | A1 | 6/2014 | Bettencourt et al. |
| 2014/0194489 | A1 | 7/2014 | Bumcrot et al. |
| 2014/0343123 | A1 | 11/2014 | Prakash et al. |
| 2015/0093444 | A1 | 4/2015 | Zhang et al. |
| 2015/0152436 | A1 | 6/2015 | Musunuru et al. |
| 2015/0174260 | A1 | 6/2015 | Yang et al. |
| 2015/0191726 | A1 | 7/2015 | Manoharan et al. |
| 2015/0247143 | A1 | 9/2015 | Fitzgerald et al. |
| 2015/0263948 | A1 | 9/2015 | Jan et al. |
| 2015/0291958 | A1 | 10/2015 | Albaek et al. |
| 2015/0315584 | A1 | 11/2015 | Macdonald et al. |
| 2015/0315594 | A1 | 11/2015 | Prakash et al. |
| 2016/0017335 | A1 | 1/2016 | Borodovsky et al. |
| 2016/0186180 | A1 | 6/2016 | Bettencourt et al. |
| 2016/0237438 | A1 | 8/2016 | Brown et al. |
| 2016/0283653 | A1 | 9/2016 | Staudt et al. |
| 2016/0354404 | A1 | 12/2016 | Hinkle et al. |
| 2017/0000815 | A1 | 1/2017 | Fitzgerald et al. |
| 2017/0002094 | A1 | 1/2017 | Sexton et al. |
| 2017/0114341 | A1 | 4/2017 | Bradshaw et al. |
| 2018/0087054 | A1 | 3/2018 | Querbes et al. |
| 2018/0148722 | A1 | 5/2018 | Fitzgerald et al. |
| 2018/0216114 | A1 | 8/2018 | Fitzgerald et al. |
| 2018/0245077 | A1 | 8/2018 | Chiu et al. |
| 2019/0062749 | A1 | 2/2019 | Zhang |
| 2019/0078088 | A1 | 3/2019 | Li et al. |
| 2019/0202855 | A1 | 7/2019 | Sakamuri et al. |
| 2019/0255091 | A1 | 8/2019 | Li et al. |
| 2019/0292547 | A1 | 9/2019 | Li et al. |
| 2020/0199591 | A1 | 6/2020 | Fitzgerald et al. |
| 2020/0338201 | A1 | 10/2020 | Zhang et al. |
| 2020/0360522 | A1 | 11/2020 | Zhang et al. |
| 2021/0032623 | A1 | 2/2021 | Zhang et al. |
| 2021/0275564 | A1 | 9/2021 | Zhang et al. |
| 2021/0277400 | A1 | 9/2021 | Zhang et al. |
| 2021/0401994 | A1 | 12/2021 | Zhang et al. |
| 2022/0049249 | A1 | 2/2022 | Zhang et al. |
| 2022/0062427 | A1 | 3/2022 | Zhang et al. |
| 2022/0186221 | A1 | 6/2022 | Zhang et al. |
| 2022/0235359 | A1 | 7/2022 | Zhang et al. |
| 2022/0315929 | A1 | 10/2022 | Zhang et al. |
| 2022/0356474 | A1 | 11/2022 | Zhang et al. |
| 2022/0389428 | A1 | 12/2022 | Zhang et al. |
| 2022/0395526 | A1 | 12/2022 | Zhang et al. |
| 2023/0076803 | A1 | 3/2023 | Zhang et al. |
| 2023/0193277 | A1 | 6/2023 | Zhang et al. |
| 2023/0257827 | A1 | 8/2023 | Zhang et al. |
| 2023/0313195 | A1 | 10/2023 | Zhang et al. |
| 2024/0200060 | A1 | 6/2024 | Zhang et al. |
| 2024/0200076 | A1 | 6/2024 | Zhang et al. |
| 2025/0057870 | A1 | 2/2025 | Liang et al. |

FOREIGN PATENT DOCUMENTS

| | | | |
|---|---|---|---|
| CA | 2 677 068 | A1 | 3/2011 |
| CN | 101603042 | A | 12/2009 |
| CN | 102006890 | A | 4/2011 |
| CN | 102016036 | A | 4/2011 |
| CN | 102083983 | A | 6/2011 |
| CN | 102124107 | A | 7/2011 |
| CN | 102140458 | A | 8/2011 |
| CN | 102140459 | A | 8/2011 |
| CN | 102140460 | A | 8/2011 |
| CN | 102140461 | A | 8/2011 |
| CN | 102344477 | A | 2/2012 |
| CN | 102439148 | A | 5/2012 |
| CN | 102719434 | A | 10/2012 |
| CN | 102753186 | A | 10/2012 |
| CN | 102140461 | B | 12/2012 |
| CN | 102869774 | A | 1/2013 |
| CN | 102140458 | B | 5/2013 |
| CN | 103380113 | A | 10/2013 |
| CN | 103890000 | A | 6/2014 |
| CN | 104107437 | A | 10/2014 |
| CN | 104232644 | A | 12/2014 |
| CN | 104328121 | A | 2/2015 |
| CN | 104717982 | A | 6/2015 |
| CN | 104854242 | A | 8/2015 |
| CN | 104922141 | A | 9/2015 |
| CN | 105324485 | A | 2/2016 |
| CN | 105378082 | A | 3/2016 |
| CN | 105392488 | A | 3/2016 |
| CN | 105452465 | A | 3/2016 |
| CN | 105517556 | A | 4/2016 |
| CN | 105713092 | A | 6/2016 |
| CN | 105814204 | A | 7/2016 |
| CN | 106132442 | A | 11/2016 |
| CN | 106146591 | A | 11/2016 |
| CN | 106232831 | A | 12/2016 |
| CN | 106255755 | A | 12/2016 |
| CN | 106460025 | A | 2/2017 |
| CN | 107075516 | A | 8/2017 |
| CN | 107109405 | A | 8/2017 |
| CN | 107250362 | A | 10/2017 |
| CN | 107854478 | A | 3/2018 |
| CN | 108064294 | A | 5/2018 |
| CN | 108064313 | A | 5/2018 |
| CN | 108220293 | A | 6/2018 |
| CN | 108239644 | A | 7/2018 |
| CN | 108265052 | A | 7/2018 |
| CN | 108271386 | A | 7/2018 |
| CN | 108348541 | A | 7/2018 |
| CN | 110945131 | A | 3/2020 |
| CN | 110959011 | A | 4/2020 |
| CN | 111050807 | A | 4/2020 |
| CN | 111973617 | A | 11/2020 |
| CN | 111973618 | A | 11/2020 |
| CN | 111973619 | A | 11/2020 |
| CN | 111979237 | A | 11/2020 |
| CN | 112423795 | A | 2/2021 |
| CN | 113330117 | A | 8/2021 |
| EP | 1 752 536 | A1 | 2/2007 |
| EP | 2194128 | A1 | 6/2010 |
| EP | 2213738 | A2 | 8/2010 |
| EP | 2376641 | A1 | 10/2011 |
| EP | 2669377 | A2 | 12/2013 |
| EP | 2990410 | A1 | 3/2016 |
| EP | 3312281 | A2 | 4/2018 |
| EP | 3315608 | A1 | 5/2018 |
| EP | 3335715 | A2 | 6/2018 |
| EP | 3409780 | A1 | 12/2018 |
| EP | 3719128 | A1 | 10/2020 |
| EP | 3862024 | A1 | 8/2021 |
| JP | 2013523149 | A | 6/2013 |
| JP | 2013537423 | A | 10/2013 |
| JP | 2016501195 | A | 1/2016 |
| JP | 2016523087 | A | 8/2016 |

(56) References Cited

FOREIGN PATENT DOCUMENTS

| | | | |
|---|---|---|---|
| JP | 2017521045 | A | 8/2017 |
| JP | 2017534290 | A | 11/2017 |
| RU | 2013134745 | A | 2/2015 |
| RU | 2558258 | C2 | 7/2015 |
| RU | 2582235 | C2 | 4/2016 |
| RU | 2015133167 | A | 3/2017 |
| RU | 2649367 | C2 | 4/2018 |
| TW | 201925471 | A | 7/2019 |
| TW | 201929905 | A | 8/2019 |
| WO | 0027795 | A1 | 5/2000 |
| WO | 2004/045543 | A2 | 6/2004 |
| WO | 2004078181 | A1 | 9/2004 |
| WO | 2005116204 | A1 | 12/2005 |
| WO | 2006006948 | A2 | 1/2006 |
| WO | 2006096018 | A1 | 9/2006 |
| WO | 2007134161 | A2 | 11/2007 |
| WO | 2008011431 | A2 | 1/2008 |
| WO | 2008109472 | A2 | 9/2008 |
| WO | 2009073809 | A2 | 6/2009 |
| WO | 2009082607 | A2 | 7/2009 |
| WO | 2009134487 | A2 | 11/2009 |
| WO | 2010012244 | A1 | 2/2010 |
| WO | 2010045509 | A2 | 4/2010 |
| WO | 2010068978 | A1 | 6/2010 |
| WO | 2010083615 | A1 | 7/2010 |
| WO | 2010101951 | A1 | 9/2010 |
| WO | 2010121074 | A1 | 10/2010 |
| WO | 2010131916 | A2 | 11/2010 |
| WO | 2010147992 | A1 | 12/2010 |
| WO | 2011005793 | A1 | 1/2011 |
| WO | 2011/028938 | A1 | 3/2011 |
| WO | 2011085271 | A2 | 7/2011 |
| WO | 2011104169 | A1 | 9/2011 |
| WO | 2011126974 | A1 | 10/2011 |
| WO | 2011139702 | A2 | 11/2011 |
| WO | 2011154331 | A1 | 12/2011 |
| WO | 2012013127 | A1 | 2/2012 |
| WO | 2012024170 | A2 | 2/2012 |
| WO | 2012037254 | A1 | 3/2012 |
| WO | 2012068176 | A1 | 5/2012 |
| WO | 2012083185 | A2 | 6/2012 |
| WO | 2012089352 | A1 | 7/2012 |
| WO | 2012/139081 | A2 | 10/2012 |
| WO | 2012130086 | A1 | 10/2012 |
| WO | 2012139469 | A1 | 10/2012 |
| WO | 2012177784 | A2 | 12/2012 |
| WO | 2013060261 | A1 | 5/2013 |
| WO | 2013061295 | A1 | 5/2013 |
| WO | 2013070771 | A1 | 5/2013 |
| WO | 2013166155 | A1 | 11/2013 |
| WO | 2014025805 | A1 | 2/2014 |
| WO | 2014076195 | A1 | 5/2014 |
| WO | 2014089313 | A1 | 6/2014 |
| WO | 2014118267 | A1 | 8/2014 |
| WO | 2014179626 | A2 | 11/2014 |
| WO | 2014179627 | A2 | 11/2014 |
| WO | 2014179629 | A2 | 11/2014 |
| WO | 2014205451 | A1 | 12/2014 |
| WO | 2015006498 | A2 | 1/2015 |
| WO | 2015006740 | A2 | 1/2015 |
| WO | 2015015496 | A1 | 2/2015 |
| WO | 2015031679 | A2 | 3/2015 |
| WO | 2015/051366 | A2 | 4/2015 |
| WO | 2015100394 | A1 | 7/2015 |
| WO | 2015113922 | A1 | 8/2015 |
| WO | 2015148580 | A2 | 10/2015 |
| WO | 2015168532 | A2 | 11/2015 |
| WO | 2015168589 | A1 | 11/2015 |
| WO | 2015188194 | A1 | 12/2015 |
| WO | 2015188197 | A2 | 12/2015 |
| WO | 2016011123 | A1 | 1/2016 |
| WO | 2016028649 | A1 | 2/2016 |
| WO | 2016/040589 | A1 | 3/2016 |
| WO | 2016077321 | A1 | 5/2016 |
| WO | 2016077349 | A1 | 5/2016 |
| WO | 2016081444 | A1 | 5/2016 |
| WO | 2016099982 | A2 | 6/2016 |
| WO | 2016149331 | A2 | 9/2016 |
| WO | 2016154127 | A2 | 9/2016 |
| WO | 2016168286 | A1 | 10/2016 |
| WO | 2016179342 | A2 | 11/2016 |
| WO | 2016/201301 | A1 | 12/2016 |
| WO | 2016188473 | A1 | 12/2016 |
| WO | 2016206626 | A1 | 12/2016 |
| WO | 2017015175 | A1 | 1/2017 |
| WO | 2017019660 | A1 | 2/2017 |
| WO | 2017019891 | A2 | 2/2017 |
| WO | 2017035340 | A1 | 3/2017 |
| WO | 2017055627 | A1 | 4/2017 |
| WO | 2017100542 | A1 | 6/2017 |
| WO | 2017120397 | A1 | 7/2017 |
| WO | 2017131236 | A1 | 8/2017 |
| WO | 2017184689 | A1 | 10/2017 |
| WO | 2017189813 | A1 | 11/2017 |
| WO | 2018/035380 | A1 | 2/2018 |
| WO | 2018027106 | A2 | 2/2018 |
| WO | 2018044350 | A1 | 3/2018 |
| WO | 2018075658 | A1 | 4/2018 |
| WO | 2018140920 | A1 | 8/2018 |
| WO | 2018191278 | A2 | 10/2018 |
| WO | 2018209848 | A1 | 11/2018 |
| WO | 2018223073 | A1 | 12/2018 |
| WO | 2019/105418 | A1 | 6/2019 |
| WO | 2019105403 | A1 | 6/2019 |
| WO | 2019105404 | A1 | 6/2019 |
| WO | 2019105419 | A1 | 6/2019 |
| WO | 2019105435 | A1 | 6/2019 |
| WO | 2019105437 | A1 | 6/2019 |
| WO | 2019128611 | A1 | 7/2019 |
| WO | 2020038377 | A1 | 2/2020 |
| WO | 2020/063198 | A1 | 4/2020 |
| WO | 2020093053 | A1 | 5/2020 |
| WO | 2020135581 | A1 | 7/2020 |
| WO | 2020147847 | A1 | 7/2020 |
| WO | 2020233651 | A1 | 11/2020 |
| WO | 2020233655 | A1 | 11/2020 |
| WO | 2020233680 | A1 | 11/2020 |
| WO | 2020238763 | A1 | 12/2020 |
| WO | 2020238766 | A1 | 12/2020 |

OTHER PUBLICATIONS

Ren , et al., "Stable Inhibition of Hepatitis B Virus Expression and Replication by Expressed siRNA", Biochemical and Biophysical Research Communications, vol. 335, No. 4, Oct. 7, 2005, pp. 1051-1059.

Ren , et al., "Synthesis of Bifunctional Cationic Compound for Gene Delivery", Tetrahedron Letters, vol. 42, No. 6, Feb. 5, 2001, pp. 1007-1010.

Office Action dated Mar. 9, 2022, issued in the corresponding Russian Patent Application No. RU 2020118025/10 (030488), 14 pages including 6 pages of English Translation.

Office Action dated May 11, 2022, issued in the corresponding Russian Patent Application No. 2020121741/04 (037329), 18 pages including 8 pages of English Translation.

Payment and Certificate of Renewal dated May 30, 2022, issued in the corresponding South African Patent Application No. 2020/03833, 1 page.

Springer , et al., "GalNAc-siRNA Conjugates: Leading the Way for Delivery of RNAi Therapeutics", Nucleic Acid Therapeutics, vol. 28, No. 3, Jun. 1, 2018, pp. 109-118.

Su , et al., "Progress on the Inhibition of Hepatitis B virus by siRNA Strategy", China Biotechnology, vol. 34, No. 9, Sep. 15, 2014, pp. 102-107.

Tangkijvanich , et al., "Low Pretreatment Serum HBsAg Level and Viral Mutations as Predictors of Response to PEG-Interferon alpha-2b Therapy in Chronic Hepatitis B", Journal of Clinical Virology, vol. 46, Issue 2, Oct. 2009, pp. 117-123.

Ui-Tei , et al., "Functional Dissection of siRNA Sequence by Systematic DNA Substitution: Modified siRNA with a DNA Seed Arm is a Powerful Tool for Mammalian Gene Silencing with

(56) References Cited

OTHER PUBLICATIONS

Significantly Reduced Off-Target Effect", Nucleic Acids Research, vol. 36, No. 7, Apr. 2008, pp. 2136-2151.
Office Action dated Aug. 14, 2020, issued in the corresponding Vietnam Patent Application No. 1-2020-03065, 3 pages including 1 page of English Translation.
Office Action dated Aug. 28, 2020, issued in the corresponding Vietnam Patent Application No. 1-2020-03777, 3 pages including 1 page of English Translation.
Watts , et al., "Chemically Modified siRNA: Tools and Applications", Drug Discovery Today, vol. 13, Nos. 19/20, Oct. 2008, pp. 842-855.
Wooddell , et al., "Hepatocyte-targeted RNAi Therapeutics for the Treatment of Chronic Hepatitis B Virus Infection", Molecular Therapy, vol. 21, No. 5, May 2013, pp. 973-985.
Wu , et al., "Cleaved High Molecular Weight Kininogen Inhibits Tube Formation of Endothelial Progenitor Cells via Suppression of Matrix Metalloproteinase 2", Journal of Thrombosis and Haemostasis, vol. 8, No. 1, Jan. 2010, pp. 185-193.
Wu, Yi , "Contact Pathway of Coagulation and Inflammation", Thrombosis Journal, vol. 13, Article No. 17, 2015, 9 pages.
Xu , et al., "Role of Angiopoietin-like 3 (ANGPTL3) in Regulating Plasma Level of Low-Density Lipoproteins", Atherosclerosis, vol. 268, Jan. 2018, pp. 196-206 (23 pages).
Yang , et al., "An Essential Role of High-Molecular-Weight Kininogen in Endotoxemia," Journal of Experimental Medicine, Sep. 4, 2017, vol. 214, No. 9, pp. 2649-2670.
Yang , et al., "A Critical Role for Plasma Kallikrein in the Pathogenesis of Autoantibody-Induced Arthritis", The Journal of the Federation of American Societies for Experimental Biology, vol. 31, No. 12, Dec. 2017, pp. 5419-5431.
Extended European Search Report dated Jul. 19, 2022, issued by the European Patent Application No. 19867686.8, 12 pages.
*Homo sapiens* Kininogen 1 (KNG1), Transcript Variant 1, mRNA, GenBank, NM 00102416.2, May 2, 2018, 8 pages.
RNAi Technology, Common knowledge with English translation, 2005, 5 pages.
Final Office Action received for U.S. Appl. No. 16/758,532, mailed on May 27, 2022, 8 pages.
Non-Final Office Action received for U.S. Appl. No. 16/758,532, mailed on Jan. 28, 2022, 28 pages.
Non-Final Office Action received for U.S. Appl. No. 16/758,532, mailed on Aug. 24, 2022, 13 pages.
Non-Final Office Action received for U.S. Appl. No. 16/758,720, mailed on Mar. 11, 2022, 21 pages.
Notice of Allowance received for U.S. Appl. No. 16/758,720, mailed on Jul. 25, 2022, 5 pages.
Non-Final Office Action received for U.S. Appl. No. 16/763,058, mailed on Nov. 16, 2021, 26 pages.
Notice of Allowance received for U.S. Appl. No. 16/763,058, mailed on Apr. 5, 2022, 7 pages.
Notice of Allowance received for U.S. Appl. No. 16/764,307, mailed on Mar. 31, 2022, 7 pages.
Office Action received for U.S. Appl. No. 16/764,307, mailed on Oct. 29, 2021, 17 pages.
Extended European Search Report dated Aug. 9, 2021, issued in the corresponding European Patent Application No. 18883362.8, 9 pages.
Beaucage , et al., "Advances in the Synthesis of Oligonucleotides by the Phosphoramidite Approach", Tetrahedron, vol. 28, No. 12, 1992, pp. 2223-2311.
Behlke, Mark A, "Chemical Modification of siRNAs for In Vivo Use", Oligonucleotides, vol. 18, No. 4, Dec. 2008, pp. 305-320.
Berthold , et al., "Cellular Delivery and Antisense Effects of Peptide Nucleic Acid Conjugated to Polyethyleneimine via Disulfide Linkers", Bioconjugate Chemistry, vol. 21, No. 10, 2010, pp. 1933-1938.
Chen , et al., "Research Progress on Factor XI as a Novel Target for Antithrombotic Therapy", Chinese Pharmacological Bulletin, English abstract, vol. 31, No. 5, May 2015, pp. 619-622.
First Office Action dated May 7, 2022, issued in the corresponding Chinese Patent Application No. 201880048597.3, 34 pages including 19 pages of English Translation.
First Office Action dated May 7, 2022, issued in the corresponding Chinese Patent Application No. 201880048600.1, 34 pages including 19 pages of English Translation.
First Office Action dated May 7, 2022, issued in the corresponding Chinese Patent Application No. 201880048949.5, 33 pages pages including 18 pages of English Translation.
First Office Action dated May 7, 2022, issued in the corresponding Chinese Patent Application No. 201880049190.2, 31 pages including 15 pages of English Translation.
First Office Action dated May 7, 2022, issued in the corresponding Chinese Patent Application No. 201880049191.7, 30 pages including 15 pages of English Translation.
First Office Action dated Jan. 30, 2022, issued in the corresponding Chinese Patent Application No. 201880049520.8, 11 pages including 5 pages of English Translation.
First Office Action dated May 7, 2022, issued in the corresponding Chinese Patent Application No. 201880049564.0, 29 pages including 14 pages of English Translation.
First Office Action dated May 7, 2022, issued in the corresponding Chinese Patent Application No. 201880049586.7, 33 pages including 14 pages of English Translation.
First Office Action dated May 7, 2022, issued in the corresponding Chinese Patent Application No. 201980010095.6, 27 pages including 12 pages of English Translation.
Office Action dated May 7, 2022, issued in the corresponding Chinese Patent Application No. 201980010175.1, 30 pages including 15 pages of English Translation.
Decision of Rejection dated Jun. 29, 2022, issued in the corresponding Chinese Patent Application No. 201980046892.X, 8 pages including 5 pages of English Translation.
First Office Action dated Jun. 23, 2021, issued in the corresponding Chinese Patent Application No. 201980046892.X, 10 pages including 6 pages of English Translation.
Second Office Action dated Mar. 16, 2022, issued in the corresponding Chinese Patent Application No. 201980046892.X, 24 pages 14 pages of including English Translation.
Decision of Rejection dated Jun. 29, 2022, issued in the corresponding Chinese Patent Application No. 201980046893.4, 8 pages including 5 pages of English Translation.
First Office Action dated Jun. 23, 2021, issued in the corresponding Chinese Patent Application No. 201980046893.4, 12 pages including 6 pages of English Translation.
Second Office Action dated Mar. 21, 2022, issued in the corresponding Chinese Patent Application No. 201980046893.4, 19 pages including 10 pages of English Translation.
Decision of Rejection dated Mar. 3, 2022, issued in the corresponding Chinese Patent Application No. 202010426194.7, 20 pages including 14 pages of English Translation.
First Office Action dated May 20, 2021, issued in the corresponding Chinese Patent Application No. 202010426194.7, 20 pages including 11 pages of English Translation.
Second Office Action dated Nov. 12, 2021, issued in the corresponding Chinese Patent Application No. 202010426194.7, 16 pages including 9 pages of English Translation.
First Office Action dated Oct. 25, 2021, issued in the corresponding Chinese Patent Application No. 202010426196.6, 16 pages including 9 pages of English Translation.
First Office Action dated May 7, 2022, issued in the corresponding Chinese Patent Application No. 202080007282.1, 33 pages including 18 pages of English Translation.
First Office Action dated May 7, 2022, issued in the corresponding Chinese Patent Application No. 202080009787.1, 50 pages including 25 pages of English Translation.
Dai , et al., "A Vital Role for Angptl3 in the PAN-Induced Podocyte Loss by Affecting Detachment and Apoptosis in Vitro", BMC Nephrology, vol. 16, Article No. 38, 2015, 10 pages.
Dar , et al., "siRNAmod: A Database of Experimentally Validated Chemically Modified siRNAs", Scientific Reports, vol. 6, Article No. 20031, Jan. 28, 2016, pp. 1-8.

(56) References Cited

OTHER PUBLICATIONS

Ding , et al., "Limited Role of Kininogen in the Host Response during Gram-Negative Pneumonia-Derived Sepsis", American Journal of Physiology Lung Cellular and Molecular Physiology, vol. 314, No. 3, Mar. 1, 2018, pp. L397-L405.
Dong , et al., "A Novel Packaging System of Recombinant AAV5/5 Vector", Chinese Journal of Biotechnology, vol. 26, No. 5, May 25, 2010, pp. 679-686.
Dong , et al., "Lipopeptide Nanoparticles for Potent and Selective siRNA Delivery in Rodents and Nonhuman Primates", Proceedings of the National Academy of Sciences, Feb. 2014, 6 pages.
Extended European Search Report dated Aug. 5, 2021, issued in the corresponding European Patent Application No. 18883153.1, 9 pages.
Extended European Search Report dated Sep. 17, 2021, issued in the corresponding European Patent Application No. 18883982.3, 9 pages.
Extended European Search Report dated Sep. 29, 2021, issued in the corresponding European Patent Application No. 18884492.2, 45 pages.
Extended European Search Report dated Oct. 7, 2021, issued in the corresponding European Patent Application No. 18896766.5, 19 pages.
Extended European Search Report dated Jun. 9, 2022, issued in the corresponding European Patent Application No. 19851738.5, 64 pages.
Supplementary European Search Report issued on Jul. 27, 2022, by the European Patent Office in European Patent Application No. 18883153. (7 pages).
Montagne et al., "Pericyte degeneration causes white matter dysfunction in the mouse CNS," Nature Medicine, 2018, vol. 24, vol. 3, pp. 326-337.
Examination Report No. 2 issued on Feb. 3, 2023, by the Australian Government IP Australia in Australian Patent Application No. 2018394875 (4 pages).
Ren et al., "Synthesis of Galactosyl Compounds for Targeted Gene Delivery", Bioorganic & Medicinal Chemistry, 2001, 9(11), pp. 2969-2978.
Extended European Search Report issued on Mar. 27, 2023, by the European Patent Office in European Patent Application No. 19902173.4 (11 pages).
Li et al., "The silencing of ApoC3 suppresses oxidative stress and inflammatory responses in placenta cells from mice with preeclampsia via inhibition of the Nf-B signaling pathway", Biomedicine & Pharmacotherapy, Aug. 31, 2018, vol. 107, pp. 1377-1384.
Notice of Reasons for Refusal issued on Jun. 1, 2023, by the Japanese Patent Office in Japanese Patent Application No. 2021-537877, with an English translation of the Notice (6 pages).
Kanasty et al., "Delivery materials for siRNA therapeutics", Nature Materials, Nov. 2023, vol. 12, pp. 967-977.
Notice of Reasons for Refusal issued on Jun. 6, 2023, by the Japanese Patent Office in Japanese Patent Application No. 2021-509880, with an English translation of the Notice (6 pages).
Durnov, et al., "Children's Oncology", Paediatric Oncology, Second Edition, Moscow Publishing House Medicine, 2002, p. 139 and its English translation. Cited in Office Action issued on Oct. 10, 2022 in Russian Application No. 2020121741). (4 pages).
Dysop, "Chemistry of Synthetic Drugs", Publishing House MIR, 1964, pp. 12-19 and its English translation. Cited in Office Action issued on Oct. 10, 2022 in Russian Application No. 2020121741). (18 pages).
Belikov, V.G., "Pharmaceutical Chemistry", textbook, Moscow, 11th Edition, MEDpress-inform, 2007, pp. 27-29 and its English translation. (Cited in Office Action issued on Oct. 10, 2022 in Russian Application No. 2020121741). (8 pages).
Chen et al., "Proof-of-concept Studies for siRNA-mediated Gene Silencing for Coagulation Factors in Rat and Rabbit", Molecular Therapy—Nucleic Acids, Jan. 27, 2015, vol. 4, No. 1, p. e224.
Ferrone et al., "IONIS-PKK Rx a Novel Antisense Inhibitor of Prekallikrein and Bradykinin Production", Nucleic Acid Therapeutics, Apr. 1, 2019, vol. 29, No. 2, pp. 82-91.
Ghosh et al., "Effectiveness and Safety of Inclisiran, A Novel Long-Acting RNA Therapeutic Inhibitor of Proprotein Convertase Subtilisin/Kexin 9", American Journal of Cardiology, Cahners Publishing Co., Newton, MA, US, Jul. 3, 2018, vol. 122, No. 7, pp. 1272-1277.
Joshi et al., "siRNA: novel therapeutics from functional genomics", Biotechnology and Genetic Engineering Reviews, Jan. 2, 2014, vol. 30, No. 1, pp. 1-30.
Pawluczyk et al., "Kallikrein gene 'knock-down' by small interfering RNA transfection induces a profibrotic phenotype in rat mesangial cells", Journal of Hypertension, Lippincott Williams & Wilkens, Ltd., Jan. 1, 2008, vol. 26, No. 1, pp. 93-101.
Revenko et al., "Selective depletion of plasma prekallikrein or coagulation factor XII inhibits thrombosis in mice without increased risk of bleeding", Blood, American Society of Hematology, Nov. 10, 2011, vol. 118, No. 19, pp. 5302-5311.
Yamasaki et al., " Novel molecular targets regulated by tumor suppressors microRNA-1 and microRNA-133a in bladder cancer", International Journal of Oncology, Feb. 29, 2012, vol. 40, pp. 1821-1830.
Supplementary European Search Report issued on Jun. 14, 2023, by the European Patent Office in European Patent Application No. 20809702.2 (12 pages).
Supplementary European Search Report issued on Jun. 16, 2023, by the European Patent Office in European Patent Application No. 20814338.8 (10 pages).
Partial Supplementary European Search Report issued on Jul. 5, 2023, by the European Patent Office in European Patent Application No. 20810635.1 (13 pages).
Partial Supplementary European Search Report issued on Jul. 10, 2023, by the European Patent Office in European Patent Application No. 20815633.1 (17 pages).
Bertrand, et al., "Comparison of antisense oligonucleotides and siRNAs in cell culture and in vivo," Biochemical and Biophysical Research Communications, 2002, vol. 296, Issue 4, pp. 1000-1004, ISSN 0006-291X.
Qui, S. et al., "Dickkopf 3 attenuates xanthine dehydrogenase expression to prevent oxidative stress-induced apoptosis," Genes to Cells, 2017, vol. 22, pp. 406-417. (cited in Extended European Search Report issued on Jan. 30, 2024, in European Patent Application No. 20813863.6).
Yasuda, T. et al., "Anti-Gout Agent Allopurinol Exerts Cytotoxicity to Human Hormone-Refractory Prostate Cancer Cells in Combination with Tumor Necrosis Factor-Related Apoptosis-Inducing Ligand," Mol Cancer Res, Dec. 2008, vol. 6, No. 12, pp. 1852-1860. (cited in Extended European Search Report issued on Jan. 30, 2024, in European Patent Application No. 20813863.6).
Hashimoto, K. et al., "Sulfotransferase-1A1-dependent bioactivation of aristolochic acid I and N-hydroxyaristolactam I in human cells," Carcinogenesis, 2016, vol. 37, No. 7, pp. 647-655. (cited in Extended European Search Report issued on Jan. 30, 2024, in European Patent Application No. 20813863.6).
Fedin A.I. et al., "Review of clinical recommendations for treatment and prevention of ischemic stroke", S. S. Korsakov Journal of Neurology and Psychiatry, 2019, vol. 119, No. 8, pp. 91-96, doi: 10.17116/jnevro201911908291, with English abstract. (Cited in Office Action issued on Mar. 6, 2024, in corresponding Russian Application No. 2021130601) (6 pages).
Meijers J.C. et al., "High levels of coagulation factor XI as a risk factor for venous thrombosis", N. Engl. J. Med., 2000, vol. 342, no. 10, pp. 696-701, doi: 10.1056/NEJM200003093421004. (Cited in Office Action issued on Mar. 6, 2024, in corresponding Russian Application No. 2021130601) (6 pages).
Soodabeh S. et al., "From in vitro Experiments to in vivo and Clinical Studies; Pros and Cons", Curr. Drug Discov. Technol., 2015, vol. 12, No. 4, pp. 218-224. (Cited in Office Action issued on Mar. 6, 2024, in corresponding Russian Application No. 2021130601) (7 pages).
Shafer A.I. et al., "Thrombotic Disorders Diagnosis and Treatment", Am. Soc. Hematol. Educ. Program, 2003, v. 1, pp. 520-539, doi

(56) References Cited

OTHER PUBLICATIONS 10.1182asheducation-2003.1.520. (Cited in Office Action issued on Mar. 6, 2024, in corresponding Russian Application No. 2021130601) (20 pages).
Sehgal, Alfica et al., "Liver as a target for oligonucleotide therapeutics", Journal of hepatology, 2013, vol. 59, pp. 1354-1359. (Cited in Office Action issued on Mar. 11, 2024, in corresponding Taiwanese Patent Application No. 109116935) (6 pages).
Diaz-Torné, Cesar et al., "New medications in development for the treatment of hyperuricemia of gout", Current opinion in rheumatology. 2015, vol. 27, No. 2, pp. 164-169. (Cited in Office Action issued on Mar. 11, 2024, in corresponding Taiwanese Patent Application No. 109116934) (6 pages).
Kojima, S. et al., "Tumour suppressors miR-1 and miR-133a target the oncogenic function of purine nucleoside phosphorylase (PNP) in prostate cancer", Br. J. Cancer, 2012, vol. 106(2), pp. 405-413. (Cited in Office Action issued on May 21, 2024, in corresponding Japanese Patent Application No. JP2021-569112) (9 pages).
Invitation to Remedy Deficiencies Pursuant to Rule 30(3) EPC / Rule 163(3) EPC dated Feb. 22, 2022, issued in the corresponding European Patent Application No. 20809029.0, 2 pages.
Communication Pursuant to Rule 159 and Rule 28 EPC Invitation to Remedy Deficiencies in the Application Documents dated Jan. 24, 2022, issued in the corresponding European Patent Application No. 20815633.1, 2 pages.
Extended European Search Report dated Sep. 16, 2021, issued in the corresponding European Patent Application No. 18883803.1, 10 pages.
Foster , et al., "Advanced siRNA Designs Further Improve In Vivo Performance of GalNAc-siRNA Conjugates", Molecular Therapy, vol. 26, No. 3, Mar. 7, 2018, pp. 708-717.
Greene , et al., "Protection for the Hydroxyl Group, Including 1,2- and 1,3-DIOLS", Protective Groups in Organic Synthesis, Third Edition, John Wiley & Sons, Inc., 1999, pp. 17-245.
Notification of Substantive Examination Result dated Dec. 2, 2021, issued in the corresponding Indonesian Patent Application No. P00202003125, 6 pages including 3 pages of English Translation.
Notification of Substantive Examination Result dated Aug. 24, 2021, issued in the corresponding Indonesian Patent Application No. P00202003131, 6 pages including 3 pages of English Translation.
Examination Report dated Nov. 24, 2021, issued in the corresponding Indian Patent Application No. 202047017398, 7 pages.
Khaitmetova, et al., "Synthesis and Study of the Properties of Polymer Complexes of Ethacizin with Carboxymethylcellulose", Chemistry of Plant Raw Materials, No. 4, 2017, 18 pages including 9 pages of English Translation.
Khan , et al., "High-Molecular-Weight Kininogen Fragments Stimulate the Secretion of Cytokines and Chemokines Through uPAR, Mac-1, and gC1qR in Monocytes", Arteriosclerosis, Thrombosis, and Vascular Biology, vol. 26, No. 10, Oct. 2006, pp. 2260-2266 (11 pages).
Khvorova , et al., "The Chemical Evolution of Oligonucleotide Therapies of Clinical Utility", Nature Biotechnology, vol. 35, No. 3, Mar. 2017, pp. 238-248.
Kim , et al., "Bifunctional Compounds for Targeted Hepatic Gene Delivery", Gene Therapy, vol. 14, No. 8, Apr. 2007, pp. 704-708.
Liu , et al., "Determination of Human Plasma Pre-Kallikrein," Journal of China Medical University, vol. 17, No. 6, 1988, pp. 432-436 with English Abstract.
Liu , et al., "Coagulation Factor XI Induces Ca2+ Response and Accelerates Cell Migration in Vascular Smooth Muscle Cells via Proteinase-Activated Receptor 1", American Journal of Physiology-Cell Physiology, vol. 316, No. 3, Mar. 1, 2019, pp. C377-C392.
Love , et al., "Lipid-Like Materials for Low-Dose, in Vivo Gene Silencing", Proceedings of the National Academy of Sciences of the United States of America, vol. 107, No. 21, May 25, 2010, 7 pages.
Matsuda , et al., "siRNA Conjugates Carrying Sequentially Assembled Trivalent N-Acetylgalactosamine Linked Through Nucleosides Elicit Robust Gene Silencing In Vivo in Hepatocytes", ACS Chemical Biology, vol. 10, No. 5, May 15, 2015, pp. 1181-1187 (A-G).
Nair , et al., "Multivalent N-Acetylgalactosamine-Conjugated siRNA Localizes in Hepatocytes and Elicits Robust RNAi-Mediated Gene Silencing", Journal of the American Chemical Society, vol. 136, No. 49, Dec. 1, 2014, pp. 16958-16961.
Nakagawa , et al., "The RNAi-Mediated Silencing of Xanthine Dehydrogenase Impairs Growth and Fertility and Accelerates Leaf Senescence in Transgenic Arabidopsis Plants", Plant & Cell Physiology, vol. 48, No. 10, Oct. 1, 2007, pp. 1484-1495.
Nakamoto , et al., "Enhanced Intercellular Delivery of cRGD-siRNA Conjugates by an Additional Oligospermine Modification", ACS Omega, vol. 3, No. 7, 2018, pp. 8226-8232.
Norata , et al., "Gene Silencing Approaches for the Management of Dyslipidaemia", Trends in Pharmacological Sciences, vol. 34, No. 4, Apr. 1, 2013, pp. 198-205.
Nordestgaard , et al., "Advances in Lipid-Lowering Therapy Through Gene-Silencing Technologies", Nature Reviews Cardiology, vol. 15, No. 5, May 2018, pp. 261-272.
Nothisen, et al., "Cationic siRNAs Provide Carrier-Free Gene Silencing in Animal Cells", Journal of the American Chemical Society, vol. 131, No. 49, 2009, pp. 17730-17731.
Papulov, Yu G, "Relationship Between Properties of Compounds With Their Structures: Math Modeling", Advances in Modern Natural Sciences, English Translation, 2006, pp. 75-76.
Paris , et al., "Conjugating Phosphospermines to siRNAs for Improved Stability in Serum, Intracellular Delivery and RNAi-Mediated Gene Silencing", Molecular Pharmaceutics, vol. 9, No. 12, 2012, pp. 3464-3475.
International Search Report and Written Opinion received for the PCT Application No. PCT/CN2018/118106, mailed on Mar. 6, 2019, 20 pages including 9 pages of English Translation.
International Search Report and Written Opinion received for the PCT Application No. PCT/CN2018/118107, mailed on Feb. 20, 2019, 22 pages including 10 pages of English Translation.
International Preliminary Report on Patentability received for the PCT Application No. PCT/CN2018/118191, mailed on Jun. 11, 2020, 7 pages.
International Search Report and Written Opinion received for the PCT Application No. PCT/CN2018/118191, mailed on Mar. 6, 2019, 23 pages including 11 pages of English Translation.
International Search Report (PCT/ISA/210) and Written Opinion received for the PCT Application No. PCTCN2018/118212, mailed on Feb. 25, 2019, 23 pages including 11 pages of English Translation.
International Search Report and Written Opinion received for the PCT Application No. PCT/CN2018/118224, mailed on Feb. 27, 2019, 13 pages of English Translation only.
International Preliminary Report on Patentability received for the PCT Application No. PCT/CN2018/118232, mailed on Jul. 2, 2020, 14 pages including 8 pages of English Translation.
International Search Report and Written Opinion received for the PCT Application No. PCT/CN2018/118232, mailed on Mar. 7, 2019, 24 pages including 12 pages of English Translation.
International Search Report and Written Opinion received for the PCT Application No. PCT/CN2018/118300, mailed on Feb. 28, 2019, 20 pages including 9 pages of English Translation.
International Search Report and Written Opinion received for the PCT Application No. PCT/CN2018/118303, mailed on Mar. 7, 2019, 22 pages including 10 pages of English Translation.
International Search Report and Written Opinion received for the PCT Application No. PCT/CN2019/101653, mailed on Nov. 21, 2019, 23 pages including 12 pages of English Translation.
International Search Report and Written Opinion received for the PCT Application No. PCT/CN2019/101656, mailed on Nov. 28, 2019, 21 pages including 10 pages of English Translation.
International Preliminary Report on Patentability received for the PCT Application No. PCT/CN2019/128686, mailed on Jul. 8, 2021, 17 pages including 9 pages of English Translation.
International Search Report and Written Opinion received for the PCT Application No. PCT/CN2019/128686, mailed on Mar. 26, 2020, 27 pages including 14 pages of English Translation.

(56) References Cited

OTHER PUBLICATIONS

International Search Report and Written Opinion received for the PCT Application No. PCT/CN2019/129016, mailed on Mar. 26, 2020, 27 pages including 14 pages of English Translation.
International Search Report and Written Opinion received for the PCT Application No. PCT/CN2020/072813, mailed on Apr. 17, 2020, 32 pages including 15 pages of English Translation.
International Search Report and Written Opinion received for the PCT Application No. PCT/CN2020/091484, mailed on Aug. 21, 2020, 29 pages including 14 pages of English Translation.
International Search Report and Written Opinion received for the PCT Application No. PCT/CN2020/091485, mailed on Aug. 25, 2020, 30 pages including 15 pages of English Translation.
International Preliminary Report on Patentability received for the PCT Application No. PCT/CN2020/091489, mailed on Sep. 3, 2021, 12 pages including 6 pages of English Translation.
International Search Report and Written Opinion received for the PCT Application No. PCT/CN2020/091489, mailed on Aug. 19, 2020, 26 pages including 11 pages of English Translation.
International Search Report and Written Opinion received for the PCT Application No. PCT/CN2020/091606, mailed on Sep. 2, 2020, 28 pages including 14 pages of English Translation.
International Search Report and Written Opinion received for the PCT Application No. PCT/CN2020/091614 , mailed on Aug. 21, 2020, 24 pages including 11 pages of English Translation.
International Search Report and Written Opinion received for the PCT Application No. PCT/CN2020/091624, mailed on Aug. 24, 2020, 26 pages including 13 pages of English Translation.
International Search Report and Written Opinion received for the PCT Application No. PCT/CN2020/091649, mailed on Aug. 28, 2020, 26 pages including 12 pages of English Translation.
Peña-Altamira , et al., "Release of Soluble and Vesicular Purine Nucleoside Phosphorylase from Rat Astrocytes and Microglia Induced by Pro-Inflammatory Stimulation with Extracellular ATP via P2X7 Receptors", Neurochemistry International, vol. 115, May 2018, pp. 37-49 (50 pages).
Pessentheiner , et al., "ANGPTL3 Targeting: The Power of Versatile Lipid-Lowering", Atherosclerosis, vol. 268, Jan. 1, 2018, pp. 185-187.
Dana et al., "Molecular Mechanisms and Biological Functions of siRNA," International Journal of Biomedical Science, vol. 13, No. 2, pp. 48-57 (2017).
Elbashir et al., "Functional anatomy of siRNAs for mediating efficient RNAi in *Drosophila melanogaster* embryo lysate," The EMBO Journal, vol. 20, No. 23, pp. 6877-6888 (2001).
Fakhr et al., "Precise and efficient siRNA design: a key point in competent gene silencing," Cancer Gene Therapy, vol. 23, pp. 73-82 (2016).
Girardet et al., "Urate Crystal Deposition Disease and Gout—New Therapies for an Old Problem," Annual Reports in Medicinal Chemistry, vol. 49, pp. 151-164 (2014).
Lorenzer et al., "Going beyond the liver: Progress and Challenges of Targeted Delivery of siRNA Therapeutics," Journal of Controlled Release, vol. 203, pp. 1-15 (2015).
Willoughby et al., "Evaluation of GalNAc-siRNA Conjugate Activity in Pre-clinical Animal Models with Reduced Asialoglycoprotein Receptor Expression," Molecular Therapy, vol. 26, No. 1, pp. 105-114 (2018).

* cited by examiner

Day 14, 3 mg/kg

Day 14, 0.3 mg/kg

Day 28, 3 mg/kg

D28, 0.3 mg/kg

DOUBLE-STRANDED OLIGONUCLEOTIDE, COMPOSITION AND CONJUGATE COMPRISING DOUBLE-STRANDED OLIGONUCLEOTIDE, PREPARATION METHOD THEREOF AND USE THEREOF

CROSS REFERENCE OF RELATED APPLICATIONS

This application is a continuation of U.S. patent application Ser. No. 16/758,720, filed on Apr. 23, 2020, now U.S. Pat. No. 11,492,620, entitled "DOUBLE-STRANDED OLIGONUCLEOTIDE, COMPOSITION AND CONJUGATE COMPRISING DOUBLE-STRANDED OLIGONUCLEOTIDE, PREPARATION METHOD THEREOF AND USE THEREOF," which in turn is a national stage application of PCT/CN2018/118212, filed on Nov. 29, 2018, which claims priority to Chinese Patent Application No. 201711249356.9, filed on Dec. 1, 2017, Chinese Patent Application No. 201711249345.0, filed on Dec. 1, 2017, Chinese Patent Application No. 201711249333.8, filed on Dec. 1, 2017, Chinese Patent Application No. 201711479058.9, filed on Dec. 29, 2017, Chinese Patent Application No. 201810951752.4, filed on Aug. 21, 2018, and Chinese Patent Application No. 201811165363.5, filed on Sep. 30, 2018. The entire content of each of the prior applications is hereby incorporated by reference.

SEQUENCE LISTING

Incorporated by reference herein in its entirety is a computer-readable sequence listing submitted via EFS-Web and identified as follows: One (87534 byte ASCII (Text)) file named "20211012 RB069PCT-ESP1V192724ZX-CNSZRB-US-updated.txt" created on Oct. 12, 2021.

BACKGROUND OF THE INVENTION

The use of double-stranded oligonucleotides as pharmaceutical active ingredients has been well-known to the public. Delivery system is one of key technologies in the development of small RNA drugs. One type of small RNA delivery system is a targeted conjugation delivery technology for liver cells.

SUMMARY OF THE INVENTION

In some embodiments, the present disclosure provides a double-stranded oligonucleotide comprising a sense strand and an antisense strand, each nucleotide in the sense strand and the antisense strand being a modified nucleotide, wherein the sense strand comprises a nucleotide sequence 1, and the antisense strand comprises a nucleotide sequence 2; the nucleotide sequence 1 and the nucleotide sequence 2 are both 19 nucleotides in length and are at least partly reverse complementary to form a double-stranded complementary region; the nucleotide sequence 2 is at least partly reverse complementary to a first nucleotide sequence segment, which refers to a segment of nucleotide sequence in the target mRNA; in the direction from 5' terminal to 3' terminal, the nucleotides at positions 7, 8 and 9 of the nucleotide sequence 1 are fluoro modified nucleotides, and each of the nucleotides at the other positions in the nucleotide sequence 1 is independently a non-fluoro modified nucleotide; the first nucleotide at 5' terminal of the nucleotide sequence 2 is the first nucleotide at 5' terminal of the antisense strand, the nucleotides at positions 2, 6, 14 and 16 of the nucleotide sequence 2 are fluoro modified nucleotides, and each of the nucleotides at the other positions in the nucleotide sequence 2 is independently a non-fluoro modified nucleotide.

In some embodiments, the present disclosure further provides a pharmaceutical composition comprising the double-stranded oligonucleotide of the present disclosure and a pharmaceutically acceptable carrier.

In some embodiments, the present disclosure further provides a conjugate comprising the double-stranded oligonucleotide the present disclosure and a ligand conjugated to the double-stranded oligonucleotide.

In some embodiments, the present disclosure provides use of the double-stranded oligonucleotide, pharmaceutical composition or conjugate of the present disclosure in the manufacture of a medicament for treating and/or preventing a pathological condition or disease caused by the expression of a specific gene in hepatocytes.

In some embodiments, the present disclosure provides a method for treating a pathological condition or disease caused by the expression of a specific gene in hepatocytes, comprising administering the double-stranded oligonucleotide, pharmaceutical composition or conjugate of the present disclosure, to a subject suffering from such a disease.

In some embodiments, the present disclosure provides is a method for inhibiting the expression of a specific gene in hepatocytes, comprising contacting the hepatocytes with the double-stranded oligonucleotide, pharmaceutical composition or conjugate of the present disclosure.

In some embodiments, the present disclosure provides is a kit comprising the double-stranded oligonucleotide, pharmaceutical composition or conjugate of the present disclosure.

Additional features and advantages of the present invention will be illustrated in detail in the following specific embodiments.

INCORPORATION BY REFERENCE

All publications, patents and patent applications mentioned in this description are herein incorporated by reference to the same extent as if each individual publication, patent and patent application were specifically and individually indicated to be incorporated by reference.

DETAILED DESCRIPTION OF THE INVENTION

Figure 1:
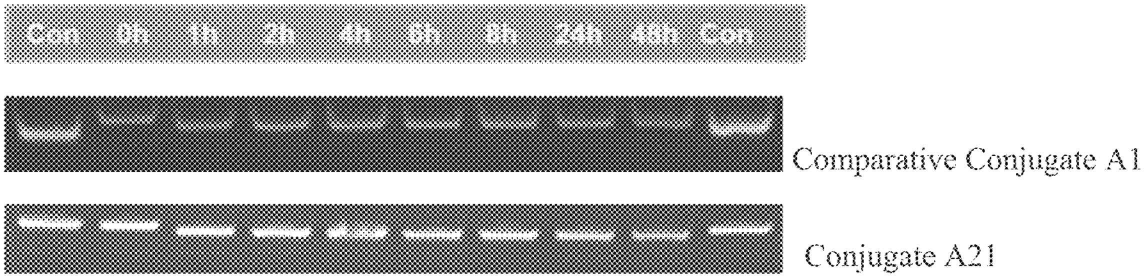
FIGS. 1 and 2 show the semiquantitative result of the stability test of the siRNA conjugates in the Tritosome in vitro.

The specific embodiments of the present disclosure are described in detail as below. It should be understood that the specific embodiments described herein are only for the purpose of illustration and explanation of the present disclosure and are not intended to limit the present disclosure in any respect.

Definitions

In the context of the present disclosure, unless otherwise specified, C, G, U, and A represent the base components of a nucleotide; m represents that the nucleotide adjacent to the left side of the letter m is a 2'-methoxy modified nucleotide; f represents that the nucleotide adjacent to the left side of the letter f is a 2'-fluoro modified nucleotide; s represents that the two nucleotides adjacent to both sides of the letter s are linked by a phosphorothioate linkage; P1 represents that the nucleotide adjacent to the right side of P1 is a 5'-phosphate nucleotide or a 5'-phosphate analog modified nucleotide, especially a vinyl phosphate modified nucleotide (expressed as VP in the Examples below), a 5'-phosphate nucleotide (expressed as P in the Examples below) or a 5'-thiophosphate modified nucleotide (expressed as Ps in the Examples below).

In the context of the present disclosure, expressions “complementary” and “reverse complementary” can be interchangeably used, and have a well-known meaning in the art, namely, the bases in one strand are complementarily paired with those in the other strand of a double-stranded nucleic acid molecule. In DNA, a purine base adenine (A) is always paired with a pyrimidine base thymine (T) (or uracil (U) in RNAs); and a purine base guanine (G) is always paired with a pyrimidine base cytosine (C). Each base pair comprises a purine and a pyrimidine. While adenines in one strand are always paired with thymines (or uracils) in another strand, and guanines are always paired with cytosines, these two strands are considered as being complementary each other; and the sequence of a strand may be deduced from the sequence of its complementary strand. Correspondingly, a “mispairing” means that in a double-stranded nucleic acid, the bases at corresponding sites are not presented in a manner of being complementarily paired.

In the context of the present disclosure, unless otherwise specified, “basically reverse complementary” means that there are no more than 3 base mispairings between two nucleotide sequences. “Substantially reverse complementary” means that there is no more than 1 base mispairing between two nucleotide sequences. “Completely complementary” means that there is no based mispairing between two nucleotide sequences.

In the context of the present disclosure, when a nucleotide sequence has “nucleotide difference” from another nucleotide sequence, the bases of the nucleotides at the same position therebetween are changed. For example, if a nucleotide base in the second sequence is A and the nucleotide base at the same position in the first sequence is U, C, G or T, these two nucleotide sequences are considered as having a nucleotide difference at this position. In some embodiments, if a nucleotide at a position is replaced with an abasic nucleotide or a nucleotide analogue, it is also considered that there is a nucleotide difference at the position.

In the context of the present disclosure, particularly in the description of the method for preparing the double-stranded oligonucleotide, pharmaceutical composition and/or oligonucleotide conjugate of the present disclosure, unless otherwise specified, “nucleoside monomer” refers to, according to the kind and order of the nucleotides in the double-stranded oligonucleotide, pharmaceutical composition and/or oligonucleotide conjugate to be prepared, unmodified or modified nucleoside monomer used in solid phase phosphoramidite synthesis (unmodified or modified RNA phosphoramidite; RNA phosphoramidites are also referred to as nucleoside phosphoramidites sometimes). Solid phase phosphoramidite synthesis is a well-known method RNA synthesis to those skilled in the art. Nucleoside monomers used in the present disclosure can all be commercially available.

As used herein, a dash (“-”) that is not positioned between two letters or symbols is used to indicate the attachment position of a substituent. For example, $—C_1$-$C_{10}$ alkyl-$NH_2$ is attached through $C_1$-$C_{10}$ alkyl.

As used herein, “optional” or “optionally” means that the subsequently described event or condition may or may not occur, and that the description includes instances wherein the event or condition may or may not occur. For example, “optionally substituted alkyl” encompasses both “alkyl” and “substituted alkyl” as defined below. Those skilled in the art would understand, with respect to any group containing one or more substituents, that such groups are not intended to introduce any substitution or substitution patterns that are sterically impractical, synthetically infeasible and/or inherently unstable.

As used herein, “alkyl” refers to straight chain and branched chain having the indicated number of carbon atoms, usually 1 to 20 carbon atoms, for example 1 to 10 carbon atoms, such as 1 to 8 or 1 to 6 carbon atoms. For example, $C_1$-$C_6$ alkyl encompasses both straight and branched chain alkyl of 1 to 6 carbon atoms. When naming an alkyl residue having a specific number of carbon atoms, all branched and straight chain forms having that number of carbon atoms are intended to be encompassed; thus, for example, “butyl” is meant to include n-butyl, sec-butyl, isobutyl and t-butyl; “propyl” includes n-propyl and isopropyl. Alkylene is a subset of alkyl, referring to the same residues as alkyl, but having two attachment positions.

As used herein, “alkenyl” refers to an unsaturated branched or straight-chain alkyl group having at least one carbon-carbon double bond which is obtained by respectively removing one hydrogen molecule from two adjacent carbon atoms of the parent alkyl. The group may be in either cis or trans configuration of the double bond. Typical alkenyl groups include, but not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In certain embodiments, an alkenyl group has 2 to 20 carbon atoms, and in other embodiments, 2 to 10, 2 to 8, or 2 to 6 carbon atoms. Alkenylene is a subset of alkenyl, referring to the same residues as alkenyl, but having two attachment positions.

As used herein, “alkynyl” refers to an unsaturated branched or straight-chain alkyl group having at least one carbon-carbon triple bond which is obtained by respectively removing two hydrogen molecules from two adjacent carbon atoms of the parent alkyl. Typical alkynyl groups include, but not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has 2 to 20 carbon atoms, and in other embodiments, 2 to 10, 2 to 8, or 2 to 6 carbon atoms. Alkynylene is a subset of alkynyl, referring to the same residues as alkynyl, but having two attachment positions.

As used herein, “alkoxy” refers to an alkyl group of the indicated number of carbon atoms attached through an oxygen bridge, such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have 1 to 10, 1 to 8, 1 to 6, or 1 to 4 carbon atoms attached through oxygen bridge.

As used herein, “aryl” refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon, including six to eighteen carbon atoms, wherein at least one ring in the ring system is fully unsaturated, i.e., it contains a cyclic, delocalized (4n+2) Tr-electron system in accordance with the Hickel theory. Aryl groups include, but not limited to, phenyl, fluorenyl, naphthyl and the like. Arylene is a subset of aryl, referring to the same residues as aryl, but having two attachment positions.

As used herein, "cycloalkyl" refers to a non-aromatic carbon ring, usually having 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "halo substituent" or "halo" refers to fluoro, chloro, bromo, and iodo, and the term "halogen" includes fluorine, chlorine, bromine, and iodine.

As used herein, "haloalkyl" refers to alkyl as defined above with the specified number of carbon atoms being substituted with one or more halogen atoms, up to the maximum allowable number of halogen atoms. Examples of haloalkyl include, but not limited to, trifluoromethyl, difluoromethyl, 2-fluoroethyl, and penta-fluoroethyl.

"Heterocyclyl" refers to a stable 3- to 18-membered non-aromatic ring radical that comprises two to twelve carbon atoms and one to six heteroatoms selected from nitrogen, oxygen and sulfur. Unless stated otherwise in the description, heterocyclyl is a monocyclic, bicyclic, tricyclic, or tetracyclic ring system, which may include fused or bridged ring systems. The heteroatoms in the heterocyclyl radical may be optionally oxidized. One or more nitrogen atoms, if present, are optionally quaternized. The heterocyclyl is partially or fully saturated. Heterocyclyl may be linked to the rest of the molecule through any atom of the ring. Examples of such heterocyclyl include, but not limited to, dioxanyl, thienyl[1,3]disulfonyl, decahydroisoquinolyl, imidazolinyl, imidazolidinyl, isothiazolidinyl, isoxazolidinyl, morpholinyl, octahydroindolyl, octahydroisoindolyl, 2-oxapiperazinyl, 2-oxapiperidinyl, 2-oxapyrimidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, trisulfonyl, tetrahydropyranyl, thiomorpholinyl, thiamorpholinyl, 1-oxa-thiomorpholinyl, and 1,1-dioxa-thiomorpholinyl.

"Heteroaryl" refers to a radical derived from a 3- to 18-membered aromatic ring radical that comprises two to seventeen carbon atoms and one to six heteroatoms selected from nitrogen, oxygen and sulfur. As used herein, heteroaryl may be a monocyclic, bicyclic, tricyclic or tetracyclic ring system, wherein at least one ring in the ring system is fully unsaturated, i.e., it contains a cyclic, delocalized (4n+2) π-electron system in accordance with the Hickel theory. Heteroaryl includes fused or bridged ring systems. The heteroatom in the heteroaryl radical is optionally oxidized. One or more nitrogen atoms, if present, are optionally quaternized. The heteroaryl is linked to the rest of the molecule through any atom of the ring. Examples of such heteroaryls include, but not limited to, azepinyl, acridinyl, benzimidazolyl, benzindolyl, 1,3-benzodioxazolyl, benzofuranyl, benzoxazolyl, benzo[d]thiazolyl, benzothiadiazolyl, benzo[b][1,4]dioxazolyl, benzo[b][1,4]oxazolyl, 1,4-benzodioxazolyl, benzonaphthofuranyl, benzodiazolyl, benzodioxaphenyl, benzopyranyl, benzopyranonyl, benzofuranyl, benzofuranonyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothienyl, furanyl, furanonyl, furo[3,2-c]pyridinyl, 5,6,7,8,9,10-hexahydrocyclohepta[d]pyrimidinyl, 5,6,7,8,9, 10-hexahydrocycloocta[d]pyridazinyl, 5,6,7,8,9,10-hexahydrocycloocta[d]pyridinyl, isothiazolyl, indazolyl, imidazolyl, indolyl, isoindolyl, indolinyl, isoindolinyl, isoquinolyl, indolizinyl, isoxazolyl, 5,8-methano-5,6,7,8-tetrahydroquinazolinyl, naphthyridinonyl, 1,6-naphthyridinonyl, oxadiazolyl, 2-oxoazepinyl, oxazolyl, oxalyl, 5,6,6a,7,8,9,10,10a-octahydrobenzo[h]quinazolinyl, 1-phenyl-1H-pyrrolyl, phenazinyl, phenothiazinyl, phenoxazinyl, phthalyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thienyl.

Various hydroxyl protecting groups can be used in the present disclosure. In general, protecting groups render chemical functionalities inert to specific reaction conditions, and can be attached to and removed from such functionalities in a molecule without substantially damaging the remainder of the molecule. Representative hydroxyl protecting groups are disclosed in Beaucage, et al., Tetrahedron 1992, 48, 2223-2311, and also in Greene and Wuts, Protective Groups in Organic Synthesis, Chapter 2, 2d ed, John Wiley & Sons, New York, 1991, each of which is hereby incorporated by reference in their entirety. In some embodiments, the protecting group is stable under basic conditions but can be removed under acidic conditions. In some embodiments, non-exclusive examples of hydroxyl protecting groups used herein include dimethoxytrityl (DMT), monomethoxytrityl, 9-phenylxanthen-9-yl (Pixyl), and 9-(p-methoxyphenyl)xanthen-9-yl (Mox). In some embodiments, non-exclusive examples of hydroxyl protecting groups used herein comprise Tr (trityl), MMTr (4-methoxytrityl), DMTr (4,4'-dimethoxytrityl), and TMTr (4,4',4"-trimethoxytrityl).

The term "subject", as used herein, refers to any animal, e.g., mammal or marsupial. Subject of the present disclosure includes, but not limited to, human, non-human primate (e.g., rhesus or other kinds of macaque), mouse, pig, horse, donkey, cow, sheep, rat and any kind of poultry.

As used herein, "treatment" or "treating" or "ameliorating" or "improving" are used interchangeably herein. These terms refer to a method for obtaining advantageous or desired result, including but not limited to, therapeutic benefit. "Therapeutic benefit" means eradication or improvement of potential disorder to be treated. Also, therapeutic benefit is achieved by eradicating or ameliorating one or more of physiological symptoms associated with the potential disorder such that an improvement is observed in the patient, notwithstanding that the patient may still be afflicted with the potential disorder.

As used herein, "prevention" and "preventing" are used interchangeably. These terms refer to a method for obtaining advantageous or desired result, including but not limited to, prophylactic benefit. For obtaining "prophylactic benefit", the conjugate or composition may be administered to the patient at risk of developing a particular disease, or to the patient reporting one or more physiological symptoms of the disease, even though the diagnosis of this disease may not have been made.

Modified Double-Stranded Oligonucleotide

In one aspect, the present disclosure provides a double-stranded oligonucleotide capable of regulating gene expression.

The double-stranded oligonucleotide of the present disclosure comprises nucleotides as basic structural units. It is well-known to those skilled in the art that the nucleotide comprises a phosphate group, a ribose group and a base. Detailed illustrations relating to such groups are omitted herein.

CN102140458B has disclosed a siRNA that specifically inhibits HBV gene and studied various chemical modification strategies of the siRNA. This study found that different modification strategies have completely different effects on the parameters of the siRNA, such as stability, biological activity and cytotoxicity. In this study, seven effective modification manners were proved. Comparing with unmodified siRNA, the siRNA obtained by one of the seven modification manners showed increased stability in blood, while maintaining substantially equal inhibitory activity as that of the unmodified siRNA.

The double-stranded oligonucleotide of the present disclosure comprises a sense strand and an antisense strand, each nucleotide in the sense strand and antisense strand being a modified nucleotide, wherein the sense strand comprises a nucleotide sequence 1, and the antisense strand comprises a nucleotide sequence 2; the nucleotide sequence 1 and the nucleotide sequence 2 are both 19 nucleotides in length and are at least partly reverse complementary to form a double-stranded complementary region; the nucleotide sequence 2 is at least partly reverse complementary to a first nucleotide sequence segment, which refers to a segment of nucleotide sequence in the target mRNA; in the direction from 5' terminal to 3' terminal, the nucleotides at positions 7, 8 and 9 of the nucleotide sequence 1 are fluoro modified nucleotides, and each of the nucleotides at the other positions in the nucleotide sequence 1 is independently a non-fluoro modified nucleotide; the first nucleotide at 5' terminal of the nucleotide sequence 2 is the first nucleotide at 5' terminal of the antisense strand, the nucleotides at positions 2, 6, 14 and 16 of the nucleotide sequence 2 are fluoro modified nucleotides, and each of the nucleotides at the other positions in the nucleotide sequence 2 is independently a non-fluoro modified nucleotide. In the context of the present disclosure, a "fluoro modified nucleotide" refers to a nucleotide formed by substituting the 2'-hydroxy of the ribose group with a fluorine atom; and a "non-fluoro modified nucleotide" refers to a nucleotide formed by substituting the 2'-hydroxy of the ribose group with a non-fluoro group, or a nucleotide analogue.

A "nucleotide analogue" refers to a group that can replace a nucleotide in a nucleic acid, while structurally differs from an adenine ribonucleotide, a guanine ribonucleotide, a cytosine ribonucleotide, a uracil ribonucleotide or thymine deoxyribonucleotide, such as an isonucleotide, a bridged nucleic acid (BNA) nucleotide or an acyclic nucleotide.

In some embodiments, the nucleotide sequence 2 is basically reverse complementary, substantially reverse complementary, or completely reverse complementary to the first nucleotide sequence segment.

In some embodiments, in the direction from 5' terminal to 3' terminal, at least the nucleotides at positions 2-19 of the nucleotide sequence 2 are complementary to the first nucleotide sequence segment. In some specific embodiments, in the direction from 5' terminal to 3' terminal, the nucleotide at position 1 of the nucleotide sequence 2 is A or U.

In some embodiments, the nucleotide sequence 1 is basically reverse complementary, substantially reverse complementary, or completely reverse complementary to the nucleotide sequence 2.

In some embodiments, the sense strand further comprises nucleotide sequence 3, and the antisense strand further comprises nucleotide sequence 4; each nucleotide in the nucleotide sequence 3 and the nucleotide sequence 4 is independently a non-fluoro modified nucleotide; the nucleotide sequence 3 and the nucleotide sequence 4 are respectively 1-4 nucleotides in length; the nucleotide sequence 3 and the nucleotide sequence 4 have equal length and are substantially reverse complementary or complete reverse complementary to each other; the nucleotide sequence 3 is linked to 5' terminal of the nucleotide sequence 1; and the nucleotide sequence 4 is linked to the 3' terminal of the nucleotide sequence 2; the nucleotide sequence 4 is substantially reverse complementary, or completely reverse complementary to a second nucleotide sequence segment, which refers to a nucleotide sequence that is adjacent to the first nucleotide sequence segment in the target mRNA and has the same length as the nucleotide sequence 4.

In some embodiments, the nucleotide sequence 3 is complete complementary to the nucleotide sequence 4, the nucleotide sequence 3 and the nucleotide sequence 4 are both 1 nucleotide in length, and the nucleotide sequence 4 is completely reverse complementary to the second nucleotide sequence segment; or the nucleotide sequence 3 is complete complementary to the nucleotide sequence 4, the nucleotide sequence 3 and the nucleotide sequence 4 are both 2 nucleotides in length, and the nucleotide sequence 4 is completely reverse complementary to the second nucleotide sequence segment; or the nucleotide sequence 3 is complete complementary to the nucleotide sequence 4, the nucleotide sequence 3 and the nucleotide sequence 4 are both 3 nucleotides in length, and the nucleotide sequence 4 is completely reverse complementary to the second nucleotide sequence segment; or the nucleotide sequence 3 is complete complementary to the nucleotide sequence 4, the nucleotide sequence 3 and the nucleotide sequence 4 are both 4 nucleotides in length, and the nucleotide sequence 4 is completely reverse complementary to the second nucleotide sequence segment.

The nucleotide sequence 3 is completely reverse complementary to the nucleotide sequence 4, the nucleotide sequence 4 is completely reverse complementary to the second nucleotide sequence segment, and once the relevant nucleotide sequence of the target mRNA is determined, the nucleotide sequence 3 and nucleotide sequence 4 are also determined.

Therefore, the sense strand or the antisense strand may independently be 19-23 nucleotides in length.

In some embodiments, the double-stranded oligonucleotide also comprises a nucleotide sequence 5; each nucleotide in the nucleotide sequence 5 is independently a non-fluoro modified nucleotide; the nucleotide sequence 5 is 1-3 nucleotides in length and is linked to 3' terminal of the antisense strand, thereby forming a 3' overhang of the antisense strand.

As such, the length ratio of the sense strand to the antisense strand in the double-stranded oligonucleotide of the present disclosure may be 19/19, 19/20, 19/21, 19/22, 20/20, 20/21, 20/22, 20/23, 21/21, 21/22, 21/23, 21/24, 22/22, 22/23, 22/24, 22/25, 23/23, 23/24, 23/25 or 23/26.

In some embodiments, the nucleotide sequence 5 is 2 nucleotides in length. Moreover, the nucleotide sequence 5 is 2 consecutive thymidine deoxynucleotides, or 2 consecutive uridine nucleotides in the direction from 5' terminal to 3' terminal, or completely reverse complementary to a third nucleotide sequence segment, which refers to a nucleotide sequence that is adjacent to the first or second nucleotide sequence segment in the target mRNA and has the same length as the nucleotide sequence 5.

Therefore, in some embodiments, the length ratio of the sense strand to the antisense strand in the double-stranded oligonucleotide of the present disclosure is 19/21 or 21/23. Here, the double-stranded oligonucleotide of the present disclosure exhibits better silencing activity against target mRNA.

In the context of the present disclosure, a "fluoro modified nucleotide" refers to a nucleotide formed by substituting the 2'-hydroxy of the ribose group with a fluorine atom, as shown by Formula (101), wherein "Base" represents a base selected from C, G, A, and U.

A "non-fluoro modified nucleotide" refers to a nucleotide formed by substituting the 2'-hydroxy of the ribose group with a non-fluoro group, or a nucleotide analogue. In some embodiments, each non-fluoro modified nucleotide is independently selected from the group consisting of a nucleotide formed by substituting the 2'-hydroxy of the ribose group thereof with a non-fluoro group, and a nucleotide analogue.

A nucleotide formed by substituting the 2'-hydroxy of the ribose group with a non-fluoro group is well-known to those skilled in the art, such as 2'-alkoxy modified nucleotide, 2'-substituted alkoxy modified nucleotide, 2'-alkyl modified nucleotide, 2'-substituted alkyl modified nucleotide, 2'-amino modified nucleotide, 2'-substituted amino modified nucleotide or 2'-deoxy nucleotide.

In some embodiments, the 2'-alkoxy modified nucleotide is a methoxy modified nucleotide (2'-OMe), as shown by Formula (102). In some embodiments, the 2'-substituted alkoxy modified nucleotide is a 2'-O-methoxyethyl modified nucleotide (2'-MOE), as shown by Formula (103). In some embodiments, the 2'-amino modified nucleotide (2'-$NH_2$) is as shown by Formula (104). In some embodiments, the 2'-deoxy nucleotide (DNA) is as shown by Formula (105).

Formula (101)

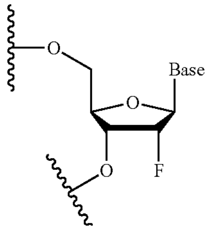

Formula (102)

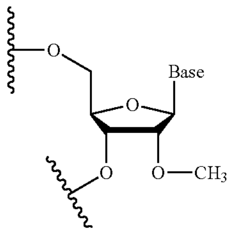

-continued

Formula (103)

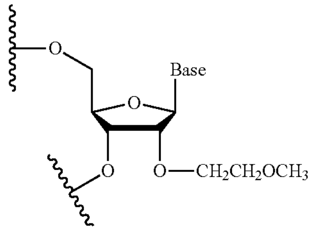

Formula (104)

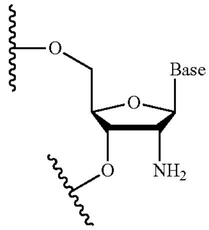

Formula (105)

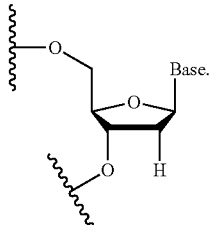

A "nucleotide analogue" refers to a group that can replace a nucleotide in the nucleic acid, while structurally differs from an adenine ribonucleotide, a guanine ribonucleotide, a cytosine ribonucleotide, a uracil ribonucleotide or thymine deoxyribonucleotide. In some embodiments, the nucleotide analogue may be an isonucleotide, a bridged nucleic acid (BNA) nucleotide or an acyclic nucleotide.

A BNA is a nucleotide that is constrained or is not accessible. BNA can contain a 5-, 6-membered or even a 7-membered ring bridged structure with a "fixed" C3'-endo sugar puckering. The bridge is typically incorporated at the 2'- and 4'-position of the ribose to afford a 2', 4'-BNA nucleotide, such as LNA, ENA and cET BNA, which are as shown by Formulae (106), (107) and (108), respectively:

Formula (106)

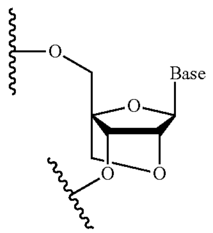

Formula (107)

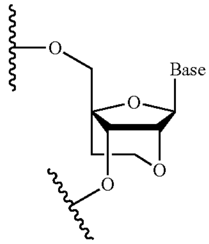

-continued

Formula (108)

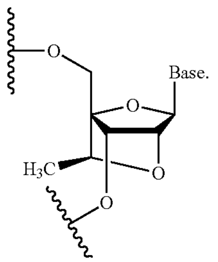

An acyclic nucleotide is a "ring-opened" nucleotide in which the sugar ring is opened, such as an unlocked nucleic acid (UNA) and a glycerol nucleic acid (GNA), which are as shown by Formulae (109) and (110), respectively:

Formula (109)

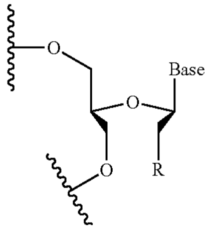

Formula (110)

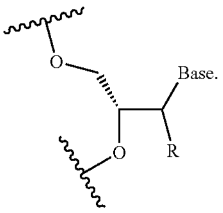

wherein R is H, OH or alkoxy (O-alkyl).

An isonucleotide is a nucleotide in which the position of the base on the ribose ring is changed, such as a compound in which the base is transposed from position-1' to position-2' or -3' on the ribose ring, as shown by Formula (111) or (112):

Formula (111)

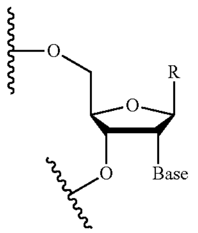

-continued

Formula (112)

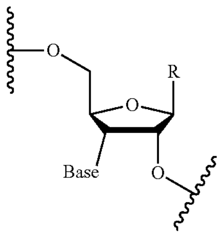

, wherein Base represents a base, such as A, U, G, C or T; R is selected from the group consisting of H, OH, F, and a non-fluoro group described above.

In some embodiments, a nucleotide analogue is selected from the group consisting of an isonucleotide, LNA, ENA, cET, UNA, and GNA. In some embodiments, each non-fluoro modified nucleotide is a methoxy modified nucleotide. In the context of the present disclosure, the methoxy modified nucleotide refers to a nucleotide formed by substituting the 2'-hydroxy of the ribose group with a methoxy group.

In the context of the present disclosure, a "fluoro modified nucleotide", a "2'-fluoro modified nucleotide", a "nucleotide in which 2'-hydroxy of the ribose group is substituted with fluoro" and a "2'-fluororibosyl" have the same meaning, referring to the nucleotide formed by substituting the 2'-hydroxy of the ribose group with fluoro, having a structure as shown by Formula (101). A "methoxy modified nucleotide", a "2'-methoxy modified nucleotide", a "nucleotide in which 2'-hydroxy of a ribose group is substituted with methoxy" and a "2'-methoxyribosyl" have the same meaning, referring to the nucleotide formed by substituting the 2'-hydroxy of the ribose group with methoxy, having a structure as shown by Formula (102).

In some embodiments, the double-stranded oligonucleotide of the present disclosure can resist ribonuclease cleavage in blood, thereby enhancing the stability of the nucleic acid in blood and allowing the nucleic acid to have stronger resistance against nuclease hydrolysis, while maintaining higher activity for regulating the target gene.

In some embodiments, the double-stranded oligonucleotides of the present disclosure realize high balance between the stability in serum and the efficiency of regulating gene expression in animal experiments; and some also have the advantages such as simpler structure and lower cost. The following are some examples.

In the direction from 5' terminal to 3' terminal, the nucleotides at positions 7, 8 and 9 of the nucleotide sequence 1 in the sense strand are fluoro modified nucleotides, and the nucleotides at the other positions in the sense strand are methoxy modified nucleotides; and the nucleotides at positions 2, 6, 14, and 16 of the nucleotide sequence 2 in the antisense strand are fluoro modified nucleotides, and the nucleotides at the other positions in the antisense strand are methoxy modified nucleotides.

In some embodiments, the double-stranded oligonucleotides of the present disclosure further comprise additional modified nucleotide(s) which would not result in significant impairment or loss of the function of the double-stranded oligonucleotides for regulating the expression of the target gene.

Currently, there are many means in the art that can be used to modify double-stranded oligonucleotides, including the ribose group modification mentioned above, backbone modification (such as phosphate group modification), base modification, and the like (see, for example, Watts, J. K., G. F. Deleavey and M. J. Damha, Chemically Modified siRNA: tools and applications. Drug Discov Today, 2008.13(19-20): p. 842-55, which is incorporated herein by reference in its entirety).

In some embodiments, at least one phosphate group in the phosphate-ribose backbone of at least one single strand of the sense strand and the antisense strand is a phosphate group with modified group(s). The phosphate group with modified group(s) is a phosphorothioate group formed by substituting at least one of oxygen atoms in a phosphodiester bond in the phosphate groups with a sulfur atom, such as the phosphorothioate structure as shown by Formula (121) below, that is, substituting a non-bridging oxygen atom in a phosphodiester bond with a sulfur atom such that the phosphodiester bond is changed to a phosphorothioate diester bond; in other words, the linkage between two nucleotides is a phosphorothioate linkage. This modification could stabilize the structure of the double-stranded oligonucleotide, while maintain high specificity and high affinity of base pairing.

Formula (121)

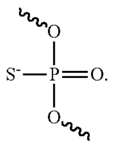

In some embodiments, in the double-stranded oligonucleotides, a phosphorothioate linkage exists in at least one of the following positions: the position between the first and the second nucleotides at either terminal of the sense or antisense strand, the position between the second and the third nucleotides at either terminal of the sense or antisense strand, or any combination thereof. In some embodiments, a phosphorothioate linkage exists at all the above positions except for 5' terminal of the sense strand. In some embodiments, a phosphorothioate linkage exists at all the above positions except for 3' terminal of the sense strand. In some embodiments, a phosphorothioate linkage exists in at least one of the following positions:

the position between the first and second nucleotides at 5' terminal of the sense strand;

the position between the second and third nucleotides at 5' terminal of the sense strand;

the position between the first and second nucleotides at 3' terminal of the sense strand;

the position between the second and third nucleotides at 3' terminal of the sense strand;

the position between the first and second nucleotides at 5' terminal of the antisense strand;

the position between the second and third nucleotides at 5' terminal of the antisense strand;

the position between the first and second nucleotides at 3' terminal of the antisense strand; and the position between the second and third nucleotides at 3' terminal of the antisense strand.

In some embodiments, the nucleotide at 5'-terminal of the antisense strand of the double-stranded oligonucleotide molecule is a 5'-phosphate nucleotide or a 5'-phosphate analogue modified nucleotide.

In some embodiments, the 5'-phosphate nucleotide has the structure as shown by Formula (122):

Formula (122)

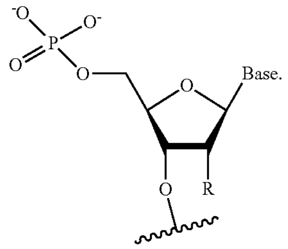

Meanwhile, common 5'-phosphate analogue modified nucleotides are well known to those skilled in the art, for example, the following nucleotides shown by Formulae (123)-(126) as disclosed in Anastasia Khvorova and Jonathan K. Watts, The chemical evolution of oligonucleotide therapies of clinical utility. Nature Biotechnology, 2017, 35(3): 238-48:

Formula (123)

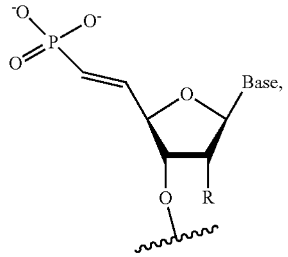

Formula (124)

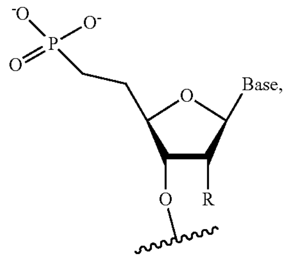

Formula (125)

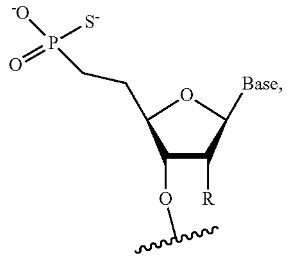

Formula (126)

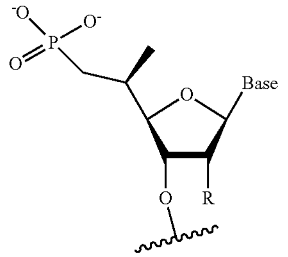

wherein R represents a group selected from the group consisting of H, OH, F, and methoxy; and "Base" represents a base selected from A, U, C, G, and T.

In some embodiments, the 5'-phosphate analogue modified nucleotide is a nucleotide containing an E-vinylphosphate (E-VP) as shown by Formula (123), or a nucleotide containing phosphorothioate as shown by Formula (125).

The modification strategies of the present disclosure are suitable for various double-stranded oligonucleotides for regulating gene expression. In some embodiments, they may be double-stranded oligonucleotides (such as siRNA) that inhibit or down-regulate gene expression; in some embodiments, they may be double-stranded oligonucleotides (such as saRNA) that activate or up-regulate gene expression.

By using the modification strategies of the present disclosure, the resultant double-stranded oligonucleotides have unexpectedly enhanced stability in blood, increased stability in lysosome, reduced off-target effect, and/or increased activity, without significantly reduced activity for regulating the expression of the target gene, while showing excellent inhibitory effect in vivo.

The modified double-stranded oligonucleotide, pharmaceutical composition and conjugate of the present disclosure can be used for regulating various abnormal gene expressions and for treating various pathological conditions or diseases caused by abnormal gene expression. These genes may be various endogenous genes in human or animal bodies, or the genes of pathogens reproduced in human or animal bodies. Double-stranded oligonucleotides with specific nucleotide sequences and said modification strategies may be designed and prepared according to the target mRNA of interest.

According to some embodiments of the present disclosure, the double-stranded oligonucleotides of the present disclosure could, for example, be the following siRNAs:

- the nucleotide sequence 1 is a sequence shown by SEQ ID NO: 1, and the nucleotide sequence 2 is a sequence shown by SEQ ID NO: 2; or
- the nucleotide sequence 1 is a sequence shown by SEQ ID NO: 3, and the nucleotide sequence 2 is a sequence shown by SEQ ID NO: 4; or
- the nucleotide sequence 1 is a sequence shown by SEQ ID NO: 5, and the nucleotide sequence 2 is a sequence shown by SEQ ID NO: 6; or
- the nucleotide sequence 1 is a sequence shown by SEQ ID NO: 7, and the nucleotide sequence 2 is a sequence shown by SEQ ID NO: 8; or
- the nucleotide sequence 1 is a sequence shown by SEQ ID NO: 9, and the nucleotide sequence 2 is a sequence shown by SEQ ID NO: 10; or
- the nucleotide sequence 1 is a sequence shown by SEQ ID NO: 11, and the nucleotide sequence 2 is a sequence shown by SEQ ID NO: 12; or
- the nucleotide sequence 1 is a sequence shown by SEQ ID NO: 13, and the nucleotide sequence 2 is a sequence shown by SEQ ID NO: 14;

(SEQ ID NO: 1)
5'- CmCmUmUmGmAmGfGfCfAmUmAmCmUmUmCmAmAmAm -3'

(SEQ ID NO: 2)
5'- UmUfUmGmAmAfGmUmAmUmGmCmCmUfCmAfAmGmGm -3'

(SEQ ID NO: 3)
5'- UmGmCmUmAmUmGfCfCfUmCmAmUmCmUmUmCmUmAm -3'

(SEQ ID NO: 4)
5'- UmAfGmAmAmGfAmUmGmAmGmGmCmAfUmAfGmCmAm -3'

(SEQ ID NO: 5)
5'- UmCmUmGmUmGmCfCfUfUmCmUmCmAmUmCmUmGmAm -3'

(SEQ ID NO: 6)
5'- UmCfAmGmAmUfGmAmGmAmAmGmGmCfAmCfAmGmAm -3'

(SEQ ID NO: 7)
5'- CmGmUmGmUmGmCfAfCfUmUmCmGmCmUmUmCmAmAm -3'

(SEQ ID NO: 8)
5'- UmUfGmAmAmGfCmGmAmAmGmUmGmCfAmCfAmCmGm -3'

(SEQ ID NO: 9)
5'- GmAmAmAmGmUmAfUfGfUmCmAmAmCmGmAmAmUmAm -3'

(SEQ ID NO: 10)
5'- UmAfUmUmCmGfUmUmGmAmCmAmUmAfCmUfUmUmCm -3'

(SEQ ID NO: 11)
5'- CmCmAmAmGmAmGfCfAfCmCmAmAmGmAmAmCmUmAm -3'

(SEQ ID NO: 12)
5'- UmAfGmUmUmCfUmUmGmGmUmGmCmUfCmUfUmGmGm -3'

(SEQ ID NO: 13)
5'- CmAmAmUmAmAmAfGfCfUmGmGmAmCmAmAmGmAmAm -3'

(SEQ ID NO: 14)
5'- UmUfCmUmUmGfUmCmCmAmGmCmUmUfUmAfUmUmGm -3' wherein C, G, U, and A represent the base components of the nucleotides; m represents that the nucleotide adjacent to the left side of the letter m is a 2'-methoxy modified nucleotide; f represents that the nucleotide adjacent to the left side of the letter f is a 2'-fluoro modified nucleotide.

According to some embodiments of the present disclosure, the double-stranded oligonucleotides of the present disclosure may be, for example, the siRNAs as shown in Tables 1A-1F:

Table 1 siRNA in some embodiments

TABLE 1A

| No | | Sequence Direction: 5'-3' | SEQ ID NO |
|---|---|---|---|
| siHBa1M1 | S | CmCmUmUmGmAmGfGfCfAmUmAmCmUmUmCmAmAmAm | 15 |
| | AS | UmUfUmGmAmAfGmUmAmUmGmCmCmUfCmAfAmGmGmUmUm | 16 |
| siHBa2M1 | S | GmAmCmCmUmUmGmAmGfGfCfAmUmAmCmUmUmCmAmAmAm | 17 |
| | AS | UmUfUmGmAmAfGmUmAmUmGmCmCmUfCmAfAmGmGmUmCmGmGm | 18 |
| siHBa1M1S | S | CmsCmsUmUmGmAmGfGfCfAmUmAmCmUmUmCmAmAmAm | 19 |
| | AS | UmsUfsUmGmAmAfGmUmAmUmGmCmCmUfCmAfAmGmGmsUmsUm | 20 |
| siHBa2M1S | S | GmsAmsCmCmUmUmGmAmGfGfCfAmUmAmCmUmUmCmAmAmAm | 21 |
| | AS | UmsUfsUmGmAmAfGmUmAmUmGmCmCmUfCmAfAmGmGmUmCmsGmsGm | 22 |

TABLE 1A-continued

| No | | Sequence Direction: 5'-3' | SEQ ID NO |
|---|---|---|---|
| siHBa1M1P1 | S | CmCmUmUmGmAmGfGfCfAmUmAmCmUmUmCmAmAmAm | 23 |
| | AS | P1-UmUfUmGmAmAfGmUmAmUmGmCmCmUfCmAfAmGmGmUmUm | 24 |
| siHBa2M1P1 | S | GmAmCmCmUmUmGmAmGfGfCfAmUmAmCmUmUmCmAmAmAm | 25 |
| | AS | P1-UmUfUmGmAmAfGmUmAmUmGmCmCmUfCmAfAmGmGmUmCmGmGm | 26 |
| SiHBa1M1SP1 | S | CmsCmsUmUmGmAmGfGfCfAmUmAmCmUmUmCmAmAmAm | 27 |
| | AS | P1-UmsUfsUmGmAmAfGmUmAmUmGmCmCmUfCmAfAmGmGmsUmsUm | 28 |
| siHBa2M1SP1 | S | GmsAmsCmCmUmUmGmAmGfGfCfAmUmAmCmUmUmCmAmAmAm | 29 |
| | AS | P1-UmsUfsUmGmAmAfGmUmAmUmGmCmCmUfCmAfAmGmGmUmCmsGmsGm | 30 |

TABLE 1B

| No | | Sequence Direction: 5'-3' | SEQ ID NO |
|---|---|---|---|
| SiHBb1 | S | UGCUAUGCCUCAUCUUCUA | 31 |
| | AS | UAGAAGAUGAGGCAUAGCAGC | 32 |
| siHBb1M1 | S | UmGmCmUmAmUmGfCfCfUmCmAmUmCmUmUmCmUmAm | 33 |
| | AS | UmAfGmAmAmGfAmUmGmAmGmGmCmAfUmAfGmCmAmGmCm | 34 |
| siHBb2M1 | S | UmGmCmUmAmUmGfCfCfUmCmAmUmCmUmUmCmUmAm | 35 |
| | AS | UmAfGmAmAmGfAmUmGmAmGmGmCmAfUmAfGmCmAmUmUm | 36 |
| siHBb1M1S | S | UmsGmsCmUmAmUmGfCfCfUmCmAmUmCmUmUmCmUmAm | 37 |
| | AS | UmsAfsGmAmAmGfAmUmGmAmGmGmCmAfUmAfGmCmAmsGmsCm | 38 |
| siHBb2M1S | S | UmsGmsCmUmAmUmGfCfCfUmCmAmUmCmUmUmCmUmAm | 39 |
| | AS | UmsAfsGmAmAmGfAmUmGmAmGmGmCmAfUmAfGmCmAmsUmsUm | 40 |
| siHBb1M1P1 | S | UmGmCmUmAmUmGfCfCfUmCmamUmCmUmUmCmUmAm | 41 |
| | AS | P1-UmAfGmAmAmGfAmUmGmAmGmGmCmAfUmAfGmCmAmGmCm | 42 |
| siHBb2M1P1 | S | UmGmCmUmAmUmGfCfCfUmCmAmUmCmUmUmCmUmAm | 43 |
| | AS | P1-UmAfGmAmAmGfAmUmGmAmGmGmCmAfUmAfGmCmAmUmUm | 44 |
| siHBb1M1SP1 | S | UmsGmsCmUmAmUmGfCfCfUmCmAmUmCmUmUmCmUmAm | 45 |
| | AS | P1-UmsAfsGmAmAmGfAmUmGmAmGmGmCmAfUmAfGmCmAmsGmsCm | 46 |
| siHBb2M1SP1 | S | UmsGmsCmUmAmUmGfCfCfUmCmAmUmCmUmUmCmUmAm | 47 |
| | AS | P1-UmsAfsGmAmAmGfAmUmGmAmGmGmCmAfUmAfGmCmAmsUmsUm | 48 |

TABLE 1C

| No | | Sequence Direction: 5'-3' | SEQ ID NO |
|---|---|---|---|
| siHBc1M1 | S | UmCmUmGmUmGmfCfUfUmCmUmCmAmUmCmUmGmAm | 49 |
| | AS | UmCfAmGmAmUfGmAmGmAmAmGmGmCfAmCfAmGmAmCmGm | 50 |
| siHBc1M1S | S | UmsCmsUmGmUmGmCfCfUfUmCmUmCmAmUmCmUmGmAm | 51 |
| | AS | UmsCfsAmGmAmUfGmAmGmAmAmGmGmCfAmCfAmGmAmsCmsGm | 52 |
| SiHBc1M1P1 | S | UmCmUmGmUmGmCfCfUfUmCmUmCmAmUmCmUmGmAm | 53 |
| | AS | P1-UmCfAmGmAmUfGmAmGmAmAmGmGmCfAmCfAmGmAmCmGm | 54 |
| siHBc1M1SP1 | S | UmsCmsUmGmUmGmCfCfUfUmCmUmCmAmUmCmUmGmAm | 55 |
| | AS | P1-UmsCfsAmGmAmUfGmAmGmAmAmGmGmCfAmCfAmGmAmsCmsGm | 56 |

TABLE 1D

| No | | Sequence Direction: 5'-3' | SEQ ID NO |
|---|---|---|---|
| siHBd1M1 | S | CmGmUmGmUmGmCfAfCfUmUmCmGmCmUmUmCmAmAm | 57 |
| | AS | UmUfGmAmAmGfCmGmAmAmGmUmGmCfAmCfAmCmGmGmUm | 58 |
| siHBd1M1S | S | CmsGmsUmGmUmGmCfAfCfUmUmCmGmCmUmUmCmAmAm | 59 |
| | AS | UmsUfsGmAmAmGfCmGmAmAmGmUmGmCfAmCfAmCmGmsGmsUm | 60 |
| siHBd1M1P1 | S | CmGmUmGmUmGmCfAfCfUmUmCmGmCmUmUmCmAmAm | 61 |
| | AS | P1-UmUfGmAmAmGfCmGmAmAmGmUmGmCfAmCfAmCmGmGmUm | 62 |
| siHBd1M1SP1 | S | CmsGmsUmGmUmGmCfAfCfUmUmCmGmCmUmUmCmAmAm | 63 |
| | AS | P1-UmsUfsGmAmAmGfCmGmAmAmGmUmGmCfAmCfAmCmGmsGmsUm | 64 |

TABLE 1E

| No | | Sequence Direction: 5'-3' | SEQ ID NO |
|---|---|---|---|
| siAN1M3 | S | CmCmAmAmGmAmGfCfAfCmCmAmAmGmAmAmCmUmAm | 65 |
| | AS | UmAfGmUmUmCfUmUmGmGmUmGmCmUfCmUfUmGmGmCmUm | 66 |
| siAN2M3 | S | AmGmCmCmAmAmGmAmGfCfAfCmCmAmAmGmAmAmCmUmAm | 67 |
| | AS | UmAfGmUmUmCfUmUmGmGmUmGmCmUfCmUfUmGmGmCmUmUmGm | 68 |
| siAN1M3S | S | CmsCmsAmAmGmAmGfCfAfCmCmAmAmGmAmAmCmUmAm | 69 |
| | AS | UmsAfsGmUmUmCfUmUmGmGmUmGmCmUfCmUfUmGmGmsCmsUm | 70 |
| siAN2M3S | S | AmsGmsCmCmAmAmGmAmGfCfAfCmCmAmAmGmAmAmCmUmAm | 71 |
| | AS | UmsAfsGmUmUmCfUmUmGmGmUmGmCmUfCmUfUmGmGmCmUmsUmsGm | 72 |
| siAN1M3P1 | S | CmCmAmAmGmAmGfCfAfCmCmAmAmGmAmAmcmUmAm | 73 |
| | AS | P1-UmAfGmUmUmCfUmUmGmGmUmGmCmUfCmUfUmGmGmCmUm | 74 |
| siAN2M3P1 | S | AmGmCmCmAmAmGmAmGfCfAfCmCmAmAmGmAmAmCmUmAm | 75 |
| | AS | P1-UmAfGmUmUmCfUmUmGmGmUmGmCmUfCmUfUmGmGmCmUmUmGm | 76 |
| siAN1M3SP1 | S | CmsCmsAmAmGmAmGfCfAfCmCmAmAmgmAmAmCmUmAm | 77 |
| | AS | P1-UmsAfsGmUmUmCfUmUmGmGmUmGmCmUfCmUfUmGmGmsCmsUm | 78 |
| siAN2M3SP1 | S | AmsGmsCmCmAmAmGmAmGfCfAfCmCmAmAmGmAmAmCmUmAm | 79 |
| | AS | P1-UmsAfsGmUmUmCfUmUmGmGmUmGmCmUfCmUfUmGmGmCmUmsUmsGm | 80 |

TABLE 1F

| No | | Sequence Direction: 5'-3' | SEQ ID NO |
|---|---|---|---|
| siAP1M2 | S | CmAmAmUmAmAmAfGfCfUmGmGmAmCmAmAmGmAmAm | 81 |
| | AS | UmUfCmUmUmGfUmCmCmAmGmCmUmUfUmAfUmUmGmGmGm | 82 |
| siAP2M2 | S | CmCmCmAmAmUmAmAmAfGfCfUmGmGmAmCmAmAmGmAmAm | 83 |
| | AS | UmUfCmUmUmGfUmCmCmAmGmCmUmUfUmAfUmUmGmGmGmAmGm | 84 |
| siAP1M2S | S | CmsAmsAmUmAmAmAfGfCfUmGmGmAmCmAmAmGmAmAm | 85 |
| | AS | UmsUfsCmUmUmGfUmCmCmAmGmCmUmUfUmAfUmUmGmsGmsGm | 86 |
| siAP2M2S | S | CmsCmsCmAmAmUmAmAmAfGfCfUmGmGmAmCmAmAmGmAmAm | 87 |
| | AS | UmsUfsCmUmUmGfUmCmCmAmGmCmUmUfUmAfUmUmGmGmGmsAmsGm | 88 |
| siAP1M2P1 | S | CmAmAmUmAmAmAfGfCfUmGmGmAmCmAmAmGmAmAm | 89 |
| | AS | P1-UmUfCmUmUmGfUmCmCmAmGmCmUmUfUmAfUmUmGmGmGm | 90 |
| siAP2M2P1 | S | CmCmCmAmAmUmAmAmAfGfCfUmGmGmAmCmAmAmGmAmAm | 91 |
| | AS | P1-UmUfCmUmUmGfUmCmCmAmGmCmUmUfUmAfUmUmGmGmGmAmGm | 92 |
| siAP1M2SP1 | S | CmsAmsAmUmAmAmAfGfCfUmGmGmAmCmAmAmGmAmAm | 93 |
| | AS | P1-UmsUfsCmUmUmGfUmCmCmAmGmCmUmUfUmAfUmUmGmsGmsGm | 94 |
| siAP2M2SP1 | S | CmsCmsCmamamUmAmAmAfGfCfUmGmGmAmCmAmAmGmAmAm | 95 |
| | AS | P1-UmsUfsCmUmUmGfUmCmCmAmGmCmUmUfUmAfUmUmGmGmGmsAmsGm | 96 |

TABLE 1G

| No | | Sequence Direction: 5'-3' | SEQ ID NO |
|---|---|---|---|
| siHBc1M1 | S | GmAmAmAmGmUmAfUfGfUmCmAmAmCmGmAmAmUmUm | 97 |
| | AS | AmAfUmUmCmGfUmUmGmAmCmAmUmAfCmUfUmUmCmUmUm | 98 |
| siHBc2M1 | S | GmAmAmAmGmUmAfUfGfUmCmAmAmCmGmAmAmUmUm | 99 |
| | AS | AmAfUmUmCmGfUmUmGmAmCmAmUmAfCmUfUmUmCmCmAm | 100 |
| siHBc3M1 | S | GmAmAmAmGmUmAfUfGfUmCmAmAmCmGmAmAmUmAm | 101 |
| | AS | UmAfUmUmCmGfUmUmGmAmCmAmUmAfCmUfUmUmCmUmUm | 102 |
| siHBc4M1 | S | GmAmAmAmGmUmAfUfGfUmCmAmAmCmGmAmAmUmAm | 103 |
| | AS | UmAfUmUmCmGfUmUmGmAmCmAmUmAfCmUfUmUmCmCmAm | 104 |
| siHBc5M1 | S | UmGmGmAmAmAmGmUmAfUfGfUmCmAmAmCmGmAmAmUmAm | 105 |
| | AS | UmAfUmUmCmGfUmUmGmAmCmAmUmAfCmUfUmUmCmCmAmUmUm | 106 |
| siHBc1M1S | S | GmsAmsAmAmGmUmAfUfGfUmCmAmAmCmGmAmAmUmUm | 107 |
| | AS | AmsAfsUmUmCmGfUmUmGmAmCmAmUmAfCmUfUmUmCmsUmsUm | 108 |
| siHBc2M1S | S | GmsAmsAmAmGmUmAfUfGfUmCmAmAmCmGmAmAmUmUm | 109 |
| | AS | AmsAfsUmUmCmGfUmUmGmAmCmAmUmAfCmUfUmUmCmsCmsAm | 110 |
| siHBc3M1S | S | GmsAmsAmAmGmUmAfUfGfUmCmAmAmCmGmAmAmUmAm | 111 |
| | AS | UmsAfsUmUmCmGfUmUmGmAmCmAmCmAfCmUfUmUmCmsUmsUm | 112 |
| siHBc4M1S | S | GmsAmsAmAmGmUmAfUfGfUmCmAmAmCmGmAmAmUmAm | 113 |
| | AS | UmsAfsUmUmCmGfUmUmGmAmCmAmCmAfCmUfUmUmCmsCmsAm | 114 |
| siHBc5M1S | S | UmsGmsGmAmAmAmGmUmAfUfGfUmCmAmAmCmGmAmAmUmAm | 115 |
| | AS | UmsAfsUmUmCmGfUmUmGmAmCmAmUmAfCmUfUmUmCmCmAmsUmsUm | 116 |
| siHBc1M1P | S | GmAmAmAmGmUmAfUfGfUmCmAmAmCmGmAmAmUmUm | 117 |
| | AS | P1-AmAfUmUmCmGfUmUmGmAmCmAmUmAfCmUfUmUmCmUmUm | 118 |
| siHBc2M1P | S | GmAmAmAmGmUmAfUfGfUmCmAmAmCmGmAmAmUmUm | 119 |
| | AS | P1-AmAfUmUmCmGfUmUmGmAmCmAmUmAfCmUfUmUmCmCmAm | 120 |
| siHBc3M1P | S | GmAmAmAmGmUmAfUfGfUmCmAmAmCmGmAmAmUmAm | 121 |
| | AS | P1-UmAfUmUmCmGfUmUmGmAmCmAmUmAfCmUfUmUmCmUmUm | 122 |
| siHBc4M1P | S | GmAmAmAmGmUmAfUfGfUmCmAmAmCmGmAmAmUmAm | 123 |
| | AS | P1-UmAfUmUmCmGfUmUmGmAmCmAmUmAfCmUfUmUmCmCmAm | 124 |
| siHBc5M1P | S | UmGmGmAmAmAmGmUmAfUfGfUmCmAmAmCmGmAmAmUmAm | 125 |
| | AS | P1-UmAfUmUmCmGfUmUmGmAmCmAmUmAfCmUfUmUmCmCmAmUmUm | 126 |
| siHBc1M1SP | S | GmsAmsAmAmGmUmAfUfGfUmCmAmAmCmGmAmAmUmUm | 127 |
| | AS | P1-AmsAfsUmUmCmGfUmUmGmAmCmAmUmAfCmUfUmUmCmsUmsUm | 128 |
| siHBc2M1SP | S | GmsAmsAmAmGmUmAfUfGfUmCmAmAmCmGmAmAmUmUm | 129 |
| | AS | P1-AmsAfsUmUmCmGfUmUmGmAmCmAmUmAfCmUfUmUmCmsCmsAm | 130 |
| siHBc3M1SP | S | GmsAmsAmAmGmUmAfUfGfUmCmAmAmCmGmAmAmUmAm | 131 |
| | AS | P1-UmsAfsUmUmCmGfUmUmGmAmCmAmUmAfCmUfUmUmCmsUmsUm | 132 |
| siHBc4M1SP | S | GmsAmsAmAmGmUmAfUfGfUmCmAmAmCmGmAmAmUmAm | 133 |
| | AS | P1-UmsAfsUmUmCmGfUmUmGmAmCmAmUmAfCmUfUmUmCmsCmsAm | 134 |
| siHBc5M1SP | S | UmsGmsGmAmAmAmGmUmAfUfGfUmCmAmAmCmGmAmAmUmAm | 135 |
| | AS | P1-UmsAfsUmUmCmGfUmUmGmAmCmAmUmAfCmUfUmUmCmCmAmsUmsUm | 136 |

*S: Sense Strand; AS: Antisense Strand

In the above tables, C, G, U, and A represent the base components of the nucleotides; in represents that the nucleotide adjacent to the left side of the letter in is a 2'-methoxy modified nucleotide; f represents that the nucleotide adjacent to the left side of the letter f is a 2'-fluoro modified nucleotide; s represents that the two nucleotides adjacent to both sides of the letter s are linked by a phosphorothioate linkage; P1 represents that the nucleotide adjacent to the right side of P1 is a 5'-phosphate nucleotide or a 5'-phosphate analogue modified nucleotide, and in some embodiments, is a vinyl phosphate modified nucleotide (expressed as VP in the Examples below), a 5'-phosphate modified nucleotide (expressed as P in the Examples below) or a phosphorothioate modified nucleotide (expressed as Ps in the Examples below).

Those skilled in the art clearly know that the double-stranded oligonucleotides of the present disclosure can be obtained by conventional methods in the art for preparing double-stranded oligonucleotides, e.g., solid phase synthesis and liquid phase synthesis. Solid phase synthesis already has commercial customization service. A modified nucleotide can be introduced into the double-stranded oligonucleotide of the present disclosure by using a nucleotide monomer having a corresponding modification, wherein the methods for preparing a nucleotide monomer having the corresponding modification and the methods for introducing a modified nucleotide into a double-stranded oligonucleotide are also well-known to those skilled in the art.

The modified double-stranded oligonucleotides of the present disclosure can be used alone, or as a pharmaceutical composition by combining with a pharmaceutically acceptable carrier, as a conjugate by binding to a conjugating molecule, or in other forms. An effective amount of the double-stranded oligonucleotide, pharmaceutical composition or conjugate are contacted with a cell to regulate expression of the target gene, or the double-stranded oligonucleotide, pharmaceutical composition or conjugate is administered to a subject to regulate expression of the target gene, thereby achieving the purpose of treating a pathological condition or disease caused by abnormal expression of the target gene.

By forming a pharmaceutical composition with a suitable carrier or forming a conjugate with a suitable conjugating molecule, the double-stranded oligonucleotide of the present disclosure could have improved stability in blood and increased targeting property, and solved its in vivo delivery problem, etc. For double-stranded oligonucleotides, carriers or conjugating molecules that can confer or improve targeting property will be very advantageous, since they can significantly increase the efficiency of regulating the expression of the target gene and decrease potential side effects of the double-stranded oligonucleotide. Furthermore, after introducing a targeting carrier or conjugating molecule, the double-stranded oligonucleotide still needs to exet function at the target site, i.e., the encapsulation/conjugation by the carrier or conjugating molecule cannot affect the activity of the double-stranded oligonucleotide (for example, in the case where the double-stranded oligonucleotide is siRNA, cannot affect the loading of the siRNA into the RNAi machinery in cells, i.e., the RISC complex). In addition, such targeting carriers or conjugating molecules also need to have good biocompatibility and minimal toxicity.

The pharmaceutical composition can be systemically distributed at various sites of the body or targetedly enriched at a specific site of the body. The conjugate generally has targeting property, and the conjugating molecule can be daptively changed according to the expression profile of the target gene in a human or animal body, so as to achieve the purpose of delivering the double-stranded oligonucleotide to the relevant site. For example, the conjugating molecule may be a conjugating molecule targeting liver, lung, kidney, or cancer cells.

In some embodiments, the present disclosure provides a pharmaceutical composition, comprising the modified double-stranded oligonucleotide above and a pharmaceutically acceptable carrier. The pharmaceutically acceptable carrier may be any suitable carrier.

In some embodiments, the present disclosure provides an oligonucleotide conjugate, comprising the modified double-stranded oligonucleotide above and a ligand conjugated to the double-stranded oligonucleotide. According to the expression profile of the target gene, different conjugating molecules may be adopted to deliver the double-stranded oligonucleotide to different organs or cells. The conjugating molecules below are suitable for delivering the double-stranded oligonucleotide to liver, thereby regulating the expression of an endogenous gene expressed in the target liver or the expression of a gene of a pathogen reproduced in the liver, so as to achieve the purpose of treating a pathological condition or disease caused by abnormal expression of the endogenous gene expressed in the liver or the gene of the pathogen reproduced in the liver.

In some embodiments, the present disclosure provides use of the above double-stranded oligonucleotide above, the above pharmaceutical composition comprising the double-stranded oligonucleotide, or the above oligonucleotide conjugate in the manufacture of a medicament for treating and/or preventing a pathological condition or disease caused by gene overexpression.

In some embodiments, the present disclosure provides a method for treating a pathological condition or disease caused by abnormal gene expression, comprising administering an effective amount of the above double-stranded oligonucleotide, the above pharmaceutical composition or the above oligonucleotide conjugate to a subject.

In some embodiments, the present disclosure provides a method for regulating the expression of a gene, comprising contacting an effective amount of the above double-stranded oligonucleotide, the above pharmaceutical composition or the above oligonucleotide conjugate with a cell expressing said gene. In some embodiments, the abnormal expression is overexpression; correspondingly, the regulation refers to inhibiting the overexpression.

In some embodiments, the above double-stranded oligonucleotide, the above pharmaceutical composition or the above oligonucleotide conjugate exhibits unexpected stability and activity in the regulation of a gene expressed in liver or in the treatment of a pathological condition or disease caused by abnormal expression of a gene in a liver cell. The gene expressed in liver includes, but not limited to, ApoB, ApoC, ANGPTL3, PCSK9, SCD1, TIMP-1, Col1A1, FVII, STAT3, p53, HBV, and HCV. In some embodiments, the specific gene is selected from the gene of hepatitis B virus, the gene of angiopoietin-like protein 3, and the gene of apolipoprotein C3. Correspondingly, the diseases are selected from chronic liver diseases, hepatitis, hepatic fibrosis, liver proliferative diseases, and dyslipidemia. In some embodiments, the dyslipidemia is hypercholesterolemia, hypertriglyceridemia, or atherosclerosis.

In some embodiments, the above double-stranded oligonucleotide, the above pharmaceutical composition or the above oligonucleotide conjugate may also be used to treat other liver diseases, including diseases characterized by undesired cell proliferation, blood diseases, metabolic diseases, and diseases characterized by inflammation. Liver proliferative diseases may be benign or malignant diseases, such as cancer, hepatocellular carcinoma (HCC), hepatic metastasis or hepatoblastoma. Liver hematology or inflammatory diseases may be diseases involving coagulation factors, complement-mediated inflammation or fibrosis. Liver metabolic diseases include dyslipidemia and irregular glucose regulation.

The present disclosure provides a kit comprising the above double-stranded oligonucleotide, the above pharmaceutical composition or the above oligonucleotide conjugate.

The following description of pharmaceutical compositions and oligonucleotide conjugates is based on the aforementioned double-stranded oligonucleotides suitable for regulating gene expression. However, the description regarding pharmaceutically acceptable carriers and ligands in drug conjugates are also applicable to systemic administration of said modified double-stranded oligonucleotides and delivery of said double-stranded oligonucleotides to the target organs or tissues, particularly liver, for regulating the expression of an endogenous gene expressed in the target organ or tissue or the expression of a gene of a pathogen reproduced in the target organ or tissue.

Pharmaceutical Composition

In one aspect, the present disclosure provides a pharmaceutical composition, comprising the above double-stranded oligonucleotide as an active ingredient, and a pharmaceutically acceptable carrier.

The pharmaceutically acceptable carrier may be a conventional carrier used in the field of double-stranded oligonucleotide administration, for example, but not limited to, one or more of magnetic nanoparticles (such as $Fe_3O_4$ and $Fe_2O_3$-based nanoparticle), carbon nanotubes, mesoporous silicon, calcium phosphate nanoparticles, polyethylenimine (PEI), polyamidoamine (PAMAM) dendrimer, poly(L-lysine) (PLL), chitosan, 1,2-dioleoyl-3-trimethylammonium-propane (DOTAP), poly(D&L-lactic/glycolic acid) copolymer (PLGA), poly(2-aminoethyl ethylene phosphate) (PPEEA), poly(2-dimethylaminoethyl methacrylate) (PDMAEMA), and derivatives thereof.

According to some embodiments, in the pharmaceutical composition of the present invention, there are no special requirements for the contents of the double-stranded oligonucleotide and the pharmaceutically acceptable carrier. In some embodiments, the ratio of the double-stranded oligonucleotide to the pharmaceutically acceptable carrier is 1:(1-500) by weight; in some embodiments, the ratio is 1:(1-50) by weight.

In some embodiments, the pharmaceutical composition of the present invention may also contain other pharmaceutically acceptable excipients, which may be one or more of various conventional formulations or compounds in the art. For example, said other pharmaceutically acceptable excipients may comprise at least one of a pH buffer, a protective agent and an osmotic pressure regulator.

The pH buffer may be a tris(hydroxymethyl) aminomethane hydrochloride buffer solution with a pH of 7.5-8.5, and/or a phosphate buffer solution with a pH of 5.5-8.5, preferably a phosphate buffer solution with a pH of 5.5-8.5.

The protective agent may be at least one of inositol, sorbitol, sucrose, trehalose, mannose, maltose, lactose, and glucose. The content of the protective agent may be from 0.01 wt % to 30 wt % on the basis of the total weight of the pharmaceutical composition.

The osmotic pressure regulator may be sodium chloride and/or potassium chloride. The content of the osmotic pressure regulator allows the osmotic pressure of the pharmaceutical composition to be 200-700 milliosmol/kg. Depending on the desired osmotic pressure, those skilled in the art can readily determine the content of the osmotic pressure regulator.

In some embodiments, the pharmaceutical composition may be a liquid formulation, for example, an injection solution; or a lyophilized powder for injection, which is mixed with a liquid excipient to form a liquid formulation upon administration. The liquid formulation may be administered by, but not limited to, subcutaneous, intramuscular or intravenous injection routes, and also may be administered to, but not limited to, lung by spray, or other organs (such as liver) via lung by spray. In some specific embodiments, the pharmaceutical composition is administered by intravenous injection.

In some embodiments, the pharmaceutical composition may be in the form of a liposome formulation. In some embodiments, the pharmaceutically acceptable carrier used in the liposome formulation comprises an amine-containing transfection compound (hereinafter also referred to as an organic amine), a helper lipid and/or a PEGylated lipid. Therein, the organic amine, the helper lipid and the PEGylated lipid may be respectively selected from one or more of the amine-containing transfection compounds or the pharmaceutically acceptable salts or derivatives thereof, the helper lipids and the PEGylated lipids as described in CN103380113A, which is incorporated herein by reference in its entirety.

In some embodiments, the organic amine may be a compound as shown by Formula (201) as described in CN103380113A or a pharmaceutically acceptable salt thereof:

Formula (201)

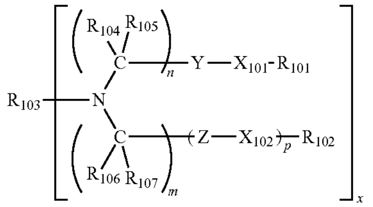

wherein:

$X_{101}$ and $X_{102}$ independently of one another are selected from O, S, N-A and C-A, wherein A is hydrogen or a $C_1$-$C_{20}$ hydrocarbon chain;

Y and Z independently of one another are selected from C═O, C═S, S═O, CH—OH and $SO_2$; $R_{101}$, $R_{102}$, $R_{103}$, $R_{104}$, $R_{105}$, $R_{106}$ and $R_{107}$ independently of one another are selected from hydrogen; a cyclic or an acyclic, substituted or unsubstituted, branched or linear aliphatic group; a cyclic or an acyclic, substituted or unsubstituted, branched or linear heteroaliphatic group; a substituted or unsubstituted, branched or linear acyl group; a substituted or unsubstituted, branched or linear aryl group, or a substituted or unsubstituted, branched or linear heteroaryl group;

x is an integer of 1-10;

n is an integer of 1-3, m is an integer of 0-20, p is 0 or 1; wherein if m and p are both 0, then $R_{102}$ is hydrogen, and if at least one of n or m has is 2, then $R_{103}$ and nitrogen in Formula (201) form a structure as shown by Formula (202) or (203):

Formula (202)

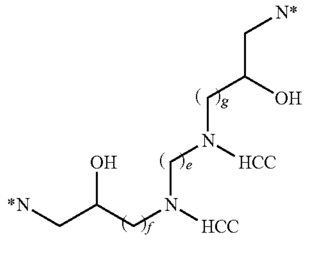

Formula (203)

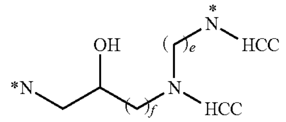

wherein g, e and f independently of one another are an integer of 1-6, "HCC" represents a hydrocarbon chain, and each * N represents a nitrogen atom shown in Formula (201).

In some embodiments, $R_{103}$ is a polyamine. In other embodiments, $R_{103}$ is a ketal. In some embodiments, $R_{101}$ and $R_{102}$ in the Formula (201) independently of one another are any of substituted or unsubstituted, branched or linear alkyl or alkenyl groups which have 3-20 carbon atoms (such as 8-18 carbon atoms) and 0-4 double bonds (such as 0-2 double bonds).

In some embodiments, if n and m independently of one another are 1-3, $R_{103}$ represents any of the following Formulae (204)-(213):

Formula (204)

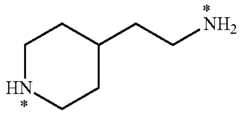

Formula (205)

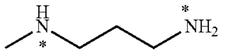

Formula (206)

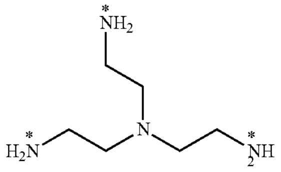

Formula (207)

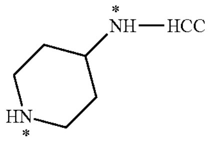

Formula (208)

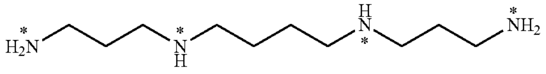

-continued

Formula (209)

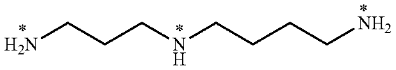

Formula (210)

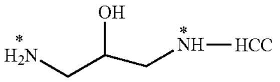

Formula (211)

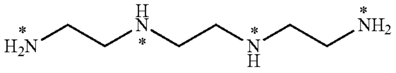

Formula (212)

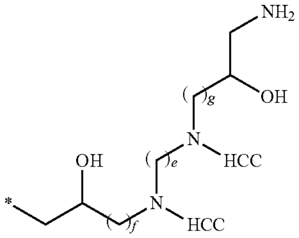

and

Formula (213)

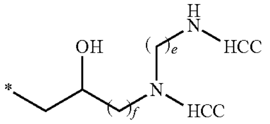

wherein each "HCC" represents a hydrocarbon chain, and each * represents a potential attachment point of $R_{103}$ to the nitrogen atom in Formula (201), where each H at any * position can be replaced to realize the attachment to the nitrogen atom in Formula (201).

The compound as shown by Formula (201) may be prepared as described in CN103380113A.

In some specific embodiments, the organic amine may be an organic amine as shown by Formula (214) and/or an organic amine as shown by Formula (215):

Formula (214)

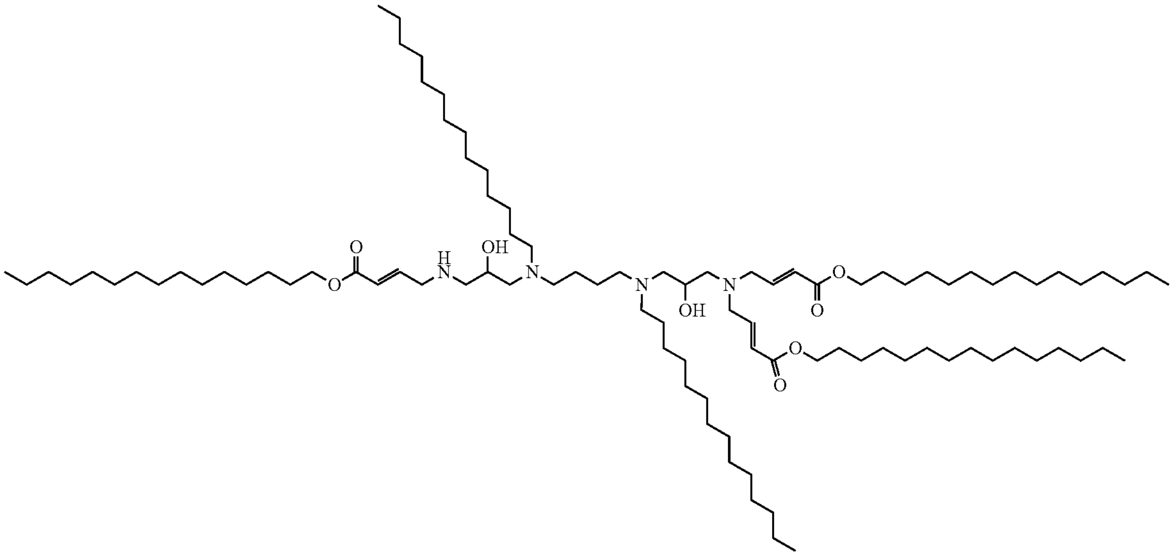

-continued (Formula 215)

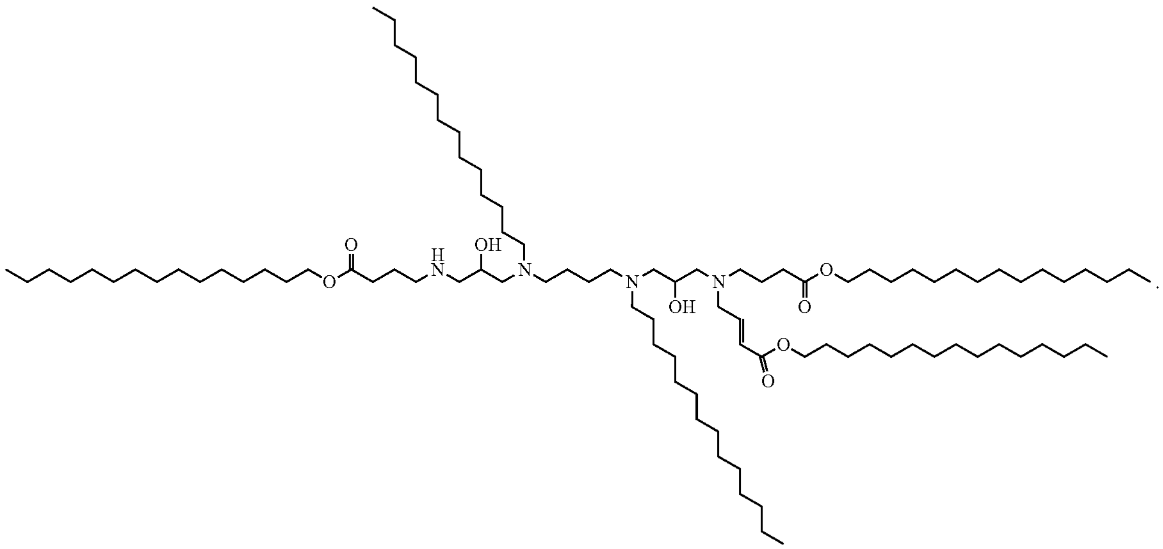

The helper lipid is cholesterol, cholesterol analogue and/or cholesterol derivatives.

The PEGylated lipid is 1,2-dipalmitoyl-sn-glycero-3-phosphatidylethanolamine-N-[methoxy(polyethylene glycol)]-2000.

In some embodiments, the molar ratio among the organic amine, the helper lipid, and the PEGylated lipid in the pharmaceutical composition is (19.7-80):(19.7-80):(0.3-50); for example, the molar ratio may be (50-70):(20-40):(3-20).

In some embodiments, the pharmaceutical composition particles formed by the double-stranded oligonucleotide of the present disclosure and the above amine-containing transfection agents have an average diameter from about 30 nm to about 200 nm, typically from about 40 nm to about 135 nm, and more typically, the average diameter of the liposome particles is from about 50 nm to about 120 nm, from about 50 nm to about 100 nm, from about 60 nm to about 90 nm, or from about 70 nm to about 90 nm, for example, the average diameter of the liposome particles is about 30, 40, 50, 60, 70, 75, 80, 85, 90, 100, 110, 120, 130, 140, 150 or 160 nm.

In some embodiments, in the pharmaceutical composition formed by the double-stranded oligonucleotide of the present disclosure and the above amine-containing transfection agents, the ratio (weight/weight ratio) of the double-stranded oligonucleotide to total lipids, e.g., the organic amines, the helper lipids and/or the PEGylated lipids, ranges from about 1:1 to about 1:50, from about 1:1 to about 1:30, from about 1:3 to about 1:20, from about 1:4 to about 1:18, from about 1:5 to about 1:17, from about 1:5 to about 1:15, from about 1:5 to about 1:12, from about 1:6 to about 1:12, or from about 1:6 to about 1:10. For example, the ratio of the double-stranded oligonucleotide of the present disclosure to total lipids is about 1:5, 1:6, 1:7, 1:8, 1:9, 1:10, 1:11, 1:12, 1:13, 1:14, 1:15, 1:16, 1:17 or 1:18 by weight.

In some embodiments, the pharmaceutical composition may be marketed with each component being separate, and used in the form of a liquid formulation. In some embodiments, the pharmaceutical composition formed by the double-stranded oligonucleotide of the present disclosure and the above pharmaceutically acceptable carrier may be prepared by various known processes, except replacing the existing double-stranded oligonucleotide with the double-stranded oligonucleotide of the present disclosure. In some specific embodiments, the pharmaceutical composition may be prepared according to the following process.

The organic amines, helper lipids and PEGylated lipids are suspended in alcohol at a molar ratio as described above and mixed homogeneously to yield a lipid solution; the alcohol is used in an amount such that the resultant lipid solution is present at a total mass concentration of 2 to 25 mg/mL (e.g., 8 to 18 mg/mL). The alcohol is a pharmaceutically acceptable alcohol, such as an alcohol that is in liquid form at about room temperature, for example, one or more of ethanol, propylene glycol, benzyl alcohol, glycerol, PEG 200, PEG 300, PEG 400, preferably ethanol.

The double-stranded oligonucleotide of the present disclosure is dissolved in a buffered salt solution to produce an aqueous solution of the double-stranded oligonucleotide. The buffered salt solution has a concentration of 0.05 to 0.5 M, such as 0.1 to 0.2 M. The pH of the buffered salt solution is adjusted to 4.0 to 5.5, such as 5.0 to 5.2. The buffered salt solution is used in an amount such that the double-stranded oligonucleotide is present at a concentration of less than 0.6 mg/ml, such as 0.2 to 0.4 mg/mL. The buffered salt may be one or more selected from the group consisting of soluble acetate and soluble citrate, such as sodium acetate and/or potassium acetate.

The lipid solution and the aqueous solution of the double-stranded oligonucleotide are mixed. The product obtained after mixing is incubated at a temperature of 40 to 60° C. for at least 2 minutes (e.g., 5 to 30 minutes) to produce an incubated lipid formulation. The volume ratio of the lipid solution to the aqueous solution of double-stranded oligonucleotide is 1:(2-5), such as 1:4.

The incubated lipid formulation is concentrated or diluted, purified to remove impurities, and then sterilized to obtain the pharmaceutical composition of the present disclosure, which has physicochemical parameters as follows: a pH of 6.5 to 8, an encapsulation percentage of more than 80%, a particle size of 40 to 200 nm, a polydispersity index of less than 0.30, and an osmotic pressure of 250 to 400 mOsm/kg; for example, the physicochemical parameters may be as follows: a pH of 7.2 to 7.6, an encapsulation percentage of more than 90%, a particle size of 60 to 100 nm, a polydispersity index of less than 0.20, and an osmotic pressure of 300 to 400 mOsm/kg.

Therein, the concentration or dilution step may be performed before, after or simultaneously with the step of impurity removal. The method for removing impurities may be any of various existing methods, for example, ultrafiltration using 100 kDa hollow fiber column, PBS at pH 7.4 as ultrafiltration exchange solution and the tangential flow system. The method for sterilization may be any of various existing methods, such as filtration sterilization on a 0.22 μm filter.

Oligonucleotide Conjugate

In one aspect, the present disclosure provides an oligonucleotide conjugate, which comprises the double-stranded oligonucleotide described above and conjugation group attached thereto.

In the context of the present disclosure, unless otherwise specified, "conjugation" refers to two or more chemical moieties each with specific function being linked to each other via a covalent linkage. Correspondingly, a "conjugate" refers to the compound formed by covalently linking individual chemical moieties. Further, an "oligonucleotide conjugate" represents a compound formed by covalently attaching a double-stranded oligonucleotide and one or more chemical moieties each with specific functions. In this context, the oligonucleotide conjugate of the present disclosure is sometimes abbreviated as a "conjugate". More specifically, in the context of the present disclosure, a "conjugating molecule" may be a specific compound capable of being conjugated to a double-stranded oligonucleotide via a reaction, thereby finally forming the oligonucleotide conjugate of the present disclosure. The type and linking mode of the ligand is well-known to those skilled in the art, and it typically serves the function of binding to the specific receptors on the surface of the target cell, thereby mediating delivery of the double-stranded oligonucleotide linked to the ligand into the target cell.

The conjugation group typically comprises at least one pharmaceutically acceptable targeting group and an optional linker. Moreover, the double-stranded oligonucleotide, the linker and the targeting group are linked in succession. In one embodiment, there are 1 to 6 targeting groups. In one embodiment, there are 2 to 4 targeting groups. The double-stranded oligonucleotide molecule may be non-covalently or covalently conjugated to the conjugation group, for example, the double-stranded oligonucleotide molecule is covalently conjugated to the conjugation group. The conjugation site between the double-stranded oligonucleotide and the conjugation group can be at 3'-terminal or 5'-terminal of the sense strand of the double-stranded oligonucleotide, or at 5'-terminal of the antisense strand, or within the internal sequence of the double-stranded oligonucleotide. In some specific embodiments, the conjugation site between the double-stranded oligonucleotide and the conjugation group is at 3'-terminal of the sense strand of the double-stranded oligonucleotide.

In some embodiments, the conjugation group is linked to the phosphate group, the 2'-hydroxy group or the base of a nucleotide. In some embodiments, the conjugation group may be linked to a 3'-hydroxy group when the nucleotides are linked via a 2'-5'-phosphodiester bond. When the conjugation group is linked to a terminal of the double-stranded oligonucleotide, the conjugation group is typically linked to a phosphate group of a nucleotide; when the conjugation group is linked to an internal sequence of the double-stranded oligonucleotide, the conjugation group is typically linked to a ribose ring or a base. For specific linking modes, reference may be made to: Muthiah Manoharan et. al. siRNA conjugates carrying sequentially assembled trivalent N-acetylgalactosamine linked through nucleosides elicit robust gene silencing in vivo in hepatocytes. ACS Chemical biology, 2015, 10(5):1181-7.

In some embodiments, the double-stranded oligonucleotide and the conjugation group can be linked by an acid-labile or reducible chemical bond, and these chemical bonds can be degraded under the acidic environment of cell endosomes, thereby rendering the double-stranded oligonucleotide to be in free state. For non-degradable conjugation modes, the conjugation group can be linked to the sense strand of the double-stranded oligonucleotide, thereby minimizing the effect of conjugation on the activity of the double-stranded oligonucleotide.

The targeting group can be linked to the double-stranded oligonucleotide molecule via an appropriate linker, and the appropriate linker can be selected by those skilled in the art according to the specific type of the targeting group. The types of these linkers and targeting groups and the linking modes with the double-stranded oligonucleotide may be found in the disclosures of WO2015006740A2, which is incorporated herein by reference in its entirety.

In some embodiments, when the targeting group is N-acetylgalactosamine, a suitable linker may have the following structure as shown by Formula (301):

Formula (301)

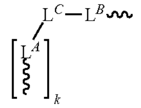

Formula (301)

wherein k is an integer of 1-3;

$L^A$ is an amide bond-comprising chain moiety that has a structure as shown by Formula (302), each $L^A$ being respectively linked to the targeting group and the $L^C$ moiety through ether bond at its two terminals:

Formula (302)

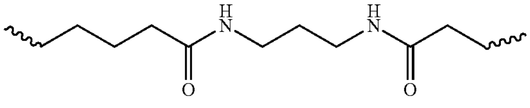

$L^B$ is an N-acylpyrrolidine-comprising chain moiety that has a structure as shown by Formula (303), the chain moiety having a carbonyl group at one terminal and being linked to the $L^C$ moiety through an amide bond, and having an oxy-group at the other terminal and being linked to the double-stranded oligonucleotide through a phosphoester bond:

Formula (303)

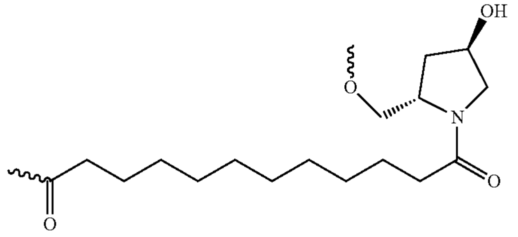

$L^C$ is a bivalent to tetravalent linking group based on hydroxymethyl aminomethane, dihydroxymethyl aminomethane or trihydroxymethyl aminomethane, $L^C$ being linked to each of the $L^A$ moieties through an ether bond via oxygen atom, and being linked to $L^B$ moiety through amide bond via nitrogen atom.

In some embodiments, when n=3 and $L^C$ is a tetravalent linking group based on trihydroxymethyl aminomethane, the oligonucleotide conjugate formed by linking N-acetylgalactosamine molecules with a double-stranded oligonucleotide molecule via $-(L^A)_3$-trihydroxymethyl aminomethane-$L^B$-as a linker has a structure as shown by Formula (304):

Formula (304)

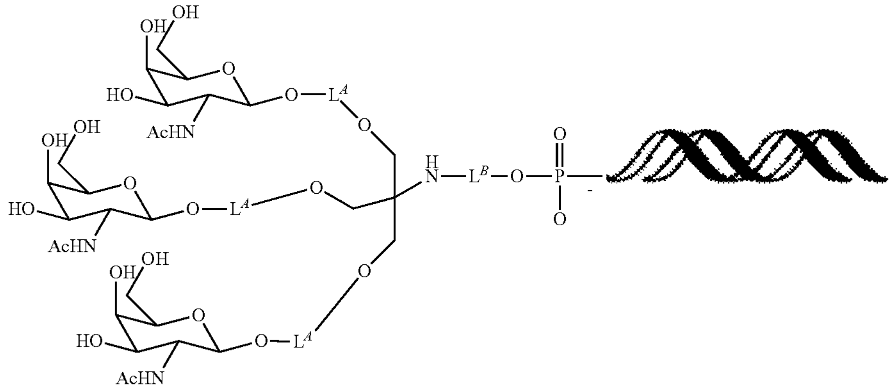

wherein the double helix structure represents a double-stranded oligonucleotide.

Likewise, the conjugation site between the double-stranded oligonucleotide and the conjugation group can be at 3'-terminal or 5'-terminal of the sense strand of the double-stranded oligonucleotide, or at 5'-terminal of the antisense strand, or within the internal sequence of the double-stranded oligonucleotide.

In some specific embodiments, the 3'-terminal of the sense strand of the double-stranded oligonucleotide of the present disclosure is covalently conjugated to three N-acetylgalactosamine (GalNAc) molecules via a linker $-(L^A)_3$-trihydroxymethyl aminomethane-$L^B$- to obtain an oligonucleotide conjugate in which the molar ratio of the double-stranded oligonucleotide molecule to the GalNAc molecule is 1:3 (hereinafter referred to as $(GalNAc)_3$-Nu), and this oligonucleotide conjugate has a structure as shown by Formula (305):

Formula (305)

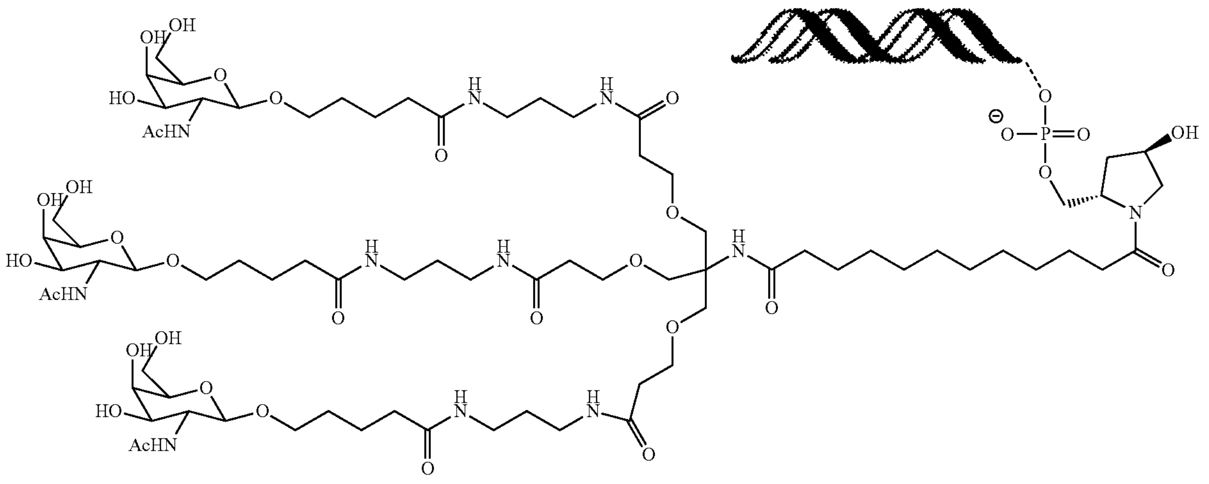

wherein the double helix structure represents a double-stranded oligonucleotide; and the linker is linked to the 3'-terminal of the sense strand of the double-stranded oligonucleotide.

In some embodiments, when the targeting group is N-acetylgalactosamine, a suitable linker may have a structure as shown by Formula (306):

Formula (306)

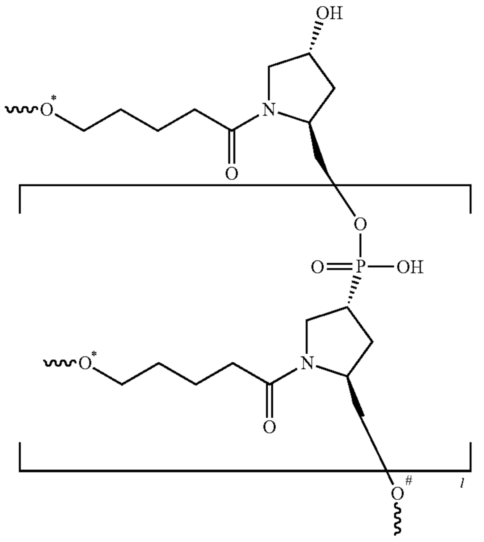

wherein 1 is an integer of 0-3;

*represents a site linked to the targeting group through ether bond on the linker; and

#represents a site linked to the double-stranded oligonucleotide via a phosphoester bond on the linker.

In some specific embodiments, when 1=2, the oligonucleotide conjugate has a structure as shown by Formula (307):

Formula (307)

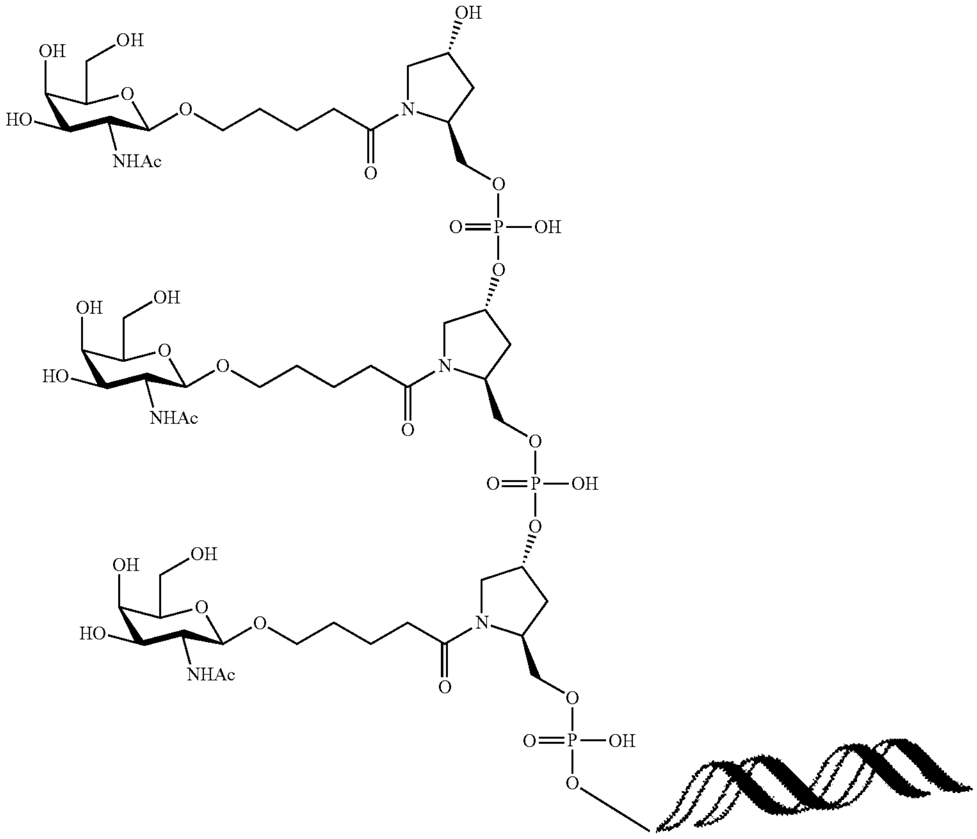

wherein the double helix structure represents a double-stranded oligonucleotide; and the linker is linked to the 3'-terminal of the sense strand of the double-stranded oligonucleotide.

The above conjugates can be synthesized according to the method described in detail in the prior art. For example, WO2015006740 A2 described in detail the preparation of various conjugates. As another example, WO2014025805A1 described the preparation method of the conjugate having the structure as shown by Formula (305). As a further example, Rajeev et al., ChemBioChem 2015, 16, 903-908, described the preparation method of the conjugate having the structure as shown by Formula (307).

In some embodiments, the conjugate has a structure as shown by Formula (308):

Formula (308)

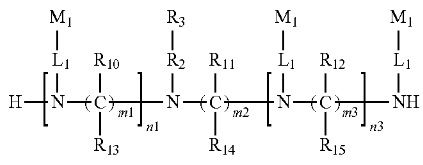

wherein n1 is an integer of 1-3, and n3 is an integer of 0-4;

m1, m2, and m3 independently of one another are an integer of 2-10;

$R_{10}$, $R_{11}$, $R_{12}$, $R_{13}$, $R_{14}$ and $R_{15}$ independently of one another are H, or selected from the group consisting of $C_1$-$C_{10}$ alkyl, $C_1$-$C_{10}$ haloalkyl, and $C_1$-$C_{10}$ alkoxy; $R_3$ is a group having a structure as shown by Formula (A59):

Formula (A59)

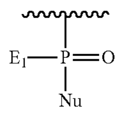

wherein, $E_1$ is OH, SH or $BH_2$;

Nu is a double-stranded oligonucleotide;

$R_2$ is a linear alkylene of 1 to 20 carbon atoms in length, wherein one or more carbon atoms are optionally replaced with one or more groups selected from the group consisting of: C(O), NH, O, S, CH═N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $R_2$ optionally has one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —$OC_1$-$C_{10}$ alkyl, —$OC_1$-$C_{10}$ alkylphenyl, —$C_1$-$C_{10}$ alkyl-OH, —$OC_1$-$C_{10}$ haloalkyl, —$SC_1$-$C_{10}$ alkyl, —$SC_1$-$C_{10}$ alkylphenyl, —$C_1$-$C_{10}$ alkyl-SH, —$SC_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), cyano, nitro, —$CO_2H$, —C(O)$OC_1$-$C_{10}$ alkyl, —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2NH$($C_1$-$C_{10}$ alkyl), —$SO_2NH$(phenyl), —$NHSO_2$($C_1$-$C_{10}$ alkyl), —$NHSO_2$(phenyl), and —$NHSO_2$($C_1$-$C_{10}$ haloalkyl);

each $L_1$ is independently a linear alkylene of 1 to 70 carbon atoms in length, wherein one or more carbon atoms are optionally replaced with one or more groups selected from the group consisting of: C(O), NH, O, S, CH═N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $L_1$ optionally has one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), cyano, nitro, —$CO_2H$, —C(O)O$C_1$-$C_{10}$ alkyl, —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2NH$($C_1$-$C_{10}$ alkyl), —$SO_2NH$(phenyl), —$NHSO_2$($C_1$-$C_{10}$ alkyl), —$NHSO_2$(phenyl), and —$NHSO_2$($C_1$-$C_{10}$ haloalkyl);

$M_1$ represents a targeting group.

In some embodiments, $L_1$ may be selected from the group consisting of groups A1-A26 and any combination thereof, wherein the structures and definitions of A1-A26 are as follows:

(A1)

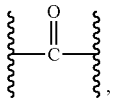

(A2)

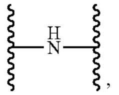

(A3)

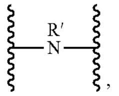

(A4)

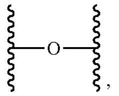

(A5)

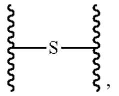

(A6)

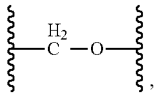

-continued (A7)

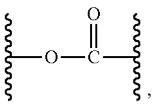

(A8)

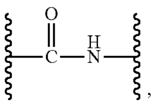

(A9)

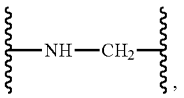

(A10)

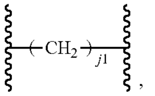

(A11)

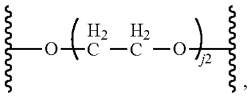

(A12)

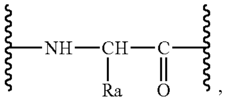

(A13)

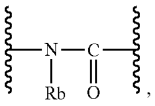

(A14)

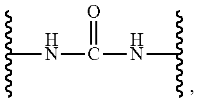

(A15)

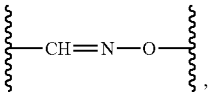

(A16)

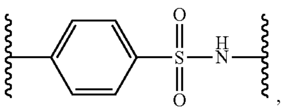

(A17)

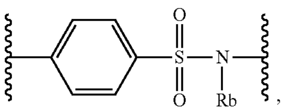

(A18)

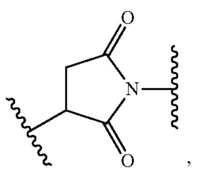

(A19)

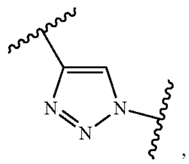

-continued
(A20)
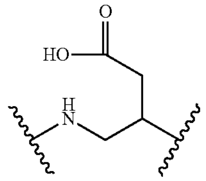
,
(A21)
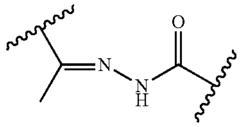
,
(A22)
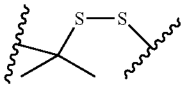
,
(A23)
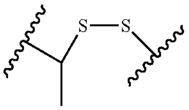
,
(A24)
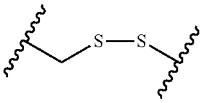
,
(A25)
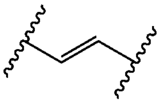
, and
(A26)
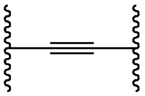
,
wherein each j1 is independently an integer of 1-20; each j2 is independently an integer of 1-20; R' is a $C_1$-$C_{10}$ alkyl; Ra is selected from the group consisting of A27-A45
(A27)
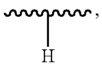
(A28)
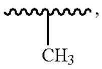
(A29)
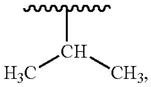
(A30)
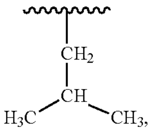
-continued
(A31)
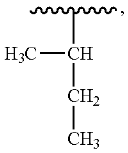
(A32)
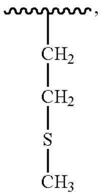
(A33)
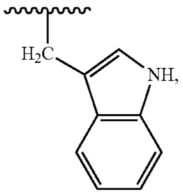
(A34)
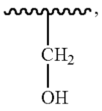
(A35)
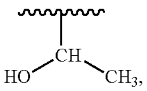
(A36)
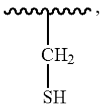
(A37)
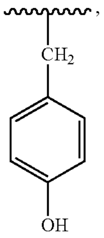
(A38)
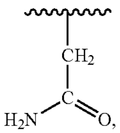
(A39)
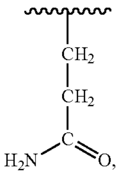

-continued (A40)

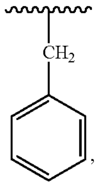

(A41)

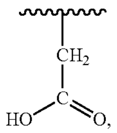

(A42)

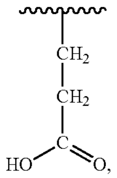

(A43)

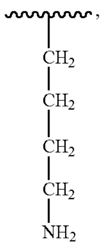

(A44)

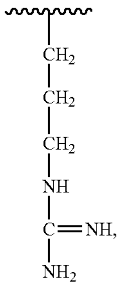

and (A45)

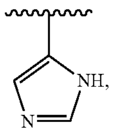

Rb is a $C_1$-$C_{10}$ alkyl; and represents a site where a group is linked to the rest of the molecule.

Those skilled in the art would understand that, though $L_1$ is defined as a linear alkyl for convenience, but it may not be a linear group or be named differently, such as an amine or alkenyl produced by the above replacement and/or substitution. For the purpose of the present disclosure, the length of $L_1$ is the number of the atoms in the chain connecting the two attaching points. For this purpose, a ring obtained by replacement of a carbon atom of the linear alkylene, such as a heterocyclylene or heteroarylene, is counted as one atom.

In some embodiments, the pharmaceutically acceptable targeting group may be a conventional ligand in the field of double-stranded oligonucleotide administration, for example, the various ligands as described in WO2009082607A2, which is incorporated herein by reference in its entirety.

In some embodiments, each ligand is independently a ligand capable of binding to a cell surface receptor. In some embodiments, at least one ligand is a ligand capable of binding to a hepatocyte surface receptor. In some embodiments, at least one ligand is a ligand capable of binding to a mammalian hepatocyte surface receptor. In some embodiments, at least one ligand is a ligand capable of binding to a human hepatocyte surface receptor. In some embodiments, at least one ligand is a ligand capable of binding to a hepatic surface asialoglycoprotein receptor (ASGP-R). The types of these ligands are well-known to those skilled in the art and they typically serve the function of binding to specific receptors on the surface of the target cell, thereby mediating delivery of the double-stranded oligonucleotide linked to the ligand into the target cell.

In some embodiments, the pharmaceutically acceptable targeting group may be any ligand that binds to the asialoglycoprotein receptor (ASGP-R) on the surface of mammalian hepatocytes. In one embodiment, each ligand is independently an asialoglycoprotein, such as asialoorosomucoid (ASOR) or asialofetuin (ASF).

In some embodiments, the pharmaceutically acceptable targeting group may be selected from one or more of the ligands fromed by the following targeting molecules or derivatives thereof: lipophilic molecules, such as cholesterol, bile acids, vitamins (such as vitamin E), lipid molecules of different chain lengths; polymers, such as polyethylene glycol; polypeptides, such as cell-penetrating peptide; aptamers; antibodies; quantum dots; saccharides, such as lactose, polylactose, mannose, galactose, N-acetylgalactosamine (GalNAc); folate; or receptor ligands expressed in hepatic parenchymal cells, such as asialoglycoprotein, asialo-sugar residue, lipoproteins (such as high density lipoprotein, low density lipoprotein), glucagon, neurotransmitters (such as adrenaline), growth factors, transferrin and the like.

In one embodiment, the ligand is a saccharide or its derivatives.

In some embodiments, at least one ligand is a saccharide. In some embodiments, each ligand is a saccharide. In some embodiments, at least one ligand is a monosaccharide, polysaccharide, modified monosaccharide, modified polysaccharide, or derivatives thereof. In some embodiments, at least one ligand may be a monosaccharide, disaccharide or trisaccharide. In some embodiments, at least one ligand is a modified saccharide. In some embodiments, each ligand is a modified saccharide. In some embodiments, each ligand is independently selected from the group consisting of polysaccharides, modified polysaccharides, monosaccharides modified monosaccharides, polysaccharide derivatives and monosaccharide derivatives. In some embodiments, each ligand or at least one ligand may be independently selected from the group consisting of glucose and its derivatives, mannose and its derivatives, galactose and its derivatives, xylose and its derivatives, ribose and its derivatives, fucose and its derivatives, lactose and its derivatives, maltose and its derivatives, arabinose and its derivatives, fructose and its derivatives, and sialic acid.

In some embodiments, each ligand may be independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O-[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-α-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose, L-4-thioribose. Other ligand selections may be found, for example, in the disclosure of CN105378082A, which is incorporated herein by reference in its entirety.

In some embodiments, the pharmaceutically acceptable targeting group in the oligonucleotide conjugate may be galactose or N-acetylgalactosamine, wherein the galactose or N-acetylgalactosamine molecules can be mono-, bi-, tri-, or tetra-valent. It should be understood that the terms mono-, bi-, tri-, or tetra-valent described herein respectively mean that the molar ratio of the double-stranded oligonucleotide molecule to the galactose or N-acetylgalactosamine molecule in the oligonucleotide conjugate is 1:1, 1:2, 1:3 or 1:4, wherein the oligonucleotide conjugate is formed from the double-stranded oligonucleotide molecule and the conjugation group containing galactose or N-acetylgalactosamine molecule as the targeting group. In some embodiments, the pharmaceutically acceptable targeting group is N-acetylgalactosamine. In some embodiments, when the double-stranded oligonucleotide of the present disclosure is conjugated to a conjugation group comprising N-acetylgalactosamine, the N-acetylgalactosamine molecule is trivalent or tetravalent. In some embodiments, when the double-stranded oligonucleotide of the present disclosure is conjugated to a conjugation group containing N-acetylgalactosamine, the N-acetylgalactosamine molecule is trivalent.

$M_1$ represents a targeting group, of which the definitions and options are the same as those described above. In some embodiments, each $M_1$ is independently selected from one of the ligands that have affinity to the asialoglycoprotein receptor on the surface of mammalian hepatocytes.

When $M_1$ is a ligand that has affinity to the asialoglycoprotein receptor (ASGP-R) on the surface of mammalian hepatocyte, in some embodiments, n1 may be an integer of 1-3, and n3 may be an integer of 0-4 to ensure that the number of the $M_1$ ligand in the conjugate may be at least 2. In some embodiments, n1+n3≥2, such that the number of the $M_1$ ligand in the conjugate may be at least 3, thereby allowing the $M_1$ ligand to more conveniently bind to the asialoglycoprotein receptor on the surface of hepatocytes, which may facilitates the endocytosis of the conjugate into cells. Experiments have shown that when the number of the $M_1$ ligand is greater than 3, the ease of binding the $M_1$ ligand to the asialoglycoprotein receptor on the surface of hepatocytes is not significantly increased. Therefore, in view of various aspects such as synthesis convenience, structure/process costs and delivery efficiency, in some embodiments, n1 is an integer of 1-2, n3 is an integer of 0-1, and n1+n3=2-3.

In some embodiments, when m1, m2, and m3 independently of one another are selected from an integer of 2-10, the steric mutual positions among many $M_1$ ligands may be fit for binding the $M_1$ ligands to the asialoglycoprotein receptor on the surface of hepatocytes. In order to make the conjugate of the present disclosure have simpler structure, easier synthesis and/or reduced cost, in some embodiments, m1, m2 and m3 independently of one another are an integer of 2-5, in some embodiments, m1=m2=m3.

Those skilled in the art would understand that when $R_{10}$, $R_{11}$, $R_{12}$, $R_{13}$, $R_{14}$, and $R_{15}$ independently of one another are selected from H, $C_1$-$C_{10}$ alkyl, $C_1$-$C_{10}$ haloalkyl, and $C_1$-$C_{10}$ alkoxy, they would not change the properties of the conjugate of the present disclosure and could all achieve the purpose of the present disclosure. In some embodiments, $R_{10}$, $R_{11}$, $R_{12}$, $R_{13}$, $R_{14}$, and $R_{15}$ independently of one another are selected from H, methyl and ethyl. In some embodiments, $R_{10}$, $R_{11}$, $R_{12}$, $R_{13}$, $R_{14}$, and $R_{15}$ are H.

According to the oligonucleotide conjugate of the present disclosure, $R_3$ is a group having the structure as shown by Formula A59, wherein $E_1$ is OH, SH or $BH_2$, and considering the availability of starting materials, in some embodiments, $E_1$ is OH or SH.

In some embodiments, $R_2$ is selected to achieve the linkage between the group as shown by Formula (A59) and the N atom on a nitrogenous backbone. In the context of the present disclosure, a "nitrogenous backbone" refers to a chain structure in which the carbon atom attached to $R_{10}$, $R_{11}$, $R_{12}$, $R_{13}$, $R_{14}$, and $R_{15}$ and the N atoms are linked to each other. In some embodiments, $R_2$ may be any linking group capable of attaching the group as shown by Formula (A59) to the N atom on a nitrogenous backbone by suitable means. In some embodiments, in the case where the oligonucleotide conjugate of the present disclosure is prepared by a solid phase synthesis process, $R_2$ group needs to have both a site linking to the N atom on the nitrogenous backbone and a site linking to the P atom in $R_3$. In some embodiments, in $R_2$, the site linking to the N atom on the nitrogenous backbone forms an amide bond with the N atom, and the site linking to the P atom in $R_3$ forms a phosphoester bond with the P atom. In some embodiments, $R_2$ is B5, B6, B5' or B6':

(B5)

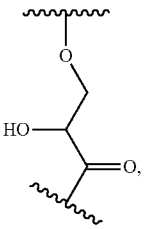

(B6)

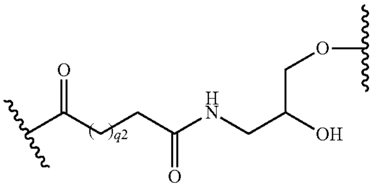

-continued (B5')

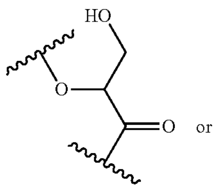

or (B6')

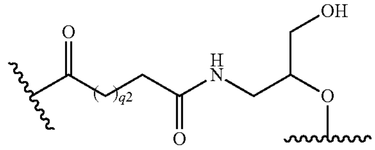

, wherein ∿∿∿ represents the site where the group is covalently linked;

$q_2$ is an integer of 1-10; in some embodiments, $q_2$ is an integer of 1-5.

$L_1$ is used to link the $M_1$ ligand to the N atom on the nitrogenous backbone, thereby providing targeting function for the oligonucleotide conjugate of the present disclosure. In some embodiments, $L_1$ is selected from the connection combinations of one or more of Formulae A1-A26. In some embodiments, $L_1$ is selected from the connection combinations of one or more of Formulae A1, A4, A5, A6, A8, A10, A11, and A13. In some embodiments, $L_1$ is selected from the connection combinations of at least two of Formula A1, A4, A8, A10, and A11. In some embodiments, $L_1$ is selected from the connection combinations of at least two of Formula A1, A8, and A10.

In some embodiments, the length of $L_1$ may be 3 to 25, 3 to 20, 4 to 15 or 5 to 12 atoms. In some embodiments, $L_1$ is 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 atoms in length.

In some embodiments, j1 is an integer of 2-10, and in some embodiments, is an integer of 3-5. In some embodiments, j2 is an integer of 2-10, and in some embodiments, is an integer of 3-5. R' is a $C_1$-$C_4$ alkyl, and in some embodiments, is one of methyl, ethyl, and isopropyl. Ra is one of A27, A28, A29, A30, and A31, and in some embodiments, is A27 or A28. Rb is a $C_1$-$C_5$ alkyl, and in some embodiments, is one of methyl, ethyl, isopropyl, and butyl. In some embodiments, j1, j2, R', Ra, and Rb of Formulae A1-A26 are respectively selected to achieve the linkage between the $M_1$ ligands and the N atom on the nitrogenous backbone, and to make the steric mutual position among the $M_1$ ligands more suitable for binding the $M_1$ ligands to the asialoglycoprotein receptor on the surface of hepatocytes.

In some embodiments, the oligonucleotide conjugate of the present disclosure has a structure as shown by Formula (403), (404), (405), (406), (407), (408), (409), (410), (411), (412), (413), (414), (415), (416), (417), (418), (419), (420), (421), or (422):

Formula (403)

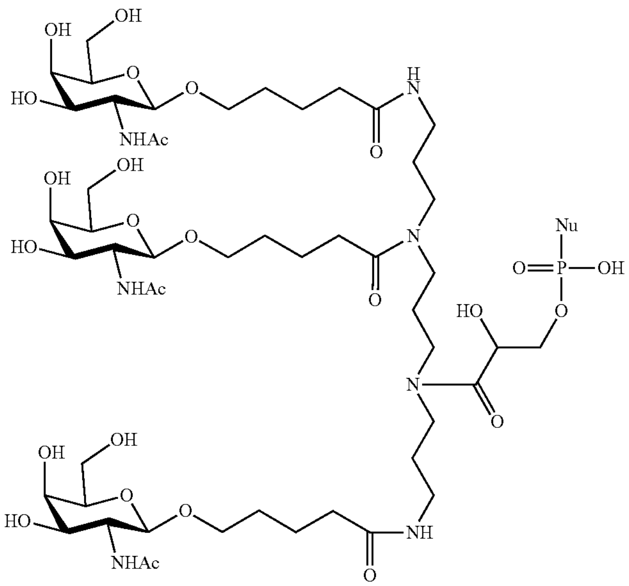

-continued
Formula (404)
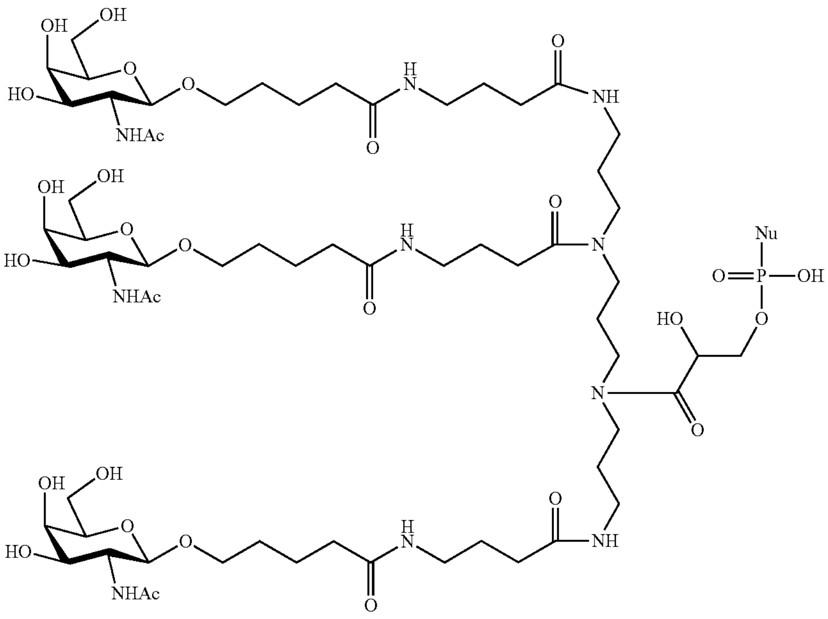
Formula (405)
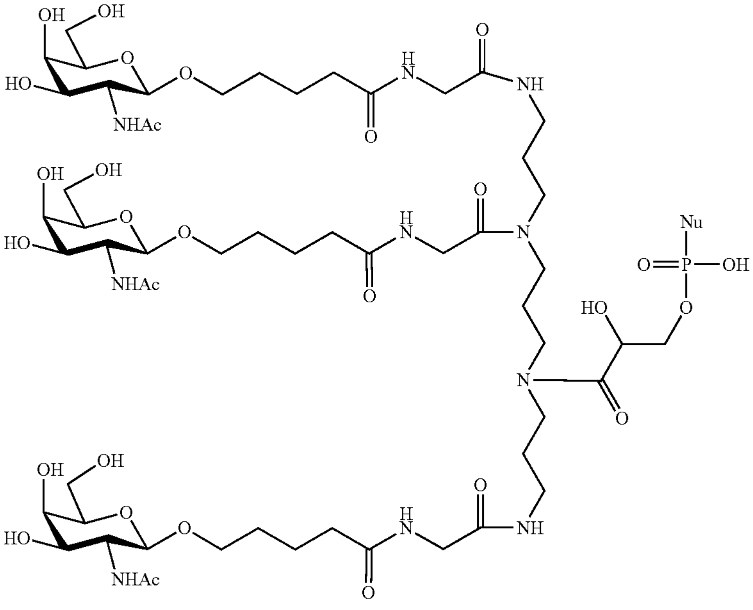

-continued
Formula (406)
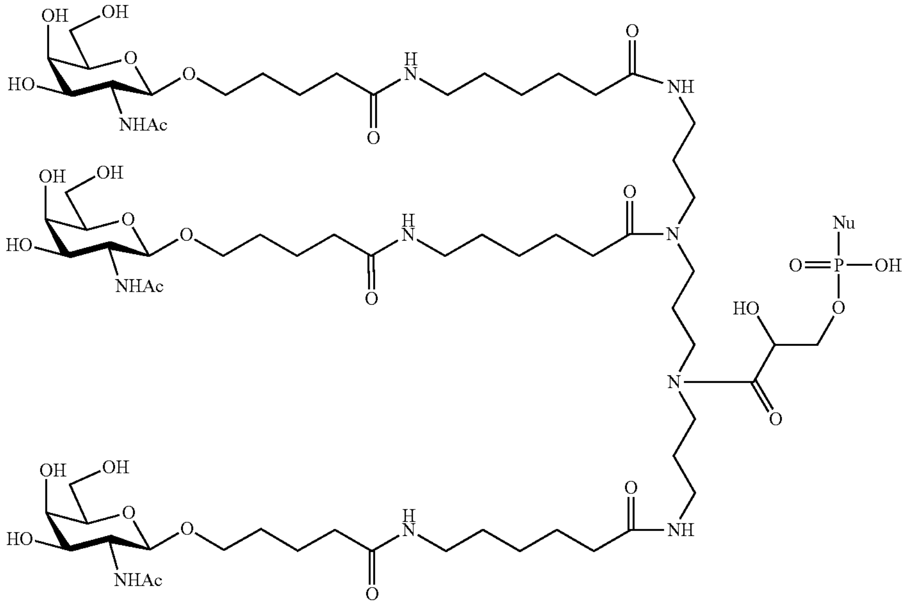
Formula (407)
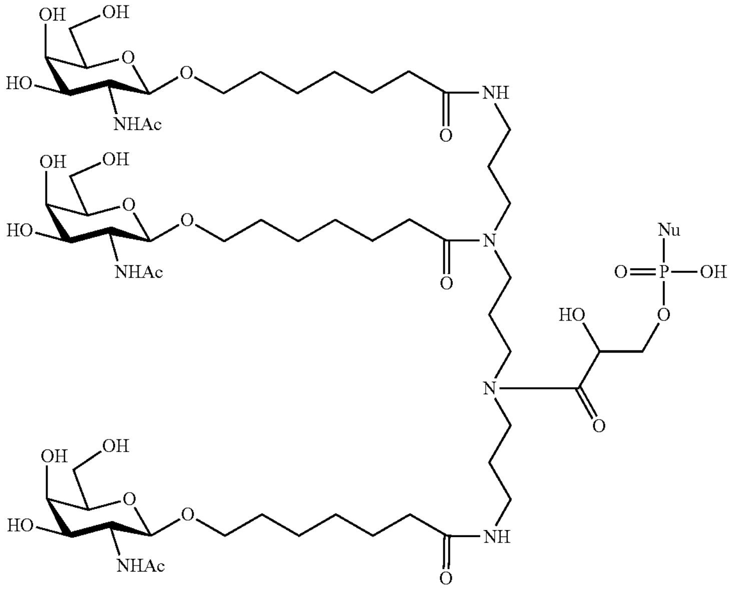

-continued
Formula (408)
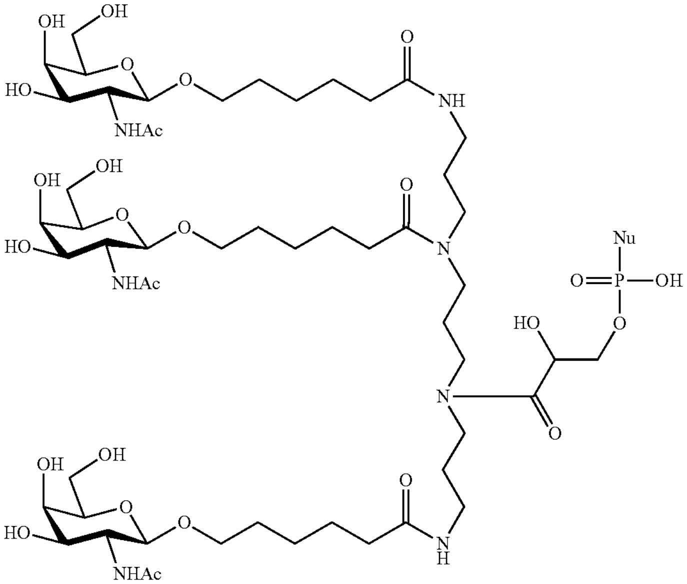
Formula (409)
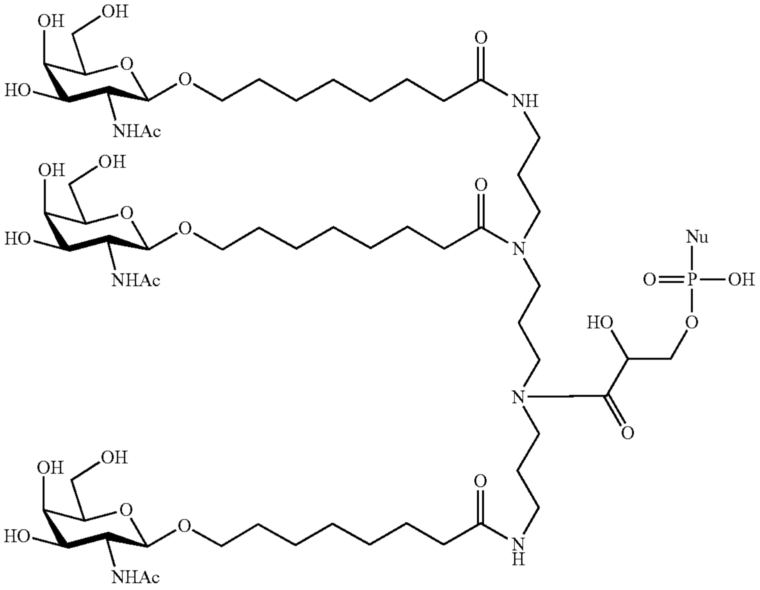

-continued
Formula (410)
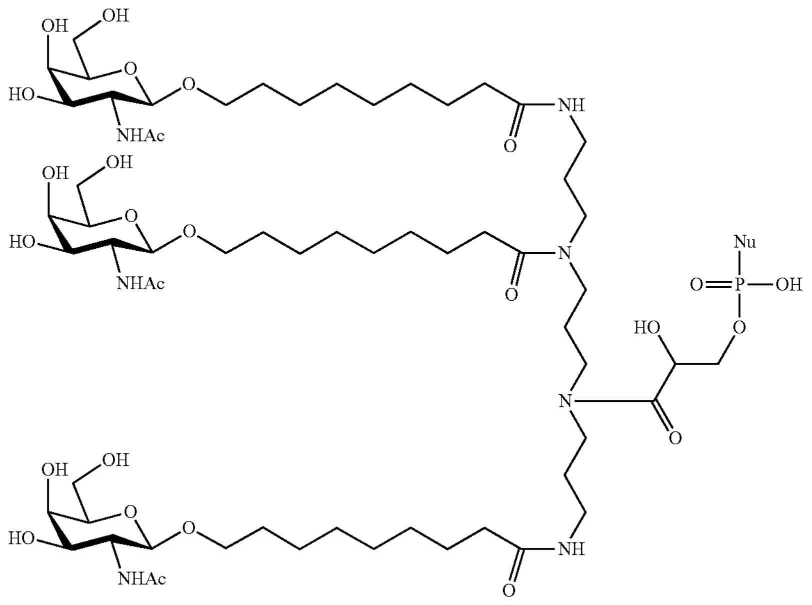
Formula (411)
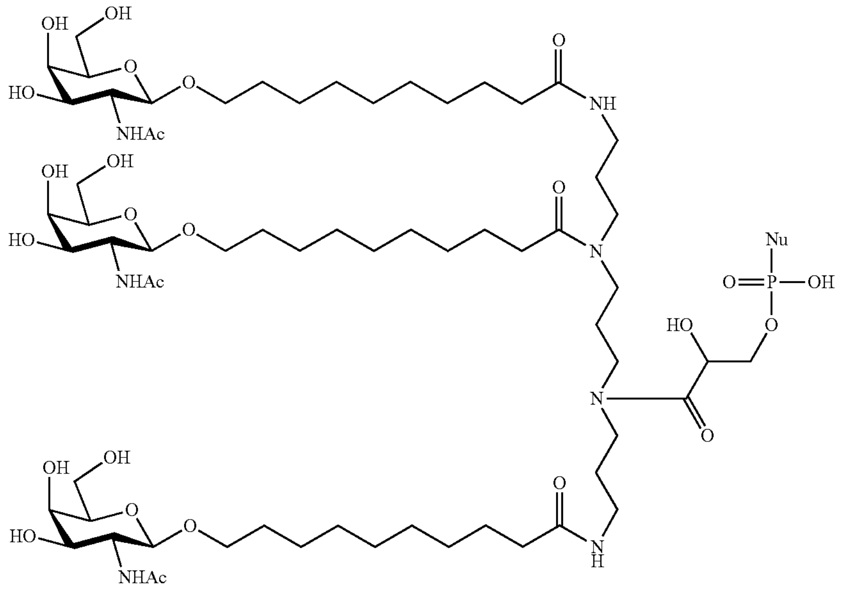

-continued
Formula (412)
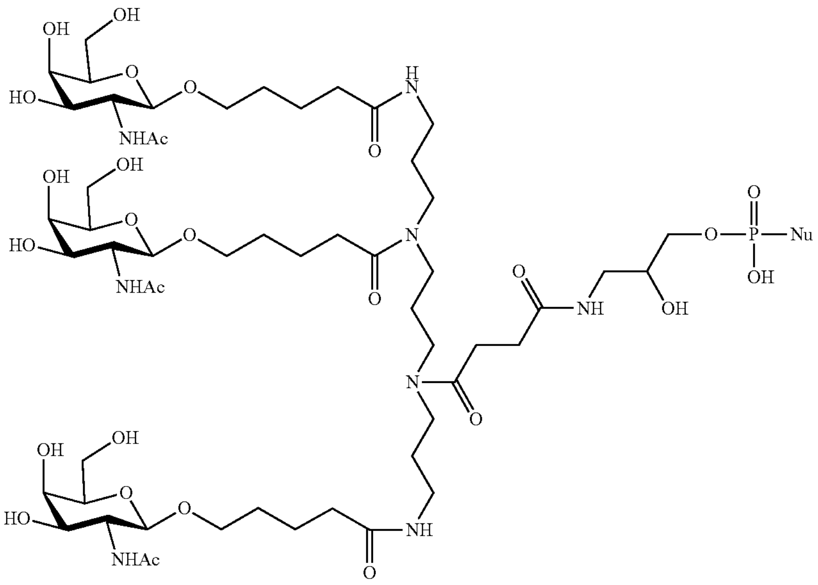
Formula (413)
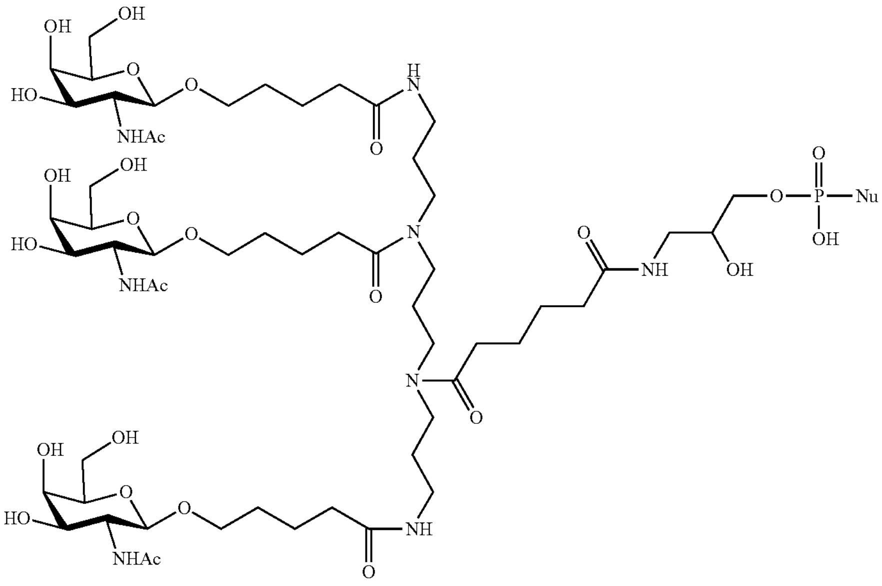

-continued
Formula (414)
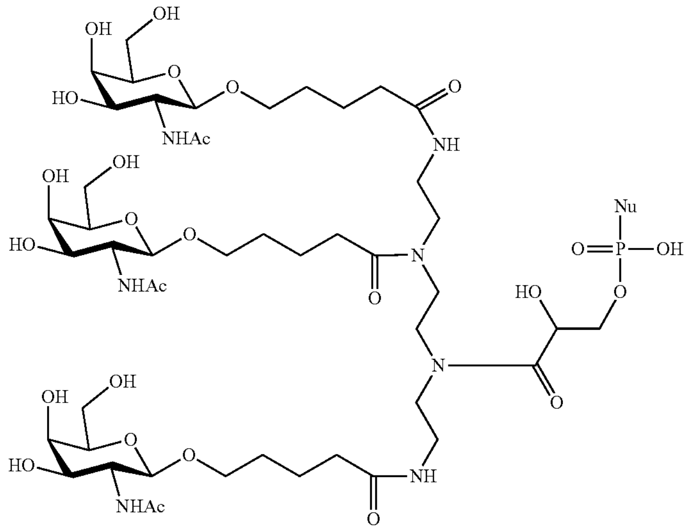
Formula (415)
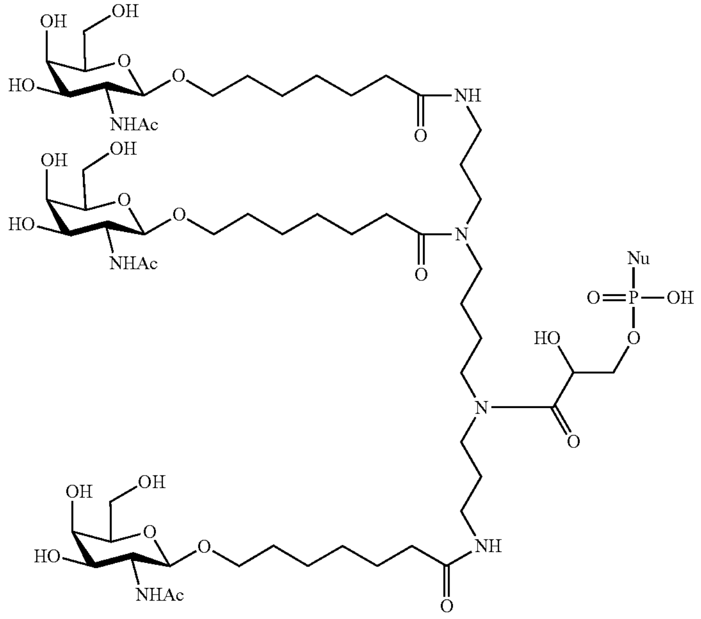

-continued
Formula (416)
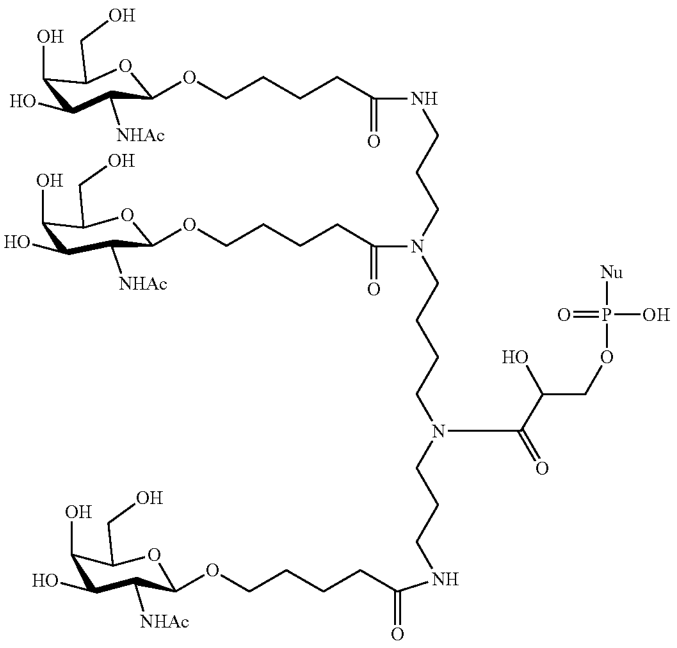
Formula (417)
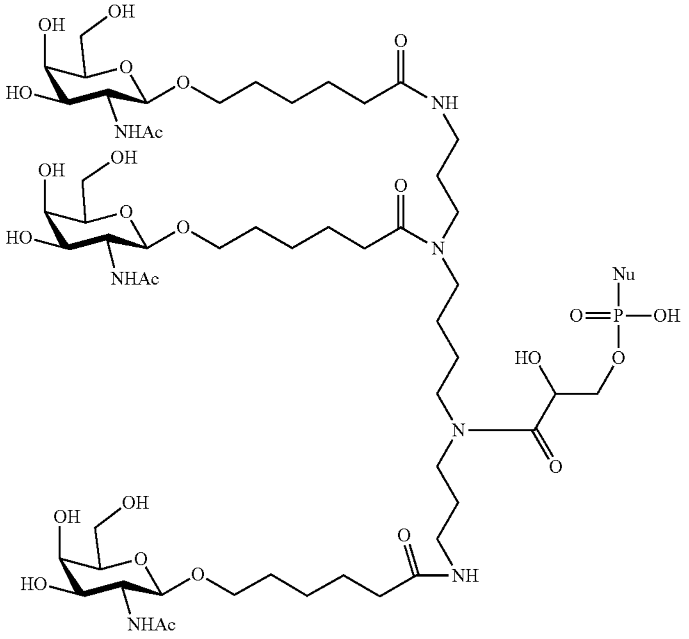

-continued
Formula (418)
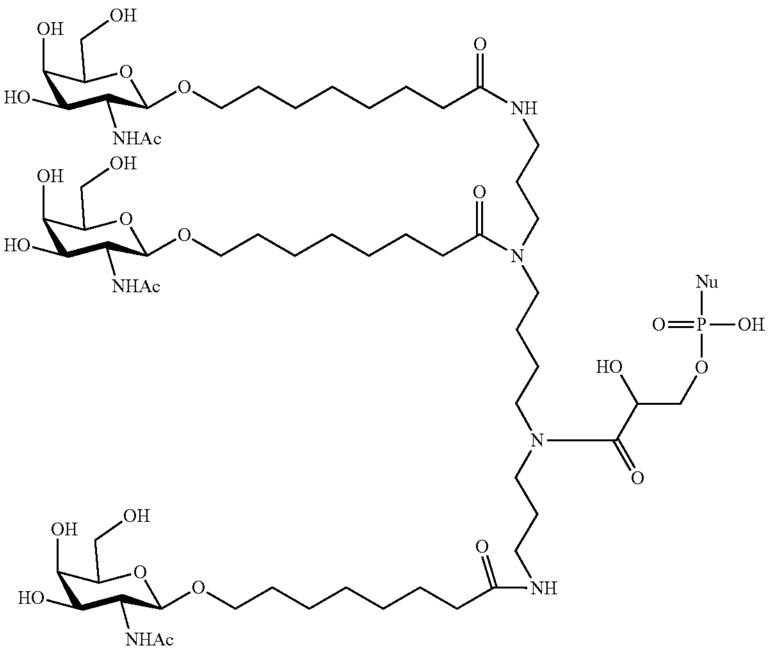
Formula (419)
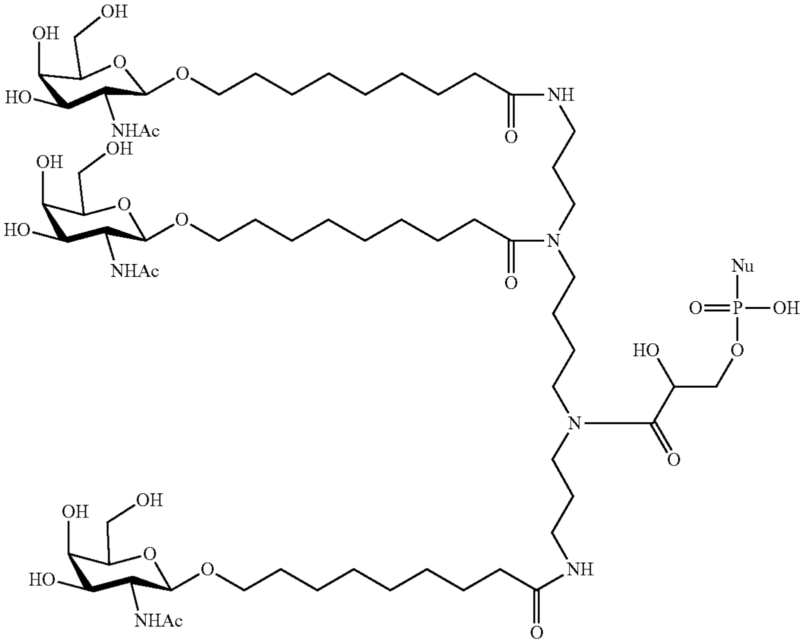

-continued
Formula (420)
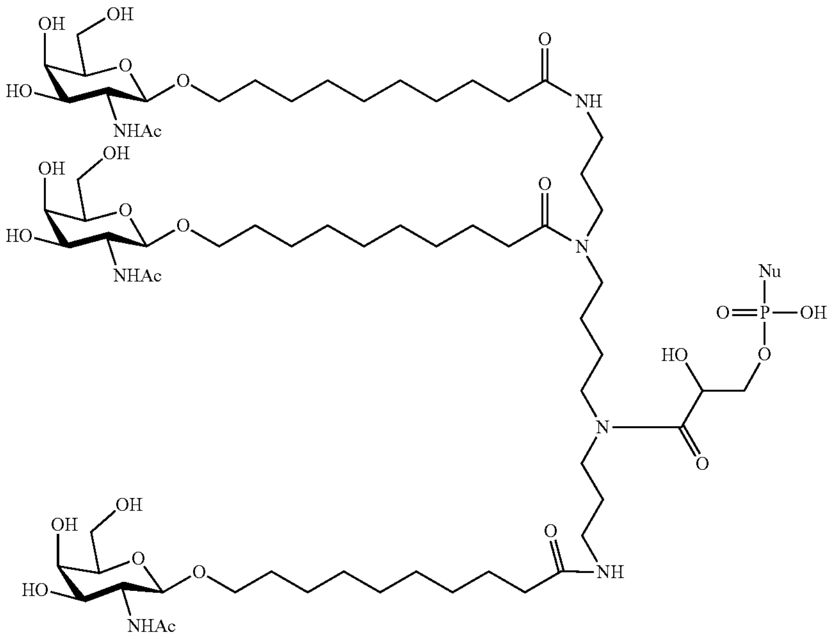
Formula (421)
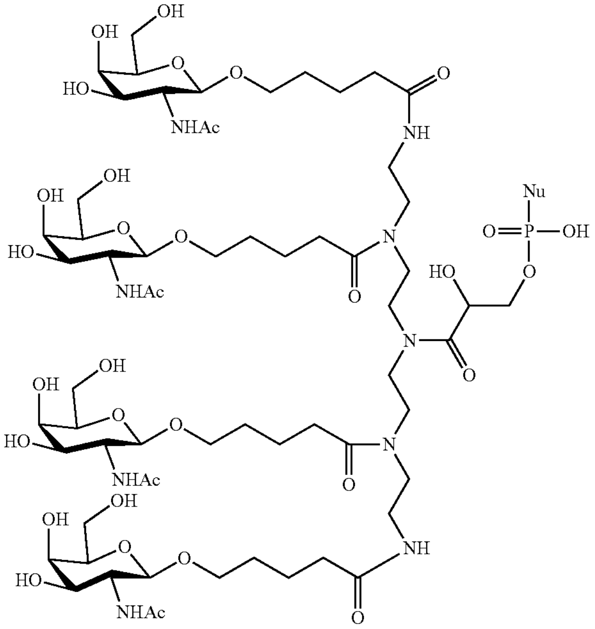

-continued

Formula (422)

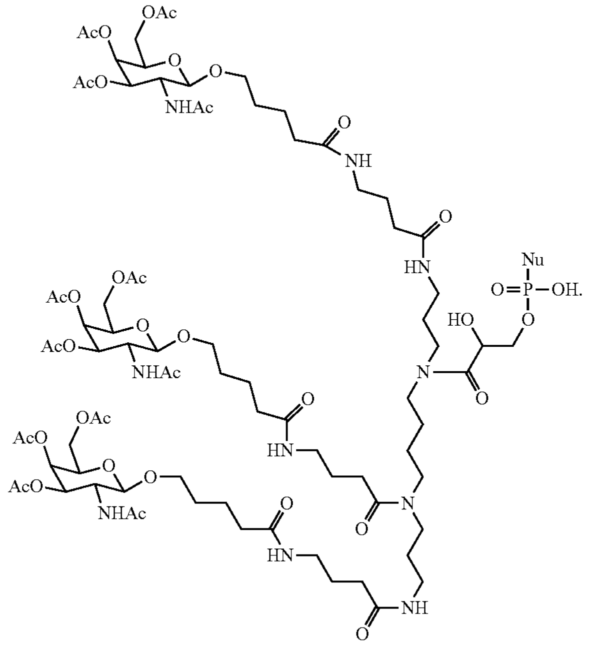

In some embodiments, the P atom in Formula A59 may be linked to any possible position in the double-stranded oligonucleotide, for example, the P atom in Formula A59 may be linked to any nucleotide in the sense or antisense strand of the double-stranded oligonucleotide. In some embodiments, the P atom in Formula A59 is linked to any nucleotide in the sense strand of the double-stranded oligonucleotide. In some embodiments, the P atom in Formula A59 is linked to a terminal of the sense or antisense strand of the double-stranded oligonucleotide. In some embodiments, the P atom in Formula A59 is linked to a terminal of the sense strand of the double-stranded oligonucleotide. Said terminal refers to the first 4 nucleotides counted from one terminal of the sense or antisense strand. In some embodiments, the P atom in Formula A59 is linked to either terminal of the sense or antisense strand of the double-stranded oligonucleotide. In some embodiments, the P atom in Formula A59 is linked to 3' terminal of the sense strand of the double-stranded oligonucleotide. In the case where the P atom in Formula A59 is linked to the above position in the sense strand of the double-stranded oligonucleotide, after entering into cells, the conjugate of the present disclosure can release a separate antisense strand of the double-stranded oligonucleotide during unwinding, thereby regulating the expression of the target gene.

The P atom in Formula A59 may be linked to any possible position of a nucleotide in the double-stranded oligonucleotide, for example, to position 5', 2' or 3', or to the base of the nucleotide. In some embodiments, the P atom in Formula A59 may be linked to position 2', 3', or 5' of a nucleotide in the double-stranded oligonucleotide by forming a phosphodiester bond. In some embodiments, the P atom in Formula A59 is linked to an oxygen atom formed by deprotonation of 3'-hydroxy of the nucleotide at 3' terminal of the sense strand in the double-stranded oligonucleotide, or the P atom in Formula A59 is linked to a nucleotide by substituting a hydrogen atom in 2'-hydroxy of a nucleotide of the sense strand in the double-stranded oligonucleotide, or the P atom in Formula A59 is linked to a nucleotide by substituting a hydrogen atom in 5'-hydroxy of the nucleotide at 5' terminal of the sense strand in the double-stranded oligonucleotide.

In the double-stranded oligonucleotide or oligonucleotide conjugate of the present disclosure, adjacent nucleotides are linked via a phosphodiester bond or phosphorothioate diester bond. The non-bridging oxygen or sulfur atom in the phosphodiester bond or phosphorothioate diester bond is negatively charged, and may be present in the form of hydroxy or sulfhydryl. Moreover, the hydrogen ion in the hydroxy or sulfhydryl may be partially or completely substituted with a cation. The cation may be any cation, such as a metal cation, an ammonium cation $NH_4^+$ or an organic ammonium cation. In order to increase solubility, in one embodiment, the cation is selected from one or more of an alkali metal cation, an ammonium cation formed by a tertiary amine and a quaternary ammonium cation. The alkali metal ion may be $K^+$ and/or $Na^+$, and the cation formed by a tertiary amine may be an ammonium cation formed by triethylamine and/or an ammonium cation formed by N,N-diisopropylethylamine. Thus, the double-stranded oligonucleotide or oligonucleotide conjugate of the present disclosure may be at least partially present in the form of salt. In one embodiment, non-bridging oxygen atom or sulfur atom in the phosphodiester bond or phosphorothioate diester bond at least partly binds to sodium ion, and thus the double-stranded oligonucleotide or oligonucleotide conjugate of the present disclosure is present or partially present in the form of sodium salt.

Those skilled in the art clearly know that a modified nucleotide may be introduced into the double-stranded oligonucleotide of the present disclosure by a nucleoside monomer with a corresponding modification. The methods for preparing a nucleoside monomer having the corresponding modification and the methods for introducing a modified nucleotide into a double-stranded oligonucleotide are also well-known to those skilled in the art. All modified nucleoside monomers may be either commercially available or prepared by known methods.

Preparation of the Oligonucleotide Conjugate as Shown by Formula (308)

The oligonucleotide conjugates of the present disclosure may be prepared by any appropriate synthesis routes.

In some embodiments, the oligonucleotide conjugate as shown by Formula (308) may be prepared by the following method, comprising: successively linking nucleoside monomers in 3' to 5' direction according to the nucleotide type and sequence in the sense strand and antisense strands of the double-stranded oligonucleotide respectively, under the condition of phosphoramidite solid phase synthesis, wherein the step of linking each nucleoside monomer includes a four-step reaction of deprotection, coupling, capping, and oxidation or sulfurization; isolating the sense strand and the antisense strand of the double-stranded oligonucleotide; and annealing, wherein the double-stranded oligonucleotide is the above double-stranded oligonucleotide of the present disclosure.

Moreover, the method further comprises: contacting the compound as shown by Formula (321) with a nucleoside monomer or a nucleotide sequence linked to a solid phase support under coupling reaction condition and in the presence of a coupling agent, thereby linking the compound as shown by Formula (321) to the nucleotide sequence through a coupling reaction. Hereinafter, the compound as shown by Formula (321) is also called a conjugating molecule.

Formula (321)

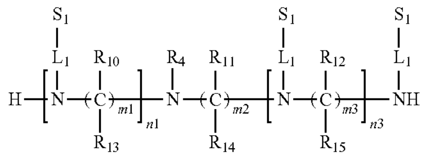

wherein, $R_4$ is a moiety capable of binding to the double-stranded oligonucleotide of the present disclosure. In some embodiments, $R_4$ is a moiety capable of binding to the double-stranded oligonucleotide of the present disclosure via a covalent bond. In some embodiments, $R_4$ is a moiety comprising any functional group that may be conjugated to a double-stranded oligonucleotide via a phosphodiester bond by a reaction;

Each $S_1$ is independently an $M_1$, which is a group formed by substituting all active hydroxyl with the group YCOO—, wherein each Y is independently selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl.

The definitions and options of n1, n3, m1, m2, m3, $R_{10}$, $R_{11}$, $R_{12}$, $R_{13}$, $R_{14}$, $R_{15}$, $L_1$, $M_1$ are respectively as described above.

$R_4$ is selected to achieve the linkage to the N atom on a nitrogenous backbone and to provide a suitable reaction site for synthesizing the oligonucleotide conjugate as shown by Formula (308). In some embodiments, $R_4$ comprises a $R_2$ linking group or protected $R_2$ linking group, and can form a functional group as shown by Formula (A59) with a double-stranded oligonucleotide via reaction.

In some embodiments, $R_4$ comprises a first functional group that can react with a group on a double-stranded oligonucleotide or a nucleoside monomer to form a phosphite ester, and a second functional group that can form a covalent bond with a hydroxy group or an amino group, or comprises a solid phase support linked via the covalent bond. In some embodiments, the first functional group is a phosphoramidite, a hydroxy or a protected hydroxy. In some embodiments, the second functional group is a phosphoramidite, a carboxyl or a carboxylate salt. In some embodiments, the second functional group is a solid phase support linked to the rest of the molecule via a covalent bond which is formed by a hydroxy group or an amino group. In some embodiments, the solid phase support is linked via a phosphoester bond, a carboxyl ester bond, or an amide bond. In some embodiments, the solid phase support is a resin.

In some embodiments, the first functional group comprises hydroxy, —$OR_k$ or a group as shown by Formula (C3); the second functional group comprises a group as shown by Formula (C1), (C2), (C3), (C1'), or (C3'):

(C1)

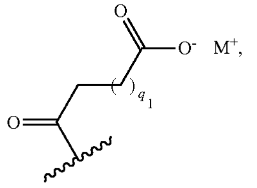

(C2)

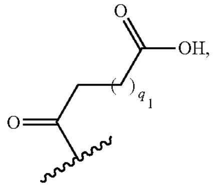

(C3)

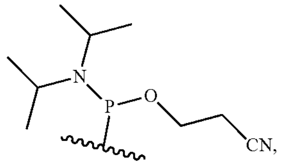

(C1')

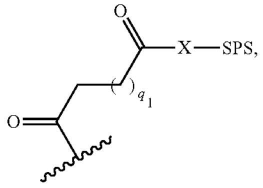

(C3')

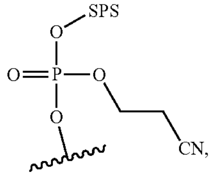

wherein $q_1$ is an integer of 1-4, X is O or NH, $M^+$ is a cation, $R_k$ is a hydroxy protecting group, SPS represents a solid phase support, and 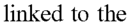 represents the site where a group is covalently linked to the rest of the molecule.

In some embodiments, the first functional group comprises a phosphoramidite group, such as the group as shown by Formula (C3). The phosphoramidite group can form a phosphite ester with a hydroxy at any position on a nucleotide (such as a 2'- or 3'-hydroxy) by coupling reaction, and the phosphite ester can form a phosphodiester bond or phosphorothioate ester bond as shown by Formula (A59) via oxidation or sulfurization, so as to conjugate the conjugating molecule to a double-stranded oligonucleotide. Thus, even if the second functional group does not exist, the compound as shown by Formula (321) will also be able to be conjugated to the nucleotide, without affecting the obtaining of the oligonucleotide conjugate as shown by Formula (308). Under such circumstances, after obtaining a sense or antisense strand of the double-stranded oligonucleotide by a method such as phosphoramidite solid phase synthesis, the compound as shown by Formula (321) is reacted with a hydroxy on the terminal nucleotide of the nucleotide sequence, and the resultant phosphite ester forms a phosphodiester bond or phosphorothioate bond by a subsequent oxidation or sulfurization, thereby conjugating the compound as shown by Formula (321) to a double-stranded oligonucleotide.

In some embodiments, the first functional group comprises a protected hydroxy group. In some embodiments, the second functional group comprises a group that can react with a solid phase support to provide a conjugating molecule comprising the solid phase support. In some embodiments, the second functional group comprises a carboxyl, a carboxylate or a phosphoramidite, such as the functional group as shown by Formula (C1), (C2) or (C3). When the second functional group comprises a carboxyl or a carboxylate, the compound as shown by Formula (321) can react via an esterification or an amidation reaction with a hydroxy or an amino group on a solid phase support such as a resin, to form a conjugating molecule comprising a solid phase support linked via a carboxylate ester bond or an amide bond. When the second functional group comprises a phosphoramidite functional group, the compound as shown by Formula (321) can be coupled with a hydroxy group on a universal solid phase support, such as a resin, and by oxidation, form a conjugating molecule comprising a solid phase support linked via a phosphodiester bond. Subsequently, starting from the above product linked to a solid phase support, the nucleoside monomers are linked sequentially by a phosphoramidite solid phase synthesis method, thereby obtaining a sense or antisense strand of the double-stranded oligonucleotide linked to the conjugation group. During the solid phase phosphoramidite synthesis, the first functional group is deprotected, and then coupled with a phosphoramidite group on a nucleoside monomer under coupling reaction condition.

In some embodiments, the first functional group comprises a hydroxy or a protected hydroxy group, and the second functional group comprises a solid phase support linked via a carboxylate ester bond, a amide bond or a phosphoester bond as shown by Formula (C1') or (C3'). Under such circumstances, starting from the compound as shown by Formula (321) in place of the solid phase support, the nucleoside monomers are linked sequentially by a phosphoramidite solid phase synthesis method, thereby obtaining a sense or antisense strand of the double-stranded oligonucleotide linked to a conjugation group.

In some embodiments, the carboxylate may be expressed as —$COO^-M^+$, wherein $M^+$ is a cation such as one of a metal cation, an ammonium cation $NH_4$J and an organic ammonium cation. In one embodiment, the metal cation may be an alkali metal cation, such as $K^+$ or $Na^+$. In order to increase solubility and facilitate the reaction, in one embodiment, the organic ammonium cation is an ammonium cation formed by a tertiary amine, or a quaternary ammonium cation, such as an ammonium cation formed by triethylamine or N,N-diisopropylethylamine. In some embodiments, the carboxylate is a triethylamine carboxylate or an N,N-diisopropylethylamine carboxylate.

In some embodiments, $R_4$ comprises a structure as shown by Formula (B9), (B10), (B9'), (B10'), (B11), (B12), (B11') or (B12'):

(B9)

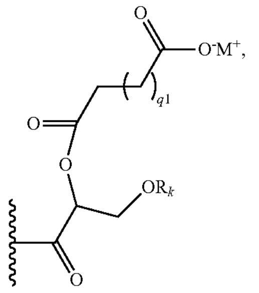

(B10)

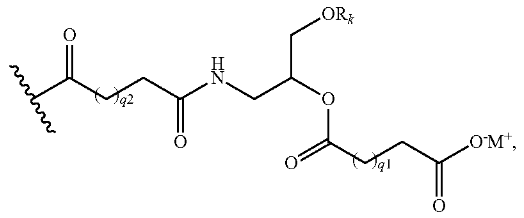

(B9')

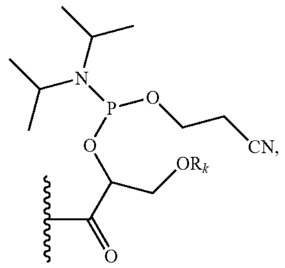

(B10')

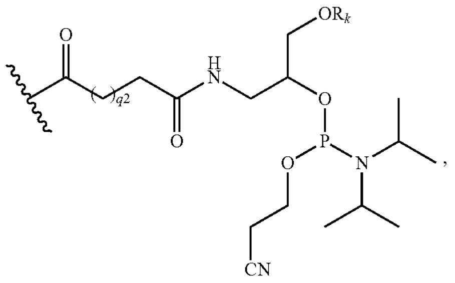

(B11)

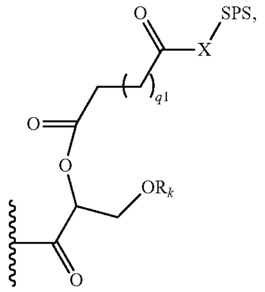

-continued (B12)

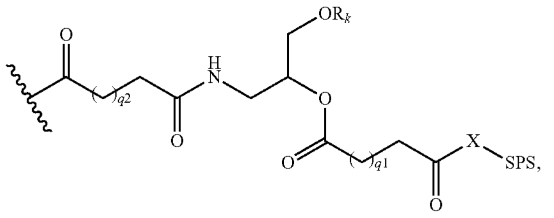

(B11')

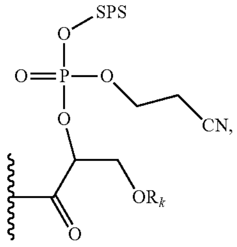

(B12')

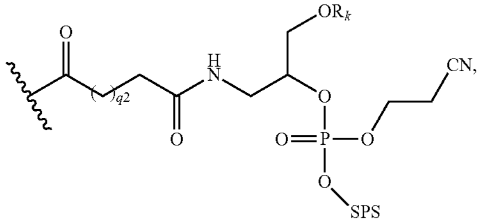

wherein $q_1$ is an integer of 1-4, $q_2$ is an integer of 1-10, X is O or NH, $M^+$ is a cation, $R_k$ is a hydroxy protecting group, SPS represents a solid phase support, and ~~~~ represents the site where a group is covalently linked to the rest of the molecule. In some embodiments, $q_1$ is 1 or 2. In some embodiments, $q_2$ is an integer of 1-5. In some embodiments, $R_4$ comprises a structure as shown by Formula (B9) or (B10). In some embodiments, $R_4$ comprises a structure as shown by Formula (B11) or (B12).

In some embodiments, $R_k$ is one or more of Tr (trityl), MMTr (4-methoxytrityl), DMTr (4,4'-dimethoxytrityl), and TMTr (4,4',4''-trimethoxytrityl). In some embodiments, $R_k$ may be DMTr, i.e., 4,4'-dimethoxytrityl.

$L_1$ is a linear alkylene of 1 to 70 carbon atoms in length, wherein one or more carbon atoms are optionally replaced with one or more groups selected from the group consisting of: C(O), NH, O, S, CH=N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $L_1$ optionally has one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —$OC_1$-$C_{10}$ alkyl, —$OC_1$-$C_{10}$ alkylphenyl, —$C_1$-$C_{10}$ alkyl-OH, —$OC_1$-$C_{10}$ haloalkyl, —$SC_1$-$C_{10}$ alkyl, —$SC_1$-$C_{10}$ alkylphenyl, —$C_1$-$C_{10}$ alkyl-SH, —$SC_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), cyano, nitro, —$CO_2$H, —C(O)$OC_1$-$C_{10}$ alkyl, —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$—$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2$NH($C_1$-$C_{10}$ alkyl), —$SO_2$NH(phenyl), —$NHSO_2$($C_1$-$C_{10}$ alkyl), —$NHSO_2$(phenyl), and —$NHSO_2$($C_1$-$C_{10}$ haloalkyl).

In some embodiments, $L_1$ is used to link the $M_1$ ligand to the N atom on the nitrogenous backbone, thereby providing liver targeting function for the oligonucleotide conjugate. In some embodiments, $L_1$ comprises any one of Formulae A1-A26, or the combination thereof.

According to the embodiments described above, those skilled in the art would easily understand that as compared with the well-known phosphoramidite solid phase synthesis methods in the art, an oligonucleotide conjugate in which a conjugating molecule is linked to any possible position of the nucleotide sequence can be obtained through the above first functional group and an optional second functional group. For example, the conjugating molecule is linked to a terminal of the nucleotide sequence or to either terminal of the nucleotide sequence. Correspondingly, unless otherwise specified, in the following description regarding conjugate preparation, when referring to the reactions such as "deprotection", "coupling", "capping", "oxidation", "sulfurization", it will be understood that the reaction conditions and agents involved in the well-known phosphoramidite solid phase synthesis methods in the art would also apply to these reactions. Exemplary reaction conditions and agents will be described in detail hereinafter.

In some embodiments, each $S_1$ is independently an $M_1$. In some embodiments, each $S_1$ is independently a group formed by protecting at least one active hydroxyl in $M_1$ with a hydroxyl protecting group. In some embodiments, $S_1$ is independently a group formed by protecting all active hydroxyls in $M_1$ with hydroxyl protecting groups. In some embodiments, any hydroxyl protecting group known to those skilled in the art may be used to protect the active hydroxyl on $M_1$. In some embodiments, the protected hydroxy is expressed as the formula YCOO—, wherein each Y is independently selected from the group consisting of $C_1$-$C_{10}$ alkyl and $C_6$-$C_{10}$ aryl, which is optionally substituted with one or more substituents selected from the group consisting of halo and $C_1$-$C_6$ alkyl. In some embodiments, each Y is independently selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and $C_1$-$C_6$ alkylphenyl.

In some embodiments, each $S_1$ is independently selected from the group consisting of Formulae A46-A54:

(A46)

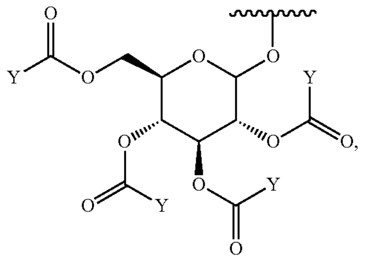

(A47)

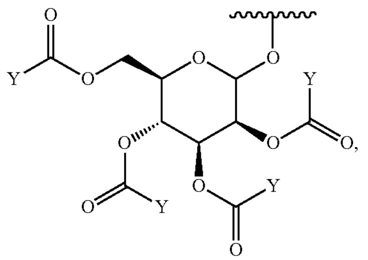

-continued (A48)

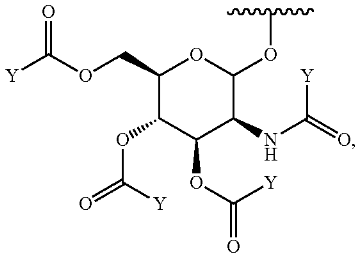

(A49)

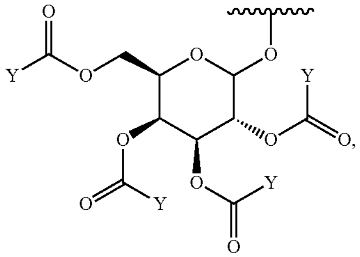

(A50)

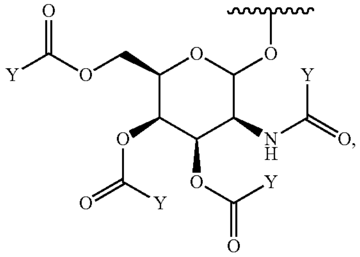

(A51)

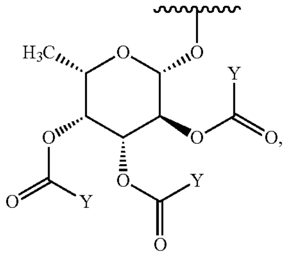

(A52)

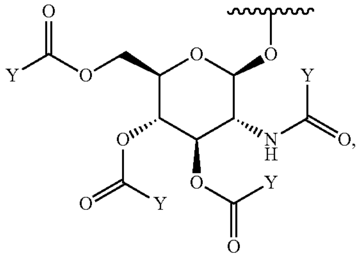

-continued (A53)

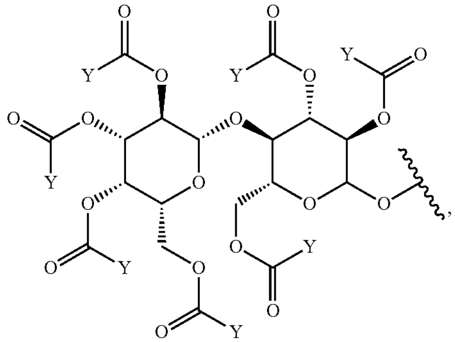

(A54)

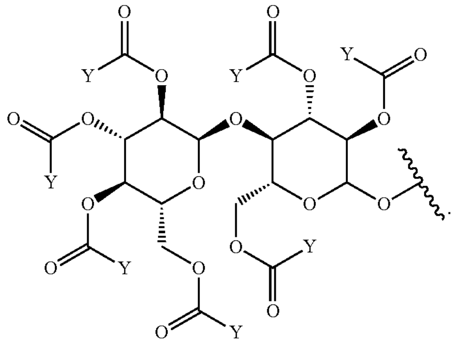

In some embodiments, $S_1$ is Formula A49 or A50.

In some embodiments, each Y is independently selected from one of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl. In some embodiments, Y is methyl.

As mentioned previously, the method for preparing the oligonucleotide conjugate of the present disclosure further comprises the following step: synthesizing the other strand of the double-stranded oligonucleotide (for example, when a sense strand of the double-stranded oligonucleotide linked to a conjugation group is synthesized in the above steps, the method further comprises synthesizing an antisense strand of the double-stranded oligonucleotide by the solid phase synthesis method, and vice versa), isolating the sense strand and the antisense strand, and annealing. In particular, in the isolation step, the solid phase support linked to the nucleotide sequence and/or conjugation group is cleaved, the necessary protecting group is removed (in this case, each $S_1$ group in the compound as shown by Formula (321) is converted to the corresponding $M_1$ ligand), a sense strand (or antisense strand) of the double-stranded oligonucleotide linked to the conjugation group and the corresponding antisense strand (or sense strand) are obtained, and the sense strand and the antisense strand are annealed to form a double-stranded RNA structure, thereby obtaining an oligonucleotide conjugate as shown by Formula (308).

In some embodiments, the method for preparing the oligonucleotide conjugate comprises the following steps: contacting the compound as shown by Formula (321) with the first nucleoside monomer at 3' terminal of the sense or antisense strand under coupling reaction condition in the presence of a coupling agent, thereby linking the compound as shown by Formula (321) to the first nucleotide in the sequence; successively linking nucleoside monomers in 3' to 5' direction to synthesize the sense or antisense strand of the double-stranded oligonucleotide according to the desired nucleotide type and sequence of the sense or antisense strand, under the condition of phosphoramidite solid phase synthesis; wherein the compound of Formula (321) is a compound in which $R_4$ comprises a first functional group comprising a protected hydroxy and a second functional group comprising a group as shown by Formula (C1') or (C3'), and the compound of Formula (321) is deprotected before linked to the first nucleoside monomer; and the linking of each nucleoside monomer comprises a four-step reaction of deprotection, coupling, capping, and oxidation or sulfurization; thus obtaining a sense or antisense strand of nucleic acid linked to the conjugation group; successively linking nucleoside monomers in 3' to 5' direction to synthesize the sense or antisense strand of nucleic acid according to the nucleotide type and sequence of the sense or antisense strand, under the condition of phosphoramidite solid phase synthesis; wherein the linking of each nucleoside monomer includes a four-step reaction of deprotection, coupling, capping, and oxidation or sulfurization; removing the protecting groups and cleaving the solid phase support; isolating and purifying the sense strand and the antisense strand of nucleic acid; and annealing.

In some embodiments, the method for preparing the oligonucleotide conjugate comprises the following steps: successively linking nucleoside monomers in 3' to 5' direction to synthesize the sense strand or the antisense strand according to the nucleotide type and sequence of the sense or antisense strand in the double-stranded oligonucleotide; wherein the linking of each nucleoside monomer comprises a four-step reaction of deprotection, coupling, capping, and oxidation or sulfurization, thus obtaining a sense strand linked to the solid phase support and an antisense strand linked to the solid phase support; contacting the compound as shown by Formula (321) with the sense strand linked to the solid phase support or the antisense strand linked to the solid phase support under coupling reaction condition in the presence of a coupling agent, thereby linking the compound as shown by Formula (321) to the sense strand or the antisense strand; wherein the compound of Formula (321) is a compound in which $R_4$ comprises a phosphoramidite group as the first functional group; removing the protecting groups and cleaving the solid phase support; respectively isolating and purifying the sense or antisense strand of the double-stranded oligonucleotide; and annealing; wherein the sense or antisense strand of the double-stranded oligonucleotide is linked to a conjugation group.

In some embodiments, the P atom in formula A59 is linked to the 3' terminal of the sense strand of the double-stranded oligonucleotide, and the method for preparing the oligonucleotide conjugate of the present disclosure comprises:

(1) removing the hydroxyl protecting group $R_k$ in the compound of Formula (321) (wherein the compound of Formula (321) is a compound in which $R_4$ comprises a first functional group and a second function group, wherein the first functional group comprises a protected hydroxy $OR_k$, and the second function group has a structure as shown by Formula (C1') or (C3')); contacting the deprotected product with a nucleoside monomer to obtain a nucleoside monomer linked to a solid phase support via the conjugation group, under coupling reaction condition in the presence of a coupling agent;

(2) starting from the nucleoside monomer linked to a solid phase support via the conjugating molecule, synthesizing a sense strand of the double-stranded oligonucleotide in 3' to 5' direction by a phosphoramidite solid phase synthesis method;

(3) synthesizing an antisense strand of the double-stranded oligonucleotide by a phosphoramidite solid phase synthesis method; and (4) isolating the sense strand and the antisense strand of the double-stranded oligonucleotide and annealing the same to obtain the oligonucleotide conjugate of the present disclosure;

wherein in step (1), the method for removing the protecting group $R_k$ in the compound of Formula (321) comprises contacting the compound of Formula (321) with a deprotection agent under deprotection condition. The deprotection condition comprises a temperature of 0-50° C., and in some embodiments, 15-35° C., and a reaction time of 30-300 seconds, and in some embodiments, 50-150 seconds. The deprotection agent may be selected from one or more of trifluoroacetic acid, trichloroacetic acid, dichloroacetic acid, and monochloroacetic acid, and in some embodiments, the deprotection agent is dichloroacetic acid. The molar ratio of the deprotection agent to the compound as shown by Formula (321) may be 10:1 to 1000:1, and in some embodiments, 50:1 to 500:1.

The coupling reaction condition and the coupling agent may be any conditions and agents suitable for the above coupling reaction. In some embodiments, the same condition and agent as those of the coupling reaction in the solid phase synthesis method can be used.

In some embodiments, the coupling reaction condition comprises a reaction temperature of 0-50° C., and in some embodiments, 15-35° C. The molar ratio of the compound of Formula (321) to the nucleoside monomer may be 1:1 to 1:50, and in some embodiments, 1:2 to 1:5. The molar ratio of the compound of Formula (321) to the coupling agent may be 1:1 to 1:50, and in some embodiments, 1:3 to 1:10. The reaction time may be 200-3000 seconds, and in some embodiments, 500-1500 seconds. The coupling agent may be selected from one or more of 1H-tetrazole, 5-ethylthio-1H-tetrazole and 5-benzylthio-1H-tetrazole, and in some embodiments, is 5-ethylthio-1H-tetrazole. The coupling reaction may be performed in an organic solvent. The organic solvent may be selected from one or more of anhydrous acetonitrile, anhydrous DMF and anhydrous dichloromethane, and in some embodiments, is anhydrous acetonitrile. The amount of the organic solvent may be 3-50 L/mol, and in some embodiments, 5-20 L/mol, with respect to the compound as shown by Formula (321).

In step (2), a sense strand S of the oligonucleotide conjugate is synthesized in 3' to 5' direction by the phosphoramidite solid phase synthesis method, starting from the nucleoside monomer linked to a solid phase support via a conjugating molecule prepared in the above steps. In this case, the conjugation group is linked to the 3' terminal of the resultant sense strand.

Other conditions for the solid phase synthesis in steps (2) and (3), including the deprotection condition for the nucleoside monomer, the type and amount of the deprotection agent, the coupling reaction condition, the type and amount of the coupling agent, the capping reaction condition, the type and amount of the capping agent, the oxidation reaction condition, the type and amount of the oxidation agent, the sulfurization reaction condition, and the type and amount of the sulfurization agent, adopt various conventional agents, amounts, and conditions in the art.

In some embodiments, for example, the solid phase synthesis in steps (2) and (3) can use the following conditions:

The deprotection condition for the nucleoside monomer comprises a reaction temperature of 0-50° C., and in some embodiments, 15-35° C., and a reaction time of 30-300 seconds, and in some embodiments, 50-150 seconds. The deprotection agent may be selected from one or more of trifluoroacetic acid, trichloroacetic acid, dichloroacetic acid, and monochloroacetic acid, and in some embodiments, is dichloroacetic acid. The molar ratio of the deprotection agent to the protecting group 4,4'-dimethoxytrityl on the solid phase support may be 2:1 to 100:1, and in some embodiments, is 3:1 to 50:1.

The coupling reaction condition comprises a reaction temperature of 0-50° C., and in some embodiments, 15-35° C. The molar ratio of the nucleic acid sequence linked to the solid phase support to the nucleoside monomer may be 1:1 to 1:50, and in some embodiments, is 1:5 to 1:15. The molar ratio of the nucleic acid sequence linked to the solid phase support to the coupling agent may be 1:1 to 1:100, and in some embodiments, is 1:50 to 1:80. The selection of the reaction time and the coupling agent can be same as above.

The capping reaction condition comprises a reaction temperature of 0-50° C., and in some embodiments, 15-35° C., and a reaction time of 5-500 seconds, and in some embodiments, 10-100 seconds. The selection of the capping agent can be same as above. The molar ratio of the total amount of the capping agent to the nucleic acid sequence linked to the solid phase support may be 1:100 to 100:1, and in some embodiments, is 1:10 to 10:1. In the case where the capping agent uses equimolar acetic anhydride and N-methylimidazole, the molar ratio of acetic anhydride, N-methylimidazole, and the nucleic acid sequence linked to the solid phase support may be 1:1:10-10:10:1, and in some embodiments, is 1:1:2-2:2:1.

The oxidation reaction condition comprises a reaction temperature of 0-50° C., and in some embodiments, 15-35° C., and a reaction time of 1-100 seconds, and in some embodiments, 5-50 seconds. In some embodiments, the oxidation agent is iodine (in some embodiments provided as iodine water). The molar ratio of the oxidation agent to the nucleic acid sequence linked to the solid phase support in the coupling step may be 1:1 to 100:1, and in some embodiments, is 5:1 to 50:1. In some embodiments, the oxidation reaction is performed in a mixed solvent in which the ratio of tetrahydrofuran:water:pyridine is 3:1:1-1:1:3. The sulfurization reaction condition comprises a reaction temperature of 0-50° C., and in some embodiments, 15-35° C., and a reaction time of 50-2000 seconds, and in some embodiments, 100-1000 seconds. In some embodiments, the sulfurization agent is xanthane hydride. The molar ratio of the sulfurization agent to the nucleic acid sequence linked to the solid phase support in the coupling step may be 10:1 to 1000:1, and in some embodiments, is 10:1 to 500:1. In some embodiments, the sulfurization reaction is performed in a mixed solvent in which the ratio of acetonitrile:pyridine is 1:3-3:1.

The method further comprises isolating the sense strand and the antisense strand of the double-stranded oligonucleotide after linking all nucleoside monomers and before the annealing. Methods for isolation are well-known to those skilled in the art and generally comprise cleaving the synthesized nucleotide sequence from the solid phase support, removing protecting groups on the bases, phosphate groups and ligands, purifying and desalting.

The conventional cleavage and deprotection methods in the synthesis of double-stranded oligonucleotides can be used to cleave the synthesized nucleotide sequence from the solid phase support, and remove the protecting groups on the bases, phosphate groups and ligands. For example, contacting the resultant nucleotide sequence linked to the solid phase support with concentrated aqueous ammonia; during deprotection, the protecting group $YCOO^-$ in groups A46-A54 is converted to a hydroxyl group, and thus the $S_1$ groups are converted to corresponding $M_1$ groups, providing the conjugate as shown by Formula (308); wherein the concentrated aqueous ammonia may be aqueous ammonia of a concentration of 25-30% by weight. The amount of the concentrated aqueous ammonia may be 0.2 ml/gmol-0.8 ml/μmol with respect to the target double-stranded oligonucleotide.

When there is at least one 2'-TBDMS protection on the synthesized nucleotide sequence, the method further comprises contacting the nucleotide sequence removed from the solid phase support with triethylamine trihydrofluoride to remove the 2'-TBDMS protection. Here, the resultant target double-stranded oligonucleotide comprises the corresponding nucleoside having free 2'-hydroxy. The amount of pure triethylamine trihydrofluoride may be 0.4 ml/gmol-1.0 ml/μmol with respect to the target double-stranded oligonucleotide. As such, the oligonucleotide conjugate as shown by Formula (308) may be obtained.

Methods for purification and desalination are well-known to those skilled in the art. For example, nucleic acid purification may be performed using a preparative ion chromatography purification column with a gradient elution of NaBr or NaCl; after collection and combination of the product, the desalination may be performed using a reverse phase chromatography purification column.

The non-bridging oxygen or sulfur atom in the phosphodiester bond or phosphorothioate diester bond between the nucleotides in the resultant oligonucleotide conjugate substantially binds to a sodium ion, and the oligonucleotide conjugate is substantially present in the form of a sodium salt. The well-known ion-exchange methods may be used, in which the sodium ion may be replaced with hydrogen ion and/or other cations, thereby providing other forms of oligonucleotide conjugates. The cations are as described above.

During synthesis, the purity and molecular weight of the nucleic acid sequence may be determined at any time, in order to better control the synthesis quality. Such determination methods are well-known to those skilled in the art. For example, the purity of the nucleic acid may be determined by ion exchange chromatography, and the molecular weight may be determined by liquid chromatography-mass spectrometry (LC-MS).

Methods for annealing are also well-known to those skilled in the art. For example, the synthesized sense strand (S strand) and antisense strand (AS strand) may be simply mixed in water for injection at an equimolar ratio, heated to 70-95° C., and then cooled at room temperature to form a double-stranded structure via hydrogen bond. Hence, the oligonucleotide conjugates of the present disclosure can be obtained.

After obtaining the conjugate of the present disclosure, in some embodiments, the oligonucleotide conjugate thus synthesized can also be characterized by the means such as molecular weight detection using the methods such as LC-MS, to confirm that the synthesized oligonucleotide conjugate is the designed oligonucleotide conjugate of interest, and the sequence of the synthesized double-stranded oligonucleotide is the sequence of the desired double-stranded oligonucleotide, for example, is one of the sequences as listed in Table 1.

The compound as shown by Formula (321) may be prepared by the following method comprising: contacting a compound as shown by Formula (313) with a cyclic anhydride in an organic solvent under esterification reaction condition in the presence of a base and an esterification catalyst; isolating the compound as shown by Formula (321) by ion exchange:

Formula (313)

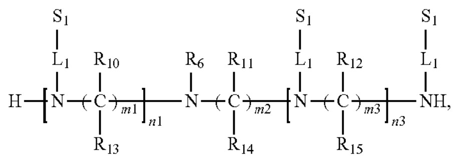

wherein the definitions and options of n1, n3, m1, m2, m3, $R_{10}$, $R_{11}$, $R_{12}$, $R_{13}$, $R_{14}$, $R_{15}$, $L_1$, $S_1$ are respectively as described above;

$R_6$ is a group for providing $R_4$ of Formula (321). In some embodiments, for example, $R_6$ has a structure as shown by Formula (A61):

(A61)

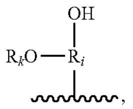

wherein, $R_i$ is any group capable of linking to the N atom on the nitrogenous backbone, linking to $R_kO$ and linking to a free hydroxy group; $R_k$ is a hydroxy protecting group. In this case, a compound as shown by Formula (321) is obtained, wherein $R_4$ comprises a first functional group as a hydroxy protecting group and a second functional group comprising a group as shown by Formula (C1) or (C2).

The esterification reaction condition includes a reaction temperature of 0-100° C. and a reaction time of 8-48 hours. In some embodiments, the esterification reaction condition comprises a reaction temperature of 10-40° C. and a reaction time of 20-30 hours.

In some embodiments, the organic solvent comprises one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in some embodiments, 5-20 L/mol, with respect to the compound as shown by Formula (313).

In some embodiments, the cyclic anhydride is one of succinic anhydride, glutaric anhydride, adipic anhydride or pimelic anhydride, and in some embodiments, the cyclic anhydride is succinic anhydride. The molar ratio of the cyclic anhydride to the compound as shown by Formula (313) is 1:1 to 10:1, and in some embodiments, 2:1 to 5:1.

The esterification catalyst may be any catalyst capable of catalyzing esterification, such as 4-dimethylaminopyridine. The molar ratio of the catalyst to the compound as shown by Formula (313) is 1:1 to 10:1, and in some embodiments, is 2:1 to 5:1.

In some embodiments, the base may be any inorganic base, organic base or combination thereof. Considering solubility and product stability, the base is an organic base of tertiary amine. In some embodiments, the organic base of tertiary amine is triethylamine or N,N-diisopropylethylamine. The molar ratio of the organic base of tertiary amine to the compound as shown by Formula (313) is 1:1 to 20:1, and in some embodiments, is 3:1 to 10:1.

The ion exchange serves the function of converting the compound as shown by Formula (321) into a desired form of carboxylic acid or carboxylic salt and the methods of ion exchange are well-known to those skilled in the art. The above conjugating molecule in which the cation is $M^+$ may be obtained by using suitable ion exchange solution and ion exchange condition, which is not described here in detail. In some embodiments, a triethylamine phosphate solution is used in the ion exchange reaction. In some embodiments, the concentration of the triethylamine phosphate solution is 0.2-0.8 M. In some embodiments, the concentration of the triethylamine phosphate solution is 0.4-0.6 M. In some embodiments, the amount of the triethylamine phosphate solution is 3-6 L/mol, and in further embodiment, 4-5 L/mol, with respect to the compound as shown by Formula (313).

The compound as shown by Formula (321) may be isolated from the reaction mixture using any suitable isolation methods. In some embodiments, the compound as shown by Formula (321) may be isolated by removal of solvent via evaporation followed by chromatography, for example, using the following chromatographic conditions for the isolation: (1) normal phase purification: 200-300 mesh silica gel filler, gradient elution of 1 wt % triethylamine in dichloromethane:methanol=100:18-100:20; or (2) reverse phase purification: C18 and C8 reverse phase filler, gradient elution of methanol:acetonitrile=0.1:1-1:0.1. In some embodiments, the solvent may be directly removed to obtain a crude product of the compound as shown by Formula (321), which may be directly used in subsequent reactions.

In some embodiments, the method for preparing the compound as shown by Formula (321) further comprises: contacting the product obtained from the above ion exchanging reaction with a solid phase support with amino or hydroxy groups in an organic solvent under condensation reaction condition in the presence of a condensing agent and an organic base of tertiary amine. In this case, a compound as shown by Formula (321) is obtained, wherein $R_4$ comprises a first functional group comprising a hydroxy protecting group and a second functional group having a structure as shown by Formula (C1').

The solid phase support is one of the supports used in solid phase synthesis of double-stranded oligonucleotides, some of which are well-known to those skilled in the art. For example, the solid phase support may be selected from the solid phase supports containing an active hydroxy or amino functional group. In some embodiments, the solid phase support is an amino or hydroxy resin. In some embodiments, the amino or hydroxy resin has the following parameters: particle size of 100-400 mesh, and surface amino or hydroxy loading of 0.2-0.5 mmol/g. The ratio of the compound as shown by Formula (321) to the solid phase support is 10 μmol compound per gram of solid phase support (μmol/g) to 400 μmol/g. In some embodiments, the ratio of compound of Formula (321) to the solid phase support is 50 μmol/g to 200 μmol/g.

The organic solvent may be any suitable solvent or mixed solvents known to those skilled in the art. In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran; the ether solvent is diethyl ether and/or methyl tertbutyl ether; the haloalkane solvent is one or more of dichloromethane, trichloromethane and 1,2-dichloroethane. In some embodiments, the organic solvent is acetonitrile. The amount of the organic solvent is 20-200 L/mol, in some embodiments, 50-100 L/mol, with respect to the compound as shown by Formula (321).

In some embodiments, the condensing agent may be benzotriazol-1-yl-oxytripyrrolidinophosphonium hexafluorophosphate, 3-diethoxyphosphoryl-1,2,3-benzotrizin-4 (3H)-one and/or O-benzotriazol-tetramethyluronium hexafluorophosphate. In some embodiments, the condensing agent is O-benzotriazol-tetramethyluronium hexafluorophosphate. The molar ratio of the condensing agent to the compound as shown by Formula (321) is 1:1 to 20:1, and in further embodiments, 1:1 to 5:1.

In some embodiments, the organic base of tertiary amine is triethylamine and/or N,N-diisopropylethylamine, and in some embodiments, N,N-diisopropylethylamine. The molar ratio of the organic base of tertiary amine to the compound as shown by Formula (321) is 1:1 to 20:1, and in some embodiments, 1:1 to 5:1.

In some embodiments, the method for preparing the compound as shown by Formula (321) further comprises: contacting the resultant condensation product with a capping agent and an acylation catalyst in an organic solvent under capping reaction condition, and isolating the compound as shown by Formula (321). The capping reaction is used to remove any active functional group that does not completely react, so as to avoid producing unnecessary by-products in subsequent reactions. The capping reaction condition comprises a reaction temperature of 0-50° C., and in some embodiments, 15-35° C., and a reaction time of 1-10 hours, and in some embodiments, 3-6 hours. The capping agent may be a capping agent used in solid phase synthesis of a nucleic acid, which is well known to those skilled in the art.

In some embodiments, the capping agent is composed of capping agent A (capA) and capping agent B (capB). The capA is N-methylimidazole, and in some embodiments, provided as a mixed solution of N-methylimidazole in pyridine/acetonitrile, wherein the volume ratio of pyridine to acetonitrile is 1:10 to 1:1, and in some embodiments, 1:3 to 1:1. In some embodiments, the ratio of the total volume of pyridine and acetonitrile to the volume of N-methylimidazole is 1:1 to 10:1, and in some embodiments, 3:1 to 7:1. In some embodiments, the capB is acetic anhydride. In some embodiments, the capB is provided as a solution of acetic anhydride in acetonitrile, wherein the volume ratio of acetic anhydride to acetonitrile is 1:1 to 1:10, and in further embodiments, 1:2 to 1:6.

In some embodiments, the ratio of the volume of the mixed solution of N-methylimidazole in pyridine/acetonitrile to the mass of the compound of Formula (321) is 5 ml/g-50 ml/g, and in some embodiments, 15 ml/g-30 ml/g. The ratio of the volume of the solution of acetic anhydride in acetonitrile to the mass of the compound of Formula (321) is 0.5 ml/g-10 ml/g, and in some embodiments, 1 ml/g-5 ml/g.

In some embodiments, the capping agent comprises equimolar acetic anhydride and N-methylimidazole. In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the organic solvent is acetonitrile. In some embodiments, the amount of the organic solvent is 10-50 L/mol, and in some embodiments, 5-30 L/mol, with respect to the compound as shown by Formula (321).

In some embodiments, the acylation catalyst may be selected from any catalyst that may be used for esterification condensation or amidation condensation, such as alkaline heterocyclic compounds. In some embodiments, the acylation catalyst is 4-dimethylaminopyridine. The mass ratio of the catalyst to the compound as shown by Formula (321) may be 0.001:1 to 1:1, and in some embodiments, 0.01:1 to 0.1:1.

In some embodiments, the compound as shown by Formula (321) may be isolated from the reaction mixture by any suitable methods. In some embodiments, the compound of Formula (321) may be obtained by thoroughly washing with an organic solvent and filtering to remove unreacted reactants, excess capping agent and other impurities, wherein the organic solvent is selected from acetonitrile, dichloromethane, or methanol. In some embodiments, the organic solvent is acetonitrile.

In some embodiments, the preparation of the conjugating molecule as shown by Formula (321) comprises contacting a compound as shown by Formula (313) with a phosphorodiamidite in an organic solvent under coupling reaction condition in the presence of a coupling agent, and isolating the compound as shown by Formula (321). In this case, a compound as shown by Formula (321) is obtained, where $R_4$ comprises a first functional group comprising a hydroxy protecting group and a second functional group having a structure as shown by Formula (C3).

In some embodiments, the coupling reaction condition comprises a reaction temperature of 0-50° C., such as 15-35° C. The molar ratio of the compound of Formula (313) to the phosphorodiamidite may be 1:1 to 1:50, such as 1:5 to 1:15. The molar ratio of the compound of Formula (313) to the coupling agent may be 1:1 to 1:100, such as 1:50 to 1:80. The reaction time may be 200-3000 seconds, such as 500-1500 seconds. The phosphorodiamidite may be, for example, bis(diisopropylamino)(2-cyanoethoxy)phosphine, which may be commercially available or synthesized according to well-known methods in the art. The coupling agent is selected from one or more of 1H-tetrazole, 5-ethylthio-1H-tetrazole and 5-benzylthio-1H-tetrazole, such as 5-ethylthio-1H-tetrazole. The coupling reaction may be performed in an organic solvent. In some embodiments, the organic solvent is selected from one or more of anhydrous acetonitrile, anhydrous DMF and anhydrous dichloromethane, such as anhydrous acetonitrile. The amount of the organic solvent may be 3-50 L/mol, such as 5-20 L/mol, with respect to the compound as shown by Formula (313). By performing the coupling reaction, the hydroxy group in the compound (313) reacts with the phosphorodiamidite to form a phosphoramidite group. In some embodiments, the solvent may be directly removed to obtain a crude product of the compound as shown by Formula (321), which may be directly used in subsequent reactions.

In some embodiments, the method for preparing the compound as shown by Formula (321) further comprises: contacting the isolated product with a solid phase support with hydroxy groups in an organic solvent under coupling reaction condition in the presence of a coupling agent, followed by capping, oxidation, and isolation, to obtain the compound as shown by Formula (321), where $R_4$ a first functional group comprising a hydroxy protecting group and a second functional group having a structure as shown by Formula (C3').

In some embodiments, the solid phase support is a well-known support in the art for solid phase synthesis of a nucleic acid, such as a deprotected commercially available universal solid phase support, such as NittoPhase®HL UnyLinker™ 300 Oligonucleotide Synthesis Support, Kinovate Life Sciences, as shown by Formula B80:

(B80)

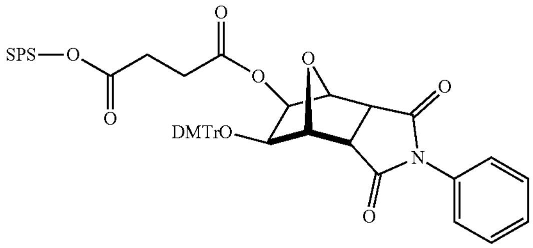

A deprotection reaction is well-known in the art. In some embodiments, the deprotection condition comprises a temperature of 0-50° C., such as 15-35° C., and a reaction time of 30-300 seconds, such as 50-150 seconds. The deprotection agent may be selected from one or more of trifluoroacetic acid, trichloroacetic acid, dichloroacetic acid, and monochloroacetic acid. In some embodiments, the deprotection agent is dichloroacetic acid. The molar ratio of the deprotection agent to the protecting group -DMTr (4,4'-dimethoxytrityl) on the solid phase support may be 2:1 to 100:1, such as 3:1 to 50:1. By such deprotection, reactive free hydroxy groups are obtained on the surface of the solid phase support, for facilitating the subsequent coupling reaction.

The coupling reaction condition and the coupling agent may be selected as above. By such a coupling reaction, the free hydroxy groups formed in the deprotection reaction reacts with the phosphoramidite groups, so as to form a phosphite ester linkage.

In some embodiments, the capping reaction condition comprises a temperature of 0-50° C., such as 15-35° C., and a reaction time of 5-500 seconds, such as 10-100 seconds. The capping reaction is performed in the presence of a capping agent. The selection and amount of the capping agent are as above.

The oxidation reaction condition may comprise a temperature of 0-50° C., such as 15-35° C., and a reaction time of 1-100 seconds, such as 5-50 seconds. The oxidation agent may be, for example, iodine (in some embodiments, provided as iodine water). In some embodiments, the molar ratio of the oxidation agent to the phosphite ester group is 1:1 to 100:1, preferably 5:1 to 50:1. In some embodiments, the oxidation reaction is performed in a mixed solvent in which the ratio of tetrahydrofuran:water:pyridine is 3:1:1-1:1:3.

In some embodiments, $R_6$ is B7 or B8:

(B7)

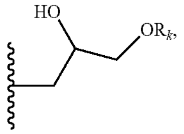

-continued (B8)

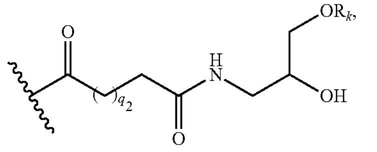

wherein $q_2$ is as defined above.

In this case, the compound shown in the Formula (313) may be prepared by the following preparation method comprising: contacting the compound as shown by Formula (314) with a compound as shown by Formula (A-1) or (A-2) in an organic solvent under amidation reaction condition in the presence of an agent for amidation condensation and an organic base of tertiary amine, and isolating:

Formula (314)

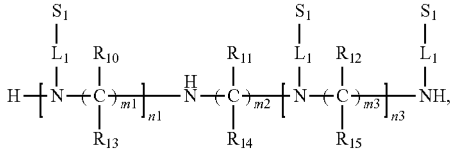

(A-1)

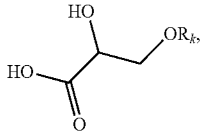

(A-2)

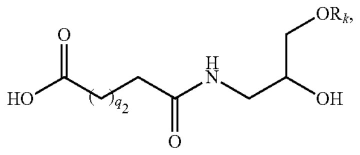

wherein the definitions and options of n1, n3, m1, m2, m3, $R_{10}$, $R_{11}$, $R_{12}$, $R_{13}$, $R_{14}$, $R_{15}$, $L_1$, $S_1$, $q_2$ and $R_k$ are respectively as described above.

The amidation reaction condition may comprise a reaction temperature of 0-100° C. and a reaction time of 1-48 hours. In some embodiments, the amidation reaction condition comprises a reaction temperature of 10-40° C. and a reaction time of 2-16 hours.

In some embodiments, the organic solvent is one or more of an alcohol solvent, an epoxy solvent, an ether solvent, an haloalkane solvent, dimethyl sulfoxide, N,N-dimethylformamide, and N,N-diisopropylethylamine. In some embodiments, the alcohol solvent is one or more of methanol, ethanol and propanol, and in further embodiments, ethanol. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in further embodiments, 3-20 L/mol, with respect to the compound as shown by Formula (314).

In some embodiments, the agent for amidation condensation is benzotriazol-1-yl-oxytripyrrolidinophosphonium hexafluorophosphate, 3-(diethoxyphosphoryloxy)-1,2,3-benzotrizin-4(3H)-one, 4-(4,6-dimethoxytriazin-2-yl)-4- methylmorpholine hydrochloride, 2-ethoxy-1-ethoxycarbonyl-1,2-dihydroquinoline (EEDQ) or O-benzotriazol-tetramethyluronium hexafluorophosphate, and in further embodiments, 3-(diethoxyphosphoryloxy)-1,2,3-benzotrizin-4(3H)-one. The molar ratio of the agent for amidation condensation to the compound as shown by Formula (314) may be 1:1 to 10:1, and in some embodiments, 2.5:1 to 5:1.

In some embodiments, the organic base of tertiary amine is triethylamine or N,N-diisopropylethylamine, and in further embodiments, N,N-diisopropylethylamine. The molar ratio of the tertiary amine to the compound as shown by Formula (314) may be 3:1 to 20:1, and in some embodiments, 5:1 to 10:1.

In some embodiments, the compounds of Formula (A-1) and (A-2) may be prepared by any suitable methods. For example, when $R_k$ is a DMTr group, the compound of Formula (A-1) may be prepared by reacting calcium glycerate with DMTrCl. Similarly, the compound of Formula (A-2) may be prepared by contacting 3-amino-1,2-propanediol with a cyclic anhydride and then reacting with DMTrCl, wherein the cyclic anhydride may have 4-13 carbon atoms, and in some embodiments, 4-8 carbon atoms. Those skilled in the art would readily understand that the selections of different cyclic anhydrides correspond to different values for $q_2$ in the compound of Formula (A-2). For example, when the cyclic anhydride is succinic anhydride, $q_2=1$; when the cyclic anhydride is glutaric anhydride, $q_2=2$, and so on.

In some variants, the compound of Formula (313) can also be prepared by successively reacting the compound as shown by Formula (314) with the cyclic anhydride, 3-amino-1,2-propanediol, and DMTrCl. Those skilled in the art would readily understand that these variants would not affect the structure and function of the compound of Formula (313), and these variants can be readily achieved by those skilled in the art on the basis of the above methods.

Similarly, the compound as shown by Formula (313) may be isolated from the reaction mixture by any suitable isolation methods. In some embodiments, the compound as shown by Formula (313) may be isolated by removal of solvent via evaporation followed by chromatography, for example, using the following two sets of chromatographic conditions for isolation: (1) normal phase purification: 200-300 mesh silica gel filler, gradient elution of petroleum ether:ethyl acetate:dichloromethane: N,N-dimethylformamide=1:1:1:0.5-1:1:1:0.6; and (2) reverse phase purification: C18 and C8 reverse phase fillers, gradient elution of methanol: acetonitrile=0.1:1-1:0.1. In some embodiments, the solvent may be directly removed to obtain a crude product of the compound as shown by Formula (313), which may be directly used in subsequent reactions.

In some embodiments, the compound as shown by Formula (314) may be prepared by the following preparation method comprising contacting the compound as shown by Formula (315) with haloacetic acid in an organic solvent under deprotection reaction condition, and then isolating:

Formula (315)

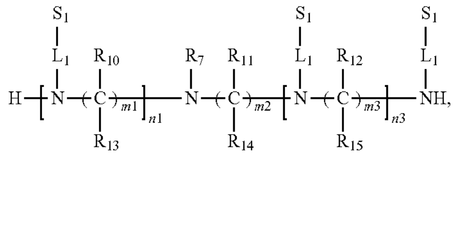

wherein $R_7$ is selected from the groups as shown by Formula (330), (331), (332) and (333), and in some embodiments, $R_7$ has the structure as shown by Formula (330):

(330)

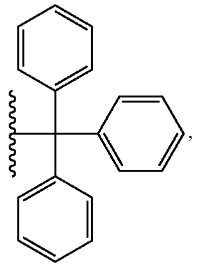

(331)

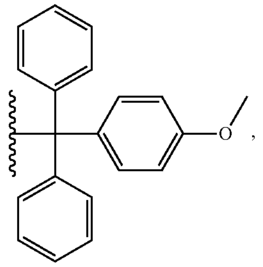

(332)

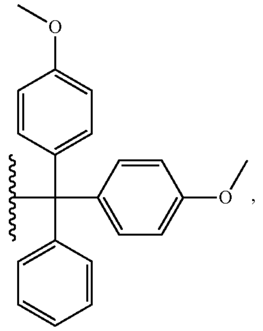

(333)

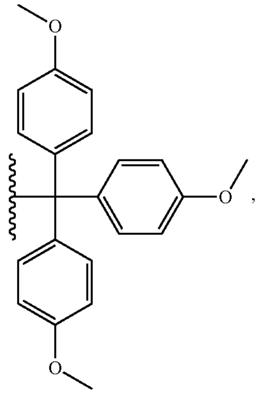

wherein the definitions and options of n1, n3, m1, m2, m3, $R_{10}$, $R_{11}$, $R_{12}$, $R_{13}$, $R_{14}$, $R_{15}$, $L_1$ and $S_1$ are respectively as described above.

The haloacetic acid may be selected from one or more of dichloroacetic acid, trichloroacetic acid, monochloroacetic acid and trifluoroacetic acid, and in some embodiments, dichloroacetic acid.

The deprotection reaction condition may comprise a reaction temperature of 0-100° C. and a reaction time of 0.1-24 hours, and in some embodiments comprises a reaction temperature of 10-40° C. and a reaction time of 0.5-16 hours.

In some embodiments, the organic solvent is one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in further embodiments, 5-20 L/mol, with respect to the compound as shown by Formula (315).

The molar ratio of the haloacetic acid to the compound as shown by Formula (315) may be 5:1 to 100:1, and in some embodiments, 10:1 to 50:1.

Similarly, the compound as shown by Formula (314) may be isolated from the reaction mixture by any suitable isolation methods. In some embodiments, the compound as shown by Formula (314) may be isolated by removal of solvent via evaporation followed by chromatography, for example, using the following two sets of chromatographic conditions for isolation, (1) normal phase purification: 200-300 mesh silica gel filler, gradient elution of dichloromethane:methanol=100:30-100:40; and (2) reverse phase purification: C18 and C8 reverse phase fillers, gradient elution of methanol: acetonitrile=0.1:1-1:0.1. In some embodiments, the solvent may be directly removed to obtain a crude product of the compound as shown by Formula (314), which may be directly used in subsequent reactions.

The compound as shown by Formula (315) may be prepared by the following method comprising contacting the compound as shown by Formula (317) with the compound as shown by Formula (316) in an organic solvent under condensation reaction condition in the presence of an agent for amidation condensation and an organic base of tertiary amine, and isolating:

Formula (316)

$$S_1—L_1—COOH$$

Formula (317)

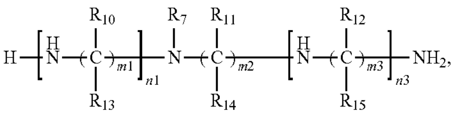

wherein the definitions and options of n1, n3, m1, m2, m3, $R_7$, $R_{10}$, $R_{11}$, $R_{12}$, $R_{13}$, $R_{14}$, $R_{15}$, $L_1$ and $S_1$ are respectively as described above.

The compound of Formula (316) can be, such as, those disclosed in J. Am. Chem. Soc. 2014, 136, 16958-16961. Alternatively, the compounds of Formula (316) may be prepared by those skilled in the art via various methods. For example, some compounds of Formula (316) may be prepared according to the methods as disclosed in Example 1 of U.S. Pat. No. 8,106,022 B2, which is incorporated herein by reference in its entirety.

In some embodiments, the condensation reaction condition comprises a reaction temperature of 0-100° C. and a reaction time of 0.1-24 hours. In some embodiments, the condensation reaction condition comprises a reaction temperature is 10-40° C. and a reaction time is 0.5-16 hours.

The molar ratio of the compound as shown by Formula (316) to the compound as shown by Formula (317) may be 2:1 to 10:1, and in some embodiments, 2.5:1 to 5:1.

In some embodiments, the organic solvent is one or more of acetonitrile, an epoxy solvent, an ether solvent, an haloalkane solvent, dimethyl sulfoxide, N,N-dimethylformamide and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is acetonitrile. The amount of the organic solvent may be 3-50 L/mol, and in some embodiments, 5-20 L/mol, with respect to the compound as shown by Formula (317).

In some embodiments, the agent for amidation condensation is benzotriazol-1-yl-oxytripyrrolidinophosphonium hexafluorophosphate, 3-(diethoxyphosphoryloxy)-1,2,3-benzotrizin-4(3H)-one (DEPBT), O-benzotriazol-tetramethyluronium hexafluorophosphate or 4-(4,6-dimethoxytriazin-2-yl)-4-methylmorpholine hydrochloride, and in further embodiments, is 4-(4,6-dimethoxytriazin-2-yl)-4-methylmorpholine hydrochloride. The molar ratio of the agent for amidation condensation to the compound as shown by Formula (317) may be 2:1 to 10:1, and in some embodiments, is 2.5:1 to 5:1.

The organic base of tertiary amine may be N-methylmorpholine, triethylamine or N,N-diisopropylethylamine, and in some embodiments, N-methylmorpholine. The molar ratio of the tertiary amine to the compound as shown by Formula (317) may be 3:1 to 20:1, and in some embodiments, is 5:1 to 10:1.

Similarly, the compound as shown by Formula (315) may be isolated from the reaction mixture by any suitable isolation methods. In some embodiments, the compound as shown by Formula (315) is isolated by removal of solvent via evaporation followed by chromatography, for example, using the following two sets of chromatographic conditions for isolation, (1) normal phase purification: 200-300 mesh silica gel filler, gradient elution of dichloromethane:methanol=100:5-100:7; (2) reverse phase purification: C18 and C8 reverse phase fillers, gradient elution of methanol: acetonitrile=0.1:1-1:0.1. In some embodiments, the solvent is directly removed to obtain a crude product of the compound as shown by Formula (315), which may be directly used in subsequent reactions.

In some embodiments, the compound of Formula (317) reacts with a sufficient amount of one compound of Formula (316) in one batch to obtain the desired compound of Formula (315), wherein all $S_1$-$L_1$ moieties are identical. In some embodiments, the compound of Formula (317) reacts with different compounds of Formula (316) in batches as desired, i.e., the compounds of Formula (316) having different $L_1$ and/or $S_1$, so as to obtain the compound of Formula (315) having two or more types of $S_1$ and/or $L_1$ therein. For example, 1 eq of the compound of Formula (317) may be firstly contacted with 2 eq of a first compound of Formula (316) to attach the first $S_1$-$L_1$ moieties to the two terminal primary amine groups in the compound of Formula (317), and then contacted with the (n3+n1−1) eq of a second compound of Formula (316) to attach the second $S_1$-$L_1$ moieties to the (n3+n1−1) secondary amine groups in the compound of Formula (317), wherein the definitions and ranges of n3 and n1 are as described above.

In some embodiments, the compound as shown by Formula (317) may be prepared by the following method comprising contacting the compound as shown by Formula (318) with aqueous methylamine solution under deprotection reaction condition in the presence of an organic solvent, and isolating:

Formula (318)

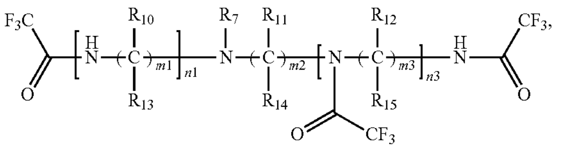

wherein the definitions and options of n1, n3, m1, m2, m3, $R_7$, $R_{10}$, $R_{11}$, $R_{12}$, $R_{13}$, $R_{14}$ and $R_{15}$ are respectively as described above.

The deprotection reaction condition may comprise a reaction temperature of 0-150° C. and a reaction time of 5-72 hours, and in some embodiments comprises a reaction temperature of 20-80° C. and a reaction time of 10-30 hours.

The organic solvent may be selected from alcohols, in some embodiments, is one of methanol, ethanol and isopropanol, and in some embodiments, methanol. The amount of the organic solvent may be 1-20 L/mol, and in some embodiments, is 1.5-10 L/mol, with respect to the compound as shown by Formula (318).

The concentration of the methylamine aqueous solution may be 30%-40% by mass, and the molar ratio of methylamine to the compound as shown by Formula (318) may be 10:1 to 500:1, and in some embodiments, 50:1 to 200:1.

Similarly, the compound as shown by Formula (317) may be isolated from the reaction mixture using any suitable isolation methods. In some embodiments, the compound as shown by Formula (317) may be isolated by removal of solvent via evaporation followed by chromatography, for example, using the following two sets of chromatographic conditions for isolation, (1) normal phase purification: 200-300 mesh silica gel filler, gradient elution of dichloromethane:methanol:aqueous ammonia (25 wt %)=1:1:0.05-1:1:0.25; and (2) reverse phase purification: C18 and C8 reverse phase fillers, gradient elution of methanol: acetonitrile=0.1:1-1:0.1. In some embodiments, the solvent may be directly removed to obtain a crude product of the compound as shown by Formula (317), which may be directly used in subsequent reactions.

The compound as shown by Formula (318) may be prepared by the following method comprising contacting the compound as shown by Formula (319) with triphenylchloromethane (TrCl), diphenylethylphenylchloromethane, phenyldiethylphenylchloromethane or triethylphenylchloromethane (in some embodiments, with triphenylchloromethane (TrCl)) under substitution reaction condition in the presence of an organic solvent, and isolating:

Formula (319)

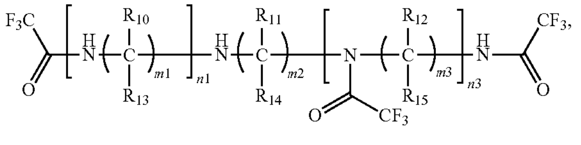

wherein the definitions and options of n1, n3, m1, m2, m3, $R_{10}$, $R_{11}$, $R_{12}$, $R_{13}$, $R_{14}$ and $R_{15}$ are respectively as described above.

The substitution reaction condition may comprise a reaction temperature of 0-100° C. and a reaction time of 5-72 hours, and in some embodiments comprises a reaction temperature of 10-40° C. and a reaction time of 10-30 hours.

Triphenylchloromethane (TrCl), diphenylethylphenylchloromethane, phenyldiethylphenylchloromethane or triethylphenylchloromethane are commercially available. The molar ratio of triphenylchloromethane (TrCl), diphenylethylphenylchloromethane, phenyldiethylphenylchloromethane or triethylphenylchloromethane to the compound as shown by Formula (319) may be 1:1 to 10:1, and in some embodiments, 1:1 to 3:1.

The organic solvent may be one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is dichloromethane. The amount of the organic solvent may be 3-50 L/mol, and in some embodiments, 5-20 L/mol, with respect to the compound as shown by Formula (319).

Similarly, the compound as shown by Formula (318) may be isolated from the reaction mixture by any suitable isolation methods. In some embodiments, the compound as shown by Formula (318) may be isolated by removal of solvent via evaporation followed by chromatography, for example, using the following two sets of chromatographic conditions for isolation, (1) normal phase purification: 200-300 mesh silica gel filler, gradient elution of methanol: dichloromethane=0.01:1-0.5:1 or gradient elution of methanol:dichloromethane:ethyl acetate:petroleum ether=0.1:1:1:1-1:1:1:1; and (2) reverse phase purification: C18 and C8 reverse phase fillers, gradient elution of methanol: acetonitrile=0.1:1-1:0.1. In some embodiments, the solvent may be directly removed to obtain a crude product of the compound as shown by Formula (318), which may be directly used in subsequent reactions.

In some embodiments, the compound as shown by Formula (319) may be prepared by the following method comprising contacting the compound as shown by Formula (320) with ethyl trifluoroacetate in an organic solvent under substitution reaction condition, and isolating:

Formula (320)

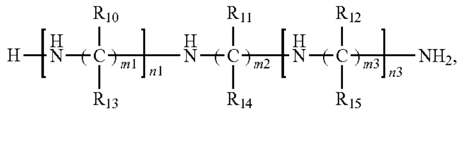

wherein the definitions and options of n1, n3, m1, m2, m3, $R_{10}$, $R_{11}$, $R_{12}$, $R_{13}$, $R_{14}$ and $R_{15}$ are respectively as described above.

In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is acetonitrile. The amount of the organic solvent may be 1-50 L/mol, and in some embodiments, 1-20 L/mol, with respect to the compound as shown by Formula (320).

The substitution reaction condition may comprise a reaction temperature of 0-100° C. and a reaction time of 5-72 hours, and in some embodiments comprises a reaction temperature of 10-40° C. and a reaction time of 10-30 hours.

The compound as shown by Formula (320) may be commercially available, or obtained by those skilled in the art via the known methods. For example, in the case that m1=m2=m3=3, n1=1, n3=2, and $R_{10}$, $R_{11}$, $R_{12}$, $R_{13}$, $R_{14}$ and $R_{15}$ are all H, the compound as shown by Formula (320) is commercially available from Alfa Aesar Inc.

The molar ratio of ethyl trifluoroacetate to the compound as shown by Formula (320) may be 2:1 to 10:1, and in some embodiments, 3:1 to 5:1.

Similarly, the compound as shown by Formula (319) may be isolated from the reaction mixture using any suitable isolation methods. In some embodiments, the compound as shown by Formula (319) may be isolated by removal of solvent via evaporation followed by chromatography, for example, using the following two sets of chromatographic conditions for isolation: (1) normal phase purification: 200-300 mesh silica gel filler, gradient elution of methanol: dichloromethane=0.01:1-0.5:1 or gradient elution of methanol: dichloromethane:ethyl acetate:petroleum ether=0.1:1:1:1-1:1:1:1; and (2) reverse phase purification: C18 and C8 reverse phase fillers, gradient elution of methanol: acetonitrile=0.1:1-1:0.1. In some embodiments, the solvent may be directly removed to obtain a crude product of the compound as shown by Formula (319), which may be directly used in subsequent reactions.

The oligonucleotide conjugate of the present disclosure may also be used in combination with other pharmaceutically acceptable excipients, which may be one or more of the various conventional formulations or compounds in the art. For details, please refer to the above description of the pharmaceutical compositions of the present disclosure.

Use of the Double-Stranded Oligonucleotide, Pharmaceutical Composition and Oligonucleotide Conjugate of the Present Disclosure In some embodiments, the present disclosure provides use of the double-stranded oligonucleotide, pharmaceutical composition and/or oligonucleotide conjugate of the present disclosure in the manufacture of a medicament for treating and/or preventing pathological conditions or diseases caused by the expression of specific genes in cells. In some embodiments, the specific gene may be a gene abnormally expressed in hepatocytes. In some embodiments, the specific gene may be an endogenous gene expressed in liver. In some embodiments, the specific gene may be the gene of a pathogen reproduced in liver. In some embodiments, the specific gene is selected from the gene ApoB, ApoC, ANGPTL3, PCSK9, SCD1, TIMP-1, Col1A1, FVII, STAT3, p53, HBV and HCV. In some embodiments, the specific gene is selected from the gene of hepatitis B virus, the gene of angiopoietin-like protein 3, and the gene of apolipoprotein C3. Correspondingly, the diseases are selected from chronic liver disease, hepatitis, hepatic fibrosis, liver proliferative diseases and dyslipidemia. In some embodiments, the dyslipidemia is hypercholesterolemia, hypertriglyceridemia, or atherosclerosis.

In some embodiments, the present disclosure provides a method for treating pathological conditions or diseases caused by abnormal expression of specific genes, comprising administering an effective amount of the double-stranded oligonucleotides, pharmaceutical compositions and/or oligonucleotide conjugates of the present disclosure to a subject in need thereof. In some embodiments, the specific gene is selected from the gene ApoB, ApoC, ANGPTL3, PCSK9, SCD1, TIMP-1, Col1A1, FVII, STAT3, p53, HBV and HCV. In some embodiments, the specific gene is selected from the gene of hepatitis B virus, the gene of angiopoietin-like protein 3, and the gene of apolipoprotein C3. Correspondingly, the diseases are selected from chronic liver disease, hepatitis, hepatic fibrosis, liver proliferative diseases and dyslipidemia. In some embodiments, the dyslipidemia is hypercholesterolemia, hypertriglyceridemia or atherosclerosis. In some embodiments, the conjugate provided by the present disclosure may also be used to treat other liver diseases, including diseases characterized by undesired cell proliferation, blood diseases, metabolic diseases, and diseases characterized by inflammation. Proliferative diseases of liver may be benign or malignant diseases such as cancer, hepatocellular carcinoma (HCC), hepatic metastasis or hepatoblastoma. Liver hematology or inflammatory diseases may be diseases that involve coagulation factors, complement-mediated inflammation or fibrosis. Liver metabolic diseases include dyslipidemia and irregular glucose regulation. In some embodiments, the method comprises administering one or more double-stranded oligonucleotides having a high degree of homology to the gene sequences involved in the diseases.

In some embodiments, the present disclosure provides a method for inhibiting the expression of specific genes in cells, comprising contacting an effective amount of the double-stranded oligonucleotide, pharmaceutical composition and/or oligonucleotide conjugate of the present disclosure with the cells.

The purpose of preventing and/or treating pathological conditions or diseases caused by the expression of specific genes in cells may be achieved through the mechanism of regulating gene expression by administering the double-stranded oligonucleotide, pharmaceutical composition and/or oligonucleotide conjugate of the present disclosure to a subject in need thereof. Therefore, the double-stranded oligonucleotide, pharmaceutical composition and/or oligonucleotide conjugate of the present disclosure may be used for preventing and/or treating the pathological conditions or diseases of the present disclosure, or for preparing a medicament for preventing and/or treating the pathological conditions or diseases of the present disclosure.

As used herein, the term "administration/administer" refers to the delivery of the double-stranded oligonucleotide, pharmaceutical composition and/or oligonucleotide conjugate into a subject's body by a method or a route that at least partly locates the double-stranded oligonucleotide, pharmaceutical composition and/or oligonucleotide conjugate at a desired site to produce a desired effect. Suitable administration routes for the methods of the present disclosure include topical administration and systemic administration. In general, topical administration results in the delivery of more double-stranded oligonucleotides, pharmaceutical compositions and/or oligonucleotide conjugates to a particular site compared with the whole body of the subject; whereas systemic administration results in the delivery of the double-stranded oligonucleotides, pharmaceutical compositions and/or oligonucleotide conjugates to substantially the whole body of the subject. Considering that the present disclosure aims to provide a means for preventing and/or treating pathological conditions or diseases caused by the expression of specific genes in hepatocytes, in some embodiments, an administration mode capable of delivering drugs to liver is used.

The administration to a subject may be achieved by any suitable routes known in the art, including but not limited to, oral or parenteral route, such as intravenous administration, intramuscular administration, subcutaneous administration, transdermal administration, intratracheal administration (aerosol), pulmonary administration, nasal administration, rectal administration and topical administration (including buccal administration and sublingual administration). The administration frequency may be once or more times daily, weekly, biweekly, triweekly, monthly, or yearly.

The dose of the double-stranded oligonucleotide, pharmaceutical composition and/or oligonucleotide conjugate of the present disclosure may be a conventional dose in the art, which may be determined according to various parameters, especially age, weight and gender of a subject. Toxicity and efficacy may be measured in cell cultures or experimental animals by standard pharmaceutical procedures, for example, by determining LD50 (the lethal dose that causes 50% population death) and ED50 (the dose that can cause 50% of the maximum response intensity in a quantitative response, and that causes 50% of the experimental subjects to have a positive response in a qualitative response). The dose range for human may be derived based on the data obtained from cell culture assays and animal studies.

When administering the double-stranded oligonucleotide, pharmaceutical composition and/or oligonucleotide conjugate of the present disclosure, for example, to male or female C57BL/6J or C3H/HeNCrlVr mice of 6-12 weeks old and 18-25 g body weight, for an oligonucleotide conjugate formed by a double-stranded oligonucleotide and pharmaceutically acceptable conjugating molecules, the amount of the double-stranded oligonucleotide may be 0.001-100 mg/kg body weight, in some embodiments 0.01-50 mg/kg body weight, in further embodiments 0.05-20 mg/kg body weight, in still further embodiments 0.1-15 mg/kg body weight, and in still yet further embodiments 0.1-10 mg/kg body weight, as calculated based on the amount of the double-stranded oligonucleotide in the double-stranded oligonucleotide, pharmaceutical composition and/or oligonucleotide conjugate. When administering the double-stranded oligonucleotide, pharmaceutical composition and/or oligonucleotide conjugate of the present disclosure, the above amounts are preferred.

In addition, the purpose of inhibiting the expression of specific genes in hepatocytes may also be achieved through the mechanism of regulating gene expression by introducing the double-stranded oligonucleotide, pharmaceutical composition and/or oligonucleotide conjugate of the present disclosure into the hepatocytes with abnormal expression of the specific genes. In some embodiments, the hepatocytes are hepatitis cells, and in some embodiments are HepG2.2.15 cells. In some embodiments, the hepatocytes may be selected from hepatoma cell lines such as Hep3B, HepG2 or Huh7, and isolated liver primary cells, and in some embodiments are Huh7 hepatoma cells.

In the case where the expression of specific genes in hepatocytes is inhibited by using the method of the present disclosure, the amount of the double-stranded oligonucleotide in the provided double-stranded oligonucleotide, pharmaceutical composition and/or oligonucleotide conjugate can be readily determined by those skilled in the art according to the desired effects. For example, in some embodiments where the double-stranded oligonucleotide, pharmaceutical composition and/or oligonucleotide conjugate is an siRNA conjugate, the amount of siRNA in the siRNA conjugate provided is an amount sufficient to reduce the expression of the target gene and result in an extracellular concentration of 1 pM to 1 μM, or 0.01 nM to 100 nM, or 0.05 nM to 50 nM or 0.05 nM to about 5 nM on the surface of the target cells. The amount required to achieve this local concentration will vary with various factors, including the delivery method, the delivery site, the number of cell layers between the delivery site and the target cells or tissues, the delivery route (topical or systemic), etc. The concentration at the delivery site may be significantly higher than that on the surface of the target cells or tissues.

Kit

In another aspect, the present disclosure provides a kit comprising the above double-stranded oligonucleotide, the above pharmaceutical composition and/or the above oligonucleotide conjugate.

In some embodiments, the kit of the present disclosure provides the double-stranded oligonucleotide in one container. In some embodiments, the kit of the present disclosure comprises a container comprising pharmaceutically acceptable excipients. In some embodiments, the k is of the present disclosure further comprises additional ingredients, such as stabilizers or preservatives. In some embodiments, the kit comprises at least one additional therapeutic agent in other container than the container comprising the double-stranded oligonucleotide of the present disclosure. In some embodiments, the kit comprises an instruction for mixing the double-stranded oligonucleotide with pharmaceutically acceptable carriers and/or adjuvants or other ingredients (if any).

In a kit of the present disclosure, the double-stranded oligonucleotides and the pharmaceutically acceptable carriers and/or adjuvants, the compositions and/or conjugates comprising said double-stranded oligonucleotides, and/or the pharmaceutically acceptable adjuvants may be provided in any form, e.g., in a liquid form, a dry form, or a lyophilized form. In some embodiments, the double-stranded oligonucleotides and the pharmaceutically acceptable carriers and/or adjuvants, the compositions and/or conjugates comprising said double-stranded oligonucleotides, and optional pharmaceutically acceptable adjuvants are substantially pure and/or sterile. In some embodiments, sterile water may be provided in the kit of the present disclosure.

Hereinafter, the present disclosure will be further illustrated with reference to the examples, but is not limited thereto.

Without wishing to be limited, the invention is described in further details in the following embodiments and the Examples regarding the exemplary embodiments where the double-stranded oligonucleotide in the compositions and/or oligonucleotide conjugates of the present disclosure is a small interfering RNA (siRNA). In this case, the double-stranded oligonucleotide, composition, and oligonucleotide conjugate of the present disclosure are an siRNA, a composition comprising an siRNA and an siRNA conjugate, respectively. In the context of the present disclosure, the siRNA, the compositions comprising siRNA and the siRNA conjugates in these embodiments are also referred to as the siRNA, the siRN compositions and the siRNA conjugates of the present disclosure just for convenience of description. It does not mean that the double-stranded oligonucleotide of the present disclosure can only be siRNA, instead, the double-stranded oligonucleotide may be other variants disclosed in the present disclosure or known to those skilled in the art, such as small activating RNA (saRNA). It can be envisaged that, based on the detailed illustration of the siRNA, the compostions comprising siRNA, and the siRNA conjugates, other functional double-stranded oligonucleotides would work similarly alone, or when forming the compositions and/or conjugates of the present disclosure.

Advantageous Effects

In some embodiments, the double-stranded oligonucleotide, composition or oligonucleotide conjugate of the present disclosure can have higher stability, lower toxicity, and/or higher activity in vivo. In some embodiments, the double-stranded oligonucleotide of the present disclosure is saRNA. In some embodiments, the saRNA, saRNA composition or saRNA conjugate of the present disclosure exhibits an improvement percentage of target gene expression of at least 20%, 30%, 40%, 50%, 60%, 70%, 80%, 90%, or 95% in vivo. In some embodiments, the double-stranded oligonucleotide of the present disclosure is siRNA. In some embodiments, the siRNA, siRNA composition or siRNA conjugate of the present disclosure exhibits an inhibition percentage of target gene expression of at least 20%, 30%, 40%, 50%, 60%, 70%, 80%, 90%, or 95% in vivo. In some embodiments, the siRNA, siRNA composition or siRNA conjugate of the present disclosure exhibits an inhibition percentage of HBV gene expression of at least 20%, 30%, 40%, 50%, 60%, 70%, 80%, 90%, or 95% in vivo. In some embodiments, the siRNA, siRNA composition or siRNA conjugate of the present disclosure exhibits an inhibition percentage of HBV gene expression in liver of at least 20%, 30%, 40%, 50%, 60%, 70%, 80%, 90%, or 95% in vivo. In some embodiments, the siRNA, siRNA composition or siRNA conjugate of the present disclosure exhibits an inhibition percentage of HBV gene expression in liver in animal models of at least 20%, 30%, 40%, 50%, 60%, 70%, 80%, 90%, or 95% in vivo. In some embodiments, the siRNA, siRNA composition or siRNA conjugate of the present disclosure exhibits an inhibition percentage of HBV surface antigen expression of at least 20%, 30%, 40%, 50%, 60%, 70%, 80%, 90%, or 95% in vivo. In some embodiments, the siRNA, siRNA composition or siRNA conjugate of the present disclosure exhibits an inhibition percentage of ANGPTL3 gene expression of at least 20%, 30%, 40%, 50%, 60%, 70%, 80%, 90%, or 95% in vivo. In some embodiments, the siRNA, siRNA composition or siRNA conjugate of the present disclosure exhibits an inhibition percentage of ANGPTL3 gene expression in liver of at least 20%, 30%, 40%, 50%, 60%, 70%, 80%, 90%, or 95% in vivo. In some embodiments, the siRNA, siRNA composition or siRNA conjugate of the present disclosure exhibits an inhibition percentage of ANGPTL3 gene expression in liver in animal models of at least 20%, 30%, 40%, 50%, 60%, 70%, 80%, 90%, or 95% in vivo. In some embodiments, the siRNA, siRNA composition or siRNA conjugate of the present disclosure exhibits an inhibition percentage of ANGPTL3 gene expression in liver in human subjects of at least 20%, 30%, 40%, 50%, 60%, 70%, 80%, 90%, or 95% in vivo. In some embodiments, the siRNA, siRNA composition or siRNA conjugate of the present disclosure exhibits an inhibition percentage of ApoC3 gene expression of at least 20%, 30%, 40%, 50%, 60%, 70%, 80%, 90%, or 95% in vivo. In some embodiments, the siRNA, siRNA composition or siRNA conjugate of the present disclosure exhibits an inhibition percentage of ApoC3 gene expression in liver of at least 20%, 30%, 40%, 50%, 60%, 70%, 80%, 90%, or 95% in vivo. In some embodiments, the siRNA, siRNA composition or siRNA conjugate of the present disclosure exhibit an inhibition percentage of ApoC3 gene expression in liver in animal models of at least 20%, 30%, 40%, 50%, 60%, 70%, 80%, 90%, or 95% in vivo. In some embodiments, the siRNA, siRNA composition or siRNA conjugate of the present disclosure exhibit an inhibition percentage of ApoC3 gene expression in liver in human subjects of at least 20%, 30%, 40%, 50%, 60%, 70%, 80%, 90%, or 95% in vivo. In some embodiments, the double-stranded oligonucleotide, composition or oligonucleotide conjugate of the present disclosure exhibits no significant off-target effect. An off-target effect may be for example inhibition of normal expression of a gene which is not the target gene. It is considered that if the binding/inhibition of the expression of an off-target gene is 50%, 40%, 30%, 20%, or 10% lower than that of the target activity, then the off-target effect is not significant.

According to some embodiments of the present disclosure, the siRNA, siRNA composition or siRNA conjugate of the present disclosure exhibits an excellent inhibitory effect. For example, according to one embodiment of the present disclosure, the siRNA conjugate of the present disclosure exhibits excellent property of inhibiting HBV gene expression: an inhibition percentage of 66.9-90.9% of HBV gene expression in the liver of HBV model mice at a dose of 1 mg/kg, along with a low off-target effect. Meanwhile, the siRNA conjugate of the present disclosure further effectively reduces the expression of HBV surface antigen and HBV DNA in HBV model mice. In particular, compared with those provided in the prior art, the specific siRNA conjugate formed by the specifically modified siRNA and the specific conjugating molecule provided by the present disclosure, exhibits an consistent and excellent inhibitory effect on HBV expression at low doses over a period of up to 140 days.

According to one embodiment of the present disclosure, the siRNA conjugate of the present disclosure exhibits excellent property of inhibiting HBV gene expression: an inhibition percentage of 81.7-89.2% of HBV gene expression in the liver of HBV model mice at a dose of 1 mg/kg, along with a low off-target effect. Meanwhile, the siRNA conjugate of the present disclosure further effectively reduces the expression of HBV surface antigen and HBV DNA in HBV model mice. In particular, compared with the conjugate formed from the conjugating molecule provided in the prior art, the specific siRNA conjugate formed by the specifically modified siRNA and the specific conjugating molecule provided by the present disclosure, exhibits an consistent and excellent inhibitory effect on HBV expression at low doses over a period of up to 84 days.

According to one embodiment of the present disclosure, the siRNA conjugate of the present disclosure exhibits excellent property of inhibiting HBV gene expression: an inhibition percentage of up to 93.8% of HBV gene expression in the liver of HBV model mice at a dose of 1 mg/kg, along with a low off-target effect. Meanwhile, the siRNA conjugate of the present disclosure further effectively reduces the expression of HBV surface antigen in HBV model mice, achieves an inhibition percentage of 90% or higher for HBV surface antigen expression even at a dose of 3 mg/kg, and effectively inhibits HBV DNA. In particular, compared with reference conjugates, the specific siRNA conjugate formed by the specifically modified siRNA and the specific conjugating molecule provided by the present disclosure, exhibits an consistent and higher inhibitory effect on HBV expression at lower doses over a period of up to 21 days.

According to one embodiment of the present disclosure, the siRNA conjugate of the present disclosure exhibits excellent property of inhibiting HBV gene expression: an inhibition percentage of up to 93.63% of gene expression for HBV X gene region in the liver of HBV model mice at a dose of 1 mg/kg, along with a low off-target effect. Meanwhile, the siRNA conjugate of the present disclosure further effectively reduces the expression of HBV surface antigen in HBV model mice, achieves an inhibition percentage of 95% or higher for HBV surface antigen expression even at a dose of 3 mg/kg, and effectively inhibits HBV DNA. In particular, compared with the conjugate formed from the conjugating molecule provided in the prior art, the specific siRNA conjugate formed by the specifically modified siRNA and the specific conjugating molecule provided by the present disclosure, exhibits an consistent and excellent inhibitory effect on HBV expression at lower doses over a period of up to 56 days and an inhibition percentage of 90% or higher for HBV X mRNA.

In some embodiment, the siRNA conjugates of the present disclosure can exhibit an excellent efficiency of inhibiting ANGPTL3 mRNA and significantly down-regulate blood lipid level. For example, in some embodiments, an inhibition percentage of up to 95% or higher for ANGPTL3 mRNA in mice is achieved on day 14 after single subcutaneous administration; in some embodiments, the maximum inhibition percentage of triglyceride (TG) is 93% and the maximum inhibition percentage of total cholesterol (CHO) is 83% after single subcutaneous administration; and the inhibition percentage of TG is maintained at 55% or higher and the inhibition percentage of CHO is maintained at 40% or higher on day 154 after administration. In particular, compared with the conjugate formed from the conjugating molecule provided in the prior art, the siRNA conjugate of the present disclosure exhibits more excellent inhibition percentage of gene expression and enhanced capability of reducing blood lipid; and the siRNA conjugate of the present disclosure exhibits consistent and excellent hypolipidemic effects at low doses and low administration frequency over a period of up to 189 days.

In some embodiments, the siRNA conjugates of the present disclosure exhibits excellent property of inhibiting ApoC3 gene expression: an inhibition percentage of at least 88% of ApoC3 gene expression in the liver of high-lipid model mice at a dose of 1 mg/kg. In particular, compared with the conjugate formed from the conjugating molecule provided in the prior art, the modified siRNA and siRNA conjugate provided by the present disclosure exhibit excellent inhibition percentage of gene expression and low off-target effect; and the siRNA conjugate of the present disclosure exhibits consistent and excellent hypolipidemic effects at low doses and low administration frequency over a period of up to 189 days.

In some embodiments, the siRNA conjugates of the present disclosure exhibit low toxicity and good safety in animal models. For example, in some embodiments, no obviously toxic response is observed even when the conjugate of the present disclosure is administered to C57BL/6J mice at a concentration of 100-fold higher than the minimal effective concentration (calculated based on the minimal effective concentration of 3 mg/kg).

The above instances indicate that the siRNA, siRNA composition and siRNA conjugate of the present disclosure can effectively reduce gene expression in the target cell and exhibit excellent delivery potency.

EXAMPLES

Hereinafter, the present disclosure will be described in detail with reference to the examples. Unless otherwise specified, the agents and culture media used in following examples are all commercially available, and the procedures used such as nucleic acid electrophoresis and real-time PCR are all performed according to methods described in Molecular Cloning (Cold Spring Harbor Laboratory Press (1989)).

HEK293A cells were provided by Nucleic acid technology laboratory, Institute of Molecular Medicine, Peking University and cultured in DMEM complete media (Hyclone company) containing 20% fetal bovine serum (FBS, Hyclone company), 0.2 v % Penicillin-Streptomycin (Gibco, Invitrogen company) at 37° C. in an incubator containing 5% $CO_{2/95}$% air.

HepG2.2.15 cells were purchased from ATCC and cultured in DMEM complete medium (Gibco) containing 10% fetal bovine serum (FBS, Gibco), 2 mM L-glutamine (Gibco) and 380 μg/ml G418 at 37° C. in an incubator containing 5% $CO_2$/95% air. Huh7 cells were purchased from ATCC and cultured in DMEM complete medium (Gibco) containing 10% fetal bovine serum (FBS, Gibco), 2 mM L-glutamine (Gibco) and 380 μg/ml G418 at 37° C. in an incubator containing 5% $CO_2$/95% air.

Unless otherwise specified, Lipofectamine™2000 (Invitrogen company) was used as a transfection agent when cells were transfected with various synthesized siRNA or siRNA conjugates below. Detailed procedures was performed with reference to the instruction provided by manufacturer.

Unless otherwise specified, ratios of the agents provided below are all calculated by volume ratio (v/v).

The animal models used are as follows:

- C57BL/6N mice: 6-8 weeks old, purchased from Beijing Vital River Laboratory Animal Technology Co., Ltd., hereinafter referred to as C57 mice;
- SD rats: provided by Beijing Vital River Laboratory Animal Technology Co., Ltd.;
- HBV transgenic mice: C57BL/6-HBV, Strain name: B6-Tg HBV/Vst (1.28 copy, genotype A), purchased from Beijing Vital River Laboratory Animal Technology Co., Ltd. Mice with COI>$10^4$ (hereinafter referred as 1.28 copy mice) are selected before experiments;
- HBV transgenic mice C57BL/6J-Tg (A1b1HBV) 44Bri/J: purchased from Department of Laboratory Animal Science, Health Science Center, Peking University;
- HBV transgenic mice M-TgHBV, purchased from Department of Animal, Shanghai Public Health Center. The preparation methods of transgenic mice are described in Ren J. et al., in J. Medical Virology. 2006, 78:551-560;
- AAV-HBV transgenic mice: AAV-HBV model prepared according to the method in the (Xiaoyan Dong et al., Chin J Biotech 2010, May 25; 26(5): 679-686) by using rAAV8-1.3HBV, D type (ayw) virus (purchased from Beijing FivePlus Molecular Medicine Institute Co. Ltd., $1\times10^{12}$ viral genome (v.g.)/mL, Lot No. 2016123011). The rAAV8-1.3HBV was diluted to $5\times10^{11}$ v.g./mL with sterile PBS before experiments. 200 μL of the diluted rAAV8-1.3HBV was injected into each mouse, i.e., $1\times10^{11}$ v.g. per mouse. The orbital blood (about 100 μL) was taken from each mouce on day 28 after virus injection to collect serum for detection of HBsAg and HBV DNA;
- Low concentration AAV-HBV transgenic mice: prepared by using substantially the same modeling method as above, except that the virus was diluted to $1\times10^{11}$ v.g./mL with sterile PBS before experiments. 100 μL virus was injected into each mouse, i.e., $1\times10^{10}$ v.g. per mouse;

BALB/c mice: 6-8 weeks old, purchased from Beijing Vital River Laboratory Animal Technology Co., Ltd.;

ob/ob mice: 6-8 weeks old, purchased from Changzhou Cavens Laboratory Animal Co., Ltd.;

Human APOC3 transgenic mice: B6; CBA-Tg(APOC3) 3707Bres/J, purchased from Jackson Laboratory, USA;

Metabolic syndrome monkey: provided by Non-human Primate Research Center, Institute of Molecular Medicine, Peking University.

Unless otherwise specified, the following data of effect experiments in intro/in vivo are expressed as $\bar{X}\pm SEM$, and the data are analyzed with statistical analysis software Graphpad prism 5.0. The data are initially tested for normal distribution and homogeneity of variance. If the data meet normal distribution (p>0.20) and homogeneity of variance (p>0.10), then comparison among groups would be performed by LSD method using single-factor analysis of variance for multiple comparisons. P<0.05 is considered as being statistically significant. If the data fail to meet normal distribution and homogeneity of variance, comparison among groups would be performed by Krushkal-Wallis H method for Non-parametric Test. If the results obtained by Krushkal-Wallis H test are statistically significant (p<0.05), pairwise comparisons among groups would be conducted after rank transformation of the data. P<0.05 is considered as being statistically significant.

Preparation Example 1 Preparation of siRNA of the Present Disclosure

In this preparation Example, siRNAs listed in Table 2 were synthesized according to the following method.

TABLE 2

Synthesized siRNAs

| siRNA | No. | | Sequence Direction: 5'-3' | SEQ ID NO |
|---|---|---|---|---|
| siRNA1 | siAN1M3SVP | S | CmsCmsAmAmGmAmGfCfAfCmCmAmAmG mAmAmCmUmAm | 137 |
| | | AS | VP-UmsAfsGmUmUmCfUmUmGmGmUmGm CmUfCmUfUmGmGmsCmsUm | 138 |
| siRNA2 | siAN1M3SP | S | CmsCmsAmAmGmAmGfCfAfCmCmAmAmG mAmAmCmUmAm | 139 |
| | | AS | P-UmsAfsGmUmUmCfUmUmGmGmUmGmC mUfCmUfUmGmGmsCmsUm | 140 |
| siRNA3 | siAN1M3SPs | S | CmsCmsAmAmGmAmGfCfAfCmCmAmAmG mAmAmCmUmAm | 141 |
| | | AS | Ps-UmsAfsGmUmUmCfUmUmGmGmUmGmC mUfCmUfUmGmGmsCmsUm | 142 |
| siRNA4 | siAN1M3S | S | CmsCmsAmAmGmAmGfCfAfCmCmAmAmG mAmAmCmUmAm | 143 |
| | | AS | UmsAfsGmUmUmCfUmUmGmGmUmGmCm UfCmUfUmGmGmsCmsUm | 144 |
| Comparative siRNA1 | siHBa1M5 | S | CmCmUmUmGAGGCmAUmACmUmUmCmA AAdTsdT | 145 |
| | | AS | UfUmUfGAAGUfAUGCCUfCAAGGdTsdT | 146 |
| Comparative siRNA2 | siHBa1 | S | CGUGUGCACUUCGCUUCAA | 147 |
| | | AS | UUGAAGCGAAGUGCACACGGU | 148 |
| Comparative siRNA3 | ANG | S | CGUGUGCACUUCGCUUCAA | 149 |
| | | AS | UUGAAGCGAAGUGCACACGGU | 150 |
| Comparative siRNA4 | 65695 | S | GUGUGCACUUCGCUUCACA | 151 |
| | | AS | UGUGAAGCGAAGUGCACACUU | 152 |

*S: sense strand; AS: antisense strand

Note:

C, G, U, and A represents the base components of the nucleotides; dT represents a deoxythymine nucleotide; m represents that the nucleotide adjacent to the left side of the letter m is a 2'-methoxy modified nucleotide; f represents that the nucleotide adjacent to the left side of the letter f is a 2'-fluoro modified nucleotide; s represents that the two nucleotides adjacent to both sides of the letter s are linked by a phosphorothioate linkage; VP represents that the nucleotide adjacent to the right side of the letter VP is a vinyl phosphate modified nucleotide; P represents that the nucleotide adjacent to the right side of the letter P is a phosphate nucleotide; Ps represents that the nucleotide adjacent to the right side of the letters Ps is a phosphorothioate modified nucleotide.

(1-1) Synthesis of a Sense Strand of siRNA

Nucleoside monomers are linked one by one in 3' to 5' direction according to the above sequences by starting the cycles using a universal solid phase support (UnyLinker™ loaded NittoPhase®HL Solid Supports, Kinovate Life Sciences Inc.). The linking of each nucleoside monomer included a four-step reaction of deprotection, coupling, capping, and oxidation. The synthesis conditions are as follows:

The nucleoside monomers are provided in a 0.1 M acetonitrile solution. The condition for deprotection reaction in each step is identical, i.e., a temperature of 25° C., a reaction time of 70 seconds, a solution of dichloroacetic acid in dichloromethane (3% v/v) as a deprotection agent, and a molar ratio of dichloroacetic acid to the protecting group on the solid phase support of 4,4'-dimethoxytrityl of 5:1.

The condition for coupling reaction in each step is identical, including a temperature of 25° C., a molar ratio of the nucleic acid sequence linked to the solid phase support to nucleoside monomers of 1:10, a molar ratio of the nucleic acid sequence linked to the solid phase support to a coupling agent of 1:65, a reaction time of 600 seconds, and 0.5 M acetonitrile solution of 5-ethylthio-1H-tetrazole as a coupling agent.

The condition for capping reaction in each step is identical, including a temperature of 25° C. and a reaction time of 15 seconds, a mixed solution of Cap 1 and Cap 2 in a molar ratio of 1:1 as a capping agent, and a molar ratio of the capping agent to the nucleic acid sequence linked to the solid phase support of 1:1:1 (anhydride: N-methylimidazole: the nucleic acid sequence linked to the solid phase support).

The condition for oxidation reaction in each step is identical, including a temperature of 25° C., a reaction time of 15 seconds, and 0.05 M iodine water as an oxidation agent; and a molar ratio of iodine to the nucleic acid sequence linked to the solid phase support in the coupling step of 30:1. The reaction is carried out in a mixed solvent in which the ratio of tetrahydrofuran:water:pyridine is 3:1:1.

When two nucleotides in the target sequence is linked via a phosphorothioate linkage, the following sulfurization reaction step is used to replace the oxidation reaction step during linking of the later of the two nucleotides: the condition for sulfurization reaction in each step is identical, including a temperature of 25° C., a reaction time of 300 seconds, and xanthane hydride as a sulfurization agent; a molar ratio of the sulfurization agent to the nucleic acid sequence linked to the solid phase support in the coupling step of 120:1. The reaction is carried out in a mixed solvent in which the ratio of acetonitrile:pyridine is 1:1.

The conditions for cleavage and deprotection are as follows: adding the synthesized nucleotide sequence linked to the support into 25 wt % aqueous ammonia to react for 16 hours at 55° C., and the aqueous ammonia is in an amount of 0.5 ml/μmol. The liquid is removed, and the residue is concentrated in vacuum to dryness. After treatment with aqueous ammonia, the product is dissolved in 0.4 ml/μmol N-methylpyrrolidone, and then added with 0.3 ml/μmol triethylamine and 0.6 ml/μmol triethylamine trihydrofluoride, with respect to the amount of the single strand nucleic acid, for removing the 2'-TBDMS protection on ribose. When 2'-positions of all nucleotides in the target sequence were modified hydroxyl groups, the step of removing the 2'-TBDMS protection on ribose is not included in the conditions for cleavage and deprotection.

Purification and desalination: purification of the nucleic acid is achieved by using a preparative ion chromatography column (Source 15Q) with a gradient elution of NaCl. Specifically, eluent A: 20 mM sodium phosphate (pH 8.1), solvent:water/acetonitrile=9:1 (v/v); eluent B: 1.5 M sodium chloride, 20 mM sodium phosphate (pH 8.1), solvent:water/acetonitrile=9:1 (v/v); elution gradient:eluent A:eluent B=100:0-50:50. The eluate is collected, combined and desalted by using a reverse phase chromatography column. The specific conditions include using a Sephadex column (filler: Sephadex-G25) for desalination and deionized water for eluting.

Detection: the purity is determined by ion exchange chromatography (IEX-HPLC); and the molecular weight is analyzed by liquid chromatography-mass spectrometry (LC-MS), and compared with the calculated value.

Thus, a sense strand S of siRNA is synthesized in the above step.

(1-2) Synthesis of an Antisense Strand

In this step, an antisense strand AS of siRNA is synthesized by using a universal solid phase support (UnyLinker™ loaded NittoPhase®HL Solid Supports, Kinovate Life Sciences Inc.) under the same conditions as that in the synthesis of the sense strand, including conditions of deprotection, coupling, capping, oxidation and/or sulfurization reaction, deprotection, cleavage, and isolation in the solid phase synthesis method.

Therein, the vinyl phosphate and 2'-methoxy modified uridine monomer (VP-Um) is synthesized according to the following method:

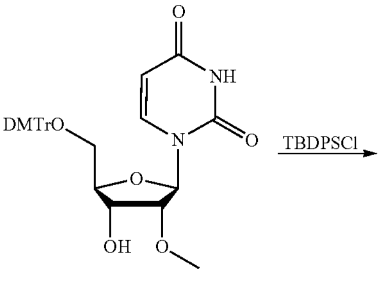

2'-OMe-U

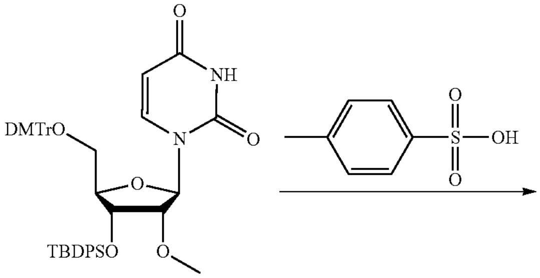

VP-U-1

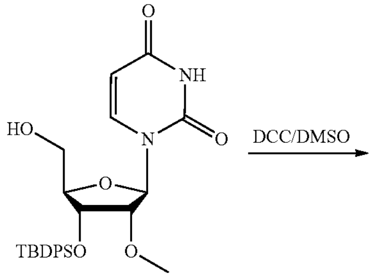

VP-U-2

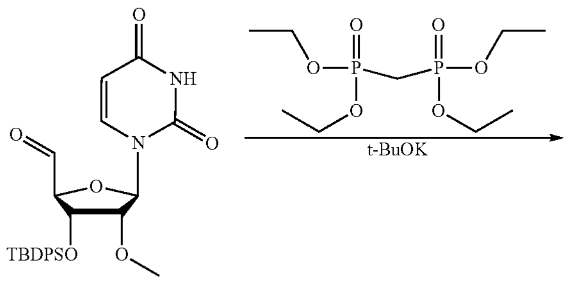

VP-U-3

-continued

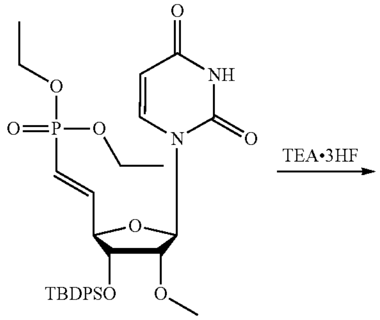

VP-U-4

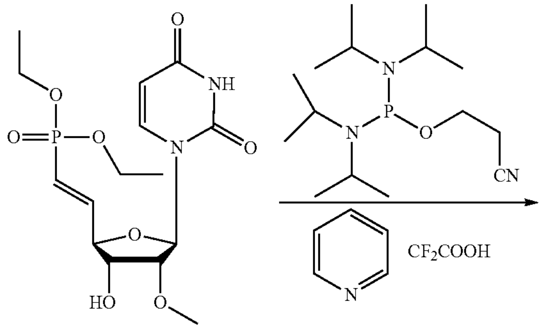

VP-U-5

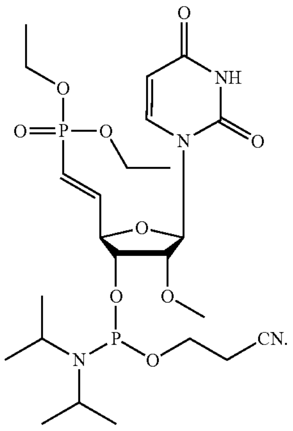

VP-U-6

(1-2-1) Synthesis of VP—U-2

A VP—U-2 molecule is synthesized according to the following method:

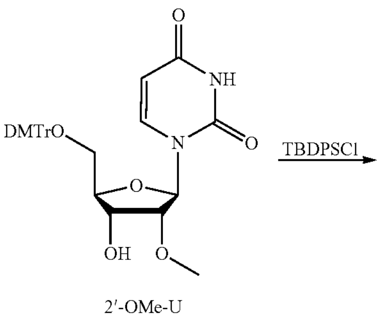

2'-OMe-U

-continued

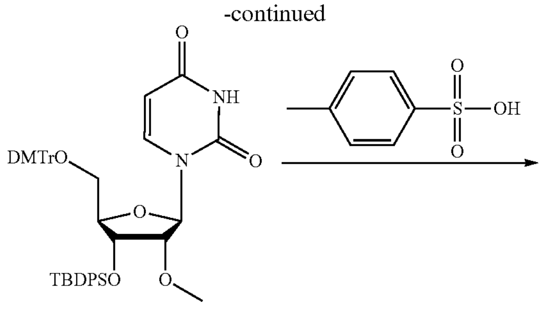

VP-U-1

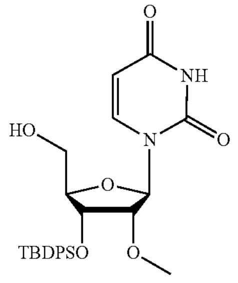

VP-U-2

A 2'-methoxy modified uracil nucleoside (2'-OMe-U, 51.30 g, 91.6 mmol), tertbutyl diphenylchlorosilane (TBDP-SCl, 50.35 g, 183.2 mmol), and imidazole (12.47 g, 183.2 mmol) were mixed and dissolved in 450 ml of N,N-dimethylformamide (DMF) to react under stirring at room temperature for 20 hours. DMF was removed by evaporation, and the residue was dissolved in 600 ml of dichloromethane and washed with 300 ml of saturated sodium bicarbonate. The aqueous phase isolated was extracted three times, each with 300 ml of dichloromethane. All organic phases were combined, washed with 5% oxalic acid until the pH of the aqueous phase is <5. The solvent was evaporated to dryness to give a crude product of VP—U-1, which was directly used in the subsequent synthesis of VP—U-2.

The crude product VP—U-1 was dissolved in 100 ml of dichloromethane, and then stirred for 10 minutes in an ice bath. 450 ml of 2% p-toluenesulfonic acid solution (with a mixed solvent of methanol and dichloromethane in a volume ratio of 3:7) pre-cooled in a refrigerator at 4° C. was added to react for 10 minutes. The reaction was quenched by addition of 200 ml of saturated sodium bicarbonate. The organic phase obtained was washed by addition of saturated sodium bicarbonate solution to pH=8. Aqueous phases were combined and extracted twice, each with 200 ml of dichloromethane. All organic phases were combined and washed once with 200 ml of saturated brine. The solvent was removed by evaporation, and the residue was purified by using a normal phase silica gel column (200-300 mesh). The column was packed with petroleum ether and eluted with a gradient elution of petroleum ether:ethyl acetate:dichloromethane:methanol=1:1:1:0.05-1:1:1:0.25. The eluate was collected, the solvent was removed by evaporation under reduced pressure, and the residue was foam-dried in a vacuum oil pump to give a total of 40.00 g of pure product VP—U-2. 1H NMR (400 MHz, DMSO-d6) δ 7.96 (d, J=7.8 Hz, 1H), 7.64 (dtd, J=5.1, 4.0, 2.2 Hz, 4H), 7.41-7.30 (m, 6H), 6.79 (d, J=4.7 Hz, 1H), 5.73 (d, J=7.6 Hz, 1H), 4.94 (t, J=7.0 Hz, 1H), 4.12 (td, J=4.6, 3.9 Hz, 1H), 4.05 (dd, J=4.8, 4.0 Hz, 1H), 3.96 (t, J=4.7 Hz, 1H), 3.68 (ddd, J=11.8, 7.0, 4.6 Hz, 1H), 3.57-3.46 (m, 1H), 3.39 (s, 3H), 1.05 (s, 8H). MS m/z: C26H33N2O6Si, $[M+H]^+$, calculated: 497.21, measured: 497.45.

(1-2-2) Synthesis of VP—U-4:

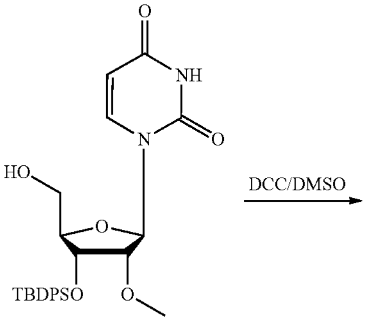

VP-U-2

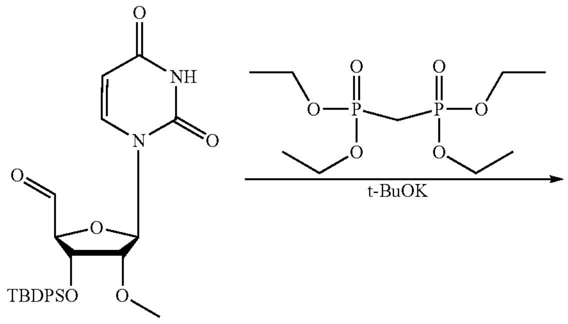

VP-U-3

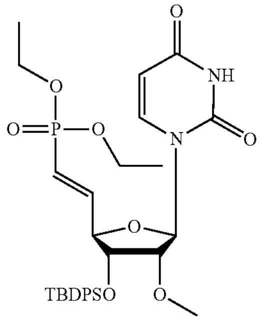

VP-U-4

VP—U-2 (19.84 g, 40.0 mmol), dicyclohexylcarbodiimide (DCC, 16.48 g, 80.0 mmol), pyridine (4.20 g, 53.2 mmol), and trifluoroacetic acid (6.61 g, 53.2 mmol) were mixed and dissolved in 200 ml of dimethyl sulfoxide (DMSO) to react under stirring at room temperature for 20 hours. Separately, tetraethyl methylenediphosphate (21.44 g, 74.4 mmol) was dissolved in 120 ml of THF, cooled in an ice bath, added with t-BuOK (11.36 g, 101.2 mmol) at a temperature of the ice bath to react for 10 min, warmed to room temperature to react for 0.5 h and added into the above reaction solution over about 1 h. The reaction was carried out at a temperature of the ice bath for 1 h and then warmed to room temperature to react for 18 h. The reaction was quenched by addition of water. The aqueous phase isolated was extracted three times, each with 200 ml of dichloromethane. All organic phases were combined and washed once with 200 ml of saturated brine. The solvent was evaporated to dryness, and the residue was purified by using a normal phase silica gel column (200-300 mesh). The column was packed with petroleum ether and eluted with a gradient elution of petroleum ether: ethyl acetate=1:1-1:4. The eluate was collected, the solvent was removed by evaporation under reduced pressure, and the residue was foam-dried in a vacuum oil pump to give a total of 14.00 g of pure product VP—U-4. 1H NMR (400 MHz, DMSO-d6) δ 7.96 (d, J=7.8 Hz, 1H), 7.64 (dtd, J=5.1, 4.0, 2.2 Hz, 4H), 7.41-7.30 (m, 6H), 6.82-6.71 (m, 2H), 5.90 (ddd, J=25.9, 15.0, 1.0 Hz, 1H), 5.73 (d, J=7.6 Hz, 1H), 4.36-4.21 (m, 3H), 4.18 (t, J=4.9 Hz, 1H), 4.05 (ddq, J=9.7, 8.5, 6.9 Hz, 2H), 3.87 (t, J=4.8 Hz, 1H), 3.39 (s, 3H), 1.32 (td, J=6.9, 0.7 Hz, 6H), 1.05 (s, 8H). MS m/z: C31H42N2O8PSi, [M+H]+, calculated: 629.24, measured: 629.51.

(1-2-3) Synthesis of VP—U-5:

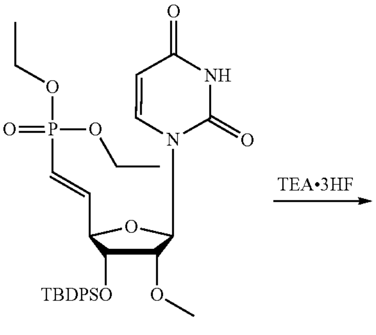

VP-U-4

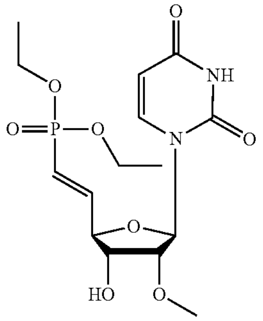

VP-U-5

VP—U-4 (14.00 g, 22.29 mmol) was dissolved in 100 ml of tetrahydrofuran, added with triethylamine trihydrofluoride (17.96 g, 111.45 mmol), and stirred at room temperature for 20 hours to react completely. The solvent was directly evaporated to dryness and the residue was dissolved in dichoromethane; the above evaporation and dissolution steps were additionally repeated twice, each with 50 ml of dichloromethane, to give a crude product. The crude product was purified by using a normal phase silica gel column (200-300 mesh). The column was packed with petroleum ether and eluted with a gradient elution of petroleum ether: ethyl acetate:dichloromethane:methanol=1:1:1:0.05-1:1:1:0.25. The eluate was collected, the solvent was removed by evaporation under reduced pressure, and the residue was foam-dried in a vacuum oil pump to give a total of 6.70 g of pure product VP—U-5. 1H NMR (400 MHz, DMSO-d6) δ 7.96 (d, J=7.8 Hz, 1H), 6.77 (dd, J=15.0, 6.2 Hz, 1H), 5.99-5.82 (m, 2H), 5.73 (d, J=7.6 Hz, 1H), 5.27 (d, J=5.1 Hz, 1H), 5.10 (dd, J=5.3, 4.7 Hz, 1H), 4.29 (ddq, J=9.8, 8.6, 7.0 Hz, 2H), 4.17 (ddd, J=6.2, 5.2, 1.0 Hz, 1H), 4.12-3.98 (m, 3H), 3.39 (s, 2H), 1.32 (td, J=6.9, 0.6 Hz, 6H). MS m/z: C15H24N2O8P, [M+H]+, calculated: 391.13, measured: 391.38.

(1-2-4) Synthesis of VP—U-6:

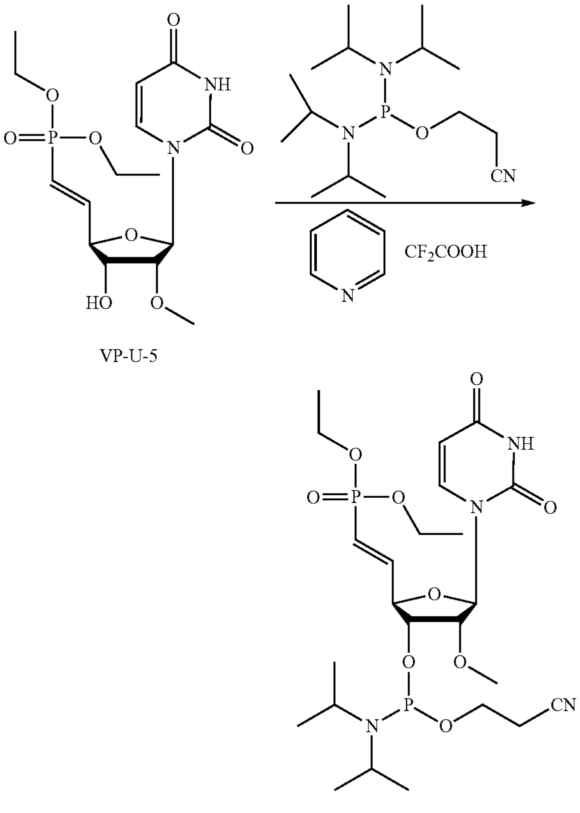

VP-U-5

VP-U-6

VP—U-5 (391 mg, 1.0 mmol), pyridine trifluoroacetate (0.232 g, 1.2 mmol), N-methylimidazole (0.099 g, 1.2 mmol), and bis(diisopropylamino)(2-cyanoethoxy)phosphine (0.452 g, 1.5 mmol) were added into 10 ml of anhydrous dichloromethane under argon atmosphere to react under stirring at room temperature for 5 hours. The solvent was evaporated to dryness, and then the residue was purified by column chromatography (200-300 mesh normal phase silica gel, with a gradient elution of dichloromethane:acetonitrile (containing 0.5 wt % triethylamine)=3:1-1:3). The eluate was collected and concentrated to remove the solvent to give a total of 508 mg of target product VP—U-6. 31P NMR (161 MHz, DMSO-d6) δ 150.34, 150.29, 17.07, 15.50. MS m/z: C24H41N4O9P2, [M+H]+, calculated: 591.23, measured: 591.55. The above data indicated that VP—U-6 was the target product VP-Um, which was involved in the synthesis of RNA strands as a nucleoside monomer.

A 5'-phosphate ester modification was linked to 5' terminal using the following method:

As a starting material, a phosphorylated structural monomer with the following structure of Formula CPR—I (provided by Suzhou GenePharma Inc., Cat #13-2601-XX) was used:

(CPR-I)

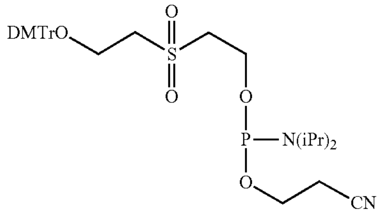

After all nucleosides of the antisense strand were linked, the monomer of Formula (CPR—I) was linked to the 5' terminal of the antisense strand by a four-step reaction of deprotection, coupling, capping, and oxidation according to the phosphoramidite solid phase synthesis method of nucleic acid. Then, cleavage and deprotection were performed under the following conditions, to give the antisense strand:

The synthesized nucleotide sequence linked to the support was added into 25 wt % aqueous ammonia to react at 55° C. for 16 hours, and the aqueous ammonia is in an amount of 0.5 ml/μmol. The liquid was removed, and the residue was concentrated in vacuum to dryness. After treatment with aqueous ammonia, the product was dissolved in 0.4 ml/μmol N-methylpyrrolidone, and then added with 0.3 ml/gmol of triethylamine and 0.6 ml/μmol of triethylamine trihydrofluoride, with respect to the amount of the single strand nucleic acid, for removing the 2'-TBDMS protection on ribose. Purification and desalination: purification of the nucleic acid was achieved by using a preparative ion chromatography column (Source 15Q) with a gradient elution of NaCl. Specifically, eluent A: 20 mM sodium phosphate (pH 8.1), solvent:water/acetonitrile=9:1 (v/v); eluent B: 1.5 M sodium chloride, 20 mM sodium phosphate (pH 8.1), solvent:water/acetonitrile=9:1 (v/v); elution gradient:eluent A:eluent B=100:0-50:50. The eluate was collected, combined and desalted by using a reverse phase chromatography column. The specific conditions included using a Sephadex column (filler: Sephadex-G25) for desalination and deionized water for eluting.

In the case where the target product has a 5'-phosphorothioate modification, the same procedure as above was adopted, except that the above oxidation reaction condition was replaced with a sulfurization reaction condition during the linking, for performing the sulfurization reaction.

The antisense strand of siRNA was similarly analyzed and detected using the same apparatus and methods as the sense strand. It was finally confirmed that the corresponding antisense strand of siRNA was obtained.

(1-3) Synthesis of siRNA

The S strand and the AS strand were mixed at an equimolar ratio, dissolved in water for injection and heated to 95° C., and then cooled at room temperature, such that the strands could form a duplex structure through hydrogen bonds.

For the sense strand and antisense strand as synthesized above, the purity was determined by ion exchange chromatography (IEX-HPLC), and the molecular weight was analyzed by LC-MS. It was confirmed that the synthesized nucleic acid sequences correspond to the respective siRNAs shown in Table 2.

Preparation Example 2 Preparation of Conjugate 1

In this preparation Example, siRNA conjugate (which is referred to as Conjugate A1 in Table 4A) was synthesized according to the following method.

(2-1) Preparation of Compound L-10:
Compound L-10 was synthesized according to the following method.
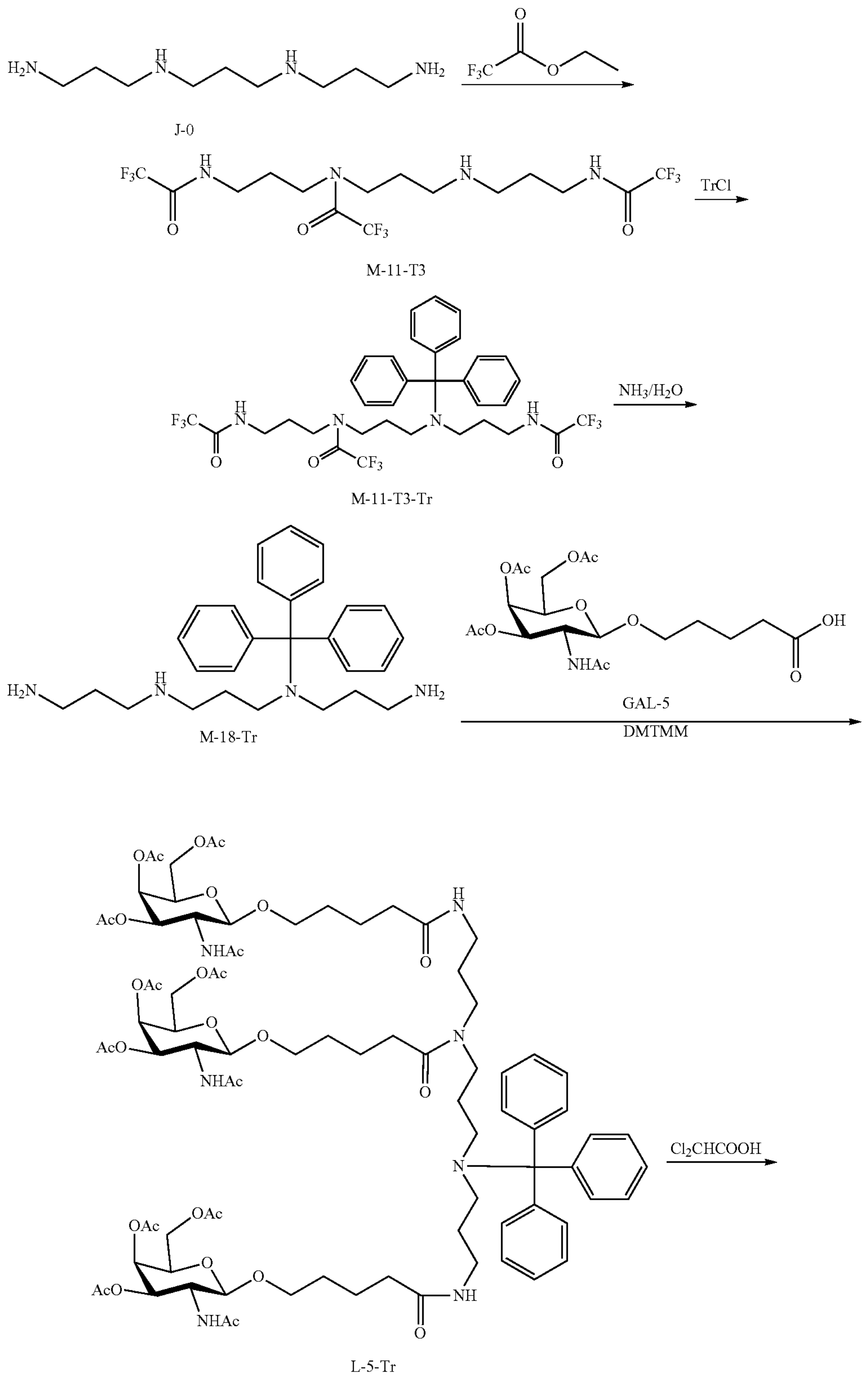
J-0
M-11-T3
M-11-T3-Tr
M-18-Tr
L-5-Tr -continued
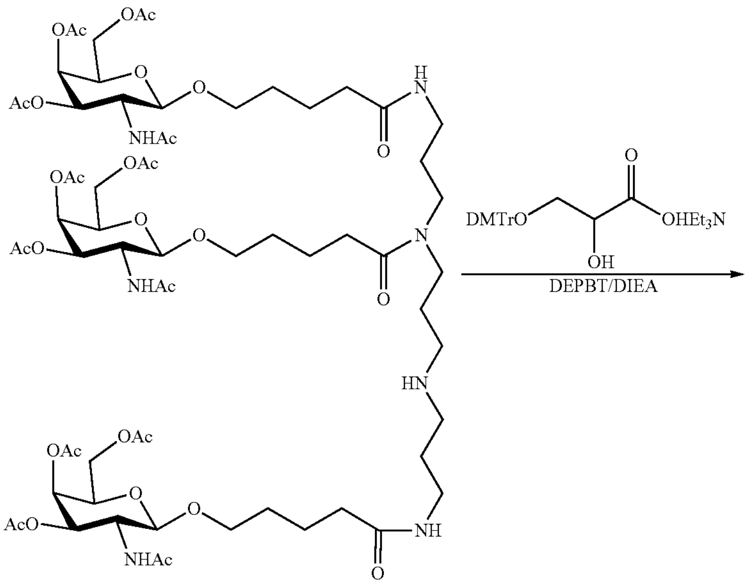
L-8
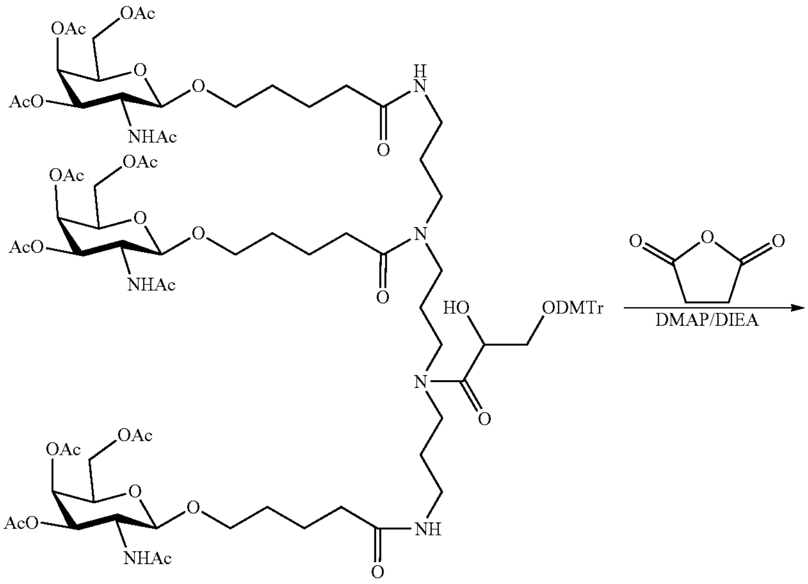
L-7

-continued
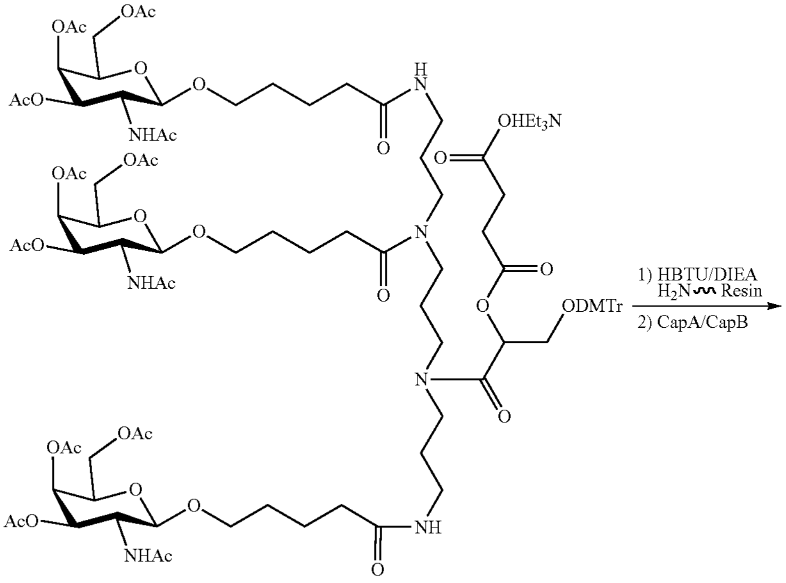
L-9
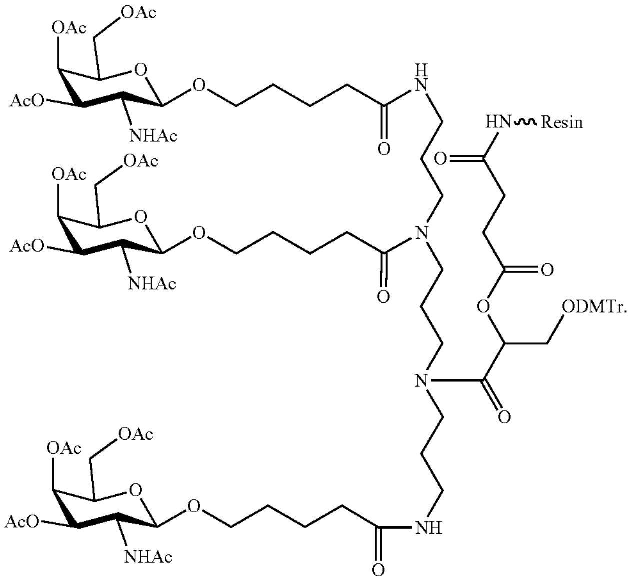
L-10

(2-1-1) Synthesis of GAL-5 (a Terminal Segment of the Conjugating Molecule)

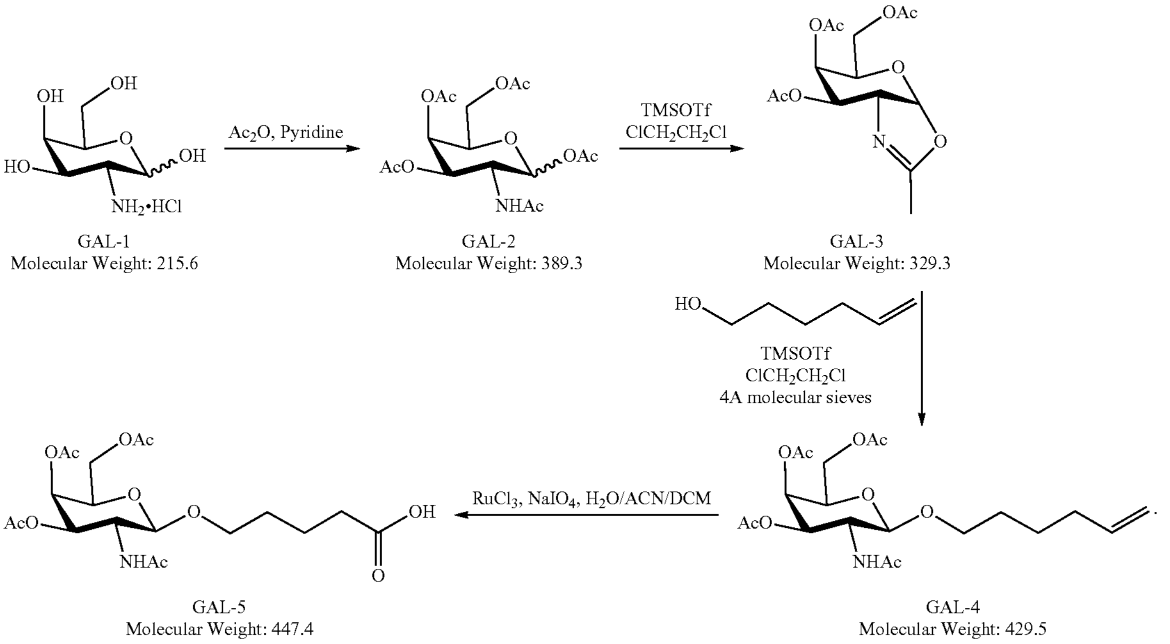

(2-1-1a) Synthesis of GAL-2

100.0 g of GAL-1 (N-acetyl-D-galactosamine hydrochloride, CAS No.: 1772-03-8, purchased from Ningbo Hongxiang Bio-Chem Co., Ltd., 463.8 mmol) was dissolved in 1000 ml of anhydrous pyridine, to which 540 ml of acetic anhydride (purchased from Enox Inc., 5565.6 mmol) was added in an ice water bath to react under stirring at room temperature for 1.5 hours. The resultant reaction solution was poured into 10 L of ice water and subjected to suction filtration under reduced pressure. The residue was washed with 2 L of ice water, and then added with a mixed solvent of acetonitrile/toluene (v/v ratio=1:1) until completely dissolved. The solvent was removed by evaporation to give 130.0 g of product GAL-2 as a white solid.

(2-1-1b) Synthesis of GAL-3

GAL-2 (35.1 g, 90.0 mmol) obtained in step (2-1-1a) was dissolved in 213 ml of anhydrous 1,2-dichloroethane, to which 24.0 g of TMSOTf (CAS No.: 27607-77-8, purchased from Macklin Inc., 108.0 mmol) was added in an ice water bath and nitrogen atmosphere to react at room temperature overnight.

The reaction solution was added with 400 ml dichloromethane for dilution, filtered with diatomite, and then added with 1 L saturated aqueous sodium bicarbonate solution and washed. An organic phase was isolated. The aqueous phase remained was extracted twice, each with 300 ml of dichloroethane, and all organic phases were combined and washed with 300 ml of saturated aqueous sodium bicarbonate solution and 300 ml of saturated brine, respectively. The organic phase resulted from washing was isolated and dried with anhydrous sodium sulfate. The solvent was removed by evaporation under reduced pressure to give 26.9 g of product GAL-3 as a light yellow viscous syrup.

(2-1-1c) Synthesis of GAL-4

GAL-3 (26.9 g, 81.7 mmol) obtained in step (2-1-1b) was dissolved in 136 ml of anhydrous 1,2-dichloroethane, added with 30 g of dry 4 Å molecular sieve powder followed by 9.0 g of 5-hexen-1-ol (CAS No.: 821-41-0, purchased from Adamas-beta Inc., 89.9 mmol), and stirred at room temperature for 30 minutes. 9.08 ml of TMSOTf (40.9 mmol) was added in an ice bath and nitrogen atmosphere to react under stirring at room temperature overnight. The 4 Å molecular sieve powder was removed by filtration. The filtrate was added with 300 ml dichloroethane for dilution, filtered with diatomite, and then added with 500 ml of saturated aqueous sodium bicarbonate solution and stirred for 10 minutes for washing. An organic phase was isolated. The aqueous phase was extracted once with 300 ml of dichloroethane. All organic phases were combined and washed with 300 ml of saturated aqueous sodium bicarbonate solution and 300 ml of saturated brine respectively. The organic phase resulted from the washing was isolated and dried with anhydrous sodium sulfate. The solvent was removed by evaporation under reduced pressure to give 41.3 g of product GAL-4 as a yellow syrup, which was directly used in the next oxidation reaction without purification.

(2-1-1d) Synthesis of GAL-5

GAL-4 (14.9 g, 34.7 mmol) obtained according to the method described in step (2-1-1c) was dissolved in a mixed solvent of 77 ml of dichloromethane and 77 ml of acetonitrile, added with 103 ml of deionized water and 29.7 g of sodium periodate (CAS No.: 7790-28-5, purchased from Aladdin Inc., 138.8 mmol) respectively, and stirred in an ice bath for 10 minutes. Ruthenium trichloride (CAS No.: 14898-67-0, available from Energy Chemical, 238 mg, 1.145 mmol) was added to react at room temperature overnight, wherein the system temperature was controlled as being no more than 30° C. The resultant reaction solution was diluted by adding 300 ml of water under stirring, and adjusted to a pH of about 7.5 by adding saturated sodium bicarbonate. The organic phase was isolated and discarded. The aqueous phase was extracted three times, each with 200 ml of dichloromethane, and the organic phase resulted from the extraction was discarded. The aqueous phase resulted from the extraction was adjusted to a pH of about 3 with citric acid solids and extracted three times, each with 200 ml of dichloromethane, and the resultant organic phases were combined and dried with anhydrous sodium sulfate. The solvent is removed by evaporation under reduced pressure to give 6.5 g of product GAL-5 as a white foamy solid. $^1$H NMR (400 MHz, DMSO) δ 12.01 (br, 1H), 7.83 (d, J=9.2 Hz, 1H), 5.21 (d, J=3.2 Hz, 1H), 4.96 (dd, J=11.2, 3.2 Hz, 1H), 4.49 (d, J=8.4 Hz, 1H), 4.07-3.95 (m, 3H), 3.92-3.85 (m, 1H), 3.74-3.67 (m, 1H), 3.48-3.39 (m, 1H), 2.20 (t, J=6.8 Hz, 2H), 2.11 (s, 3H), 2.00 (s, 3H), 1.90 (s, 3H), 1.77 (s, 3H), 1.55-1.45 (m, 4H).

(2-1-2) Synthesis of M-11-T3:

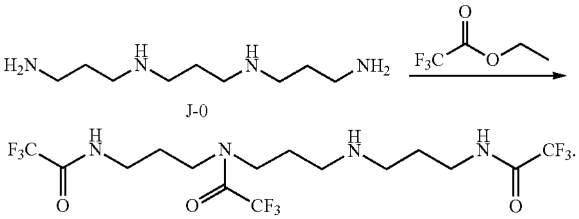

J-0

M-11-T3

J-0 (1.883 g, 10 mmol, purchased from Alfa Aesar) was dissolved in 25 ml of acetonitrile, added with triethylamine (4.048 g, 40 mmol), and cooled to 0° C. in an ice water bath. Ethyl trifluoroacetate (5.683 g, 40 mmol) was added to react at room temperature for 22 hours. The solvent was removed by evaporation under reduced pressure, and the residue was foam-dried in a vacuum oil pump for 18 hours to give 5.342 g of crude solid product M-11-T3, which was directly used in subsequent reaction without further purification. MS m/z: C15H22F9N4O3, [M+H]+, calculated: 477.35, measured: 477.65.

(2-1-3) Synthesis of M-11-T3-Tr:

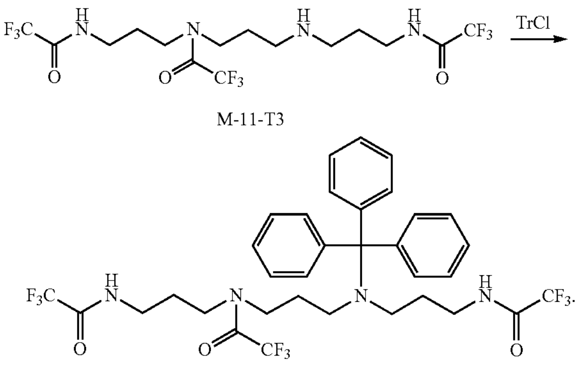

M-11-T3

M-11-T3-Tr

The crude product M-11-T3 (5.342 g, 10 mmol) was dissolved in 50 ml of dichloromethane. The resultant reaction solution was added with TrCl (3.345 g, 12 mmol) and triethylamine (1.518 g, 15 mmol) to react under stirring at room temperature for 20 hours. The reaction solution was washed twice, each with 20 ml of saturated sodium bicarbonate and once with 20 ml of saturated brine. The resultant organic phase was dried with anhydrous sodium sulfate and filtered. The organic solvent was removed by evaporation under reduced pressure, and the residue was foam-dried in a vacuum oil pump overnight to give 7.763 g of crude solid product M-11-T3-Tr. MS m/z: C34H36F9N4O3, [M+Na]+, calculated: 741.25, measured: 741.53. The crude solid product M-11-T3-Tr was then used in the next step for synthesis of M-18-Tr without purification.

(2-1-4) Synthesis of M-18-Tr:

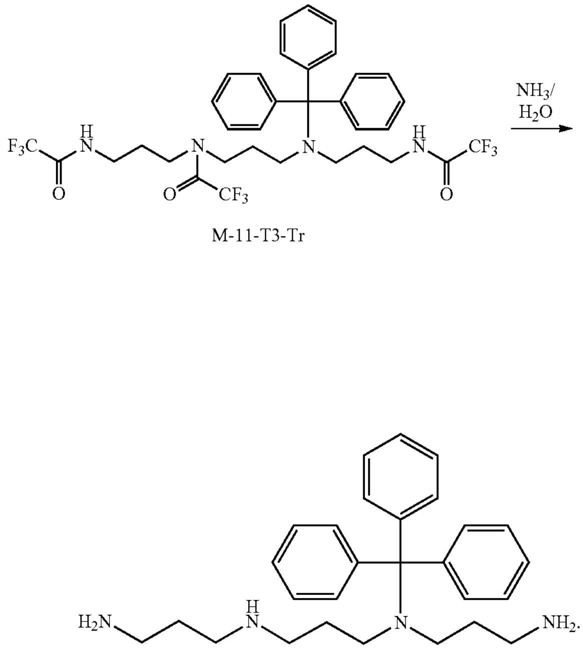

M-11-T3-Tr

M-18-Tr

The crude product M-11-T3-Tr (7.763 g, 10 mmol) obtained in step (2-1-3) was dissolved in 100 ml of methanol, and added with 100 ml of aqueous methylamine solution (40 mass %) to react under stirring at 50° C. for 23 hours. Insoluble particles were removed by filtration. The solvent was removed by evaporation under reduced pressure, and the residue was added with 200 ml of mixed solvent of DCM:methanol in a volume ratio of 1:1, washed with 50 ml of saturated sodium bicarbonate. The aqueous phase obtained was extracted three times, each with 50 ml of dichloromethane. All organic phases were combined, dried with anhydrous sodium sulfate and filtered. The solvent was removed by evaporation under reduced pressure, and the residue was foam-dried in a vacuum oil pump overnight, and purified by using a normal phase silica gel column (200-300 mesh). The column was packed with petroleum ether and added with 1 wt % triethylamine for neutralizing the acidity of silica gel, and eluted with a gradient elution of dichloromethane:methanol:aqueous ammonia (25 wt %)=1:1:0.05-1:1:0.25. The eluate was collected, the solvent was removed by evaporation under reduced pressure, and the residue was foam-dried in a vacuum oil pump to give 2.887 g of pure product M-18-Tr. $^1$H NMR (400 MHz, DMSO) δ7.47-7.39 (m, 6H), 7.32-7.24 (m, 6H), 7.19-7.12 (m, 3H), 2.60-2.47 (m, 4H), 2.46-2.19 (m, 13H), 1.70-1.55 (m, 4H), 1.40 (p, J=6.8 Hz, 2H). MS m/z: C28H39N$_4$, [M+H]+, calculated: 431.65, measured: 432.61.

(2-1-5) Synthesis of L-5-Tr:

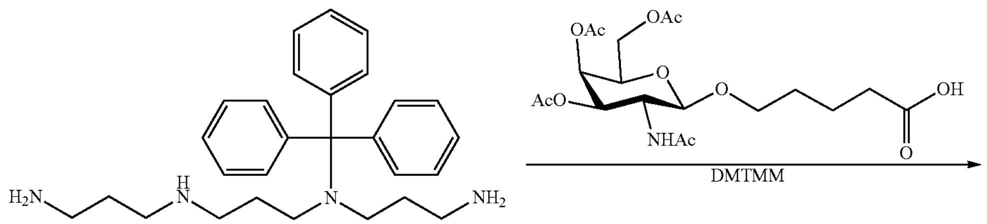

M-18-Tr

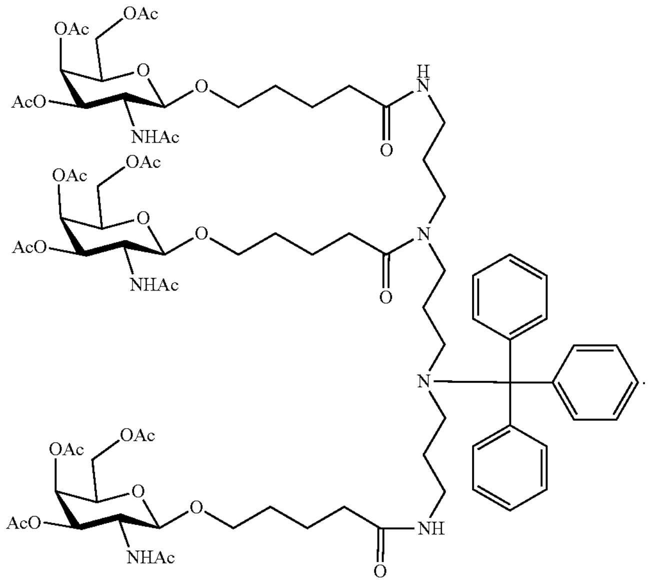

L-5-Tr

M-18-Tr (2.02 g, 4.69 mmol) obtained in step (2-1-4) and GAL-5 (6.93 g, 15.48 mmol) obtained in step (2-1-1) were mixed and dissolved in 47 ml of acetonitrile, and added with N-methylmorpholine (3.13 g, 30.96 mmol) and 4-(4,6-dimethoxytriazin-2-yl)-4-methylmorpholine hydrochloride (DMTMM, 4.28 g, 15.48 mmol) to react under stirring at room temperature for 2 hours. The resultant reaction solution was diluted with 200 ml of dichloromethane. The organic phase was washed with 100 ml of a saturated sodium bicarbonate solution and 100 ml of saturated brine, dried with anhydrous sodium sulfate, and filtered. Then the solvent was removed by evaporation under reduced pressure to give a crude product. The crude product was purified by using a normal phase silica gel column (200-300 mesh). The column was packed with petroleum ether, added with 1 wt % triethylamine for neutralizing the acidity of silica gel, and eluted with a gradient elution of dichloromethane:methanol=100:5-100:7. The eluate was collected, and evaporated to dryness under reduced pressure to give 7.49 g of pure product L-5-Tr. $^1$H NMR (400 MHz, DMSO) 37.83-7.10 (m, 4H), 7.67-7.60 (m, 1H), 7.44-7.34 (m, 6H), 7.33-7.24 (m, 6H), 7.20-7.15 (m, 3H), 5.22 (s, 3H), 4.97 (d, J=11.3 Hz, 3H), 4.49 (d, J=8.4 Hz, 3H), 4.06-3.07 (m, 9H), 3.95-3.83 (m, 3H), 3.77-3.64 (m, 3H), 3.45-3.35 (m, 3H), 3.12-2.87 (m, 8H), 2.30-2.15 (m, 3H), 2.11-1.98 (m, 22H), 1.95-1.84 (m, 11H), 1.81-1.61 (m, 14H), 1.54-1.36 (m, 14H). MS m/z: C85H119N7030, [M+H]+, calculated: 1718.81, measured: 1718.03.

(2-1-6) Synthesis of L-8:

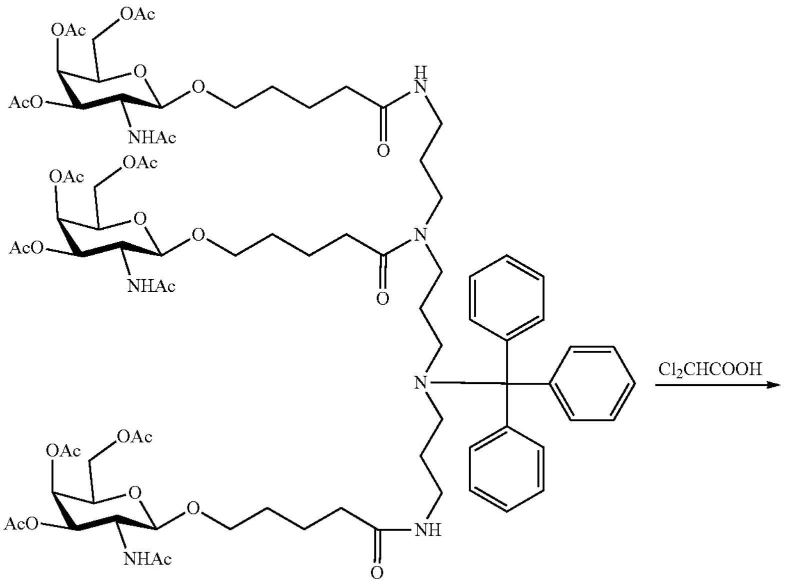

L-5-Tr

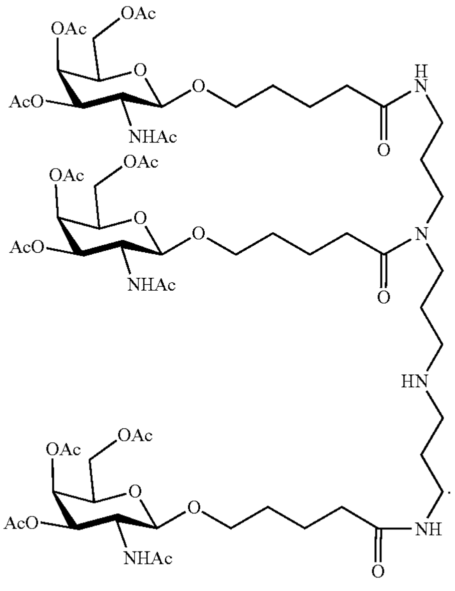

L-8

L-5-Tr (5.94 g, 3.456 mmol) obtained in step (2-1-5) was dissolved in 69 ml of dichloromethane, and added with dichloroacetic acid (13.367 g, 103.67 mmol) to react at room temperature for 2 hours. The resultant reaction solution was diluted by adding 100 ml of dichloromethane, washed and adjusted to pH 7-8 with saturated sodium bicarbonate solution. The aqueous phase isolated was extracted six times, each with 30 ml of dichloromethane. All organic phases were combined, dried with anhydrous sodium sulfate, and filtered. Then the solvent was removed by evaporation under reduced pressure to give a crude product. The crude product was purified by using a normal phase silica gel column (200-300 mesh). The column was added with 10 wt % triethylamine for neutralizing the acidity of silica gel and equilibrated with 1 wt % triethylamine, and eluted with a gradient elution of dichloromethane:methanol=100:30-100:40. The eluate was collected, and the solvent was removed by evaporation under reduced pressure to give 4.26 g of pure product L-8. $^{1}$H NMR (400 MHz, DMSO) δ 7.84 (d, J=9.0 Hz, 3H), 7.27-7.23 (m, 1H), 7.13-7.18 (m, 1H), 5.22 (d, J=3.1 Hz, 3H), 4.97 (dd, J=11.3, 3.1 Hz, 3H), 4.48 (d, J=8.4 Hz, 3H), 4.09-3.98 (m, 9H), 3.88 (dd, J=19.3, 9.3 Hz, 3H), 3.75-3.66 (m, 3H), 3.44-3.38 (m, 3H), 3.17-3.30 (m, 4H), 3.10-2.97 (m, 4H), 2.35-2.20 (m, 6H), 2.15-2.08 (m, 9H), 2.07-1.98 (m, 13H), 1.94-1.87 (m, 9H), 1.81-1.74 (m, 9H), 1.65-1.42 (m, 18H). MS m/z: C85H119N7O30, [M+H]+, calculated: 1477.59, measured: 1477.23.

(2-1-7a) Synthesis of A-1

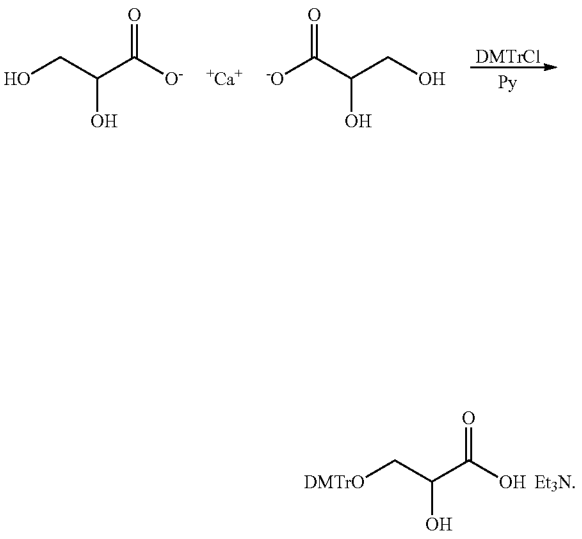

A-1

DMTrCl (4,4'-dimethoxytrityl chloride, 38.12 g, 112.5 mmol) was dissolved in 450 ml of anhydrous pyridine, and added with calcium DL-glycerate hydrate (12.88 g, 45.0 mmol) to react at 45° C. for 22 hours. The resultant reaction solution was filtered. The residue was rinsed with 200 ml of DCM, and the filtrate was concentrated to dryness under reduced pressure. The residue was redissolved in 500 ml of dichloromethane and washed twice, each with 200 ml of 0.5 M triethylamine phosphate (pH=7-8). The aqueous phase isolated was extracted twice, each with 200 ml of dichloromethane. All organic phases were combined, dried with anhydrous sodium sulfate, and filtered. The solvent was removed by evaporation under reduced pressure, and the residue was purified by using a normal phase silica gel column (200-300 mesh) which was eluted with a gradient elution of petroleum ether:ethyl acetate:dichloromethane:methanol=1:1:1:0.35-1:1:1:0.55. The eluate was collected, and the solvent was removed by evaporation under reduced pressure. The residue was redissolved in 500 ml of dichloromethane, and washed once with 200 ml of 0.5 M triethylamine phosphate. The aqueous phase isolated was extracted twice, each with 200 ml of dichloromethane. All organic phases were combined, dried with anhydrous sodium sulfate, and filtered. The solvent was removed by evaporation under reduced pressure (reduced pressure in a vacuum oil pump) to dryness overnight to give 20.7 g of product A-1 as a white solid. $^1$H NMR (400 MHz, DMSO-d6) δ 7.46 (ddd, J=6.5, 2.3, 1.1 Hz, 1H), 7.40-7.28 (m, 7H), 6.89-6.81 (m, 4H), 4.84 (d, J=5.0 Hz, 1H), 4.36-4.24 (m, 1H), 4.29 (s, 6H), 3.92 (dd, J=12.4, 7.0 Hz, 1H), 3.67 (dd, J=12.3, 7.0 Hz, 1H), 2.52 (q, J=6.3 Hz, 6H), 1.03 (t, J=6.3 Hz, 9H). MS m/z: C24H23O6, [M−H]−, calculated: 407.15, measured: 406.92.

(2-1-7b) Synthesis of L-7:

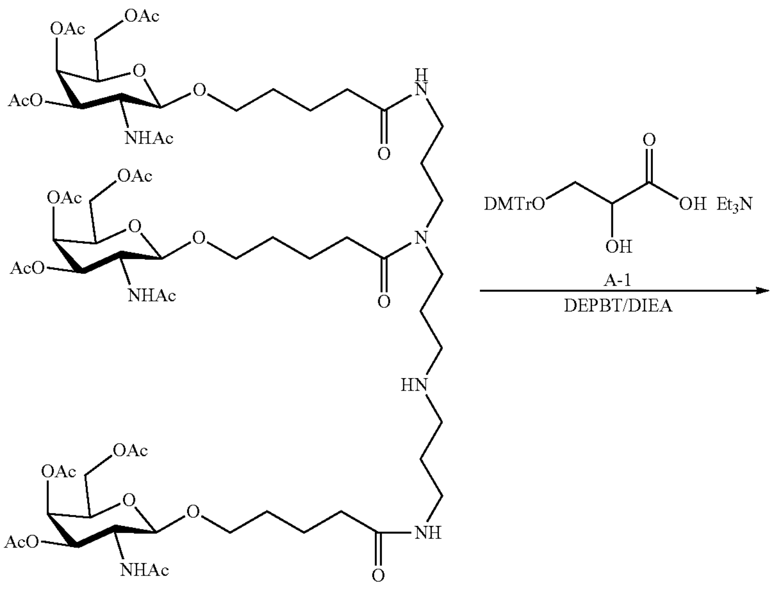

L-8

-continued

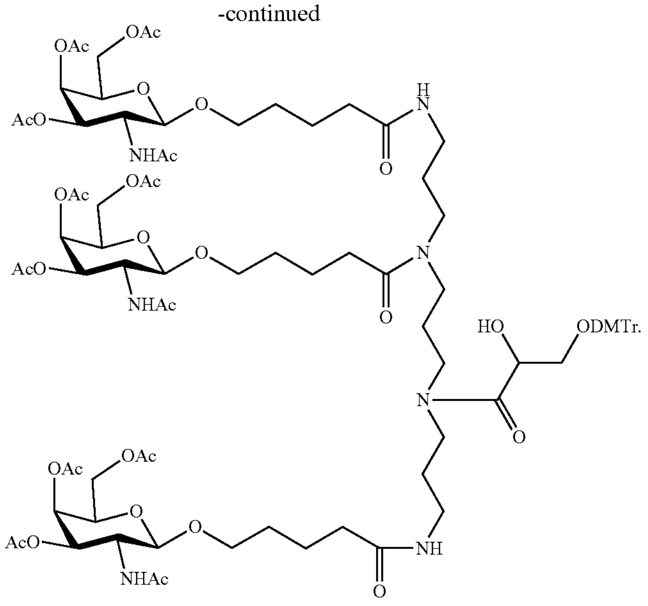

L-7

L-8 (2.262 g, 1.532 mmol) obtained in step (2-1-6) and A-1 (2.342 g, 4.596 mmol) obtained in step (2-1-7a) were mixed and dissolved in 16 ml of dichloromethane, added with 3-(diethoxyphosphoryloxy)-1,2,3-benzotrizin-4(3H)-one (DEPBT, 1.375 g, 4.596 mmol), and further added with diisopropylethylamine (1.188 g, 9.191 mmol) to react under stirring at 25° C. for 2 hours. The organic phase was washed with 10 ml of saturated sodium bicarbonate. The aqueous phase isolated was extracted three times, each with 10 ml of dichloromethane. All organic phases were combined and washed with 10 ml of saturated brine, and the aqueous phase isolated was extracted twice, each with 10 ml of dichloromethane, and the obtained organic phases were combined, dried with anhydrous sodium sulfate and filtered. The solvent was removed by evaporation under reduced pressure, and the residue was foam-dried in a vacuum oil pump overnight to give 4.900 g of crude product. The crude product was subjected to a column purification. The column was filled with 120 g normal phase silica gel (200-300 mesh), added with 20 ml triethylamine for neutralizing the acidity of silica gel, equilibrated with petroleum ether containing 1 wt % triethylamine, and eluted with a gradient elution of petroleum ether:ethyl acetate:dichloromethane: N,N-dimethylformamide=1:1:1:0.5-1:1:1:0.6. The eluate was collected, and the solvent was removed by evaporation under reduced pressure to give 2.336 g of pure product L-7. $^{1}$H NMR (400 MHz, DMSO) δ7.90-7.78 (m, 4H), 7.75-7.64 (m, 1H), 7.38-7.18 (m, 9H), 6.91-6.83 (m, 4H), 5.25-5.10 (m, 4H), 4.97 (dd, J=11.2, 3.2 Hz, 3H), 4.48-4.30 (m, 4H), 4.02 (s, 9H), 3.93-3.84 (m, 3H), 3.76-3.66 (m, 9H), 3.45-3.35 (m, 3H), 3.24-2.98 (m, 10H), 2.30-2.20 (m, 2H), 2.11-1.88 (m, 31H), 1.80-1.40 (m, 28H). MS m/z: C90H128N7O35, [M-DMTr]+, calculated: 1564.65, measured: 1564.88.

(2-1-8) Synthesis of L-9:

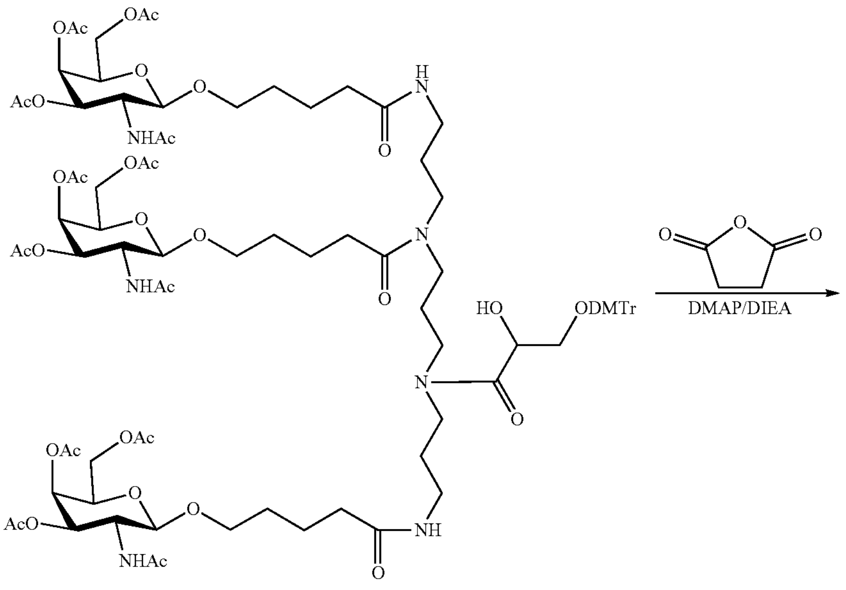

L-7

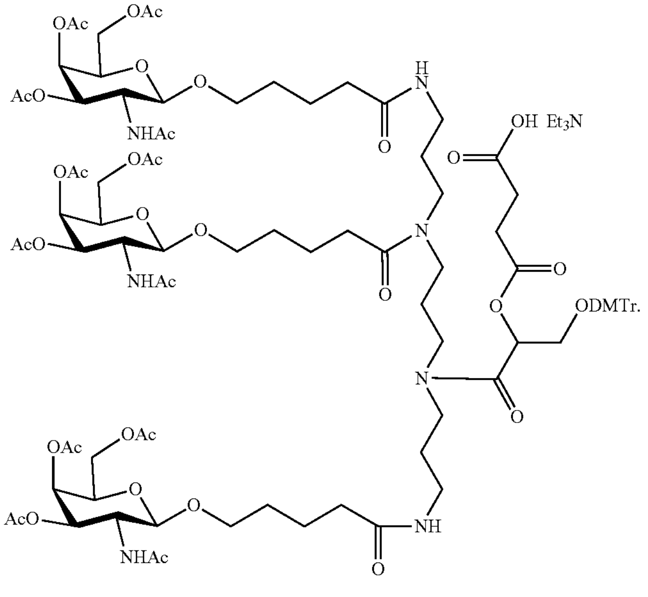

L-9

L-7 (2.300 g, 1.26 mmol) obtained in step (2-1-7b), succinic anhydride (0.378 g, 3.78 mmol) and 4-dimethylaminopyridine (DMAP, 0.462 g, 3.78 mmol) were mixed and dissolved in 13 ml of dichloromethane, further added with DIPEA (0.814 g, 6.30 mmol), and stirred at 25° C. for 24 hours. The resultant reaction solution was washed with 5 ml of 0.5 M triethylamine phosphate. The aqueous phase isolated was extracted three times, each with 5 ml of dichloromethane. All organic phases were combined and removed by evaporation under reduced pressure to give 2.774 g of crude product. The crude product was subjected to a column purification. The column was filled with 60 g normal phase silica gel (200-300 mesh), added with 1 wt % triethylamine for neutralizing the acidity of silica gel, equilibrated with dichloromethane and eluted with a gradient elution of 1 wt % triethylamine-containing dichloromethane:methanol=100:18-100:20. The eluate was collected, and the solvent was removed by evaporation under reduced pressure to give 1.874 g of pure product of L-9 conjugating molecule (compound conjugating molecule 1). $^1$H NMR (400 MHz, DMSO) δ 8.58 (d, J=4.2 Hz, 1H), 7.94-7.82 (m, 3H), 7.41-7.29 (m, 5H), 7.22 (d, J=8.1 Hz, 5H), 6.89 (d, J=8.3 Hz, 4H), 5.49-5.37 (m, 1H), 5.21 (d, J=3.0 Hz, 3H), 4.97 (d, J=11.1 Hz, 3H), 4.49 (d, J=8.2 Hz, 3H), 4.02 (s, 9H), 3.88 (dd, J=19.4, 9.4 Hz, 3H), 3.77-3.65 (m, 9H), 3.50-3.39 (m, 6H), 3.11-2.90 (m, 5H), 2.61-2.54 (m, 4H), 2.47-2.41 (m, 2H), 2.26-2.17 (m, 2H), 2.15-1.95 (m, 22H), 1.92-1.84 (m, 9H), 1.80-1.70 (m, 10H), 1.65-1.35 (m, 17H), 1.31-1.19 (m, 4H), 0.96 (t, J=7.1 Hz, 9H). MS m/z: C94H132N7O38, [M-DMTr]+, calculated: 1664.72, measured: 1665.03.

(2-1-9) Synthesis of Compound L-10:

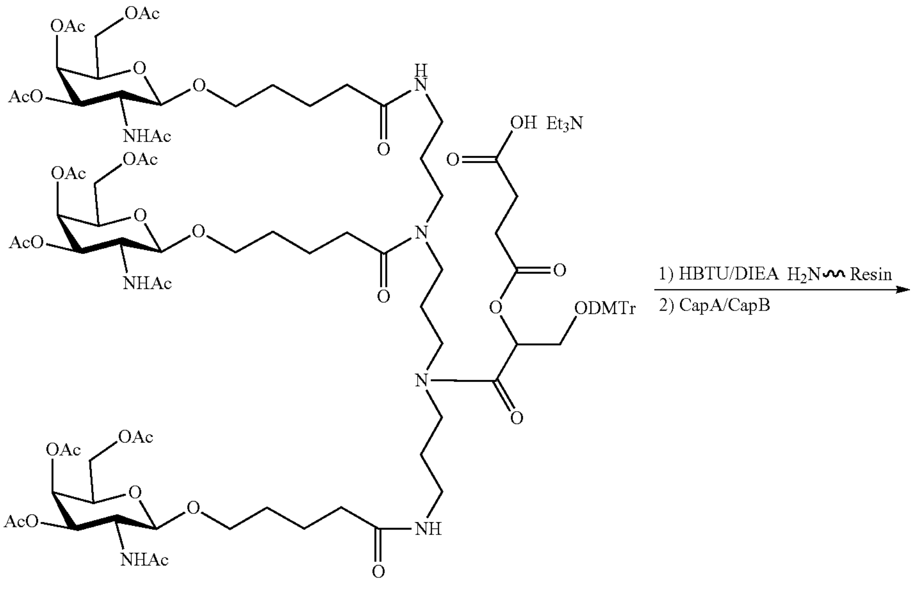

L-9

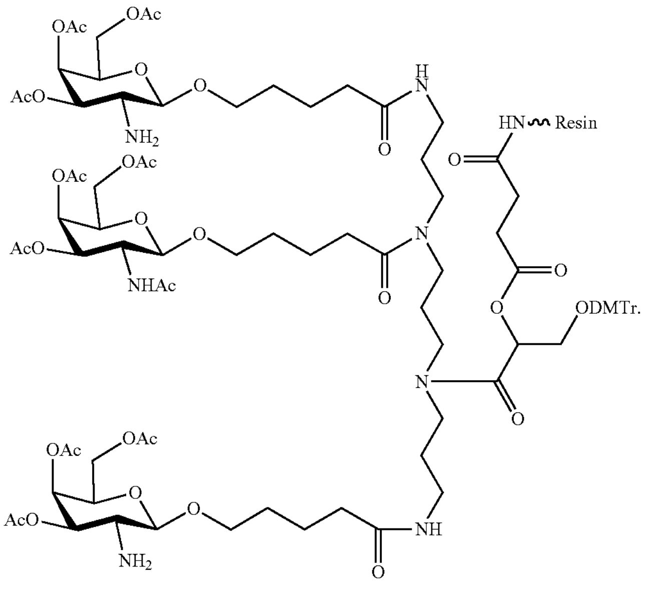

L-10

In this step, a compound L-10 was prepared by linking the L-9 conjugating molecule to a solid phase support.

The L-9 conjugating molecule (0.233 g, 0.1126 mmol) obtained in step (1-1-8), 0-benzotriazol-tetramethyluronium hexafluorophosphate (HBTU, 0.064 g, 0.1689 mmol) and diisopropylethylamine (DIPEA, 0.029 g, 0.2252 mmol) were mixed and dissolved in 19 ml of acetonitrile, and stirred at room temperature for 5 minutes. The resultant reaction solution was added with Aminomethyl resin (H2NResin, 0.901 g, 100-200 mesh, amino loading: 400 μmol/g, purchased from Tianjin Nankai HECHENG S&T Co., Ltd.). A reaction was performed on a shaker at 25° C. and 220 rpm/min for 15 hours, and the reaction mixture was filtered. The residue was rinsed twice (each with 30 ml of DCM), three times (each with 30 ml of acetonitrile), and once (with 30 ml of ethyl ether), and dried in a vacuum oil pump for 2 hours. Then starting materials (CapA, CapB, 4-dimethylaminopyridine (DMAP) and acetonitrile) were added according to the charge ratios shown in Table 3 for a capping reaction. The reaction was performed on a shaker at 25° C. and 200 rpm/min for 5 hours. The reaction solution was filtered. The residue was rinsed three times, each with 30 ml of acetonitrile, subjected to suction filtration to dryness, and dried overnight under a reduced pressure in a vacuum oil pump to give 1.100 g of compound L-10 (i.e., L-9 conjugating molecule linked to a solid phase support), with a loading of 90.8 μmol/g.

TABLE 3

The charge ratios of capping reaction

| Starting Materials | Amount | Specs | Lot No. | Manufacturer |
|---|---|---|---|---|
| CapA | 20 ml | — | — | — |
| CapB | 2.3 ml | — | — | — |
| DMAP | 0.01 g | analytical pure | I1422139 | Aladdin |
| acetonitrile | 2.3 ml | spectroscopic pure | O15161001 | CINC (Shanghai) Co., Ltd |

In the above table, CapA and CapB are solutions of capping agents. CapA is a solution of 20% by volume of N-methylimidazole in a mixture of pyridine/acetonitrile, wherein the volume ratio of pyridine to acetonitrile is 3:5. CapB is a solution of 20% by volume of acetic anhydride in acetonitrile.

In the following synthesis, the sequences of the sense strand and antisense strand correspond to S Sequence and AS Sequence of Conjugate 1 as shown in Table 4, respectively.

(2-2) Synthesis of a Sense Strand

Nucleoside monomers were linked one by one in 3' to 5' direction according to the arrangement sequence of nucleotides in the sense strand by the phosphoramidite solid phase synthesis method, starting the cycles from the Compound L-10 prepared in the above step. The linking of each nucleoside monomer included a four-step reaction of deprotection, coupling, capping, and oxidation or sulfurization. Therein, when two nucleotides is linked via a phosphoester linkage, a four-step reaction of deprotection, coupling, capping, and oxidation was included during linking of the later nucleoside monomer; and when two nucleotides is linked via a phosphorothioate linkage, a four-step reaction of deprotection, coupling, capping, and sulfurization was included during linking of the later nucleoside monomer. The conditions of the above reactions were the same as those used for the synthesis of the sense strand in Preparation Example 1 as described above.

(2-3) Synthesis of an Antisense Strand

An antisense strand AS of Conjugate 1 was synthesized by starting the cycles using a universal solid phase support (UnyLinker™ loaded NittoPhase®HL Solid Supports, Kinovate Life Sciences Inc.) via the phosphoramidite solid phase synthesis method. The reaction conditions of deprotection, coupling, capping, oxidation or sulfurization, cleavage, deprotection, purification and desalination in the solid phase synthesis method were the same as those used for the synthesis of the antisense strand in Preparation Example 1 as described above.

After completion of the synthesis, for the sense strand and antisense strand synthesized above, the purity was determined by ion exchange chromatography (IEX-HPLC), and the molecular weight was analyzed by LC-MS. The measured molecular weight values were compared with the calculated values for validating the synthesized sense strand and antisense strand.

(2-4) Synthesis of Conjugate A1

The S strand and AS strand were respectively dissolved in water for injection to give a solution of 40 mg/m. They are mixed at an equimolar ratio, heated at 50° C. for 15 min, and then cooled at room temperature, such that they could form a double stranded structure via hydrogen bonds. The conjugate was diluted to a concentration of 0.2 mg/mL with ultra-pure water (prepared by Milli-Q ultra-pure water instrument, with resistivity of 18.2MΩ*cm (25° C.)). The molecular weight was measured by LC-MS instrument (purchased from Waters Corp., model: LCT Premier). As a result, the calculated values of the molecular weight for S and AS were 7516.37 and 7061.57 respectively, and the measured values thereof were 7516.6 and 7060.49 respectively. Since the measured values were in conformity with the calculated values, it was indicated that the target Conjugate A1 with a structure as shown by Formula (403) was obtained.

Preparation Example 3 Preparation of the Conjugates of the Present Disclosure and Comparative Conjugates Conjugates A2-A7, B1-B2, C2, C12-C13, D2, D12-D13, E1-E4, F1-F3, G1-G3 and Comparative Conjugates A2, C1, D1, E1, F1, G1 listed in Tables 4A-4G were synthesized by using the same methods as those in Preparation Example 2, and it is expected that Conjugates A8-A11, B3-B7, C1, C3, D1, D3, E5-E9, F4-F11, G4-G9 listed in Tables 4A-4G can be prepared, except that: the siRNA sequences of these conjugates were the corresponding sequences shown in Tables 4A-4G, respectively. After completion of the synthesis, the resultant conjugates were confirmed by using the same detection methods as those in Preparation Example 2.

Conjugate A2: Calculated values S:7516.37, AS:7065.58, Measured values S:7516.6, AS:7064.5;

Conjugate A3: Calculated values S:7504.34, AS:7139.68, Measured values S:7515.6, AS:7138.9;

Conjugate A4: Calculated values S:7516.37, AS:7081.64, Measured values S:7515.6, AS:7080.9;

Conjugate A5: Calculated values S:8218.83, AS:7703.05, Measured values S:8218, AS:7702.5;

Conjugate A6: Calculated values S:7516.37, AS:6985.58, Measured values S:7516.5, AS:6984.9;

Conjugate B1: Calculated values S:7407.22, AS:7208.77, Measured values S:7406.4, AS:7208.1;

Conjugate B2: Calculated values S:7407.22, AS:7170.72, Measured values S:7406.5, AS:7170.1, Conjugate C2: Calculated values S:7485.3, AS:7161.7, Measured values S:7484.4, AS:7160.9;

Conjugate D2: Calculated values S:7423.22, AS:7207.78, Measured values S:7422.6, AS:7207.2;

Conjugate F2: Calculated values S:7649.55, AS:6995.47, Measured values S:7648.8, AS:6994.8;

Conjugate F3: Calculated values S:7649.55, AS:7011.53, Measured values S:7648.8, AS:7010.9;

Conjugate E1: Calculated values S:7584.5, AS:7007.46, Measured values S:7584, AS:7006.2;

Conjugate E2: Calculated values S:7584.5, AS:7011.47, Measured values S:7584, AS:7011.3;

Conjugate E4: Calculated values S:7572.47, AS:6907.41, Measured values S:7571.8, AS:6906.9;

Since the measured values of the molecular weight are in conformity with the calculated values, it is indicated that the target conjugates are obtained. These conjugates all have a structure as shown by Formula (403).

Table 4 siRNA conjugates

TABLE 4A

| Example | No | | Sequence Direction: 5'-3' | SEQ ID NO |
|---|---|---|---|---|
| Conjugate A1 | L10-siHBa1M1SVP | S | CmsCmsUmUmGmAmGfGfCfAmUmAmCm UmUmCmAmAmAm | 153 |
| | | AS | VP-UmsUfsUmGmAmAfGmUmAmUmGmC mCmUfCmAfAmGmGmsUmsUm | 154 |
| Conjugate A2 | L10-siHBa1M1SP | S | CmsCmsUmUmGmAmGfGfCfAmUmAmCm UmUmCmAmAmAm | 155 |
| | | AS | P-UmsUfsUmGmAmAfGmUmAmUmGmCm CmUfCmAfAmGmGmsUmsUm | 156 |
| Conjugate A3 | L10-siHBa1M1SPsT | S | CmsCmsUmUmGmAmGfGfCfAmUmAmCm UmUmCmAmAmAm | 157 |
| | | AS | Ps-TmsUfsUmGmAmAfGmUmAmUmGmCm CmUfCmAfAmGmGmsUmsUm | 158 |
| Conjugate A4 | L10-siHBa1M1SPs | S | CmsCmsUmUmGmAmGfGfCfAmUmAmCm UmUmCmAmAmAm | 159 |
| | | AS | Ps-UmsUfsUmGmAmAfGmUmAmUmGmCm CmUfCmAfAmGmGmsUmsUm | 160 |
| Conjugate A5 | L10-siHBa2M1S | S | GmsAmsCmCmUmUmGmAmGfGfCfAmUm AmCmUmUmCmAmAmAm | 161 |
| | | AS | UmsUfsUmGmAmAfGmUmAmUmGmCmC mUfCmAfAmGmGmUmCmsGmsGm | 162 |
| Conjugate A6 | L10-siHBa1M1S | S | CmsCmsUmUmGmAmGfGfCfAmUmAmCm UmUmCmAmAmAm | 163 |
| | | AS | UmsUfsUmGmAmAfGmUmAmUmGmCmC mUfCmAfAmGmGmsUmsUm | 164 |
| Conjugate A7 | L10-siHBa2M1SVP | S | GmsAmsCmCmUmUmGmAmGfGfCfAmUm AmCmUmUmCmAmAmAm | 165 |
| | | AS | VP-UmsUfsUmGmAmAfGmUmAmUmGmC mCmUfCmAfAmGmGmUmCmsGmsGm | 166 |
| Conjugate A8 | L10-siHBa1M1 | S | CmCmUmUmGmAmGfGfCfAmUmAmCmU mUmCmAmAmAm | 167 |
| | | AS | UmUfUmGmAmAfGmUmAmUmGmCmCm UfCmAfAmGmGmUmUm | 168 |
| Conjugate A9 | L10-siHBa2M1 | S | GmAmCmCmUmUmGmAmGfGfCfAmUmA mCmUmUmCmAmAmAm | 169 |
| | | AS | UmUfUmGmAmAfGmUmAmUmGmCmCm UfCmAfAmGmGmUmCmGmGm | 170 |
| Conjugate A10 | L10-siHBa1M1VP | S | CmCmUmUmGmAmGfGfCfAmUmAmCmU mUmCmAmAmAm | 171 |
| | | AS | VP-UmUfUmGmAmAfGmUmAmUmGmCm CmUfCmAfAmGmGmUmUm | 172 |
| Conjugate A11 | L10-siHBa2M1VP | S | GmAmCmCmUmUmGmAmGfGfCfAmUmA mCmUmUmCmAmAmAm | 173 |
| | | AS | VP-UmUfUmGmAmAfGmUmAmUmGmCm CmUfCmAfAmGmGmUmCmGmGm | 174 |
| Conjugate A12 | P10-siHBa1M1SVP | S | CmsCmsUmUmGmAmGfGfCfAmUmAmCm UmUmCmAmAmAm | 175 |
| | | AS | VP-UmsUfsUmGmAmAfGmUfAmUmGmCm CmUfCmAfAmGmGmsUmsUm | 176 |
| Conjugate A13 | R5-siHBa1M1SVP | S | CmCmUmUmGfAmGfGfCfAmUmAmCmUm UmCmAmAmAm | 177 |
| | | AS | VP-UmUfUmGmAmAfGmUfAfUmGmCmC mUfCmAfAmGmGmUmUm | 178 |
| Conjugate A14 | LA5-siHBa1M1SVP | S | CmsCmsUmUmGmAmGfGfCfAmUmAmCm UmUmCmAmAmAm | 179 |
| | | AS | VP-UmsUfsUmGmAmAfGmUmAmUmGmC mCmUfCmAfAmGmGmsUmsUm | 180 |
| Conjugate A15 | LB5-siHBa1M1SVP | S | CmCmUmUmGfAmGfGfCfAmUmAmCmUm UmCmAmAmAm | 181 |
| | | AS | VP-UmUfUmGmAmAfGmUfAfUmGmCmC mUfCmAfAmGmGmUmUm | 182 |

TABLE 4A-continued

| Example | No | | Sequence Direction: 5'-3' | SEQ ID NO |
|---|---|---|---|---|
| Conjugate A16 | V8-siHBa1M1SVP | S | CmCmUmUmGfAmGfGfCfAmUmAmCmUm UmCmAmAmAm | 183 |
| | | AS | VP-UmUfUmGmAmAfGmUfAfUmGmCmC mUfCmAfAmGmGmUmUm | 184 |
| Conjugate A17 | W8-siHBa1M1SVP | S | CmCmUmUmGfAmGfGfCfAmUmAmCmUm UmCmAmAmAm | 185 |
| | | AS | VP-UmUfUmGmAmAfGmUfAfUmGmCmC mUfCmAfAmGmGmUmUm | 186 |
| Conjugate A18 | X8-siHBa1M1SVP | S | CmCmUmUmGfAmGfGfCfAmUmAmCmUm UmCmAmAmAm | 187 |
| | | AS | VP-UmUfUmGmAmAfGmUfAfUmGmCmC mUfCmAfAmGmGmUmUm | 188 |
| Conjugate A19 | Z5-siHBa1M1SVP | S | CmCmUmUmGfAmGfGfCfAmUmAmCmUm UmCmAmAmAm | 189 |
| | | AS | VP-UmUfUmGmAmAfGmUfAfUmGmCmC mUfCmAfAmGmGmUmUm | 190 |
| Conjugate A20 | FIN-siHBa2M1SVP | S | GmsAmsCmCmUmUmGmAmGfGfCfAmUm AmCmUmUmCmAmAmAm | 191 |
| | | AS | VP-UmsUfsUmGmAmAfGmUmAmUmGmC mCmUfCmAfAmGmGmUmCmsGmsGm | 192 |
| Conjugate A21 | FIN-siHBa1M1SVP | S | CmsCmsUmUmGmAmGfGfCfAmUmAmCm UmUmCmAmAmAm | 193 |
| | | AS | VP-UmsUfsUmGmAmAfGmUmAmUmGmC mCmUfCmAfAmGmGmsUmsUm | 194 |
| Conjugate A22 | FIN-siHBa2M1S | S | GmsAmsCmCmUmUmGmAmGfGfCfAmUm AmCmUmUmCmAmAmAm | 195 |
| | | AS | UmsUfsUmGmAmAfGmUmAmUmGmCmC mUfCmAfAmGmGmUmCmsGmsGm | 196 |
| Conjugate A23 | FIN-siHBa1M1S (X2UR8 NON-VP) | S | CmsCmsUmUmGmAmGfGfCfAmUmAmCm UmUmCmAmAmAm | 197 |
| | | AS | UmsUfsUmGmAmAfGmUmAmUmGmCmC mUfCmAfAmGmGmsUmsUm | 198 |
| Comparative Conjugate A1 | FIN-siHBa1M3 | S | CmCmUmUmGAGGCmAUmACmUmUmCm AAAdT-S-dT | 199 |
| | | AS | UfUmUfGAAGUfAUGCCUfCAAGGdT-S-dT | 200 |
| Comparative Conjugate A2 | L10-siHBa1M2SVP | S | CmsCmsUmUmGfAmGfGfCfAmUmAmCmU mUmCmAmAmAm | 201 |
| | | AS | VP-UmsUfsUmGmAmAfGmUfAfUmGmCm CmUfCmAfAmGmGmsUmsUm | 202 |
| Comparative Conjugate A3 | AD-66810 | S | GmsUmsGmUmGfCmAfCfUfUmCmGmCmU mUmCmAmCmAm | 203 |
| | | AS | UmsGfsUmGmAmAfGmCfGfAmAmGmUmG fCmAfCmAmCmsUmsUm | 204 |

TABLE 4B

| Conjugate | No | | Sequence Direction: 5'-3' | SEQ ID NO |
|---|---|---|---|---|
| Conjugate B1 | L10-siHBb1M1SVP | S | UmsGmsCmUmAmUmGfCfCfUmCmAmUm CmUmUmCmUmAm | 205 |
| | | AS | UmsAfsGmAmAmGfAmUmGmAmGmGmC mAfUmAfGmCmAmsGmsCm | 206 |
| Conjugate B2 | L10-siHBb2M1SVP | S | UmsGmsCmUmAmUmGfCfCfUmCmAmUm CmUmUmCmUmAm | 207 |
| | | AS | UmsAfsGmAmAmGfAmUmGmAmGmGmC mAfUmAfGmCmAmsUmsUm | 208 |
| Conjugate B3 | L10-siHBb1M1S | S | UmGmCmUmAfUmGfCfCfUmCmAmUmCm UmUmCmUmAm | 209 |
| | | AS | UmAfGmAmAmGfAmUfGfAmGmGmCmAf UmAfGmCmAmGmCm | 210 |

TABLE 4B-continued

| Conjugate | No | | Sequence Direction: 5'-3' | SEQ ID NO |
|---|---|---|---|---|
| Conjugate B4 | L10-siHBb2M1S | S | UmGmCmUmAfUmGfCfCfUmCmAmUmCm UmUmCmUmAm | 211 |
| | | AS | UmAfGmAmAmGfAmUfGfAmGmGmCmAf UmAfGmCmAmUmUm | 212 |
| Conjugate B5 | L10-siHBb4M1SVP | S | GmsCmsUmGmCmUmAmUmGfCfCfUmCm AmUmCmUmUmCmUmAm | 213 |
| | | AS | VP-UmsAfsGmAmAmGfAmUmGmAmGmG mCmAfUmAfGmCmAmGmCmsGmsCm | 214 |
| Conjugate B6 | L10-siHBb1M1SP | S | UmsGmsCmUmAmUmGfCfCfUmCmAmUm CmUmUmCmUmAm | 215 |
| | | AS | VP-UmsAfsGmAmAmGfAmUmGmAmGmG mCmAfUmAfGmCmAmsUmsUm | 216 |
| Conjugate B7 | L10-siHBb1M1SPs | S | UmsGmsCmUmAmUmGfCfCfUmCmAmUm CmUmUmCmUmAm | 217 |
| | | AS | VP-UmsAfsGmAmAmGfAmUmGmAmGmG mCmAfUmAfGmCmAmsUmsUm | 218 |
| Conjugate B8 | P10-siHBb2M1SVP | S | UmsGmsCmUmAmUmGfCfCfUmCmAmUm CmUmUmCmUmAm | 219 |
| | | AS | VP-UmsAfsGmAmAmGfAmUmGmAmGmG mCmAfUmAfGmCmAmsUmsUm | 220 |
| Conjugate B9 | R5-siHBb2M1SVP | S | UmsGmsCmUmAmUmGfCfCfUmCmAmUm CmUmUmCmUmAm | 221 |
| | | AS | VP-UmsAfsGmAmAmGfAmUmGmAmGmG mCmAfUmAfGmCmAmsUmsUm | 222 |
| Conjugate B10 | LA5-siHBb2M1SVP | S | UmsGmsCmUmAmUmGfCfCfUmCmAmUm CmUmUmCmUmAm | 223 |
| | | AS | VP-UmsAfsGmAmAmGfAmUmGmAmGmG mCmAfUmAfGmCmAmsUmsUm | 224 |
| Conjugate B11 | LB5-siHBb2M1SVP | S | UmsGmsCmUmAmUmGfCfCfUmCmAmUm CmUmUmCmUmAm | 225 |
| | | AS | VP-UmsAfsGmAmAmGfAmUmGmAmGmG mCmAfUmAfGmCmAmsUmsUm | 226 |
| Conjugate B12 | V8-siHBb2M1SVP | S | UmsGmsCmUmAmUmGfCfCfUmCmAmUm CmUmUmCmUmAm | 227 |
| | | AS | VP-UmsAfsGmAmAmGfAmUmGmAmGmG mCmAfUmAfGmCmAmsUmsUm | 228 |
| Conjugate B13 | W8-siHBb2M1SVP | S | UmsGmsCmUmAmUmGfCfCfUmCmAmUm CmUmUmCmUmAm | 229 |
| | | AS | VP-UmsAfsGmAmAmGfAmUmGmAmGmG mCmAfUmAfGmCmAmsUmsUm | 230 |
| Conjugate B14 | X8-siHBb2M1SVP | S | UmsGmsCmUmAmUmGfCfCfUmCmAmUm CmUmUmCmUmAm | 231 |
| | | AS | VP-UmsAfsGmAmAmGfAmUmGmAmGmG mCmAfUmAfGmCmAmsUmsUm | 232 |
| Conjugate B15 | Z5-siHBb2M1SVP | S | UmsGmsCmUmAmUmGfCfCfUmCmAmUm CmUmUmCmUmAm | 233 |
| | | AS | VP-UmsAfsGmAmAmGfAmUmGmAmGmG mCmAfUmAfGmCmAmsUmsUm | 234 |
| Conjugate B16 | FIN-siHBb1M1SVP | S | UmsGmsCmUmAmUmGfCfCfUmCmAmUmC mUmUmCmUmAm | 235 |
| | | AS | VP-UmsAfsGmAmAmGfAmUmGmAmGmGm CmAfUmAfGmCmAmsGmsCm | 236 |
| Conjugate B17 | FIN-siHBb2M1SVP | S | UmsGmsCmUmAmUmGfCfCfUmCmAmUmC mUmUmCmUmAm | 237 |
| | | AS | VP-UmsAfsGmAmAmGfAmUmGmAmGmGm CmAfUmAfGmCmAmsUmsUm | 238 |
| Comparative Conjugate B1 | FIN-NC | S | UUCUCCGAACGUGUCACGU | 239 |
| | | AS | ACGUGACACGUUCGGAGAAUU | 240 |

TABLE 4C

| Conjugate | No | | Sequence direction 5'-3' | SEQ NO NO |
|---|---|---|---|---|
| Conjugate C1 | L10-siHBc1M1 | S | UmCmUmGmUmGmCfCfUfUmCmUmCmAmUmCm UmGmAm | 241 |
| | | AS | UmCfAmGmAmUfGmAmGmAmAmGmGmCfAmCf AmGmAmCmGm | 242 |
| Conjugate C2 | L10-siHBc1M1SVP | S | UmsCmsUmGmUmGmCfCfUfUmCmUmCmAmUmC mUmGmAm | 243 |
| | | AS | VP-UmsCfsAmGmAmUfGmAmGmAmAmGmGmCf AmCfAmGmAmsCmsGm | 244 |
| Conjugate C3 | L10-siHBc2M1SVP | S | CmsGmsUmCmUmGmUmGmCfCfUfUmCmUmCmA mUmCmUmGmAm | 245 |
| | | AS | VP-UmsCfsAmGmAmUfGmAfGfAmAmGmGmCfA mCfAmGmAmsCmsGmGmGm | 246 |
| Conjugate C4 | P10-siHBc1M1SVP | S | UmsCmsUmGmUmGmCfCfUfUmCmUmCmAmUmC mUmGmAm | 247 |
| | | AS | VP-UmsCfsAmGmAmUfGmAmGmAmAmGmGmCf AmCfAmGmAmsCmsGm | 248 |
| Conjugate C5 | R5-siHBc1M1SVP | S | UmsCmsUmGmUmGmCfCfUfUmCmUmCmAmUmC mUmGmAm | 249 |
| | | AS | VP-UmsCfsAmGmAmUfGmAmGmAmAmGmGmCf AmCfAmGmAmsCmsGm | 250 |
| Conjugate C6 | LA5-siHBc1M1SVP | S | UmsCmsUmGmUmGmCfCfUfUmCmUmCmAmUmC mUmGmAm | 251 |
| | | AS | VP-UmsCfsAmGmAmUfGmAmGmAmAmGmGmCf AmCfAmGmAmsCmsGm | 252 |
| Conjugate C7 | LB5-siHBc1M1SVP | S | UmsCmsUmGmUmGmCfCfUfUmCmUmCmAmUmC mUmGmAm | 253 |
| | | AS | VP-UmsCfsAmGmAmUfGmAmGmAmAmGmGmCf AmCfAmGmAmsCmsGm | 254 |
| Conjugate C8 | V8-siHBc1M1SVP | S | UmsCmsUmGmUmGmCfCfUfUmCmUmCmAmUmC mUmGmAm | 255 |
| | | AS | VP-UmsCfsAmGmAmUfGmAmGmAmAmGmGmCf AmCfAmGmAmsCmsGm | 256 |
| Conjugate C9 | W8-siHBc1M1SVP | S | UmsCmsUmGmUmGmCfCfUfUmCmUmCmAmUmC mUmGmAm | 257 |
| | | AS | VP-UmsCfsAmGmAmUfGmAmGmAmAmGmGmCf AmCfAmGmAmsCmsGm | 258 |
| Conjugate C10 | X8-siHBc1M1SVP | S | UmsCmsUmGmUmGmCfCfUfUmCmUmCmAmUmC mUmGmAm | 259 |
| | | AS | VP-UmsCfsAmGmAmUfGmAmGmAmAmGmGmCf AmCfAmGmAmsCmsGm | 260 |
| Conjugate C11 | Z5-siHBc1M1SVP | S | UmsCmsUmGmUmGmCfCfUfUmCmUmCmAmUmC mUmGmAm | 261 |
| | | AS | VP-UmsCfsAmGmAmUfGmAmGmAmAmGmGmCf AmCfAmGmAmsCmsGm | 262 |
| Conjugate C12 | L10-siHBc1M1SP | S | UmsCmsUmGmUmGmCfCfUfUmCmUmCmAmUmC mUmGmAm | 263 |
| | | AS | P-UmsCfsAmGmAmUfGmAmGmAmAmGmGmCfA mCfAmGmAmsCmsGm | 264 |
| Conjugate C13 | L10-siHBc1M1SPs | S | UmsCmsUmGmUmGmCfCfUfUmCmUmCmAmUmC mUmGmAm | 265 |
| | | AS | Ps-UmsCfsAmGmAmUfGmAmGmAmamGmGmCfA mCfAmGmAmsCmsGm | 266 |
| Conjugate C14 | FIN-siHBc1M1SVP | S | UmsCmsUmGmUmGmCfCfUfUmCmUmCmAmUmC mUmGmAm | 267 |
| | | AS | VP-UmsCfsAmGmAmUfGmAmGmAmAmGmGmCf AmCfAmGmAmsCmsGm | 268 |
| Comparative Conjugate C1 | L10-NC | S | GUGUGCACUUCGCUUCACA | 269 |
| | | AS | UGUGAAGCGAAGUGCACACUU | 270 |

TABLE 4D

| Conjugate | No | | Sequence Direction 5'-3' | SEQ ID NO |
|---|---|---|---|---|
| Conjugate D1 | L10-SiHBd1M1 | S | CmGmUmGmUmGmCfAfCfUmUmCmGmCmUmUmCmAmAm | 271 |
| | | AS | UmUfGmAmAmGfCmGmAmAmGmUmGmCfAmCfAmCmGmGmUm | 272 |
| Conjugate D2 | L10-SiHBd1M1SVP | S | CmsGmsUmGmUmGmCfAfCfUmUmCmGmCmUmUmCmAmAm | 273 |
| | | AS | VP-UmsUfsGmAmAmGfCmGmAmAmGmUmGmCfAmCfAmCmGmsGmsUm | 274 |
| Conjugate D3 | L10-SiHBd2M1SVP | S | AmsCmsCmGmUmGmUmGmCfAfCfUmUmCmGmCmUmUmCmAmAm | 275 |
| | | AS | VP-UmsUfsGmAmAmGfCmGmAmAmGmUmGmCfAmCfAmCmGmGmUmsCmsCm | 276 |
| Conjugate D4 | P10-siHBd1M1SVP | S | CmsGmsUmGmUmGmCfAfCfUmUmCmGmCmUmUmCmAmAm | 277 |
| | | AS | VP-UmsUfsGmAmAmGfCmGmAmAmGmUmGmCfAmCfAmCmGmsGmsUm | 278 |
| Conjugate D5 | R5-s1HBd1M1SVP | S | CmsGmsUmGmUmGmCfAfCfUmUmCmGmCmUmUmCmAmAm | 279 |
| | | AS | VP-UmsUfsGmAmAmGfCmGmAmAmGmUmGmCfAmCmAmCmGmsGmsUm | 280 |
| Conjugate D6 | LA5-siHBd1M1SVP | S | CmsGmsUmGmUmGmCfAfCfUmUmCmGmCmUmUmCmAmAm | 281 |
| | | AS | VP-UmsUfsGmAmAmGfCmGmAmAmGmUmGmCfAmCfAmCmGmsGmsUm | 282 |
| Conjugate D7 | LB5-siHBd1M1SVP | S | CmsGmsUmGmUmGmCfAfCfUmUmCmGmCmUmUmCmAmAm | 283 |
| | | AS | VP-UmsUfsGmAmAmGfCmGmAmAmGmUmGmCfAmCfAmCmGmsGmsUm | 284 |
| Conjugate D8 | V8-siHBd1M1SVP | S | CmsGmsUmGmUmGmCfAfCfUmUmCmGmCmUmUmCmAmAm | 285 |
| | | AS | VP-UmsUfsGmAmAmGfCmGmAmAmGmUmGmCfAmCfAmCmGmsGmsUm | 286 |
| Conjugate D9 | W8-siHBd1M1SVP | S | CmsGmsUmGmUmGmCfAfCfUmUmCmGmCmUmUmCmAmAm | 287 |
| | | AS | VP-UmsUfsGmAmAmGfCmGmAmAmGmUmGmCfAmCfAmCmGmsGmsUm | 288 |
| Conjugate D10 | X8-siHBd1M1SVP | S | CmsGmsUmGmUmGmCfAfCfUmUmCmGmCmUmUmCmAmAm | 289 |
| | | AS | VP-UmsUfsGmAmAmGfCmGmAmAmGmUmGmCfAmCfAmCmGmsGmsUm | 290 |
| Conjugate D11 | Z5-siHBd1M1SVP | S | CmsGmsUmGmUmGmCfAfCfUmUmCmGmCmUmUmCmAmAm | 291 |
| | | AS | VP-UmsUfsGmAmAmGfCmGmAmAmGmUmGmCfAmCfAmCmGmsGmsUm | 292 |
| Conjugate D12 | L10-siHBd1M1SP | S | CmsGmsUmGmUmGmCfAfCfUmUmCmGmCmUmUmCmAmAm | 293 |
| | | AS | P-UmsUfsGmAmAmGfCmGmAmAmGmUmGmCfAmCfAmCmGmsGmsUm | 294 |
| Conjugate D13 | L10-siHBd1M1SPs | S | CmsGmsUmGmUmGmCfAfCfUmUmCmGmCmUmUmCmAmAm | 295 |
| | | AS | Ps-UmsUfsGmAmAmGfCmGmAmAmGmUmGmCfAmCfAmCmGmsGmsUm | 296 |
| Conjugate D14 | FIN-siHBd1M1SVP | S | CmsGmsUmGmUmGmCfAfCfUmUmCmGmCmUmUmCmAmAm | 297 |
| | | AS | VP-UmsUfsGmAmAmGfCmGmAmAmGmUmGmCfAmCfAmCmGmsGmsUm | 298 |
| Comparative Conjugate D1 | L10-NC | S | GUGUGCACUUCGCUUCACA | 299 |
| | | AS | UGUGAAGCGAAGUGCACACU | 300 |

TABLE 4E

| Conjugate | No | | Sequence Direction 5'-3' | SEQ ID NO |
|---|---|---|---|---|
| Conjugate E1 | L10-siAN1M3SVP | S | CmsCmsAmAmGmAmGfCfAfCmCmAmAmGmAmAmCmUmAm | 301 |
| | | AS | VP-UmsAfsGmUmUmCfUmUmGmGmUmGmCmUfCmUfUmGmGmsCmsUm | 302 |
| Conjugate E2 | L10-siAN1M3SP | S | CmsCmsAmAmGmAmGfCfAfCmCmAmAmGmAmAmCmUmAm | 303 |
| | | AS | P-UmsAfsGmUmUmCfUmUmGmGmUmGmCmUfCmUfUmGmGmsCmsUm | 304 |
| Conjugate E3 | L10-siAN1M3SPs | S | CmsCmsAmAmGmAmGfCfAfCmCmAmAmGmAmAmCmUmAm | 305 |
| | | AS | Ps-UmsAfsGmUmUmCfUmUmGmGmUmGmCmUfCmUfUmGmGmsCmsUm | 306 |
| Conjugate E4 | L10-siAN1M3S | S | CmsCmsAmAmGmAmGfCfAfCmCmAmAmGmAmAmCmUmAm | 307 |
| | | AS | UmsAfsGmUmUmCfUmUmGmGmUmGmCmUfCmUfUmGmGmsCmsUm | 308 |
| Conjugate E5 | L10-siAN1M3VP | S | CmCmAmAmGmAmGfCfAfCmCmAmAmGmAmAmCmUmAm | 309 |
| | | AS | VP-UmAfGmUmUmCfUmUmGmGmUmGmCmUfCmUfUmGmGmCmUm | 310 |
| Conjugate E6 | L10-siAN2M2S | S | AmsGmsCmCmAmAmGfAmGfCfAfCmCmAmAmGmAmAmCmUmAm | 311 |
| | | AS | UmsAfsGmUmUmCfUmUmGmGmUmGmCmUfCmUfUmGmGmCmUmsUmsGm | 312 |
| Conjugate E7 | L10-siAN2M1SVP | S | AmsGmsCmCmAmAmGfAmGfCfAfCmCmAmAmGmAmAmCmUmAm | 313 |
| | | AS | VP-UmsAfsGmUmUmCfUmUfGfGmUmGmCmUfCmUfUmGmGmCmUmsUmsGm | 314 |
| Conjugate E8 | L10-siAN1M2SVP | S | CmsGmsAmAmGfAmGfCfAfCmCmAmAmGm | 315 |

TABLE 4E-continued

| Conjugate | No | | Sequence Direction 5'-3' | SEQ ID NO |
|---|---|---|---|---|
| | | | AmAmCmUmAm | |
| | | AS | VP-UmsAfsGmUmUmCfUmUmGmGmUmGmCmUfCmUfUmGmGmsCmsUm | 316 |
| Conjugate E9 | L10-siAN2M3SVP | S | AmsGmsCmCmAmAmGmAmGfCfAfCmCmAmAmGmAmAmCmUmAm | 317 |
| | | AS | VP-UmsAfsGmUmUmCfUmUmGmGmUmGmCmUfCmUfUmGmGmCmUmsUmsGm | 318 |
| Conjugate E10 | P10-siAN1MASVP | S | CmsCmsAmAmGmAmGfCfAfCmCmAmAmGmAmAmCmUmAm | 319 |
| | | AS | VP-UmsAfsGmUmUmCfUmUmGmGmUmGmCmUfCmUmGmGmsCmsUm | 320 |
| Conjugate E11 | R5-siAN1M3SVP | S | CmsCmsAmAmGmAmGfCfAfCmCmAmAmGmAmAmCmUmAm | 321 |
| | | AS | VP-UmsAfsGmUmUmCfUmUmGmGmUmGmCmUfCmUfUmGmGmsCmsUm | 322 |
| Conjugate E12 | LA5-siAN1M3SVP | S | CmsCmsAmAmGmAmGfCfAfCmCmAmAmGmAmAmCmUmAm | 323 |
| | | AS | VP-UmsAfsGmUmUmCfUmUmGmGmUmGmCmUfCmUfUmGmGmsCmsUm | 324 |
| Conjugate E13 | LB5-siAN1M3SVP | S | CmsCmsAmAmGmAmGfCfAfCmCmAmAmGmAmAmCmUmAm | 325 |
| | | AS | VP-UmsAfsGmUmUmCfUmUmGmGmUmGmCmUfCmUfUmGmGmsCmsUm | 326 |
| Conjugate E14 | V8-siAN1M3SVP | S | CmsCmsAmAmGmAmGfCfAfCmCmAmAmGmAmAmCmUmAm | 327 |
| | | AS | VP-UmsAfsGmUmUmCfUmUmGmGmUmGmCmUfCmUfUmGmGmsCmsUm | 328 |
| Conjugate E15 | W8-siAN1M3SVP | S | CmsCmsAmAmGmAmGfCfAfCmCmAmAmGmAmAmCmUmAm | 329 |
| | | AS | VP-UmsAfsGmUmUmCfUmUmGmGmUmGmC | 330 |

TABLE 4E-continued

| Conjugate | No | | Sequence Direction 5'-3' | SEQ ID NO |
|---|---|---|---|---|
| | | | mUfCmUfUmG mGmsCmsUm | |
| Conjugate E16 | X8-siAN1M3SVP | S | CmsCmsAmAm GmAmGfCfAf CmCmAmAmGm AmAmCmUmAm | 331 |
| | | AS | VP-UmsAfsG mUmUmCfUmU mGmGmUmGmC mUfCmUfUmG mGmsCmsUm | 332 |
| Conjugate E17 | Z5-siAN1M3SVP | S | CmsCmsAmAm GmAmGfCfAf CmCmAmAmGm AmAmCmUmAm | 333 |
| | | AS | VP-UmsAfsG mUmUmCfUmU mGmGmUmGmC mUfCmUfUmG mGmsCmsUm | 334 |
| Conjugate E18 | FIN-siAN1M3SVP | S | CmsCmsAmAm GmAmGfCfAf CmCmAmAmGm AmAmCmUmAm | 335 |
| | | AS | VP-UmsAfsG mUmUmCfUmU mGmGmUmGmC mUfCmUfUmG mGmsCmsUm | 336 |
| Conjugate E19 | FIN-siAN2M3SVP | S | AmsGmsCmCm AmAmGmAmGf CfAfCmCmAm AmGmAmAmCm UmAm | 337 |
| | | AS | VP-UmsAfsG mUmUmCfUmU mGmGmUmGmC mUfCmUfUmG mGmCmUmsUm sGm | 338 |
| Conjugate E20 | FIN-siAN1M3S | S | CmsCmsAmAm GmAmGfCfAf CmCmAmAmGm AmAmCmUmAm | 339 |
| | | AS | UmsAfsGmUm UmCfUmUmGm GmUmGmCmUf CmUfUmGmGm sCmsUm | 340 |
| Comparative Conjugate E1 | L10-siHBV X1M1SVP | S | CmsCmsUmUm GfAmGfGfCf AmUmAmCmUm UmCmAmAmAm | 341 |
| | | AS | VP-UmsUfsU mGmAmAfGmU fAfUmGmCmC mUfCmAfAmG mGmsUmsUm | 342 |
| Comparative Conjugate E2 | (GalNAc)$_3$-65695 | S | AmsCmsAmUm AmUmUfUmGf AfUfCmAmGm UmCmUmUmUm UmUm | 343 |
| | | AS | AmsAfsAmAm AmGfAmCmUm GmAmUmCmAf AmAfUmAmUm GmUmsUmsGm | 344 |

TABLE 4F

| Conjugate | No | | Sequence Direction: 5'-3' | SEQ ID NO |
|---|---|---|---|---|
| Conjugate F1 | L10-siAP1M2SVP | S | CmsAmsAmUm AmAmAfGfCf UmGmGmAmCm AmAmGmAmAm | 345 |
| | | AS | VP-UmsUfsC mUmUmGfUmC mCmAmGmCmU mUfUmAfUmU mGmsGmsGm | 346 |
| Conjugate F2 | L10-siAP1M2SP | S | CmsAmsAmUm AmAmAfGfCf UmGmGmAmCm AmAmGmAmAm | 347 |
| | | AS | P-UmsUfsCm UmUmGfUmCm CmAmGmCmUm UfUmAfUmUm GmsGmsGm | 348 |
| Conjugate F3 | L10-siAP1M2SPs | S | CmsAmsAmUm AmAmAfGfCf UmGmGmAmCm AmAmGmAmAm | 349 |
| | | AS | Ps-UmsUfsC mUmUmGfUmC mCmAmGmCmU mUfUmAfUmU mGmsGmsGm | 350 |
| Conjugate F4 | L10-siAP1M2 | S | CmAmAmUmAm AmAfGfCfUm GmGmAmCmAm AmGmAmAm | 351 |
| | | AS | UmUfCmUmUm GfUmCmCmAm GmCmUmUfUm AfUmUmGmGm Gm | 352 |
| Conjugate F5 | L10-siAP2M2 | S | CmCmCmAmAm UmAmAmAfGf CfUmGmGmAm CmAmAmGmAm Am | 353 |
| | | AS | UmUfCmUmUm GfUmCmCmAm GmCmUmUfUm AfUmUmGmGm GmAmGm | 354 |
| Conjugate F6 | L10-siAP1M2VP | S | CmAmAmUmAm AmAfGfCfUm GmGmAmCmAm AmGmAmAm | 355 |
| | | AS | VP-UmUfCmU mUmGfUmCmC mAmGmCmUmU fCmAfUmUmG mGmGm | 356 |
| Conjugate F7 | L10-siAP2M2VP | S | CmCmCmAmAm UmAmAmAfGf CfUmGmGmAm CmAmAmGmAm Am | 357 |
| | | AS | VP-UmUfCmC mUmGfUmCmC mAmGmCmUmU fUmAfUmUmG mGmGmAmGm | 358 |
| Conjugate F8 | L10-SiAP1M2S | S | CmsAmsAmUm AmAmAfGfCf UmGmGmAmCm AmAmGmAmAm | 359 |

TABLE 4F-continued

| Conjugate | No | | Sequence Direction: 5'-3' | SEQ ID NO |
|---|---|---|---|---|
| | | AS | UmsUfsCmUmUmGfUmCmCmAmGmCmUmUfUmAfUmUmGmsGmsGm | 360 |
| Conjugate F9 | L10-siAP2M2S | S | CmsCmsCmAmAmUmAmAmAfGfCfUmGmGmAmCmAmAmGmAmAm | 361 |
| | | AS | UmsUfsCmUmUmGfUmCmCmAmGmCmUmUfUmAfUmUmGmGmGmsAmsGm | 362 |
| Conjugate F10 | L10-SiAP1M2SVP | S | CmsAmsAmUmAmAmAfGfCfUmGmGmAmCmAmAmGmAmAm | 363 |
| | | AS | VP-UmsUfsCmUmUmGfUmCmCmAmGmCmUmUfUmAfUmUmGmsGmsGm | 364 |
| Conjugate F11 | L10-siAP2M2SVP | S | CmsCmsCmAmAmCmAmAmAfGfCfUmGmGmAmCmAmAmGmAmAm | 365 |
| | | AS | VP-UmsUfsCmUmUmGfUmCmCmAmGmCmUmUfUmAfUmUmGmGmGmsAmsGm | 366 |
| Conjugate F12 | P10-siAP1M2SVP | S | CmsAmsAmUmAmAmAfGfCfUmGmGmAmCmAmAmGmAmAm | 367 |
| | | AS | VP-UmsUfsCmUmUmGfUmCmCmAmGmCmUmUfUmAfUmUmGmsGmsGm | 368 |
| Conjugate F13 | R5-siAP1M2SVP | S | CmsAmsAmUmAmAmAfGfCfUmGmGmAmCmAmAmGmAmAm | 369 |
| | | AS | VP-UmsUfsCmUmUmGfUmCmCmAmGmCmUmUfUmAfUmUmGmsGmsGm | 370 |
| Conjugate F14 | LA5-siAP1M2SVP | S | CmsAmsAmUmAmAmAfGfCfUmGmCmAmCmAmAmGmAmAm | 371 |
| | | AS | VP-UmsUfsCmUmUmGfUmCmCmAmGmCmUmUfUmAfUmUmGmsGmsGm | 372 |
| Conjugate F15 | LB5-siAP1M2SVP | S | CmsAmsAmUmAmAmAfGfCfUmGmGmAmCmAmAmGmAmAm | 373 |
| | | AS | VP-UmsUfsCmUmUmGfUmCmCmAmGmCmUmUfUmAfUmUmGmsGmsGm | 374 |
| Conjugate F16 | V8-siAP1M2SVP | S | CmsAmsAmUmAmAmAfGfCfUmGmGmAmCmAmAmGmAmAm | 375 |
| | | AS | VP-UmsUfsCmUmUmGfUmCmCmAmGmCmUmUfUmAfUmUmGmsGmsGm | 376 |
| Conjugate F17 | W8-siAP1M2SVP | S | CmsAmsAmUmAmAmAfGfCfUmGmGmAmCmAmAmGmAmAm | 377 |
| | | AS | VP-UmsUfsCmUmUmGfUmCmCmAmGmCmUmUfUmAfUmUmGmsGmsGm | 378 |
| Conjugate F18 | X8-siAP1M2SVP | S | CmsAmsAmUmAmAmAfGfCfUmGmGmAmCmAmAmGmAmAm | 379 |
| | | AS | VP-UmsUfsCmUmUmGfUmCmCmAmGmCmUmUfUmAfUmUmGmsGmsGm | 380 |
| Conjugate F19 | Z5-siAP1M2SYP | S | CmsAmsAmUmAmAmAfGfCfUmGmGmAmCmAmAmGmAmAm | 381 |
| | | AS | VP-UmsUfsCmUmUmGfUmCmCmAmGmCmUmUfUmAfUmUmGmsGmsGm | 382 |
| Conjugate F20 | FIN-siAP2M2S | S | CmsCmsCmAmAmUmAmAmAfGfCfUmGmGmAmCmAmAmGmAmAm | 383 |
| | | AS | UmsUfsCmUmUmGfUmCmCmAmGmCmUmUfUmAfUmUmGmGmGmsAmsGm | 384 |
| Comparative Conjugate F1 | L10-siHBV X1M1SVP | S | CmsCmsUmUmGfAmGfGfCfAmUmAmCmUmUmCmAmAmAm | 385 |
| | | AS | VPUmsUfsUmGmAmAfGmUfAfUmGmCmCmUfCmAfAmGmGmsUmsUm | 386 |
| Comparative Conjugate F2 | (GalNAc)$_3$-69535 | S | GmsCmsUmUmAmAmAmAmGfGmGfAmCmAmGmUmAmUmUmCmAm | 387 |
| | | AS | UmsGfsAmAmUmAmCmUmGmUmCmCfCmUf | 388 |

TABLE 4F-continued

| Conjugate | No | | Sequence Direction: 5'-3' | SEQ ID NO |
|---|---|---|---|---|
| | | | UmUmUmAmAm GmCmsAmsAm | |

TABLE 4G

| Conjugate | No | | Sequence Direction: 5'-3' | SEQ ID NO |
|---|---|---|---|---|
| Conjugate G1 | L10-siHB3M1SVP | S | GmsAmsAmAm GmUmAfUfGf UmCmAmAmCm GmAmAmUmAm | 389 |
| | | AS | VP-UmsAfsU mUmCmGfUmU mGmAmCmAmU mAfCmUfUmU mCmsUmsUm | 390 |
| Conjugate G2 | L10-siHB3M1SP | S | GmsAmsAmAm GmUmAfUfGf UmCmAmAmCm GmAmAmUmAm | 391 |
| | | AS | P-UmsAfsUm UmCmGfUmUm GmAmCmAmCm AfCmUfUmUm CmsUmsUm | 392 |
| Conjugate G3 | L10-siHB3M1SPs | S | GmsAmsAmAm GmUmAfUfGf UmCmAmAmCm GmAmAmUmAm | 393 |
| | | AS | Ps-UmsAfsU mUmCmGfUmU mGmAmCmAmU mAfCmUfUmU mCmsUmsUm | 394 |
| Conjugate G4 | L10-siHB3M1VP | S | GmAmAmAmGm UmAfUfGfUm CmAmAmCmGm AmAmUmAm | 395 |
| | | AS | VP-UmAfUmU mCmGfUmUmG mAmCmAmUmA fCmUfUmUmC mUmUm | 396 |
| Conjugate G5 | L10-siHB3M1P | S | GmAmAmAmGm UmAfUfGfUm CmAmAmCmGm AmAmUmAm | 397 |
| | | AS | P-UmAfUmUm CmGfUmUmGm AmCmAmUmAf CmUfUmUmCm UmUm | 398 |
| Conjugate G6 | L10-siHB3M1 | S | GmAmAmAmGm UmAfUfGfUm CmAmAmCmGm AmAmUmAm | 399 |
| | | AS | UmAfUmUmCm GfUmUmGmAm CmAmUmAfCm UfUmUmCmUm Um | 400 |
| Conjugate G7 | L10-siHB3M1S | S | GmsAmsAmAm GmUmAfUfGf UmCmAmAmCm GmAmAmUmAm | 401 |

TABLE 4G-continued

| Conjugate | No | | Sequence Direction: 5'-3' | SEQ ID NO |
|---|---|---|---|---|
| | | AS | UmsAfsUmUm CmGfUmUmGm AmCmAmUmAf CmUfUmUmCm sUmsUm | 402 |
| Conjugate G8 | L10-siHB2M1SP | S | GmsAmsAmAm GmUmAfUfGfU mCmAmAmCmG mAmAmUmUm | 403 |
| | | AS | P-AmsAfsUm UmCmGfUmUm GmAmCmAmUm AfCmUfUmUm CmsCmsAm | 404 |
| Conjugate G9 | L10-siHB5M1SVP | S | UmsGmsGmAm AmAmGmUmAf UfGfUmCmAm AmCmGmAmAm UmAm | 405 |
| | | AS | VP-UmsAfsU mUmCmGfUmU mGmAmCmAmU mAf CmUfUmUmCm CmAmsUmsUm | 406 |
| Conjugate G10 | P10-siHB3M1SVP | S | GmsAmsAmAm GmUmAfUfGfU mCmAmAmCmG mAmAmUmAm | 407 |
| | | AS | VP-UmsAfsU mUmCmGfUmU mGmAmCmAmU mAfCmUfUmU mCmsUmsUm | 408 |
| Conjugate G11 | R5-siHB3M1SVP | S | GmsAmsAmAm GmUmAfUfGf UmCmAmAmCm GmAmAmUmAm | 409 |
| | | AS | VP-UmsAfsU mUmCmGfUmU mGmAmCmAmU mAfCmUfUmU mCmsUmsUm | 410 |
| Conjugate G12 | LA5-siHB3M1SVP | S | GmsAmsAmAm GmUmAfUfGf UmCmAmAmCm GmAmAmUmAm | 411 |
| | | AS | VP-UmsAfsU mUmCmGfUmU mGmAmCmAmU mAfCmUfUmU mCmsUmsUm | 412 |
| Conjugate G13 | LB5-siHB3M1SVP | S | GmsAmsAmAm GmUmAfUfGfUm CmAmAmCmGm AmAmUmAm | 413 |
| | | AS | VP-UmsAfsU mUmCmGfUmU mGmAmCmAmU mAfCmUfUmU mCmsUmsUm | 414 |
| Conjugate G14 | V8-siHB3M1SVP | S | GmsAmsAmAm GmUmAfUfGf UmCmAmAmCm GmAmAmUmAm | 415 |
| | | AS | VP-UmsAfsU mUmCmGfUmU mGmAmCmAmU mAfCmUfUmU mCmsUmsUm | 416 |

TABLE 4G-continued

| Conjugate | No | | Sequence Direction: 5'-3' | SEQ ID NO |
|---|---|---|---|---|
| Conjugate G15 | W8-siHB3M1SVP | S | GmsAmsAmAm GmUmAfUfGf UmCmAmAmCm GmAmAmUmAm | 417 |
| | | AS | VP-UmsAfsU mUmCmGfUmU mGmAmCmAmU mAfCmUfUmU mCmsUmsUm | 418 |
| Conjugate G16 | X8-siHB3M1SVP | S | GmsAmsAmAm GmUmAfUfGf UmCmAmAmCm GmAmAmUmAm | 419 |
| | | AS | VP-UmsAfsU mUmCmGfUmUm GmAmCmAmUm AfCmUfUmUm CmsUmsUm | 420 |
| Conjugate G17 | Z5-siHB3M1SVP | S | GmsAmsAmAm GmUmAfUfGf UmCmAmAmCm GmAmAmUmAm | 421 |
| | | AS | VP-UmsAfsU mUmCmGfUmU mGmAmCmAmU mAfCmUfUmU mCmsUmsUm | 422 |
| Comparative Conjugate G1 | NC | S | UUCUCCGAAC GUGUCACGU | 423 |
| | | AS | ACGUGACACG UUCGGAGAAU U | 424 |

*S: sense strand; AS: antisense strand

Note:

C, G, U, and A represents the base components of the nucleotides; m represents that the nucleotide adjacent to the left side of the letter m is a 2'-methoxy modified nucleotide; f represents that the nucleotide adjacent to the left side of the letter f is a 2'-fluoro modified nucleotide; s represents that the two nucleotides adjacent to both sides of the letter s are linked by a phosphorothioate linkage; VP represents that the nucleotide adjacent to the right side of the letter VP is a vinyl phosphate modified nucleotide; P represents that the nucleotide adjacent to the right side of the letter P is a phosphate nucleotide; Ps represents that the nucleotide adjacent to the right side of the letters Ps is a phosphorothioate modified nucleotide.

In the following Preparation Examples 4-12, various conjugating molecules were synthesized and were respectively used to replace Compound L-10 in Preparation Example 2; and it is expected that Conjugates A12-A19, B8-B15, C4-C11, D4-D11, E10-E17, F12-F19, and G10-G17 listed in Tables 4A-4G can be prepared based on the corresponding sequences listed in Tables 4A-4G.

Preparation Example 4 Preparation of P10 Conjugates

In this Preparation Example, it is expected that Conjugates A12, B8, C4, D4, E10, F12 and G10 (hereinafter referred to as P-10 Conjugates) can be synthesized according to the following process.

(4-1) Synthesis of P-10 Compounds

P-10 Compounds were synthesized according to the following process:

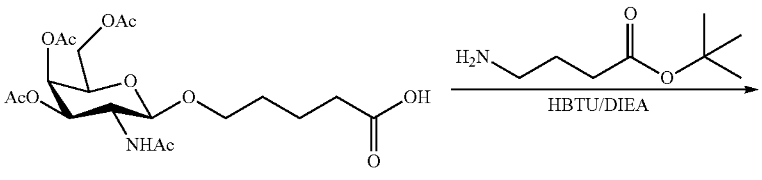

GAL-5

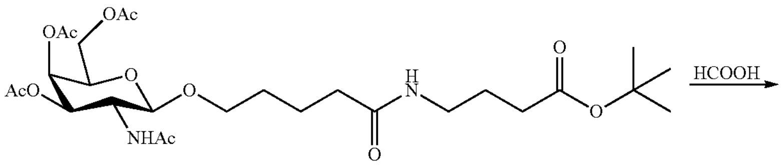

GAL5-C4-1

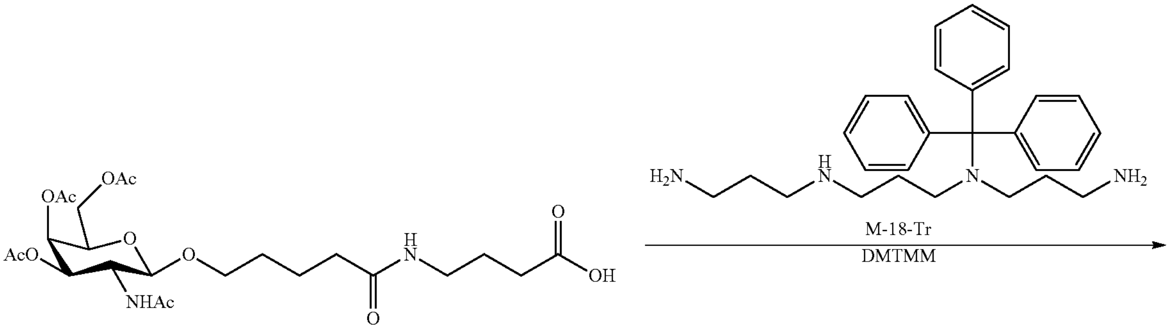

GAL5-C4-2

-continued
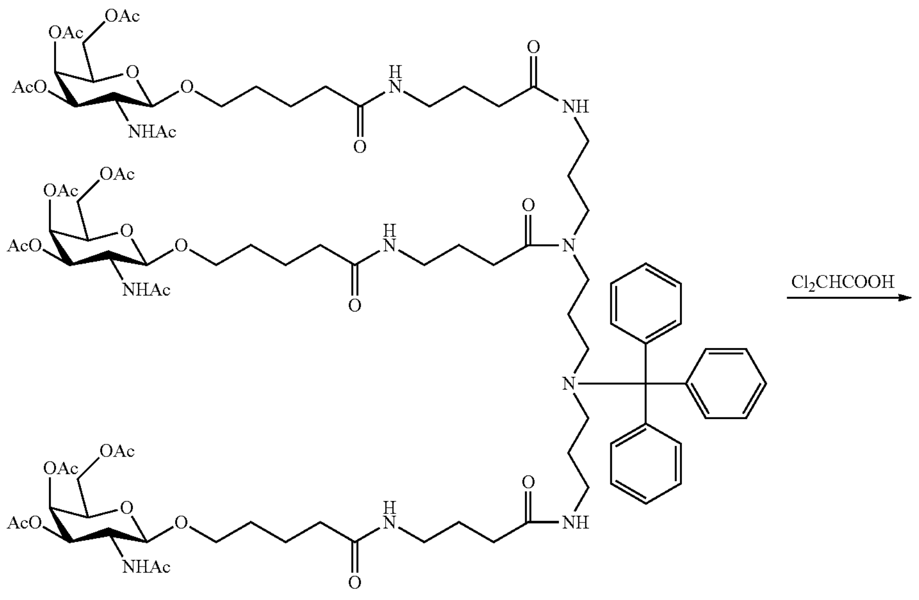
P-6
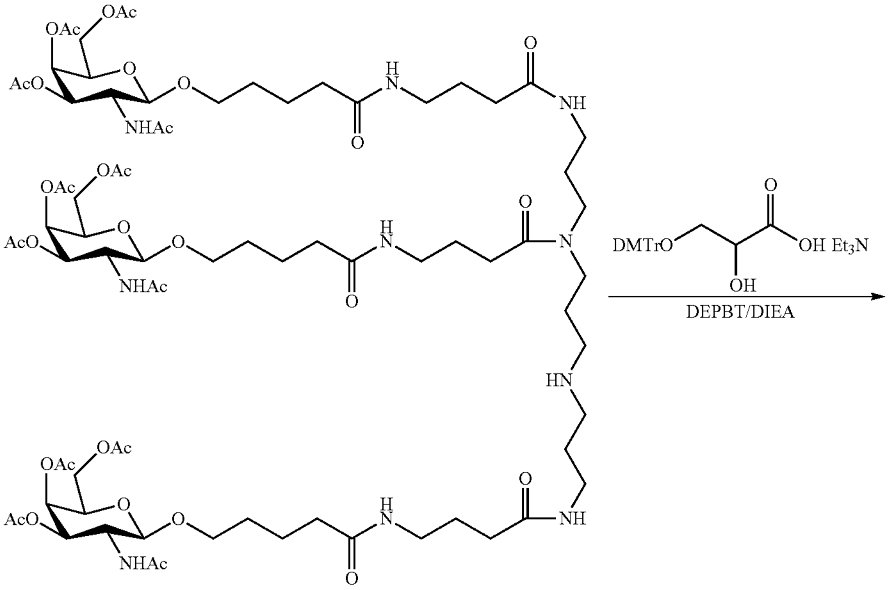
P-7

-continued
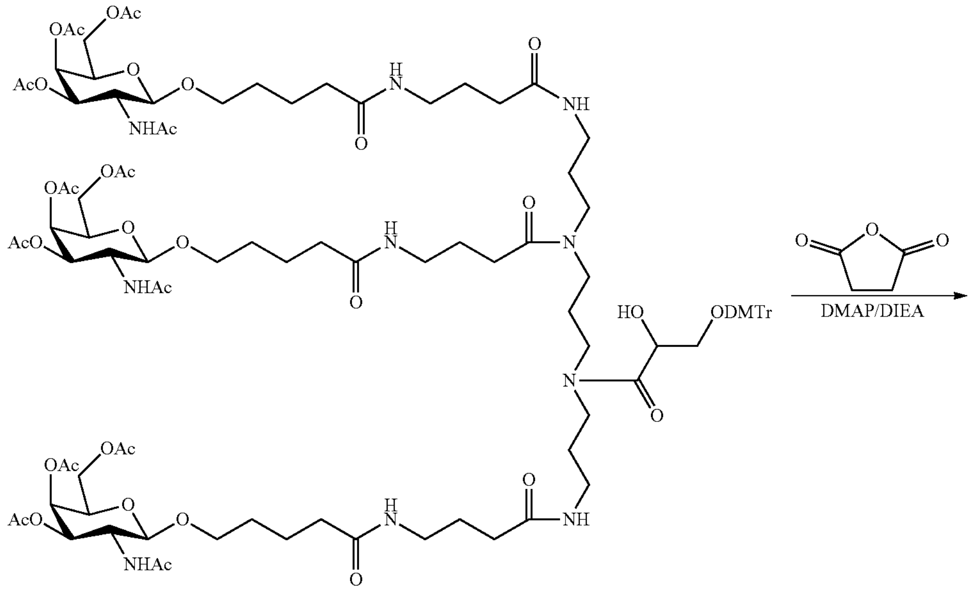
P-8
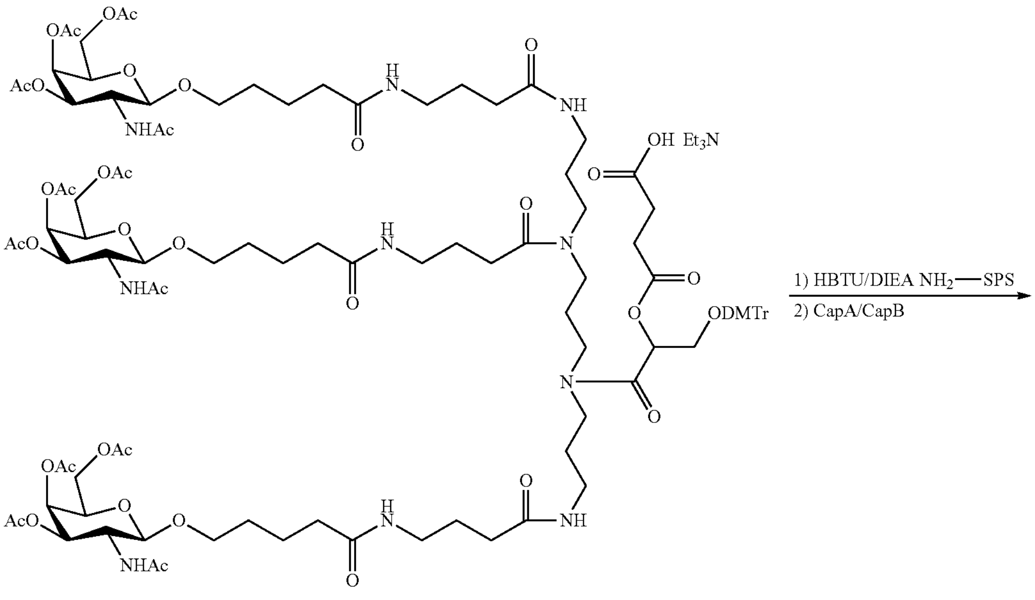
P-9

-continued

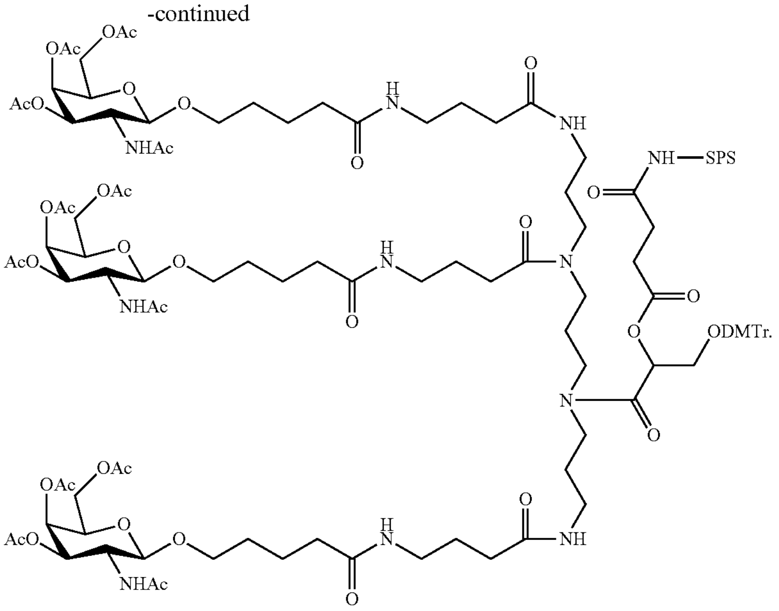

P-10

(4-1-1) Synthesis of GAL5-C4-1

GAL-5 (13.43 g, 30.0 mmol) obtained according to the method described in step (2-1-1) above, t-butyl 4-aminobutyrate hydrochloride (5.87 g, 30.0 mmol), O-benzotriazol-tetramethyluronium hexafluorophosphate (13.65 g, 36.0 mmol) and diisopropylethylamine (11.63 g, 90.0 mmol) were added into 40 ml of N,N-dimethylformamide, dissolved homogeneously and then stirred at room temperature to react for 5 hours. The resultant reaction solution was added with 300 ml of saturated aqueous sodium bicarbonate solution, extracted three times, each with 200 ml of ethyl acetate. All organic phases were combined and washed once with 200 ml of saturated brine. The organic phase was isolated and dried with anhydrous sodium sulfate. The solvent was removed by evaporation under reduced pressure to dryness to give 30.3 g of crude product GAL5-C4-1 as oil, which was directly used in the next reaction.

(4-1-2) Synthesis of GAL5-C4-2

The crude product GAL5-C4-1 (30.3 g, 30 mmol) obtained in step (4-1-1) was dissolved in 180 ml of formic acid and stirred at room temperature to react for 16 hours. The solvent was evaporated to dryness. The residue was purified by column chromatography (200-300 mesh normal phase silica gel, with a gradient elution of dichloromethane: methanol=100:18-100:20). The eluate was collected and concentrated to remove the solvents to give a total of 14.84 g of the target product GAL5-C4-2.

(4-1-3) Synthesis of P-6:

M-18-Tr (2.02 g, 4.69 mmol) obtained according to the method described in step (2-1-4) and GAL5-C4-2 (8.24 g, 15.48 mmol) obtained in step (4-1-2) were mixed and dissolved in 47 ml of acetonitrile, added with N-methylmorpholine (3.13 g, 30.96 mmol) followed by 4-(4,6-dimethoxytriazin-2-yl)-4-methylmorpholine hydrochloride (DMTMM, 4.28 g, 15.48 mmol) to react under stirring at room temperature for 2 hours. The resultant reaction solution was diluted with 20 ml of dichloromethane. The resultant organic phase was washed with 10 ml of saturated sodium bicarbonate solution and 10 ml of saturated brine, respectively. All organic phases were combined, dried with anhydrous sodium sulfate, and filtered. The solvent was removed by evaporation under reduced pressure to give a crude product, which was purified by using a normal phase silica gel column (200-300 mesh). The column was packed with petroleum ether, added with 1 wt % triethylamine for neutralizing the acidity of silica gel, and eluted with a gradient elution of dichloromethane:methanol=100:5-100:7. The eluate was collected, and the solvent was removed by evaporation under reduced pressure to give a total of 8.27 g of pure product P-6.

(4-1-4) Synthesis of P-7:

P-6 (6.82 g, 3.456 mmol) obtained in step (4-1-3) above was dissolved in 69 ml of dichloromethane, and added with dichloroacetic acid (13.367 g, 103.67 mmol) to react at room temperature for 2 hours. The resultant reaction solution was diluted by adding 100 ml of dichloromethane, washed and adjusted to pH 7-8 with saturated sodium bicarbonate solution. The aqueous phase isolated was extracted six times, each with 30 ml of dichloromethane. All organic phases were combined, dried with anhydrous sodium sulfate, and filtered. Then the solvent was removed by evaporation under reduced pressure to give a crude product. The crude product was purified by using a normal phase silica gel column (200-300 mesh). The column was added with 10 wt % triethylamine for neutralizing the acidity of silica gel, equilibrated with 1 wt % triethylamine and eluted with a gradient elution of dichloromethane:methanol=100:30-100:40. The eluate was collected, and the solvent was removed by evaporation under reduced pressure to give a total of 4.82 g of P-7. MS m/z: $C_{78}$H127N10O33, [M+H]+, calculated: 1732.91, measured: 1735.73.

(4-1-5) Synthesis of P-8:

(A-1)

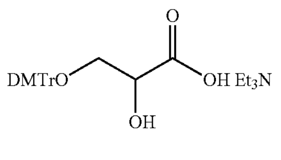

P-7 (2.653 g, 1.532 mmol) and A-1 (2.342 g, 4.596 mmol) were mixed and dissolved in 16 ml of dichloromethane, and added with 3-diethoxyphosphoryl-1,2,3-benzotrizin 4(3H)-one (DEPBT) (1.375 g, 4.596 mmol) followed by diisopropylethylamine (1.188 g, 9.191 mmol) to react under stirring at 25° C. for 2 hours. The organic phase was washed with 10 ml of saturated sodium bicarbonate. The aqueous phase isolated was extracted three times, each with 10 ml of dichloromethane. All organic phases were combined and washed with 10 ml of saturated brine. The aqueous phase isolated was extracted twice, each with 10 ml of dichloromethane, and the obtained organic phases were combined, dried with anhydrous sodium sulfate and filtered. The solvent was removed by evaporation under reduced pressure, and foam-dried in a vacuum oil pump overnight to give a crude product. The crude product was subjected to a column purification. The column was filled with 120 g normal phase silica gel (200-300 mesh), added with 20 ml triethylamine for neutralizing the acidity of silica gel, equilibrated with petroleum ether containing 1 wt % triethylamine and eluted with a gradient elution of petroleum ether:ethyl acetate: dichloromethane: N,N-dimethylformamide=1:1:1:0.5-1:1:1:0.6. The eluate was collected, and the solvent was removed by evaporation under reduced pressure to give a total of 2.793 g of pure product P-8.

(4-1-6) Synthesis of P-9:

P-8 (490 mg, 0.231 mmol), succinic anhydride (69 mg, 0.693 mmol) and 4-dimethylaminopyridine (DMAP, 68 mg, 0.554 mmol) were mixed and dissolved in 2.3 ml of dichloromethane, and added with diisopropylethylamine (DIEA, 149 mg, 1.155 mmol) to react under stirring at 25° C. for 21 hours. The resultant reaction solution was added with 50 ml dichloromethane for dilution and then washed with 100 ml of 0.5 M triethylamine phosphate. The aqueous phase isolated was extracted three times, each with 10 ml of dichloromethane. All organic phases were combined, and the solvent was removed by evaporation under reduced pressure to give a crude product. The crude product was subjected to a column purification. The column was filled with 80 g normal phase silica gel (200-300 mesh), added with 1 wt % triethylamine for neutralizing the acidity of silica gel and equilibrated with dichloromethane, and eluted with a gradient elution of dichloromethane containing 1 wt % triethylamine:methanol=100:18-100:20. The eluate was collected, and the solvent was removed by evaporation under reduced pressure to give a total of 200 mg of pure product P-9 conjugating molecule. MS m/z: C106H153N10O41, [M-DMTr]+, calculated: 1921.05, measured: 1920.97.

(4-1-7) Synthesis of P-10:

P-10 was prepared by using the same method as that in step (2-1-9) of Preparation Example 2, except that: P-9 conjugating molecule was used to replace L-9 conjugating molecule, thereby obtaining P-9 conjugating molecule linked to a solid phase support.

(4-2) Synthesis of P10 Conjugates

Conjugates were prepared by using the same methods as those in steps (2-2), (2-3A) and (2-4) of Preparation Example 2, except that P-10 Compound was used to replace L-10 Compound to start the synthesis of a sense strand. It is expected that Conjugates A12, B8, C4, D4, E10, F12 and G10 with a structure as shown by Formula (404) can be obtained.

Preparation Example 5 Preparation of R5 Conjugates

In this Preparation Example, Conjugates A13, B9, C5, D5, E11, F13 and G11 (hereinafter referred to as R5 Conjugates) can be synthesized by the following method.

(5-1) Synthesis of R-5 Compound

R-5 Compound was synthesized by the following method:

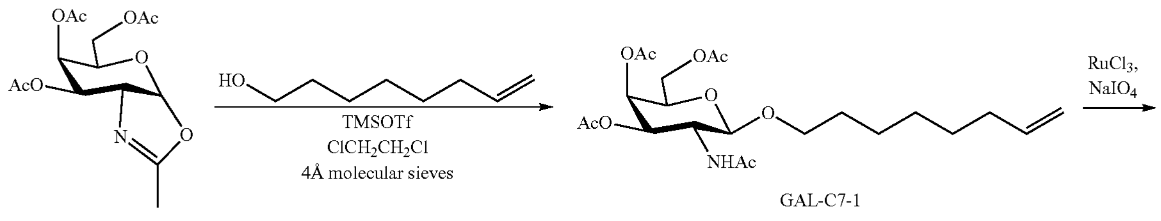

GAL-3

GAL-C7-1

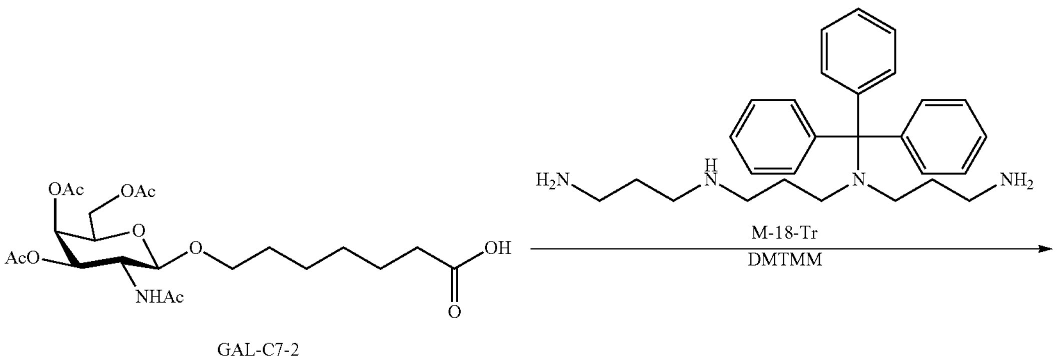

GAL-C7-2

-continued
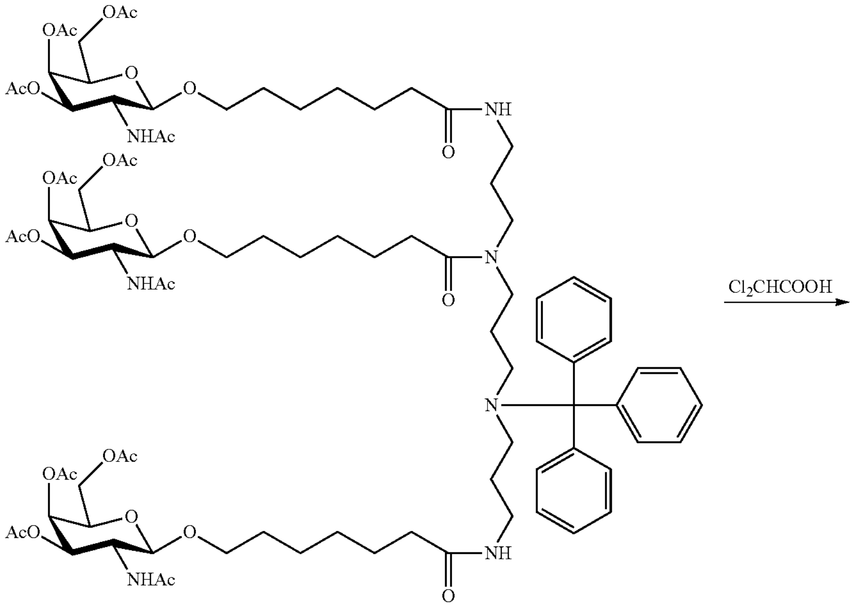
R-1
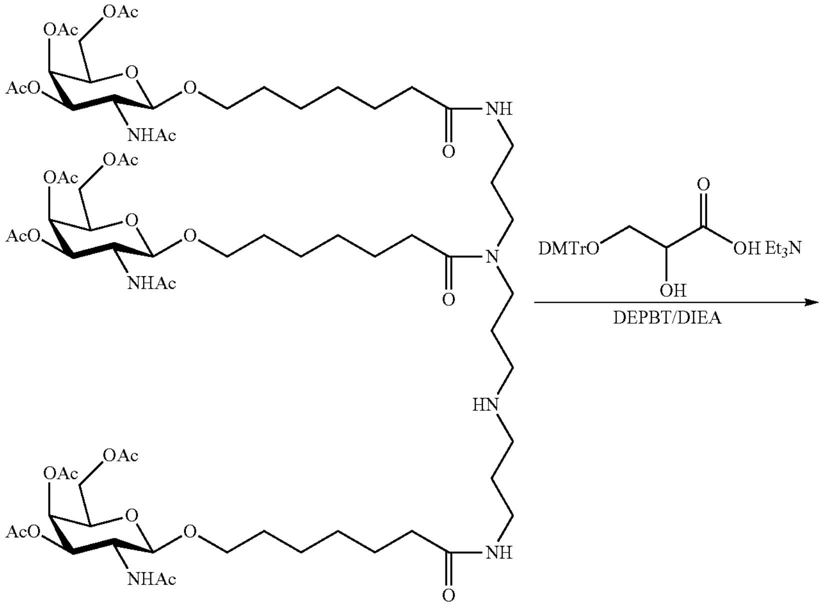
R-2

-continued
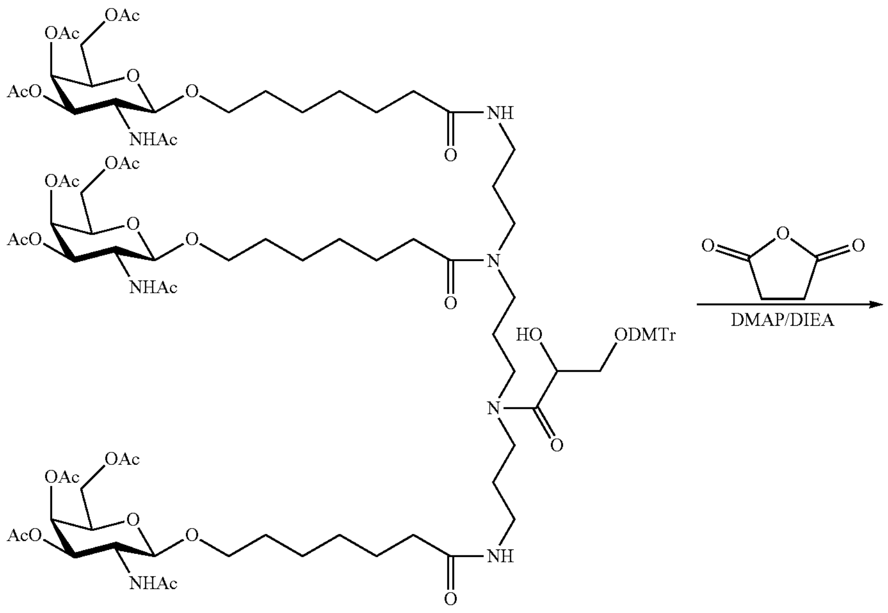
R-3
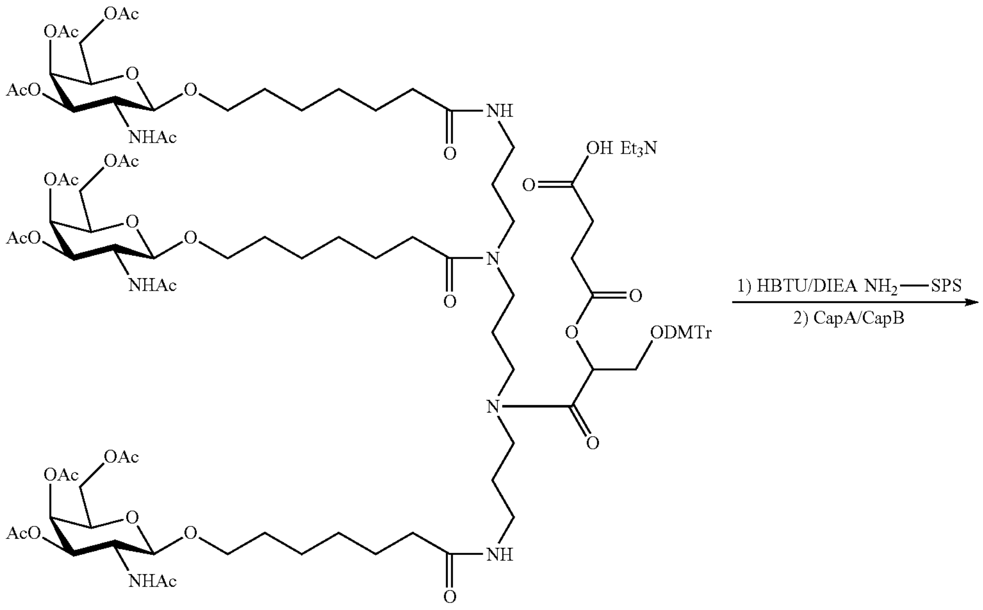
R-4

-continued

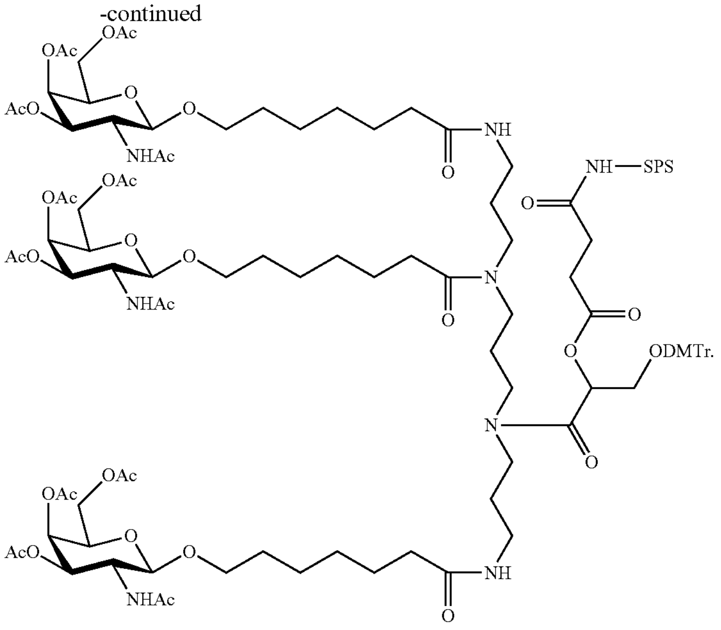

R-5

(5-1-1) Synthesis of GAL-C7-1

GAL-3 (26.4 g, 80.2 mmol) obtained according to the method described in step (2-1-1b) was dissolved in 134 ml of anhydrous 1,2-dichloroethane, and added with 60 g of 4 Å molecular sieve powder followed by 7-octen-1-ol (11.3 g, 88.2 mmol) to react under stirring at room temperature for 10 minutes. Trimethylsilyl trifluoromethanesulphonate (8.9 g, 40.1 mmol) was added in an ice bath and nitrogen atmosphere to react under stirring at room temperature for 24 hours. The 4 Å molecular sieve powder was removed by filtration. 500 ml of saturated aqueous sodium bicarbonate solution was added to the filtrate for washing. An organic phase was isolated. The aqueous phase was extracted once with 100 ml of dichloromethane. All organic phases were combined and washed once with 250 ml of saturated brine. The organic phase was isolated and dried with anhydrous sodium sulfate. The solvent was removed by evaporation under reduced pressure to dryness to give 33.3 g of product GAL-C7-1 as a yellow syrup, which was directly used in the next oxidation reaction without purification.

(5-1-2) Synthesis of GAL-C7-2

GAL-C7-1 (33.3 g, 72.8 mmol) obtained in step (5-1-1) was dissolved in a mixed solvent of 160 ml of dichloromethane and 160 ml of acetonitrile, added with 216 ml of water and solid sodium periodate (62.3 g, 291.2 mmol) respectively, stirred in an ice water bath for 10 minutes, and added with a catalyst ruthenium trichloride (498 mg, 2.4 mmol). The reaction was naturally warmed to room temperature and stirred for 23 hours. The resultant reaction solution was diluted by adding 200 ml of water under stirring, and adjusted to pH 7.5 by adding saturated sodium bicarbonate. The organic phase was solated and discarded. The aqueous phase was extracted three times, each with dichloromethane. The organic phases resulted from the extraction were discarded. The aqueous phase resulted from the extraction was adjusted to a pH of about 3 with citric acid solid and extracted three times, each with 200 ml of dichloromethane, and the resultant organic phases were combined and dried with anhydrous sodium sulfate. The solvent was removed by evaporation under reduced pressure, and then the residue was purified by column chromatography (200-300 mesh normal phase silica gel, with a gradient elution of dichloromethane:methanol=100:18-100:20) to give 22.4 g of product GAL-C7-2 as a white foamy solid. MS m/z: C21H32NO11, [M+H]+, calculated: 476.50, measured: 475.94.

(5-1-3) Synthesis of R-1:

M-18-Tr (2.02 g, 4.69 mmol) obtained according to the method described in step (2-1-4) and GAL-C7-2 (7.36 g, 15.48 mmol) were mixed and dissolved in 47 ml of acetonitrile, added with N-methylmorpholine (3.13 g, 30.96 mmol) followed by 4-(4,6-dimethoxytriazin-2-yl)-4-methylmorpholine hydrochloride (DMTMM, 4.28 g, 15.48 mmol) to react under stirring at room temperature for 2 hours. The resultant reaction solution was diluted with 200 ml of dichloromethane. The organic phase was washed with 100 ml of saturated sodium bicarbonate solution and 100 ml of saturated brine, respectively. All organic phases were combined, dried with anhydrous sodium sulfate, and filtered. The solvent was removed by evaporation under reduced pressure to give a crude product, which was purified by using a normal phase silica gel column (200-300 mesh). The column was packed with petroleum ether, added with 1 wt % triethylamine for neutralizing the acidity of silica gel, and eluted with a gradient elution of dichloromethane:methanol=100:5-100:7. The eluate was collected and the solvent was removed by evaporation under reduced pressure to give 7.82 g of pure product R-1.

(5-1-4) Synthesis of R-2:

R-1 (6.23 g, 3.456 mmol) was dissolved in 69 ml of dichloromethane, and added with dichloroacetic acid (13.367 g, 103.67 mmol) to react at room temperature for 2 hours. The resultant reaction solution was diluted by adding 100 ml of dichloromethane, washed and adjust to pH 7-8 with saturated sodium bicarbonate solution. The aqueous phase isolated was extracted six times, each with 30 ml of dichloromethane. All organic phases were combined, dried with anhydrous sodium sulfate, and filtered. Then the solvent was removed by evaporation under reduced pressure to give a crude product. The crude product was purified by using a normal phase silica gel column (200-300 mesh). The column was added with 10 wt % triethylamine for neutralizing the acidity of silica gel and equilibrated with 1 wt % triethylamine, and eluted with a gradient elution of dichloromethane:methanol=100:30-100:40. The solvent was removed by evaporation under reduced pressure to give 4.49 g of pure product R-2.

(5-1-5) Synthesis of R-3:

R-2 (2.391 g, 1.532 mmol) and A-1 (2.342 g, 4.596 mmol) were mixed and dissolved in 16 ml of dichloromethane, and added with 3-(diethoxyphosphoryloxy)-1,2,3-benzotrizin-4 (3H)-one (DEPBT, 1.375 g, 4.596 mmol) followed by diisopropylethylamine (1.188 g, 9.191 mmol) to react under stirring at 25° C. for 2 hours The organic phase was washed with 10 ml of saturated sodium bicarbonate. The aqueous phase isolated was extracted three times, each with 10 ml of dichloromethane. The organic phase was washed with 10 ml of saturated brine. The aqueous phase isolated was extracted twice, each with 10 ml of dichloromethane, and the obtained organic phases were combined, dried with anhydrous sodium sulfate and filtered. The solvent was removed by evaporation under reduced pressure, and the residue was foam-dried in a vacuum oil pump overnight to give a crude product. The crude product was subjected to a column purification. The column was filled with 120 g normal phase silica gel (200-300 mesh), added with 20 ml triethylamine for neutralizing the acidity of silica gel and equilibrated with petroleum ether containing 1 wt % triethylamine, and eluted with a gradient elution of petroleum ether:ethyl acetate: dichloromethane: N,N-dimethylformamide=1:1:1:0.5-1:1:1:0.6. The solvent was removed by evaporation under reduced pressure to give 2.642 g of pure product R-3.

(5-1-6) Synthesis of R-4:

R-3 (795 mg, 0.4074 mmol), succinic anhydride (82 mg, 0.8148 mmol) and 4-dimethylaminopyridine (DMAP, 100 mg, 0.8148 mmol) were mixed and dissolved in 4 ml of dichloromethane, and added with diisopropylethylamine (DIEA, 100 mg, 0.8148 mmol) to react under stirring at 25° C. for 18 hours. The resultant reaction solution was washed with 5 ml of 0.5 M triethylamine phosphate. The aqueous phase was extracted three times, each with 5 ml of dichloromethane. All organic phases were combined, and the solvent was removed by evaporation under reduced pressure to give a crude product. The crude product was subjected to a column purification. The column was filled with 30 g normal phase silica gel (200-300 mesh), added with 1 wt % triethylamine for neutralizing the acidity of silica gel and equilibrated with dichloromethane, and eluted with a gradient elution of dichloromethane containing 1 wt % triethylamine:methanol=100:18-100:20. The eluate was collected, and the solvent was removed by evaporation under reduced pressure to give 505 mg of pure product of R-4 conjugating molecule.

(5-1-7) Synthesis of R-5 Conjugating Molecule

R-5 was prepared by using the same method as that in step (2-1-9) of Preparation Example 2, except that: R-4 conjugating molecule was used to replace L-9 conjugating molecule, thereby obtaining R-4 conjugating molecule linked to a solid phase support.

(5-2) Synthesis of R5 Conjugates

R5 Conjugates were prepared by using the same methods as those in steps (2-2), (2-3A) and (2-4) of Preparation Example 2, except that R-5 Compound was used to replace L-10 Compound to start the synthesis of a sense strand. It is expected that Conjugates A13, B9, C5, D5, E11, F13 and G11 with a structure as shown by Formula (407) can be obtained.

Preparation Example 6 Preparation of LA-5 Conjugates

In this Preparation Example, Conjugates A14, B10, C6, D6, E12, F14 and G12 (hereinafter referred to as LA-5 Conjugates) can be synthesized by the following method.

It is expected that LA-5 Compounds can be synthesized by the following process route:

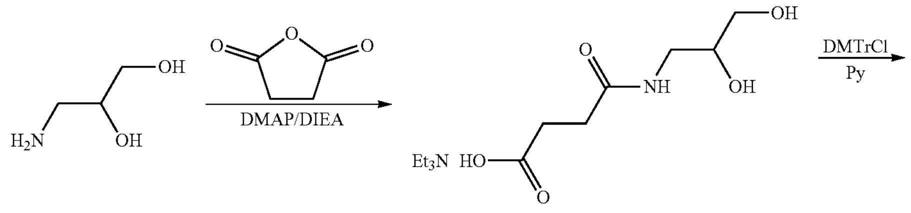

LA-1

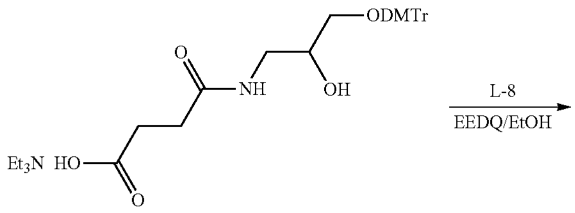

LA-2

-continued
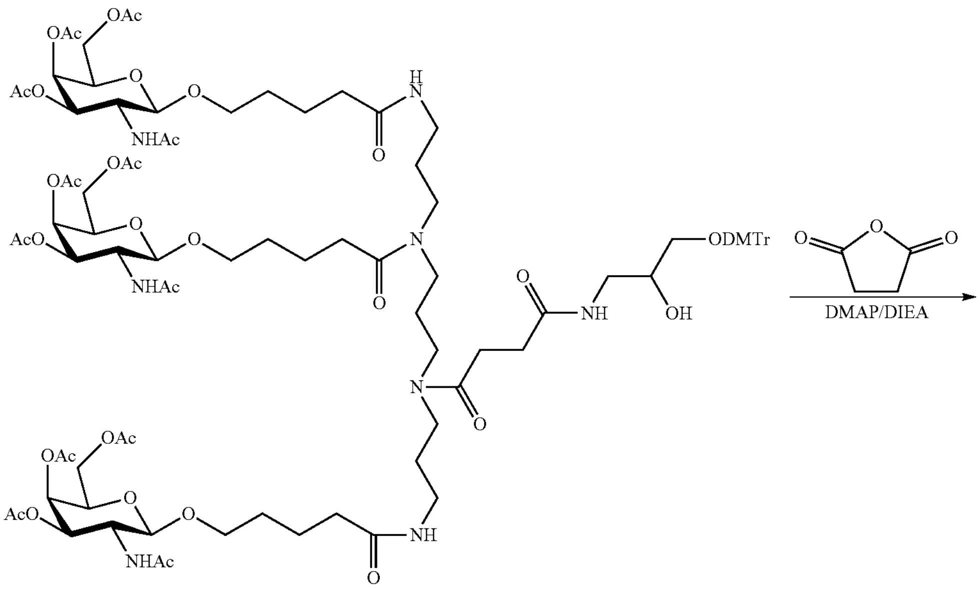
LA-3
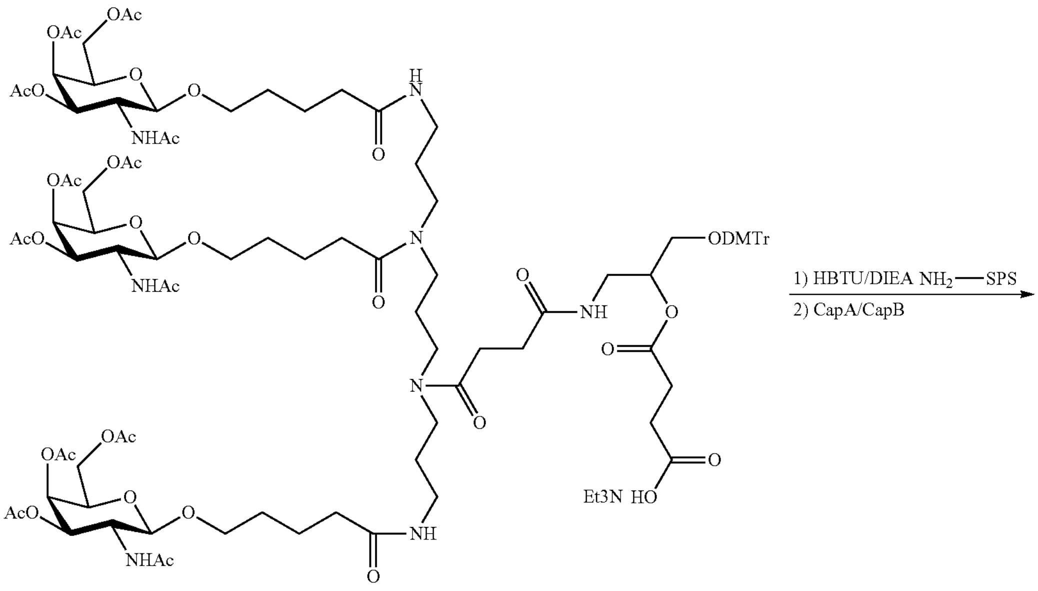
LA-4

-continued

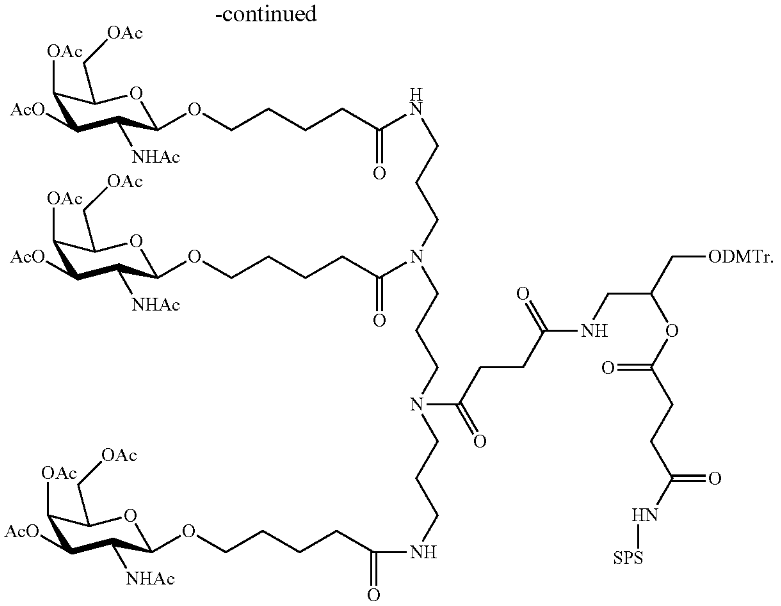

LA-5

LA Conjugates were prepared by using the same methods as those in steps (2-2), (2-3A) and (2-4) of Preparation Example 2, except that LA-5 Compound was used to replace L-10 Compound to start the synthesis of a sense strand. It is expected that Conjugates A14, B10, C6, D6, E12, F14 and G12 with a structure as shown by Formula (412) can be obtained.

Preparation Example 7 Preparation of LB-5 Conjugates

In this Preparation Example, Conjugates A15, B11, C7, D7, E13, F15 and G13 (hereinafter referred to as LB-5 Conjugates) can be synthesized by the following method.

(7-1) Synthesis of LB-5 Compounds

LB-5 Compounds were synthesized by the following method:

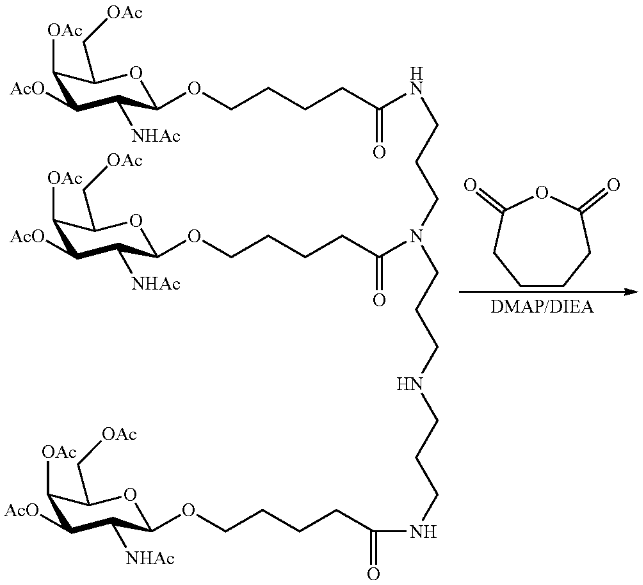

L-8

-continued
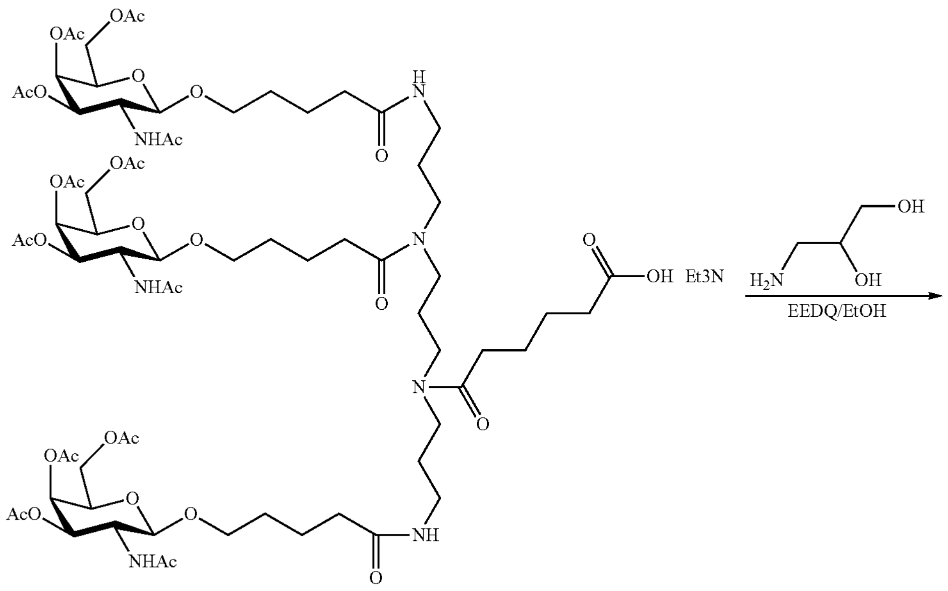
LB-1
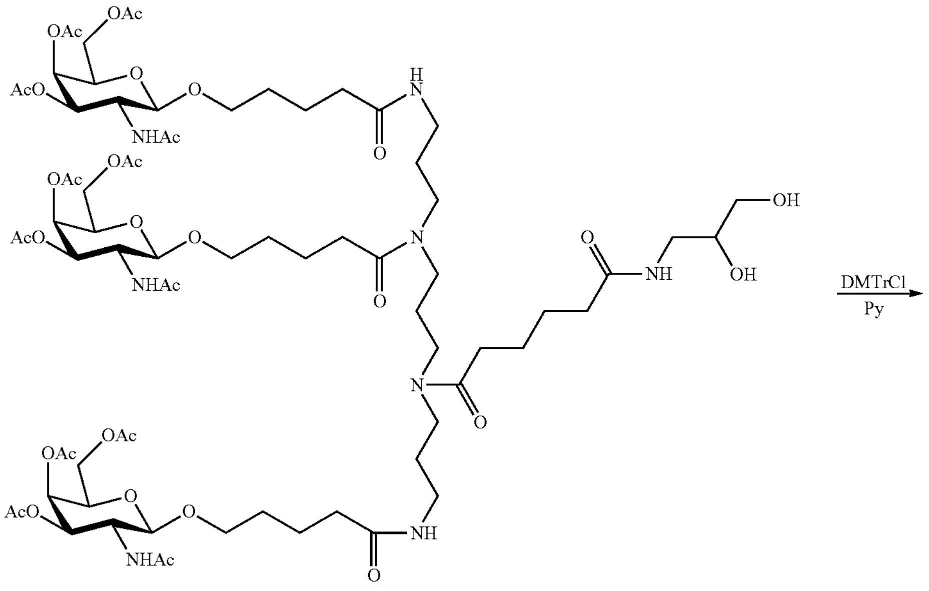
LB-2

-continued
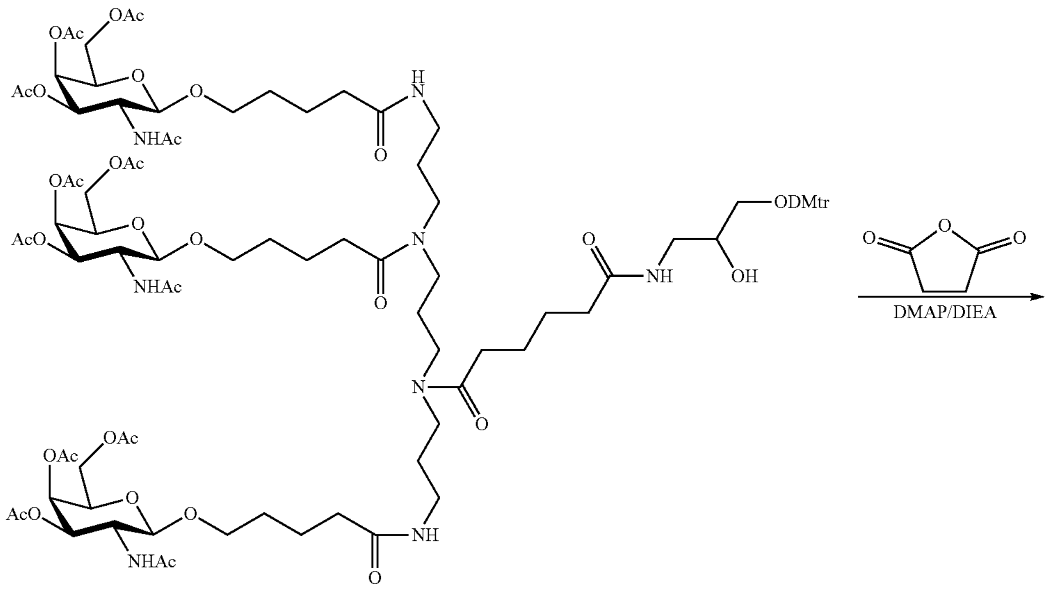
LB-3
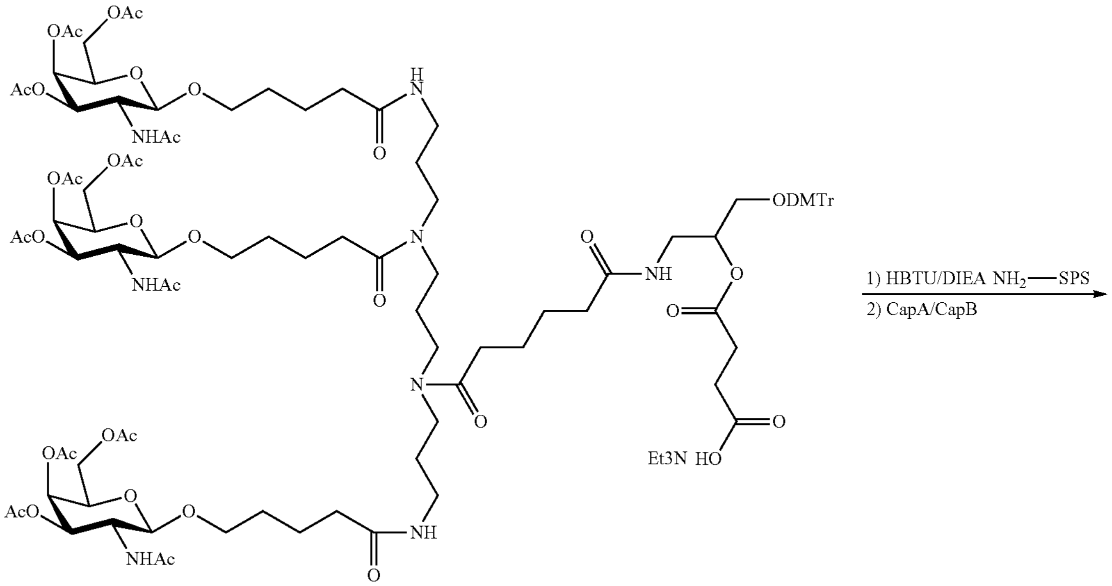
LB-4

-continued

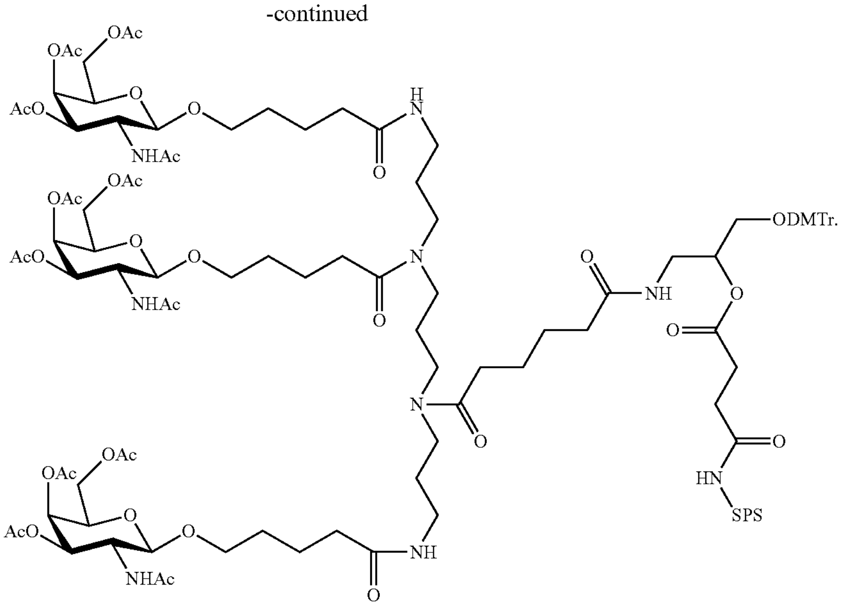

LB-5

(7-1-1) Synthesis of LB-1

L-8 (5.0 g, 3.386 mmol) obtained according to the method described in step (2-1-6), adipic anhydride (870 mg, 6.772 mmol) and 4-dimethylaminopyridine (DMAP, 827 mg, 6.772 mmol) were mixed and dissolved in 130 ml of dichloromethane, and added with diisopropylethylamine (DIEA, 2.2 g, 16.931 mmol) to react under stirring at 25° C. for 4 hours. The resultant reaction solution was added with 70 ml dichloromethane for dilution and then washed with 0.5 M triethylamine phosphate. The aqueous phase isolated was extracted four times, each with 10 ml of dichloromethane. All organic phases were combined, and the solvent was removed by evaporation under reduced pressure to give a crude product. The crude product was subjected to a column purification. The column was filled with 120 g normal phase silica gel (200-300 mesh), added with 1 wt % triethylamine for neutralizing the acidity of silica gel and equilibrated with dichloromethane, and eluted with a gradient elution of petroleum ether:ethyl acetate:dichloromethane:methanol=1:1:1:0.2-1:1:1:1. The solvent was removed by evaporation under reduced pressure to give 4.267 g of pure product LB-1.

(7-1-2) Synthesis of LB-2:

LB-1 (4.697 g, 2.753 mmol, combination of 2 batches) obtained according to the method described in step (7-1-1), 3-amino-1,2-propanediol (313 mg, 3.442 mmol), 4-(4,6-dimethoxytriazin-2-yl)-4-methylmorpholine hydrochloride (DMTMM, 953 mg, 3.442 mmol) and N-methylmorpholine (700 mg, 6.884 mmol) were sequentially added to the mixture of 30 ml of acetonitrile and 3 ml of methanol to react under stirring at room temperature overnight. The solvent was evaporated to dryness, and the residue was purified by column chromatography (200-300 mesh normal phase silica gel, with a gradient elution of dichloromethane:methanol=1:0.07-1:0.5). The eluate was collected and concentrated to remove the solvents to give 3.27 g of target product LB-2.

(7-1-3) Synthesis of LB-3:

LB-2 (2.27 g, 1.353 mmol) was dissolved in 14 ml of anhydrous pyridine, and added with 4,4'-dimethoxytrityl chloride (688 mg, 2.03 mmol) to react under stirring at room temperature overnight. The reaction was quenched by addition of 150 ml of methanol. The solvent was evaporated to dryness, and the residue was purified by column chromatography (200-300 mesh normal phase silica gel, with a gradient elution of dichloromethane:methanol=1:0.05-1:0.2).

The eluate was collected and concentrated to remove the solvent to give 1.647 g of target product LB-3.

(7-1-4) Synthesis of LB-4:

LB-3 (822 mg, 0.415 mmol), succinic anhydride (83 g, 0.83 mmol) and 4-dimethylaminopyridine (DMAP, 102 mg, 0.83 mmol) were mixed and dissolved in 4 ml of dichloromethane, added with DIEA (270 mg, 2.075 mmol), and stirred at 25° C. to react overnight. The resultant reaction solution was washed with 0.5 M triethylamine phosphate three times. The aqueous phase isolated was extracted three times, each with 2 ml of dichloromethane. All organic phases were combined, and the solvent was removed by evaporation under reduced pressure to give a crude product. The crude product was subjected to a column purification. The column was filled with normal phase silica gel (200-300 mesh), added with 5 wt % triethylamine for neutralizing the acidity of silica gel and equilibrated with petroleum ether, and eluted with a gradient elution of 1 wt % triethylamine-containing dichloromethane:methanol=100:5-100:20. The solvent was removed by evaporation under reduced pressure to give 787 mg of pure product LB-4 conjugating molecule.

(7-1-5) Synthesis of LB-5:

LB-5 was prepared by using the same method as that in step (2-1-9) of Preparation Example 2, except that: LB-4 conjugating molecule was used to replace L-9 conjugating molecule, thereby obtaining LB-4 conjugating molecule linked to a solid phase support.

(7-2) Synthesis of LB-5 Conjugates

LB-5 Conjugates were prepared by using the same methods as those in steps (2-2), (2-3A) and (2-4) of Preparation Example 2, except that LB-5 Compound was used to replace L-10 compound to start the synthesis of a sense strand. It is expected that Conjugates A15, B11, C7, D7, E13, F15 and G13 with a structure as shown by Formula (413) can be obtained.

Preparation Example 8, Synthesis of V8 Conjugates
In this Preparation Example, it is expected that Conjugates A16, B12, C8, D8, E14, F16 and G14 (hereinafter referred to as V8 Conjugates) can be synthesized by the following method.
It is expected that V-8 Compounds can be synthesized by the following process route:
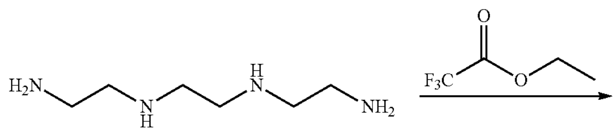
V-0
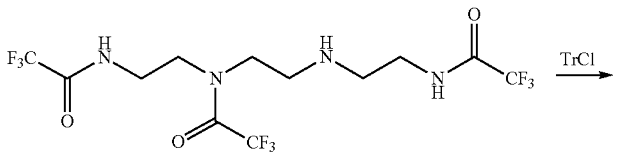
V-1
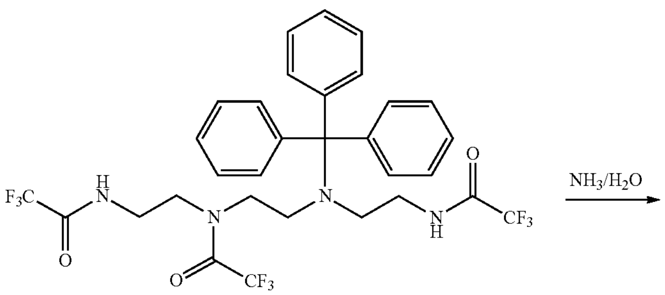
V-2
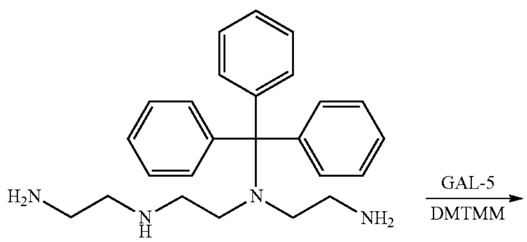
V-3

-continued
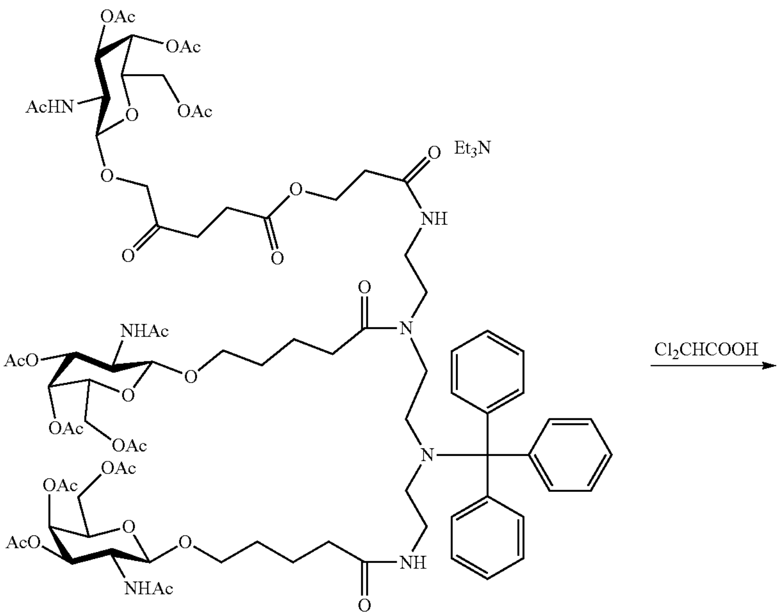
V-4
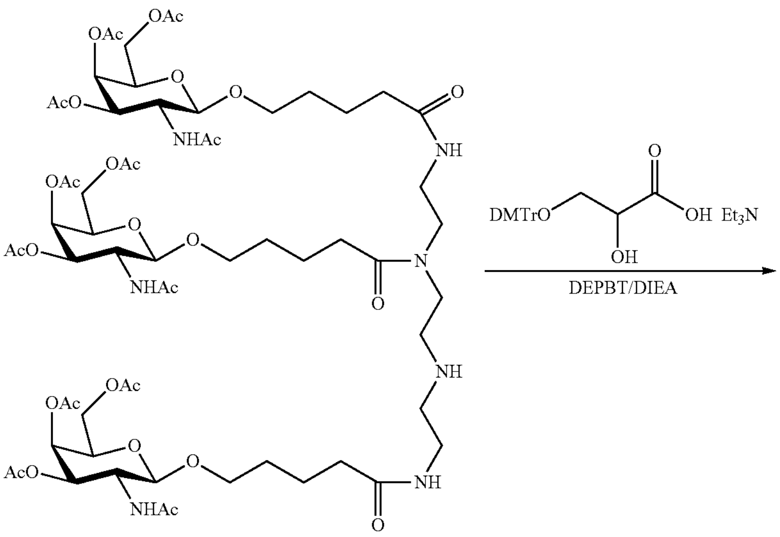
V-5

-continued
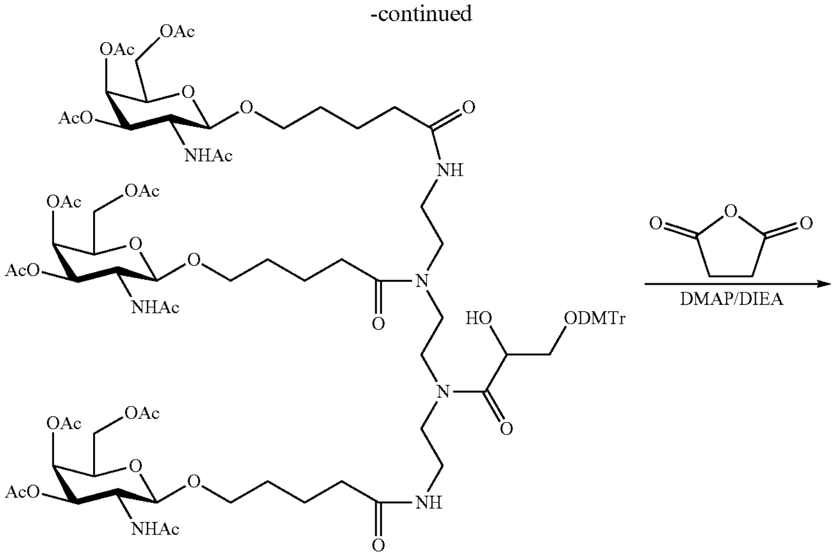
V-6
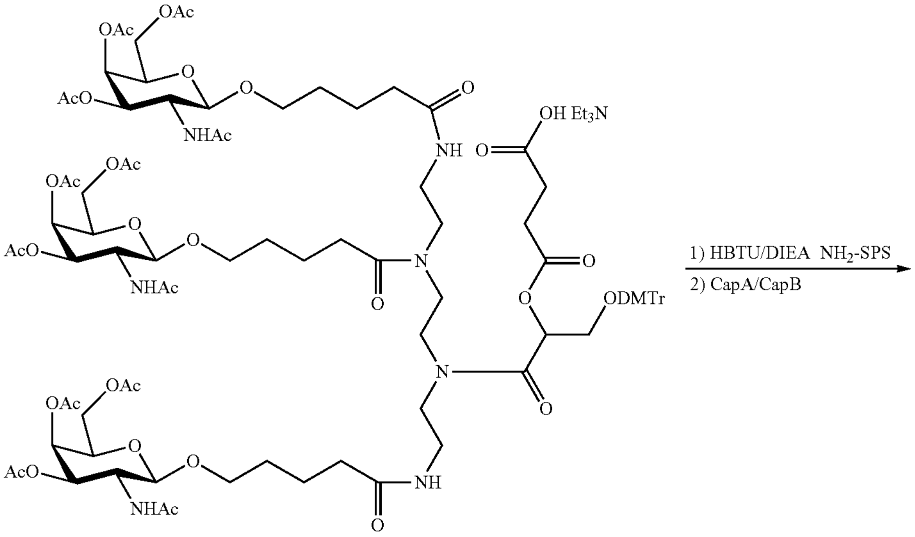
V-7
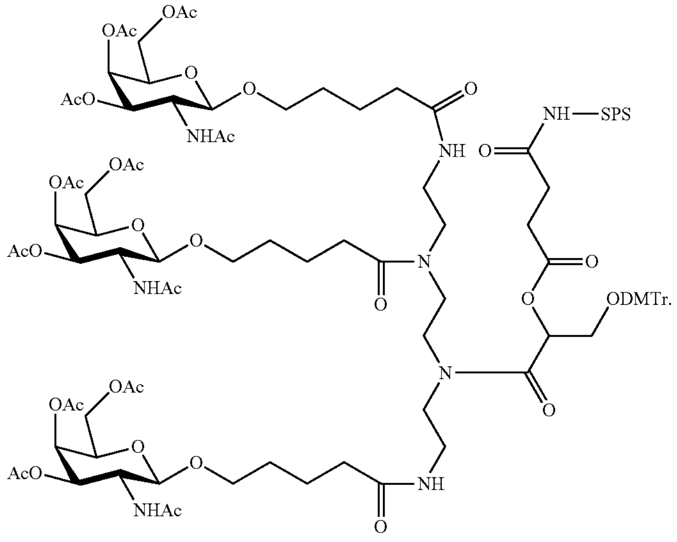
V-8

V8 Conjugates were prepared by using the same methods as those in steps (2-2), (2-3A) and (2-4) of Preparation Example 2, except that V-8 Compound was used to replace L-10 Compound to start the synthesis of a sense strand. It is expected that Conjugates A15, B12, C8, D8, E14, F16 and G14 (hereinafter referred to as V8 Conjugates) with a structure as shown by Formula (414) can be obtained.

Preparation Example 9 Synthesis of W8 Conjugates

In this Preparation Example, it is expected that Conjugates A17, B13, C9, D9, E15, F17 and G15 (hereinafter referred to as W8 Conjugates) can be synthesized by the following method.

(9-1) Synthesis of W-8 Compounds

W-8 Compounds were synthesized by the following method:

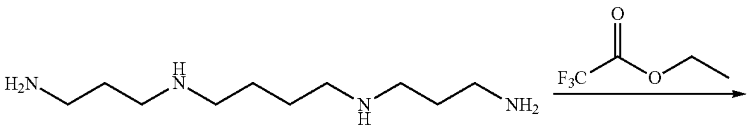

W-0

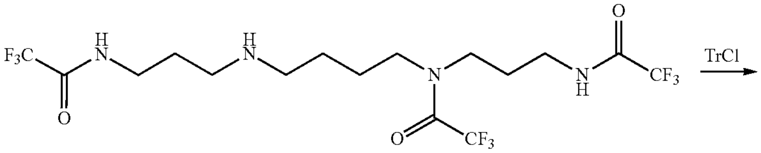

W-1

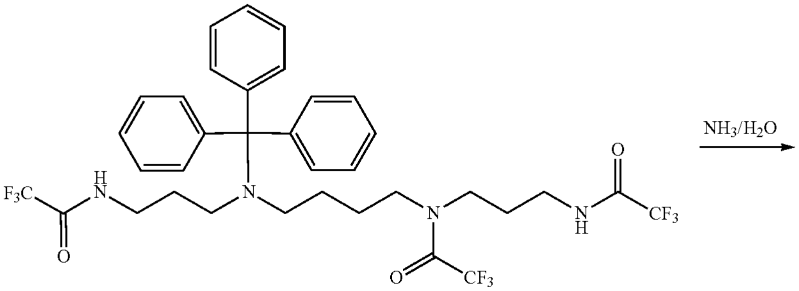

W-2

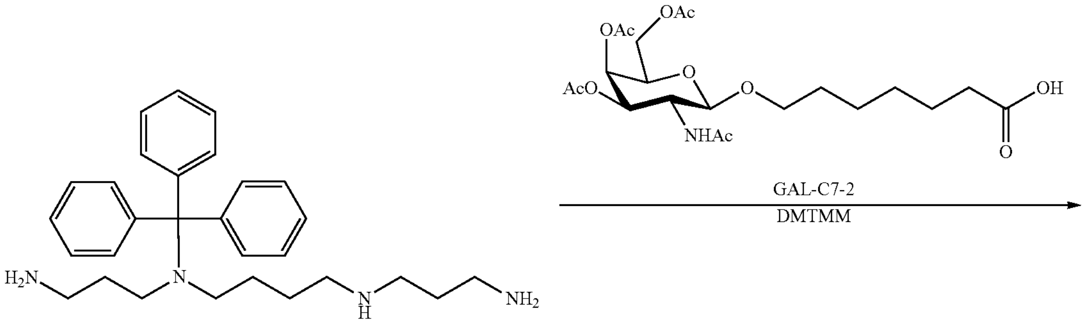

W-3

-continued
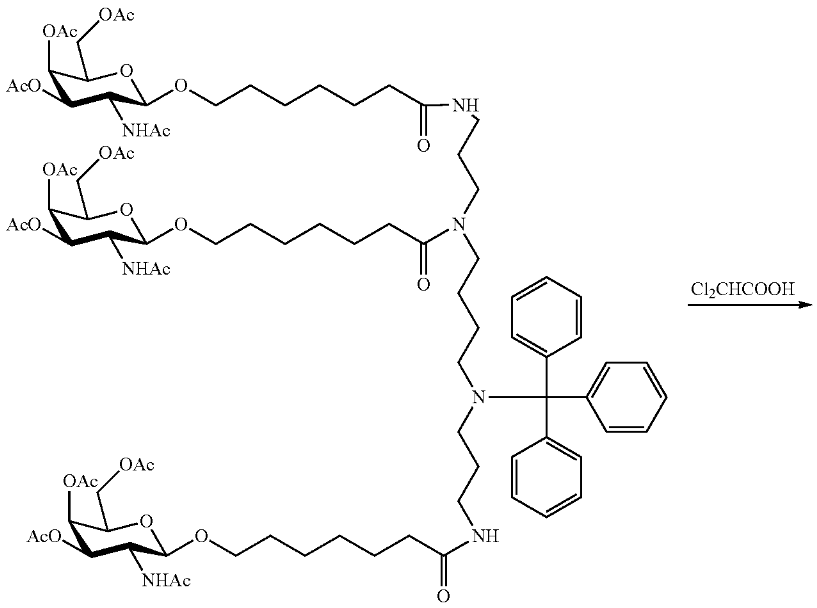
W-4
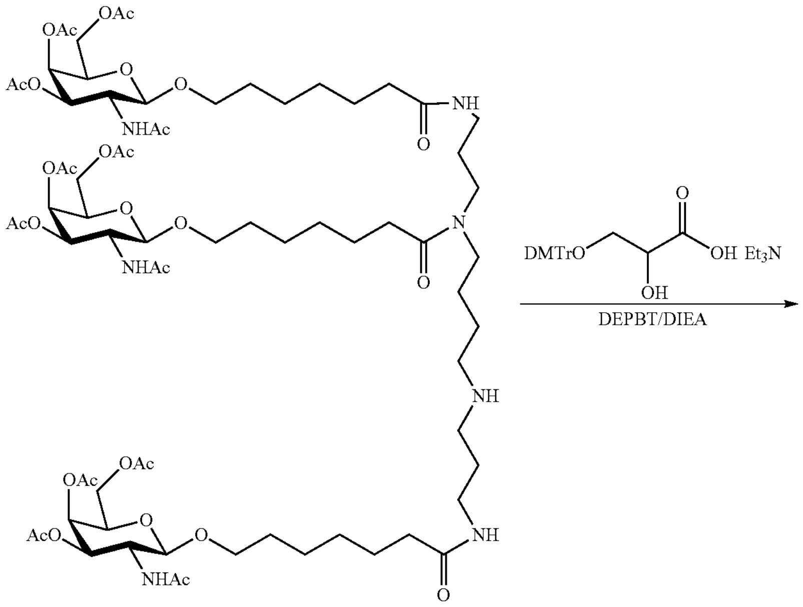
W-5

-continued
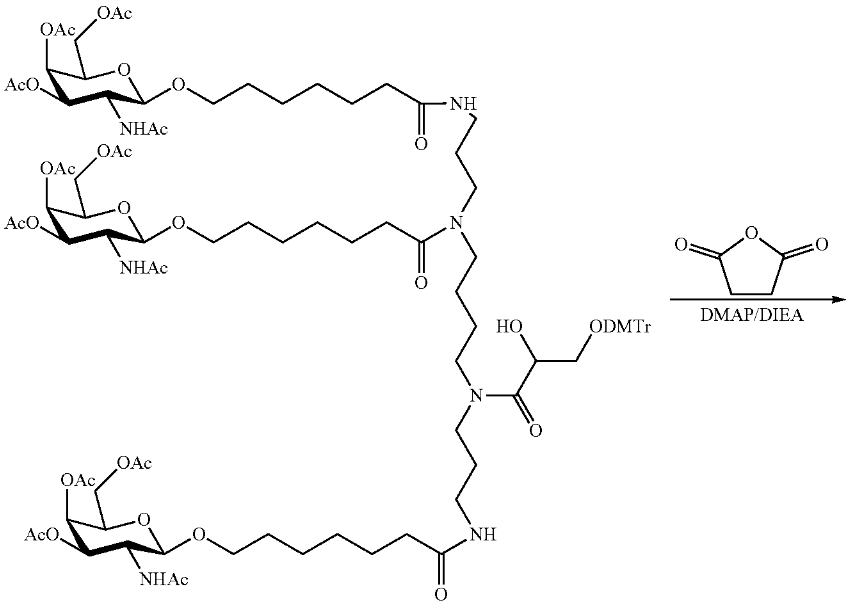
W-6
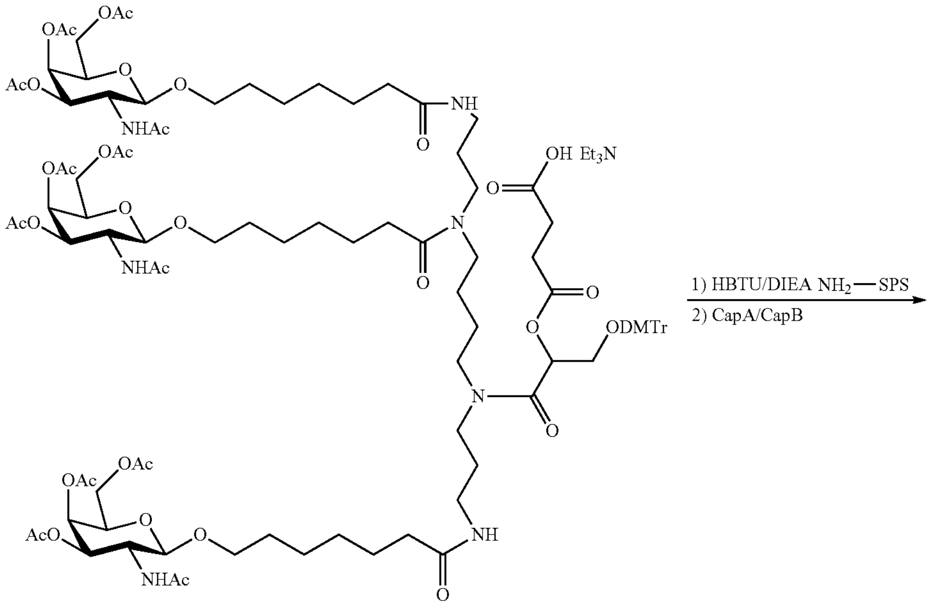
W-7

-continued

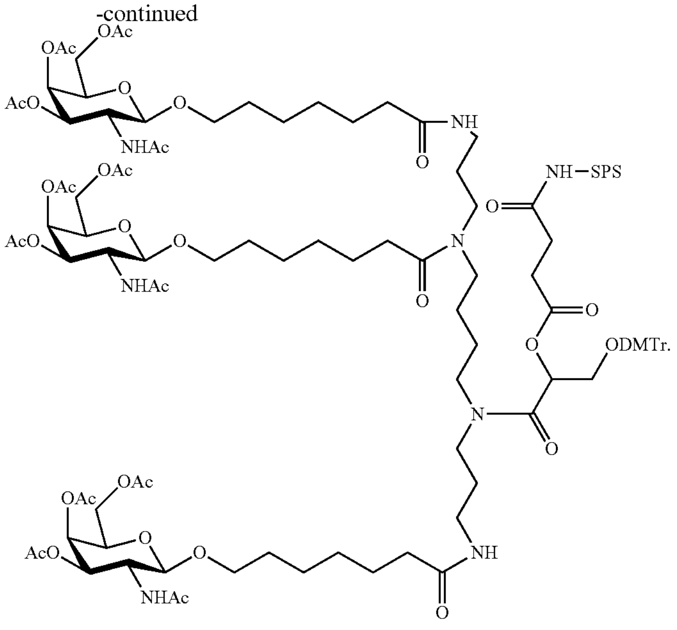

W-8

(9-1-1) Synthesis of W-1

W-0 (2.024 g, 10 mmol) was dissolved in 25 ml of acetonitrile, added with triethylamine (4.048 g, 40 mmol), and cooled to about 0° C. in an ice water bath. Ethyl trifluoroacetate (5.683 g, 40 mmol) was added to react at room temperature for 22 hours. The solvent was removed by evaporation under reduced pressure, and the residue was foam-dried in a vacuum oil pump for 18 hours to give 5.835 g of crude solid product W-1.

(9-1-2) Synthesis of W-2:

The crude product W-1 (5.835 g, 10 mmol) was dissolved in 50 ml of dichloromethane. The resultant reaction solution was added with TrCl (3.345 g, 12 mmol) and triethylamine (1.518 g, 15 mmol) to react under stirring at room temperature for 20 hours. The resultant reaction solution was washed twice, each with 20 ml of saturated sodium bicarbonate and once with 20 ml of saturated brine. All organic phases were combined, dried with anhydrous sodium sulfate and filtered. The organic solvent was removed by evaporation under reduced pressure, and the residue was foam-dried in a vacuum oil pump overnight to give 8.012 g of crude solid product W-2. The crude solid product W-2 was used in the next deprotection reaction without treatment.

(9-1-3) Synthesis of W-3:

The crude product W-2 (8.012 g, 10 mmol) was dissolved in 100 ml of methanol, and added with 100 ml of aqueous methylamine solution (40 wt %) to react under stirring at 50° C. for 23 hours. Insoluble particles were removed by filtration. The solvent was removed by evaporation under reduced pressure. The residue was added with 200 ml of mixed solvent of DCM:methanol in a volume ratio of 1:1, and the resultant organic phase was washed with 50 ml of saturated sodium bicarbonate. The aqueous phase isolated was extracted three times, each with 50 ml of dichloromethane. All organic phases were combined, dried with anhydrous sodium sulfate and filtered. The solvent was removed by evaporation under reduced pressure, and the residue was foam-dried in a vacuum oil pump overnight, and purified by using a normal phase silica gel column (200-300 mesh). The column was packed with petroleum ether, added with 1 wt % triethylamine for neutralizing the acidity of silica gel, and eluted with a gradient elution of dichloromethane:methanol: aqueous ammonia (25 wt %)=1:1:0.05-1:1:0.25. The eluate was collected. The solvent was removed by evaporation under reduced pressure, and the residue was foam-dried in a vacuum oil pump to give 3.062 g of pure product W-3.

(9-1-4) Synthesis of W-4:

W-3 (0.675 g, 1.517 mmol) and GAL-C7-2 (2.60 g, 5.46 mmol) were mixed and dissolved in 47 ml of acetonitrile, added with diisopropylethylamine (1.57 g, 12.14 mmol) followed by 3-(diethoxyphosphoryloxy)-1,2,3-benzotrizin-4 (3H)-one (DEPBT, 1.816 g, 6.04 mmol) to react under stirring at room temperature for 2.5 hours. The resultant reaction solution was diluted with 100 ml of dichloromethane. The organic phase obtained was washed with 80 ml of saturated sodium bicarbonate solution and 80 ml of saturated brine, respectively. All organic phases were combined, dried with anhydrous sodium sulfate, and filtered. The solvent was removed by evaporation under reduced pressure to give a crude product, which was purified by using a normal phase silica gel column (200-300 mesh). The column was packed with petroleum ether, added with 1 wt % triethylamine for neutralizing the acidity of silica gel, and eluted with a gradient elution of dichloromethane:methanol=100:5-100:7. The eluate was collected, and the solvent was removed by evaporation under reduced pressure to give 1.610 g of pure product W-4.

(9-1-5) Synthesis of W-5:

W-4 (1.61 g, 0.886 mmol) was dissolved in 125 ml of dichloromethane, and added with dichloroacetic acid (3.5 ml, 42.43 mmol) to react at room temperature for 1 hour. The resultant reaction solution was neutralized by adding 150 ml of pyridine. The solvent was removed by evaporation under reduced pressure to give a crude product. The crude product was purified by using a normal phase silica gel column (200-300 mesh). The column was added with 10 wt % triethylamine for neutralizing the acidity of silica gel, equilibrated with 1 wt % triethylamine and eluted with a gradient elution of dichloromethane:methanol=100:30-100:40. The eluate was collected, and the solvent was removed by evaporation under reduced pressure to give 1.26 g of pure product W-5.

(9-1-6) Synthesis of W-6:

W-5 (1.25 g, 0.793 mmol) and A-1 (1.21 g, 2.38 mmol) obtained according to the method described in step (2-1-7a) were mixed and dissolved in 12 ml of dichloromethane, and added with 3-(diethoxyphosphoryloxy)-1,2,3-benzotrizin-4 (3H)-one (DEPBT, 0.712 g, 2.38 mmol) followed by diisopropylethylamine (0.615 g, 4.76 mmol) to react under stirring at 25° C. for 3 hours. The organic phase was washed with 80 ml of saturated sodium bicarbonate. The aqueous phase isolated was extracted three times, each with 10 ml of dichloromethane. All organic phases were combined and washed with 10 ml of saturated brine. The obtained organic phases were combined, dried with anhydrous sodium sulfate and filtered. The solvent was removed by evaporation under reduced pressure, and the residue was foam-dried in a vacuum oil pump overnight to give a crude product. The crude product was subjected to a column purification. The column was filled with 185 g normal phase silica gel (200-300 mesh), added with 20 ml triethylamine for neutralizing the acidity of silica gel, equilibrated with petroleum ether containing 1 wt % triethylamine and eluted with a gradient elution of petroleum ether:ethyl acetate:dichloromethane: N,N-dimethylformamide=1:1:1:0.1-1:1:1:0.7. The eluate was collected, and the solvent was removed by evaporation under reduced pressure to give 1.57 g of pure product W-6.

(9-1-7) Synthesis of W-7:

W-6 (1.238 g, 0.63 mmol), succinic anhydride (0.189 g, 1.89 mmol) and 4-dimethylaminopyridine (DMAP, 0.231 g, 1.89 mmol) were mixed and dissolved in 7 ml of dichloromethane, and added with DIEA (0.407 g, 3.15 mmol) to react under stirring at 25° C. for 24 hours. The resultant reaction solution was washed with 5 ml of 0.5 M triethylamine phosphate. The aqueous phase isolated was extracted three times, each with 5 ml of dichloromethane. All organic phases were combined, and the solvent was removed by evaporation under reduced pressure to give a crude product. The crude product was subjected to a column purification. The column was filled with 30 g normal phase silica gel (200-300 mesh), added with 1 wt % triethylamine for neutralizing the acidity of silica gel, equilibrated with dichloromethane and eluted with a gradient elution of 1 wt % triethylamine-containing dichloromethane:methanol=100:18-100:20. The eluate was collected, and the solvent was removed by evaporation under reduced pressure to give 1.033 g of pure product W-7 conjugating molecule. MS m/z: C101H146N7O38, [M-DMTr]+, calculated: 1763.92, measured: 1763.21.

(9-1-8) Synthesis of W-8

W-8 was prepared by using the same method as that in step (2-1-9) of Preparation Example 2, except that: W-7 conjugating molecule was used to replace L-9 conjugating molecule, thereby obtaining W-7 conjugating molecule linked to a solid phase support.

(9-2) Synthesis of W-8 Conjugates

W-8 Conjugates were prepared by using the same methods as those in steps (2-2), (2-3A) and (2-4) of Preparation Example 2, except that W-8 Compound was used to replace L-10 Compound to start the synthesis of a sense strand. It is expected that Conjugates A17, B13, C9, D9, E15, F17 and G15 with a structure as shown by Formula (415) can be obtained.

Preparation Example 10 Synthesis of X8 Conjugates

In this Preparation Example, it is expected that Conjugates A18, B14, C10, D10, E16, F18 and G16 (hereinafter referred to as X8 Conjugates) can be synthesized by the following method.

It is expected that X-8 Compounds can be synthesized by the following process route:

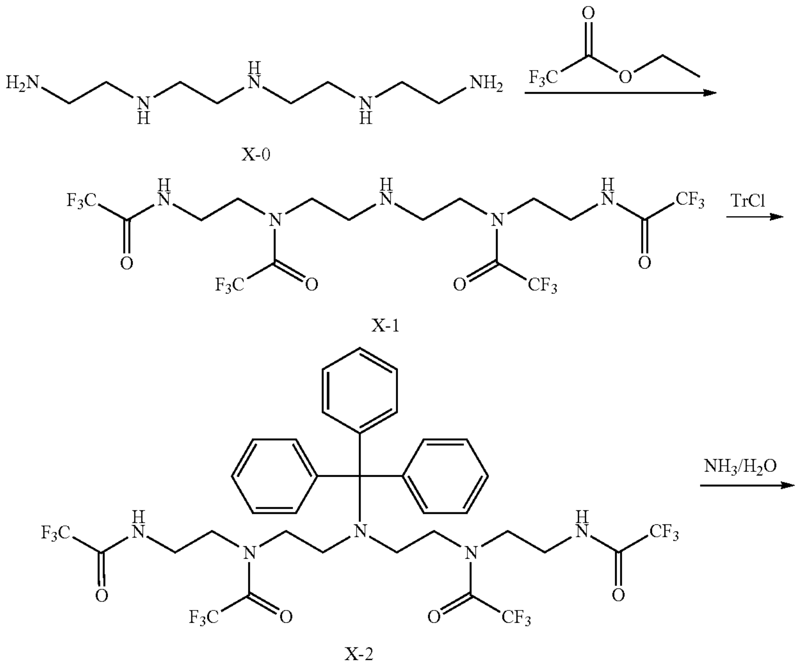

X-0

X-1

X-2

-continued
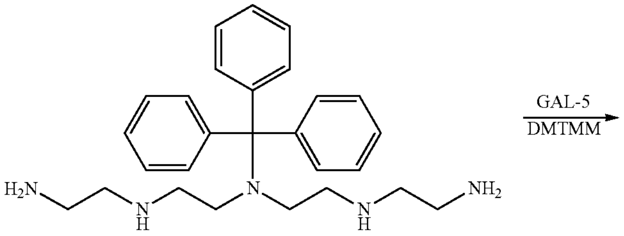
X-3
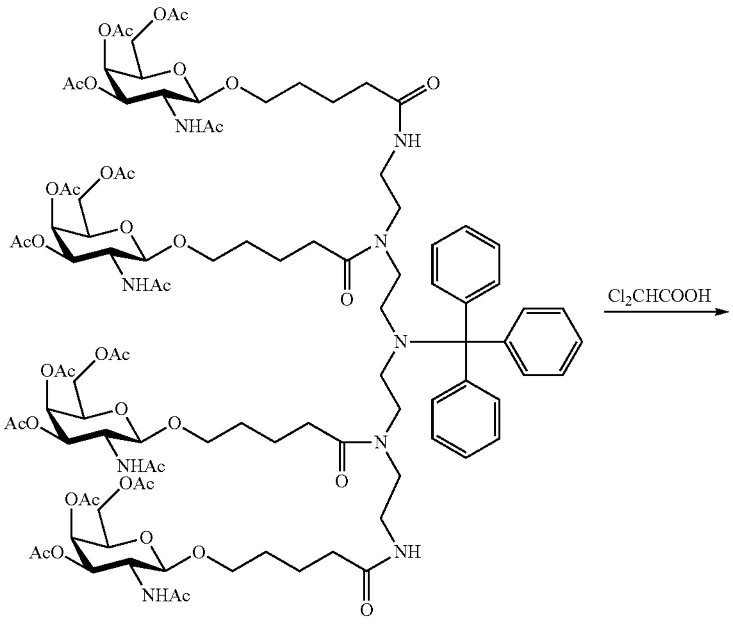
X-4
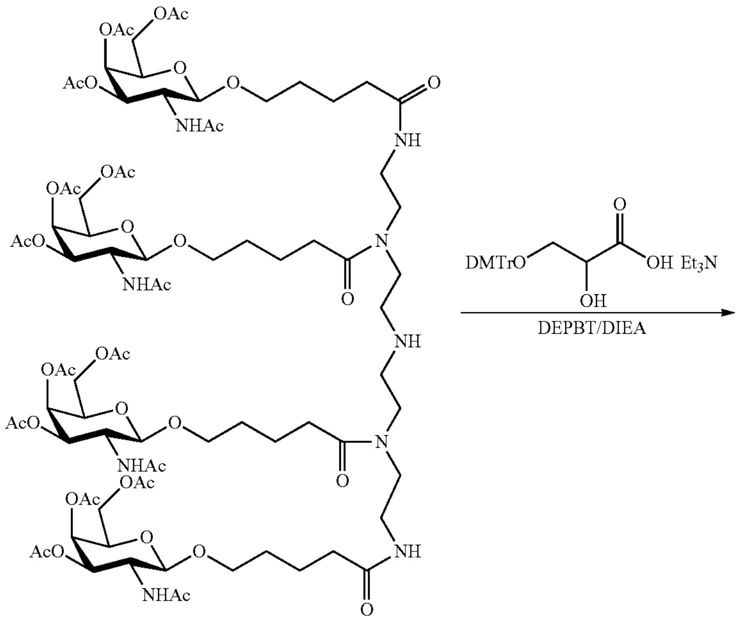
X-5

-continued
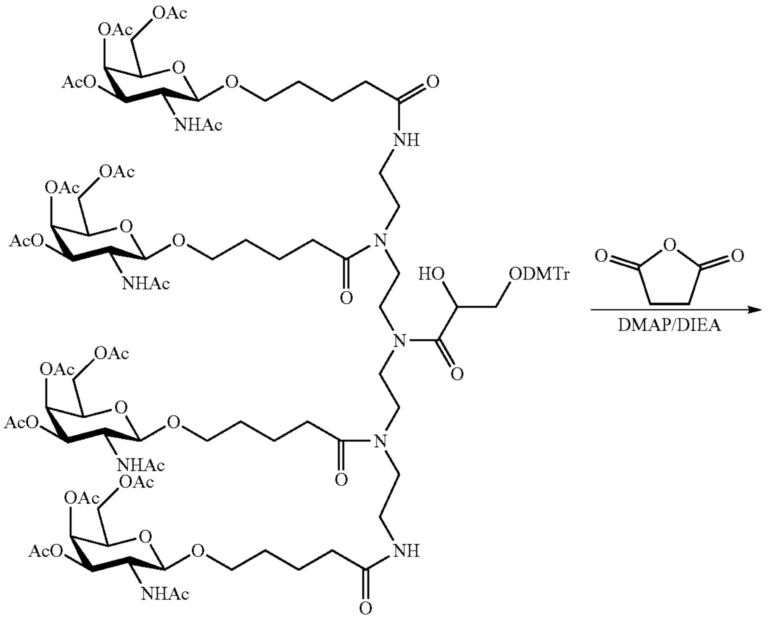
X-6
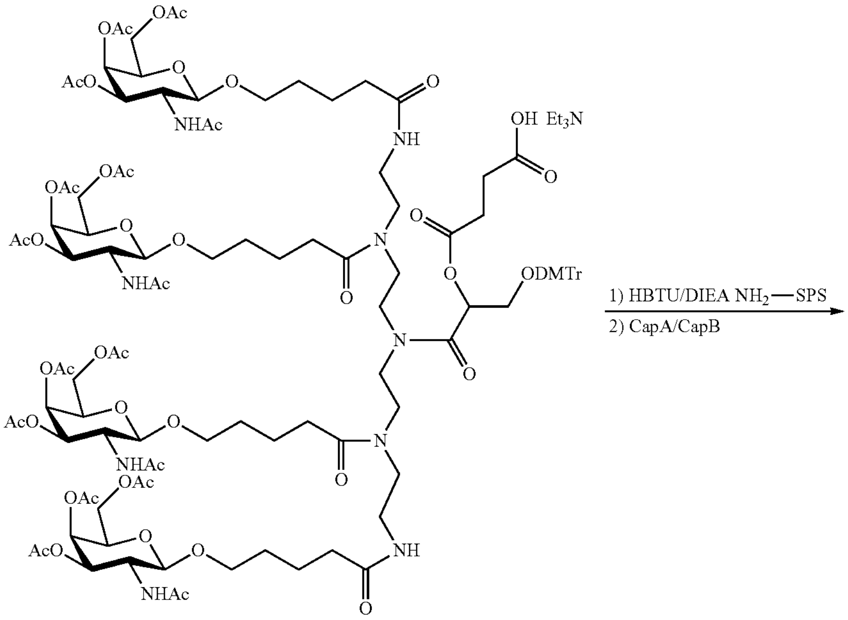
X-7

-continued

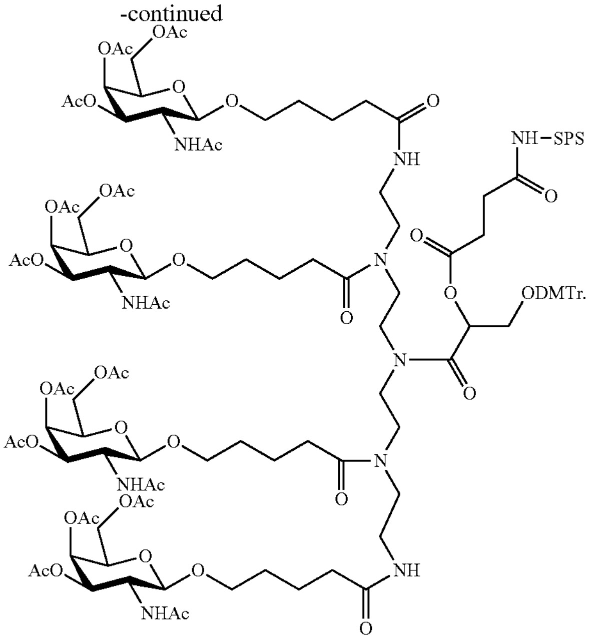

X-8

X-8 Conjugates were prepared by using the same methods as those in steps (2-2), (2-3A) and (2-4) of Preparation Example 2, except that X-8 Compound was used to replace L-10 Compound to start the synthesis of a sense strand. It is expected that Conjugates A18, 1B14, C10, D10, E16, F18 and G16 with a structure as shown by Formula (421) can be obtained.

Preparation Example 11 Synthesis of Z-5 Conjugates

In this Preparation Example, it is expected that Conjugates A19, B15, C11, D11, E12, F14 and G12 (hereinafter referred to as Z5 Conjugates) can be synthesized by the following method.

(11-1) Synthesis of Z-5 Compounds

Z-5 Compounds can be synthesized by the following method:

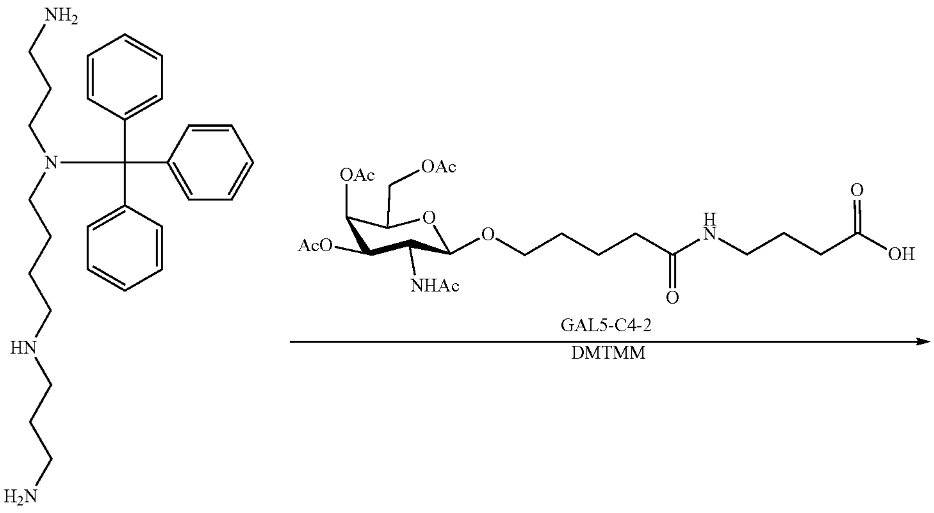

W-3

-continued
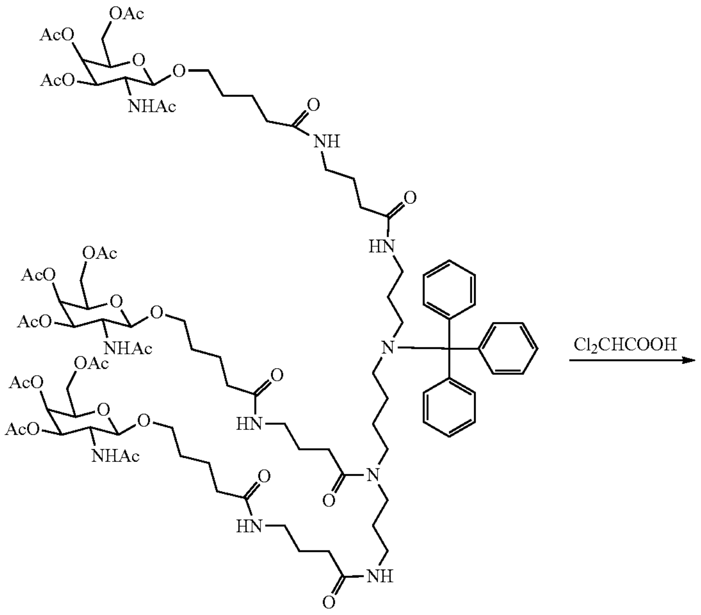
Z-1
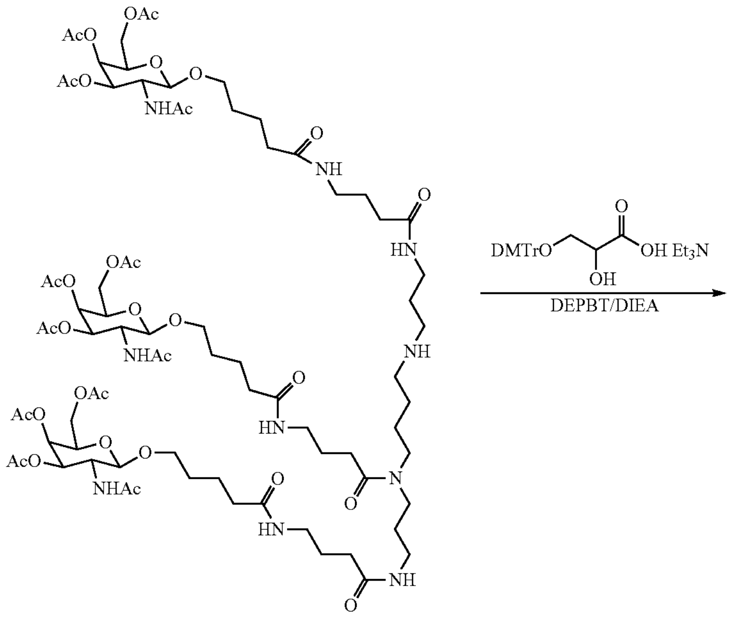
Z-2

-continued
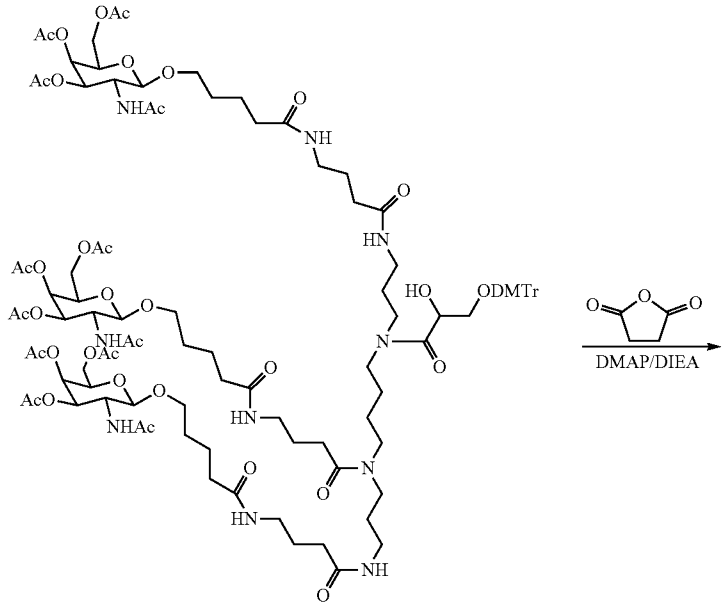
Z-3
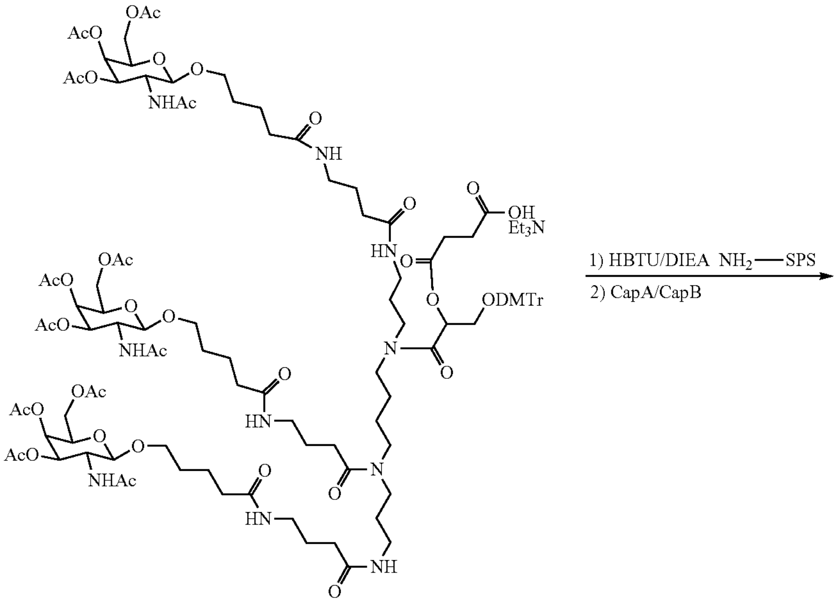
Z-4

-continued

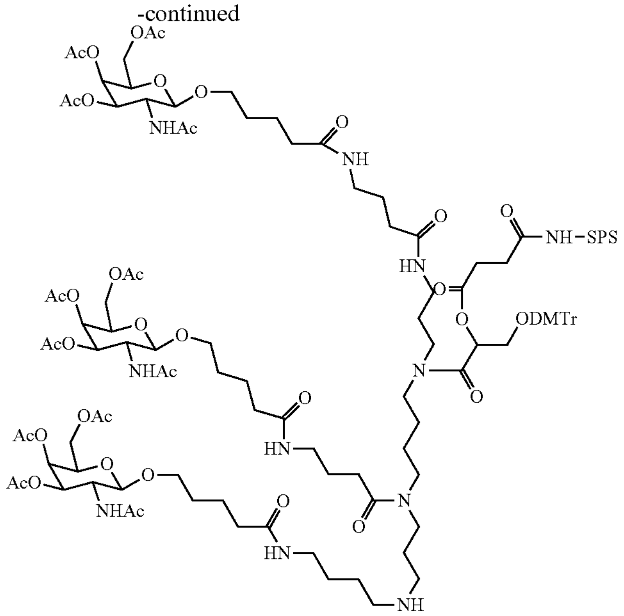

Z-5

(11-1-1) Synthesis of Z-1

W-3 (1.50 g, 3.37 mmol) obtained according to the method described in step (9-1-3) and GAL5-C4-2 (7.18 g, 13.48 mmol) obtained according to the method described in step (4-1-2) were mixed and dissolved in 34 ml of dichloromethane, and added with diisopropylethylamine (3.48 g, 26.96 mmol) followed by 3-(diethoxyphosphoryloxy)-1,2,3-benzotrizin-4(3H)-one (DEPBT, 4.04 g, 13.48 mmol) to react under stirring at room temperature for 4.5 hours. The resultant liquid solution was diluted with 100 ml of dichloromethane. The organic phase was washed with 80 ml of saturated sodium bicarbonate solution and 80 ml of saturated brine, respectively. All organic phases were combined, dried with anhydrous sodium sulfate, and filtered. The solvent was removed by evaporation under reduced pressure to give a crude product, which was purified by using a normal phase silica gel column (200-300 mesh). The column was packed with petroleum ether, added with 1 wt % triethylamine for neutralizing the acidity of silica gel, and eluted with a gradient elution of dichloromethane:methanol=30:1-15:1. The eluate was collected and removed by evaporation under reduced pressure to give 3.97 g of pure product Z-1. MS m/z: C98H143N10O33, [M+H]+, calculated: 1987.98, measured: 1987.90.

(11-1-2) Synthesis of Z-2:

Z-1 (3.97 g, 2.00 mmol) was dissolved in 250 ml of dichloromethane, and added with dichloroacetic acid (10.941 g, 84.85 mmol) to react at room temperature for 1 hour. Pyridine was added to neutralize the resultant reaction solution to neutral. The solvent was removed by evaporation under reduced pressure to give a crude product. The column was loaded with 200 g 200-300 mesh normal phase silica gel, and added with 10 wt % pyridine for neutralizing the acidity of silica gel, equilibrated with 1 wt % pyridine and eluted with a gradient elution of dichloromethane:methanol=10:1-2:1. The eluate was collected, and the solvent was removed by evaporation under reduced pressure to give 3.49 g of pure product Z-2. MS m/z: C79H129N10O33, [M+H]+, calculated: 1746.94, measured: 1746.90.

(11-1-3) Synthesis of Z-3:

Z-2 (3.49 g, 2.0 mmol) and A-1 (3.06 g, 6.0 mmol) obtained according to the method described in step (2-1-7a) were mixed and dissolved in 30 ml of dichloromethane, and added with 3-(diethoxyphosphoryloxy)-1,2,3-benzotrizin-4(3H)-one (DEPBT, 1.80 g, 6.0 mmol) followed by diisopropylethylamine (1.55 g, 12.0 mmol) to react for 3 hours under stirring at 25° C. The resultant reaction solution was added with 100 ml dichloromethane for dilution. The organic phase was washed twice with 30 ml of saturated sodium bicarbonate. The aqueous phase was extracted with 10 ml of dichloromethane. All organic phases were combined and washed with 50 ml of saturated brine. The obtained organic phases were combined and dried with anhydrous sodium sulfate, and filtered. The solvent was removed by evaporation under reduced pressure, and the residue was foam-dried in a vacuum oil pump overnight to give a crude product. The crude product was subjected to a column purification. The column was filled with 200 g normal phase silica gel (200-300 mesh), added with 20 ml triethylamine for neutralizing the acidity of silica gel. The column was equilibrated with petroleum ether containing 1 wt % triethylamine and eluted with a gradient elution of dichloromethane:methanol=25:1-15:1. The eluate was collected, and the solvent was removed by evaporation under reduced pressure to give 2.2 g of pure product Z-3. MS m/z: C103H151N10O38, [M+H]+, calculated: 2136.02, measured: 2136.20.

(11-1-4) Synthesis of Z-4:

Z-3 (2.10 g, 0.983 mmol) was dissolved in 14.8 ml of dichloromethane containing DIEA (0.635 g, 4.915 mmol), 4-dimethylaminopyridin (DMAP, 240 mg, 1.966 mmol) was added to the resultant solution and stirred until the solution is clear. Succinic anhydride (197 mg, 1.966 mmol) was added to react under stirring at 25° C. for 18 hours. The resultant reaction solution was added with 50 ml dichloromethane for dilution, and washed with 80 ml of 0.5 M triethylamine phosphate. The aqueous phase was extracted twice, each with 50 ml of dichloromethane. All organic phases were combined, and the solvent was removed by evaporation under reduced pressure to give a crude product.

The crude product was subjected to a column purification. The column was filled with 188 g normal phase silica gel (200-300 mesh), added with 1 wt % triethylamine for neutralizing the acidity of silica gel, equilibrated with dichloromethane and eluted with a gradient elution of dichloromethane containing 1 wt % triethylamine:methanol=10:1-3:1. The eluate was collected, and the solvent was removed by evaporation under reduced pressure to give 1.95 g of pure product Z-4 conjugating molecule. MS m/z: C107H155N10O41, [M+H]+, calculated: 1935.07, measured: 1935.29.

(11-1-5) Synthesis of Z-5

Z-5 was prepared by using the same method as that in step (2-1-9) of Preparation Example 2, except that: Z-4 conjugating molecule was used to replace L-9 conjugating molecule, thereby obtaining Z-4 conjugating molecule linked to a solid phase support.

(11-2) Synthesis of Z-5 Conjugates

Z-5 Conjugates were prepared by using the same methods as those in steps (2-2), (2-3A) and (2-4) of Preparation Example 2, except that Z-5 Compound was used to replace L-10 Compound to start the synthesis of a sense strand. It is expected that Conjugates A19, B15, C11, D11, E17, F19 and G17 with a structure as shown by Formula (422) can be obtained.

Preparation Example 12 Preparation of FIN Conjugates

In this Preparation Example, Conjugates A20-A23, B16-B17, C14, D14, E18-E20, F20 and Comparative Conjugates A1 and B1 (hereinafter referred to as FIN Conjugates) listed in Tables 4A-4G were synthesized. For the sequences of the conjugated siRNA in these conjugates, please refer to the corresponding sequences listed in Tables 4A-4G.

(12-1) Synthesis of FIN-2 Conjugating Molecule

FIN-2 conjugating molecule was synthesized with reference to the preparation method described in Rajeev et al., ChemBioChem 2015, 16, 903-908 according to the following process route:

(12-1-1) Synthesis of Compound PRO-10

(12-1-1a) Synthesis of PRO-7

2.93 g of PRO-6 (L-hydroxyproline, CAS No.: 51-35-4, purchased from Energy Chemical, 22.4 mmol) was dissolved in 22.5 ml of 1,4-dioxane (CAS No.: 123-91-1) and added with 34 ml of 10% (w/w) aqueous $Na_2CO_3$ solution in the form of suspension. 6.95 g of Fmoc-Cl (9-fluorenylmethyl chloroformate, CAS No.: 28920-43-6, purchased from Energy Chemical, 26.8 mmol) was dissolved in 34 ml of 1,4-dioxane, added into the above suspension in an ice bath, and naturally warmed to room temperature for reacting overnight. The reaction solution was poured into 150 ml of ice water, and extracted three times, each with 100 ml of methyl t-butyl ether, and the resultant organic phases were discarded. The aqueous phase remained was adjusted to pH≤5 with concentrated hydrochloric acid, extracted twice, each with 100 ml of ethyl acetate. The obtained organic phases were combined and dried with anhydrous sodium sulfate. The solvent was removed by evaporation under reduced pressure to give 7.83 g of product PRO-7 as a white foamy solid. $^1H$ NMR (400 MHz, DMSO-$d_6$) δ 7.91 (t, J=7.2 Hz, 2H), 7.67 (d, J=7.5 Hz, 2H), 7.48-7.39 (m, 2H), 7.38-7.27 (m, 2H), 5.17 (s, 1H), 4.27 (s, 2H), 4.23-4.11 (m, 2H), 3.55-3.41 (m, 3H), 2.31-2.10 (m, 1H), 2.08-1.88 (m, 1H). HRMS (ESI) m/z calculated. for $C_{20}H_{19}NO_5$ [M−H]− 352.1190, measured: 352.1033.

(12-1-1b) Synthesis of PRO-8

7.83 g of PRO-7 (22.2 mmol) was dissolved in 80 ml of THF (CAS No.: 109-99-9), heated to 65° C. in an oil bath, added with 36.6 ml of 2 mol/L solution of BH3-Me2S in THF (CAS No. 13292-87-0, purchased from J&K Scientific Ltd., 73.2 mmol) under reflux, and refluxed continually to react for 3 hours. The reaction solution was poured out, and the remaining solid was dissolved in methanol. To the resultant reaction solution, mehtanol was added under stirring until no gas emits, stirred continually for 30 minutes. The solvent was removed by evaporation under reduced pressure, and then the residue was purified with petroleum ether three times to give 7.1 g of product PRO-8 as a white

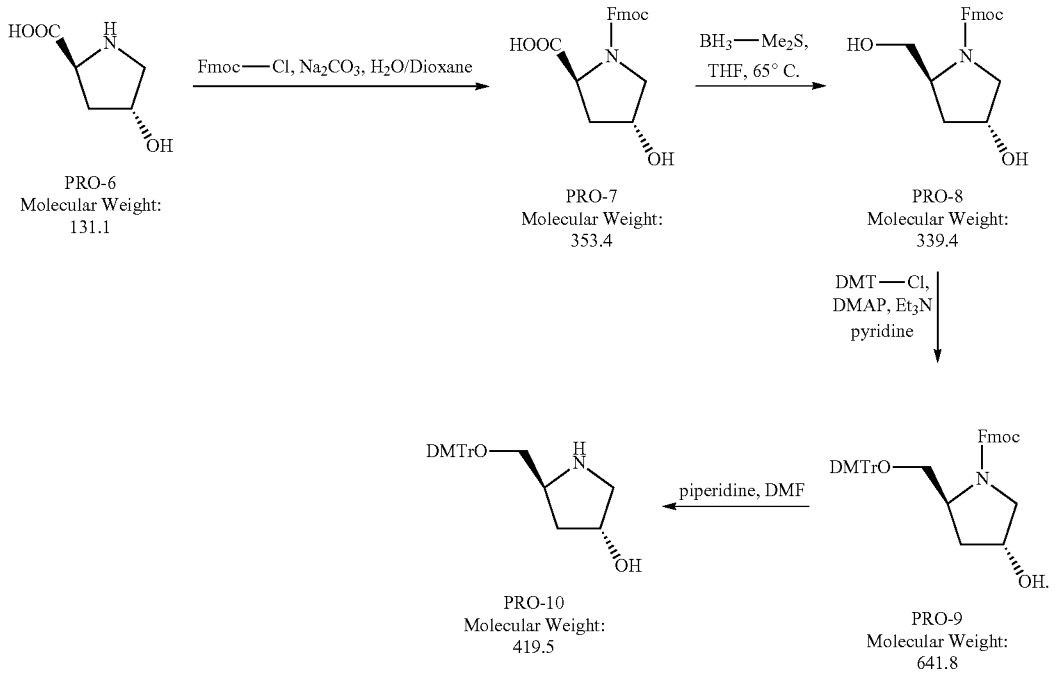

solid. $^1$H NMR (400 MHz, DMSO-$d_6$) δ 7.91 (t, J=6.7 Hz, 2H), 7.67 (d, J=7.2 Hz, 2H), 7.49-7.39 (m, 2H), 7.38-7.26 (m, 2H), 5.18 (dd, J=6.1, 3.8 Hz, 1H), 4.28 (s, 2H), 4.23-4.13 (m, 2H), 3.55-3.38 (m, 2H), 2.32-2.11 (m, 1H), 2.08-1.89 (m, 1H). HRMS (ESI) m/z, calculated for $C_{20}H_{21}NO_4$ $[M+Na]^+$ 362.1368, measured: 362.1012.

(12-1-1c) Synthesis of PRO-9

7.1 g of PRO-8 (21 mmol) was dissolved in 100 ml of pyridine, and added with 14.2 g of DMTr-Cl (4,4'-dimethoxytrityl chloride, 42 mmol) to react under stirring at room temperature for 5 hours. The solvent was removed by evaporation under reduced pressure. The resultant crude product was dissolved in ethyl acetate and filtered to remove salt impurities. The solvent was removed by evaporation under reduced pressure, and then the residue was purified by using a silica gel column. For purification, the crude product dissolved in DCM was loaded onto the silica gel column pretreated with pyridine to alkalify the column. DMTr-Cl was eluted with DCM containing 1% (v/v) pyridine, and then the product was eluted with ethyl acetate. The eluate was collected, and the solvent was removed by evaporation under reduced pressure to give 8.2 g of product PRO-9 as a white solid. HRMS (ESI) m/z, calculated for $C_{41}H_{39}NO_6$ [M+Na]+ 664.2675, measured: 664.2348; C18 RP-HPLC (Lot No.: JJS160324-1); purity: 94.20%.

(12-1-1d) Synthesis of PRO-10

8.2 g of PRO-9 (12.8 mmol) was dissolved in 64 ml of DMF and added with 40 ml of piperidine (384 mmol) to react under stirring at room temperature for 30 minutes. The reaction solution was poured into 300 ml of ice water and extracted three times, each with 150 ml of ethyl acetate. The resultant organic phases were combined and washed with 200 ml of saturated brine, and the organic phase resulted from washing was dried with anhydrous sodium sulfate. The solvent was removed by evaporation under reduced pressure, and then the residue was purified by using a silica gel column. For purification, the crude product dissolved in DCM was loaded onto the silica gel column pretreated with pyridine to alkalify the column. Fmoc was eluted with DCM containing 1% (v/v) pyridine, and then the product was eluted with ethyl acetate. The eluate was collected, and the solvent was removed by evaporation under reduced pressure to give 4.65 g of product PRO-10 as a white solid. $^1$H NMR (400 MHz, DMSO-$d_6$) δ 7.40 (d, J=7.2 Hz, 2H), 7.35-7.18 (m, 7H), 6.93-6.84 (m, 4H), 4.56 (d, J=3.9 Hz, 1H), 4.12 (s, 1H), 3.74 (s, 6H), 3.46-3.37 (m, 1H), 2.88 (ddd, J=18.5, 10.0, 5.5 Hz, 2H), 2.75 (dd, J=8.7, 5.8 Hz, 1H), 2.62 (dd, J=11.0, 2.7 Hz, 1H), 1.74-1.65 (m, 1H), 1.40 (ddd, J=12.9, 8.5, 5.9 Hz, 1H); HRMS (ESI) m/z calculated for $C_{26}H_{29}NO_4$ $[M+Na]^+$ 442.1994, measured: 442.1999; C18 RP-HPLC (Lot No.: JJS160329-1), purity: 97.07%.

(12-1-2) Synthesis of FIN-1

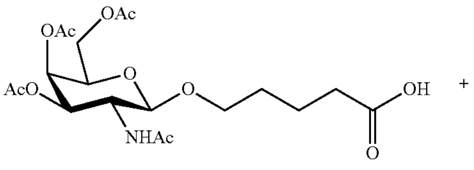

GAL-5
Molecular Weight:
447.4

-continued

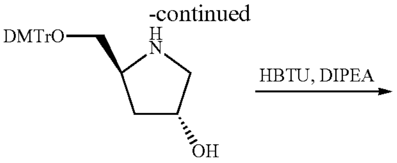

PRO-10
Molecular Weight:
419.5

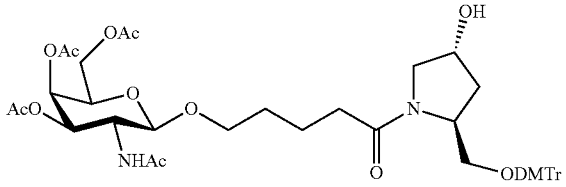

FIN-1
Molecular Weight:
848.9

GAL-5 (4.5 g, 10 mmol) obtained according to the method described in step (2-1-1) was dissolved in 40 ml of DMF, sequentially added with 3.9 g of DIEA (N,N-diisopropylethylamine, CAS No.: 7087-68-5, purchased from Aladdin Inc., 30 mmol) and 3.8 g of HBTU (benzotriazol-N,N,N',N'-tetramethyluronium hexafluorophosphate, CAS No.: 94790-37-2, purchased from Aladdin Inc., 11 mmol), and stirred at room temperature for 10 minutes. PRO-10 (4.2 g, 10 mmol) obtained in step (11-1-1d) was dissolved in 40 ml of DMF, and then added into the above reaction solution. The resultant reaction solution was dried by addition of anhydrous sodium sulfate and stirred at room temperature for 2 hours. The reaction solution was poured into 120 ml of ice water and extracted three times, each with 60 ml of ethyl acetate. The resultant organic phases were combined, washed with 20 ml of water and 20 ml of saturated brine, respectively. The organic phase obtained from washing was isolated and dried with anhydrous sodium sulfate. The solvent was removed by evaporation under reduced pressure, and then the residue was purified by using a silica gel column. For purification, a sample was loaded onto the silica gel column pretreated with pyridine to alkalify the column, and was eluted with dichloromethane (DCM) solution containing 1% (v/v) triethylamine and 1% (v/v) methanol. The eluate was collected, and the solvent was removed by evaporation under reduced pressure to give 6.5 g of product FIN-1 as a light yellow foamy solid. $^1$H NMR (400 MHz, DMSO-$d_6$) δ 7.83 (d, J=9.2 Hz, 1H), 7.32 (t, J=6.6 Hz, 4H), 7.20 (td, J=8.9, 3.5 Hz, 5H), 6.93-6.84 (m, 4H), 5.21 (d, J=3.2 Hz, 1H), 5.04-4.90 (m, 2H), 4.49 (s, 1H), 4.40 (d, J=4.4 Hz, 0.8H), 4.31 (d, J=5.0 Hz, 0.2H), 4.15 (s, 1H), 4.03 (s, 3H), 3.93 (s, 1H), 3.74 (s, 7H), 3.59 (dt, J=12.0, 6.0 Hz, 1H), 3.50-3.40 (m, 1H), 3.39-3.25 (m, 3H), 3.13 (dd, J=8.9, 5.2 Hz, 1H), 3.00 (dq, J=9.3, 5.3, 4.3 Hz, 1H), 2.22 (s, 2H), 2.07 (s, 3H), 1.99 (s, 3H), 1.90 (s, 4H), 1.74 (s, 3H), 1.50 (s, 3H), 1.36 (s, 1H). C18 RP-HPLC (Lot Number: LJ160422), purity: 95.45%.

(12-1-3) Synthesis of FIN-2

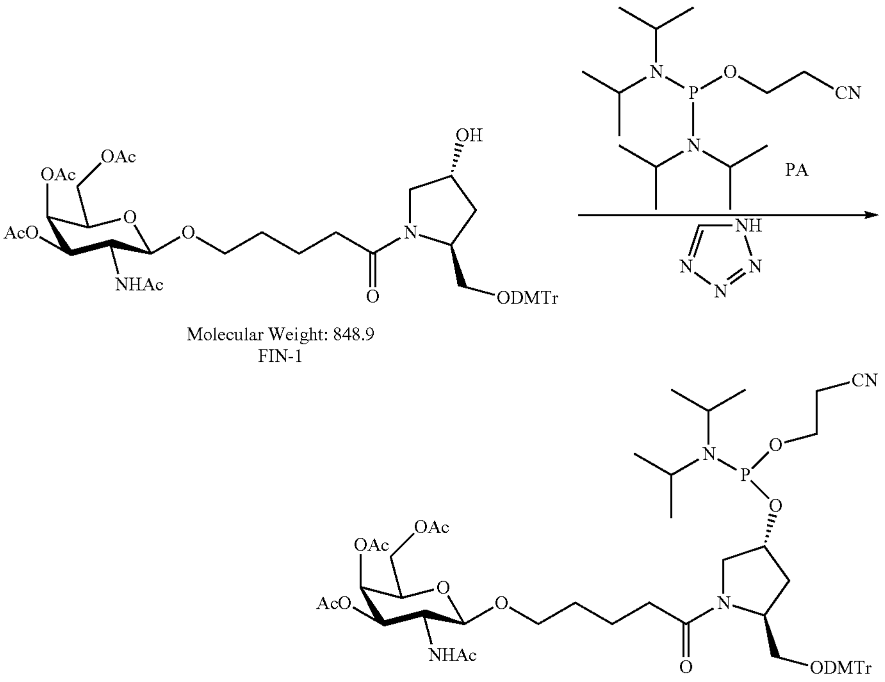

Molecular Weight: 848.9
FIN-1

Molecular Weight: 1049.2
FIN-2

FIN-1 (3.0 g, 3.53 mmol) obtained in step (12-1-2) and acetonitrile were heated for azeotropic dehydration, subjected to suction drying under reduced pressure, dissolved in 10 ml of DMF (dried by immersing in a molecular sieve), added with 2.13 g of PA (bis(diisopropylamino)(2-cyanoethoxy)phosphine, Adamas Inc., product No. 11356B, 7.06 mmol)) and 346 mg tetrazole (CAS No.: 288-94-8, purchased from Aladdin Inc., 4.94 mmol) under nitrogen atmosphere, and stirred to reaction at room temperature. The reaction was supplemented with 10 ml of DMF and continually stirred to react for 1 hour. The solvent was removed by evaporation under reduced pressure, and then the residue was purified by silica gel column chromatography. For purification, the crude product dissolved in DCM was loaded onto the silica gel column pretreated with pyridine to alkalify the column, and eluted with ethyl acetate. The eluate was collected, and the solvent was removed by evaporation under reduced pressure to give 4.5 g of crude product as a colorless syrup. The crude product was completely dissolved in 50% (v/v) aqueous acetonitrile solution and purified by using a medium pressure column (C-18, 330 g, 300 Å) pretreated with a solution of 1% (v/v) pyridine in acetonitrile to alkalify the column. A product peak was collected by gradient elution and the solvent was removed by evaporation under reduced pressure to give 2.2 g of product FIN-2 conjugating molecule as a white powder. $^{31}P$ NMR (162 MHz, $CDCl_3$) δ 148.04, 147.94, 147.62, 147.19, purity of $^{31}P$ NMR: 92%; purity of C18 RP-HPLC: 90.54%.

(12-2) Linking FIN-2 Conjugating Molecule to a Solid Phase Support

The conjugation group (FIN_FIN_FIN) was linked to the 3' terminal of the sense strand of RNA by linking the FIN-2 conjugating molecule obtained in step (12-1-3) to a universal solid phase support (UnyLinker™ loaded NittoPhase®HL Solid Supports) by using the nucleic acid solid phase synthesis method through three reaction cycles.

The linking of conjugation group FIN_FIN_FIN was proformed according to the method described in Rajeev et al., Chem Bio Chem 2015, 16, 903-908. Specifically, the hydroxy protecting group was initially removed from the above-mentioned universal solid phase support and then the solid phase support, which was subsequently brought into contact and coupled with the FIN-2 conjugating molecule under coupling reaction condition in the presence of a coupling agent, and a FIN conjugating molecule linked to the solid phase support was obtained after the capping and oxidation reaction. Moreover, the hydroxy protecting group DMTr was removed from the FIN conjugating molecule linked to the solid phase support, and the solid phase support was further brought into contact and coupled with another FIN-2 conjugating molecule, followed by capping and oxidation reaction. By repeating the above steps of Deprotection-Coupling-Capping-Oxidation, a third FIN-2 conjugating molecule was linked, and thus a conjugation group (FIN_FIN_FIN) linked to the solid phase support was obtained.

In the reactions described above, the reaction conditions of the deprotection, coupling, capping and oxidation as well as the amounts of the solvents and agents are the same as those of the above solid phase synthesis method of nucleic acid in Preparation Example 1.

(12-3) Synthesis of Conjugates F1-F5

The subject conjugates were prepared by the same methods as those in steps (2-2), (2-3A) and (2-4) of Preparation Example 2, except that: 1) the sense strand was synthesized starting from the compound obtained in step (12-2); and 2) the conjugated siRNAs had the sequences corresponding to Conjugates A20-A23, B16-B17, C14, D14, E18-E20 and F20 and Comparative Conjugates A1 and B1 as shown in Tables 4A-4G.

The molecular weight was measured by LC-MS instrument (Liquid Chromatography-Mass Spectrometry, purchased from Waters Corp., Model: LCT Premier). The results showed that the measured values were in conformity with the calculated values, and thus it was confirmed that the synthesized conjugates were the designed compounds of interest, which have a structure as shown by Formula (307).

Preparation Example 13 Preparation of Comparative Conjugates A3, E2 and F2

In this Preparation Example, Comparative Conjugates A3, E2 and F2 were synthesized. The conjugated siRNAs in these conjugates had sequences shown in Tables 4A, 4E and 4F.

(13-1) Synthesis of $(GalNAc)_3$ Conjugating Molecule

Compound 30, i.e., the conjugating molecule containing the above mentioned linker $-(L^A)_3$-trihydroxymethyl aminomethane-$L^B$- and the targeting group N-acetylgalactosamine molecule (wherein each $L^A$ can be linked to one N-acetylgalactosamine molecule such that one linker can be linked to three N-acetylgalactosamine molecules), was synthesized according to the preparation method described in WO2014025805A1. This conjugating molecule can also be referred to as $(GalNAc)_3$ conjugating molecule, and the structure of compound 30 was shown as follows:

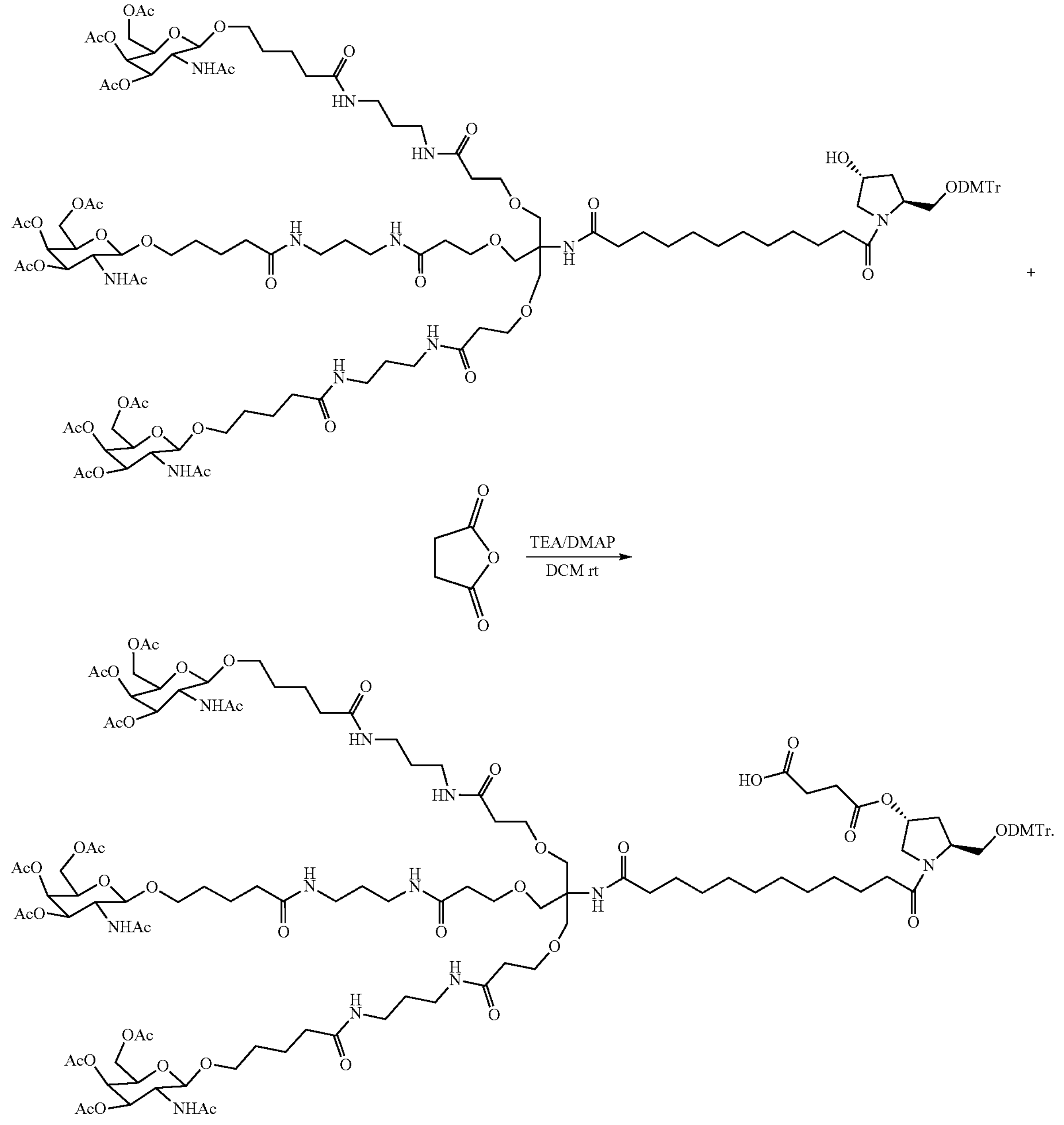

(13-2) Linking $(GalNAc)_3$ Conjugating Molecule to a Solid Phase Support

The $(GalNAc)_3$ conjugating molecule was linked to a solid phase support by the same method as that in step (2-1-9) of Preparation Example 2, thereby obtaining $(GalNAc)_3$ conjugating molecule linked to a solid phase support.

(13-3) Synthesis of Comparative Conjugates A3, E2 and F2

Comparative Conjugates A3, E2 and F2 were prepared by the same methods as those in steps (2-2), (2-3A) and (2-4) of Preparation Example 2, except that: 1) the sense strand was synthesized starting from the compound obtained in step (13-2); and 2) the conjugated siRNAs had sequences shown under NOs. A3, E2 and F2 in Tables 4A, 4E and 4F.

The molecular weight was measured by LC-MS instrument (Liquid Chromatography-Mass Spectrometry, purchased from Waters Corp., Model: LCT Premier). The results showed that the measured values were in conformity with the calculated values, and thus it was confirmed that the synthesized conjugates were the designed compounds of interest, which have a structure as shown by Formula (305).

After the preparation of the above conjugates of the present disclosure, they were lyophilized to solid powder via standard process and stored until used. When being used, they can be reconstituted with, for example, water for injection to a solution at a desired concentration.

The properties of the above siRNA and siRNA conjugates of the present disclosure prepared were studied by the examples below.

The effect experiments of the siRNA conjugates in Table 4A are illustrated as follows.

Experimental Example A1—The toxicity of the siRNA conjugates of the present disclosure.

In C57BL/6J mice, Conjugate A1 (0.9 wt % NaCl aqueous solution, administration volume of 10 mL/kg, concentrations of 10 mg/mL and 20 mg/mL, wherein each concentration was used for 6 mice: three male and three female) was subcutaneously administered to each mouse, with a single dose of 100 mg/kg or 200 mg/kg (based on siRNA). Continuous clinical observation was performed during treatment period, which shows no animal death and no clinical symptoms associated with adverse drug responses. 24 h after the administration, blood samples were taken for clinical pathology test and the mice were dissected. The results show that no abnormalities were found in clinical pathology test and gross anatomy. Thus, the above results indicate the conjugates of the present disclosure have a relatively low toxicity at animal level.

Experimental Example A2 This experiment illustrated the stability of the siRNA conjugates of the present disclosure.

(Experimental Example A2-1) Stability of the siRNA conjugates of the present disclosure in the lysosome lysate in vitro.

Preparation of test samples treated with the lysosome lysate: Comparative Conjugate A1 and Conjugate A21 (each provided in the form of 0.9 wt % NaCl aqueous solution in which the concentration of siRNA is 20 μM, 6 μl for each group) were individually mixed well with 27.2 μL of sodium citrate aqueous solution (pH 5.0), 4.08 μL of deionized water and 2.72 μL of Tritosomes (purchased from Xenotech Inc., Cat No. R0610LT, Lot No. 1610069), and incubated at a constant temperature of 37° C. 5 μL samples were taken at each time point of 0 h, 1 h, 2 h, 4 h, 6 h, 8 h, 24 h and 48 h respectively, added to 15 μL of 9 M urea for denaturation, and added with 4 μL of 6×loading buffer (purchased from Solarbio Inc., Cat No. 20160830), then immediately cryopreserved in a −80° C. freezer to quench the reaction. 0 h represents the moment when the sample was taken immediately after the samples to be tested are mixed well with the lysosome lysate.

Preparation of control samples untreated with the lysosome lysate: 1.5 μL each of the conjugates above at equal moles (20 μM) was mixed well with 7.5 μL of sodium citrate aqueous solution (pH 5.0) and 1 μL of deionized water, added to 30 μL of 9 M urea solution for denaturation, and added with 8 μL of 6×loading buffer, then immediately cryopreserved in a −80° C. freezer to quench the reaction. The control sample for each conjugate is marked as Con in the electrophoretogram.

16 wt % of non-denatured polyacrylamide gel was prepared. 20 μL each of the test samples and the control samples described above was loaded onto the gel to perform electrophoresis under 20 mA constant current for 10 minutes and then under 40 mA constant current for 30 minutes. After finishing the electrophoresis, the gel was placed on a shaker and stained with Gelred dye (BioTium, Cat No. 13G1203) for 10 minutes. The gel was subjected to imaging, observation and photocopying. The results are shown in FIG. 1.

FIG. 1 shows the semiquantitative detection result of the in vitro stability of the tested siRNA conjugates in the Tritosome. The results indicate that the conjugates of the present disclosure can remain undegraded for a long time in Tritosome, showing good stability.

(Experimental Example A2-2) Stability of the siRNA conjugates in the lysosome lysate in vitro.

The stability was measured using the same method as that in Experimental Example 2-1, except that the samples to be tested are Conjugates A1, A6 and Comparative siRNA1, and the time period of incubation with Tritosomes is 0 h, 5 min, 15 min, 30 min, 1 h, 2 h, 4 h and 8 h, respectively.

Figure 2:
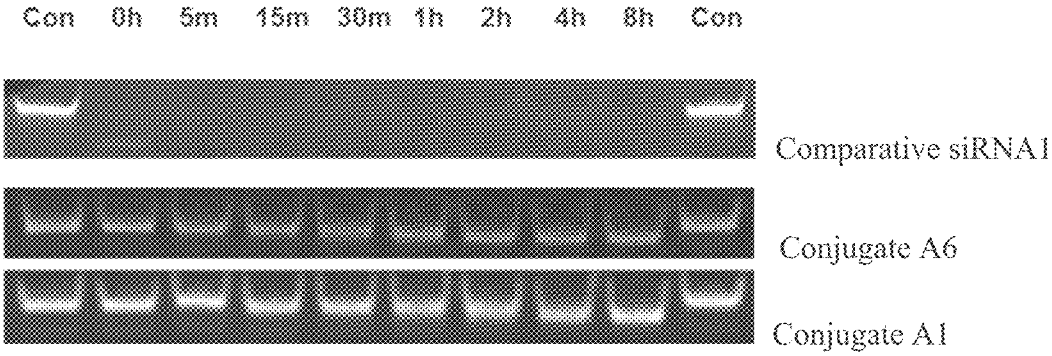

The results of the electrophoresis of non-denatured polyacrylamide gel are shown in FIG. 2.

FIG. 2 shows the semiquantitative detection result of the in vitro stability of the tested siRNA conjugates in the Tritosome. The results indicate that the conjugates of the present disclosure can remain undegraded for a long time in Tritosome, showing good stability.

As can be seen from the results of FIGS. 1 and 2, the siRNAs having specific modification according to the present disclosure exhibit satisfactory stability in the lysosome lysate in vitro.

(Experimental Example A2-3) Stability in human plasma

Conjugates A1, A6, and Comparative siRNA2 (each provided in the form of 0.9 wt % NaCl aqueous solution in which the concentration of siRNA is 20 μM, 12 μl for each group) were individually mixed well with 108 μL of 90% human plasma (diluted in PBS) and incubated at a constant temperature of 37° C. 10 μL samples were taken at each time point of 0 h, 2 h, 4 h, 6 h, 8 h, 24 h, 48 h and 72 h, respectively, and immediately frozen in liquid nitrogen and cryopreserved in a −80° C. freezer. After sampling at each time point, each cryopreserved sample was diluted 5-fold with 1×PBS (pH 7.4) and then taken in a volume of 10 μL for use. Meanwhile, each of the samples to be tested was taken at equal moles (2 μM, 2 μL) and mixed well with 8 μL of 1×PBS (pH 7.4), thus obtaining 10 μL of samples untreated with human plasma (marked as Con). 20 wt % of non-denatured polyacrylamide gel was prepared. Each cryopreserved sample above was mixed with 4 μL of loading buffer (aqueous solution of 20 mM EDTA, 36 wt % glycerol, and 0.06 wt % bromophenol blue) and then loaded onto the above gel to perform electrophoresis under 80 mA constant current for 60 minutes. After finishing the electrophoresis, the gel was stained with 1×Sybr Gold dye (Invitrogen, Cat No. 11494) for 15 minutes followed by imaging. The results are shown in FIG. 3.

Figure 3:
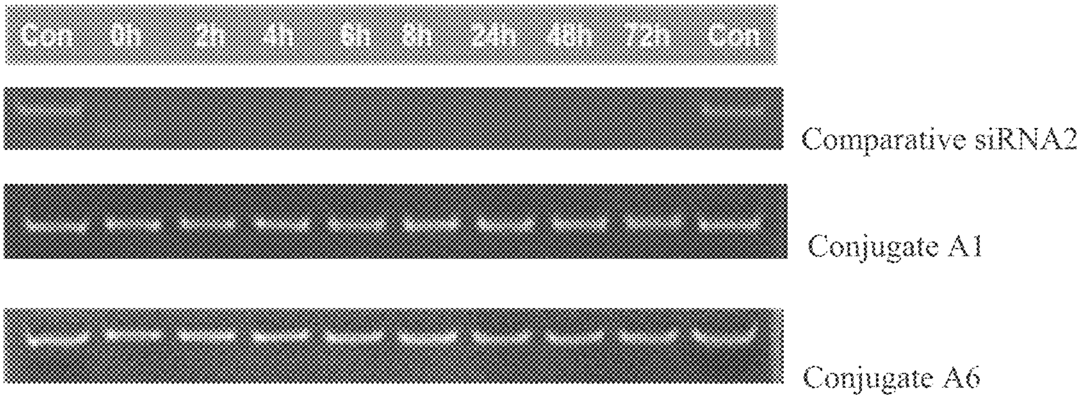
FIGS. 3 and 4 show the semiquantitative result of the stability test of the siRNA conjugates in human plasma in vitro.

FIG. 3 shows the semiquantitative detection result of the in vitro stability of the tested conjugates in human plasm.

As can be seen from the results of FIG. 3, in human plasma, the conjugates of the present disclosure remain undegraded at up to 72 hours, showing excellent stability in human plasma.

(Experimental Example A2-4) Stability of the conjugates in the monkey plasma

Conjugates A1, A6, and Comparative siRNA2 (each provided in the form of 0.9 wt % NaCl aqueous solution in which the concentration of siRNA is 20 μM, 12 μl for each group) were individually mixed well with 108 μL of 90% cynomolgus monkey plasma (Monkey plasma, purchased form HONGQUAN Bio, Cat No. HQ70082, diluted in PBS) and incubated at a constant temperature of 37° C. 10 μL samples were taken at each time point of 0 h, 2 h, 4 h, 6 h, 8 h, 24 h, 48 h and 72 h, respectively, and immediately frozen in liquid nitrogen and cryopreserved in a −80° C. freezer. After sampling at each time point, each sample was diluted 5-fold with 1×PBS (pH 7.4) and then taken in a volume of 10 μL for use. Meanwhile, each of the samples to be tested was taken at equal moles (2 μM, 2 μL) and mixed well with 8 μL of 1×PBS (pH 7.4), thus obtaining 10 μL of samples untreated with monkey plasma (marked as Con). 20 wt % of non-denatured polyacrylamide gel was prepared. Each cryopreserved sample was all mixed with 4 μL of loading buffer (aqueous solution of 20 mM EDTA, 36 wt % glycerol, and 0.06 wt % bromophenol blue) and then loaded onto the above gel to perform electrophoresis under 80 mA constant current for 60 minutes. After finishing the electrophoresis, the gel was stained with 1×Sybr Gold dye (Invitrogen, Cat No. 11494) for 15 minutes followed by imaging. The results are shown in FIG. 4.

Figure 4:
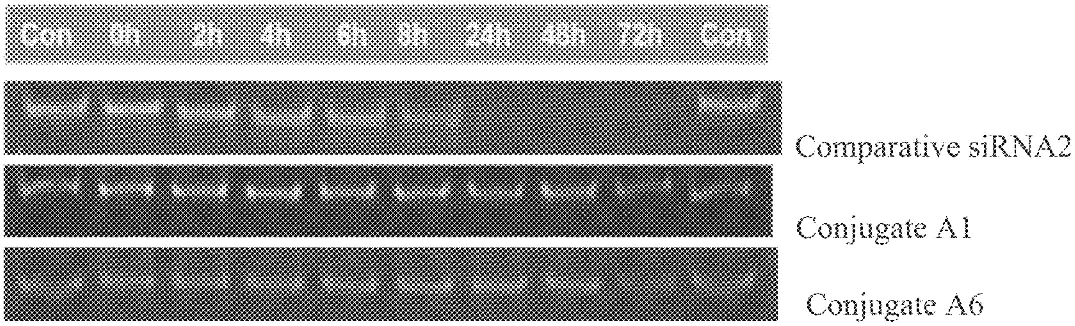

FIG. 4 shows the semiquantitative detection result of the in vitro stability of the tested siRNA in the monkey plasma.

As can be seen from the results of FIG. 4, in cynomolgus monkey plasma, the siRNA conjugates of the present disclosure remain undegraded at up to 72 hours, showing excellent stability in monkey plasma.

(Experimental Example A2-5) This experiment illustrated the stability of the siRNA conjugates of the present disclosure in the lysosome lysate in vitro.

1) Detection of the Stability in Murine Lysosome Lysate

Preparation of test samples treated with the lysosome lysate: Conjugate A2 and Comparative siRNA2 (20 μM, each 6 μL) were individually mixed well with 27.2 μL of sodium citrate aqueous solution (pH 5.0), 4.08 μL of deionized water and 2.72 μL of murine lysosome lysate (Rat Liver Tritosomes, purchased from Xenotech Inc., Cat No. R0610.LT, Lot No. 1610069, at a final concentration of acid phosphatase of 0.2 mU/μL), and incubated at a constant temperature of 37° C. 5 μL mixed solution was taken at each time point of 0 h, 1 h, 2 h, 4 h, 6 h, and 24 h, respectively, added to 15 μL of 9 M urea solution for denaturation, and added with 4 μL of 6×loading buffer (purchased from Solarbio Inc., Cat No. 20160830), then immediately cryopreserved in a −80° C. freezer to quench the reaction. 0 h represents the moment when the sample was taken immediately after the samples to be tested are mixed well with the lysosome lysate.

Preparation of control samples untreated with the lysosome lysate: 1.5 μL each of the Conjugate A2 and Comparative siRNA2 (20 μM) at equal moles was mixed well with 7.5 μL of sodium citrate aqueous solution (pH 5.0) and 1 μL of deionized water, added to 30 μL of 9 M urea solution for denaturation, and added with 8 μL of 6×loading buffer, then immediately cryopreserved in a −80° C. freezer to quench the reaction. The control sample for each conjugate is marked as M to be compared with the electrophoresis results of the sample.

Figure 5:
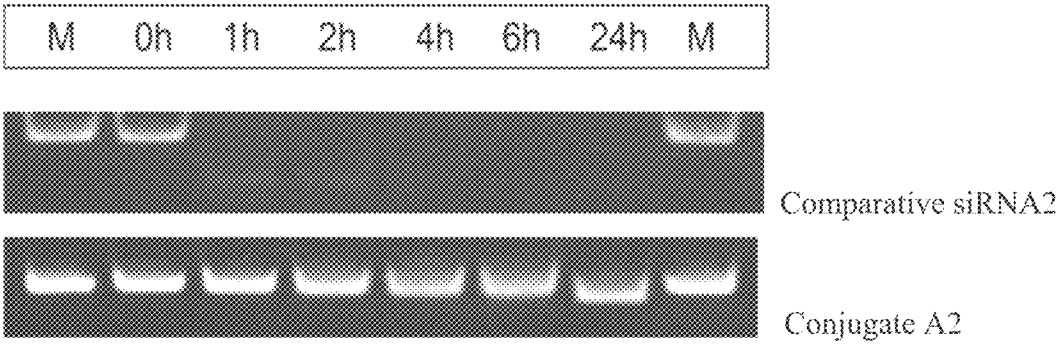
FIGS. 5 and 6 show the semiquantitative result of the stability test of the siRNA conjugates in monkey plasma in vitro.

16 wt % of non-denatured polyacrylamide gel was prepared. 20 μL each of the test sample and the control sample described above was loaded onto the gel to perform electrophoresis under 20 mA constant current for 10 minutes and then under 40 mA constant current for 30 minutes. After finishing the electrophoresis, the gel was placed on a shaker and stained with Gelred dye (BioTium, Cat No. 13G1203) for 10 minutes. The gel was subjected to imaging, observation and photocopying. The results are shown in FIG. 5.

2) Detection of the Stability in Human Lysosome Lysate

Figure 6:
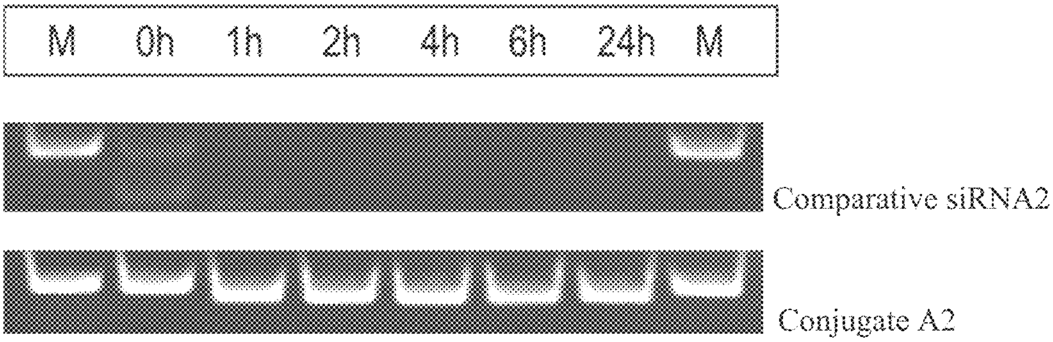

The stability of Comparative siRNA2 and Conjugate A2 in the human lysosome lysate was measured using the same method as that in 1), except that the murine lysosome lysate was replaced with the human lysosome lysate (Human Liver Lysosomes, purchased from Xenotech Inc., Cat No. $R^{0610}$.L, Lot No. 1610316). The results are shown in FIG. 6.

The results indicate that the siRNA conjugates of the present disclosure can remain undegraded for at least 24 hours both in human-origined lysosome lysate and in murine lysosome lysate, showing satisfactory stability.

Experimental Example A3 The results of the pharmacokinetic study of conjugate A1 of the present disclosure in rats in vivo In this Experimental Example, Conjugate A1 was administered to rats in each experimental group (10 rats in each group, five male and five female) by subcutaneous injection, respectively, with a single dose of 10 mg/kg and 50 mg/kg. Subsequently, the drug concentration in plasma, liver and kidney tissues of rats were measured at each time point.

The SD rats used in this experimental example were provided by Beijing Vital River Laboratory Animal Technology Co., Ltd.

Firstly, SD rats were randomly divided into groups according to the body weight and gender by using the PRISTIMAdata system version 7.2.0, and then respectively administered with each group of the conjugates according to the designed dosage. The drug dosages for all animals were calculated according to the body weigh (single administration (subcutaneously), administration dosage of 10 mg/kg and 50 mg/kg, in the form of 0.9% NaCl aqueous solution containing 1 mg/ml and 5 mg/ml conjugates, and administration volume of 10 mL/kg). Rat whole blood was collected from the jugular vein before administration and at 5 minutes (+30 seconds), 30 minutes (±1 minute), 1 hour (+2 minutes), 2 hours (+2 minutes), 6 hours (+5 minutes), 24 hours (+10 minutes), 48 hours (+20 minutes), 72 hours (+20 minutes), 120 hours (+30 minutes), and 168 hours (+30 minutes) after administration. Then the whole blood samples were centrifugated at 1800×g at 2-8° C. for 10 minutes to separate plasma. About 70 μL volume of the plasma sample was placed in one tube, and the remaining of the sample was placed in another, both of which were cryopreserved at −70° C. to −86° C. for detection. Liver and kidney tissues of rats were collected at about 24, 48, 72, 120, and 168 hours after administration by the method comprising anesthetizing the rats with pentobarbital sodium according to the weight thereof (60 mg/kg, intraperitoneal injection), euthanizing the rats by blood collection from abdominal aorta, and performing gross anatomy. The liver and kidney of each rat were sampled and stored in 1 mL cryotube at below −68° C. until detection and analysis.

The concentrations of the Conjugate A1 in plasma, liver and kidney tissues of rats were detected quantitatively by High Performance Liquid Chromatography with Fluorescence Detection (HPLC-FLD) according to the following steps:

(1) grinding the tissue until a tissue mass of no more than 80 mg was obtained, then adding Tissue and Cell Lysis Solution (supplier: Epicentre, Cat No. MTC096H) to prepare a tissue homogenate of 66.7 mg/mL;

(2) subjecting the tissue homogenate to a sonication (150 W, 30 s) to disrupt cells;

(3) for tissue samples, adding 75 μL of tissue samples to a 96-well PCR plate, adding 5 μL of proteinase K (supplier: Invitrogen, Cat No. 25530-015) and 10 μL of mixed aqueous solution of 10 wt % acetonitrile and 0.01 wt % Tween 20; for plasma samples, adding 20 μL of plasma to a 96-well PCR plate, adding 45 μL of Tissue and Cell Lysis Solution, 5 μL of proteinase K, and 20 μL of mixed aqueous solution of 10 wt % acetonitrile and 0.01 wt % Tween 20;

(4) blocking the plates and placing them in a PCR instrument (supplier: Applied Biosystems, model: GeneAmp® PCR system 9700) and incubating at 65° C. for 45 minutes;

(5) after finishing incubation, adding 10 μl of 3 M KCl aqueous solution (supplier: Sigma-aldrich, Cat No. 60135-250ML), shaking well, and centrifuging at 3200 rcf at 4° C. for 15 minutes;

(6) for tissue samples, adding 80 μL of supernatant into 120 μL of hybridization mixture solution (formula: 0.5 mL of 6 μM PNA probe (supplier: TAHE-PNA), 1 mL of 200 mM Trizma/pH=8, 5 mL of 8 M urea aqueous solution, 3.5 mL of $H_2O$, 2 mL of acetonitrile); for plasma samples, adding 40 μL of supernatant into 160 μL of hybridization mixture solution (formula: 0.5 mL of 6 μM PNA probe, 1 mL of 200 mM Trizma/pH=8, 5 mL of 8 M urea aqueous solution, 7.5 mL of $H_2O$, 2 mL of acetonitrile);

(7) blocking the plates and placing them in a PCR instrument, incubating at 95° C. for 15 minutes, then immediately placing on ice for 5 minutes;

(8) transferring the samples to new 96-well plates with conical bottom, shaking well, and centrifuging at 3200 rcf for 1 minute;

(9) injecting the samples for detection and quantitatively analyzing by using HPLC-FLD (liquid-phase system supplier: Thermo Fisher, chromatography model: ultimate 3000).

Figure 7:
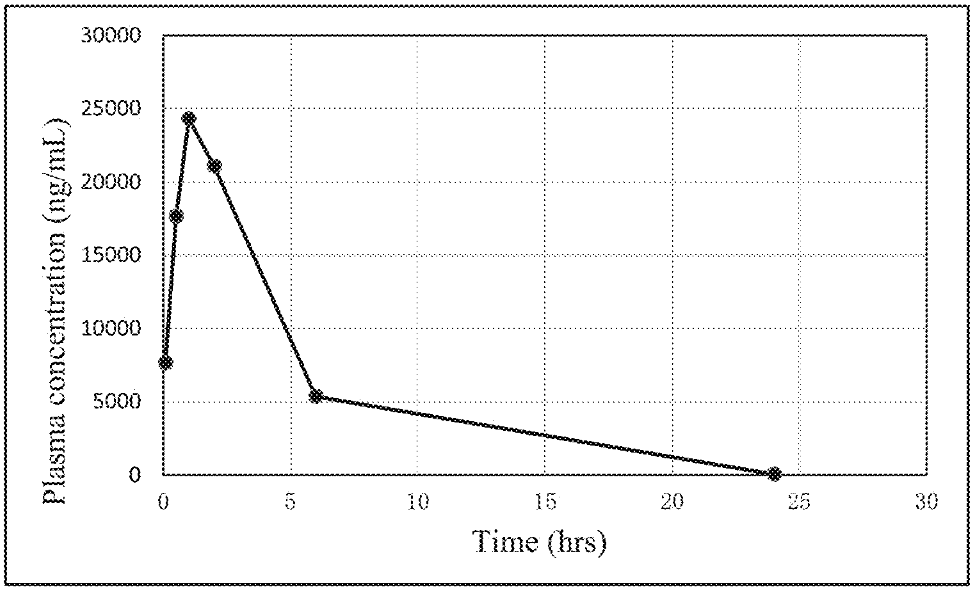
FIGS. 7-10 are metabolic curves over time showing PK/TK plasma or tissue concentration for: Conjugate A1 in rat plasma at a dosage of 10 mg/kg (FIG. 7); Conjugate A1 in rat liver and kidney at a dosage of 10 mg/kg (FIG. 8); Conjugate A1 in rat plasma at a dosage of 50 mg/kg (FIG. 9); Conjugate A1 in rat liver and kidney at a dosage of 50 mg/kg (FIG. 10).

The analyzed results can be found in FIGS. 7-10, which show metabolic curves over time of PK/TK plasma concentrations in rat plasma and PK/TK tissue concentrations in rat liver and kidney for Conjugate A1 at a dosage of 10 mg/kg or 50 mg/kg, respectively. Specifically, FIG. 7 is a metabolic curve over time showing PK/TK plasma concentration for Conjugate A1 in rat plasma at a dosage of 10 mg/kg.

Figure 8:
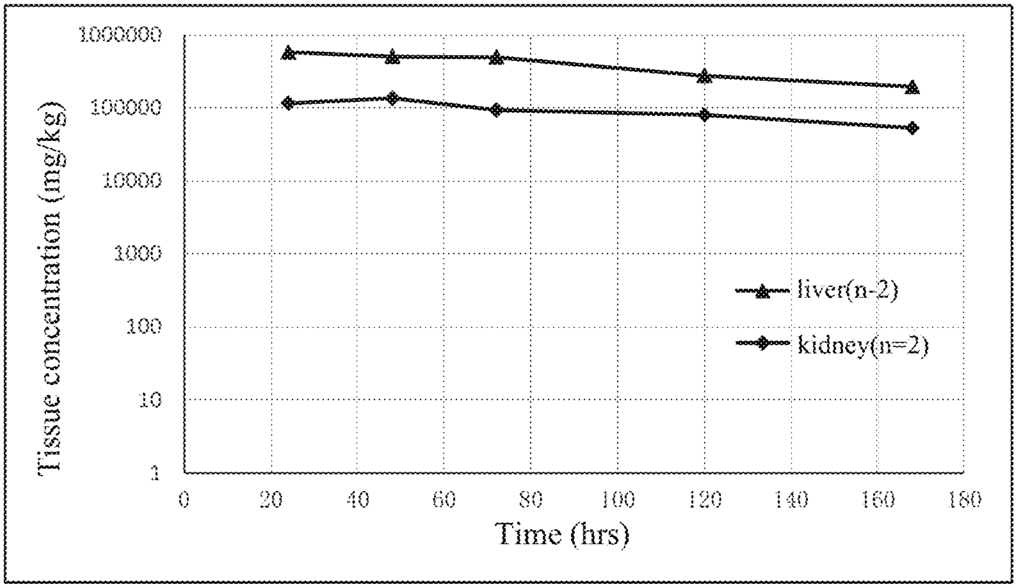

FIG. 8 is a metabolic curve over time showing PK/TK tissue concentrations for Conjugate A1 in rat liver and kidney at a dosage of 10 mg/kg.

Figure 9:
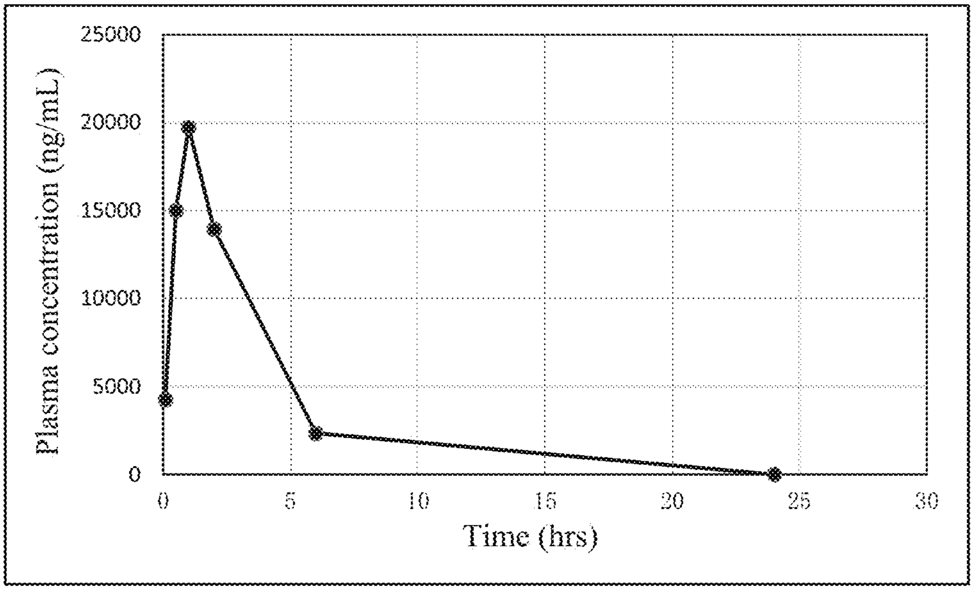

FIG. 9 is a metabolic curve over time showing PK/TK plasma concentration for Conjugate A1 in rat plasma at a dosage of 50 mg/kg.

Figure 10:
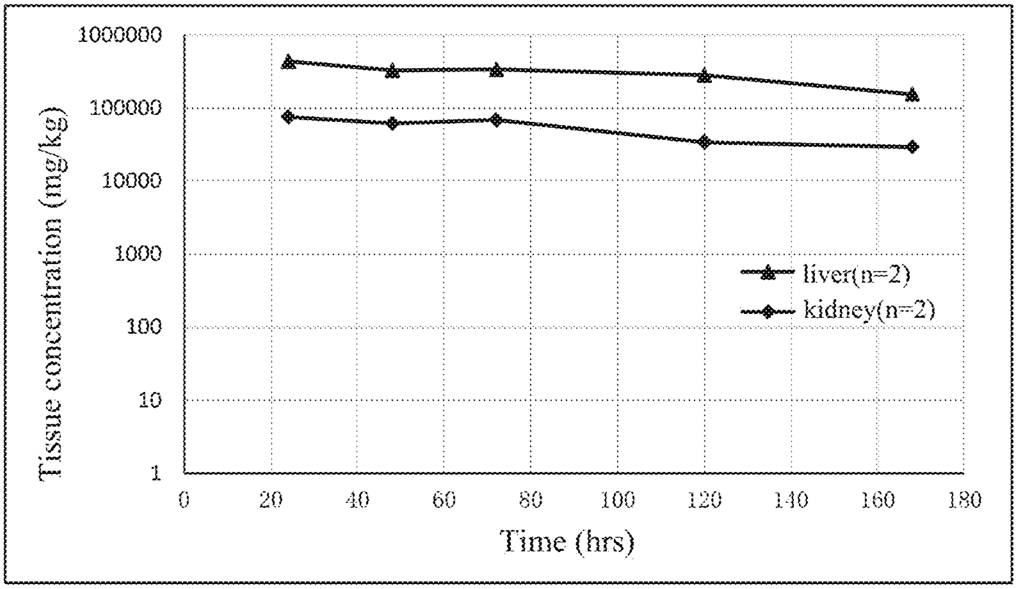

FIG. 10 is a metabolic curve over time showing PK/TK tissue concentrations for Conjugate A1 in rat liver and kidney at a dosage of 50 mg/kg.

As can be seen from the results of FIGS. 7-10, the concentrations for Conjugate A1 in rat plasma were rapidly decreased below the detection limit within several hours, while the concentrations in rat liver tissue were maintained at a relatively high and stable level over at least 168 hours, either at a low dosage (10 mg/kg) or at a relatively high dosage (50 mg/kg). This shows that the siRNA conjugate of the present disclosure can be specifically and significantly enriched in liver and remain stable, showing a high degree of targeting.

Experimental Example A4—This experiment illustrated the inhibitory efficiency of the RNA conjugates of the present disclosure against the expression of HBV mRNA in vivo.

In this experimental example, the inhibition efficiency of Conjugates A5 and A7 against the expression of HBV mRNA in HBV transgenic mice C57BL/6J-Tg(A1b1HBV)44Bri/J was investigated.

HBsAg content in mouse serum was measured using Hepatitis B Virus Surface Antigen Assay Kit (Enzyme-linked Immunosorbent Assay, ELISA) (Shanghai Kehua Bio-engineering Co., Ltd.). Mice with S/COV>10 were selected and randomly divided into groups (all female, 4 mice in each group) and respectively numbered as Conjugate A5 and Conjugate A7, and a normal saline (NS) group was added as a control group. The drug dosages for all animals were calculated according to the body weight (single administration (subcutaneously), administration dosage of 1 mg/kg and 0.1 mg/kg, in the form of 0.9% NaCl aqueous solution containing 0.2 mg/ml and 0.02 mg/ml conjugates, and administration volume of 5 mL/kg). Animals were sacrificed on day 14 after administration. The liver was collected and kept with RNA later (Sigma Aldrich), and the liver tissue was homogenized with a tissue homogenizer. Then the total RNA was extracted and obtained by using Trizol according to the standard procedures for total RNA extraction.

The expression level of HBV mRNA in liver tissue was detected by real-time fluorescent qPCR. Specifically, the extracted total RNA was reverse transcribed into cDNA by using ImProm-II™ reverse transcription kit (Promega) according to the instruction, and then the inhibitory efficiency of siRNAs against the expression of HBV mRNA in liver tissue was detected by using the fluorescent qPCR kit (Beijing Cowin Biosicences Co., Ltd). In this fluorescent qPCR method, β-actin gene was used as an internal control gene, the HBV and β-actin were detected by using primers for HBV and β-actin, respectively.

Sequences of primers for detection are shown in Table 5A.

TABLE 5A

Sequences of primers for detection

| Genes | Upstream Primers | Downstream Primers |
|---|---|---|
| HBV | 5'-CCGTCT GTGCCTTCT CATCT-3' (SEQ ID NO: 425) | 5'-TAATCTCC TCCCCCAACTC C-3' (SEQ ID NO: 426) |
| β-actin | 5'-AGCTTC TTTGCAGCT CCTTCGTT G-3' (SEQ ID NO: 427) | 5'-TTCTGACC CATTCCCACCA TCACA-3' (SEQ ID NO: 428) |

In this fluorescent qPCR method, the expression of HBV mRNA was expressed as the remaining expression of HBV X gene and calculated by the following equation:

The remaining expression of *HBV X* gene=(the copy number of *HBV X* gene in the test group/the copy number of β-actin gene in the test group)/(the copy number of *HBV* gene in the control group/the copy number of β-actin gene in the control group)×100%,which is marked as *HBV X*/β-actin mRNA expression in the figures.

Figure 11:
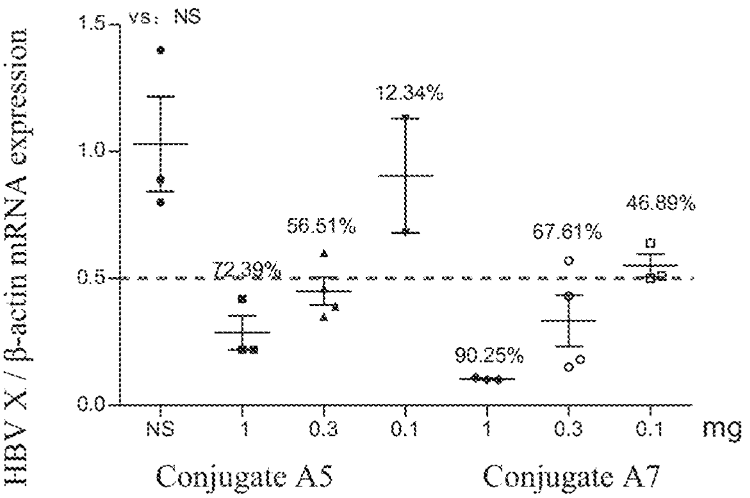
FIGS. 11-14 respectively show inhibitory effect of the conjugates of the present disclosure on HBV mRNA in 44BriHBV models.

Then, the inhibition percentage of the conjugate against mRNA was calculated according to the equation:

The inhibition percentage of the conjugate against mRNA=(1−the remaining expression of *HBV X* gene)×100%, wherein the control group was a group of control mice administered with NS in this experiment and each test group was a group of mice administered with different siRNA conjugates, respectively. The results are shown in FIG. 11.

Figure 12:
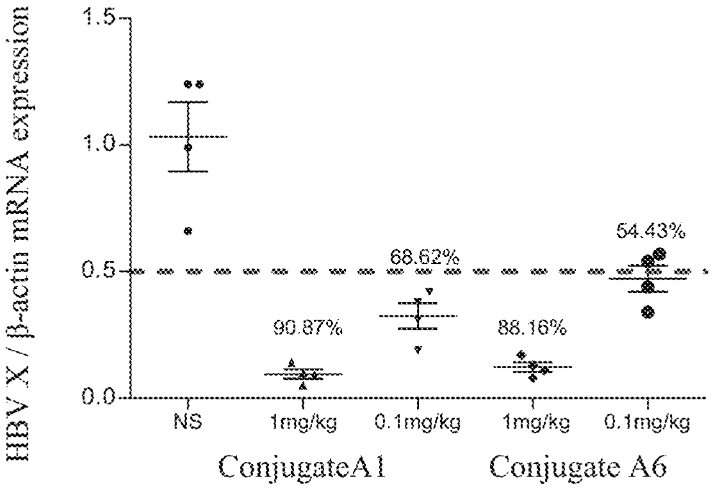
Figure 13:
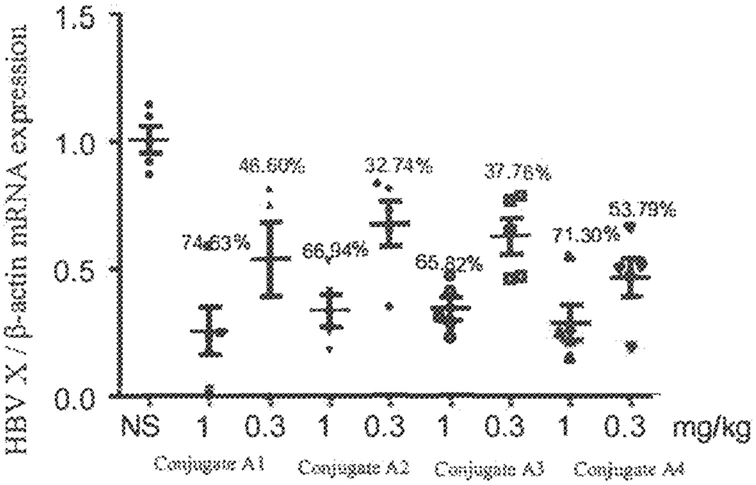

In other experiments, several tests were further performed according to the following conditions:

Tests were performed by using the same method described above, except that the siRNA conjugate administered was replaced with Conjugates A1 and A6 for testing, and the data were collected on day 14. The results are shown in FIG. 12; and Tests were performed by using the same method described above, except that the siRNA conjugate administered was replaced with Conjugates A1, A2, A3 and A4 for testing (5 mice in each group), and the data are collected on day 28. Each conjugate was administered in the two dosages of 1 mg/kg and 0.3 mg/kg (wherein the administration volume remained the same, while the concentrations of the conjugate solutions were respectively adjusted). The results are respectively shown in FIG. 13.

Figure 14:
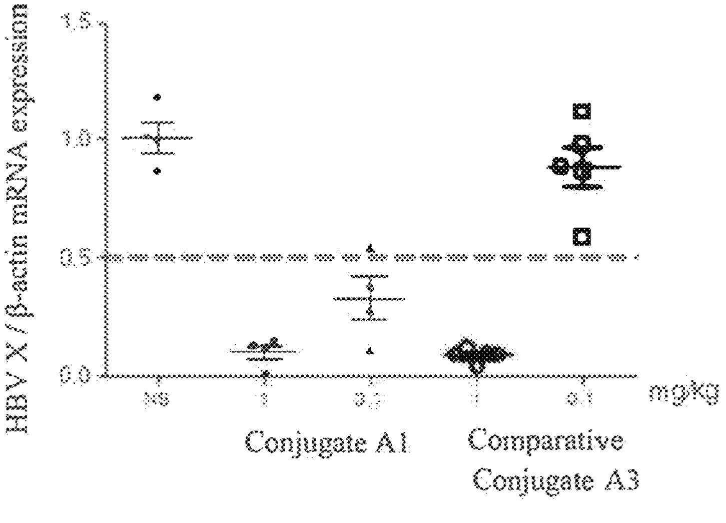

Tests were performed by using the same method described above, except that the siRNA conjugate administered was replaced with Conjugate A1 and Comparative Conjugate A3 for testing, and the data are collected on day 14. Each conjugate was administered in the two dosages of 1 mg/kg and 0.1 mg/kg (wherein the administration volume remained the same, while the concentrations of the conjugate solutions were respectively adjusted). The results are respectively shown in FIG. 14.

As can be seen from the above results, in several experiments with different testing time points, all conjugates of the present disclosure described above show high inhibitory activity against the expression of HBV mRNA in mice in vivo.

Experimental Example A5 This experiment illustrated a test about the relationship between time and inhibitory efficiency of the siRNA conjugates of the present disclosure against the expression of HBsAg and HBV DNA in HBV transgenic mice serum.

An AAV-HBV mouse was used. After successful establishment of the animal models, these mice were randomly divided into groups based on HBsAg content in serum (5 mice in each group). Conjugate A1, Comparative Conjugate A2, Comparative Conjugate A3 and NS as a blank control were respectively administered to each group. The drug dosages for all animals were calculated according to the body weight (single administration (subcutaneously), administration dosage of 3 mg/kg and 1 mg/kg, in the form of 0.9% NaCl aqueous solution containing 0.3 mg/ml and 0.1 mg/ml conjugates, and administration volume of 5 mL/kg). The blood was taken from mouse orbital venous plexus before administration (marked as D0) and on days 7, 14, 21, 28, 56, 84, 112, 140, 154, 168 and 182 after administration, and HBsAg level in serum was measured for each time point. During the experiment, the detection of a subject is ended if the HBsAg content in serum in the test result is close to or more than the original value.

About 100 μl orbital blood was taken each time, and the serum was no less than 20 μl after centrifugation. The expression level of HBsAg in serum was measured by using HBsAg CLIA kit (Autobio, CL0310). The expression level of HBV DNA was measured by extraction of the DNA from the serum with reference to the instruction of QIAamp 96 DNA Blood Kit followed by qPCR.

The normalized HBsAg expression level=(the content of HBsAg after administration/the content of HBsAg before administration)×100%.

The inhibition percentage against HBsAg=(1−the content of HBsAg after administration/the content of HBsAg before administration)×100%, wherein the content of HBsAg was expressed in equivalents (*UI*) of HBsAg per milliliter (ml) of serum.

The normalized *HBV DNA* expression level=(the content of *HBV DNA* after administration/the content of *HBV DNA* before administration)×100%.

The inhibition percentage against *HBV DNA*=(1−the content of *HBV DNA* after administration/the content of *HBV DNA* before administration)×100%, wherein the content of HBV DNA was expressed in copies of HBV DNA per milliliter (ml) of serum.

Figure 15:
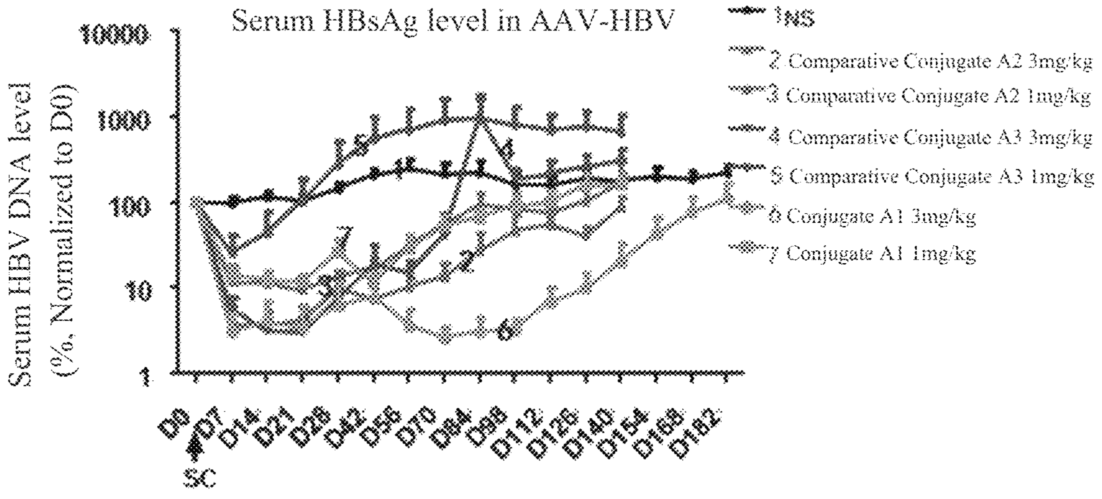
FIGS. 15-16 respectively show inhibitory effect over time of the conjugates of the present disclosure on serum HBsAg and HBV DNA in AAV-HBV models.
Figure 16:
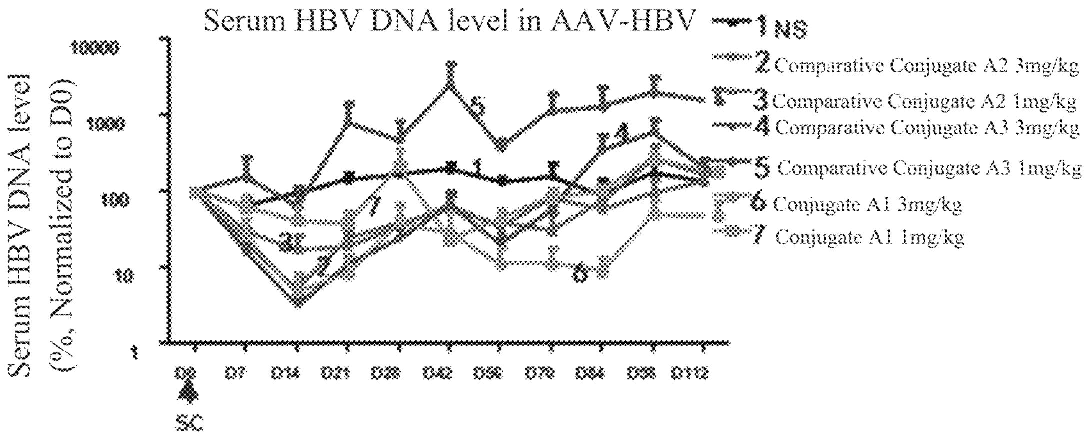

The results are shown in FIGS. 15 and 16.

As can be seen from the results of FIG. 15, the NS negative control group showed no inhibitory effect at different time points after administration; in contrast, each conjugate showed excellent inhibitory effect on HBsAg at different time points after administration. In particular, Conjugate A1 consistently showed high inhibition percentage against HBsAg in serum over a period of up to 140 days, indicating stable and effective inhibition against the expression of HBV gene over a longer time period.

As can be seen from the results of FIG. 16, the Conjugate A1 also showed efficient inhibition against the expression of HBV DNA and maintained higher inhibition percentage over a period of up to 84 days.

In contrast, although Comparative Conjugates A2 and A3 achieved similar mRNA inhibitory effects to the individual conjugates in the experiments in vivo, the duration of the inhibitory effects as shown in FIGS. 15 and 16 were significantly shorter than that of Conjugates 1 and 6 at the same dose level.

Figure 17:
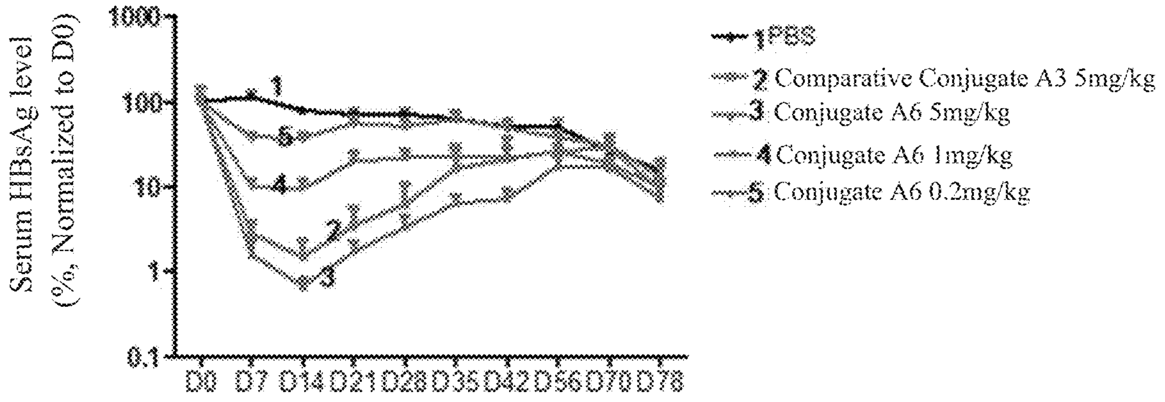
FIG. 17 shows inhibitory effect over time of the conjugates of the present disclosure on serum HBsAg in M-Tg models.
Figure 18:
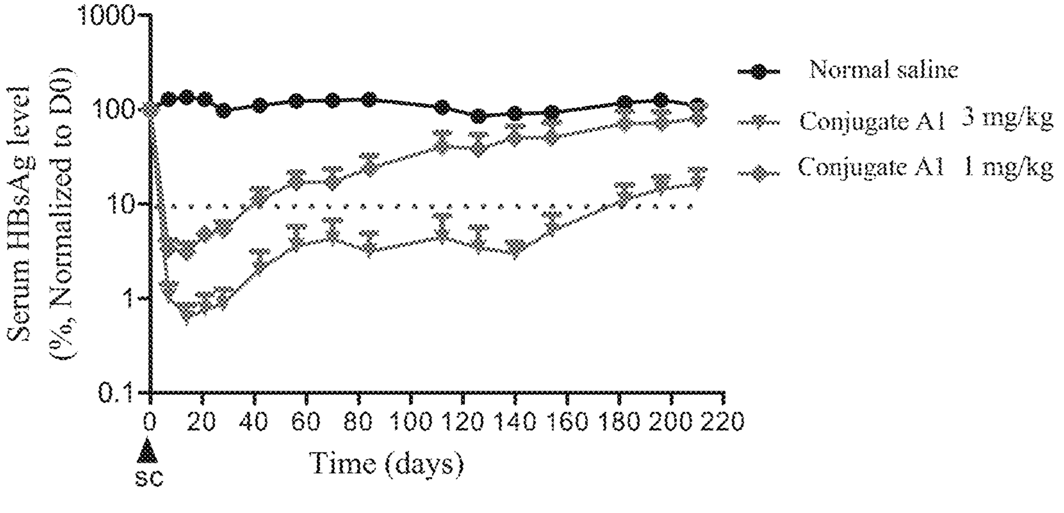
FIGS. 18-19 respectively show inhibitory effect over time of the conjugates of the present disclosure on serum HBsAg and HBV DNA in 1.28 copy HBV-Tg models.
Figure 19:
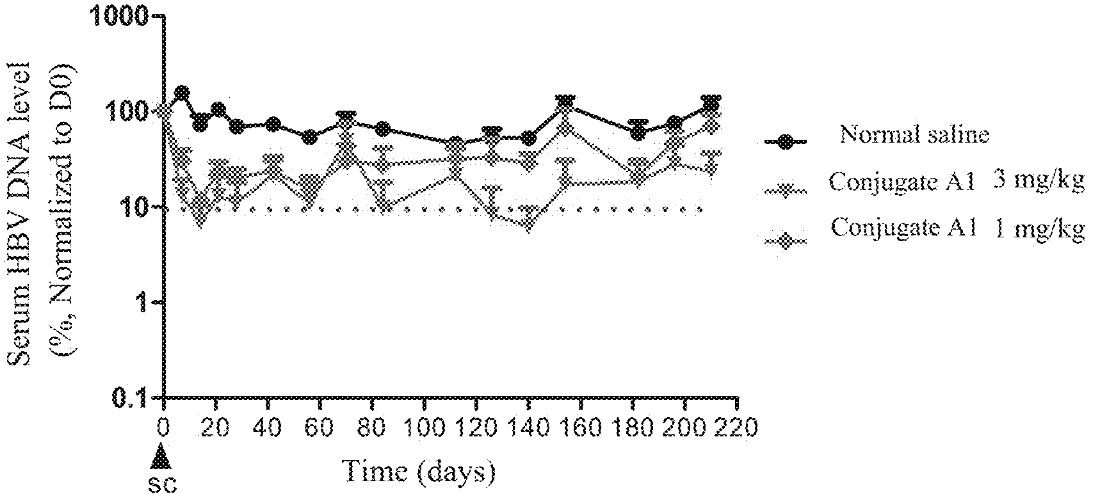
Figure 20A:
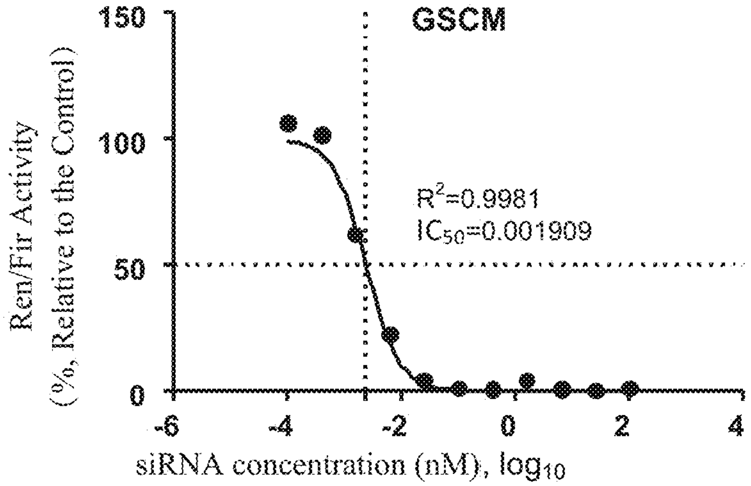
FIGS. 20A, 20B, 20C, and 20D respectively show inhibitory effect of Conjugate A1 at different concentrations on the expression of GSCM, GSSM, PSCM and PSSM.
Figure 20B:
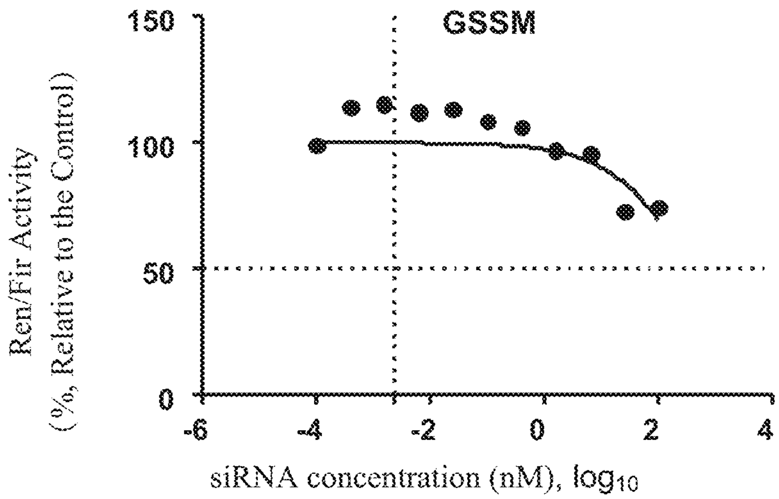
Figure 20C:
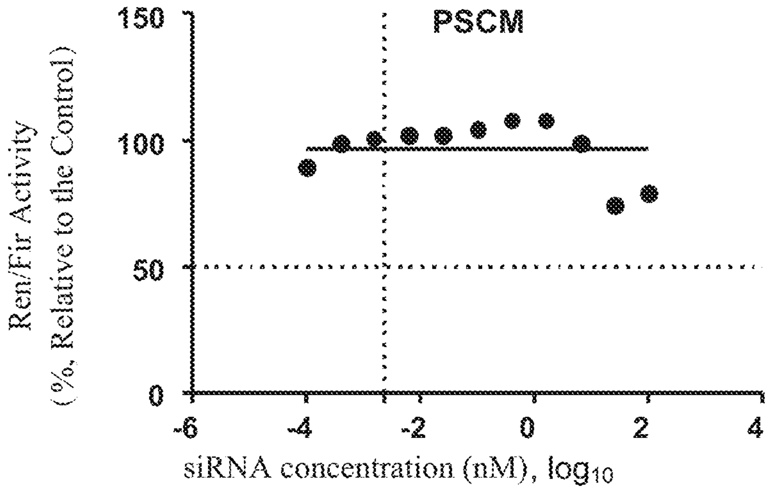
Figure 20D:
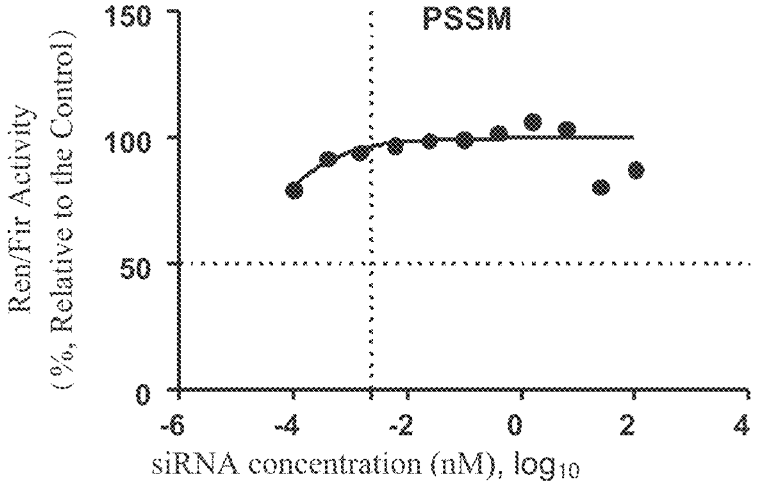

According to the same methods as described above, two more tests were further performed, wherein serum HBsAg was measured, except that:

In M-Tg models, the administration doses of Conjugate A6 are 5 mg/kg, 1 mg/kg and 0.2 mg/kg, and Comparative Conjugate A3 is 5 mg/kg; the test continued until day 78; and the results are shown in FIG. 17;

In 1.28 copy model mouse, the administration doses of Conjugate A1 are 3 mg/kg and 1 mg/kg; the test continued until day 210; and the results are shown in FIGS. 18 and 19.

For the various administration doses described above, each conjugate was administered in the same administration volume, while concentration of the solution was correspondingly adjusted, so as to be administered in the corresponding dose.

From the results of FIGS. 15-19, it can be seen that the siRNA conjugates of the present disclosure showed consistent and efficient inhibitory efficiency on serum HBsAg in various animal models, and regular dose dependency.

Experimental Example A6 This experiment illustrated that the siRNA conjugate of the present disclosure not only has higher activity in vitro, but also shows low off-target effect (A6-1) HEK293A cells used in this experimental example were provided by Nucleic Acid Technology Laboratory, Institute of Molecular Medicine, Peking University and cultured in DMEM complete media (Hyclone company) containing 20% fetal bovine serum (FBS, Hyclone company), 0.2 v % Penicillin-Streptomycin (Gibco, Invitrogen company) at 37° C. in an incubator containing 5% $CO_2$/95% air.

In this experimental example, Conjugate A1 was investigated in in vitro psiCHECK system for the on-target activity and off-target effect. Specifically, Conjugate A1 was tested for the activity of targeting completely matching target sequence (of which the nucleotide sequence is completely complementary with the full length nucleotide sequence of the sense/antisense strand of Conjugate A1) or targeting matching target sequence in seed region (of which the nucleotide sequence is complementary with the nucleotide sequence of positions 1-8 of the sense/antisense strand of Conjugate A1).

According to the method described by Kumico Ui-Tei et. al., Functional dissection of siRNA sequence by systematic DNA substitution: modified siRNA with a DNA seed arm is a powerful tool for mammalian gene silencing with significantly reduced off-target effect. Nucleic Acids Research, 2008.36(7), 2136-2151, plasmids for detection were constructed and co-transfected with the siRNA conjugates to be detected into HEK293A cells; and the expression levels of the dual luciferase reporter gene reflect the on-target activity and off-target effect of the siRNA conjugates. Specific steps are as follows:

[1] Construction of Plasmids for Detection

Four recombinant plasmids were constructed using psiCHECK™-2 (Promega™) plasmid, in which GSCM represents the on-target plasmid; and PSCM, GSSM and PSSM represent the off-target plasmids:

(1) GSCM, containing a target sequence, wherein the target sequence is fully complementary with all 21 nucleotide sequences of the antisense strand in the conjugate to be detected (which is Conjugate A1 in this example).

(2) PSCM, containing a target sequence, wherein the target sequence is identical with all 21 nucleotide sequences of the antisense strand in the Conjugate A1.

(3) GSSM, containing a target sequence, wherein the target sequence is fully complementary with the nucleotide sequence at positions 1-8 from 5' terminal of the antisense strand in the Conjugate A1, while the remaining part of the target sequence corresponds to the nucleotide sequence at positions 9-21 from 5' terminal of the antisense strand in the Conjugate A1, but is completely mismatched; that is, when the nucleotide at any position in positions 9-21 from 5' terminal of the antisense strand in the Conjugate A1 is G, C, A or U, the nucleotide at the corresponding position in the target sequence is T, A, C or G.

(4) PSSM, containing a target sequence, wherein the target sequence is fully complementary with the nucleotide sequence at positions 1-8 from the 5' terminal of the sense strand in the Conjugate A1, while the remaining part of the target sequence corresponds to the nucleotide sequence at positions 9-19 from 5' terminal of the sense strand in the Conjugate A1, but is completely mismatched; that is, when the nucleotide at any position in positions 9-19 from 5' terminal of the sense strand in the Conjugate A1 is G, C, A or U, the nucleotide at the corresponding position in the target sequence is T, A, C or G. In order to have the same length as the target sequence in GSSM, two CC were added at 3' terminal of the target sequence in PSSM.

The target sequence was inserted into the Xho I/Not I site of the psiCHECK™-2 plasmid.

[2] Transfection

In a 96-well plate, siRNA and each of the above plasmids were co-transfected according to the instruction of Lipofectamine™ 2000 (Invitrogen), each plasmid corresponding to several specific concentrations of Conjugate A1. Specifically, 10 ng of plasmid was transfected per well, using 0.2 μL of Lipofectamine™ 2000 per well; for the on-target plasmid GSCM, the final concentration (based on the concentration of siRNA) of Conjugate A1 was from 100 nM to 0.0001 nM (4-fold serial dilutions of 11 concentrations), 3 replicate wells per group.

[3] Detection 24 hours after co-transfection, the HEK293A cells were lysed by using a dual luciferase reporter gene assay kit (Promega, Cat No. E2940) according to the instruction to detect the expression level of the dual luciferase reporter gene. For the test group of each specific concentration, those untreated with the conjugate were used as control (con). The *Renilla* luciferase protein level (Ren) was normalized to the firefly luciferase protein level (Fir).

The dose-response curves were plotted by the activity results measured at different siRNA concentrations, and the curves were fitted using the function log(inhibitor) vs. response-Variable slope of Graphpad 5.0 software. The $IC_{50}$ of the siRNA targeting GSCM was calculated based on the dose-response curve with the formula below:

$$Y = \text{Bot} + \frac{\text{Top}-\text{Bot}}{1 + 10^{(LogIC50-X)\times HillSlope}}$$

wherein:

Y is the expression level of remaining mRNA,

X is the logarithm of the concentration of transfected siRNA,

Bot is the Y value at the bottom of the steady stage,

Top is the Y value at the top of the steady stage,

Log $IC_{50}$ is the X value at which Y is the median value between the bottom and the top of the steady stage, and HillSlope is the slope of the curve.

The $IC_{50}$ of the Conjugate A1 targeting GSCM was determined via calculation based on the dose-response curve. The results are shown in FIGS. 20A-20D, which indicate that the $IC_{50}$ value of Conjugate A1 corresponding to GSCM was 0.0019 nM. Conjugate A1 corresponding to PSCM, GSSM or PSSM shows no significant inhibitory effect at each siRNA concentration, indicating that the siRNA conjugate of the present disclosure not only has higher activity in vitro, but also exhibits low off-target effect.

According to the above results, Conjugate A1 shows superior inhibitory effect on the expression of the target mRNA in the on-target plasmid with low $IC_{50}$; while shows no inhibitory effect on the expression of the three off-target plasmids. Thus, Conjugate A1 not only has superior inhibitory efficiency of the target mRNA, but also exhibits low off-target effect.

The effect experiment of the siRNA conjugates in Table 4B was illustrated as follows.

Experimental Example B1 This experiment illustrated inhibitory activity in vitro of the siRNA conjugates of the present disclosure.

Experimental Example B1-1 On-target activity in in vitro psiCHECK system

HEK293A cells used in this experimental example were provided by Nucleic Acid Technology Laboratory, Institute of Molecular Medicine, Peking University and cultured in DMEM complete media (Hyclone company) containing 20% fetal bovine serum (FBS, Hyclone company), 0.2 v % Penicillin-Streptomycin (Gibco, Invitrogen company) at 37° C. in an incubator containing 5% $CO_2$/95% air.

In this experimental example, Conjugates B16 and B17 were investigated in in vitro psiCHECK system for the on-target activity and off-target effect. Specifically, Conjugates B16 and B17 were tested for the activity of targeting completely matching target sequence (of which the nucleotide sequence is completely complementary with the full length nucleotide sequence of the sense/antisense strand of the conjugates) or targeting matching target sequence in seed region (of which the nucleotide sequence is complementary with the nucleotide sequence of positions 1-8 of the sense/antisense strand of the conjugates).

According to the method described by Kumico Ui-Tei et. al., Functional dissection of siRNA sequence by systematic DNA substitution: modified siRNA with a DNA seed arm is a powerful tool for mammalian gene silencing with significantly reduced off-target effect. Nucleic Acids Research, 2008.36(7), 2136-2151, plasmids for detection were constructed and co-transfected with the siRNA conjugates to be detected into HEK293A cells; and the expression levels of the dual luciferase reporter gene reflect the on-target activity of the siRNA conjugates. Specific steps are as follows:

[1] Construction of a Plasmid for Detection

An on-target plasmid was constructed using psiCHECK™-2 (Promega™) plasmid. This plasmid contains a target sequence, which is fully complementarily paired with all 21 nucleotide sequences of the antisense strand in the conjugate to be detected (i.e., Conjugate B16 or B17).

The target sequence was inserted into the Xho I/Not I site of the psiCHECK™-2 plasmid.

[2] Transfection

In a 96-well plate, siRNA conjugate and the above plasmid were co-transfected according to the instruction of Lipofectamine™ 2000 (Invitrogen), respectively. Specifically, 10 ng of plasmid was transfected per well, using 0.2 μL of Lipofectamine™ 2000 per well; the final concentrations (based on the concentration of siRNA) of the conjugates were 0.1 nM, 0.05 nM and 0.01 nM, and those untreated with the conjugates in each group were used as control, with 3 replicate wells per group.

NC is a universal negative control B01001 with no homology to the target gene sequence (GenePharma Co., Ltd).

Figure 21:
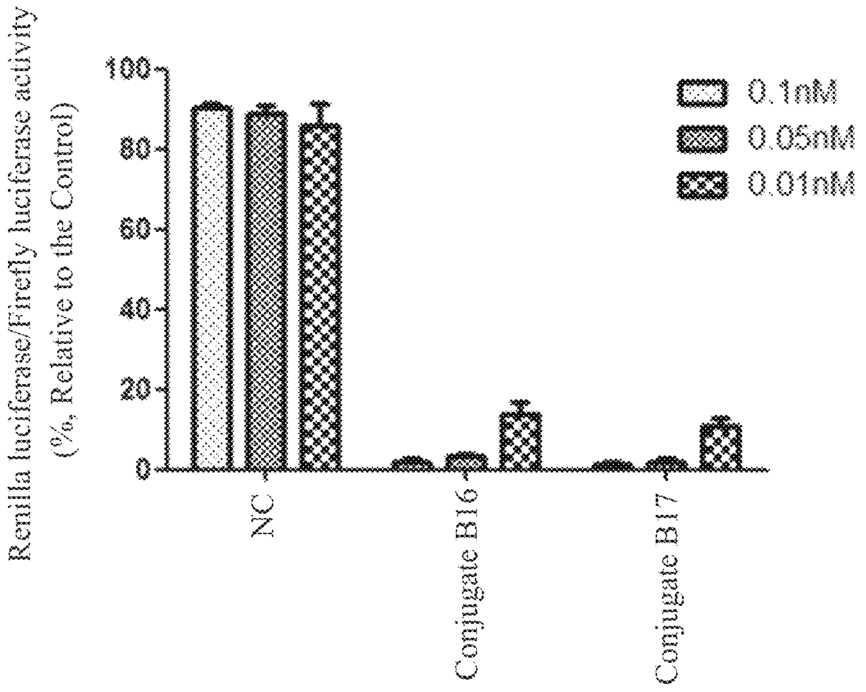
FIGS. 21-22 respectively show in intro inhibitory effect of the conjugates of the present disclosure on target mRNA and off-target mRNA.

[3] Detection 24 hours after co-transfection, the HEK293A cells were lysed by using a dual luciferase reporter gene assay kit (Promega, Cat No. E2940) according to the instruction to detect the expression level of the dual luciferase reporter gene. The *Renilla* luciferase protein level (Ren) was normalized to the firefly luciferase protein level (Fir). The results are shown in FIG. 21.

The results indicated that Conjugates B16 and B17 both have good inhibitory activity in intro.

Experimental Example B1-2 On-target activity and off-target effect in in vitro psiCHECK system In this experimental example, on-target activity and off-target effect of Conjugate B2 in in vitro psiCHECK system was investigated.

Conjugate B2 was tested by the method described in Experimental Example A6, except that 4 target sequences were constructed which correspondings to Conjugate B2; and the concentrations were diluted from 0.1 nM to 0.0001 nM; each group of plasmids corresponds to 11 concentrations of siRNA. The test results are shown in FIG. 22.

Figure 22:
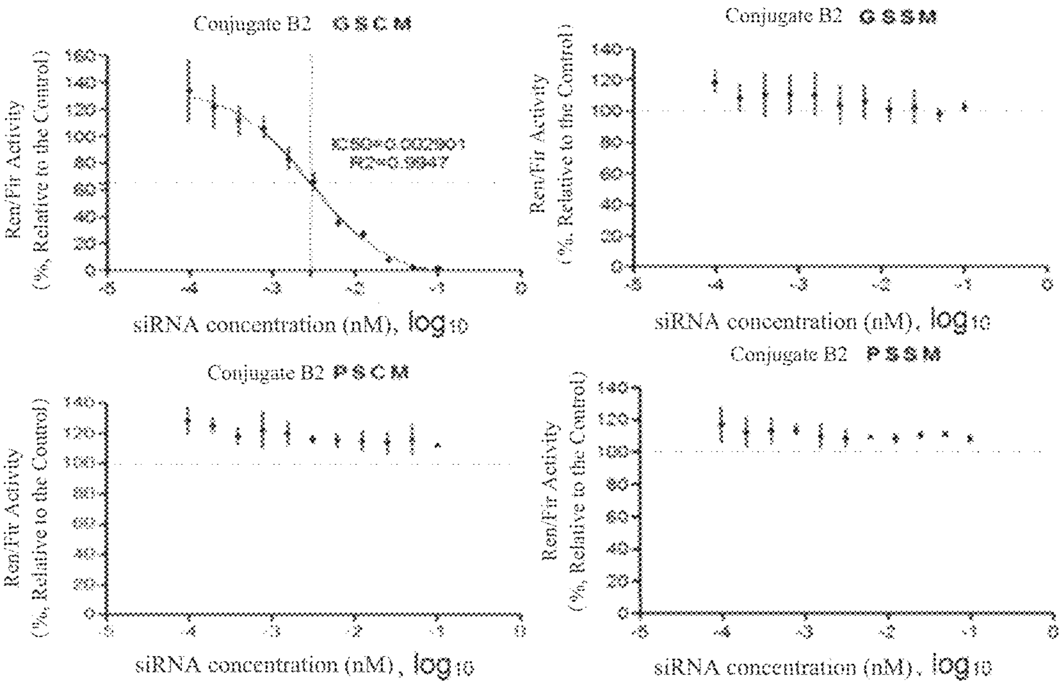

As can be seen from FIG. 22, Conjugate B2 not only has excellent inhibitory effect on the target mRNA, but also exhibits low off-target effect.

Experimental Example B2 This experiment illustrated the stability of the siRNA conjugates of the present disclosure (Experimental Example B2-1) Stability of the siRNA conjugates in the lysosome lysate in vitro.

Preparation of test samples treated with the lysosome lysate: Conjugates B1 and B2 (each provided in the form of 0.9 wt % NaCl aqueous solution in which the concentration of siRNA is 20 μM, 6 μl for each group, respectively) were individually mixed well with 27.2 μL of sodium citrate aqueous solution (pH 5.0), 4.08 μL of deionized water and 2.72 μL of Tritosomes (commercially available from Xenotech Inc., Cat No. R0610LT, Lot No. 1610069), and incubated at a constant temperature of 37° C. 5 μL samples were taken at each time point of 0 h, 5 min, 15 min, 30 min, 1 h, 2 h, 4 h, and 8 h respectively, added to 15 μL of 9 M urea aqueous solution for denaturation, and added with 4 μL of 6×loading buffer (purchased from Solarbio Inc., Cat No. 20160830), then immediately cryopreserved in a −80° C. freezer to quench the reaction. 0 h represents the moment when the sample was taken immediately after the samples to be tested are mixed well with the lysosome lysate.

Preparation of control samples untreated with the lysosome lysate: 1.5 μL for each of the corresponding conjugates (20 μM) at equal moles was mixed well with 7.5 μL of sodium citrate aqueous solution (pH 5.0) and 1 μL of deionized water, added to 30 μL of 9 M urea solution for denaturation, and added with 8 μL of 6×loading buffer, then immediately cryopreserved in a −80° C. freezer to quench the reaction. The control sample is marked as Con in the electrophoretogram.

16 wt % of non-denatured polyacrylamide gel was prepared. 20 μL each of the test sample and the control sample described above was loaded onto the gel to perform electrophoresis under 20 mA constant current for 10 minutes and then under 40 mA constant current for 30 minutes. After finishing the electrophoresis, the gel was placed on a shaker and stained with Gelred dye (BioTium, Cat No. 13G1203) for 10 minutes. The gel was subjected to imaging, observation and photocopying. The results are shown in FIG. 23.

Figure 23:
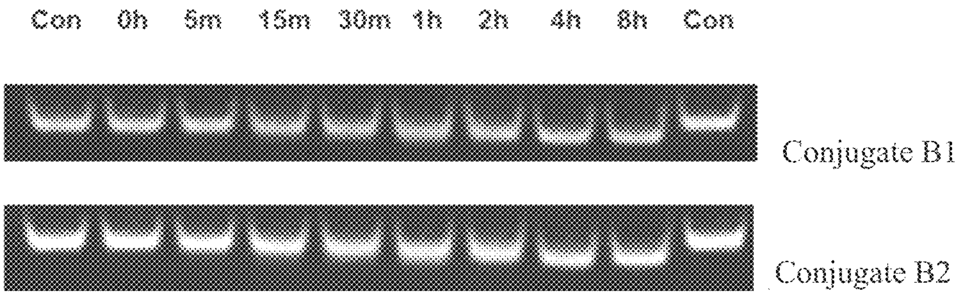
FIGS. 23-25 respectively show the results of the stability tests of the conjugates of the present disclosure in vitro.

FIG. 23 shows the semiquantitative detection result of the in vitro stability of the tested siRNA conjugates in the Tritosome. The results indicate that the conjugates of the present disclosure can remain undegraded for a long time in Tritosome, showing good stability.

(Experimental Example B2-2) Stability of the siRNA conjugates in human plasma

Conjugates B1 and B2 (each provided in the form of 0.9 wt % NaCl aqueous solution in which the concentration of siRNA is 20 μM, 12 μl for each group) were individually mixed well with 108 μL of 90% human plasma (diluted in PBS) and incubated at a constant temperature of 37° C. 10 μL samples were taken at each time point of 0 h, 2 h, 4 h, 6 h, 8 h, 24 h, 48 h and 72 h, respectively, and immediately frozen in liquid nitrogen and cryopreserved in a −80° C. freezer. After sampling at each time point, each cryopreserved sample was diluted 5-fold with 1×PBS (pH 7.4) and then taken in a volume of 10 μL for use. Meanwhile, the siRNA conjugate was taken at equal moles (siRNA concentration of 2 μM, 2 μL) and mixed well with 8 μL of 1×PBS (pH 7.4), thus obtaining 10 μL of sample untreated with human plasma (marked as Con).

20 wt % of non-denatured polyacrylamide gel was prepared. Each cryopreserved sample above was all mixed with 4 μL of loading buffer (aqueous solution of 20 mM EDTA, 36 wt % glycerol, and 0.06 wt % bromophenol blue) and then loaded onto the gel to perform electrophoresis under 80 mA constant current for 60 minutes. After finishing the electrophoresis, the gel was stained with 1×Sybr Gold dye (Invitrogen, Cat No. 11494) for 15 minutes followed by imaging. The results are shown in FIG. 24.

Figure 24:
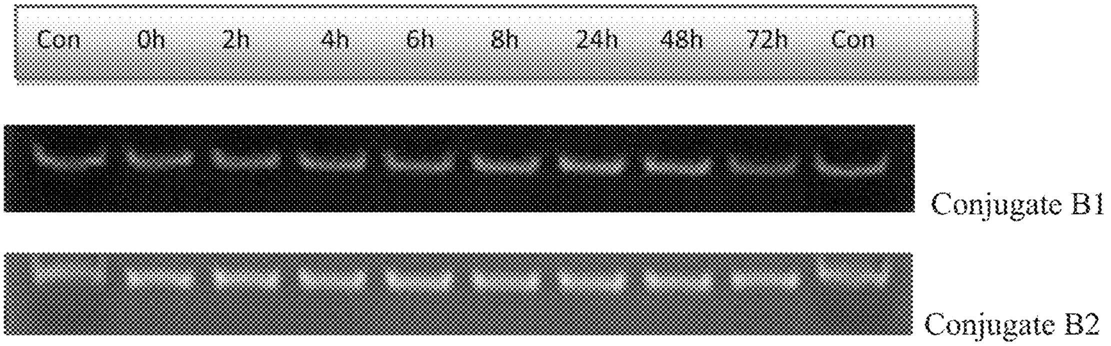

FIG. 24 shows the semiquantitative detection result of the in vitro stability of the tested conjugates in human plasm.

As can be seen from the results of FIG. 24, the conjugates of the present disclosure remain undegraded at up to 72 hours in human plasma, showing excellent stability in human plasma.

(Experimental Example B2-3) Stability of siRNA conjugates in the monkey plasma

In another experiment, the stability of Conjugates B1 and B2 in monkey plasma (Monkey plasma, purchased form HONGQUAN Bio, Cat No. HQ70082, diluted in PBS) was measured using the same method as that in Experimental Example 2-2. The results are shown in FIG. 25.

Figure 25:
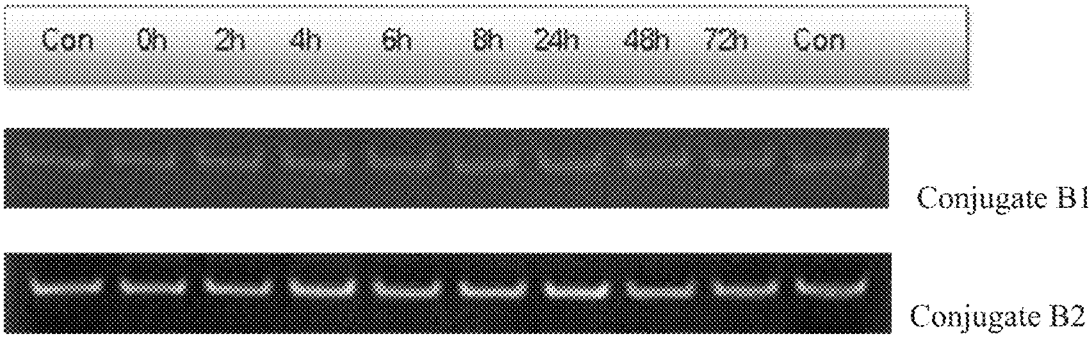

FIG. 25 shows the semiquantitative detection result of the in vitro stability of the tested siRNA in the monkey plasma.

As can be seen from the results of FIG. 25, in cynomolgus monkey plasma, the siRNA conjugates of the present disclosure remain undegraded at up to 72 hours, showing excellent stability in monkey plasma.

Experimental Example B3 This experiment illustrated the inhibition of the conjugates of the present disclosure against the expression of HBV mRNA in mice.

In this experimental example, the inhibitory efficiency of Conjugate B1 against the expression level of HBV mRNA in HBV transgenic mice C57BL/6J-Tg (A1b1HBV) 44Bri/J were investigated.

At first, C57BL/6J-Tg (A1b1HBV) 44Bri/J mice were randomly divided into groups based on HBsAg content in serum (all female, 4 mice in each group) and respectively numbered, and a normal saline (NS) group was added as a control group. The drug dosages for all animals were calculated according to the body weight (single administration (subcutaneously), administration dosage of 1 mg/kg and 0.1 mg/kg Conjugate B1, in the form of 0.9% NaCl aqueous solution containing 0.2 mg/ml and 0.02 mg/ml conjugates, and administration volume of 5 mL/kg). Animals were sacrificed on day 7 after administration. The liver was collected and kept with RNA later (Sigma Aldrich), and the liver tissue was homogenized with a tissue homogenizer. Then the total RNA was extracted and obtained by using Trizol according to the standard procedure for total RNA extraction.

The expression level of HBV mRNA in liver tissue was measured by real-time fluorescent qPCR. Specifically, the extracted total RNA was reverse transcribed into cDNA by using ImProm-II™ reverse transcription kit (Promega) according to the instruction, and then the inhibitory efficiency of siRNAs against the expression of HBV mRNA in liver tissue was measured by using the fluorescent qPCR kit (Beijing Cowin Biosicences Co., Ltd). In this fluorescent qPCR method, a gene encoding glyceraldehyde-3-phosphate dehydrogenase (GAPDH) was used as an internal control gene, the HBV and GAPDH were detected by using primers for HBV and GAPDH, respectively.

Sequences of primers for detection are shown in Table 5B.

TABLE 5B

Sequences of primers for detection

| Genes | Upstream Primers | Downstream Primers |
|---|---|---|
| HBV | 5'-CCGTCT GTGCCTTCT CATCT-3' (SEQ ID NO: 425) | 5'-TAATCTCC TCCCCCAACTC C-3' (SEQ ID NO: 426) |
| GAPDH | 5'-AACTTTG GCATTGTGGA AGGGCTC-3' (SEQ ID NO: 431) | 5'-TGGAAGA GTGGGAGTTG CTGTTGA-3' (SEQ ID NO: 432) |

In this fluorescent qPCR method, the inhibitory activity of siRNA was expressed as the remaining expression of HBV gene and calculated by the following equation:

The remaining expression of *HBV* gene=(the copy number of *HBV* gene in the test group/the copy number of GAPDH in the test group)/(the copy number of *HBV* gene in the control group/the copy number of GAPDH in the control group)×100%.

Figure 26:
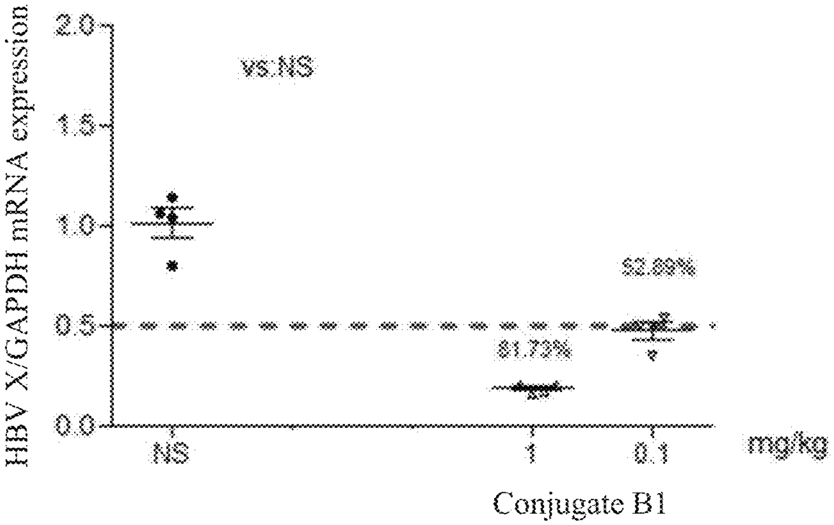
FIGS. 26-28 show inhibitory effect of the conjugates of the present disclosure on HBV mRNA in vivo.

Then, the inhibition percentage against mRNA was calculated according to the following equation:

The inhibition percentage against mRNA=(1−the remaining expression of *HBV* gene)×100%, wherein the control group was a group of control mice administered with NS in this experiment and each test group was a group of mice administered with different siRNA conjugates, respectively. The results are shown in FIG. 26.

Figure 27:
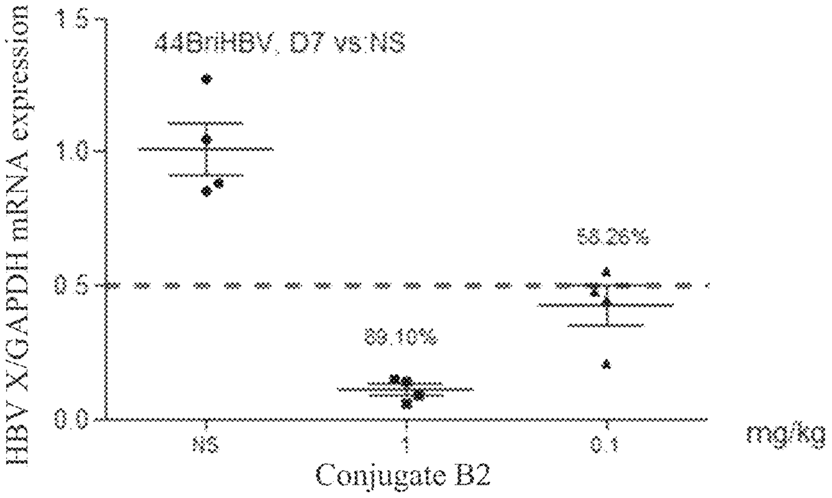
Figure 28:
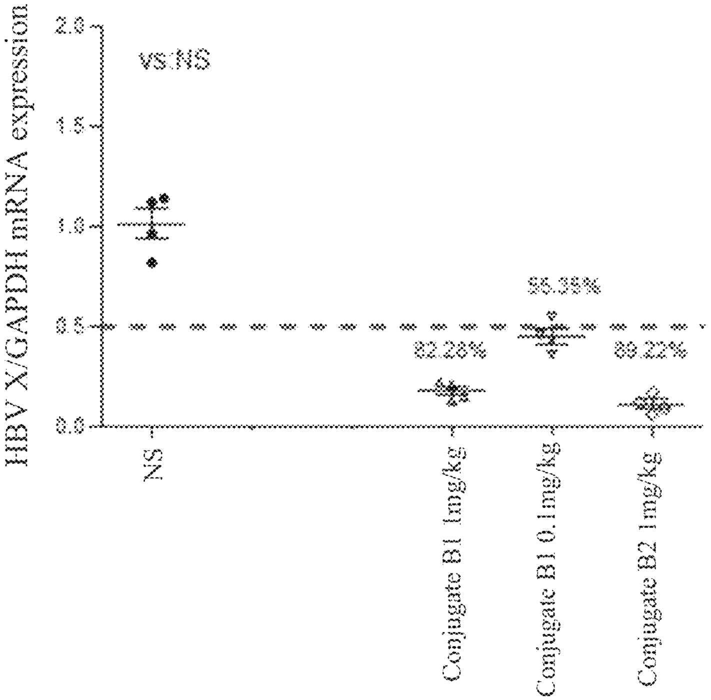

In other experiments, two tests were further performed according to the following conditions:

Tests were performed by using the same method described above, except that the siRNA conjugate administered was replaced with Conjugate B2 for testing, and the data were collected on day 7. The results are shown in FIG. 27; and the siRNA conjugate administered was replaced with Conjugates B1 and B2 for testing; the Conjugate B1 was administered respectively in the two dosages of 1 mg/kg and 0.1 mg/kg;

Conjugate B2 was administered in the dosage of 1 mg/kg; and the sequences for detection were replaced with the sequences shown in Table 5C. The results are shown in FIG. 28.

TABLE 5C

Sequences of primers for detection

| Genes | Upstream Primers | Downstream Primers |
|---|---|---|
| HBV S | 5'-CGTTTCT CCTGGCTCAG TTTA-3' (SEQ ID NO: 429) | 5'-CAGCGGT AAAAAGGGAC TCAA-3' (SEQ ID NO: 430) |
| GAPDH | 5'-AACTTTGG CATTGTGGAAG GGCTC-3' (SEQ ID NO: 431) | 5'-TGGAAGAGT GGGAGTTGCTG TTGA-3' (SEQ ID NO: 432) |

As can be seen from FIGS. 27 and 28, all conjugates of the present disclosure described above show good inhibitory effect on the target mRNA. Moreover, the inhibitory effects thereof against different kinds of HBV mRNA remain substantially the same.

Experimental Example B4 This experiment illustrated a test about the relationship between time and inhibitory efficiency of the siRNA conjugates of the present disclosure against the expression of HBsAg and HBV DNA in HBV transgenic mice serum.

For low-concentration AAV-HBV model mouse, the mice were randomly divided into groups based on HBsAg content in serum (5 mice in each group). Conjugate B2 and NS as a blank control were respectively administered to each group. The drug dosages for all animals were calculated according to the body weight (single administration (subcutaneously), administration dosage of 3 mg/kg and 1 mg/kg, in the form of 0.9% NaCl aqueous solution containing 0.6 mg/ml and 0.2 mg/ml conjugates, and administration volume of 5 mL/kg). The blood was taken from mouse orbital venous plexus before administration and on days 7, 14, 21, 28, 56, 84, 98, 112, 126, and 140 after administration, and HBsAg level in serum was measured for each time point.

About 100 μl orbital blood was taken each time, and the serum was no less than 20 μl after centrifugation. The expression level of HBsAg in serum was measured by using HBsAg CLIA kit (Autobio, CL0310). The expression level of HBV DNA was measured by extraction of the DNA from the serum with reference to the instruction of QIAamp 96 DNA Blood Kit followed by qPCR.

The inhibition percentage against HBsAg was calculated according to the following equation:

The inhibition percentage against HBsAg=(1−the content of HBsAg after administration/the content of HBsAg before administration)×100%, wherein the content of HBsAg was expressed in equivalents (*UI*) of HBsAg per milliliter (ml) of serum.

The inhibition percentage against HBV DNA was calculated according to the following equation:

The inhibition percentage against *HBV DNA*=(1−the content of *HBV DNA* after administration/the content of *HBV DNA* before administration)×100%, wherein the content of HBV DNA was expressed in copies of HBV DNA per milliliter (ml) of serum.

Figure 29:
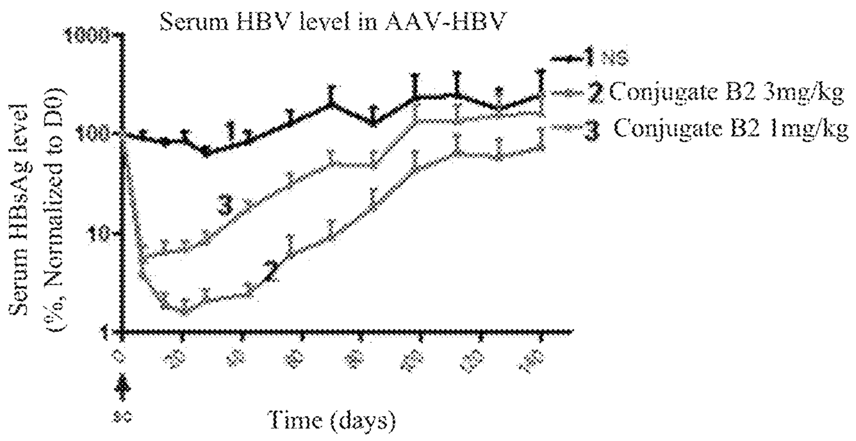
FIGS. 29-31 show inhibitory effect over time of the conjugates of the present disclosure on the expression of HBsAg and HBV DNA in the sera of different HBV transgenic mice.

The results are shown in FIG. 29.

As can be seen from the results of FIG. 29, the NS negative control group shows no inhibitory effect at different time points after administration; in contrast, Conjugate B2 shows excellent inhibitory effect on HBsAg at different time points after administration. In particular, Conjugate B2 consistently shows high inhibition percentage against HBsAg in serum over a period of up to 100 days, indicating stable and effective inhibition against the expression of HBV gene over a longer time period.

According to the same methods as described above, further tests were performed. In 1.28 copy model mouse, the administration doses of Conjugate B2 are 3 mg/kg and 1 mg/kg, using 0.9 wt % NaCl aqueous solution containing 0.6 mg/ml and 0.2 mg/ml conjugates, with administration volume of 5 mL/kg. The administration period continued until day 85; and the inhibitory effects against HBsAg and HBV DNA were measured according to the method described above. The results are shown in FIGS. 30 and 31.

Figure 30:
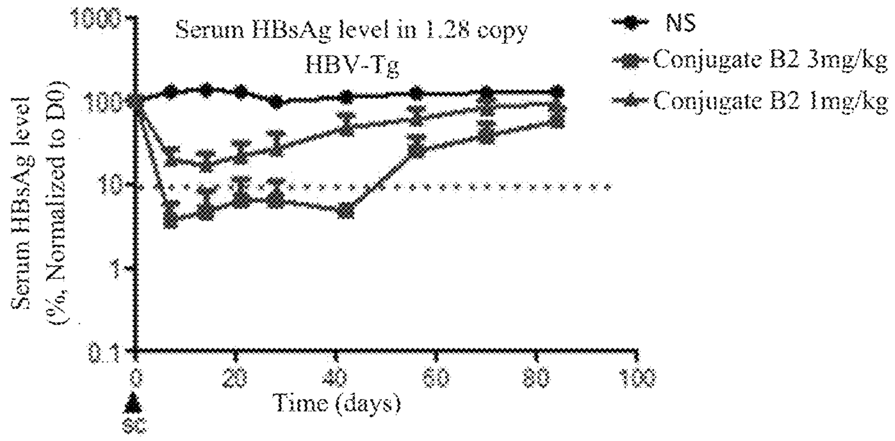
Figure 31:
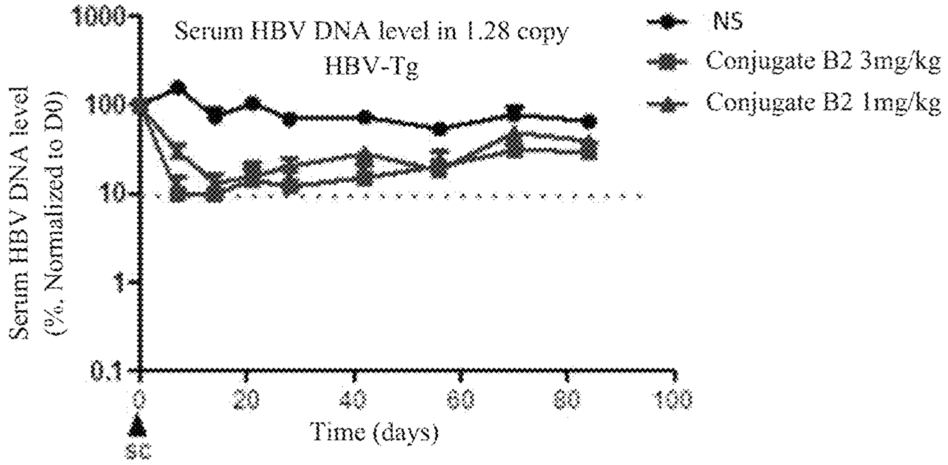

As can be seen from FIGS. 30 and 31, in 1.28 copy model mouse, Conjugate B2 of the present disclosure consistently showed high inhibition against the expression of HBV gene and HBV DNA over a period of 85 days.

Hereinbelow, an experiment for verifying the properties of the siRNA conjugates shown in Table 4C is described:

Experimental Example C1 This experiment illustrated the stability of the siRNA conjugates Shown in Table 4C (Experimental Example C1-1) Stability of the siRNA conjugates in the lysosome lysate in vitro.

Preparation of test samples treated with the lysosome lysate: Conjugate C2 (provided in the form of 0.9 wt % NaCl aqueous solution in which the concentration of siRNA is 20 μM, 6 μl for each group) was individually mixed well with 27.2 μL of sodium citrate aqueous solution (pH 5.0), 4.08 μL of deionized water and 2.72 μL of Tritosomes (purchased from Xenotech Inc., Cat No. R0610LT, Lot No. 1610069), and incubated at a constant temperature of 37° C. 5 μL samples were taken at each time point of 0 h, 5 min, 15 min, 30 min, 1 h, 2 h, 4 h, and 8 h respectively, added to 15 μL of 9 M urea aqueous solution for denaturation, and added with 4 μL of 6×loading buffer (purchased from Solarbio Inc., Cat No. 20160830) was added, then immediately cryopreserved in a −80° C. freezer to quench the reaction. 0 h represents the moment when the sample was taken immediately after the samples to be tested are mixed well with the lysosome lysate.

Preparation of control samples untreated with the lysosome lysate: 1.5 μL of Conjugate C2 at equal moles (20 μM) was mixed well with 7.5 μL of sodium citrate aqueous solution (pH 5.0) and 1 μL of deionized water, added to 30 μL of 9 M urea solution for denaturation, and added with 8 μL of 6×loading buffer, then immediately cryopreserved in a −80° C. freezer to quench the reaction. The control sample is marked as Con in the electrophoretogram.

16 wt % of non-denatured polyacrylamide gel was prepared. 20 μL each of the test sample and the control sample described above was loaded onto the gel to perform electrophoresis under 20 mA constant current for 10 minutes and then under 40 mA constant current for 30 minutes. After finishing the electrophoresis, the gel was placed on a shaker and stained with Gelred dye (BioTium, Cat No. 13G1203) for 10 minutes. The gel was subjected to imaging, observation and photocopying. The results are shown in FIG. 32.

Figure 32:
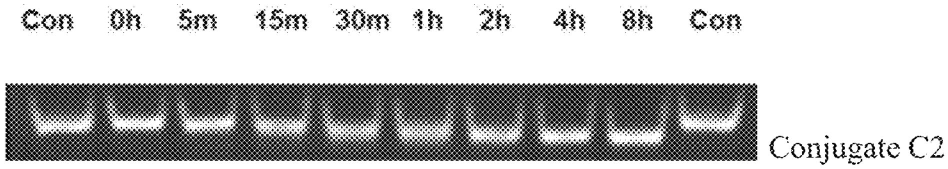
FIGS. 32-34 respectively show the results of the stability tests of the conjugates of the present disclosure in vitro.

FIG. 32 shows the semiquantitative detection result of the in vitro stability of the tested siRNA conjugates in the Tritosome. The result shows that the conjugate of the present disclosure can remain undegraded for a long time in lysosome, showing good stability.

(Experimental Example C1-2) Stability of siRNA conjugates in human plasma

Conjugate C2 (provided in the form of 0.9 wt % NaCl aqueous solution at 20 μM with regard to siRNA, 12 μl for each group) was individually mixed well with 108 μL of 90% human plasma (diluted in PBS) and incubated at a constant temperature of 37° C. 10 μL samples were taken at each time point of 0 h, 2 h, 4 h, 6 h, 8 h, 24 h, 48 h and 72 h, respectively, and immediately frozen in liquid nitrogen and cryopreserved in a −80° C. freezer. After sampling at each time point, each cryopreserved sample was diluted 5-fold with 1×PBS (pH 7.4) and then taken in a volume of 10 μL for use. Meanwhile, the siRNA conjugate was taken at equal moles (siRNA concentration of 2 μM, 2 μL) and mixed well with 8 μL of 1×PBS (pH 7.4), thus obtaining 10 μL of samples untreated with human plasma (marked as Con).

20 wt % of non-denatured polyacrylamide gel was prepared. Each cryopreserved sample above was all mixed with 4 μL of loading buffer (aqueous solution of 20 mM EDTA, 36 wt % glycerol, and 0.06 wt % bromophenol blue) and then loaded onto the gel to perform electrophoresis under 80 mA constant current for 60 minutes. After finishing the electrophoresis, the gel was stained with 1×Sybr Gold dye (Invitrogen, Cat No. 11494) for 15 minutes followed by imaging. The results are shown in FIG. 33.

Figure 33:
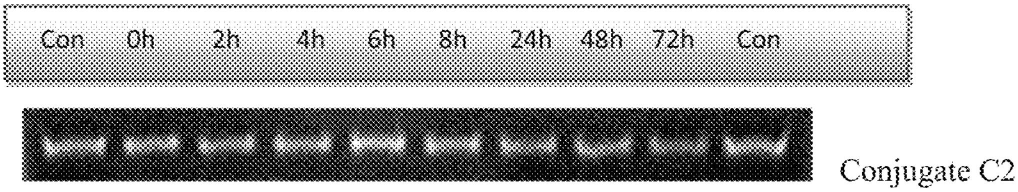

As can be seen from the results of FIG. 33, in human plasma, the conjugates of the present disclosure remained undegraded at up to 72 hours, showing excellent stability in human plasma.

(Experimental Example C1-3) Stability of siRNA conjugates in the monkey plasma

In another experiment, the stability of Conjugate C2 in monkey plasma (Monkey plasma, purchased form HONGQUAN Bio, Cat No. HQ70082, diluted in PBS) was measured using the same method as that in Experimental Example C1-2. The results are shown in FIG. 34.

Figure 34:
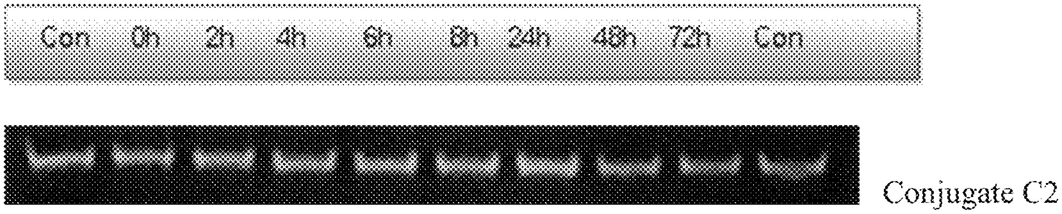

FIG. 34 shows the semiquantitative detection result of the in vitro stability of the tested siRNA in the monkey plasma.

As can be seen from the results of FIG. 34, in cynomolgus monkey plasma, the siRNA conjugates of the present disclosure remained undegraded at up to 72 hours, showing excellent stability in monkey plasma.

Figure 35:
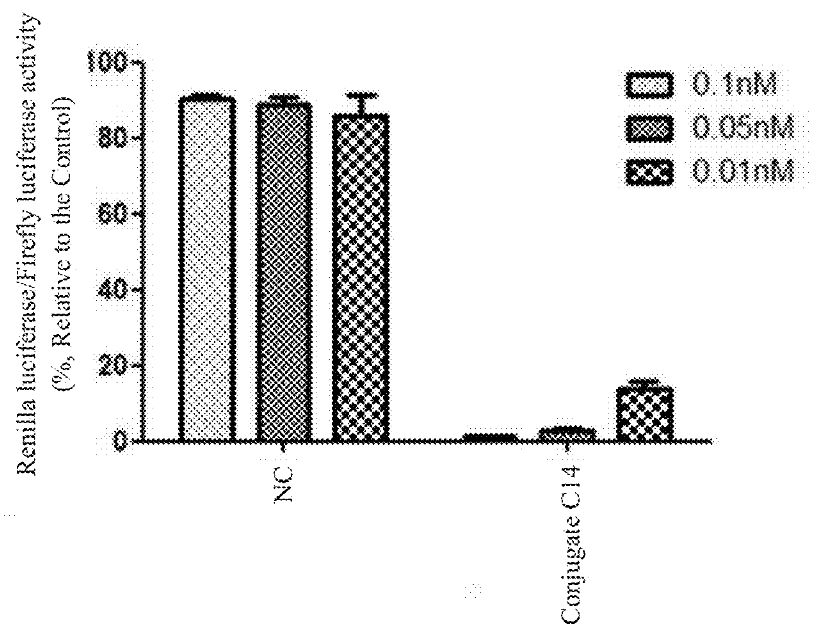
FIGS. 35-36 show in intro inhibitory effect of the conjugates of the present disclosure on target mRNA and off-target mRNA.

Experimental Example C2 This experimental example illustrated inhibitory activity in vitro of the siRNA conjugates of the present disclosure (Experimental Example C2-1) On-target activity in in vitro psiCHECK system Conjugate C14 was tested by the method described in Experimental Example B1-2, except that the target sequences were constructed using the sequences of Conjugate C14. The test results are shown in FIG. 35. The results indicate that Conjugate C14 has good inhibitory activity in vitro.

(Experimental Example C2-2) Measurement of $IC_{50}$ in in vitro psiCHECK system Conjugate C2 was tested by the method described in Experimental Example A6, except that the target sequences were constructed using the sequences of Conjugate C2; and the concentrations were diluted from 0.1 nM to 0.0001 nM, each group of sequences was tested at 11 concentrations. The results are shown in FIG. 36.

Figure 36:
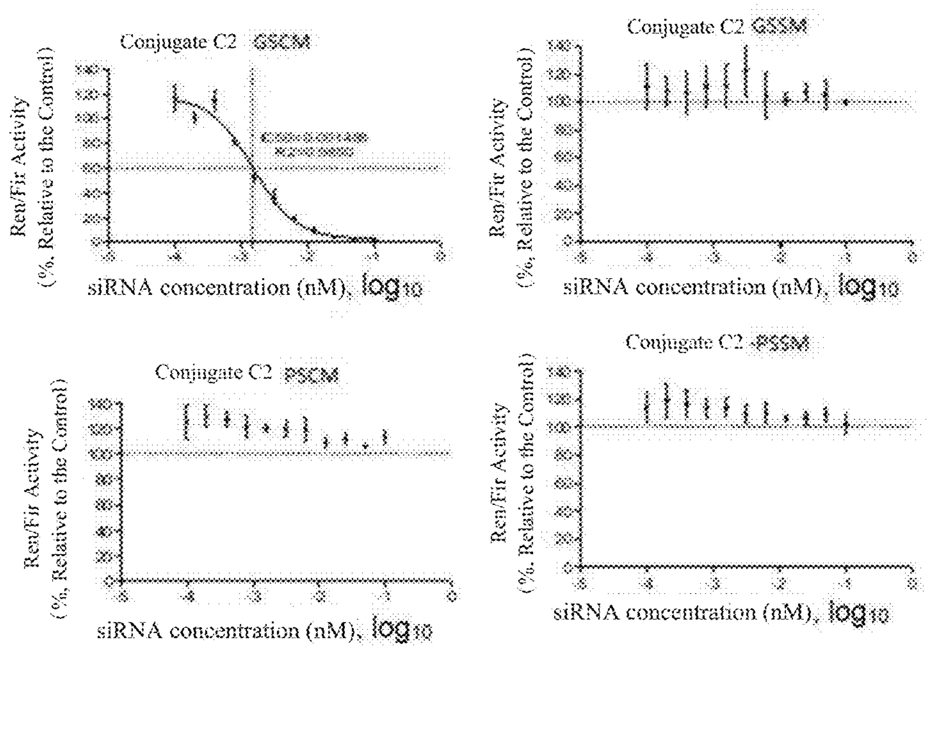

As can be seen from the FIG. 36, Conjugate C2 not only had excellent inhibitory effect on the target mRNA, but also exhibited low off-target effect.

Experimental Example C3—This experimental example illustrated the inhibition of the conjugates of the present disclosure against expression of HBV mRNA in mice.

In this experimental example, the inhibition efficiency of Conjugate C2 against the expression level of HBV mRNA in HBV transgenic mice C57BL/6J-Tg(A1b1HBV)44Bri/J was investigated.

At first, C57BL/6J-Tg (A1b1HBV) 44Bri/J mice were randomly divided into groups (all female, 4 mice in each group) and numbered individually, and a normal saline (NS) group was added as a control group. The drug dosages for all animals were calculated according to the body weight (single administration (subcutaneously), administration dosage of 1 mg/kg and 0.1 mg/kg Conjugate C2, in the form of 0.9% NaCl aqueous solution containing 0.2 mg/ml and 0.02 mg/ml conjugates, and administration volume of 5 mL/kg). Animals were sacrificed on day 7 after administration. The liver was collected and kept with RNA later (Sigma Aldrich), and the liver tissue was homogenized with a tissue homogenizer. Then the total RNA was extracted and obtained by using Trizol according to the standard procedure for total RNA extraction.

The expression level of HBV mRNA in liver tissue was measured by real-time fluorescent qPCR. Specifically, the extracted total RNA was reverse transcribed into cDNA by using ImProm-II™ reverse transcription kit (Promega) according to the instruction, and then the inhibitory efficiency of siRNAs against the expression of HBV mRNA in liver tissue was measured by using the fluorescent qPCR kit (Beijing Cowin Biosicences Co., Ltd). In this fluorescent qPCR method, β-actin gene was used as an internal control gene, the HBV and 0-actin were detected by using primers for HBV and β-actin, respectively.

Sequences of primers for detection are shown in Table 5A.

In this fluorescent qPCR method, the inhibitory activity of siRNA was expressed as the remaining expression of HBV gene and calculated by the following equation:

The remaining expression of *HBV* gene=(the copy number of *HBV* gene in the test group/the copy number of β-actin gene in the test group)/(the copy number of *HBV* gene in the control group/ the copy number of β-actin gene in the control group)×100%,which is marked as the expression of *HBV X*/β-actin mRNA in the figure.

Then, the inhibition percentage against mRNA was calculated according to the following equation:

The inhibition percentage against mRNA=(1−the remaining expression of *HBV* gene)×100%, wherein the control group was a group of control mice administered with NS in this experiment and each test group was a group of mice administered with different siRNA conjugates, respectively. The results are shown in FIG. 37.

Figure 37:
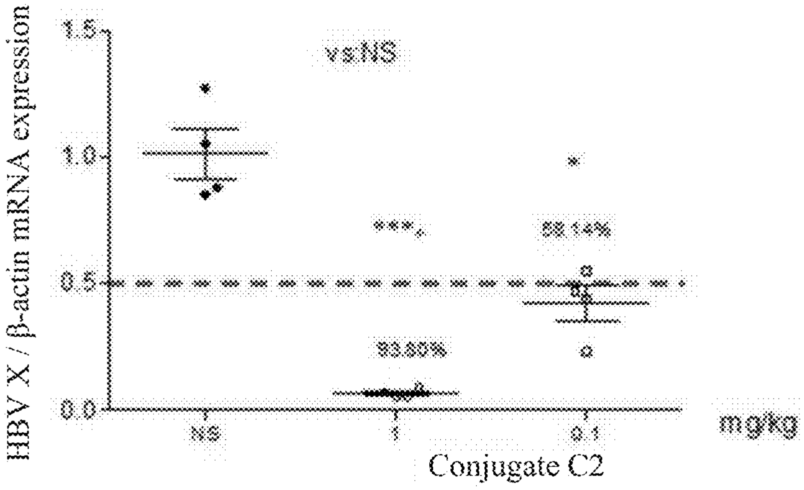
FIG. 37 shows in vivo inhibitory effect of the conjugates of the present disclosure on mRNA in 44BriHBV models.

As can be seen from the results of FIG. 37, the inhibition percentage of the conjugates of the present disclosure against the target mRNA was up to 93.8%, exhibiting good inhibitory effect.

Experimental Example C4 This experimental example illustrated the inhibitory effect of the siRNA conjugates of the present disclosure (single administration) against HBsAg and HBV X mRNA in M-Tg model mice.

HBV transgenic (M-TgHBV) mice (purchased from Department of Animal, Shanghai Public Health Center) were randomly divided into groups based on HBsAg content in serum (6 mice in each group, all male) and respectively numbered as a normal saline (NS) control group, Conjugate C2 1 mg/kg and 3 mg/kg groups. The drug dosages for all animals were calculated according to the body weight (single administration (subcutaneously), and administration volume of 10 mL/kg). The blood was taken from mouse orbital venous plexus before administration (marked as D0) and on days 7, 14, 21, 28, 42, 56, 70, and 85 after administration, and HBsAg level in serum was measured for each time point.

About 0.5 ml orbital blood was taken each time, and the serum was no less than 200 μl after centrifugation. The content of HBsAg in serum was measured by using HBsAg CLIA kit (Autobio, CL0310).

The normalized HBsAg level in serum=(the content of HBsAg after administration in the test group/the content of HBsAg before administration in the test group)×100%.

The inhibition percentage against HBsAg=(1−the content of HBsAg after administration/the content of HBsAg before administration)×100%, wherein the content of HBsAg was expressed in equivalents (UI) of HBsAg per milliliter (ml) of serum.

Figure 38:
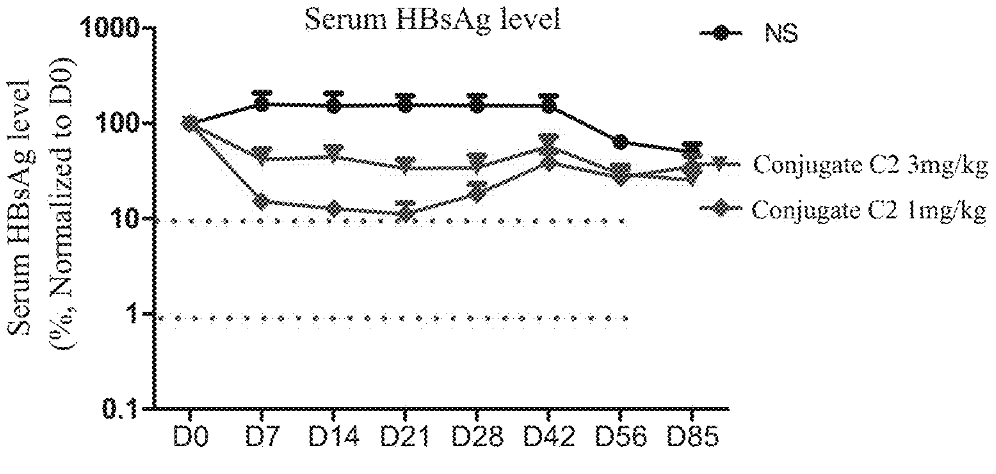
FIG. 38 shows inhibitory effect over time of the conjugates of the present disclosure on the expression of HBsAg in mice.
Figure 39:
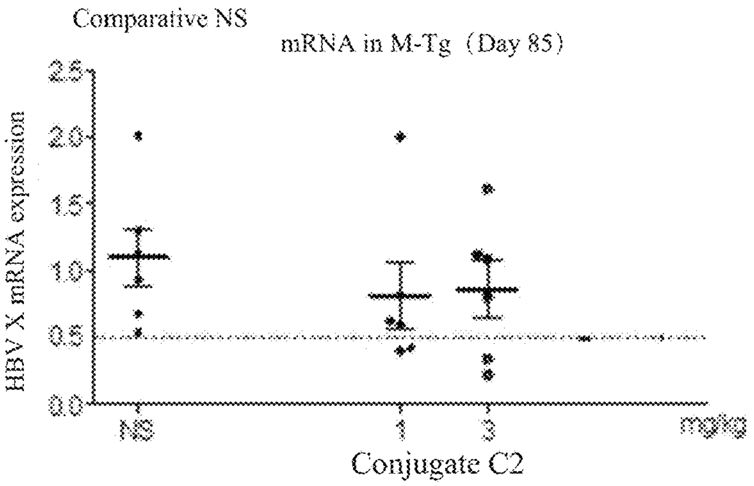
FIG. 39 shows in vivo inhibitory effect of the conjugates of the present disclosure on mRNA in M-Tg mouse models.

The following FIGS. 38 and 39 show the test results of the inhibitory effect of the tested siRNA conjugate in a single administration against HBsAg and HBV X mRNA in M-Tg model mice.

As can be seen from the results of FIGS. 38 and 39, Conjugate C2 administered at 3 mg/kg maintained higher inhibition percentage against HBsAg over a period of 21 days, exhibiting an inhibition percentage of up to 90% or higher; and Conjugate C2 administered at 3 mg/kg still showed higher inhibition percentage against HBV X mRNA on day 85.

Hereinbelow, an effect experiment of the siRNA conjugates shown in Table 4D was described.

Experimental Example D1 this experiment illustrated stability of the siRNA conjugates of the present disclosure Experimental Example (D1-1) Stability of the siRNA conjugates in the lysosome lysate in vitro.

According to the method described in Experimental Example C1-1, the stability of Conjugate D2 in the lysosome lysate in vitro was measured. The results are shown in FIG. 40.

Figure 40:
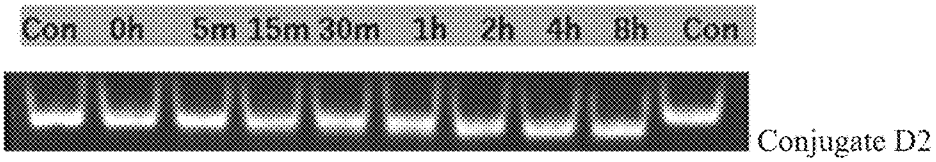
FIGS. 40-42 show the results of the stability tests of the conjugates of the present disclosure in vitro.

FIG. 40 shows the semiquantitative detection result of the in vitro stability of the tested siRNA conjugates in the lysosome. The result showed that the conjugates of the present disclosure can remain undegraded for a long time in lysosome, showing good stability.

Experimental Example (D1-2) Stability of the siRNA conjugates in the human/monkey plasma According to the method described in Experimental Examples C1-2 and C1-3, the stability of Conjugate D2 respectively in the human plasma in vitro and in the cynomolgus monkey plasma in vitro was measured. The results are shown in FIGS. 41 and 42.

Figure 41:
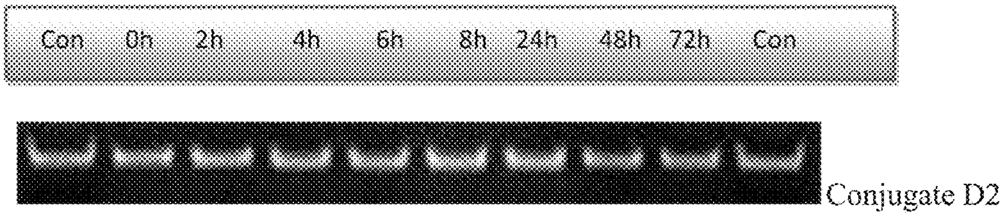
Figure 42:
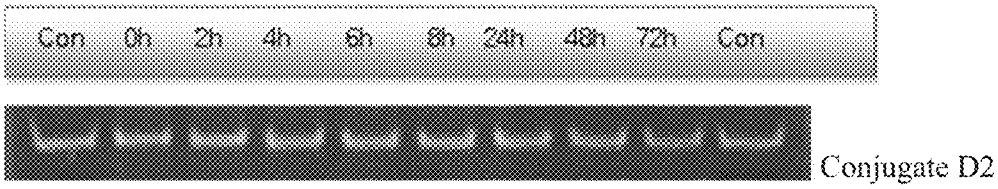

As can be seen from the results of FIGS. 41 and 42, in the human/monkey plasma, the conjugates of the present disclosure remained undegraded at up to 72 hours, showing excellent stability.

Experimental Example D2 This experimental example illustrated inhibitory activity in vitro of the siRNA conjugates of the present disclosure.

(Experimental Example D2-1) On-target activity in in vitro psiCHECK system

HEK293A cells as used herein were provided by Nucleic acid technology laboratory, Institute of Molecular Medicine, Peking University and cultured in DMEM complete media (Hyclone company) containing 20% fetal bovine serum (FBS, Hyclone company), 0.2 v % Penicillin-Streptomycin (Gibco, Invitrogen company) at 37° C. in an incubator containing 5% $CO_2$/95% air.

Figure 43:
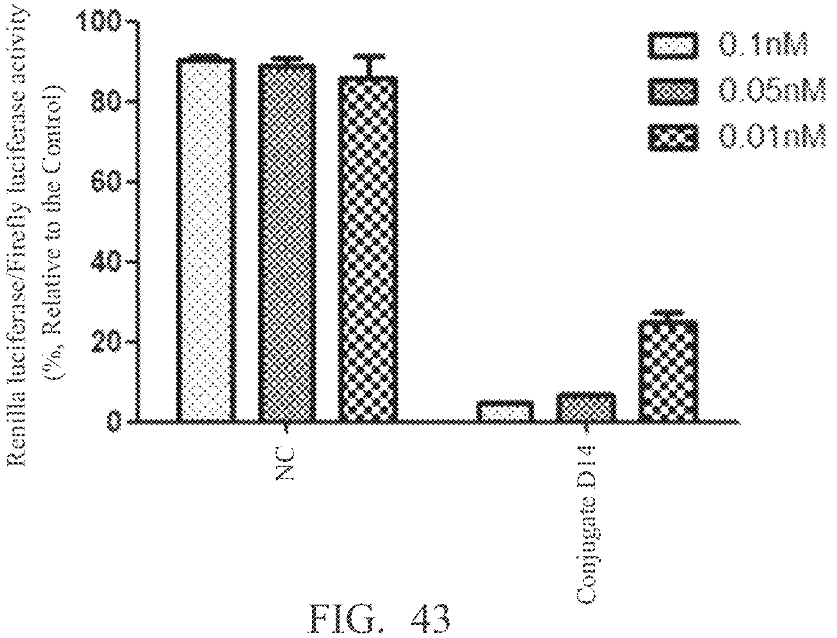
FIGS. 43-44 show in intro inhibitory effect of the conjugates of the present disclosure on target mRNA and off-target mRNA.

Conjugate D14 was tested by the method described in Experimental Example A6, except that target sequences were constructed based on the sequences of Conjugate D14; and for each sequence, the concentration was diluted from 0.1 nM to 0.0001 nM, and each sequence was tested at 11 concentrations. The results are shown in FIG. 43, indicating that Conjugate D14 has good inhibitory activity in vitro.

(Experimental Example D2-2) Measurement of $IC_{50}$ in in vitro psiCHECK system In this experimental example, the $IC_{50}$ of Conjugate D2 in in vitro psiCHECK system was investigated.

Figure 44:
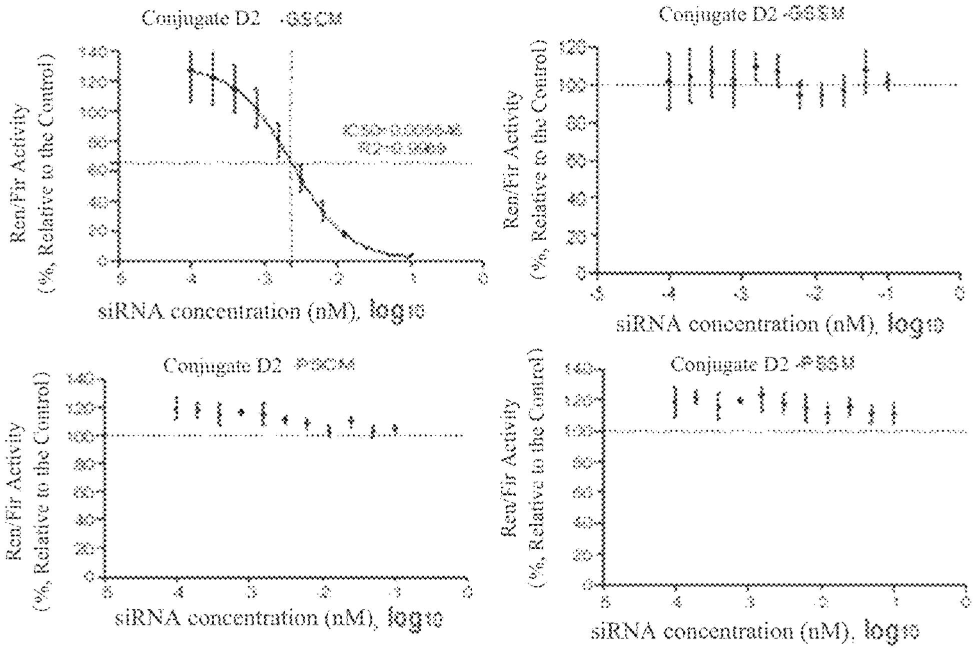

Conjugate D2 was tested according to the method described in Experimental Example B1-2, except that four target sequences were constructed based on the sequences of Conjugate D2; and for each sequence, the concentration was diluted from 0.1 nM to 0.0001 nM, and each sequence was tested at 11 concentrations. The results are shown in FIG. 44, indicating that Conjugate D2 not only has excellent inhibitory effect on the target mRNA, but also shows low off-target effects.

Experimental Example D3 This experimental example illustrated the inhibition of the conjugate of the present disclosure against the expression of HBV mRNA in mice.

In this experimental example, the inhibition efficiency of Conjugate D2 against the expression level of HBV mRNA in HBV transgenic mice C57BL/6J-Tg(A1b1HBV)44Bri/J was investigated.

Conjugate D2 was tested using the method described in Experimental Example C3. The results are shown in FIG. 45.

Figure 45:
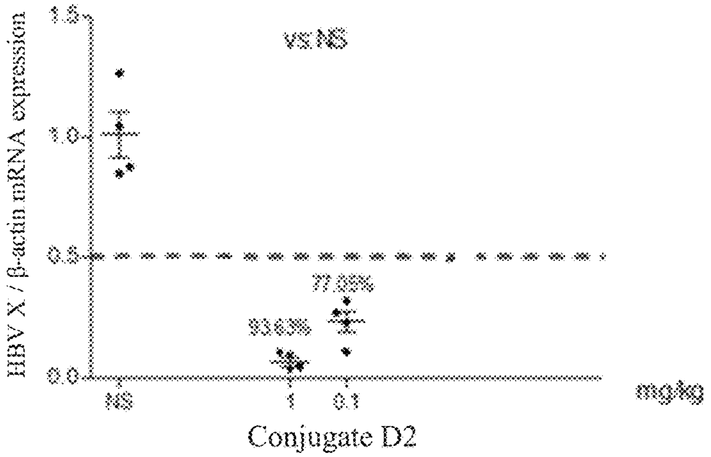
FIG. 45 shows in vivo inhibitory effect of the conjugates of the present disclosure on HBV mRNA.

As can be seen from the results of FIG. 45, the conjugates of the present disclosure showed good inhibitory effect on the target mRNA. Specifically, Conjugate D2 showed, at the dosage of 1 mg/kg, an inhibition percentage against the target mRNA of up to 93.63%; and at the dosage of a much lower concentration (0.1 mg/kg), also resulted in an inhibition percentage of 77.05%, showing good inhibitory effect.

Experimental Example D4 This experimental example illustrated the inhibitory effect of the siRNA conjugates of the present disclosure administered in a single dose against HBsAg and HBV X mRNA in M-Tg model mice.

HBV transgenic (M-TgHBV) mice (purchased from Department of Animal, Shanghai Public Health Center) were randomly divided into groups based on HBsAg content in serum (6 mice in each group, all male) and respectively numbered as a normal saline (NS) control group, Conjugate D2 1 mg/kg and 3 mg/kg groups. The drug dosages for all animals were calculated according to the body weight(single administration (subcutaneously), and administration volume of 10 mL/kg). The blood was taken from mouse orbital venous plexus before administration and on days 7, 14, 21, 28, 42, 56, 70, and 85 after administration, and HBsAg level in serum was measured for each time point.

About 0.5 ml orbital blood was taken each time, and the serum was no less than 200 μl after centrifugation. The content of HBsAg in serum was measured by using HBsAg CLIA kit (Autobio, CL0310). The remaining amount of HBsAg expression was calculated according to the following equation:

The remaining amount of HBsAg expression=(the content of HBsAg in the test group/the content of HBsAg in the *NS* control group)×100%, wherein the content of HBsAg was expressed in equivalents (*UI*) of HBsAg per milliliter (ml) of serum.

Figure 46:
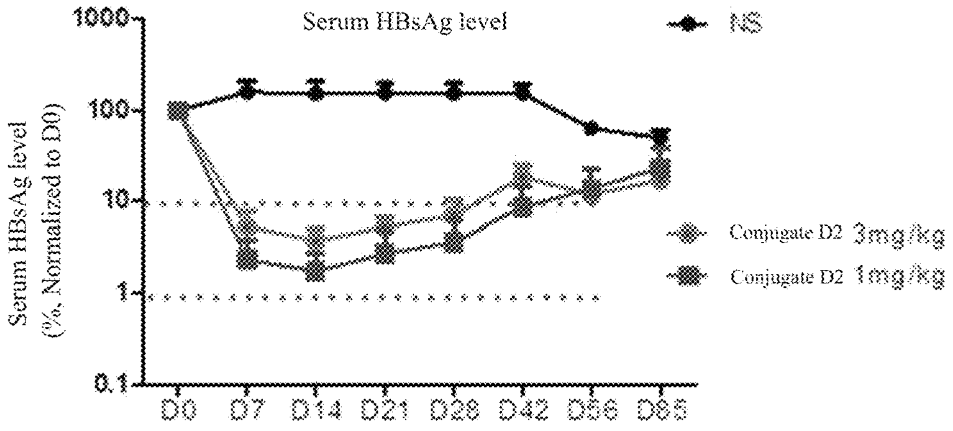
FIG. 46 shows inhibitory effect over time of the conjugates of the present disclosure on HBsAg expression in HBV transgenic mice serum.
Figure 47:
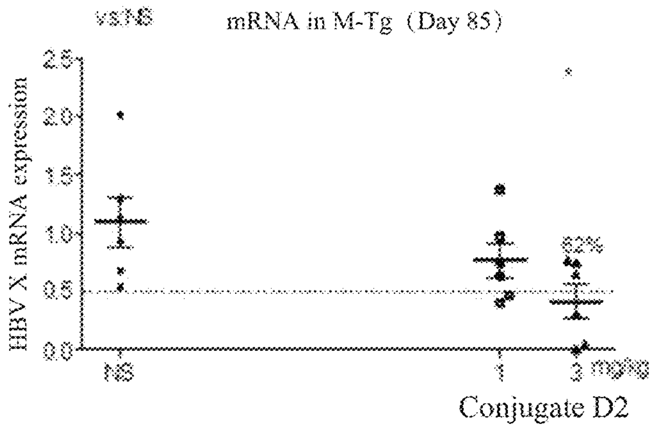
FIG. 47 shows inhibitory effect of the conjugates of the present disclosure on HBV mRNA in M-Tg mouse models.
Figure 48A:
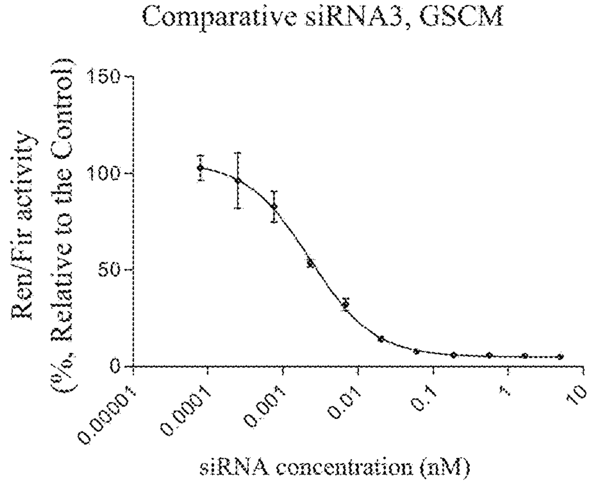
FIGS. 48A-48D show inhibitory effect of comparative siRNA3 on target mRNA and off-target mRNA in intro.
Figure 48B:
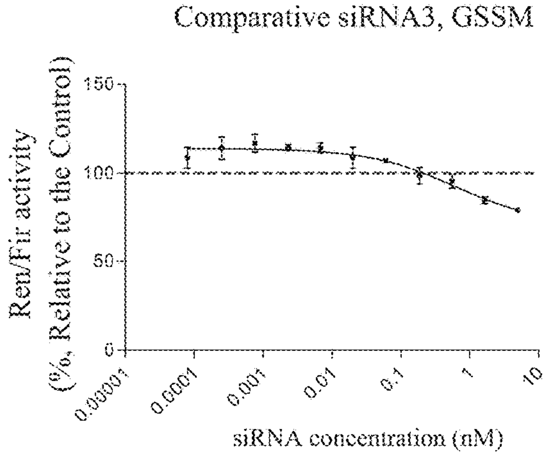
Figure 48C:
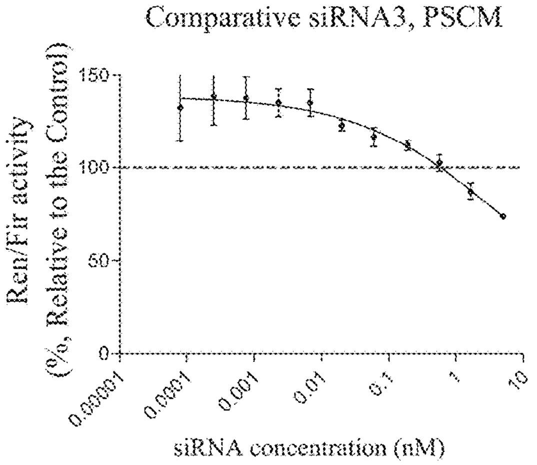
Figure 48D:
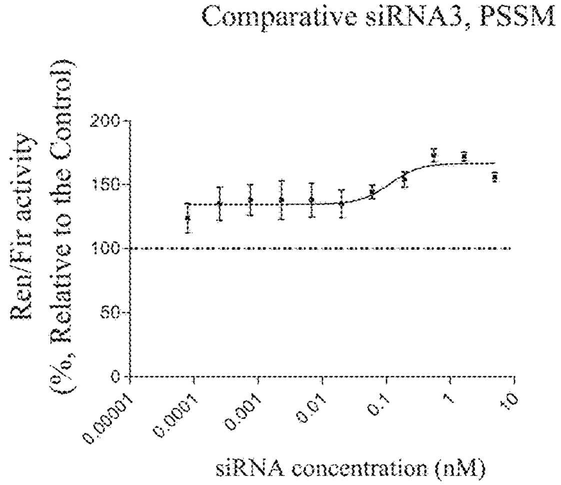
Figure 49A:
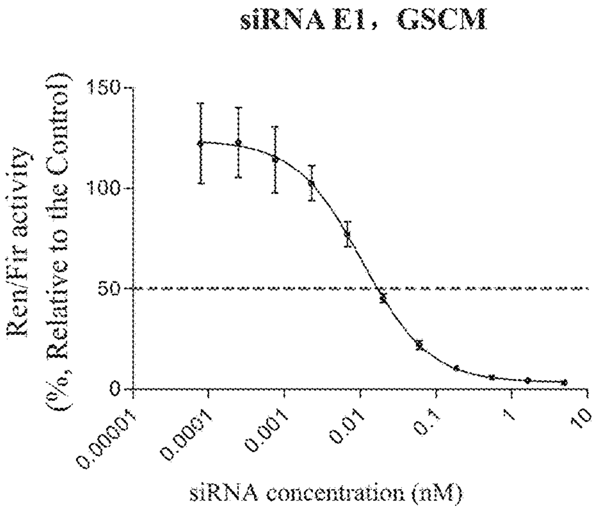
FIGS. 49A-49D show inhibitory effect of the siRNA E1 of the present disclosure on target mRNA and off-target mRNA in intro.
Figure 49B:
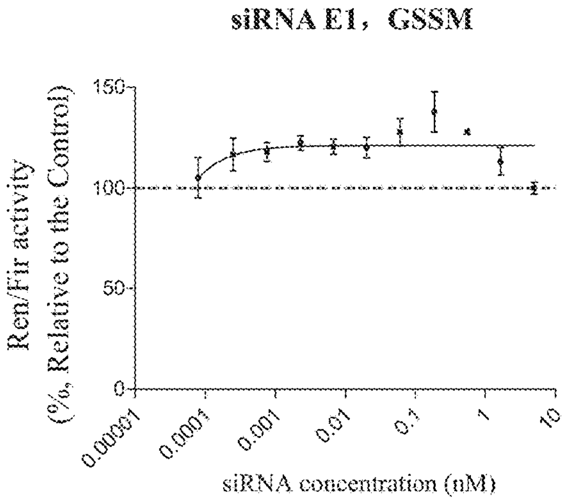
Figure 49C:
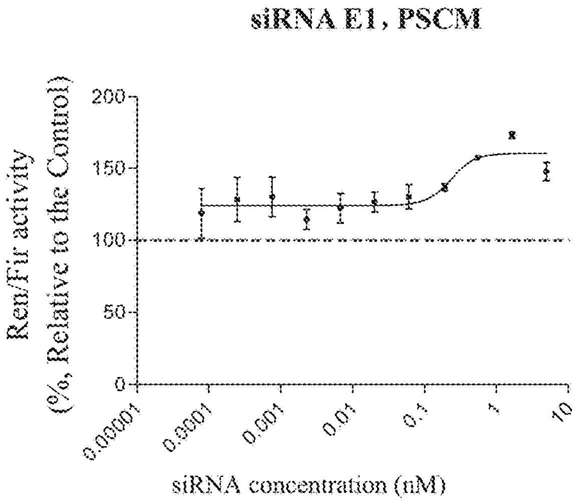
Figure 49D:
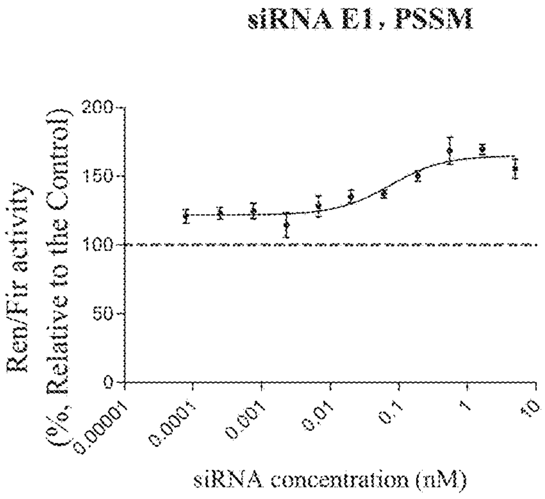

The following FIGS. 46 and 47 show the test results of the inhibitory effect of the tested siRNA conjugate administered in a single administration against HBsAg and HBV X mRNA in M-Tg model mice.

As can be seen from the results of FIGS. 46 and 47: Conjugate D2 administered at 3 mg/kg maintained higher inhibition against HBsAg over a period of 50 days, exhibiting an inhibition percentage of 90% or higher and the maximum inhition percentage of 95% or higher; and Conjugate D2 administered at 3 mg/kg still showed an inhibition percentage of 62% against HBV X mRNA on day 85.

Hereinbelow, an experiment for verifying the effects of the siRNA conjugates shown in Table 4E was described.

Experimental Example E1 Detection for the inhibitory activity and off-target effect of siRNA in in vitro psiCHECK system In this experimental example, siRNAs E1, E4 and Comparative siRNA3 were investigated in in vitro psiCHECK system for the on-target activity and off-target effect. Specifically, the activities of three siRNA targeting completely matching target sequences or targeting matching target sequence in seed region were tested, respectively.

Tests were conducted by using the method described in Experimental Example B1-2, except that four target sequences were constructed based on the sequences to be tested; the testing concentration was diluted from 5 nM to 0.00008 nM (3-fold serial dilutions), totaling 11 concentrations. The inhibitory effects of Comparative siRNA3 against the expressions of four recombinant plasmids were shown in FIGS. 48A-48D, while the inhibitory effects of siRNA E1 against the expressions of four recombinant plasmids were shown in FIGS. 49A-49D. As can be seen from these Figures, the unmodified Comparative siRNA3 at 5 nM exhibited an inhibition percentage of about 20% against the expressions of GSSM and PSCM, indicating low off-target effects both in the seed region of the antisense strand and in the sense strand. However, the modified siRNA E1 provided by the present disclosure showed no off-target effect; and siRNAE4, consistent with siRNA E1, showed no off-target effect.

The dose-response curves were plotted by the activity results measured at different siRNA concentrations, and the curves were fitted using the function log(inhibitor) vs. response-Variable slope of Graphpad 5.0 software. The $IC_{50}$ of the siRNA t targeting GSCM to be detected was calculated below based on the dose-response curve with the formula below. The results are shown in Table 5:

$$Y = \text{Bot} + \frac{\text{Top}-\text{Bot}}{1 + 10^{(LogIC50-X)\times HillSlope}}$$

wherein

Y is the expression level of remaining mRNA,

X is the logarithm of the concentration of transfected siRNA,

Bot is the Y value at the bottom of the steady stage,

Top is the Y value at the top of the steady stage,

Log $IC_{50}$ is the X value at which Y is the median value between the bottom and the top of the steady stage, and HillSlope is the slope of the curve.

TABLE 6E

| $IC_{50}$ value of siRNA against GSCM | | |
|---|---|---|
| siRNA | No. | $IC_{50}$ value against GSCM |
| siRNA E1 | siAN1M3SVP | 0.017 nM |
| siRNA E4 | siAN1M3S | 0.024 nM |
| Comp. siRNA 3 | siAN1 | 0.0028 nM |

As can be seen from Table 6E, the modified siRNA of the present disclosure showed very high inhibitory activity in in vitro psiCHECK system, with $IC_{50}$ ranging between 3 and 30 μM.

Meanwhile, even at a concentration of 5 nM, no off-target effect was observed in the siRNAs to be detected.

Experimental Example E2 Detection of inhibitory activity of siRNA and siRNA conjugate in in vitro cell system Experimental Example E2-1 Detection of the inhibitory efficiency of siRNA in Huh 7 cell against the expression level of ANGPTL 3 mRNA The siRNAs (siRNA E1, E2 and E4 and Comparative siRNA4) to be detected were transfected to Human hepatoma cell lines Huh7 by using Lipofectamine™ 2000. The final concentrations of siRNAs were 5 nM, 0.25 nM and 0.05 nM, respectively, 2 replicate wells per concentration. Cells untreated with siRNA were used as a blank control.

The expression levels of ANGPTL3 mRNAs in Huh 7 cells transfected with siRNAs at various concentrations were measured by PCR (Quantitative Real-Time PCR), respectively. Specific steps were as follows: 24 hours after cultivation of transfected cells, the total RNA was extracted and obtained by using Trizol (Thermo Fisher) according to the standard procedure for total RNA extraction; 1 μg of the total RNA was individually extracted and reverse transcribed into cDNA by using reverse transcription kit (Promega, Cat No. A3500) according to the instruction thereof. The expression level of ANGPTL3 mRNA was detected based on the template cDNA according to the steps described in the instruction by using 2×Ultra SYBR Mixture (with ROX) (Beijing Cowin Biosciences Co., Ltd, Cat No. CW 0956). Therein, the PCR primers of GAPDH for amplifying ANGPTL3 and as an internal control gene are shown in Table 5E.

TABLE 5E

| Primer Information | | | |
|---|---|---|---|
| Genes | Primer types | Nucleotide Sequences (5' →3') | SEQ ID NO |
| Human ANGPTL3 | Upstream Primer | ACCAACTATACGCTACAT | 433 |
| | Downstream Primer | CCTCCTGAATAACCCTCT | 434 |
| Human GAPDH | Upstream Primer | GGTCGGAGTCAACGGATTT | 435 |
| | Downstream Primer | CCAGCATCGCCCCACTTGA | 436 |

The expression level of ANGPTL3 mRNA was calculated by the following equation:

the expression level of ANGPTL3 mRNA=(the expression level of ANGPTL3 mRNA in the test group/the expression level of GAPDH mRNA in the test group)/(the expression level of ANGPTL3 mRNA in the control group/the expression level of GAPDH mRNA in the control group)×100%.

The inhibition percentage of siRNA against the expression level of ANGPTL3 mRNA is (1−the expression level of ANGPTL3 mRNA)×100%. Therein, Huh7 cells individually treated with siRNAs at various concentrations were used in the test groups, and Huh 7 cells untreated with siRNAs were used in the control group (marked as "Blank" in FIG. 50A). The results are shown in FIG. 50A.

Figure 50A:
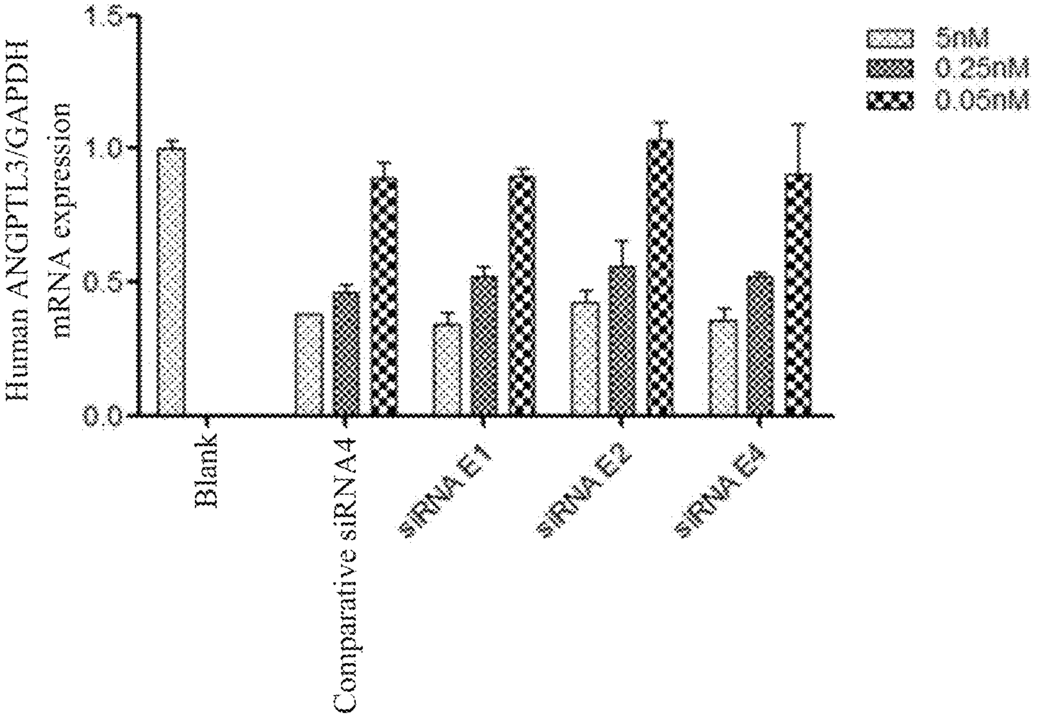
FIGS. 50A-50B respectively show inhibitory effect of the siRNA and siRNA conjugates of the present disclosure on ANGPTL3 mRNA in intro.

As can be seen from FIG. 50A, the modified siRNAs provided by the present disclosure showed higher inhibitory activity in the Huh7 cell lines.

Experimental Example E2-2 Detection of the inhibitory efficiency of siRNA conjugate against the expression level of ANGPTL3 mRNA in Huh7 cells Detection was conducted by the same method as in Experimental Example E2-1, except that the samples to be detected were Conjugates E18 and E19, and the final concentrations of the conjugates (calculated based on the amount of siRNA) were 50 nM and 5 nM. The in vitro inhibitory activity of each conjugate is shown in FIG. 50B.

Figure 50B:
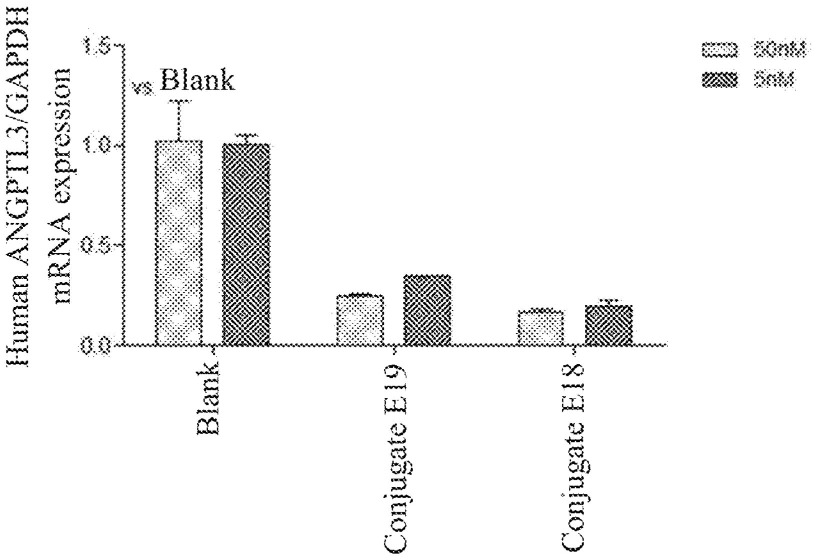

As can be seen from FIG. 50B, the siRNA conjugates provided by the present invention showed higher inhibitory activity in Huh7 cell lines, and the conjugates at 5 nM showed an inhibition percentage of 60-80% against the expression level of ANGPTL3 mRNA.

Experimental Example E2-3 Measurement of $IC_{50}$ of siRNA conjugate against ANGPTL3 mRNA in Huh7 cells Detection was conducted by the same method as that in Experimental Example E2-1, except that the samples to be detected were Conjugates E18 and E19. The final concentrations of the conjugates (calculated based on the amount of siRNAs) were diluted five-fold from 50 nM to 0.016 nM, with the lowest concentration being set at 0.00001 nM (totaling 7 concentrations), 3 replicate wells per group.

In further experiments, the sample to be detected was Conjugate E2. The final concentration of the conjugate (calculated based on the amount of siRNA) was double diluted from 2 nM to 0.0078 nM (totaling 9 concentrations), 2 replicate wells per group.

In still further experiments, the samples to be detected were conjugates E1 and E4. The final concentrations of the conjugates (calculated based on the amount of siRNA) were double diluted from 0.5 nM to 0.03125 nM, with the highest concentration being set at 5 nM (totaling 6 concentrations), 2 replicate wells per group.

The $IC_{50}$ value was calculated by the same method as that in Experimental Example 1 according to the measured inhibition percentages of siRNA conjugates at different concentrations against the expression level of ANGPTL3 mRNA. The $IC_{50}$ value of the conjugates to be detected in in vitro Huh7 cells can be obtained. The results are shown in Table 7E.

TABLE 7E $IC_{50}$ of siRNA conjugates against ANGPTL3 mRNA

| Conjugate | NO. | $IC_{50}$ |
|---|---|---|
| Conjugate E18 | FIN-siAN1M3SVP | 0.0851 nM |
| Conjugate E19 | FIN-siAN2M3SVP | 0.1419 nM |
| Conjugate E2 | L10-siAN1M3SP | 0.1271 nM |
| Conjugate E1 | L10-siAN1M3SVP | 0.2137 nM |
| Conjugate E4 | L10-siAN1M3S | 0.3833 nM |

As can be seen from Table 7E, the siRNA conjugates of the present invention showed very high inhibitory activity in in vitro cell lines, with $IC_{50}$ ranging from 0.085 to 0.383 nM.

Experimental Example E3 Detection of the stability of siRNAs and siRNA conjugates in plasma and lysosome Experimental Example E3-1 Detection of the stability of siRNAs in lysosome In this experimental example, the stabilitie of siRNAs E1, E2 and E4 in murine lysosome lysate were investigated.

Preparation of test samples treated with the lysosome lysate: 6 μL each of the siRNAs (at 20 μM) was individually mixed well with 27.2 μL of sodium citrate aqueous solution (pH 5.0), 4.08 μL of deionized water and 2.72 μL of murine lysosome lysate (Rat Liver Tritosomes, purchased from Xenotech Inc., Cat No. R0610LT, Lot No. 1610069, at a final concentration of acid phosphatase of 0.2 mU/μL), and incubated at a constant temperature of 37° C. 5 μL samples were taken at each time point of 0 h, 1 h, 2 h, 4 h, 6 h, and 24 h respectively, added to 15 μL of 9 M urea aqueous solution for denaturation, and added with 4 μL of 6×loading buffer (purchased from Solarbio Inc., Cat No. 20160830), then immediately cryopreserved in a −80° C. freezer to quench the reaction. 0 h represents the moment when the sample was taken immediately after the samples to be tested are mixed well with the lysosome lysate.

Preparation of control samples untreated with the lysosome lysate: 1.5 μL each of the conjugates at equal moles (20 μM) was mixed well with 7.5 μL of sodium citrate aqueous solution (pH 5.0) and 1 μL of deionized water, added to 30 μL of 9 M urea solution for denaturation, and added with 8 μL of 6×loading buffer, then immediately cryopreserved in a −80° C. freezer to quench the reaction. The control sample for each siRNA was marked as Con in the electrophoretogram.

16 wt % of non-denatured polyacrylamide gel was prepared. 20 μL each of the test samples and the control samples described above was loaded onto the gel to perform electrophoresis under 20 mA constant current for 10 minutes and then under 40 mA constant current for 30 minutes. After finishing the electrophoresis, the gel was placed on a shaker and stained with Gelred dye (BioTium, Cat No. 13G1203) for 10 minutes. The gel was subjected to imaging, observation and photocopying. The results are shown in FIG. 51A.

Figure 51A:
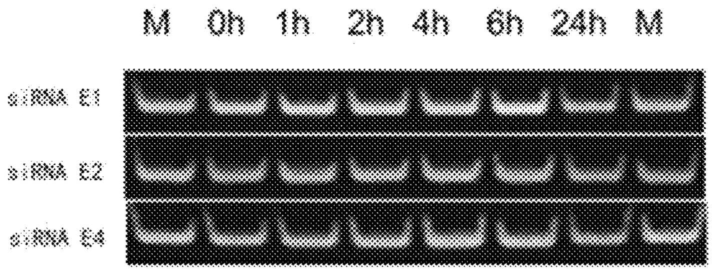
FIGS. 51A-51D respectively show the results of the stability tests of the conjugates of the present disclosure in vitro.

As can be seen from FIG. 51A, the modified siRNAs of the present invention remained stable for at least 24 hours in murine lysosome.

Experimental Example E3-2 Detection of the stability of siRNA conjugates in lysosome In this experimental example, the stability of Conjugates E1 and E4 in murine lysosome lysate was investigated.

Detection was conducted according to the same method as that in experimental example 3-1, except that: the samples to be detected were Conjugates E1 and E4, and the concentration of the conjugates were calculated based on the amount of siRNA, and the time points for detection were 0 h, 5 minutes, 15 minutes, 30 minutes, 1 h, 2 h, 4 h and 6 h. The gel image was shown in FIG. 51B.

Figure 51B:
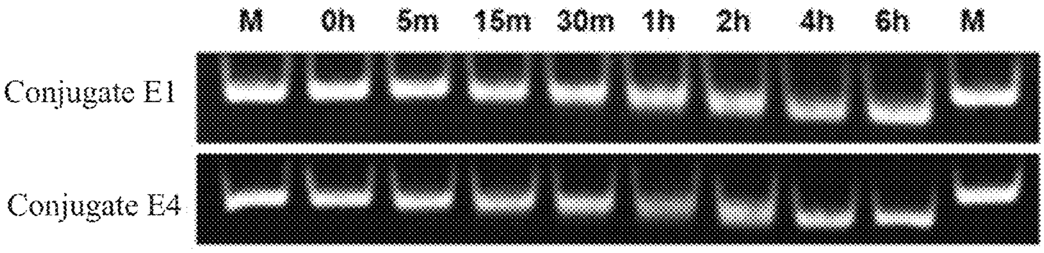

As can be seen from FIG. 51B, the siRNA conjugates of the present invention remained undegraded for at least 1 hour in murine lysosome, and then the major band of the electrophoresis was only slightly shifted downward. In view of the high stability of the corresponding siRNA in the lysosome lysate, it is considered that the downward shifting of the band may be the cleavage of a monosaccharide on the conjugation group. The siRNA conjugates of the present disclosure show satisfactory stability.

Experimental Example E3-3 Detection of the stability of siRNA conjugates in plasma In this experimental example, the stability of Conjugates E1 and E4 in human plasma was investigated.

Conjugates E1 and E4 and Comparative siRNA3 (the concentration of siRNA or siRNA conjugate is 20 μM, 12 μl, and the conjugate is calculated based on the amount of siRNA) were individually mixed well with 108 μL of 90% human plasma (diluted in PBS) and incubated at a constant temperature of 37° C. 10 μL samples were taken at each time point of 0 h, 2 h, 4 h, 6 h, 8 h, 24 h, 48 h and 72 h, respectively, and immediately frozen in liquid nitrogen and cryopreserved in a −80° C. freezer for use. After sampling at each time point, each cryopreserved sample was diluted 5-fold with 1×PBS (pH 7.4) and then taken in a volume of 10 μL for use. Meanwhile, the siRNAs (2 μM, 2 μL) or siRNA conjugate (at the siRNA concentration of 2 μM, 2 μL) was taken at equal moles and mixed well with 8 μL of 1×PBS, thus obtaining 10 μL of samples untreated with human plasma (marked as M).

20 wt % of non-denatured polyacrylamide gel was prepared. Each of the above samples was mixed with 4 μL of loading buffer (aqueous solution of 20 mM EDTA, 36 wt % glycerol, and 0.06 wt % bromophenol blue) and then loaded onto the gel to perform electrophoresis for under 80 mA constant current about 60 minutes. After finishing the electrophoresis, the gel was placed on the shaker and stained with 1×Sybr Gold dye (Invitrogen, Cat No. 11494) for 15 minutes followed. The gel was subjected to imaging, observation and photocopying. The results are shown in FIG. 51C.

Figure 51C:
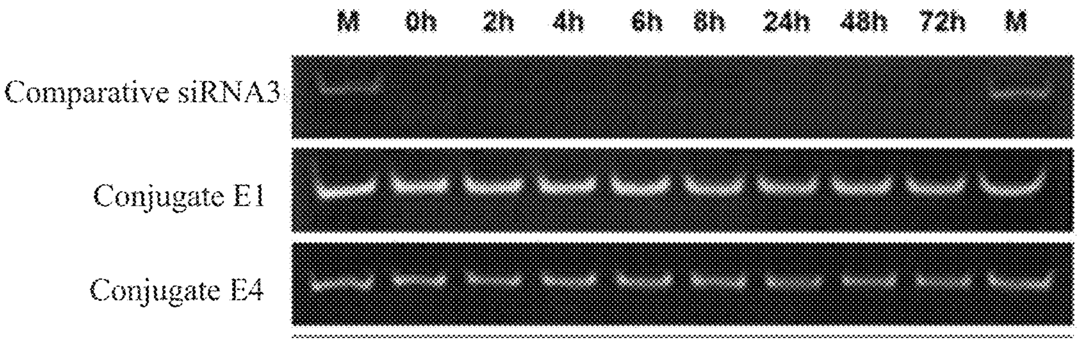

As can be seen from FIG. 51C, the siRNA conjugates of the present invention remained undegraded at up to 72 hours in human plasma, showing excellent stability in human plasma.

Figure 51D:
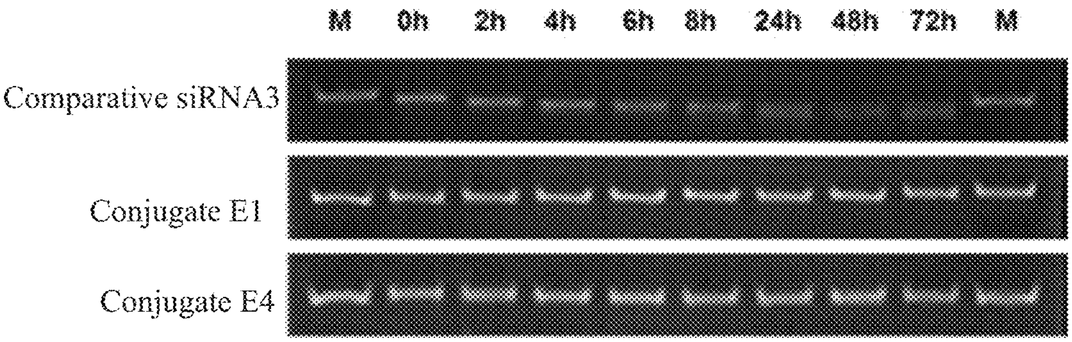

In further experiments, the stability of Conjugates E1 and E4 in monkey plasma was detected by using the same method described above. The results are shown in FIG. 51D.

The results indicate that the siRNA conjugates of the present invention can stay stably for at least 72 hours both in human plasma and in monkey plasma, showing excellent stability.

Experimental Example E4 Detection of the inhibitory efficiency of siRNA conjugates against the expression level of ANGPTL3 mRNA in mice in vivo, and detection of the inhibitory effect on blood lipid Experimental Example E4-1 Determination of $ED_{50}$ of siRNA conjugates against ANGPTL3 mRNA in normal mice C57 in vivo In this experimental example, the inhibitory activity of Conjugates E18 and E19 in normal mice C57 in vivo was investigated.

Normal mice C57 of 6-8 weeks old were randomly divided into groups (5 mice in each group). Conjugates E18, E19 and PBS were individually administered to the mice in each group. The drug dosages for all animals were calculated according to the body weight (single administration (subcutaneously), administration dosage of 10 mg/kg, 3 mg/kg, 1 mg/kg, 0.3 mg/kg and 0.1 mg/kg for each siRNA conjugate (calculated based on the amount of siRNA)). Moreover, the lowest dosage for Conjugates E18 and E19 was 0.003 mg/kg. Each test group was administered in the administration volume of 10 mL/kg. Each siRNA conjugate was individually administered in the form of PBS aqueous solution. The drug concentration of the conjugate to be formulated was calculated according to administered dosage and volume. Mice were sacrificed on day 3 after administration. The liver was collected and kept with RNA later (Sigma Aldrich), and the liver tissue was homogenized with a tissue homogenizer. Then the total RNA was extracted and obtained by using Trizol (Thermo Fisher) according to the standard procedure for total RNA extraction.

The expression level of ANGPTL3 mRNA in liver tissue was measured by real-time fluorescent qPCR. Specifically, cDNA was obtained by reverse transcription using reverse transcription kit (Promega, Cat No. A3500) according to the instruction thereof. The expression level of ANGPTL3 mRNA was measured based on the template cDNA according to the steps in the instruction by using 2×Ultra SYBR Mixture (with ROX) (Beijing Cowin Biosciences Co., Ltd, Cat No. CW 0956). Therein, the PCR primers of GAPDH for amplifying ANGPTL3 and as an internal control gene are shown in Table 8E.

TABLE 8E sequences of primers

| Genes | SEQ ID NO. | Nucleotide Sequences (5' →3') |
|---|---|---|
| Mouse ANGPTL3 | 437 | GAGGAGCAGCTAACCAACTTAAT |
| | 438 | TCTGCATGTGCTGTTGACTTAAT |
| Mouse GAPDH | 439 | AACTTTGGCATTGTGGAAGGGCTC |
| | 440 | TGGAAGAGTGGGAGTTGCTGTTGA |

The expression level of ANGPTL3 mRNA was calculated by the equation: the expression level of ANGPTL3 mRNA=[(the expression level of ANGPTL3 mRNA in the test group/the expression level of GAPDH mRNA in the test group)/(the expression level of ANGPTL3 mRNA in the control group/the expression level of GAPDH mRNA in the control group)]×100%.

The inhibition percentage of the conjugates against the expression level of ANGPTL3 mRNA was calculated by the equation:

the inhibition percentage=[1−(the expression level of ANGPTL3 mRNA in the test group/the expression level of β-actin mRNA in the test group)/(the expression level of ANGPTL3 mRNA in the control group/the expression level of β-actin mRNA in the control group)×100%.

Therein, the control group was a group of control mice administered with PBS in this experiment and each test group was a group of mice administered with different siRNA conjugate, respectively.

$ED_{50}$ was calculated by the same method as in Experimental Example E1 according to the inhibition percentages of siRNA conjugates at different concentrations against the expression level of ANGPTL3 mRNA. The $ED_{50}$ value of the conjugates to be detected in normal mice in vivo can be obtained. The results are shown in Table 9E.

TABLE 9E $ED_{50}$ of siRNA conjugates against the ANGPTL3 mRNA in liver tissue of normal mice c57

| Conjugates | NO. | ED50 |
|---|---|---|
| ConjugateE18 | FIN-siAN1M3SVP | 0.1403 nM |
| ConjugateE19 | FIN-siAN2M3SVP | 0.1595 nM |

As can be seen from Table 9E, the inhibitory activity of the tested conjugates in normal mice in vivo was highly consistent with that of the corresponding conjugates in in vitro cell line described in Experimental Example 2-3, with ED50 ranging between 0.1403 and 0.1595 nM, indicating that the siRNA conjugates of the present invention showed very high inhibitory activity in normal mice in vivo.

Experimental Example E4-2 Inhibitory efficiency of the siRNA conjugates against the expression level of ANGPTL3 mRNA in normal mice BALB/c in vivo, and the effect on blood lipid In this experimental example, the inhibitory percentage of Conjugates E18 and E20 against ANGPTL3 mRNA in liver tissue in normal mice BALB/c in vivo, and the effect on blood lipid were investigated.

Normal mice BALB/c of 6-8 weeks old were randomly divided into groups (10 mice in each group). Conjugates E18, E20, Comparative Conjugate E2, and PBS were individually administered to the mice in each group. The drug dosages for all animals were calculated according to the body weight (single administration (subcutaneously), two administration dosage of 3 mg/kg and 0.3 mg/kg for the siRNA conjugates (calculated based on the amount of siRNA), and the administration volume of 10 mL/kg). Each siRNA conjugate was administered in the form of PBS aqueous solution. The drug concentration of the conjugate to be formulated was calculated according to administered dosage and volume. The blood was taken from mouse orbital vein before administration and on days 7 and 14 after administration, the blood lipid level in serum was tested at each time point. Five mice were respectively sacrificed on days 7 and 14 after administration, and the liver tissue was collected to detect the expression level of ANGPTL3 mRNA in liver.

About 100 μl orbital blood was taken each time, and the serum was obtained after centrifugation. The contents of total cholesterol (CHO) and triglyceride (TG) in serum were further measured by using a PM1P000/3 full-automatic serum biochemical analyzer (SABA, Italy).

The normalized blood lipid level=(the blood lipid content in the test group after administration/the blood lipid content in the test group before administration)×100%.

Inhibition percentage against blood lipid level=(1−the blood lipid content in the test group after administration/the blood lipid content in the test group before administration)×100%. Blood lipid refers to total cholesterol or triglyceride.

Figure 52A:
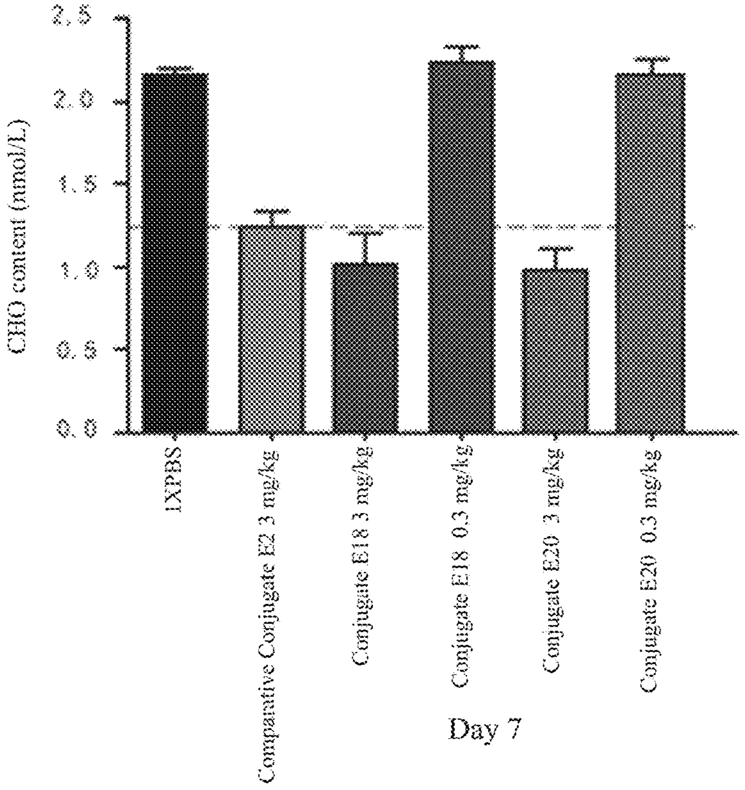
FIGS. 52A-52D show inhibition percentages of the conjugates of the present disclosure against blood lipid, represented by total cholesterol (CHO) and triglyceride (TG) in serum.
Figure 52B:
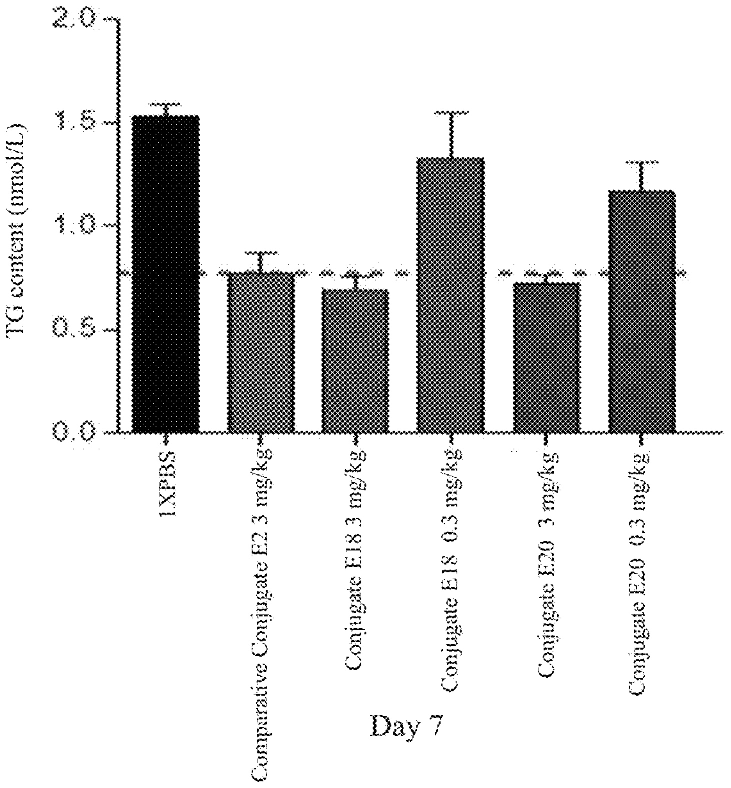
Figure 52C:
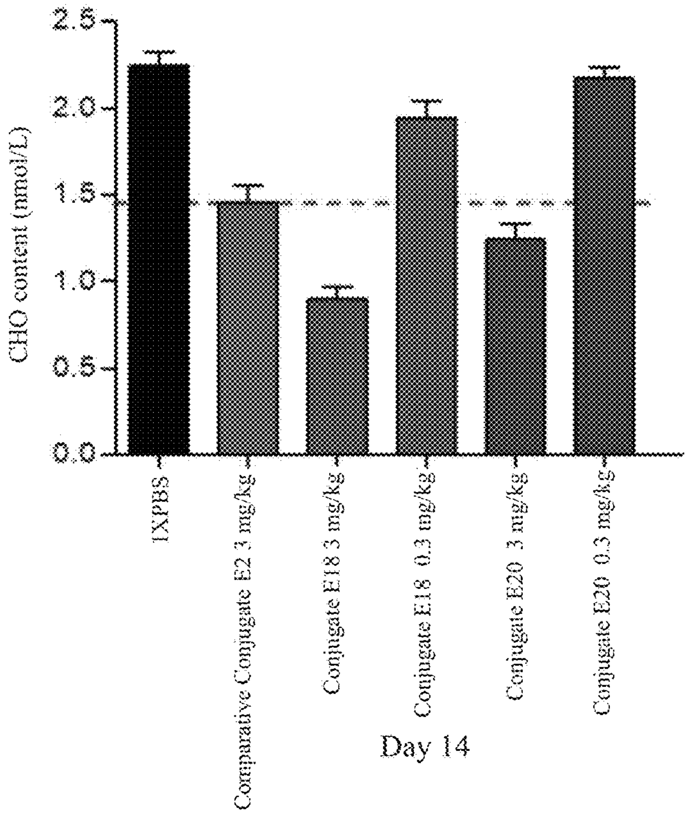
Figure 52D:
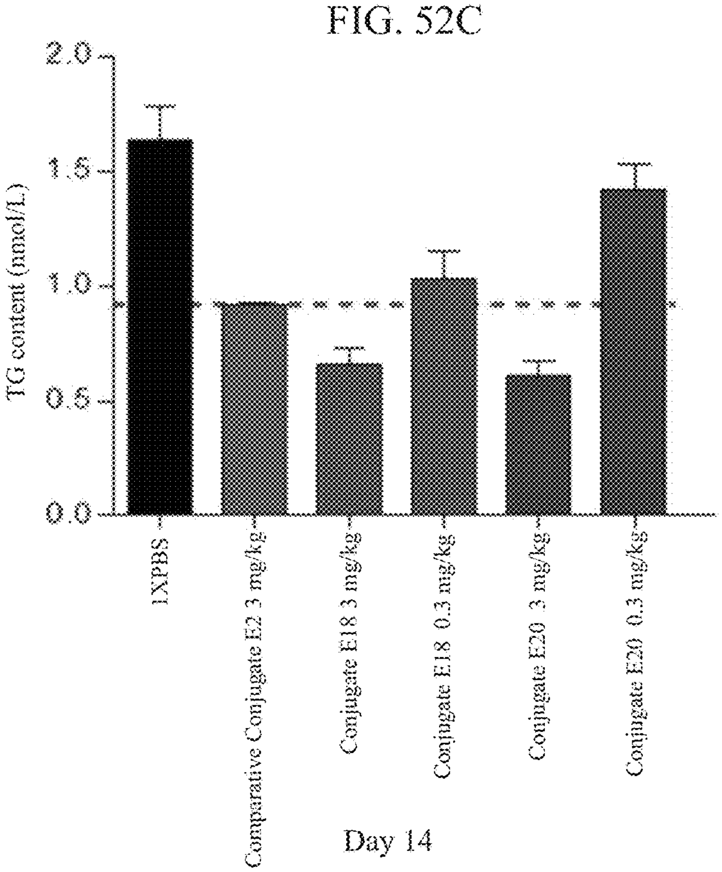
Figure 53A:
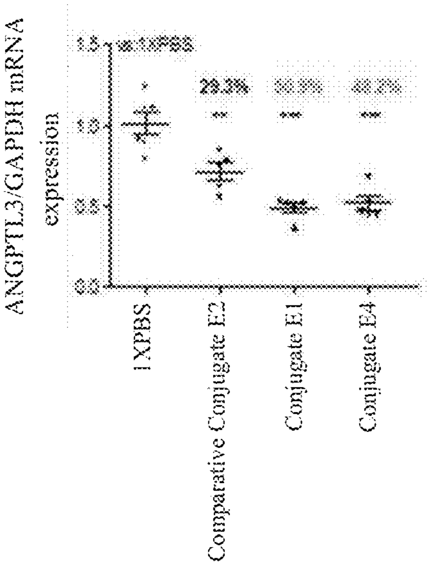
FIGS. 53A-53D show inhibition percentages of the conjugates of the present disclosure against ANGPTL3 mRNA in vivo.
Figure 53B:
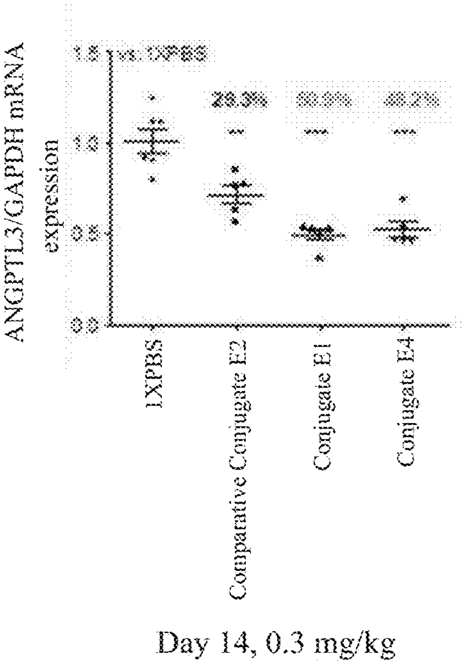
Figure 53C:
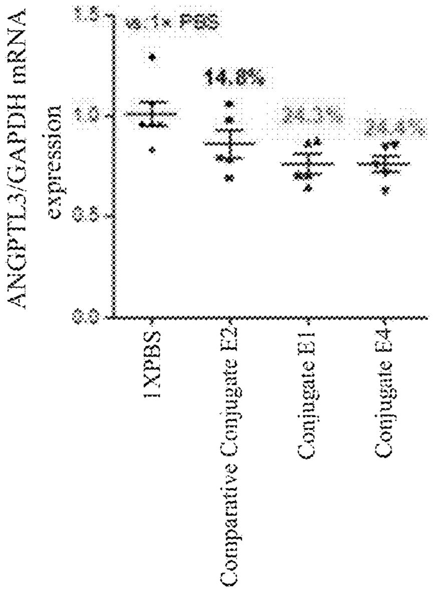
Figure 53D:
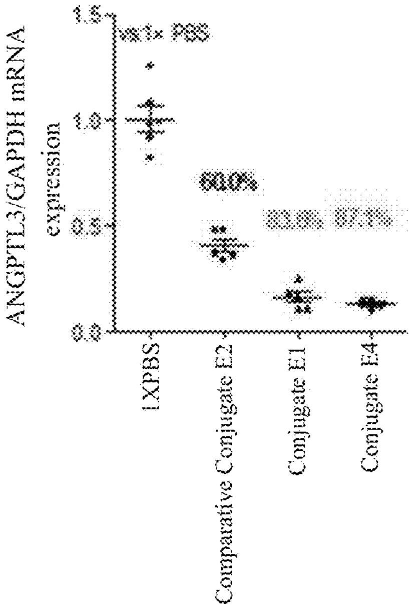
Figure 54A:
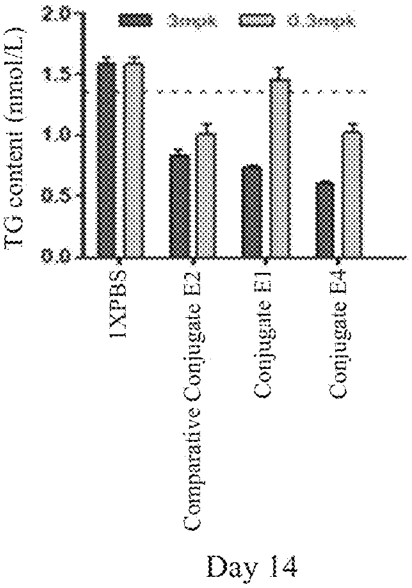
FIGS. 54A-54D respectively show inhibition percentages of the conjugates of the present disclosure against blood lipid, represented by total cholesterol (CHO) and triglyceride (TG) in serum.
Figure 54B:
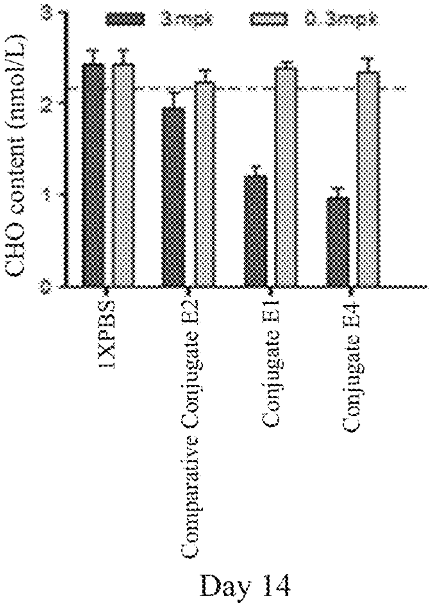
Figure 54C:
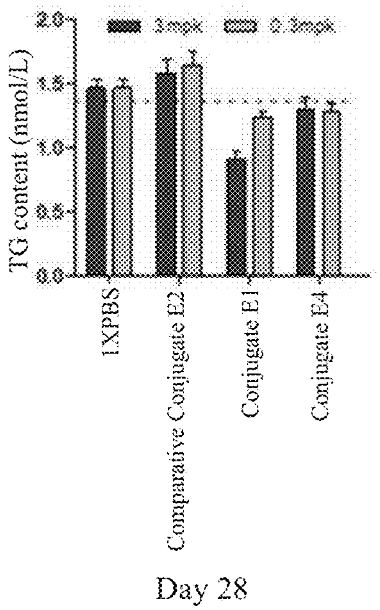
Figure 54D:
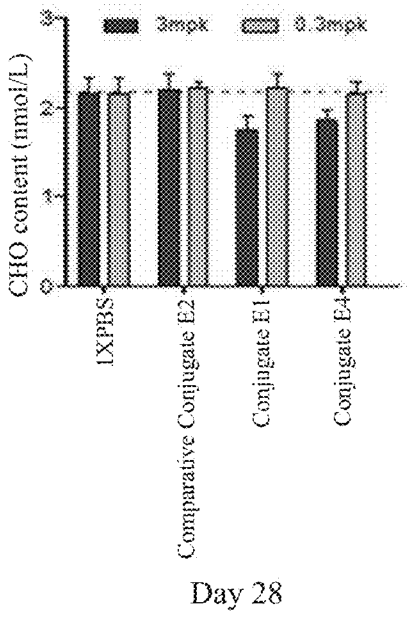

The blood lipid contents of mice on day 7 after administration are shown in FIGS. 52A-52B, and the blood lipid contents of mice on day 14 after administration are shown in FIGS. 52C-52D.

As can be seen from FIGS. 52A-52D, the tested siRNA conjugates significantly reduced the blood lipid level in normal mice. On day 14 after administration, the siRNA conjugates of the present invention at the dose of 3 mg/kg showed stronger ability to reduce blood lipid level as compared with the positive control (Comparative Conjugate E2).

The inhibitory efficiency of siRNA conjugates against the expression level of ANGPTL3 mRNA in liver was measured by real-time fluorescent qPCR using the same method as that in Experimental Example E4-1. The results are shown in Table 10E.

TABLE 10E inhibitory efficiency of siRNA conjugates against ANGPTL3 mRNA in liver tissue of normal mice BALB/c

| Conjugates | NO. | Dose (mg/kg) | Inhibition percentage against mRNA on day 7 (%) | Inhibition percentage against mRNA on day 14 (%) |
|---|---|---|---|---|
| Comparative Conjugate E2 | $(GalNAc)_3$-65695 | 3 | 96.6 | 91.2 |
| Conjugate E18 | FIN-siAN1M3SVP | 3 | 96.7 | 97.4 |
| Conjugate E20 | FIN-siAN1M3S | 3 | 98.3 | 95.8 |
| Conjugate E18 | FIN-siAN1M3SVP | 0.3 | 70.6 | 46.5 |
| Conjugate E20 | FIN-siAN1M3S | 0.3 | 68.0 | 34.0 |

In further experiments, the blood lipid and the expression level of ANGPTL3 mRNA were measured by the same methods described above, except that the administered conjugates were Conjugates E1, E4 and Comparative Conjugate E2; and the time for detection was on days 14 and 28 after administration. The inhibitory effect of each conjugate against ANGPTL3 mRNA is shown in FIGS. 53A-53D, and the inhibitory effect on blood lipid is shown in FIGS. 54A-54D.

As can be seen from FIGS. 53A-53D, on day 14 after administration, the siRNA conjugates of the present disclosure at high dose showed an inhibition percentage of up to 95% against ANGPTL3 mRNA, i.e. showing inhibitory indensity significantly higher than Comparative Conjugate E2. For the siRNA conjugates at low doses, the tested siRNA conjugates, observed for an extended time period until day 28 after administration, all showed strong inhibitory effect on ANGPTL3 mRNA in liver tissue of normal mice, and the inhibitory intensity was significantly higher than that of the Comp. Conjugate.

As can be seen from FIGS. 54A-54D, in the serum of the mice treated with siRNA conjugates of the present invention, the contents of both CHO and TG were reduced significantly, and blood lipid level reduction was at least observed until 28 days after administration. The siRNA conjugates of the present disclosure at a dose of 3 mg/kg showed stronger ability to reduce blood lipid level than the positive control (Comparative Conjugate E2).

Experimental Example E4-3 Inhibitory efficiency of siRNA conjugates against the expression level of ANGPTL3 mRNA in obese mice in vivo and the effect on blood lipid In this experimental example, the inhibition percentage of Conjugate E18 against ANGPTL3 mRNA in liver tissue of ob/ob mice in vivo and the effect on blood lipid were investigated.

Figure 55A:
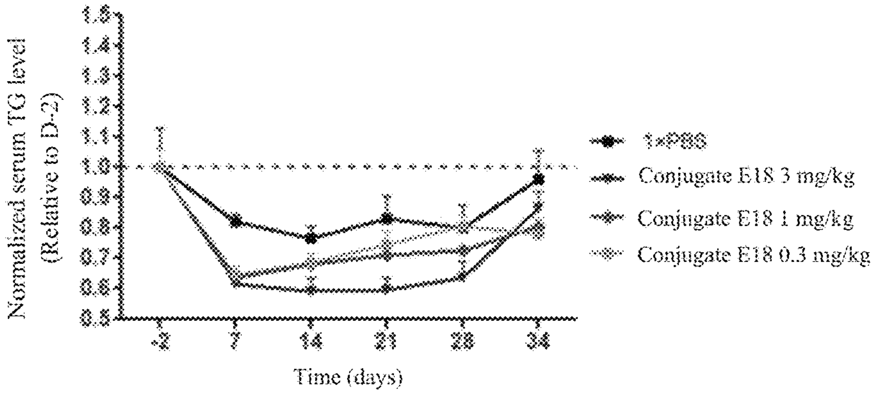
FIGS. 55A and 55B show inhibition percentages over time of the conjugates of the present disclosure against blood lipid, represented by total cholesterol (CHO) and triglyceride (TG) in serum.
Figure 55B:
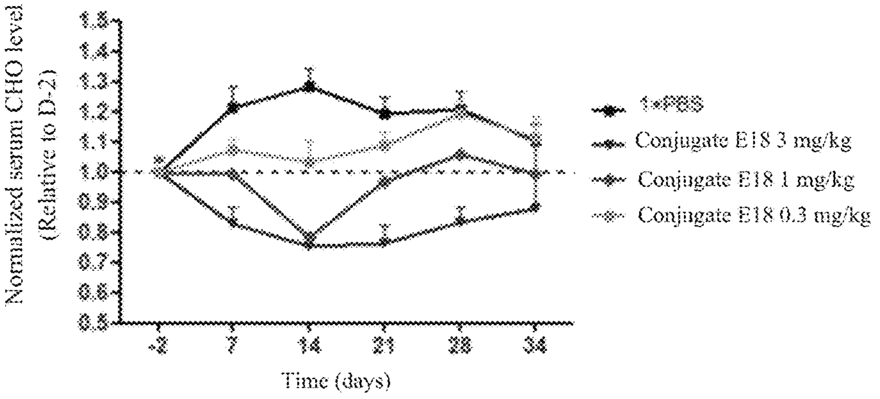
Figure 55C:
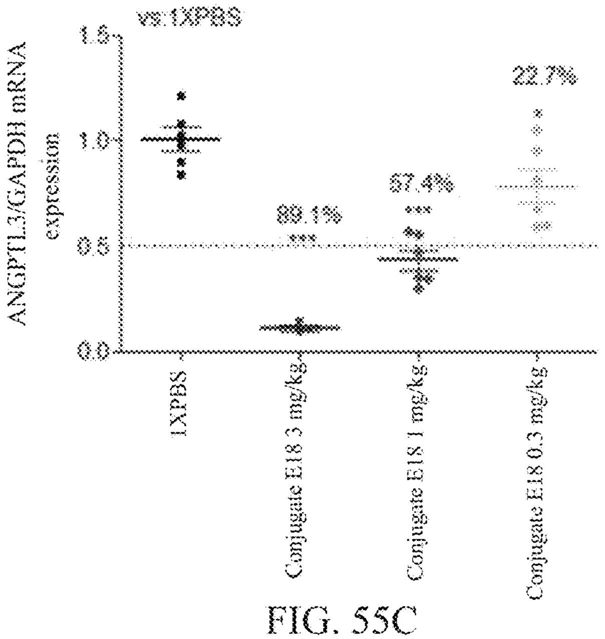
FIG. 55C shows the inhibition percentage against ANGPTL3 mRNA expression.

The expression level of ANGPTL3 mRNA and the blood lipid of ob/ob mice were measured by the same method described in Experimental Example E4-2, except that: ob/ob mice of 6-8 weeks old (6 mice in each group) were adopted; the conjugate administered was Conjugate E18, of which the administration dosages were 3 mg/kg, 1 mg/kg and 0.3 mg/kg; and the blood was taken two days before administration (marked as day −2) and on day 7, 14, 21, 28 and 34 after administration; the mice were sacrificed on day 34. The inhibitory effects of Conjugate E18 on blood lipid are shown in FIGS. 55A-55B; and the inhibitory effect on ANGPTL3 mRNA is shown in FIG. 55C.

As can be from the figures, in the mice treated with siRNA conjugates of the present invention, the contents of both CHO and TG were reduced significantly, and certain blood lipid reduction effect was at least observed until 34 days after administration. Meanwhile, on day 34 after administration, the siRNA conjugate can still effectively inhibit the expression of ANGPTL3 mRNA.

Experimental Example E4-4 Effect of siRNA conjugates on blood lipid in high-fat model mice in vivo In this experimental example, the inhibition percentage of Conjugate E1 against ANGPTL3 mRNA in liver tissue of human APOC3 transgenic mice and the effect thereof on blood lipid were investigated.

Human APOC3 transgenic mice Tg(APOC3)3707Bre were randomly divided into groups based on TG content>2 mmol/L in serum (6 mice in each group). Conjugate E1, Comparative Conjugate E1 and PBS blank control were individually administered to the mice in each group. The drug dosages for all animals were calculated according to the body weight (single administration (subcutaneously), administration dosage of 3 mg/kg and 1 mg/kg for the siRNA conjugates (calculated based on the amount of siRNA), and administration volume of 5 mL/kg). Each siRNA conjugate was administered in the form of PBS aqueous solution. The concentration of the conjugate to be formulated was calculated based on the administered dosage and volume. The blood was taken from mouse orbital venous plexus before administration (marked as day −1) and on days 7, 14, 21, 28, 35, 56, 70, 84, 98, 112, 126, 140, 154, and 168 after administration, and the blood lipid level was measured for each time point by using the same method as in Experimental Example 4-2. The results are shown in FIGS. 56A and 56B.

Figure 56A:
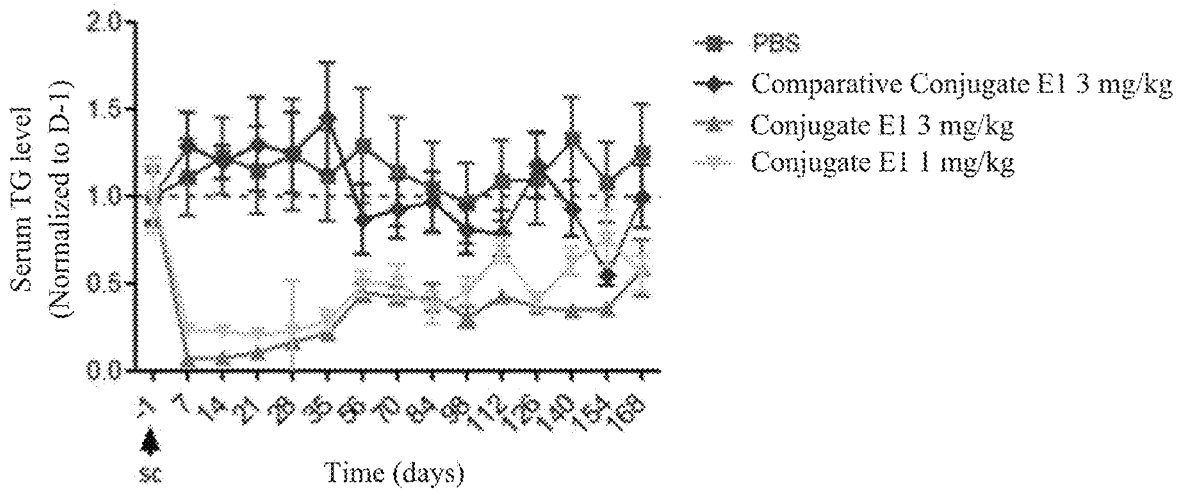
FIGS. 56A and 56B show inhibition percentages over time of the conjugates of the present disclosure against blood lipid, represented by total cholesterol (CHO) and triglyceride (TG) in serum.
Figure 56B:
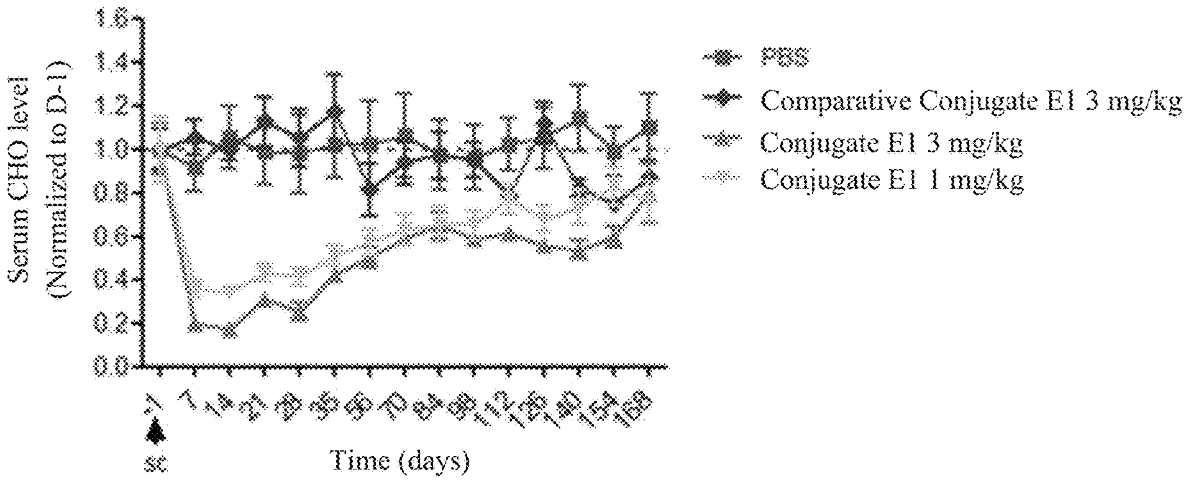

As can be seen from FIGS. 56A and 56B, the PBS blank control group and Comparative Conjugate E1 negative control group showed no inhibitory effect on blood lipid at different time points after administration; in contrast, Conjugate E1 significantly reduced the contents of TG and CHO. For TG, the high dose group showed the maximum inhibition percentage of 92.9% on day 7 after administration, and the low dose group showed the maximum inhibition percentage of 79.1% on day 21 after administration. The high dose group consistently showed an inhibition percentage of 55% or higher against TG over a period of up to 154 days after single administration; the low dose group consistently showed an inhibition percentage of 55% or higher against TG over a period of up to 98 days after single administration. For CHO, the high dose group showed the maximum inhibition percentage of 82.9% on day 14 after administration, and the low dose group showed the maximum inhibition percentage of 65.9% on day 14 after administration. The high dose group showed an inhibition percentage of 40% or higher against CHO over a period of up to 154 days after single administration, and the low dose group showed an inhibition percentage 40% or higher against CHO over a period of up to 56 days after single administration. FIGS. 56A and 56B indicated that Conjugate E1 allowed continuous, stable and efficient reduction effect on blood lipid level within 168 days after single administration.

In other experiments, the same method above was used, except that: the conjugates to be administered were Conjugate E2 and Comparative Conjugate E2. Blood lipid test continued until day 70 after administration, and the results were shown in FIGS. 57A-57D.

Figure 57A:
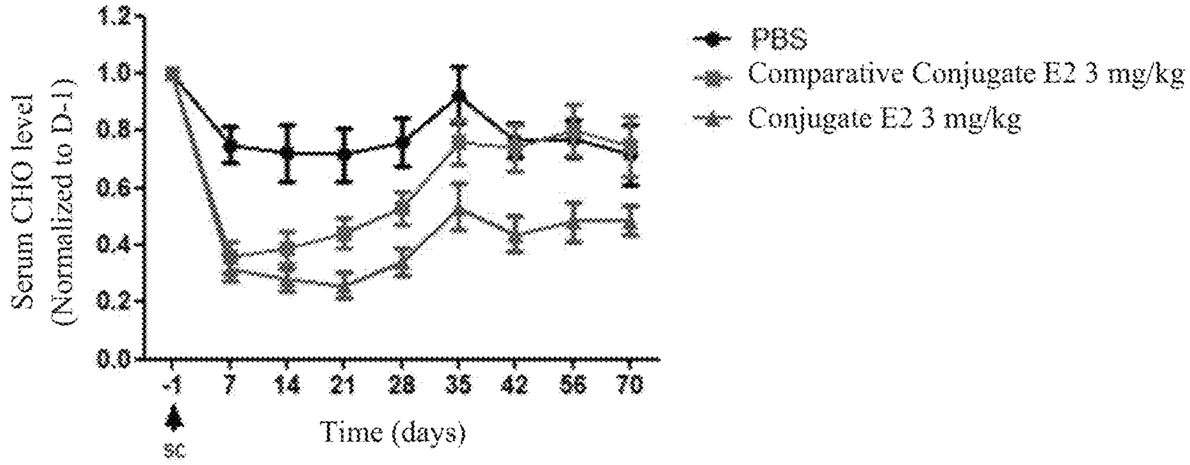
FIGS. 57A-57D show inhibition percentages over time of the conjugates of the present disclosure against blood lipid, represented by total cholesterol (CHO) and triglyceride (TG) in serum.
Figure 57B:
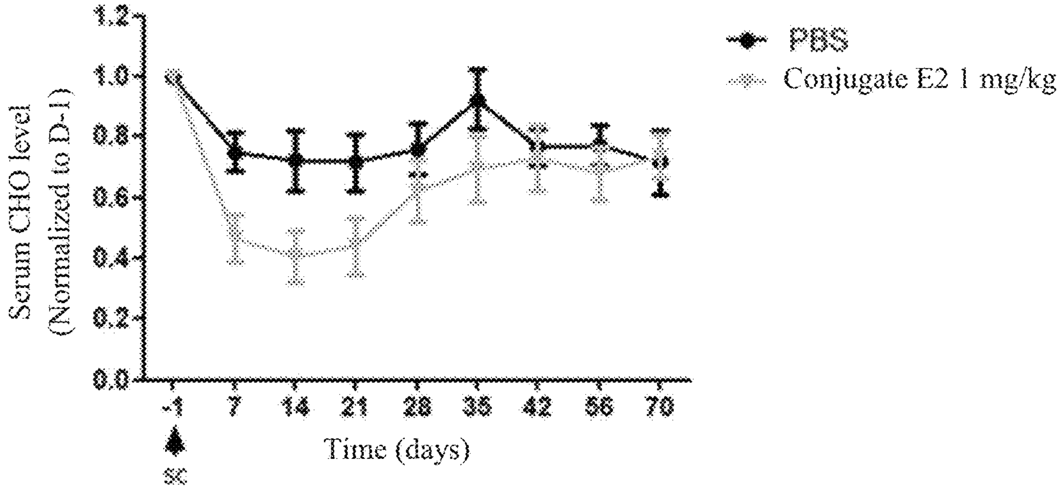

FIGS. 57A-57B showed the inhibitory effects of Conjugate E2 at two doses on CHO at different time points after administration. The group of mice administered with high dose showed the maximum inhibitory percentage against CHO of up to 74.3% on day 21 after single administration; and the inhibitory percentage against CHO was consistently maintained at 50% or higher over a period of up to 70 days after administration. The group of mice administered with low dose showed the maximum inhibitory percentage against CHO of 59.5% on day 14 after administration.

Figure 57C:
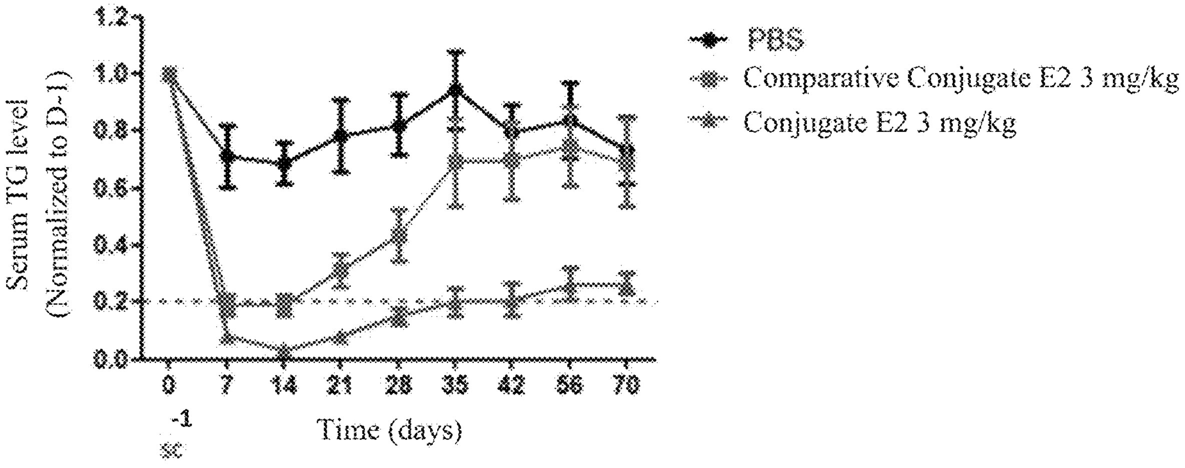
Figure 57D:
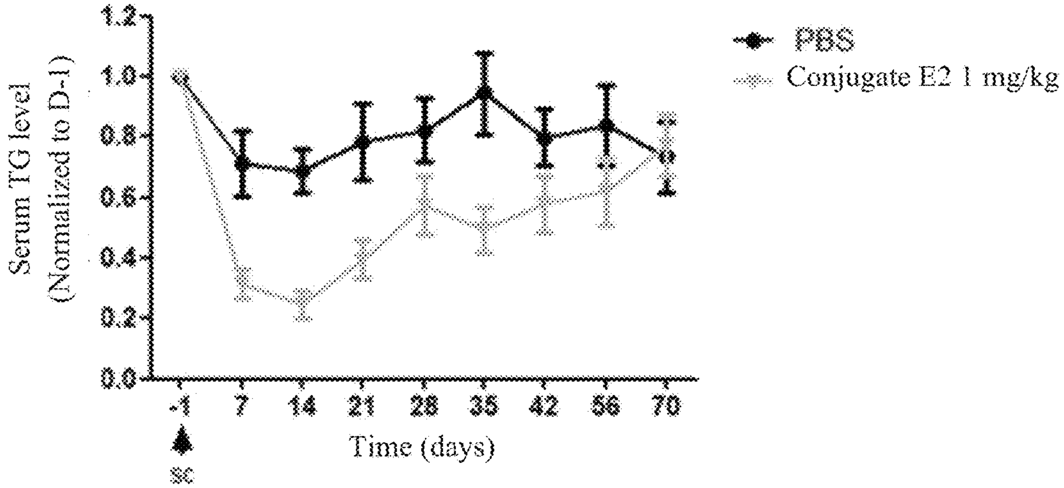

FIGS. 57C and 57D showed the inhibitory effects of Conjugate E2 at two doses on TG at different time points after administration. The group of mice administered with high dose showed the maximum inhibitory percentage against TG of up to 96.3% on day 14 after single administration; and the inhibitory percentage against TG was consistently maintained at 70% or higher over a period of up to 70 days after administration. The group of mice administered with low dose showed the maximum inhibitory percentage against TG of 75.3% on day 14 after administration.

As can be seen from FIGS. 57A-57D, Conjugate E2 consistently reduced the blood lipid level over a period of 70 days after single administration, and was obviously superior to Comparative Conjugate E2 at equal dose.

Experimental Example E5 Detection of the inhibitory efficiency of the siRNA conjugate against the expression level of ANGPTL3 mRNA and the inhibitory effect on blood lipid in non-human primates in vivo 12 Monkeys with metabolic syndrome (all male) were randomly divided into groups, with 8 monkeys being administered with Conjugate E2, 4 monkeys being administered with Comparative Conjugate E1. Each siRNA conjugate was dissolved in normal saline for injection to have a drug concentration of 100 mg/ml (calculated based on the amount of siRNA). The drug dosages for all animals were calculated according to the body weight. A single dose was administered subcutaneously, with the dosage of 9 mg/kg, the injection amount of 0.09 mL/kg and the administration volume of no more than 2 ml for each administration site.

The blood was taken from the vein once a week during three weeks before administration to measure indicators such as the blood lipid level, liver function, and blood routine examination. These indicators were re-measured respectively on days 7, 14, 21, 28 and 35 after administration.

The normalized blood lipid level=(1−the blood lipid content in the test group after administration/the blood lipid content in the test group before administration)×100%. The blood lipid refers to total cholesterol or triglyceride.

The blood lipid content before administration is the mean value of the blood lipid during 3 weeks before administration, and is a baseline value marked as D0. The inhibitory effects against blood lipids are shown in FIGS. 58A and 58B.

Figure 58A:
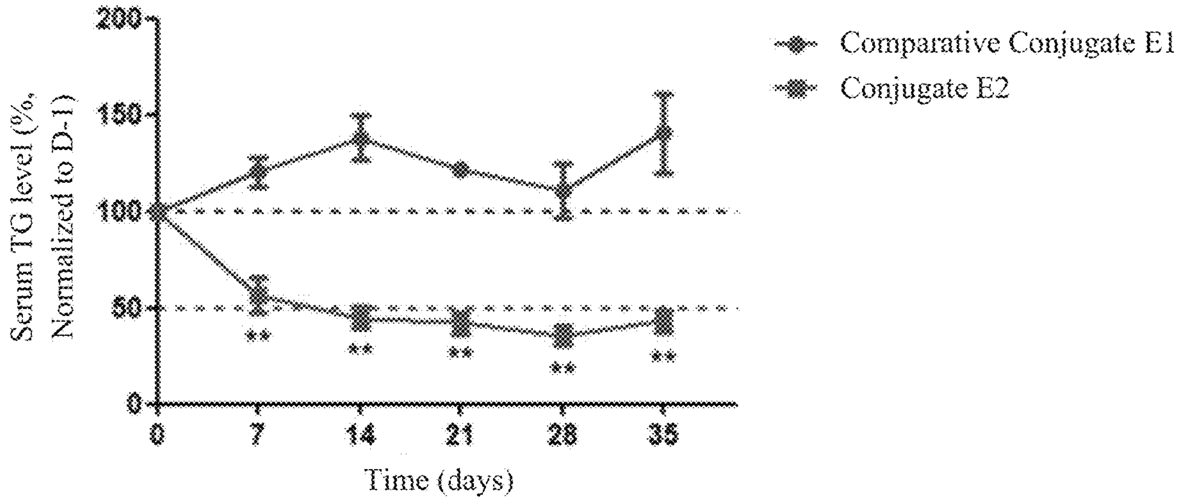
FIGS. 58A and 58B show inhibition percentages over time of the conjugates of the present disclosure against blood lipid, represented by total cholesterol (CHO) and triglyceride (TG) in serum.
Figure 58B:
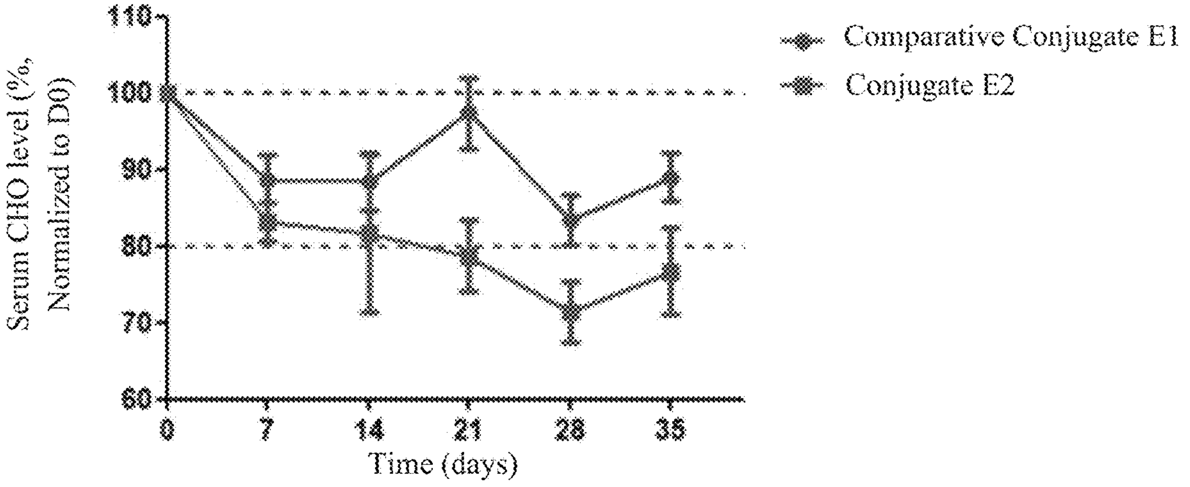

FIGS. 58A and 58B showed that Conjugate E2 resulted in the maximum inhibition percentage of 68% against TG and the maximum inhibition percentage of 30% against CHO on day 28 after single administration compared with that before administration.

In the very day of administration (marked as before administration) and on day 28 after administration, a Percutanous transhepatic biopsy was performed to measure the mRNA expression level of the ANGPTL3 in the liver tissue. The expression was measured by real-time fluorescent qPCR using the same method as described in Experimental Example 4-1, except that the detection primers are different. The detection primers used herein are shown in Table 11E. The inhibition percentage against ANGPTL3 mRNA is shown in FIG. 58C.

TABLE 11E

| Sequences of the primers | | |
|---|---|---|
| Genes | SEQ ID NO. | Nucleotide sequence (5' → 3') |
| Monkey ANGPTL3 | 441 | CTGGTGGTGGCATGATGAGT |
| | 442 | CTCTTCTCCGCTCTGGCTTAG |
| Monkey GAPDH | 443 | GGGAGCCAAAAGGGTCATCA |
| | 444 | CGTGGACTGTGGTCATGAGT |

Figure 58C:
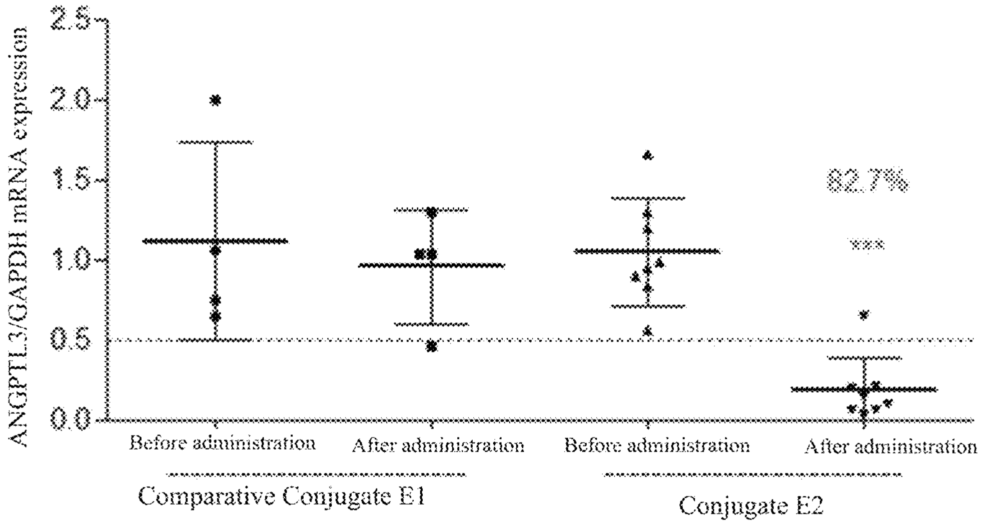
FIG. 58C shows the inhibition percentage against ANGPTL3 mRNA expression.

FIG. 58C showed that Conjugate E2 resulted in an inhibition percentage of up to 83% against ANGPTL3 mRNA on day 28 after single administration compared with that before administration.

Further indicators were measured at each time point after administration, no abnormal changes in the blood platelet, glutamic-pyruvic transaminase and glutamic oxalacetic transaminase were found, indicating that Conjugate E2 had relatively good safety; and no obvious toxic side effect was observed.

As can be seen from FIGS. 58A-58C, Conjugate E2 showed the effects of significantly reducing blood lipid level and inhibiting ANGPTL3 gene expression in non-human primate, and at the same time exhibited relatively good safety.

The above results indicated that the siRNAs and conjugates provided by the present invention can effectively inhibit the expression of ANGPTL3 mRNA in liver and reduce the content of total cholesterol or triglyceride in blood, and thus can prevent and/or treat blood lipid abnormalities and have good clinical application prospect.

Hereinbelow, an experiment for verifying the effects of the siRNA conjugates shown in Table 4F is illustrated.

Experimental Example F1 This experiment investigates the inhibitory activity in vitro of the siRNA conjugates of the present invention.

Experimental Example F1-1 On-target activity in in vitro psiCHECK system

In this experimental example, Conjugate F20 was investigated in in vitro psiCHECK system for on-target activity. Specifically, Conjugate F20 was tested for the activity of targeting completely matching target sequence (of which the nucleotide sequence is completely complementary with the full length nucleotide sequence of the antisense strand of the conjugate).

Figure 59:
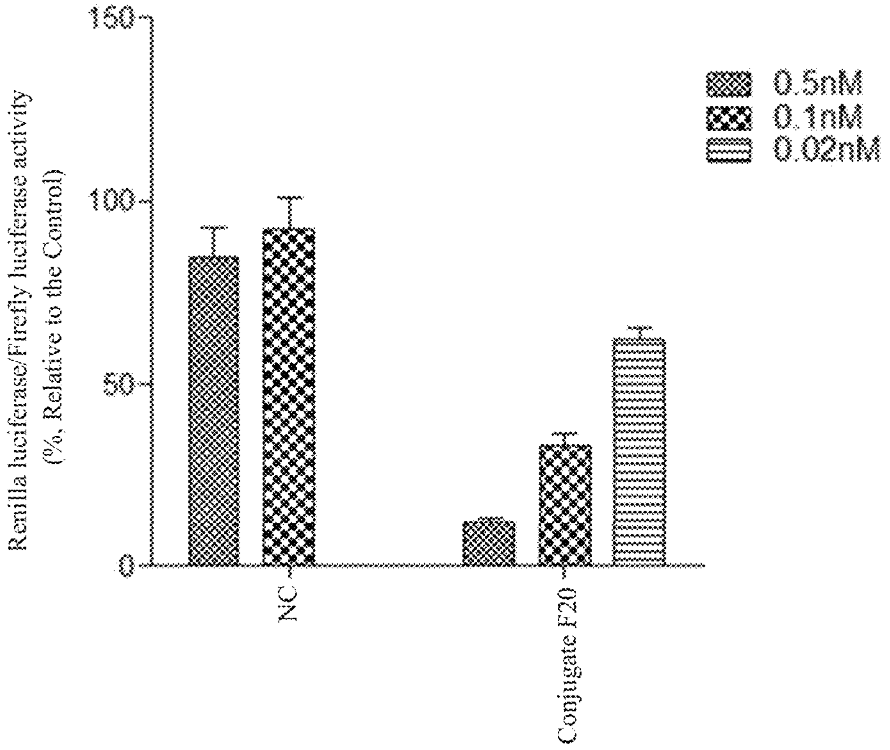
FIG. 59 shows inhibition percentage of the conjugates of the present disclosure against APOC3 expression in vitro.

Conjugate F20 was tested using the method as described in Experimental Example A1-6. The results are shown in FIG. 59, indicating that Conjugate F20 has good inhibitory activity in vitro.

Experimental Example F1-2 measurement of $IC_{50}$ in in vitro psiCHECK system

This experimental example investigates the $IC_{50}$ value of Conjugate F1 in in vitro psiCHECK system.

The on-target plasmid of Conjugate F1 was constructed using the same method as described in Experimental Example F1-1. The final concentration of Conjugate F1 (calculated based on the concentration of siRNA) was double diluted from 1 nM to 0.001 nM to give 11 concentrations. The dose-response curves were plotted by the activity results measured at different siRNA concentrations, and the curves were fitted using function log(inhibitor) vs. response-Variable slope of Graphpad 5.0 software. The $IC_{50}$ value of Conjugate F1 was calculated based on the dose-response curves with the formula below:

$$Y = \mathrm{Bot} + \frac{\mathrm{Top} - \mathrm{Bot}}{1 + 10^{(LogIC50 - X) \times HillSlope}}$$

wherein

Y is the expression level of remaining mRNA,

X is the logarithm of the concentration of transfected siRNA,

Bot is the Y value at the bottom of the steady stage,

Top is the Y value at the top of the steady stage,

Log $IC_{50}$ is the X value at which Y is median value between the bottom and the top of the steady stage, and HillSlope is the slope of the curve.

It was thus calculated that Conjugate F1 had an $IC_{50}$ value of 0.0174 nM in in vitro psiCHECK system, indicating that the siRNA conjugate of the present disclosure has higher activity in intro.

Experimental Example F1-3 measurement of IC50 in in vitro cell lines

In this experimental example, the inhibitory efficiency of Conjugate F2 against the expression level of APOC3 mRNA in in vitro Huh 7 cells was investigated.

Conjugate F2 was transfected to Human hepatoma cell lines Huh7 by using Lipofectamine™ 2000. The final concentration of siRNA conjugate was diluted 3-fold from 3 nM to 0.004 nM to give 7 concentrations, 2 replicate wells per concentration.

The expression levels of APOC3 mRNAs in Huh 7 cells transfected with Conjugate F2 at various concentrations were measured by PCR (Quantitative Real-Time PCR), respectively. Specific steps were as follows: 24 hours after cultivation of transfected cells, the total RNA was extracted and obtained by using Trizol (Thermo Fisher) according to the standard procedure for total RNA extraction; 1 μg of the total RNA was individually extracted and reverse transcribed into cDNA by using reverse transcription kit (Promega, Cat No. A3500) according to the instruction thereof. The expression level of APOC3 mRNA was detected based on the template cDNA according to the steps described in the instruction by using 2×Ultra SYBR Mixture (with ROX) (Beijing Cowin Biosciences Co., Ltd, Cat No. CW 0956). Therein, the PCR primers of j-actin for amplifying APOC3 and as an internal control gene are shown in Table 5F.

TABLE 5F

| Sequences of the primers for detection | | |
|---|---|---|
| Genes | Upstream Primers | Downstream Primers |
| Human APOC3 | 5'-GTGACCGATGGCT TCAGTTC-3' (SEQ ID NO: 445) | 5'-ATGGATAGGCAGGT GGACTT-3' (SEQ ID NO: 446) |
| Human β-actin | 5'-CCAACCGCGAGAA GATGA-3' (SEQ ID NO: 447) | 5'-CCAGAGGCGTACA GGGATAG-3' (SEQ ID NO: 448) |

The expression level of APOC3 mRNA was calculated by the following equation:

the expression level of APOC3 mRNA=[(the expression level of APOC3 mRNA in the test group/the expression level of β-actin mRNA in the test group)/(the expression level of APOC3 mRNA in the control group/the expression level of β-actin mRNA in the control group)]×100%.

Therein, Huh7 cells individually treated with Conjugate F2 at various concentrations were used in the test groups, and Huh 7 cells untreated with Conjugate F2 were used in the control group.

The $IC_{50}$ value was calculated by the same method as in Experimental Example F1-2 according to the measured inhibition percentages of Conjugate F2 at different concentrations against the expression level of APOC3 mRNA. The $IC_{50}$ value of Conjugate F2 in in vitro Huh7 cells was obtained to be 0.0085 nM, suggesting that the siRNA conjugate of the present disclosure has higher activity in intro.

Experimental Example F2 This experimental example illustrated the inhibitory efficiency of the siRNA conjugate of the present invention against the expression level of APOC3 mRNA in vivo.

Experimental Example F2-1 This experimental example investigated the inhibition percentage of Conjugate F1 against the expression level of APOC3 mRNA in liver tissue of human APOC3 transgenic mice in vivo.

Human APOC3 transgenic mice (B6; CBA-Tg(APOC3) 3707Bres/J) were randomly divided into groups based on TG content>2 mmol/L (5 mice in each group). Conjugate F1, Comparative Conjugate F1 and Normal saline (NS) were individually administered to the mice in each group. The drug dosages for all animals were calculated according to the body weight (single administration (subcutaneously), two administration dosage of 1 mg/kg and 0.1 mg/kg for the siRNA conjugates (calculated based on the amount of siRNA)). Each conjugate was administered at the concentrations of 0.2 mg/mL and 0.02 mg/mL in the form of 0.9 wt % NaCl aqueous solution and the administration volume of 5 mL/kg. The mice were sacrificed on day 14 after administration. The liver was collected and kept with RNA later (Sigma Aldrich), and the liver tissue was homogenized with a tissue homogenizer. Then the total RNA was extracted and obtained by using Trizol according to the standard procedure for total RNA extraction.

The expression level of APOC3 mRNA in liver tissue was measured by the real-time fluorescent qPCR method as described in Experimental Example F1-3. In this fluorescent qPCR method, β-actin gene was used as an internal control gene, the expression levels of APOC3 and β-actin were measured by using primers for APOC3 and β-actin, respectively.

The sequences of primers for detection are shown in Table 6F.

TABLE 6F

| Genes | Upstream Primers | Downstream Primers |
|---|---|---|
| Human APOC3 | 5'-GTGACCGATGG CTTCAGTTC-3' (SEQ ID NO: 449) | 5'-ATGGATAGGCAG GTGGACTT-3' (SEQ ID NO: 450) |
| Mouse β-actin | 5'-AGCTTCTTTGC AGCTCCTTCGTTG-3' (SEQ ID NO: 451) | 5'-TTCTGACCCATTC CCACCATCACA-3' (SEQ ID NO: 452) |

Figure 60:
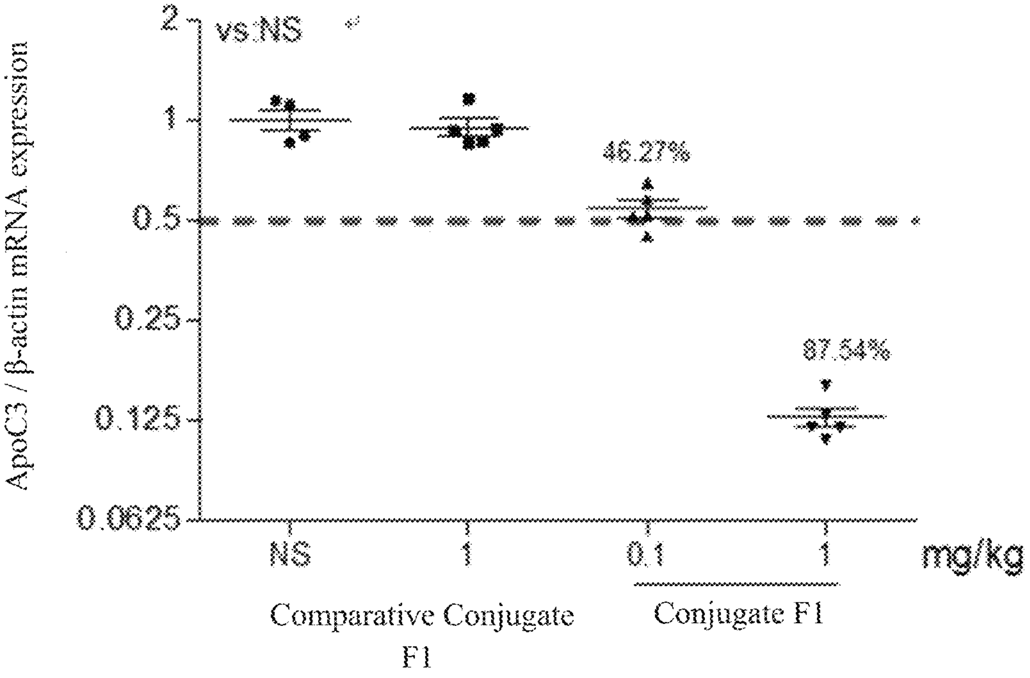
FIG. 60 shows inhibition percentage against APOC3 expression in liver tissue on day 14.

The inhibition percentage of the conjugate against APOC3 mRNA was calculated according to the equation:

the inhibition percentage=(the expression level of APOC3 mRNA in the test group/the expression level of β-actin mRNA in the test group)/(the expression level of APOC3 mRNA in the control group/the expression level of β-actin mRNA in the control group)×100%, wherein the control group was a group of control mice administered with NS in this experiment and each test group was a group of mice administered with different siRNA conjugates, respectively. The results were shown in FIG. 60.

The results indicated that Conjugate F1 showed inhibitory effect on human APOC3 gene in transgenic mice.

Experimental Example F2-2 This experimental example investigated the inhibition percentage of Conjugate F1 against the expression level of APOC3 mRNA in liver tissue of cynomolgus monkey in vivo, and the effect on blood lipid level.

CTI Biotechnology (Suzhou) Co., Ltd. was authorized to perform this experimental example. Cynomolgus monkeys (body weight: 2-4 kg, age: 3-5 years old) were randomly divided into two groups, one male and one female per group. Conjugate F1 and Comparative Conjugate F2 were administered individually. The drug dosages for all animals were calculated according to the body weight (single administration (subcutaneously), administration dosage of 3 mg/kg for the siRNA conjugates (calculated based on the amount of siRNA), in the form of 3 mg/ml in the form of NaCl solution for injection (Shandong Kelun Pharmaceutical Co., Ltd.), and administration volume of 1 mL/kg). The very day on which the first dose is administered is defined as Test Day 1 (D1), and one day before administration is defined as Day 0 (DO).

The blood samples were taken from the vein of the animals before administration and on day 7, 14, 21 and 28 after administration. The contents of the substances to be detected in serum were measured at each time point. The substances to be detected include blood lipids (total cholesterol (CHO) and triglyceride (TG)), and transaminases (glutamic pyruvic transaminase (ALT) and glutamic oxaloacetic transaminase (AST). The substances to be detected were normalized. The inhibition percentage of each substance to be detected was calculated by the equation:

the inhibition percentage=(1−the content of the substance to be detected in the test group after administration)/the content of the substance to be detected in the test group before administration)×100%, wherein the inhibition percentage against triglyceride (TG) is shown in Table 7F.

TABLE 7F

| | | Content of TG (mmol/L) | | | | | Inhibition percentage against TG (%) | | | |
|---|---|---|---|---|---|---|---|---|---|---|
| Conjugate | Time point | D0 | D7 | D14 | D21 | D28 | D7 | D14 | D21 | D28 |
| Conjugate 1 | Male M | 0.88 | 0.32 | 0.35 | 0.42 | 0.3 | 63.6 | 60.2 | 52.3 | 65.9 |
| | Female F | 0.75 | 0.31 | 0.4 | 0.52 | 0.23 | 58.7 | 46.7 | 30.7 | 69.3 |

Transaminase content was measured at each detection point after administration, and no abnormality on liver function was found.

The animals were sacrificed on day 28 after administration, and the liver was collected. No abnormalities were found in gross anatomy. RNA was extracted from liver tissue by the same method as that described in Experimental Example F2-1, and the expression level of APOC3 mRNA in liver was measured. The sequences of the primers for detection are shown in Table 8F.

TABLE 8F

| Genes | Upstream Primers | Downstream Primers |
|---|---|---|
| Monkey APOC3 | 5'-TTGAACCCTGA GGCCAAACC-3' (SEQ ID NO: 453) | 5'-CGGTAGGAGG GCACTGAGAA-3' (SEQ ID NO: 454) |
| Monkey GAPDH | 5'-GGGAGCCAAA AGGGTCATCA-3' (SEQ ID NO: 455) | 5'-CGTGGACTGTG GTCATGAGT-3' (SEQ ID NO: 456) |

The expression level of APOC3 mRNA can be measured by real-time fluorescent qPCR. Relative to the Comparative Conjugate F2, Conjugate F1 resulted in an inhibition percentage of 55.3% against APOC3 mRNA in the female animals and an inhibition percentage of 78.5% against APOC3 mRNA in the male animals.

This experiment indicated that Conjugate F1 also exhibited significantly inhibitory effect on APOC3 gene in non-human primate and showed significantly inhibitory effect on TG in serum, and at the same time no abnormalities on liver function were observed.

Experimental Example F3 This experiment investigated the effects of the siRNA conjugate of the present invention on blood lipid content in vivo.

Experimental Example F3-1 This experiment investigated the effects of Conjugate F1 on the contents of total cholesterol (CHO) and triglyceride (TG) in serum of human APOC3 transgenic mice in vivo.

Human APOC3 transgenic mice (B6; CBA-Tg(APOC3) 3707Bres/J) with TG content each being >2 mmol/L were randomly divided into groups (7 mice for each group): (1) NS control group; (2) Conjugate F1 3 mg/kg group; (3) Conjugate F1 1 mg/kg group. The drug dosages for all animals were calculated according to the body weight (single administration (subcutaneously), in form of 0.9 wt % NaCl aqueous solution containing 0.6 mg/ml and 0.2 mg/ml the siRNA conjugate, and administration volume of 5 mL/kg).

The blood was taken from mouse orbital venous plexus before administration (marked as day 0) and on days 7, 14, 21, 28, 35, 42, 49, 63, 77, 91, 112, 133, 147, 154, 161, 175 and 189 after administration respectively. The contents of total cholesterol (CHO) and triglyceride (TG) in serum were measured at each time point.

About 100 μl orbital blood was taken each time, and the serum was no less than 20 μl after centrifugation. The contents of total cholesterol (CHO) and triglyceride (TG) in serum were further measured by using a PM1P000/3 full-automatic serum biochemical analyzer (SABA, Italy).

The normalized blood lipid level=(the blood lipid content in the test group after administration/the blood lipid content in the test group before administration)×100%.

The inhibition percentage against blood lipid level=(1−the blood lipid content in the test group after administration/the blood lipid content in the test group before administration)×100%. Blood lipid refers to total cholesterol (CHO) or triglyceride (TG).

Figure 61A:
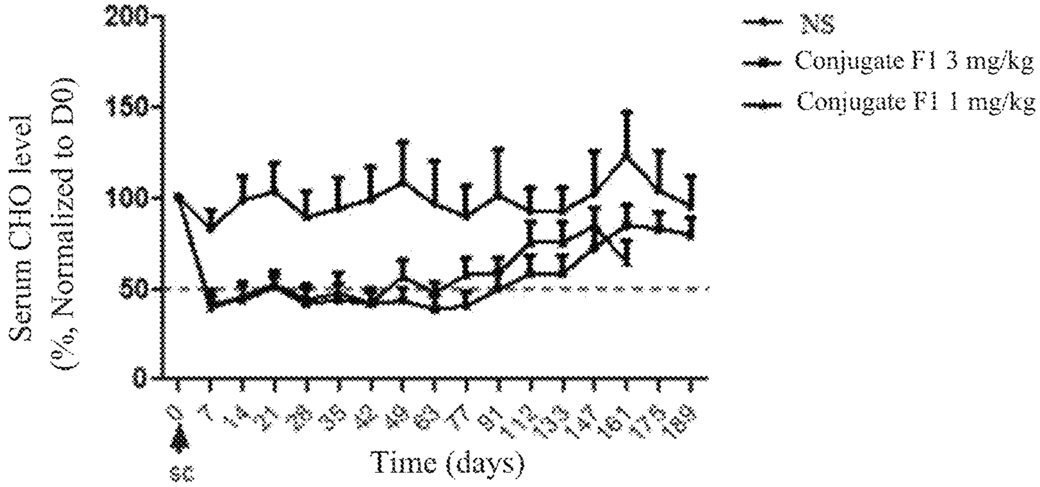
FIGS. 61A and 61B show inhibition percentages over time of the conjugates of the present disclosure against blood lipid, represented by total cholesterol (CHO) and triglyceride (TG) in serum.
Figure 61B:
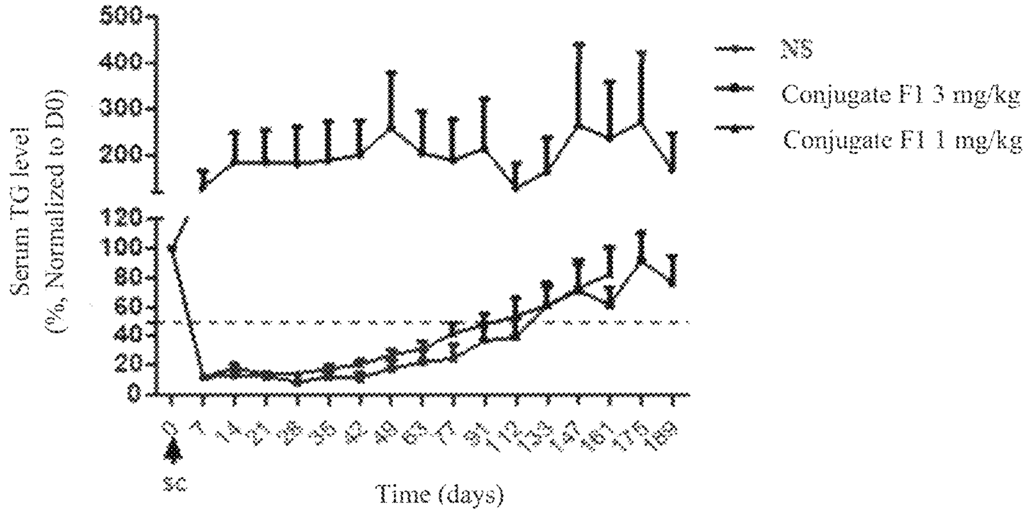

The measured results are shown in FIGS. 61A and 61B.

As can be seen from FIGS. 61A and 61B, Conjugate F1 showed the effect of significantly reducing the contents of TG and CHO in mouse serum at different time points after administration over a period of up to 189 days, indicating that the conjugate has stable and effective inhibition against the expression of APOC3 gene over a longer time period.

Experimental Example F3-2 This experimental example investigated the effects of Conjugate F2 on the contents of total cholesterol (CHO) and triglyceride (TG) in human APOC3 transgenic mice serum in vivo.

Detection was performed according to the same method as described in Experimental Example F3-1, except that: 8 mice for each group, the conjugate to be administered was Conjugate F2; five doses (0.1, 0.3, 1, 3 and 9 mg/kg) were individually administered; the administration volume remained unchanged and thus the concentration of conjugate solution was corresponding adjusted; the test continued until day 112. The results are shown in FIGS. 62A and 62B.

Figure 62A:
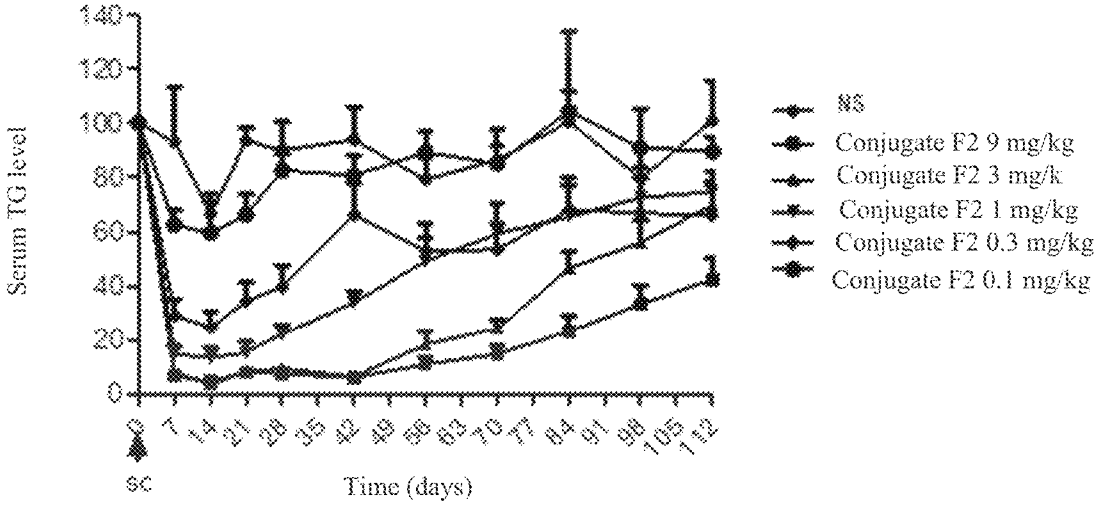
FIGS. 62A and 62B show inhibition percentages over time of the conjugates of the present disclosure against blood lipid, represented by total cholesterol (CHO) and triglyceride (TG) in serum.
Figure 62B:
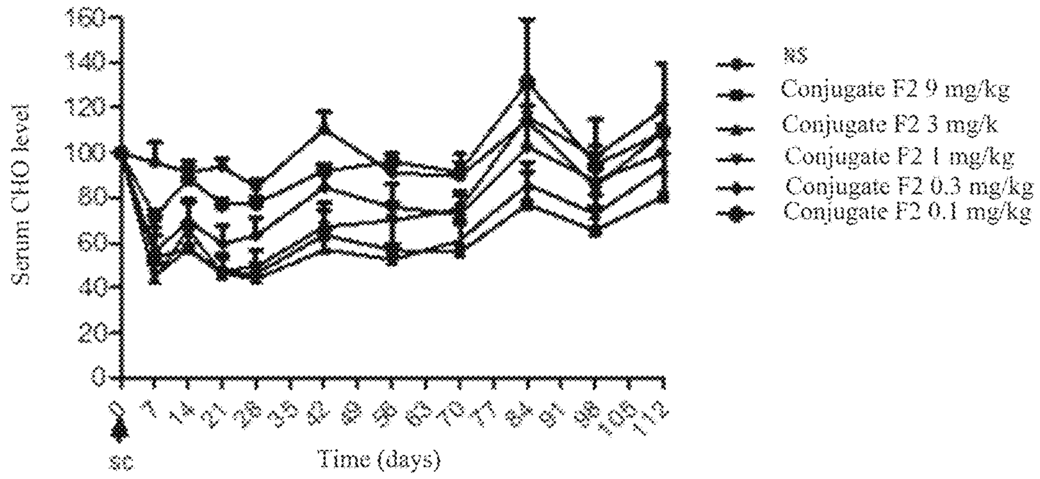
Figure 63A:
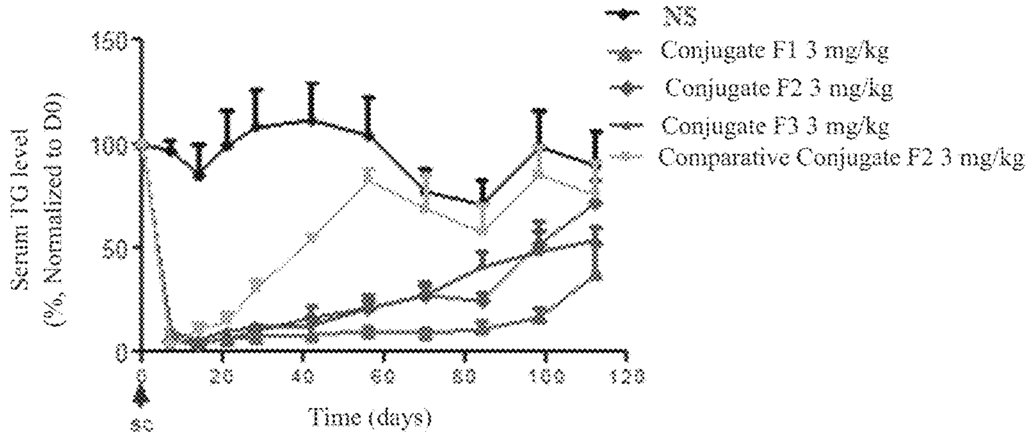
FIGS. 63A-63D show inhibition percentages over time of the conjugates of the present disclosure at different dosages against blood lipid, represented by total cholesterol (CHO) and triglyceride (TG) in serum.
Figure 63B:
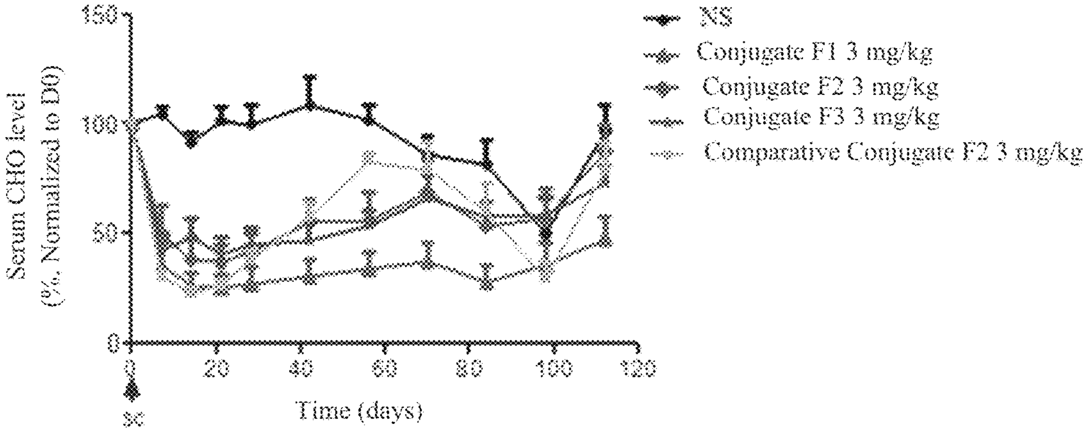
Figure 63C:
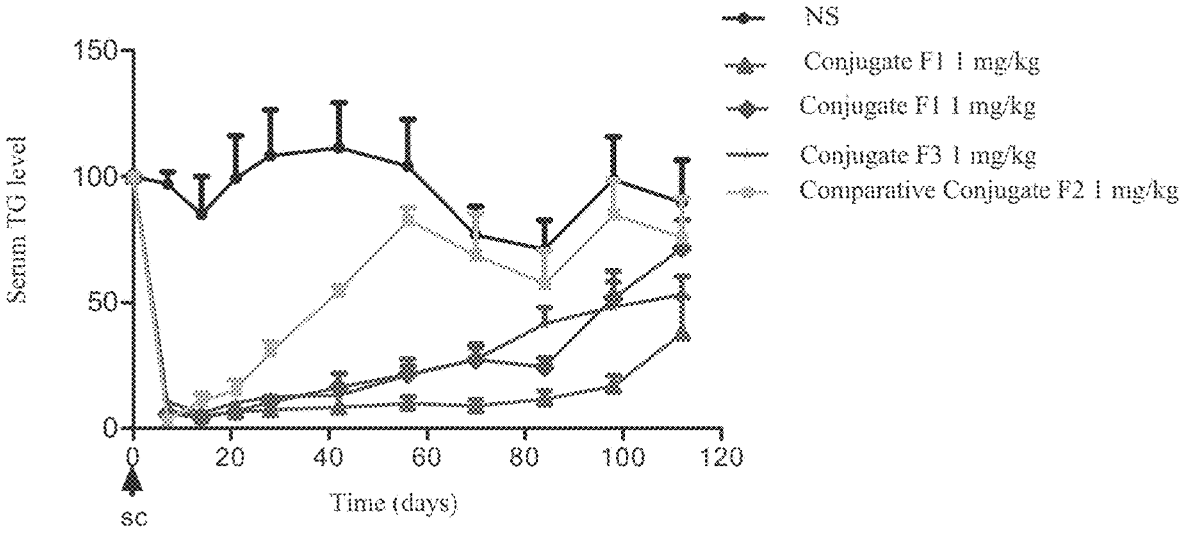
Figure 63D:
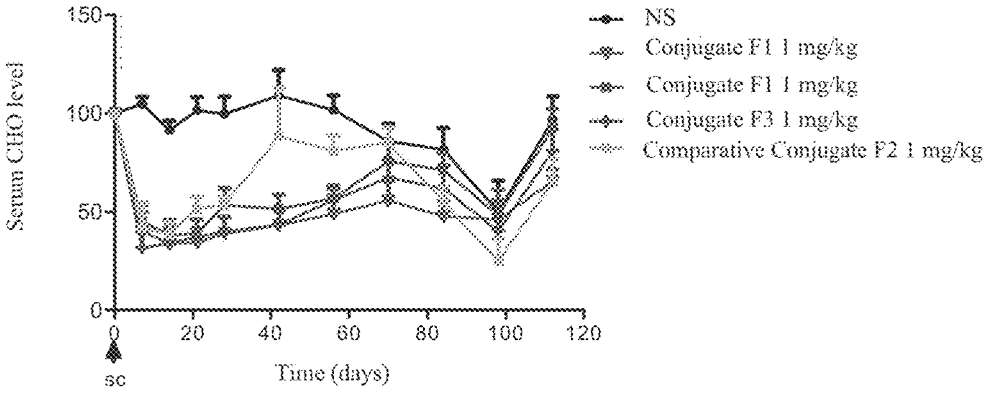

As can be seen from the results of FIGS. 62A and 62B, Conjugate F2 significantly reduced the contents of TG and CHO in transgenic mice over a period of up to 112 days, and there was obvious dose-dependent response in the reduction effect.

Experimental Example F3-3 This experimental example compared the effects of Conjugates F1-F3 on the contents of total cholesterol (CHO) and triglyceride (TG) in human APOC3 transgenic mice serum in vivo.

The contents of total cholesterol (CHO) and triglyceride (TG) in mouse serum were measured using the same method as that in Experimental Example F3-1, except that: 6 mice for each group, Conjugates F1, F2 and F3 and Comparative Conjugate F2 were individually administered; two doses (1 mg/kg and 3 mg/kg) were administered for each conjugate; the administration volume remained unchanged and thus the concentration of conjugate solution was correspondingly adjusted; the test continued until day 112. The results are shown in FIGS. 63A-63D.

As can be seen from the results of FIGS. 63A-63D, the Conjugates F1-F3 of the present disclosure at different doses showed the effect of consistently reducing the blood lipid level in the transgenic mice in up to 112 days, and this reduction effect as a whole was superior to that of Comparative Conjugate F2.

The above results indicated that the conjugates provided by the present invention effectively inhibited the expression of APOC3 mRNA in liver and reduced the content of total cholesterol or triglyceride in blood, and thus can prevent and/or treat blood lipid abnormalities and have good clinical application prospect.

Hereinbelow, an experiment for verifying the effects of the siRNA conjugates shown in Table 4G was illustrated.

Experimental Example G1 This experimental example indicated that the siRNA conjugate of the present disclosure not only has higher activity in vitro, but also shows low off-target effect.

HEK293A cells used in this experimental example were provided by Nucleic Acid Technology Laboratory, Institute of Molecular Medicine, Peking University, and cultured in DMEM complete media (Hyclone company) containing 20% fetal bovine serum (FBS, Hyclone company), 0.2 v % Penicillin-Streptomycin (Gibco, Invitrogen company) at 37° C. in an incubator containing 5% $CO_2$/95% air.

In this experimental example, Conjugate G2 was investigated in in vitro psiCHECK system for the on-target activity and off-target effect. Specifically, Conjugate G2 was tested for the activity of targeting completely matching target sequence (of which the nucleotide sequence is completely complementary with the full length nucleotide sequence of the sense/antisense strand of Conjugate G2) or targeting seed region matching target sequence (of which the nucleotide sequence is complementary with the nucleotide sequence of positions 1-8 of the sense/antisense strand of Conjugate G2).

Conjugate G2 was tested according to the method described in Experimental Example A1-6, except that four target sequences were constructed based on the sequences of Conjugate G2. For the on-target plasmid GSCM, the final concentration of Conjugate G2 (calculated based on the concentration of siRNA) was double diluted from 1 nM to 0.000977 nM to give 11 concentrations; and for the other 3 off-target plasmids, the final concentration of Conjugate G2 was 4-fold diluted from 10 nM to 0.000038 nM to give 10 concentrations.

For GSCM, the $IC_{50}$ value of Conjugate G2 was 0.0513 nM ($R^2$=0.9911); for PSCM, GSSM, and PSSM, Conjugate G2 showed no obvious inhibitory effect at each siRNA concentration, indicating that the siRNA conjugate of the present disclosure not only has higher activity in vitro, but also shows low off-target effect.

Experimental Example G2 This experimental example illustrated stability of the siRNA conjugates of the present disclosure in the lysosome lysate in vitro.

1) Detection of the Stability in Murine Lysosome Lysate

Preparation of test samples treated with the lysosome lysate: 6 μl each of Conjugate G2 and Comparative siRNA1 (20 μM) were individually mixed well with 27.2 μL of sodium citrate aqueous solution (pH 5.0), 4.08 μL of deionized water and 2.72 μL of murine lysosome lysate (Rat Liver Tritosomes, purchased from Xenotech Inc., Cat No. R0610.LT, Lot No. 1610069, at a final concentration of acid phosphatase of 0.2 mU/μL), and incubated at a constant temperature of 37° C. 5 μL mixed solutions were taken at each time point of 0 h, 1 h, 2 h, 4 h, 6 h, and 24 h, respectively, added to 15 μL of 9 M urea aqueous solution for denaturation, and added with 4 μL of 6×loading buffer (purchased from Solarbio Inc., Cat No. 20160830), then immediately cryopreserved in a −80° C. freezer to quench the reaction. 0 h represents the moment when the sample was taken immediately after the samples to be tested are mixed well with the lysosome lysate.

Preparation of control samples untreated with the lysosome lysate: 1.5 μL each of the Conjugate G2 and Comparative siRNA1 (20 μM) at equal moles was mixed well with 7.5 μL of sodium citrate aqueous solution (pH 5.0) and 1 μL of deionized water, added to 30 μL of 9 M urea solution for denaturation, and added with 8 μL of 6×loading buffer, then immediately cryopreserved in a −80° C. freezer to quench the reaction. The control sample for each conjugate is marked as M to be compared with the electrophoresis results of the sample.

16 wt % of non-denatured polyacrylamide gel was prepared. 20 μL each of the test sample and the control sample described above was loaded onto the gel to perform electrophoresis for 10 minutes under 20 mA constant current and then for 30 minutes under 40 mA constant current. After finishing the electrophoresis, the gel was placed on a shaker and stained with Gelred dye (BioTium, Cat No. 13G1203) for 10 minutes. The gel was subjected to imaging, observation and photocopying. The results are shown in FIG. 64.

2) Detection of the Stability in Human-Origined Lysosome Lysate

The stability of Comparative siRNA1 and Conjugate G2 in the human lysosome lysate was measured using the same method as in 1), except that the murine lysosome lysate was replaced with the human lysosome lysate (Human Liver Lysosomes, purchased from Xenotech Inc., Cat No. R0610.L, Lot No. 1610316). The results are shown in FIG. 65.

Figure 64:
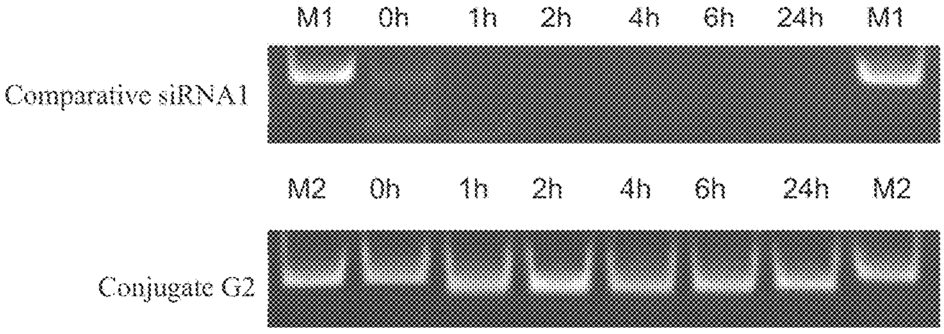
FIGS. 64-65 show the results of the stability tests of the conjugates of the present disclosure in vitro.
Figure 65:
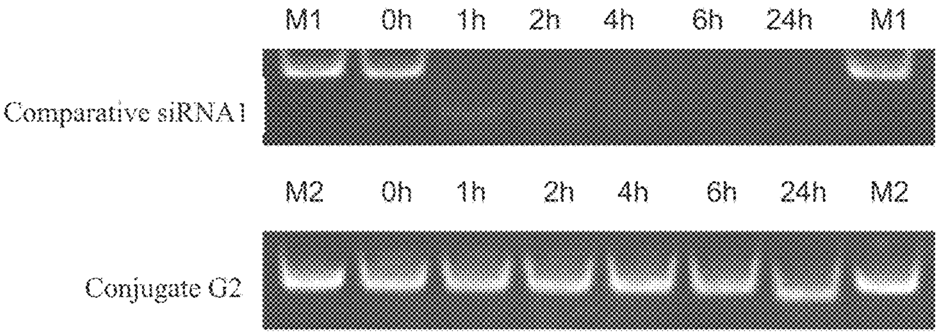

The results of FIGS. 64 and 65 indicated that the siRNA conjugates of the present disclosure can remain undegraded for at least 24 hours either in human lysosome lysate or murine lysosome lysate, showing satisfactory stability.

Experimental Example G3 This experimental example illustrated the inhibitory efficiency of the siRNA conjugates of the present disclosure against the expression level of HBV mRNA in HBV model mice.

1) In this experimental example, the inhibition efficiency of Conjugates G1 and G2 against the expression level of HBV mRNA in HBV model mice C57BL/6J-Tg(A1b1HBV) 44Bri/J was investigated.

The C57BL/6J-Tg (A1b1HBV) 44Bri/J mice used herein were purchased from Department of Laboratory Animal Science, Peking University Health Science Center. Conjugate G2 was formulated with 0.9% NaCl aqueous solution into a solution with a concentration of 0.2 mg/ml (calculated based on the concentration of siRNA); and Conjugate 1 was formulated with 0.9% NaCl aqueous solution into solutions with the concentrations of 0.2 mg/ml and 0.06 mg/ml (calculated based on the concentration of siRNA).

HBsAg content in mouse serum was measured using Hepatitis B Virus Surface Antigen Assay Kit (Enzyme-linked Immunosorbent Assay, ELISA) (Shanghai Kehua Bio-engineering Co., Ltd.). Mice with S/COV>10 were selected and randomly divided into two groups (all female, 6 mice in each group) and respectively numbered as the control group and the test group. Each group of the animals was administered subcutaneously with the respective drugs on day 1 in the volume of 5 mL/kg. The drug dosages for all animals were calculated according to the body weight. Therein, mice in the control group were administered with normal saline; and mice in the test group were administered with Conjugate G2, with the administration dose being 1 mg/kg. All the animals were sacrificed on day 28 after administration, and were subjected to gross anatomy to observe whether the organs in the body were diseased. The diseased tissues by visual observation were kept in 10% formalin for further pathological observation. The liver was collected and kept with RNA later (Sigma Aldrich), the liver tissue was homogenized with a tissue homogenizer, and then total RNAs were extracted and obtained by using Trizol according to the standard procedure for total RNA extraction.

The expression level of HBV mRNA in liver tissue was measured by real-time fluorescent qPCR. Specifically, the extracted total RNA was reverse transcribed into cDNA by using ImProm-II™ reverse transcription kit (Promega) according to the instruction, and then the inhibitory efficiency of siRNAs against the expression of HBV mRNA in liver tissue was measured by using the fluorescent qPCR kit (Beijing Cowin Biosicences Co., Ltd). In this fluorescent qPCR method, β-actin gene was used as an internal control gene, the HBV and β-actin were detected by using primers for HBV and β-actin, respectively.

Sequences of primers for detection are shown in Table 5A.

In this fluorescent qPCR method, the inhibitory activity of siRNA was expressed as the inhibition percentage against HBV mRNA and calculated by the equation:

the inhibition percentage against *HBV* mRNA=(1−the remaining expression of *HBV* gene)×100%;

The remaining expression of HBV gene=(the copy number of HBV gene in the test group/the copy number of β-actin gene in the test group)/(the copy number of HBV gene in the control group/the copy number of β-actin gene in the control group)×100%.

The results are shown in Table 6G below.

The inhibitory efficiency in vivo of Conjugate 1 at different doses (n=5) against the expression level of HBV mRNA was detected using the same method. The results are shown in Table 6G below.

TABLE 6G

| siRNA Conjugate | NO. | Dose (mg/kg) | Inhibition percentage against HBV P mRNA in liver (%) |
|---|---|---|---|
| Conjugate G2 | L10-siHB3M1SP | 1 | 77.41 |
| Conjugate G1 | L10-siHB3M1SVP | 1 | 88.27 |
| Conjugate G1 | L10-siHB3M1SVP | 0.3 | 57.95 |

As can be seen from the results shown above, all conjugates of the present disclosure showed high inhibitory activity against HBV mRNA in mice in vivo, indicating good in vivo delivery efficiency of the siRNA conjugates of the present disclosure.

2) The inhibitory efficiency in vivo of Conjugates G3-G20 against HBV mRNA was detected using the same method as in 1). It can be expected that Conjugates G3-G20 also exhibit higher inhibitory activity against HBV mRNA.

Experimental Example G4 This experiment illustrated a test about the relationship between time and the inhibitory efficiency of the siRNA conjugates of the present disclosure against the expression levels of HBsAg, HBeAg and HBV DNA in HBV model mice serum.

HBV model mice C57B/6N-Tg (1.28 HBV)/Vst (genotype A) used in this experimental example was purchased from Beijing Vitalstar Biotechnology Co., Ltd. Conjugate G1 was formulated with 0.9% NaCl aqueous solution into solutions with the concentrations of 0.6 mg/ml and 0.2 mg/ml (calculated based on the concentration of siRNA).

The mice with HBsAg content in serum $>10^4$ COI (half female, half male) were selected and randomly divided into three groups (6 mice in each group), which are respectively numbered as the control group, the high-dose group and the low-dose group. The drugs were individually administered subcutaneously to the mice in each group on day 1, with the administration volume being 5 mL/kg. The drug dosages for all animals were calculated according to the body weight.

All the animals were administered before noon. If it is necessary to take the blood, the administration would be conducted after the blood have been taken. Therein, the mice in the control group were injected with normal saline; and the mice in the test groups were injected with different doses of Conjugate G1: 3 mg/kg for the high-dose group and 1 mg/kg for the low-dose group. The blood was taken from mouse orbital venous plexus before administration and on days 7, 13, 21, 28, 42, 56, 70, 84, 98, 112, 126, 140, and 154 after administration, and HBsAg, HBeAg and HBV DNA levels in serum were measured for each time point.

About 100 μl orbital blood was taken each time; and the serum was no less than 20 μl after centrifugation, resuspended with PBS to 500 μl and delivered to Clinical Laboratory Center of Beijing DIAN Diagnostics to measure the contents of HBsAg, HBeAg and HBV DNA in serum, which were expressed in COI, COI and IU/m1, respectively.

The normalized levels of the indicators to be measured (HBeAg, HBeAg and HBV DNA) were calculated according to the equation: the normalized level of the indicator to be measured=(the remaining content of the indicator to be measured after administration/the content of the indicator to be measured before administration)×100%.

The inhibition percentage of the indicator to be measured=(1−the normalized level of the indicator to be measured)×100%.

The experimental data are expressed as $\overline{X}$±SEM, and the data are analyzed with Graphpad prism 5.0 statistical analysis software. The data are initially tested for normal distribution and homogeneity of variance. If the data meet normal distribution ($p>0.2$) and homogeneity of variance ($p>0.10$), then comparison among groups would be performed by LSD method using single-factor analysis of variance for multiple comparisons. $P<0.05$ is considered as being statistically significant. If the data fail to meet normal distribution and homogeneity of variance, comparison among groups would be performed by Krushkal-Wallis H method for Non-parametric Test. If the results obtained by Krushkal-Wallis H test are statistically significant ($p<0.05$), pairwise comparisons among multiple groups would be conducted after rank transformation. $P<0.05$ is considered to be statistically significant.

Figure 66:
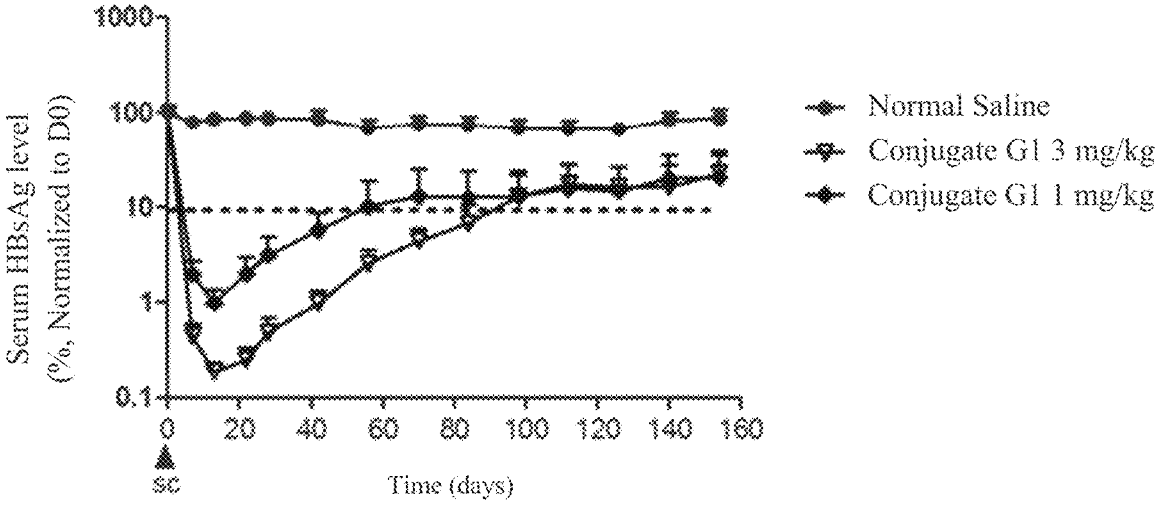
FIGS. 66-68 show inhibition percentages over time of the conjugates of the present disclosure at different dosages against serum surface antigen, serum e antigen and HBV DNA.
Figure 67:
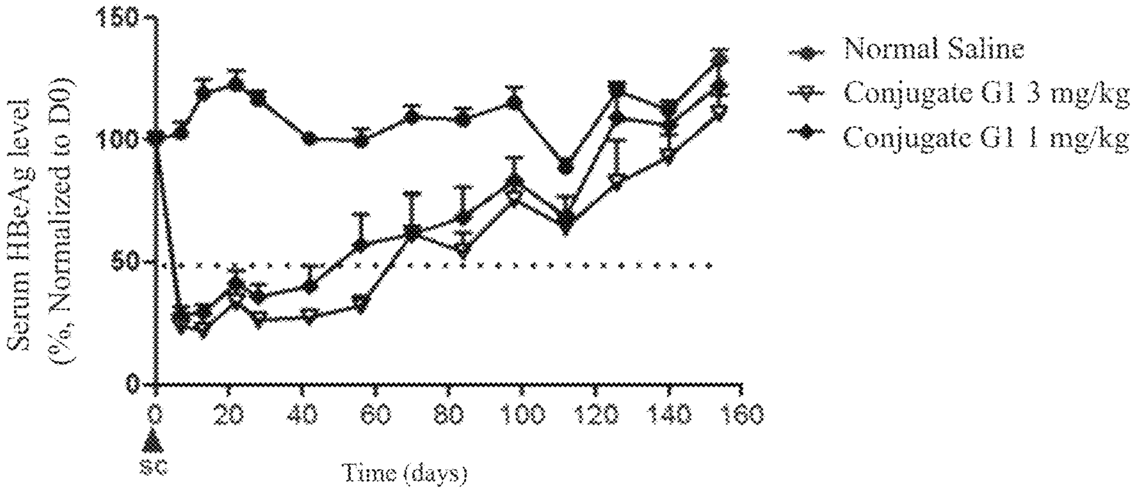
Figure 68:
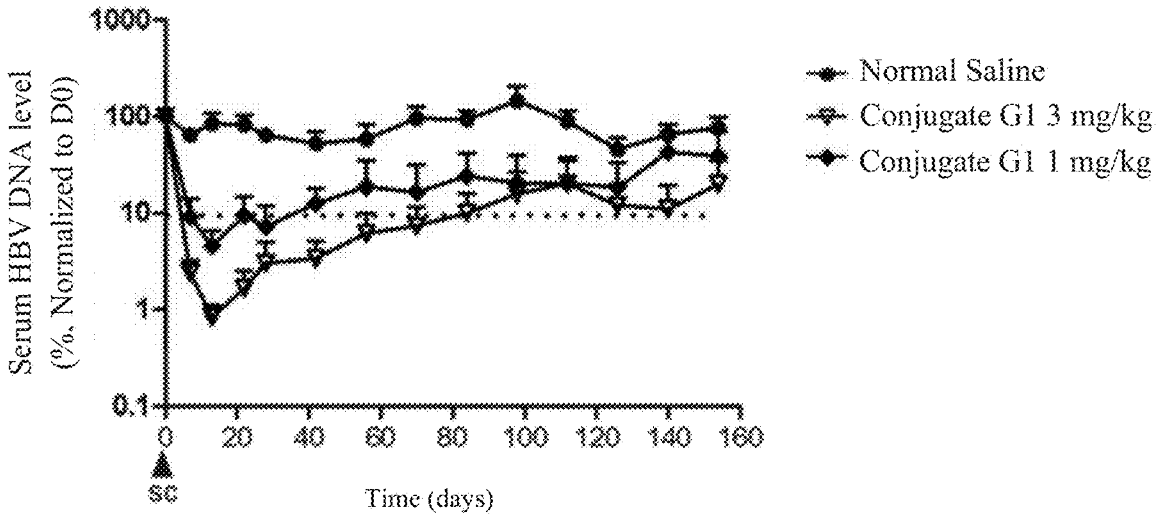

The results are shown in FIGS. 66-68.

As can be seen from FIG. 66, the negative control group administered with normal saline showed no inhibitory effect on HBsAg at different time points after administration. In contrast, Conjugate G1 at the two doses both showed excellent inhibitory effects on HBsAg at different time points after administration. For the high dose group, the maximum inhibitory percentage against HBsAg was up to 99.8% on day 13 after single administration; the inhibitory percentage against HBsAg was still maintained at 90% or higher over a period of up to 84 days after administration; and until the end of the observation, the inhibitory percentage against HBsAg was still up to 80.1%. For the low dose group, the maximum inhibitory percentage against HBsAg was 99.0% on day 13 after administration; until the end of the observation on day 154, the inhibitory percentage against HBsAg was still up to 60.8%.

As can be seen from FIG. 67, Conjugate G1 likewise inhibited the expression of HBeAg, wherein the high-dose group showed an inhibition percentage of about 50% against HBeAg in serum on day 70 after administration; and until the end of the observation on day 154, the inhibitory efficiency against HBeAg was rebound to the level before administration.

As can be seen from FIG. 68, Conjugate G1 further efficiently inhibited the expression of HBV DNA and maintained higher inhibit ratio over an observation period of up to 154 days. The high-dose group showed the maximum inhibition percentage of up to 99.2% against HBV DNA on day 13 after single administration; the inhibitory percentage against HBV DNA was still maintained at 90% or higher over a period of up to 84 days after administration; and until the end of the observation, the inhibitory percentage against HBV DNA was still up to 77.0%. The low-dose group showed the maximum inhibitory percentage against HBV DNA of up to 95.4% on day 13 after administration; until the end of the observation on day 154, the inhibitory percentage against HBV DNA was still up to 79.4%.

The results described above indicated that the conjugates of the present disclosure showed stable and effective inhibition against the expression of HBV gene over a longer time period, and in particular exhibited long-time and effective inhibition against surface antigen, showing excellent effects.

Embodiments of the present disclosure are described above in detail, but the present disclosure is not limited to the specific details of the above-described embodiments. Various simple variations of the technical solution of the present disclosure can be made within the scope of the technical concept of the present disclosure, and these simple variations are within the scope of the present disclosure.

It is to be noted that each of the specific technical features described in the above embodiments can be combined in any suitable manner as long as no contradiction is caused. In order to avoid unnecessary repetition, the various possible combination manners are no longer described in the present disclosure.

In addition, the various different embodiments of the present disclosure may also be carried out in any combination as long as it does not contravene the idea of the present disclosure, which should also be regarded as the disclosure of the present disclosure.

The invention claimed is:

1. A double-stranded oligonucleotide, which comprises a sense strand and an antisense strand, each nucleotide in the sense strand and antisense strand being a modified nucleotide, wherein the sense strand comprises a nucleotide sequence 1, and the antisense strand comprises a nucleotide sequence 2; the nucleotide sequence 1 and the nucleotide sequence 2 are both 19 nucleotides in length and are at least partly reverse complementary to form a double-stranded region; the nucleotide sequence 2 is at least partly reverse complementary to a first nucleotide sequence segment, which refers to a segment of nucleotide sequence in a target mRNA; in the direction from 5' terminal to 3' terminal, the nucleotides at positions 7, 8 and 9 of the nucleotide sequence 1 are fluoro modified nucleotides, and each of the nucleotides at the other positions in the nucleotide sequence 1 is independently a non-fluoro modified nucleotide; the first nucleotide at 5' terminal of the nucleotide sequence 2 is the first nucleotide at 5' terminal of the antisense strand, the nucleotides at positions 2, 6, 14 and 16 of the nucleotide sequence 2 are fluoro modified nucleotides, and each of the nucleotides at the other positions in the nucleotide sequence 2 is independently a non-fluoro modified nucleotide, wherein in the double-stranded oligonucleotide, at least one phosphate group is a phosphorothioate, and the phosphorothioate linkage exists in at least one of the following positions:

the position between the first and second nucleotides at 5' terminal of the sense strand;

the position between the second and third nucleotides at 5' terminal of the sense strand;

the position between the first and second nucleotides at 3' terminal of the sense strand;

the position between the second and third nucleotides at 3' terminal of the sense strand;

the position between the first and second nucleotides at 5' terminal of the antisense strand;

the position between the second and third nucleotides at 5' terminal of the antisense strand;

the position between the first and second nucleotides at 3' terminal of the antisense strand; and the position between the second and third nucleotides at 3' terminal of the antisense strand;

wherein the double-stranded oligonucleotide is an saRNA or an siRNA.

2. The double-stranded oligonucleotide according to claim 1, wherein in the direction from 5' terminal to 3' terminal, at least the nucleotides at positions 2-19 of the nucleotide sequence 2 are complementary to the first nucleotide sequence segment, or wherein in the direction from 5' terminal to 3' terminal, the nucleotide at position 1 of the nucleotide sequence 2 is A or U.

3. The double-stranded oligonucleotide according to claim 1, wherein the sense strand further comprises nucleotide sequence 3, and the antisense strand further comprises nucleotide sequence 4; each nucleotide in the nucleotide sequence 3 and the nucleotide sequence 4 is independently a non-fluoro modified nucleotide; the nucleotide sequence 3 and the nucleotide sequence 4 are respectively 1-4 nucleotides in length; the nucleotide sequence 3 and the nucleotide sequence 4 have equal length and are substantially reverse complementary or completely reverse complementary to each other; the nucleotide sequence 3 is linked to the 5' terminal of the nucleotide sequence 1; and the nucleotide sequence 4 is linked to the 3' terminal of the nucleotide sequence 2; the nucleotide sequence 4 is substantially reverse complementary, or completely reverse complementary to a second nucleotide sequence segment, which refers to a nucleotide sequence that is adjacent to the first nucleotide sequence segment in the target mRNA and has the same length as the nucleotide sequence 4.

4. The double-stranded oligonucleotide according to claim 1, wherein the double-stranded oligonucleotide also comprises a nucleotide sequence 5; each nucleotide in the nucleotide sequence 5 is independently a non-fluoro modified nucleotide; the nucleotide sequence 5 is 1-3 nucleotides in length and is linked to 3' terminal of the antisense strand, thereby forming a 3' overhang of the antisense strand.

5. The double-stranded oligonucleotide according to claim 4, wherein the nucleotide sequence 5 is 2 nucleotides in length; and in the direction from 5' terminal to 3' terminal, the nucleotide sequence 5 is 2 consecutive thymidine deoxynucleotides or 2 consecutive uridine nucleotides, or is completely reverse complementary to a third nucleotide sequence segment, which refers to a nucleotide sequence that is adjacent to the first or second nucleotide sequence segment in the target mRNA and has the same length as the nucleotide sequence 5.

6. The double-stranded oligonucleotide according to claim 1, wherein each non-fluoro modified nucleotide is a methoxy modified nucleotide, wherein the methoxy modified nucleotide refers to a nucleotide formed by substituting the 2'-hydroxy of the ribose group of the nucleotide with a methoxy group.

7. The double-stranded oligonucleotide according to claim 1, wherein the nucleotide at 5'-terminal of the antisense strand is a 5'-phosphate nucleotide or a 5'-phosphate analogue modified nucleotide.

8. The double-stranded oligonucleotide according to claim 1, wherein the target mRNA is one of the mRNAs corresponding to the following genes: ApoB, ApoC, ANGPTL3, PCSK9, SCD1, TIMP-1, Col1A1, FVII, STAT3, p53, HBV, and HCV.

9. The double-stranded oligonucleotide according to claim 8, wherein, the nucleotide sequence 1 is a sequence shown by SEQ ID NO: 1, and the nucleotide sequence 2 is a sequence shown by SEQ ID NO: 2; or the nucleotide sequence 1 is a sequence shown by SEQ ID NO: 3, and the nucleotide sequence 2 is a sequence shown by SEQ ID NO: 4; or the nucleotide sequence 1 is a sequence shown by SEQ ID NO: 5, and the nucleotide sequence 2 is a sequence shown by SEQ ID NO: 6; or the nucleotide sequence 1 is a sequence shown by SEQ ID NO: 7, and the nucleotide sequence 2 is a sequence shown by SEQ ID NO: 8; or the nucleotide sequence 1 is a sequence shown by SEQ ID NO: 9, and the nucleotide sequence 2 is a sequence shown by SEQ ID NO: 10; or the nucleotide sequence 1 is a sequence shown by SEQ ID NO: 11, and the nucleotide sequence 2 is a sequence shown by SEQ ID NO: 12; or the nucleotide sequence 1 is a sequence shown by SEQ ID NO: 13, and the nucleotide sequence 2 is a sequence shown by SEQ ID NO: 14;

(SEQ ID NO: 1)
5'-CmCmUmUmGmAmGfGfCfAmUmAmCmUmUmCmAmAmAm-3'

(SEQ ID NO: 2)
5'-UmUfUmGmAmAfGmUmAmUmGmCmCmUfCmAfAmGmGm-3'

-continued (SFQ ID NO: 3)
5'-UmGmCmUmAmUmGfCfCfUmCmAmUmCmUmUmCmUmAm-3'

(SEQ ID NO: 4)
5'-UmAfGmAmAmGfAmUmGmAmGmGmCmAfUmAfGmCmAm-3'

(SEQ ID NO: 5)
5'-UmCmUmGmUmGmCfCfUfUmCmUmCmAmUmCmUmGmAm-3'

(SEQ ID NO: 6)
5'-UmCfAmGmAmUfGmAmGmAmAmGmGmCfAmCfAmGmAm-3'

(SEQ ID NO: 7)
5'-CmGmUmGmUmGmCfAfCfUmUmCmGmCmUmUmCmAmAm-3'

(SEQ ID NO: 8)
5'-UmUfGmAmAmGfCmGmAmAmGmUmGmCfAmCfAmCmGm-3'

(SEQ ID NO: 9)
5'-GmAmAmAmGmUmAfUfGfUmCmAmAmCmGmAmAmUmAm-3'

(SEQ ID NO: 10)
5'-UmAfUmUmCmGfUmUmGmAmCmAmUmAfCmUfUmUmCm-3'

(SEQ ID No: 11)
5'-CmCmAmAmGmAmGfCfAfCmCmAmAmGmAmAmCmUmAm-3'

(SEQ ID No: 12)
5'-UmAfGmUmUmCfUmUmGmGmUmGmCmUfCmUfUmGmGm-3'

(SEQ ID No: 13)
5'-CmAmAmUmAmAmAfGfCfUmGmGmAmCmAmAmGmAmAm-3'

(SEQ ID No: 14)
5'-UmUfCmUmUmGfUmCmCmAmGmCmUmUfUmAfUmUmGm-3' wherein C, G, U, and A represent the base components of the nucleotides; m represents that the nucleotide adjacent to the left side of the letter m is a 2'-methoxy modified nucleotide; f represents that the nucleotide adjacent to the left side of the letter f is a 2'-fluoro modified nucleotide.

10. A pharmaceutical composition, wherein the pharmaceutical composition comprises the double-stranded oligonucleotide according to claim 1 and a pharmaceutically acceptable carrier.

11. An oligonucleotide conjugate, comprising the double-stranded oligonucleotide according to claim 1 and a conjugation group conjugated to the double-stranded oligonucleotide.

12. The oligonucleotide conjugate according to claim 11, wherein the oligonucleotide conjugate has a structure as shown by Formula (308):

Formula (308)

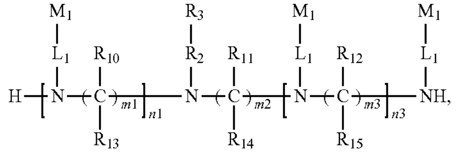

wherein n1 is an integer of 1-3, and n3 is an integer of 0-4;

m1, m2, and m3 independently of one another are an integer of 2-10;

$R_{10}$, $R_{11}$, $R_{12}$, $R_{13}$, $R_{14}$, and $R_{15}$ independently of one another are H, or selected from the group consisting of $C_1$-$C_{10}$ alkyl, $C_1$-$C_{10}$ haloalkyl and $C_1$-$C_{10}$ alkoxy;

$R_3$ is a group having a structure as shown by Formula (A59):

Formula (A59)

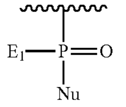

wherein, $E_1$ is OH, SH or $BH_2$;

Nu is a double-stranded oligonucleotide;

$R_2$ is a linear alkylene of 1 to 20 carbon atoms in length, wherein one or more carbon atoms are optionally replaced with one or more groups selected from the group consisting of: C(O), NH, O, S, CH=N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $R_2$ optionally has one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —$OC_1$-$C_{10}$ alkyl, —$OC_1$-$C_{10}$ alkylphenyl, —$C_1$-$C_{10}$ alkyl-OH, —$OC_1$-$C_{10}$ haloalkyl, —$SC_1$-$C_{10}$ alkyl, —$SC_1$-$C_{10}$ alkylphenyl, —$C_1$-$C_{10}$ alkyl-SH, —$SC_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), cyano, nitro, —$CO_2H$, —C(O)$OC_1$-$C_{10}$ alkyl, —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2NH$($C_1$-$C_{10}$ alkyl), —$SO_2NH$(phenyl), —$NHSO_2$($C_1$-$C_{10}$ alkyl), —$NHSO_2$(phenyl), and —$NHSO_2$($C_1$-$C_{10}$ haloalkyl);

each $L_1$ is independently a linear alkylene of 1 to 70 carbon atoms in length, wherein one or more carbon atoms are optionally replaced with one or more groups selected from the group consisting of: C(O), NH, O, S, CH=N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $L_1$ optionally has one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —$OC_1$-$C_{10}$ alkyl, —$OC_1$-$C_{10}$ alkylphenyl, —$C_1$-$C_{10}$ alkyl-OH, —$OC_1$-$C_{10}$ haloalkyl, —$SC_1$-$C_{10}$ alkyl, —$SC_1$-$C_{10}$ alkylphenyl, —$C_1$-$C_{10}$ alkyl-SH, —$SC_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), cyano, nitro, —$CO_2H$, —C(O)$OC_1$-$C_{10}$ alkyl, —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2NH$($C_1$-$C_{10}$ alkyl), —$SO_2NH$(phenyl), —$NHSO_2$($C_1$-$C_{10}$ alkyl), —$NHSO_2$(phenyl), and —$NHSO_2$($C_1$-$C_{10}$ haloalkyl);

~~~ represents the site where a group is linked to the rest of the molecule;

$M_1$ represents a targeting group.

13. The oligonucleotide conjugate according to claim 12, wherein each $L_1$ is independently selected from the group consisting of groups A1-A26, and any combination thereof:
~~~

-continued
(A1)
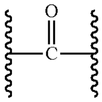,
(A2)
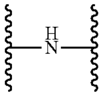,
(A3)
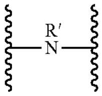,
(A4)
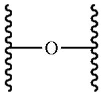,
(A5)
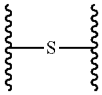,
(A6)
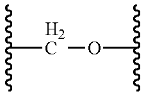,
(A7)
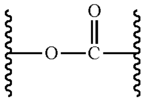,
(A8)
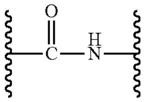,
(A9)
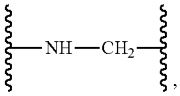,
(A10)
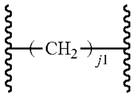,
(A11)
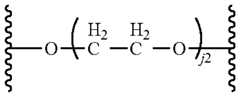,
(A12)
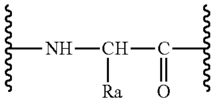,
(A13)
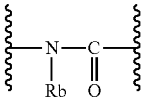,
(A14)
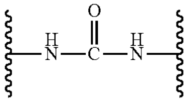,
(A15)
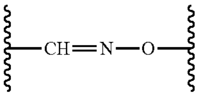,
(A16)
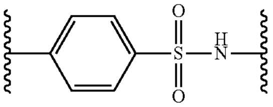,
(A17)
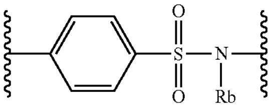,
(A18)
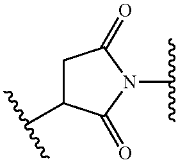,
(A19)
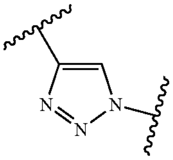,
(A20)
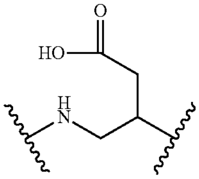,
(A21)
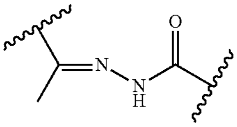,
(A22)
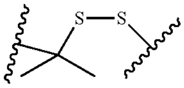,
(A23)
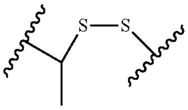,
(A24)
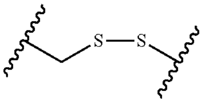,
(A25)
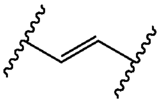, and -continued
(A26)
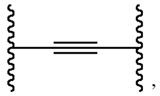
wherein each j1 is independently an integer of 1-20; each j2 is independently an integer of 1-20;
R' is a $C_1$-$C_{10}$ alkyl;
Ra is selected from the group consisting of A27-A45:
(A27)
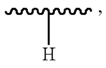
(A28)
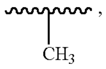
(A29)
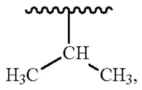
(A30)
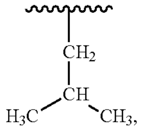
(A31)
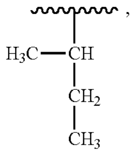
(A32)
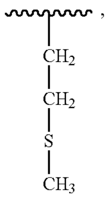
(A33)
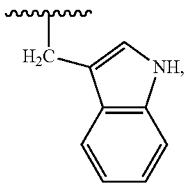
(A34)
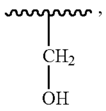
(A35)
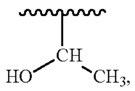
-continued
(A36)
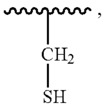
(A37)
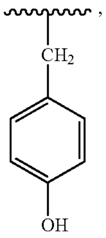
(A38)
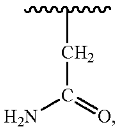
(A39)
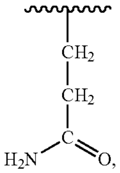
(A40)
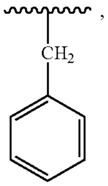
(A41)
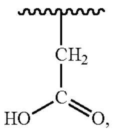
(A42)
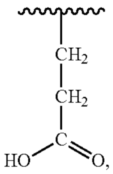
(A43)
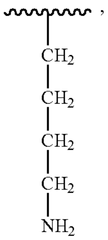

-continued (A44)

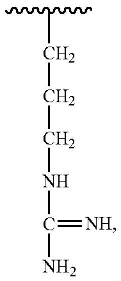

and (A45)

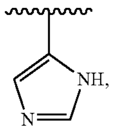

Rb is a $C_1$-$C_{10}$ alkyl.

14. The oligonucleotide conjugate according to claim 13, wherein L1 is selected from A1, A4, A5, A6, A8, A10, A11, and A13, and any connection combination thereof; or L1 is selected from the connection combinations of at least two of A1, A4, A8, A10, and A11; or L1 is selected from the connection combinations of at least two of A1, A8 and A10.

15. The oligonucleotide conjugate according to claim 12, wherein L1 is 3 to 25 atoms in length, or L1 is 4 to 15 atoms in length.

16. The oligonucleotide conjugate according to claim 12, wherein n1 is an integer of 1 or 2; n3 is an integer of 0 or 1; and n1+n3=2-3.

17. The oligonucleotide conjugate according to claim 12, wherein m1, m2 and m3 independently of one another are an integer of 2-5, or m1=m2=m3.

18. The oligonucleotide conjugate according to claim 12, wherein each of the targeting groups is selected from ligands capable of binding to cell surface receptor; or each of the targeting groups is selected from ligands that have affinity to the asialoglycoprotein receptor (ASGP-R) on the surface of mammalian hepatocyte; or at least one or each of the targeting groups is galactose or N-acetylgalactosamine (GalNAc).

19. The oligonucleotide conjugate according to claim 12, wherein R10, R11, R12, R13, R14, and R15 independently of one another are selected from H, methyl or ethyl.

20. The oligonucleotide conjugate according to claim 12, wherein R2 forms an amide bond with the N atom on the nitrogenous backbone; or R2 is B5, B6, B5' or B6':

(B5)

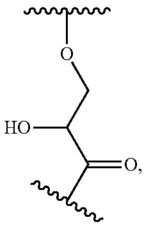

(B6)

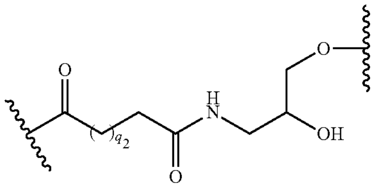

(B5')

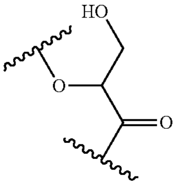

or (B6')

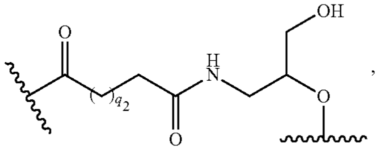

, wherein 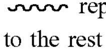 represents the site where a group is linked to the rest of the molecule;

q2 is an integer of 1-10.

21. The oligonucleotide conjugate according to claim 12, wherein the conjugate has a structure as shown by Formula (403), (404), (405), (406), (407), (408), (409), (410), (411), (412), (413), (414), (415), (416), (417), (418), (419), (420), (421), or (422):

Formula (403)
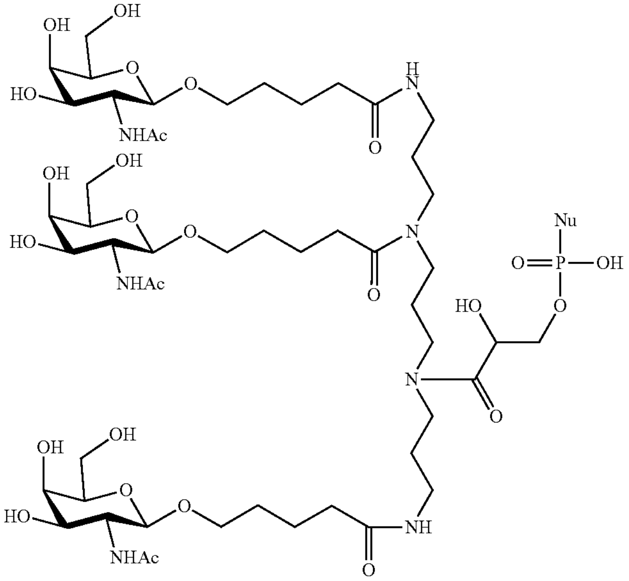
Formula (404)
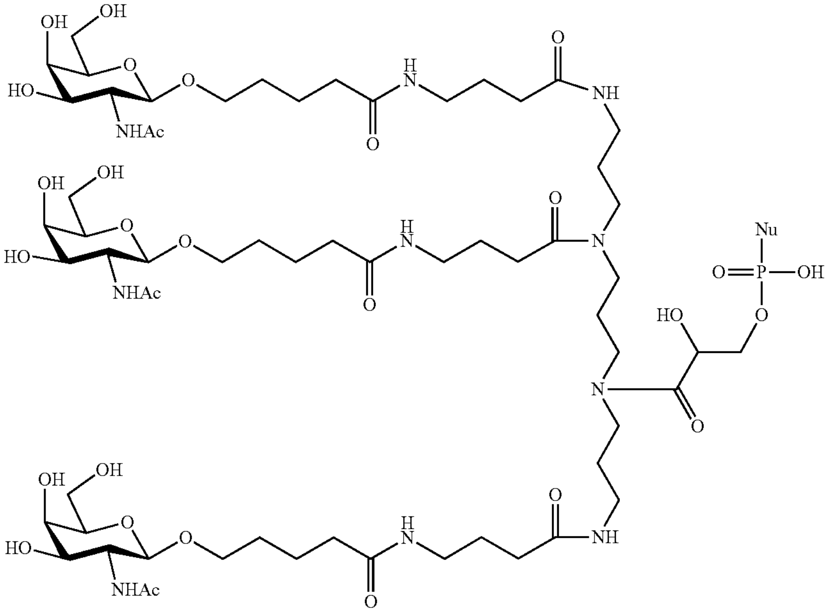

-continued
Formula (405)
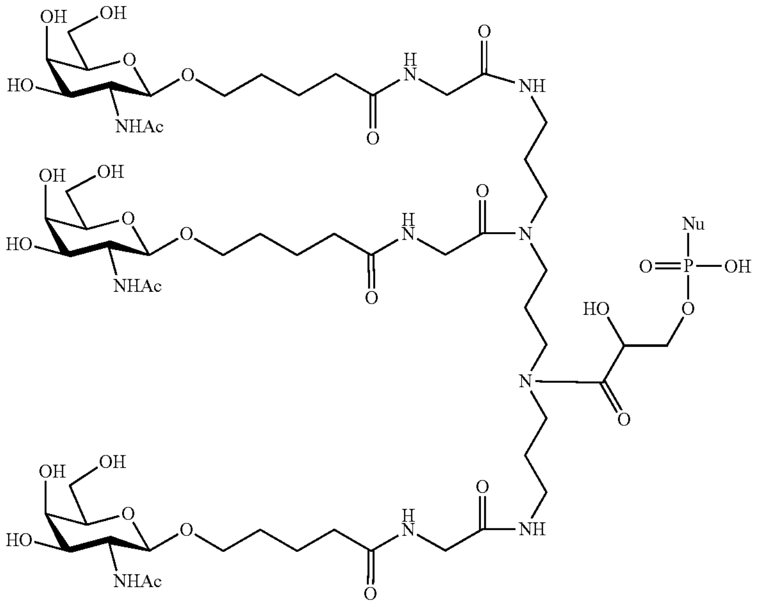
Formula (406)
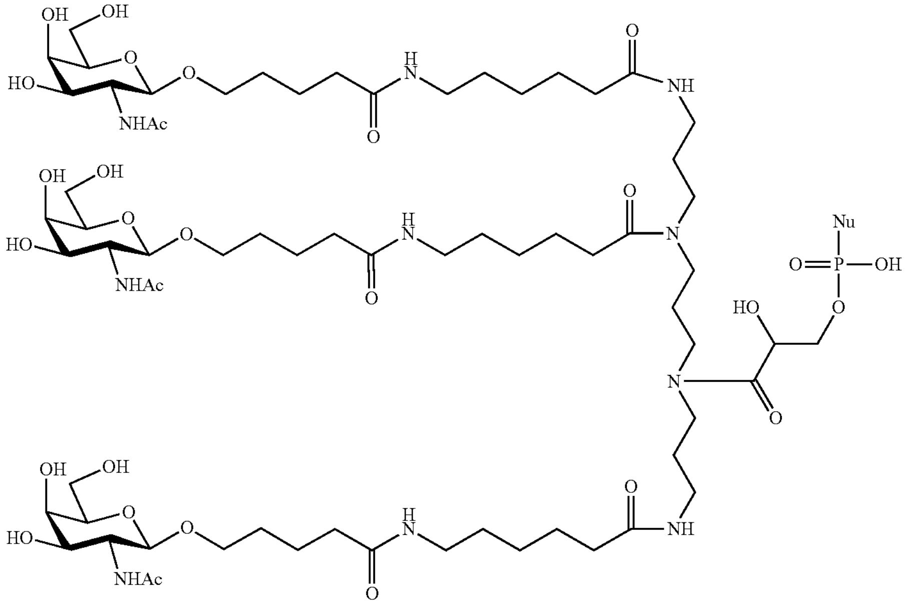

-continued
Formula (407)
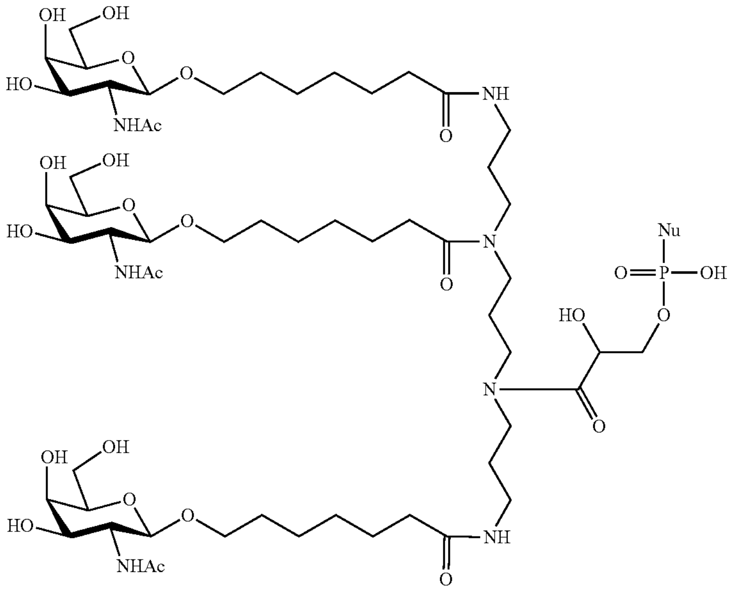
Formula (408)
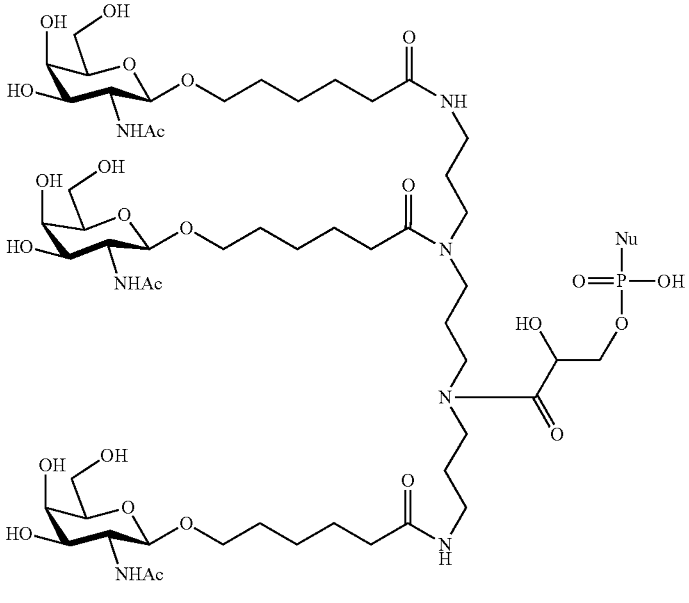

-continued
Formula (409)
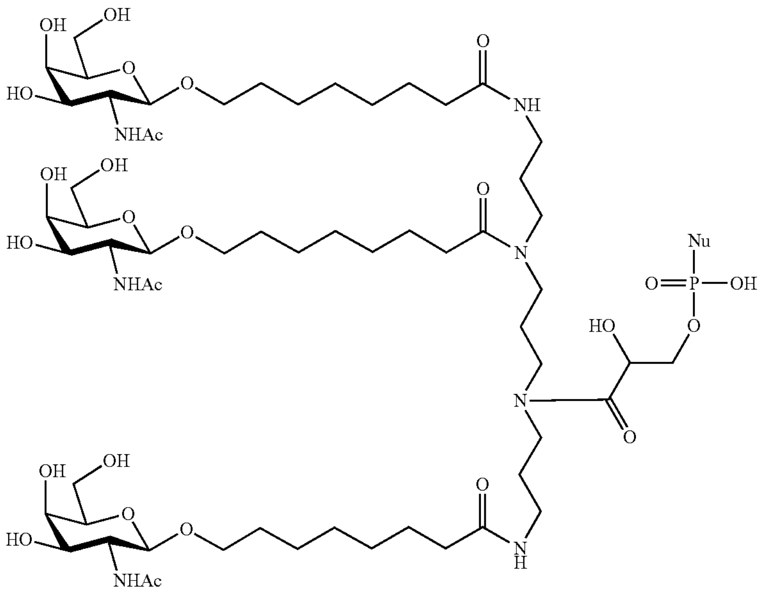
Formula (410)
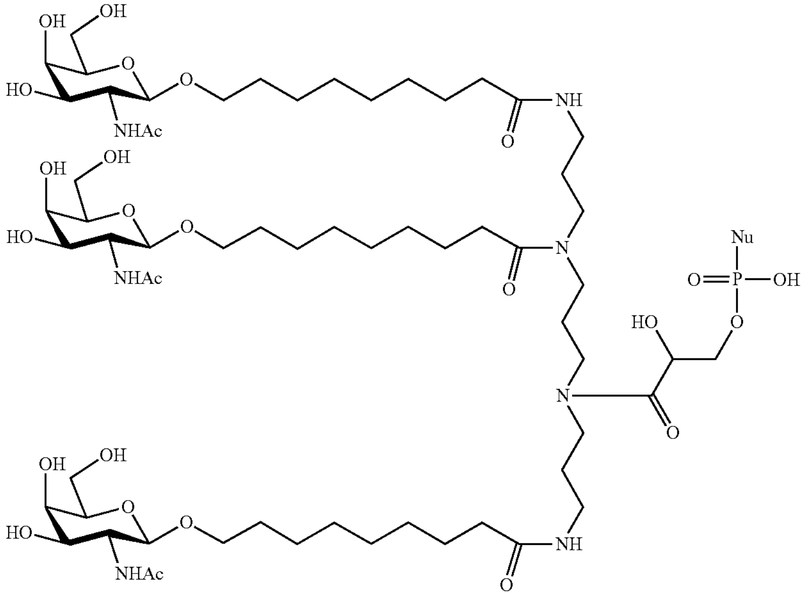

-continued
Formula (411)
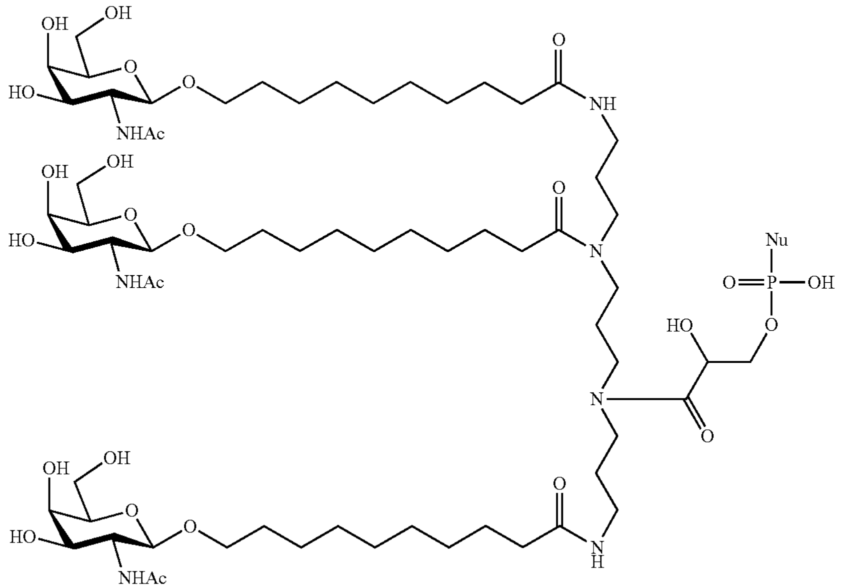
Formula (412)
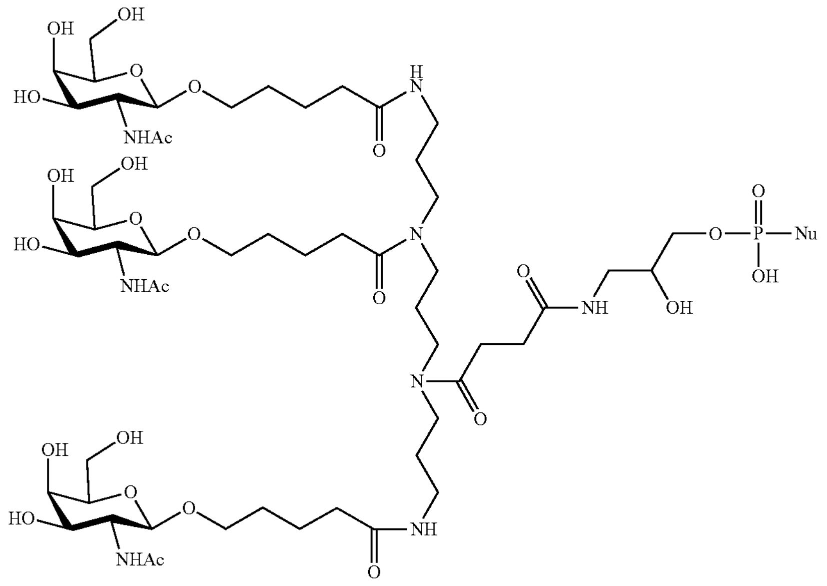

-continued
Formula (413)
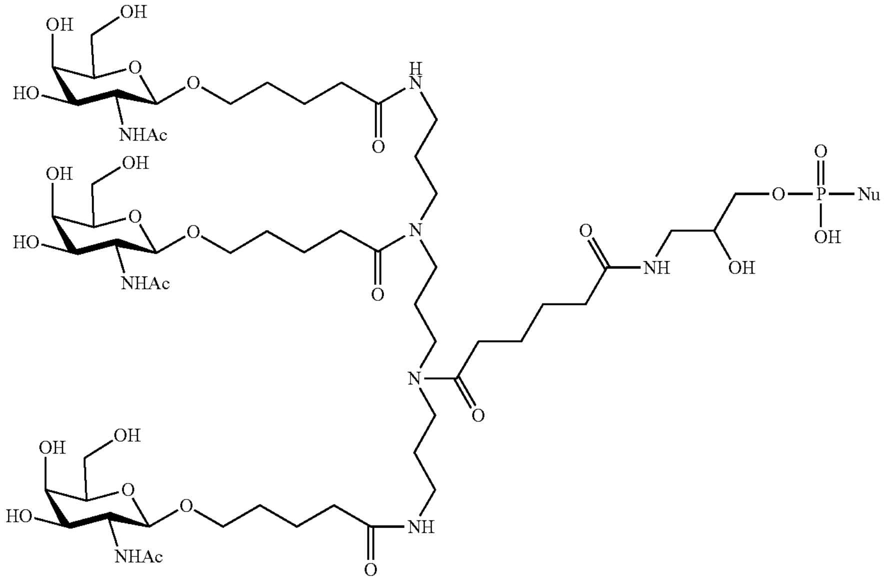
Formula (414)
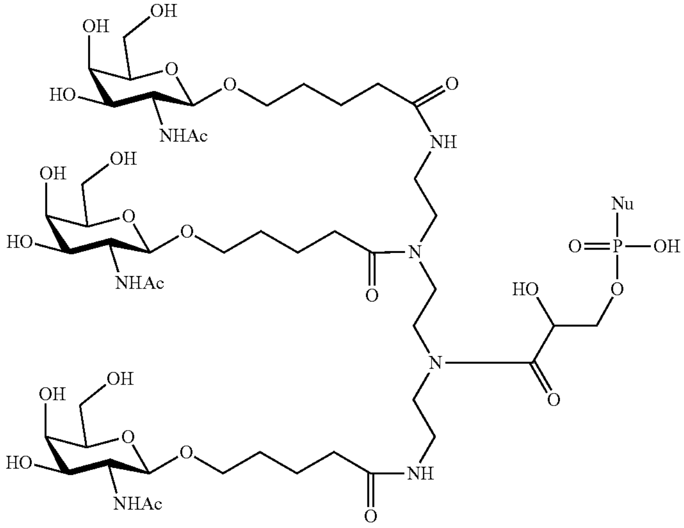

-continued
Formula (415)
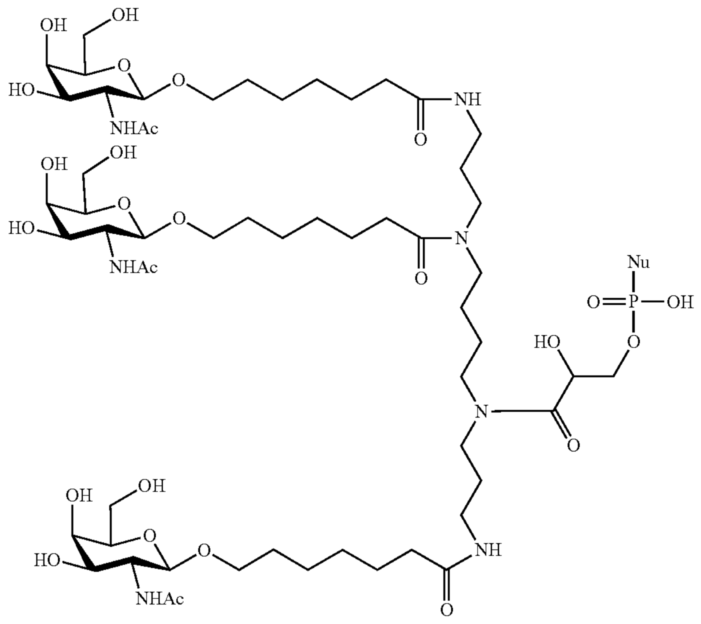
Formula (416)
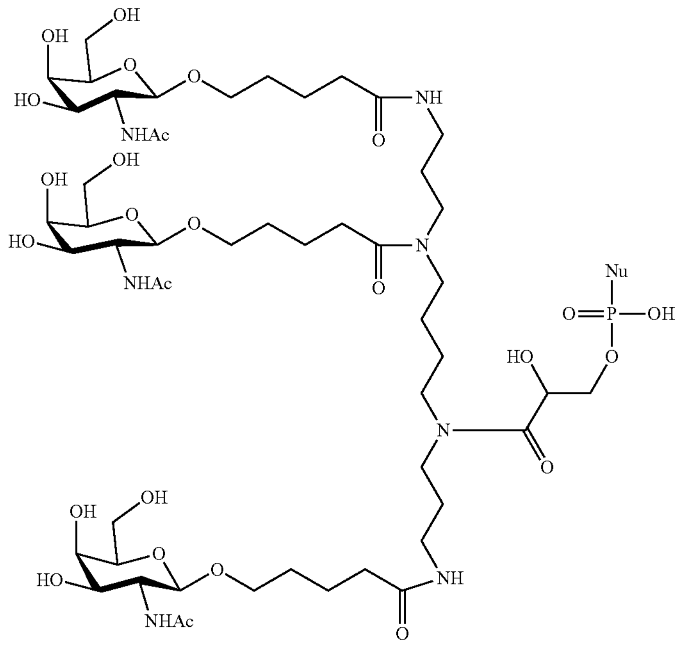

-continued
Formula (417)
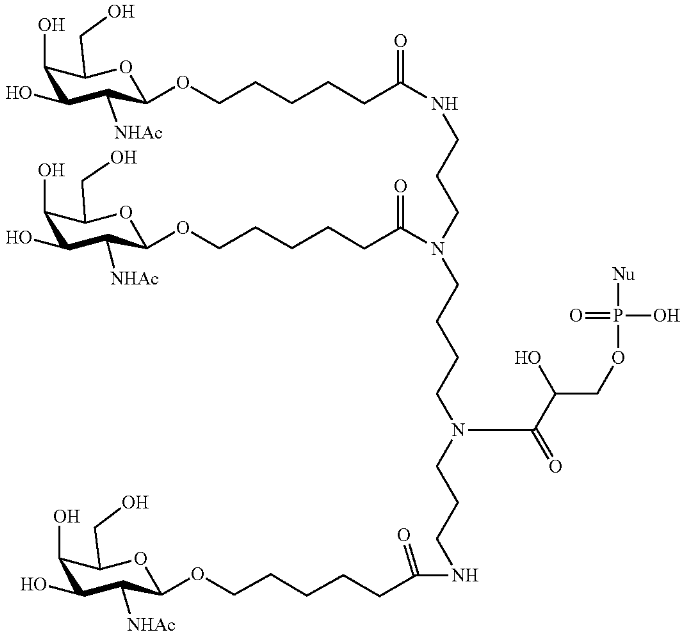
Formula (418)
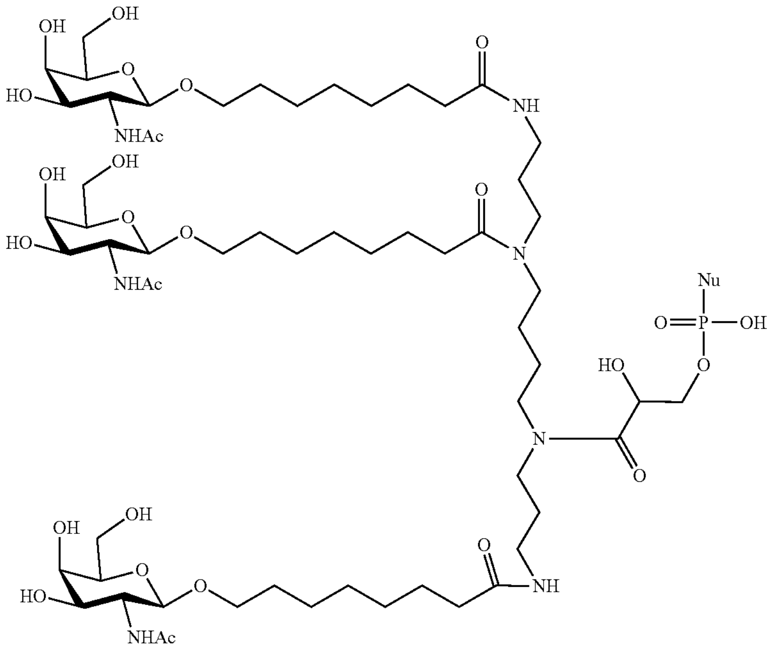

-continued
Formula (419)
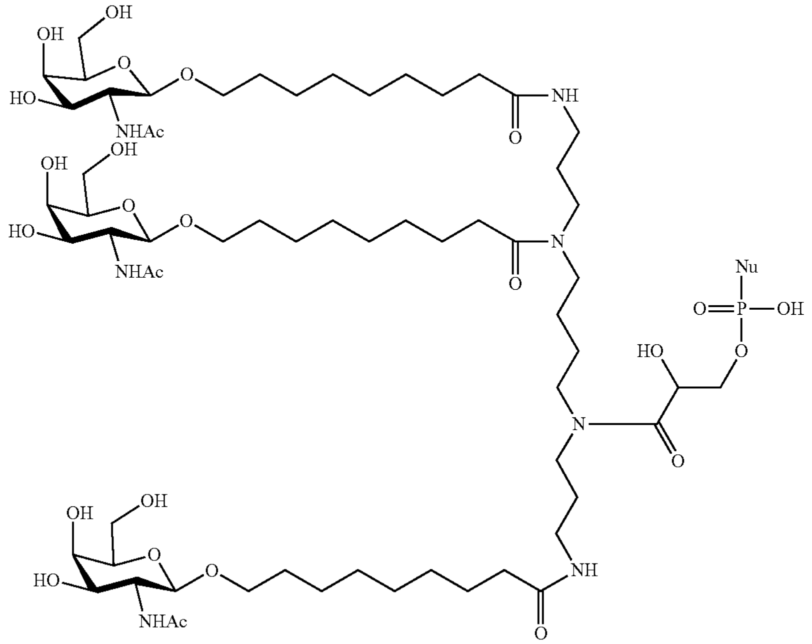
Formula (420)
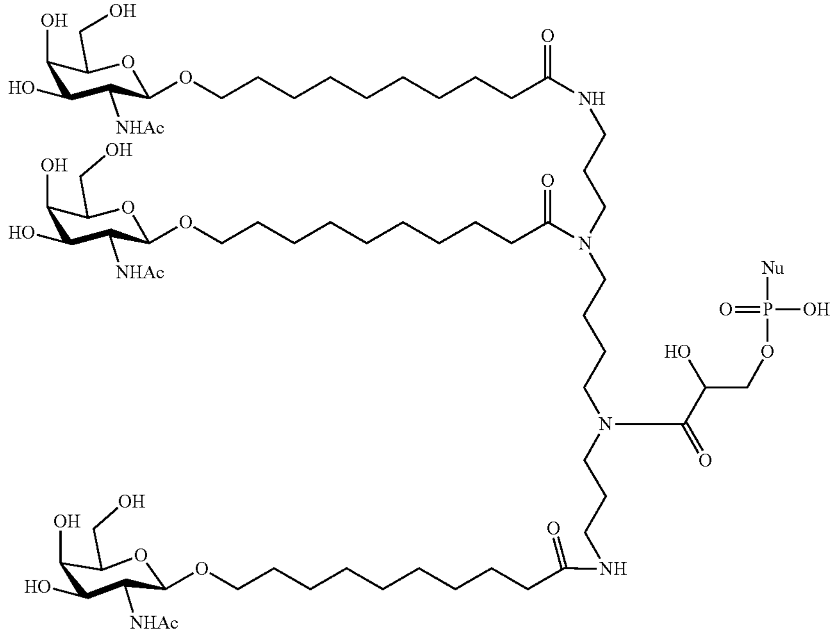

-continued

Formula (421)

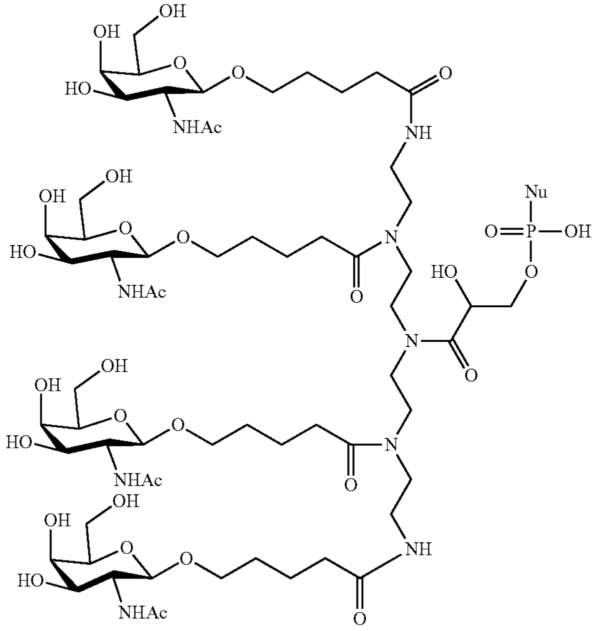

Formula (422)

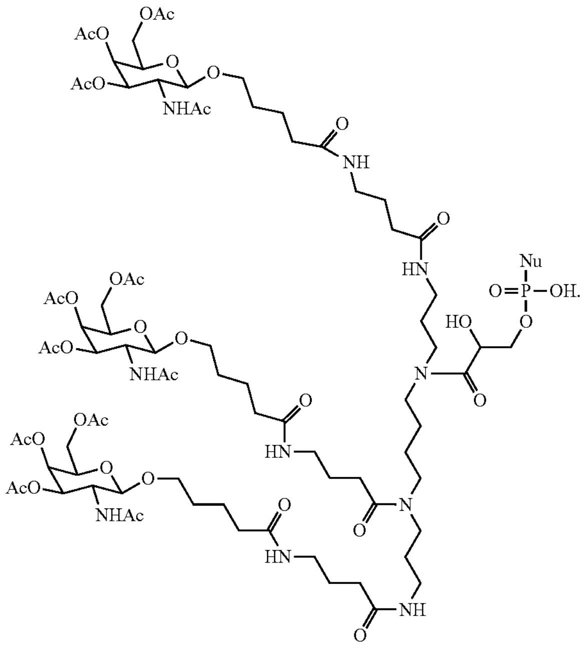

22. A method for treating a pathological condition or disease caused by abnormal gene expression, comprising administering an effective amount of the double-stranded oligonucleotide according to claim 1 and/or an oligonucleotide conjugate comprising the double-stranded oligonucleotide and a conjugation group conjugated to the double-stranded oligonucleotide, to a subject in need thereof.

23. The method according to claim 22, wherein the gene is selected from the group consisting of the gene of hepatitis B virus, the gene of angiopoietin-like protein 3, and the gene of apolipoprotein C3.

24. The method according to claim 22, wherein the disease is selected from chronic diseases, inflammations, fibrotic diseases, proliferative diseases and dyslipidemia.

25. A method for inhibiting the expression of a gene in a subject or a cell, comprising contacting the subject or the cell with an effective amount of the double-stranded oligonucleotide according to claim 1 and/or an oligonucleotide conjugate comprising the double-stranded oligonucleotide and a conjugation group conjugated to the double-stranded oligonucleotide.

* * * * *

SEQUENCE LISTING

```
Sequence total quantity: 456
SEQ ID NO: 1           moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 1
ccttgaggca tacttcaaa                                          19

SEQ ID NO: 2           moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 2
tttgaagtat gcctcaagg                                          19

SEQ ID NO: 3           moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 3
tgctatgcct catcttcta                                          19

SEQ ID NO: 4           moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 4
tagaagatga ggcatagca                                          19

SEQ ID NO: 5           moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 5
tctgtgcctt ctcatctga                                          19

SEQ ID NO: 6           moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 6
tcagatgaga aggcacaga                                          19
```

-continued

```
SEQ ID NO: 7            moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 7
cgtgtgcact tcgcttcaa                                          19

SEQ ID NO: 8            moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 8
ttgaagcgaa gtgcacacg                                          19

SEQ ID NO: 9            moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 9
gaaagtatgt caacgaata                                          19

SEQ ID NO: 10           moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 10
tattcgttga catactttc                                          19

SEQ ID NO: 11           moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 11
ccaagagcac caagaacta                                          19

SEQ ID NO: 12           moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 12
tagttcttgg tgctcttgg                                          19

SEQ ID NO: 13           moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 13
caataaagct ggacaagaa                                          19

SEQ ID NO: 14           moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 14
```

```
ttcttgtcca gctttattg                                                19

SEQ ID NO: 15          moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 15
ccttgaggca tacttcaaa                                                19

SEQ ID NO: 16          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 16
tttgaagtat gcctcaaggt t                                             21

SEQ ID NO: 17          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 17
gaccttgagg catacttcaa a                                             21

SEQ ID NO: 18          moltype = RNA  length = 23
FEATURE                Location/Qualifiers
misc_feature           1..23
                       note = Modified siRNA
source                 1..23
                       mol_type = other RNA
                       organism = synthetic construct
SEQUENCE: 18
tttgaagtat gcctcaaggt cgg                                           23

SEQ ID NO: 19          moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 19
ccttgaggca tacttcaaa                                                19

SEQ ID NO: 20          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 20
tttgaagtat gcctcaaggt t                                             21

SEQ ID NO: 21          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 21
gaccttgagg catacttcaa a                                             21

SEQ ID NO: 22          moltype = RNA  length = 21
FEATURE                Location/Qualifiers
misc_feature           1..21
                       note = Modified siRNA
source                 1..21
                       mol_type = other RNA
                       organism = synthetic construct
```

```
SEQUENCE: 22
gaccttgagg catacttcaa a                                              21

SEQ ID NO: 23           moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 23
tttgaagtat gcctcaaggt cgg                                            23

SEQ ID NO: 24           moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 24
tttgaagtat gcctcaaggt t                                              21

SEQ ID NO: 25           moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 25
gaccttgagg catacttcaa a                                              21

SEQ ID NO: 26           moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 26
tttgaagtat gcctcaaggt cgg                                            23

SEQ ID NO: 27           moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 27
ccttgaggca tacttcaaa                                                 19

SEQ ID NO: 28           moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 28
tttgaagtat gcctcaaggt t                                              21

SEQ ID NO: 29           moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 29
gaccttgagg catacttcaa a                                              21

SEQ ID NO: 30           moltype = RNA  length = 23
FEATURE                 Location/Qualifiers
misc_feature            1..23
                        note = Modified siRNA
source                  1..23
                        mol_type = other RNA
```

-continued

```
                      organism = synthetic construct
SEQUENCE: 30
tttgaagtat gcctcaaggt cgg                                          23

SEQ ID NO: 31         moltype = RNA  length = 19
FEATURE               Location/Qualifiers
misc_feature          1..19
                      note = Modified siRNA
source                1..19
                      mol_type = other RNA
                      organism = synthetic construct
SEQUENCE: 31
tgctatgcct catcttcta                                               19

SEQ ID NO: 32         moltype = RNA  length = 21
FEATURE               Location/Qualifiers
misc_feature          1..21
                      note = Modified siRNA
source                1..21
                      mol_type = other RNA
                      organism = synthetic construct
SEQUENCE: 32
tagaagatga ggcatagcag c                                            21

SEQ ID NO: 33         moltype = RNA  length = 19
FEATURE               Location/Qualifiers
misc_feature          1..19
                      note = Modified siRNA
source                1..19
                      mol_type = other RNA
                      organism = synthetic construct
SEQUENCE: 33
tgctatgcct catcttcta                                               19

SEQ ID NO: 34         moltype = RNA  length = 21
FEATURE               Location/Qualifiers
misc_feature          1..21
                      note = Modified siRNA
source                1..21
                      mol_type = other RNA
                      organism = synthetic construct
SEQUENCE: 34
tagaagatga ggcatagcag c                                            21

SEQ ID NO: 35         moltype = RNA  length = 19
FEATURE               Location/Qualifiers
misc_feature          1..19
                      note = Modified siRNA
source                1..19
                      mol_type = other RNA
                      organism = synthetic construct
SEQUENCE: 35
tgctatgcct catcttcta                                               19

SEQ ID NO: 36         moltype = RNA  length = 21
FEATURE               Location/Qualifiers
misc_feature          1..21
                      note = Modified siRNA
source                1..21
                      mol_type = other RNA
                      organism = synthetic construct
SEQUENCE: 36
tagaagatga ggcatagcat t                                            21

SEQ ID NO: 37         moltype = RNA  length = 19
FEATURE               Location/Qualifiers
misc_feature          1..19
                      note = Modified siRNA
source                1..19
                      mol_type = other RNA
                      organism = synthetic construct
SEQUENCE: 37
tgctatgcct catcttcta                                               19

SEQ ID NO: 38         moltype = RNA  length = 21
FEATURE               Location/Qualifiers
misc_feature          1..21
                      note = Modified siRNA
source                1..21
```

```
                        mol_type = other RNA
                        organism = synthetic construct
SEQUENCE: 38
tagaagatga ggcatagcag c                                              21

SEQ ID NO: 39           moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 39
tgctatgcct catcttcta                                                 19

SEQ ID NO: 40           moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 40
tagaagatga ggcatagcat t                                              21

SEQ ID NO: 41           moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 41
tgctatgcct catcttcta                                                 19

SEQ ID NO: 42           moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 42
tagaagatga ggcatagcag c                                              21

SEQ ID NO: 43           moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 43
tgctatgcct catcttcta                                                 19

SEQ ID NO: 44           moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 44
tagaagatga ggcatagcat t                                              21

SEQ ID NO: 45           moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 45
tgctatgcct catcttcta                                                 19

SEQ ID NO: 46           moltype = RNA  length = 21
FEATURE                 Location/Qualifiers
misc_feature            1..21
                        note = Modified siRNA
```

```
source                  1..21
                        mol_type = other RNA
                        organism = synthetic construct
SEQUENCE: 46
tagaagatga ggcatagcag c                                               21

SEQ ID NO: 47           moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 47
tgctatgcct catcttcta                                                  19

SEQ ID NO: 48           moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 48
tagaagatga ggcatagcat t                                               21

SEQ ID NO: 49           moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 49
tctgtgcctt ctcatctga                                                  19

SEQ ID NO: 50           moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 50
tcagatgaga aggcacagac g                                               21

SEQ ID NO: 51           moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 51
tctgtgcctt ctcatctga                                                  19

SEQ ID NO: 52           moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 52
tcagatgaga aggcacagac g                                               21

SEQ ID NO: 53           moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 53
tctgtgcctt ctcacctga                                                  19

SEQ ID NO: 54           moltype = RNA  length = 21
FEATURE                 Location/Qualifiers
misc_feature            1..21
```

```
                         note = Modified siRNA
source                   1..21
                         mol_type = other RNA
                         organism = synthetic construct
SEQUENCE: 54
tcagatgaga aggcacagac g                                            21

SEQ ID NO: 55            moltype = RNA  length = 19
FEATURE                  Location/Qualifiers
misc_feature             1..19
                         note = Modified siRNA
source                   1..19
                         mol_type = other RNA
                         organism = synthetic construct
SEQUENCE: 55
tctgtgcctt ctcatctga                                               19

SEQ ID NO: 56            moltype = RNA  length = 21
FEATURE                  Location/Qualifiers
misc_feature             1..21
                         note = Modified siRNA
source                   1..21
                         mol_type = other RNA
                         organism = synthetic construct
SEQUENCE: 56
tcagatgaga aggcactgac g                                            21

SEQ ID NO: 57            moltype = RNA  length = 19
FEATURE                  Location/Qualifiers
misc_feature             1..19
                         note = Modified siRNA
source                   1..19
                         mol_type = other RNA
                         organism = synthetic construct
SEQUENCE: 57
cgtgtgcact tcgcttcaa                                               19

SEQ ID NO: 58            moltype = RNA  length = 21
FEATURE                  Location/Qualifiers
misc_feature             1..21
                         note = Modified siRNA
source                   1..21
                         mol_type = other RNA
                         organism = synthetic construct
SEQUENCE: 58
ttgaagcgaa gtgcacacgg t                                            21

SEQ ID NO: 59            moltype = RNA  length = 19
FEATURE                  Location/Qualifiers
misc_feature             1..19
                         note = Modified siRNA
source                   1..19
                         mol_type = other RNA
                         organism = synthetic construct
SEQUENCE: 59
cgtgtgcact tcgcttcaa                                               19

SEQ ID NO: 60            moltype = RNA  length = 21
FEATURE                  Location/Qualifiers
misc_feature             1..21
                         note = Modified siRNA
source                   1..21
                         mol_type = other RNA
                         organism = synthetic construct
SEQUENCE: 60
ttgaagcgaa gtgcacacgg t                                            21

SEQ ID NO: 61            moltype = RNA  length = 19
FEATURE                  Location/Qualifiers
misc_feature             1..19
                         note = Modified siRNA
source                   1..19
                         mol_type = other RNA
                         organism = synthetic construct
SEQUENCE: 61
cgtgtgcact tcgcttcaa                                               19

SEQ ID NO: 62            moltype = RNA  length = 21
FEATURE                  Location/Qualifiers
```

```
misc_feature          1..21
                      note = Modified siRNA
source                1..21
                      mol_type = other RNA
                      organism = synthetic construct
SEQUENCE: 62
ttgaagcgaa gtgcacacgg t                                             21

SEQ ID NO: 63         moltype = RNA  length = 19
FEATURE               Location/Qualifiers
misc_feature          1..19
                      note = Modified siRNA
source                1..19
                      mol_type = other RNA
                      organism = synthetic construct
SEQUENCE: 63
cttgtgcact tcgcttcaa                                                19

SEQ ID NO: 64         moltype = RNA  length = 21
FEATURE               Location/Qualifiers
misc_feature          1..21
                      note = Modified siRNA
source                1..21
                      mol_type = other RNA
                      organism = synthetic construct
SEQUENCE: 64
ttgaagcgaa gtgcacacgg t                                             21

SEQ ID NO: 65         moltype = RNA  length = 19
FEATURE               Location/Qualifiers
misc_feature          1..19
                      note = Modified siRNA
source                1..19
                      mol_type = other RNA
                      organism = synthetic construct
SEQUENCE: 65
ccaagagcac caagaacta                                                19

SEQ ID NO: 66         moltype = RNA  length = 21
FEATURE               Location/Qualifiers
misc_feature          1..21
                      note = Modified siRNA
source                1..21
                      mol_type = other RNA
                      organism = synthetic construct
SEQUENCE: 66
tagttcttgg tgctcttggc t                                             21

SEQ ID NO: 67         moltype = RNA  length = 21
FEATURE               Location/Qualifiers
misc_feature          1..21
                      note = Modified siRNA
source                1..21
                      mol_type = other RNA
                      organism = synthetic construct
SEQUENCE: 67
agccaagagc agcaagaact a                                             21

SEQ ID NO: 68         moltype = RNA  length = 23
FEATURE               Location/Qualifiers
misc_feature          1..23
                      note = Modified siRNA
source                1..23
                      mol_type = other RNA
                      organism = synthetic construct
SEQUENCE: 68
tagttcttgg tgctcttggc ttg                                           23

SEQ ID NO: 69         moltype = RNA  length = 19
FEATURE               Location/Qualifiers
misc_feature          1..19
                      note = Modified siRNA
source                1..19
                      mol_type = other RNA
                      organism = synthetic construct
SEQUENCE: 69
ccaagagcac caagaacta                                                19

SEQ ID NO: 70         moltype = RNA  length = 21
```

-continued

```
FEATURE                Location/Qualifiers
misc_feature           1..21
                       note = Modified siRNA
source                 1..21
                       mol_type = other RNA
                       organism = synthetic construct
SEQUENCE: 70
tagttcttgg tgctcttggc t                                                21

SEQ ID NO: 71          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 71
agccaagagc accaagaact a                                                21

SEQ ID NO: 72          moltype = RNA  length = 23
FEATURE                Location/Qualifiers
misc_feature           1..23
                       note = Modified siRNA
source                 1..23
                       mol_type = other RNA
                       organism = synthetic construct
SEQUENCE: 72
tagttcttgg tgctcttggc ttg                                              23

SEQ ID NO: 73          moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 73
ccaagagcac caagaacta                                                   19

SEQ ID NO: 74          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 74
tagttcttgg tgctcttggc t                                                21

SEQ ID NO: 75          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 75
agccaagagc accaagaact a                                                21

SEQ ID NO: 76          moltype = RNA  length = 23
FEATURE                Location/Qualifiers
misc_feature           1..23
                       note = Modified siRNA
source                 1..23
                       mol_type = other RNA
                       organism = synthetic construct
SEQUENCE: 76
tagttcttgg tgctcttggc ttg                                              23

SEQ ID NO: 77          moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 77
ccaagagcac caagaacta                                                   19
```

```
SEQ ID NO: 78          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 78
tagttcttgg tgctcttggc t                                      21

SEQ ID NO: 79          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 79
agccaagagc accaagaact a                                      21

SEQ ID NO: 80          moltype = RNA  length = 23
FEATURE                Location/Qualifiers
misc_feature           1..23
                       note = Modified siRNA
source                 1..23
                       mol_type = other RNA
                       organism = synthetic construct
SEQUENCE: 80
tagttcttgg tgctcttggc ttg                                    23

SEQ ID NO: 81          moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 81
caataaagct ggacaagaa                                         19

SEQ ID NO: 82          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 82
ttcttgtcca gctttattgg g                                      21

SEQ ID NO: 83          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 83
cccaataaag ctggacaaga a                                      21

SEQ ID NO: 84          moltype = RNA  length = 23
FEATURE                Location/Qualifiers
misc_feature           1..23
                       note = Modified siRNA
source                 1..23
                       mol_type = other RNA
                       organism = synthetic construct
SEQUENCE: 84
ttcttgtcca gctttattgg gag                                    23

SEQ ID NO: 85          moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 85
ctataaagct ggacaagaa                                         19
```

```
SEQ ID NO: 86          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 86
ttcttgtcca gctttattgg g                                            21

SEQ ID NO: 87          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 87
cccaataaag ctggacaaga a                                            21

SEQ ID NO: 88          moltype = RNA  length = 23
FEATURE                Location/Qualifiers
misc_feature           1..23
                       note = Modified siRNA
source                 1..23
                       mol_type = other RNA
                       organism = synthetic construct
SEQUENCE: 88
ttcttgtcca gctttattgg gag                                          23

SEQ ID NO: 89          moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 89
caataaagct ggacaagaa                                               19

SEQ ID NO: 90          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 90
ttcttgtcca gctttattgg g                                            21

SEQ ID NO: 91          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 91
cccaataaag ctggacaaga a                                            21

SEQ ID NO: 92          moltype = RNA  length = 23
FEATURE                Location/Qualifiers
misc_feature           1..23
                       note = Modified siRNA
source                 1..23
                       mol_type = other RNA
                       organism = synthetic construct
SEQUENCE: 92
ttcttgtcca gctttattgg gag                                          23

SEQ ID NO: 93          moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 93
```

```
caataaagct ggacaagaa                                           19

SEQ ID NO: 94          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 94
ttcttgtcca gctttattgg g                                        21

SEQ ID NO: 95          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 95
cccaataaag ctggacaaga a                                        21

SEQ ID NO: 96          moltype = RNA  length = 23
FEATURE                Location/Qualifiers
misc_feature           1..23
                       note = Modified siRNA
source                 1..23
                       mol_type = other RNA
                       organism = synthetic construct
SEQUENCE: 96
ttcttgtcca gctttattgg gag                                      23

SEQ ID NO: 97          moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 97
gaaagtatgt caacgaatt                                           19

SEQ ID NO: 98          moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 98
aattcgttga catactttct t                                        21

SEQ ID NO: 99          moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 99
gaaagtatgt caacgaatt                                           19

SEQ ID NO: 100         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 100
aattcgttga catactttcc a                                        21

SEQ ID NO: 101         moltype = RNA  length = 19
FEATURE                Location/Qualifiers
misc_feature           1..19
                       note = Modified siRNA
source                 1..19
                       mol_type = other RNA
                       organism = synthetic construct
```

```
SEQUENCE: 101
gaaagtatgt caacgaata                                                 19

SEQ ID NO: 102         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 102
tattcgttga catactttct t                                              21

SEQ ID NO: 103         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 103
gaaagtatgt caacgaata                                                 19

SEQ ID NO: 104         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 104
tattcgttga catactttcc a                                              21

SEQ ID NO: 105         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 105
tggaaagtat gtcaacgatt a                                              21

SEQ ID NO: 106         moltype = RNA  length = 23
FEATURE                Location/Qualifiers
misc_feature           1..23
                       note = Modified siRNA
source                 1..23
                       mol_type = other RNA
                       organism = synthetic construct
SEQUENCE: 106
tattcgttga catactttcc att                                            23

SEQ ID NO: 107         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 107
gaaagtatgt caacgaatt                                                 19

SEQ ID NO: 108         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 108
aattcgttga catactttct t                                              21

SEQ ID NO: 109         moltype = RNA  length = 19
FEATURE                Location/Qualifiers
misc_feature           1..19
                       note = Modified siRNA
source                 1..19
                       mol_type = other RNA
```

```
                       organism = synthetic construct
SEQUENCE: 109
gaaagtatgt caacgaatt                                          19

SEQ ID NO: 110         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 110
aattcgttga catactttcc a                                       21

SEQ ID NO: 111         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 111
gaaagtatgt caacgaata                                          19

SEQ ID NO: 112         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 112
tattcgttga catactttct t                                       21

SEQ ID NO: 113         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 113
gaaagtatgt caacgaata                                          19

SEQ ID NO: 114         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 114
tattcgttga catactttcc a                                       21

SEQ ID NO: 115         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 115
tggaaagtat gtcaacgatt a                                       21

SEQ ID NO: 116         moltype = RNA  length = 23
FEATURE                Location/Qualifiers
misc_feature           1..23
                       note = Modified siRNA
source                 1..23
                       mol_type = other RNA
                       organism = synthetic construct
SEQUENCE: 116
tattcgttga catactttcc att                                     23

SEQ ID NO: 117         moltype = RNA  length = 18
FEATURE                Location/Qualifiers
misc_feature           1..18
                       note = Modified siRNA
source                 1..18
```

```
                        mol_type = other RNA
                        organism = synthetic construct
SEQUENCE: 117
gaaagtatgt caacgatt                                                18

SEQ ID NO: 118          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 118
aattcgttga catactttct t                                            21

SEQ ID NO: 119          moltype = RNA  length = 18
FEATURE                 Location/Qualifiers
misc_feature            1..18
                        note = Modified siRNA
source                  1..18
                        mol_type = other RNA
                        organism = synthetic construct
SEQUENCE: 119
gaaagtatgt caacgatt                                                18

SEQ ID NO: 120          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 120
aattcgttga catactttcc a                                            21

SEQ ID NO: 121          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 121
gaaagtatgt caacgaata                                               19

SEQ ID NO: 122          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 122
tattcgttga catactttct t                                            21

SEQ ID NO: 123          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 123
gaaagtatgt caacgaata                                               19

SEQ ID NO: 124          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 124
tattcgttga catactttcc a                                            21

SEQ ID NO: 125          moltype = RNA  length = 21
FEATURE                 Location/Qualifiers
misc_feature            1..21
                        note = Modified siRNA
```

```
source                  1..21
                        mol_type = other RNA
                        organism = synthetic construct
SEQUENCE: 125
tggaaagtat gtcaacgaat a                                             21

SEQ ID NO: 126          moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 126
tattcgttga catactttcc att                                           23

SEQ ID NO: 127          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 127
gaaagtatgt caacgaatt                                                19

SEQ ID NO: 128          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 128
aattcgttga catactttct t                                             21

SEQ ID NO: 129          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 129
gaaagtatgt caacgaatt                                                19

SEQ ID NO: 130          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 130
aattcgttga catactttcc a                                             21

SEQ ID NO: 131          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 131
gaaagtatgt caacgaata                                                19

SEQ ID NO: 132          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 132
tattcgttga cttactttct t                                             21

SEQ ID NO: 133          moltype = RNA  length = 19
FEATURE                 Location/Qualifiers
misc_feature            1..19
```

-continued

```
                        note = Modified siRNA
source                  1..19
                        mol_type = other RNA
                        organism = synthetic construct
SEQUENCE: 133
gaaagtatgt caacgaata                                          19

SEQ ID NO: 134          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 134
tattcgttga catactttcc a                                       21

SEQ ID NO: 135          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 135
tggaaagtat gtcaacgaat a                                       21

SEQ ID NO: 136          moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 136
tattcgttga catactttcc att                                     23

SEQ ID NO: 137          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 137
ccaagagcac caagaacta                                          19

SEQ ID NO: 138          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 138
tagttcttgg tgctcttggc t                                       21

SEQ ID NO: 139          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 139
ccaagagcac caagaacta                                          19

SEQ ID NO: 140          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 140
tagttcttgg tgctcttggc t                                       21

SEQ ID NO: 141          moltype = RNA  length = 19
FEATURE                 Location/Qualifiers
```

-continued

```
misc_feature           1..19
                       note = Modified siRNA
source                 1..19
                       mol_type = other RNA
                       organism = synthetic construct
SEQUENCE: 141
ccaagagcac caagaacta                                               19

SEQ ID NO: 142         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 142
tagttcttgg tgctcttggc t                                            21

SEQ ID NO: 143         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 143
ccaagagcac caagaacta                                               19

SEQ ID NO: 144         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 144
tagttcttgg tgctcttggc t                                            21

SEQ ID NO: 145         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 145
ccttgaggca tacttcaaa                                               19

SEQ ID NO: 146         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 146
tttgaagtat gcctcaagg                                               19

SEQ ID NO: 147         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 147
cgtgtgcact tcgcttcaa                                               19

SEQ ID NO: 148         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 148
ttgaagcgaa gtgcacacgg t                                            21

SEQ ID NO: 149         moltype = RNA  length = 19
```

-continued

```
FEATURE                Location/Qualifiers
misc_feature           1..19
                       note = Modified siRNA
source                 1..19
                       mol_type = other RNA
                       organism = synthetic construct
SEQUENCE: 149
cgtgtgcact tcgcttcaa                                              19

SEQ ID NO: 150         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 150
ttgaagcgaa gtgcacacgg t                                           21

SEQ ID NO: 151         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 151
gtgtgcactt cgcttcaca                                              19

SEQ ID NO: 152         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 152
tgtgaagcga agtgcacact t                                           21

SEQ ID NO: 153         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 153
ccttgaggca tacttcaaa                                              19

SEQ ID NO: 154         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 154
tttgaagtat gcctcaaggt t                                           21

SEQ ID NO: 155         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 155
ccttgaggca tacttcaaa                                              19

SEQ ID NO: 156         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 156
tttgaagtat gcctcaaggt t                                           21
```

```
SEQ ID NO: 157          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 157
ccttgaggca tacttcaaa                                              19

SEQ ID NO: 158          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 158
tttgaagtat gctccaaggt t                                           21

SEQ ID NO: 159          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 159
ccttgaggca tacttcaaa                                              19

SEQ ID NO: 160          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 160
tttgaagtat gcctcaaggt t                                           21

SEQ ID NO: 161          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 161
gaccttgagg catacttcaa a                                           21

SEQ ID NO: 162          moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 162
tttgaagtat gcctcaaggt cgg                                         23

SEQ ID NO: 163          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 163
ccttgaggca tacttcaaa                                              19

SEQ ID NO: 164          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 164
tttgaagtat gcctcaaggt t                                           21
```

-continued

```
SEQ ID NO: 165          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 165
gaccttgagg catacttcaa a                                              21

SEQ ID NO: 166          moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 166
tttgaagtat gcctcaaggt cgg                                            23

SEQ ID NO: 167          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 167
ccttgaggca tacttcaaa                                                 19

SEQ ID NO: 168          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 168
tttgaagtat gcctcaaggt t                                              21

SEQ ID NO: 169          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 169
gaccttgagg catacttcaa a                                              21

SEQ ID NO: 170          moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 170
tttgaagtat gcctcaaggt cgg                                            23

SEQ ID NO: 171          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 171
ccttgaggca tacttcaaa                                                 19

SEQ ID NO: 172          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 172
```

```
tttgaagtat gcctcaaggt t                                            21

SEQ ID NO: 173          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 173
gaccttgagg catacttcaa a                                            21

SEQ ID NO: 174          moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 174
tttgaagtat gcctcaaggt cgg                                          23

SEQ ID NO: 175          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 175
ccttgaggca tacttcaaa                                               19

SEQ ID NO: 176          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 176
tttgaagtat gcctcaaggt t                                            21

SEQ ID NO: 177          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 177
ccttgaggca tacttcaaa                                               19

SEQ ID NO: 178          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 178
tttgaagtat gcctcaaggt t                                            21

SEQ ID NO: 179          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 179
ccttgaggca tacttcaaa                                               19

SEQ ID NO: 180          moltype = RNA  length = 21
FEATURE                 Location/Qualifiers
misc_feature            1..21
                        note = Modified siRNA
source                  1..21
                        mol_type = other RNA
                        organism = synthetic construct
```

```
SEQUENCE: 180
tttgaagtat gcctcaaggt t                                              21

SEQ ID NO: 181         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 181
ccttgaggca tacttcaaa                                                 19

SEQ ID NO: 182         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 182
tttgaagtat gcctcaaggt t                                              21

SEQ ID NO: 183         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 183
ccttgaggca tacttcaaa                                                 19

SEQ ID NO: 184         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 184
tttgaagtat gcctcaaggt t                                              21

SEQ ID NO: 185         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 185
ccttgaggca tacttcaaa                                                 19

SEQ ID NO: 186         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 186
tttgaagtat gcctcaaggt t                                              21

SEQ ID NO: 187         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 187
ccttgaggca tacttcaaa                                                 19

SEQ ID NO: 188         moltype = RNA  length = 21
FEATURE                Location/Qualifiers
misc_feature           1..21
                       note = Modified siRNA
source                 1..21
                       mol_type = other RNA
```

```
                         organism = synthetic construct
SEQUENCE: 188
tttgaagtat gcctcaaggt t                                                21

SEQ ID NO: 189           moltype = RNA  length = 19
FEATURE                  Location/Qualifiers
misc_feature             1..19
                         note = Modified siRNA
source                   1..19
                         mol_type = other RNA
                         organism = synthetic construct
SEQUENCE: 189
ccttgaggca tacttcaaa                                                   19

SEQ ID NO: 190           moltype = RNA  length = 21
FEATURE                  Location/Qualifiers
misc_feature             1..21
                         note = Modified siRNA
source                   1..21
                         mol_type = other RNA
                         organism = synthetic construct
SEQUENCE: 190
tttgaagtat gcctcaaggt t                                                21

SEQ ID NO: 191           moltype = RNA  length = 21
FEATURE                  Location/Qualifiers
misc_feature             1..21
                         note = Modified siRNA
source                   1..21
                         mol_type = other RNA
                         organism = synthetic construct
SEQUENCE: 191
gaccttgagg catacttcaa a                                                21

SEQ ID NO: 192           moltype = RNA  length = 23
FEATURE                  Location/Qualifiers
misc_feature             1..23
                         note = Modified siRNA
source                   1..23
                         mol_type = other RNA
                         organism = synthetic construct
SEQUENCE: 192
tttgaagtat gcctcaaggt cgg                                              23

SEQ ID NO: 193           moltype = RNA  length = 19
FEATURE                  Location/Qualifiers
misc_feature             1..19
                         note = Modified siRNA
source                   1..19
                         mol_type = other RNA
                         organism = synthetic construct
SEQUENCE: 193
ccttgaggca tacttcaaa                                                   19

SEQ ID NO: 194           moltype = RNA  length = 21
FEATURE                  Location/Qualifiers
misc_feature             1..21
                         note = Modified siRNA
source                   1..21
                         mol_type = other RNA
                         organism = synthetic construct
SEQUENCE: 194
tttgaagtat gcctcaaggt t                                                21

SEQ ID NO: 195           moltype = RNA  length = 21
FEATURE                  Location/Qualifiers
misc_feature             1..21
                         note = Modified siRNA
source                   1..21
                         mol_type = other RNA
                         organism = synthetic construct
SEQUENCE: 195
gaccttgagg catacttcaa a                                                21

SEQ ID NO: 196           moltype = RNA  length = 23
FEATURE                  Location/Qualifiers
misc_feature             1..23
                         note = Modified siRNA
source                   1..23
```

```
                        mol_type = other RNA
                        organism = synthetic construct
SEQUENCE: 196
tttgaagtat gcctcaaggt cgg                                     23

SEQ ID NO: 197          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 197
ccttgaggca tacttcaaa                                          19

SEQ ID NO: 198          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 198
tttgaagtat gcctcaaggt t                                       21

SEQ ID NO: 199          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 199
ccttgaggca tacttcaaa                                          19

SEQ ID NO: 200          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 200
tttgaagtat gcctcaagg                                          19

SEQ ID NO: 201          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 201
ccttgaggca tacttcaaa                                          19

SEQ ID NO: 202          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 202
tttgaagtat gcctcaaggt t                                       21

SEQ ID NO: 203          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 203
gtgtgcactt cgcttcaca                                          19

SEQ ID NO: 204          moltype = RNA  length = 21
FEATURE                 Location/Qualifiers
misc_feature            1..21
                        note = Modified siRNA
```

-continued

```
source                  1..21
                        mol_type = other RNA
                        organism = synthetic construct
SEQUENCE: 204
tgtgaagcga agtgcacact t                                                   21

SEQ ID NO: 205          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 205
tgctatgcct catcttcta                                                      19

SEQ ID NO: 206          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 206
tagaagatga ggcatagcag c                                                   21

SEQ ID NO: 207          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 207
tgctatgcct catcttcta                                                      19

SEQ ID NO: 208          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 208
tagaagatga ggcatagcat t                                                   21

SEQ ID NO: 209          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 209
tgctatgcct catcttcta                                                      19

SEQ ID NO: 210          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 210
tagaagatga ggcatagcag c                                                   21

SEQ ID NO: 211          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 211
tgctatgcct catcttcta                                                      19

SEQ ID NO: 212          moltype = RNA  length = 21
FEATURE                 Location/Qualifiers
misc_feature            1..21
```

```
                        note = Modified siRNA
source                  1..21
                        mol_type = other RNA
                        organism = synthetic construct
SEQUENCE: 212
tagaagatga ggcatagcat t                                        21

SEQ ID NO: 213          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 213
gctgctatgc ctcatcttct a                                        21

SEQ ID NO: 214          moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 214
tagaagatga ggcatagcag cgc                                      23

SEQ ID NO: 215          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 215
tgctatgcct catcttcta                                           19

SEQ ID NO: 216          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 216
tagaagatga ggcatagcat t                                        21

SEQ ID NO: 217          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 217
tgctatgcct catcttcta                                           19

SEQ ID NO: 218          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 218
tagaagatga ggcatagcat t                                        21

SEQ ID NO: 219          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 219
tgctatgcct catcttcta                                           19

SEQ ID NO: 220          moltype = RNA  length = 21
FEATURE                 Location/Qualifiers
```

-continued

```
misc_feature           1..21
                       note = Modified siRNA
source                 1..21
                       mol_type = other RNA
                       organism = synthetic construct
SEQUENCE: 220
tagaagatga ggcatagcat t                                              21

SEQ ID NO: 221         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 221
tgctatgcct catcttcta                                                 19

SEQ ID NO: 222         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 222
tagaagatga ggcatagcat t                                              21

SEQ ID NO: 223         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 223
tgctatgcct catcttcta                                                 19

SEQ ID NO: 224         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 224
tagaagatga ggcatagcat t                                              21

SEQ ID NO: 225         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 225
tgctatgcct catcttcta                                                 19

SEQ ID NO: 226         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 226
tagaagatga ggcatagcat t                                              21

SEQ ID NO: 227         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 227
tgctatgcct catcttcta                                                 19

SEQ ID NO: 228         moltype = RNA  length = 21
```

-continued

```
FEATURE                Location/Qualifiers
misc_feature           1..21
                       note = Modified siRNA
source                 1..21
                       mol_type = other RNA
                       organism = synthetic construct
SEQUENCE: 228
tagaagatga ggcatagcat t                                        21

SEQ ID NO: 229         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 229
tgctatgcct catcttcta                                           19

SEQ ID NO: 230         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 230
tagaagatga ggcatagcat t                                        21

SEQ ID NO: 231         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 231
tgctatgcct catcttcta                                           19

SEQ ID NO: 232         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 232
tagaagatga ggcatagcat t                                        21

SEQ ID NO: 233         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 233
tgctatgcct catcttcta                                           19

SEQ ID NO: 234         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 234
tagaagatga ggcatagcat t                                        21

SEQ ID NO: 235         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 235
tgctatgcct catcttcta                                           19
```

```
SEQ ID NO: 236          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 236
tagaagatga ggcatagcag c                                            21

SEQ ID NO: 237          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 237
tgctatgcct catcttcta                                               19

SEQ ID NO: 238          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 238
tagaagatga ggcatagcat t                                            21

SEQ ID NO: 239          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 239
ttctccgaac gtgtcacgt                                               19

SEQ ID NO: 240          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 240
acgtgacacg ttcggagaat t                                            21

SEQ ID NO: 241          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 241
tctgtgcctt ctcatctga                                               19

SEQ ID NO: 242          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 242
tcagatgaga aggcacagac g                                            21

SEQ ID NO: 243          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 243
tctgtgcctt ctcatctga                                               19
```

```
SEQ ID NO: 244          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 244
tcagatgaga aggcacagac g                                            21

SEQ ID NO: 245          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 245
cgtctgtgcc ttctcatctg a                                            21

SEQ ID NO: 246          moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 246
tcagatgaga aggcacagac ggg                                          23

SEQ ID NO: 247          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 247
tctgtgcctt ctcatctga                                               19

SEQ ID NO: 248          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 248
tcagatgaga aggcacagac g                                            21

SEQ ID NO: 249          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 249
tctgtgcctt ctcatctga                                               19

SEQ ID NO: 250          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 250
tcagatgaga aggcacagac g                                            21

SEQ ID NO: 251          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 251
```

```
tctgtgcctt ctcatctga                                            19

SEQ ID NO: 252          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 252
tcagatgaga aggcacagac g                                         21

SEQ ID NO: 253          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 253
tctgtgcctt ctcatctga                                            19

SEQ ID NO: 254          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 254
tcagatgaga aggcacagac g                                         21

SEQ ID NO: 255          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 255
tctgtgcctt ctcatctga                                            19

SEQ ID NO: 256          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 256
tcagatgaga aggcacagac g                                         21

SEQ ID NO: 257          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 257
tctgtgcctt ctcatctga                                            19

SEQ ID NO: 258          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 258
tcagatgaga aggcacagac g                                         21

SEQ ID NO: 259          moltype = RNA  length = 19
FEATURE                 Location/Qualifiers
misc_feature            1..19
                        note = Modified siRNA
source                  1..19
                        mol_type = other RNA
                        organism = synthetic construct
```

```
SEQUENCE: 259
tctgtgcctt ctcatctga                                           19

SEQ ID NO: 260          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 260
tcagatgaga aggcacagac g                                        21

SEQ ID NO: 261          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 261
tctgtgcctt ctcatctga                                           19

SEQ ID NO: 262          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 262
tcagatgaga aggcacagac g                                        21

SEQ ID NO: 263          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 263
tctgtgcctt ctcatctga                                           19

SEQ ID NO: 264          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 264
tcagatgaga aggcacagac g                                        21

SEQ ID NO: 265          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 265
tctgtgcctt ctcatctga                                           19

SEQ ID NO: 266          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 266
tcagatgaga aggcacagac g                                        21

SEQ ID NO: 267          moltype = RNA  length = 19
FEATURE                 Location/Qualifiers
misc_feature            1..19
                        note = Modified siRNA
source                  1..19
                        mol_type = other RNA
```

```
                       organism = synthetic construct
SEQUENCE: 267
tctgtgcctt ctcatctga                                              19

SEQ ID NO: 268         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 268
tcagatgaga aggcacagac g                                           21

SEQ ID NO: 269         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 269
gtgtgcactt cgcttcaca                                              19

SEQ ID NO: 270         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 270
tgtgaagcga agtgcacact t                                           21

SEQ ID NO: 271         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 271
cgtgtgcact tcgcttcaa                                              19

SEQ ID NO: 272         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 272
ttgaagcgaa gtgcacacgg t                                           21

SEQ ID NO: 273         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 273
cgtgtgcact tcgcttcaa                                              19

SEQ ID NO: 274         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 274
ttgaagcgaa gtgcacacgg t                                           21

SEQ ID NO: 275         moltype = RNA  length = 21
FEATURE                Location/Qualifiers
misc_feature           1..21
                       note = Modified siRNA
source                 1..21
```

```
                        mol_type = other RNA
                        organism = synthetic construct
SEQUENCE: 275
accgtgtgca cttcgcttca a                                21

SEQ ID NO: 276          moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 276
ttgaagcgaa gtgcacacgg tcc                              23

SEQ ID NO: 277          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 277
cgtgtgcact tcgcttcaa                                   19

SEQ ID NO: 278          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 278
ttgaagcgaa gtgcacacgg t                                21

SEQ ID NO: 279          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 279
cgtgtgcact tcgcttcaa                                   19

SEQ ID NO: 280          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 280
ttgaagcgaa gtgcacacgg t                                21

SEQ ID NO: 281          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 281
cgtgtgcact tcgcttcaa                                   19

SEQ ID NO: 282          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 282
ttgaagcgaa gtgcacacgg t                                21

SEQ ID NO: 283          moltype = RNA  length = 19
FEATURE                 Location/Qualifiers
misc_feature            1..19
                        note = Modified siRNA
```

```
source                  1..19
                        mol_type = other RNA
                        organism = synthetic construct
SEQUENCE: 283
cgtgtgcact tcgcttcaa                                                19

SEQ ID NO: 284          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 284
ttgaagcgaa gtgcacacgg t                                             21

SEQ ID NO: 285          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 285
cgtgtgcact tcgcttcaa                                                19

SEQ ID NO: 286          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 286
ttgaagcgaa gtgcacacgg t                                             21

SEQ ID NO: 287          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 287
cgtgtgcact tcgcttcaa                                                19

SEQ ID NO: 288          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 288
ttgaagcgaa gtgcacacgg t                                             21

SEQ ID NO: 289          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 289
cgtgtgcact tcgcttcaa                                                19

SEQ ID NO: 290          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 290
ttgaagcgaa gtgcacacgg t                                             21

SEQ ID NO: 291          moltype = RNA  length = 19
FEATURE                 Location/Qualifiers
misc_feature            1..19
```

```
                        note = Modified siRNA
source                  1..19
                        mol_type = other RNA
                        organism = synthetic construct
SEQUENCE: 291
cgtgtgcact tcgcttcaa                                              19

SEQ ID NO: 292          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 292
ttgaagcgaa gtgcacacgg t                                           21

SEQ ID NO: 293          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 293
cgtgtgcact tcgcttcaa                                              19

SEQ ID NO: 294          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 294
ttgaagcgaa gtgcacacgg t                                           21

SEQ ID NO: 295          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 295
cgtgtgcact tcgcttcaa                                              19

SEQ ID NO: 296          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 296
ttgaagcgaa gtgcacacgg t                                           21

SEQ ID NO: 297          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 297
cgtgtgcact tcgcttcaa                                              19

SEQ ID NO: 298          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 298
ttgaagcgaa gtgcacacgg t                                           21

SEQ ID NO: 299          moltype = RNA  length = 19
FEATURE                 Location/Qualifiers
```

```
misc_feature           1..19
                       note = Modified siRNA
source                 1..19
                       mol_type = other RNA
                       organism = synthetic construct
SEQUENCE: 299
gtgtgcactt cgcttcaca                                              19

SEQ ID NO: 300         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 300
tgtgaagcga agtgcacact t                                           21

SEQ ID NO: 301         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 301
ccaagagcac caagaacta                                              19

SEQ ID NO: 302         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 302
tagttcttgg tgctcttggc t                                           21

SEQ ID NO: 303         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 303
ccaagagcac caagaacta                                              19

SEQ ID NO: 304         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 304
tagttcttgg tgctcttggc t                                           21

SEQ ID NO: 305         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 305
ccaagagcac caagaacta                                              19

SEQ ID NO: 306         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 306
tagttcttgg tgctcttggc t                                           21

SEQ ID NO: 307         moltype = RNA  length = 19
```

```
FEATURE                Location/Qualifiers
misc_feature           1..19
                       note = Modified siRNA
source                 1..19
                       mol_type = other RNA
                       organism = synthetic construct
SEQUENCE: 307
ccaagagcac caagaacta                                       19

SEQ ID NO: 308         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 308
tagttcttgg tgctcttggc t                                    21

SEQ ID NO: 309         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 309
ccaagagcac caagaacta                                       19

SEQ ID NO: 310         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 310
tagttcttgg tgctcttggc t                                    21

SEQ ID NO: 311         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 311
agccaagagc accaagaact a                                    21

SEQ ID NO: 312         moltype = RNA  length = 23
FEATURE                Location/Qualifiers
misc_feature           1..23
                       note = Modified siRNA
source                 1..23
                       mol_type = other RNA
                       organism = synthetic construct
SEQUENCE: 312
tagttcttgg tgctcttggc ttg                                  23

SEQ ID NO: 313         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 313
agccaagagc accaagaact a                                    21

SEQ ID NO: 314         moltype = RNA  length = 23
FEATURE                Location/Qualifiers
misc_feature           1..23
                       note = Modified siRNA
source                 1..23
                       mol_type = other RNA
                       organism = synthetic construct
SEQUENCE: 314
tagttcttgg tgctcttggc ttg                                  23
```

```
SEQ ID NO: 315          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 315
ccaagagcac caagaacta                                                19

SEQ ID NO: 316          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 316
tagttcttgg tgctcttggc t                                             21

SEQ ID NO: 317          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 317
agccaagagc accaagaact a                                             21

SEQ ID NO: 318          moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 318
tagttcttgg tgctcttggc ttg                                           23

SEQ ID NO: 319          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 319
ccaagagcac caagaacta                                                19

SEQ ID NO: 320          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 320
tagttcttgg tgctcttggc t                                             21

SEQ ID NO: 321          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 321
ccaagagcac caagaacta                                                19

SEQ ID NO: 322          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 322
tagttcttgg tgctcttggc t                                             21
```

```
SEQ ID NO: 323          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 323
ccaagagcac caagaacta                                              19

SEQ ID NO: 324          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 324
tagttcttgg tgctcttggc t                                           21

SEQ ID NO: 325          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 325
ccaagagcac caagaacta                                              19

SEQ ID NO: 326          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 326
tagttcttgg tgctcttggc t                                           21

SEQ ID NO: 327          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 327
ccaagagcac caagaacta                                              19

SEQ ID NO: 328          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 328
tagttcttgg tgctcttggc t                                           21

SEQ ID NO: 329          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 329
ccaagagcac caagaacta                                              19

SEQ ID NO: 330          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 330
```

```
tagttcttgg tgctcttggc t                                            21

SEQ ID NO: 331         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 331
ccaagagcac caagaacta                                               19

SEQ ID NO: 332         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 332
tagttcttgg tgctcttggc t                                            21

SEQ ID NO: 333         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 333
ccaagagcac caagaacta                                               19

SEQ ID NO: 334         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 334
tagttcttgg tgctcttggc t                                            21

SEQ ID NO: 335         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 335
ccaagagcac caagaacta                                               19

SEQ ID NO: 336         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 336
tagttcttgg tgctcttggc t                                            21

SEQ ID NO: 337         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 337
agccaagagc accaagaact a                                            21

SEQ ID NO: 338         moltype = RNA  length = 23
FEATURE                Location/Qualifiers
misc_feature           1..23
                       note = Modified siRNA
source                 1..23
                       mol_type = other RNA
                       organism = synthetic construct
```

```
SEQUENCE: 338
tagttcttgg tgctcttggc ttg                                             23

SEQ ID NO: 339          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 339
ccaagagcac caagaacta                                                  19

SEQ ID NO: 340          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 340
tagttcttgg tgctcttggc t                                               21

SEQ ID NO: 341          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 341
ccttgaggca tacttcaaa                                                  19

SEQ ID NO: 342          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 342
tttgaagtat gcctcaaggt t                                               21

SEQ ID NO: 343          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 343
acatatttga tcagtctttt t                                               21

SEQ ID NO: 344          moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 344
aaaaagactg atcaaatatg ttg                                             23

SEQ ID NO: 345          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 345
caataaagct ggacaagaa                                                  19

SEQ ID NO: 346          moltype = RNA  length = 21
FEATURE                 Location/Qualifiers
misc_feature            1..21
                        note = Modified siRNA
source                  1..21
                        mol_type = other RNA
```

```
                         organism = synthetic construct
SEQUENCE: 346
ttcttgtcca gctttattgg g                                              21

SEQ ID NO: 347           moltype = RNA  length = 19
FEATURE                  Location/Qualifiers
misc_feature             1..19
                         note = Modified siRNA
source                   1..19
                         mol_type = other RNA
                         organism = synthetic construct
SEQUENCE: 347
caataaagct ggacaagaa                                                 19

SEQ ID NO: 348           moltype = RNA  length = 21
FEATURE                  Location/Qualifiers
misc_feature             1..21
                         note = Modified siRNA
source                   1..21
                         mol_type = other RNA
                         organism = synthetic construct
SEQUENCE: 348
ttcttgtcca gctttattgg g                                              21

SEQ ID NO: 349           moltype = RNA  length = 19
FEATURE                  Location/Qualifiers
misc_feature             1..19
                         note = Modified siRNA
source                   1..19
                         mol_type = other RNA
                         organism = synthetic construct
SEQUENCE: 349
caataaagct ggacaagaa                                                 19

SEQ ID NO: 350           moltype = RNA  length = 21
FEATURE                  Location/Qualifiers
misc_feature             1..21
                         note = Modified siRNA
source                   1..21
                         mol_type = other RNA
                         organism = synthetic construct
SEQUENCE: 350
ttcttgtcca gctttattgg g                                              21

SEQ ID NO: 351           moltype = RNA  length = 19
FEATURE                  Location/Qualifiers
misc_feature             1..19
                         note = Modified siRNA
source                   1..19
                         mol_type = other RNA
                         organism = synthetic construct
SEQUENCE: 351
caataaagct ggacaagaa                                                 19

SEQ ID NO: 352           moltype = RNA  length = 21
FEATURE                  Location/Qualifiers
misc_feature             1..21
                         note = Modified siRNA
source                   1..21
                         mol_type = other RNA
                         organism = synthetic construct
SEQUENCE: 352
ttcttgtcca gctttattgg g                                              21

SEQ ID NO: 353           moltype = RNA  length = 21
FEATURE                  Location/Qualifiers
misc_feature             1..21
                         note = Modified siRNA
source                   1..21
                         mol_type = other RNA
                         organism = synthetic construct
SEQUENCE: 353
cccaataaag ctggacaaga a                                              21

SEQ ID NO: 354           moltype = RNA  length = 23
FEATURE                  Location/Qualifiers
misc_feature             1..23
                         note = Modified siRNA
source                   1..23
```

```
                        mol_type = other RNA
                        organism = synthetic construct
SEQUENCE: 354
ttcttgtcca gctttattgg gag                                             23

SEQ ID NO: 355          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 355
caataaagct ggacaagaa                                                  19

SEQ ID NO: 356          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 356
ttcttgtcca gctttattgg g                                               21

SEQ ID NO: 357          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 357
cccaataaag ctggacaaga a                                               21

SEQ ID NO: 358          moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 358
ttcttgtcca gctttattgg gag                                             23

SEQ ID NO: 359          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 359
caataaagct ggacaagaa                                                  19

SEQ ID NO: 360          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 360
ttcttgtcca gctttattgg g                                               21

SEQ ID NO: 361          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 361
cccaataaag ctggacaaga a                                               21

SEQ ID NO: 362          moltype = RNA  length = 23
FEATURE                 Location/Qualifiers
misc_feature            1..23
                        note = Modified siRNA
```

```
source                  1..23
                        mol_type = other RNA
                        organism = synthetic construct
SEQUENCE: 362
ttcttgtcca gctttattgg gag                                           23

SEQ ID NO: 363          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 363
caataaagct ggacaagaa                                                19

SEQ ID NO: 364          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 364
ttcttgtcca gctttattgg g                                             21

SEQ ID NO: 365          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 365
cccaataaag ctggacaaga a                                             21

SEQ ID NO: 366          moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 366
ttcttgtcca gctttattgg gag                                           23

SEQ ID NO: 367          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 367
caataaagct ggacaagaa                                                19

SEQ ID NO: 368          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 368
ttcttgtcca gctttattgg g                                             21

SEQ ID NO: 369          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 369
caataaagct ggacaagaa                                                19

SEQ ID NO: 370          moltype = RNA  length = 21
FEATURE                 Location/Qualifiers
misc_feature            1..21
```

```
                        note = Modified siRNA
source                  1..21
                        mol_type = other RNA
                        organism = synthetic construct
SEQUENCE: 370
ttcttgtcca gctttattgg g                                                21

SEQ ID NO: 371          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 371
caataaagct ggacaagaa                                                   19

SEQ ID NO: 372          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 372
ttcttgtcca gctttattgg g                                                21

SEQ ID NO: 373          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 373
caataaagct ggacaagaa                                                   19

SEQ ID NO: 374          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 374
ttcttgtcca gctttattgg g                                                21

SEQ ID NO: 375          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 375
caataaagct ggacaagaa                                                   19

SEQ ID NO: 376          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 376
ttcttgtcca gctttattgg g                                                21

SEQ ID NO: 377          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 377
caataaagct ggacaagaa                                                   19

SEQ ID NO: 378          moltype = RNA  length = 21
FEATURE                 Location/Qualifiers
```

```
misc_feature          1..21
                      note = Modified siRNA
source                1..21
                      mol_type = other RNA
                      organism = synthetic construct
SEQUENCE: 378
ttcttgtcca gctttattgg g                                     21

SEQ ID NO: 379        moltype = RNA  length = 19
FEATURE               Location/Qualifiers
misc_feature          1..19
                      note = Modified siRNA
source                1..19
                      mol_type = other RNA
                      organism = synthetic construct
SEQUENCE: 379
caataaagct ggacaagaa                                        19

SEQ ID NO: 380        moltype = RNA  length = 21
FEATURE               Location/Qualifiers
misc_feature          1..21
                      note = Modified siRNA
source                1..21
                      mol_type = other RNA
                      organism = synthetic construct
SEQUENCE: 380
ttcttgtcca gctttattgg g                                     21

SEQ ID NO: 381        moltype = RNA  length = 19
FEATURE               Location/Qualifiers
misc_feature          1..19
                      note = Modified siRNA
source                1..19
                      mol_type = other RNA
                      organism = synthetic construct
SEQUENCE: 381
caataaagct ggacaagaa                                        19

SEQ ID NO: 382        moltype = RNA  length = 21
FEATURE               Location/Qualifiers
misc_feature          1..21
                      note = Modified siRNA
source                1..21
                      mol_type = other RNA
                      organism = synthetic construct
SEQUENCE: 382
ttcttgtcca gctttattgg g                                     21

SEQ ID NO: 383        moltype = RNA  length = 21
FEATURE               Location/Qualifiers
misc_feature          1..21
                      note = Modified siRNA
source                1..21
                      mol_type = other RNA
                      organism = synthetic construct
SEQUENCE: 383
cccaataaag ctggacaaga a                                     21

SEQ ID NO: 384        moltype = RNA  length = 23
FEATURE               Location/Qualifiers
misc_feature          1..23
                      note = Modified siRNA
source                1..23
                      mol_type = other RNA
                      organism = synthetic construct
SEQUENCE: 384
ttcttgtcca gctttattgg gag                                   23

SEQ ID NO: 385        moltype = RNA  length = 19
FEATURE               Location/Qualifiers
misc_feature          1..19
                      note = Modified siRNA
source                1..19
                      mol_type = other RNA
                      organism = synthetic construct
SEQUENCE: 385
ccttgaggca tacttcaaa                                        19

SEQ ID NO: 386        moltype = RNA  length = 21
```

-continued

```
FEATURE                Location/Qualifiers
misc_feature           1..21
                       note = Modified siRNA
source                 1..21
                       mol_type = other RNA
                       organism = synthetic construct
SEQUENCE: 386
tttgaagtat gcctcaaggt t                                              21

SEQ ID NO: 387         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 387
gcttaaaagg gacagtattc a                                              21

SEQ ID NO: 388         moltype = RNA  length = 23
FEATURE                Location/Qualifiers
misc_feature           1..23
                       note = Modified siRNA
source                 1..23
                       mol_type = other RNA
                       organism = synthetic construct
SEQUENCE: 388
tgaatactgt cccttttaag caa                                            23

SEQ ID NO: 389         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 389
gaaagtatgt caacgaata                                                 19

SEQ ID NO: 390         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 390
tattcgttga catactttct t                                              21

SEQ ID NO: 391         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 391
gaaagtatgt caacgaata                                                 19

SEQ ID NO: 392         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 392
tattcgttga catactttct t                                              21

SEQ ID NO: 393         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 393
gaaagtatgt caacgaata                                                 19
```

-continued

```
SEQ ID NO: 394          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 394
tattcgttga catactttct t                                              21

SEQ ID NO: 395          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 395
gaaagtatgt caacgaata                                                 19

SEQ ID NO: 396          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 396
tattcgttga catactttct t                                              21

SEQ ID NO: 397          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 397
gaaagtatgt caacgaata                                                 19

SEQ ID NO: 398          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 398
tattcgttga catactttct t                                              21

SEQ ID NO: 399          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 399
gaaagtatgt caacgaata                                                 19

SEQ ID NO: 400          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 400
tattcgttga catactttct t                                              21

SEQ ID NO: 401          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 401
gaaagtatgt caacgaata                                                 19
```

```
SEQ ID NO: 402          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 402
tattcgttga catactttct t                                            21

SEQ ID NO: 403          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 403
gaaagtatgt caacgaatt                                               19

SEQ ID NO: 404          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 404
aattcgttga catactttcc a                                            21

SEQ ID NO: 405          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 405
tggaaagtat gtcaacgaat a                                            21

SEQ ID NO: 406          moltype = RNA  length = 23
FEATURE                 Location/Qualifiers
misc_feature            1..23
                        note = Modified siRNA
source                  1..23
                        mol_type = other RNA
                        organism = synthetic construct
SEQUENCE: 406
tattcgttga catactttcc att                                          23

SEQ ID NO: 407          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 407
gaaagtatgt caacgaata                                               19

SEQ ID NO: 408          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 408
tattcgttga catactttct t                                            21

SEQ ID NO: 409          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 409
```

```
gaaagtatgt caacgaata                                               19

SEQ ID NO: 410          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 410
tattcgttga catactttct t                                            21

SEQ ID NO: 411          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 411
gaaagtatgt caacgaata                                               19

SEQ ID NO: 412          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 412
tattcgttga catactttct t                                            21

SEQ ID NO: 413          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 413
gaaagtatgt caacgaata                                               19

SEQ ID NO: 414          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 414
tattcgttga catactttct t                                            21

SEQ ID NO: 415          moltype = RNA  length = 19
FEATURE                 Location/Qualifiers
misc_feature            1..19
                        note = Modified siRNA
source                  1..19
                        mol_type = other RNA
                        organism = synthetic construct
SEQUENCE: 415
gaaagtatgt caacgaata                                               19

SEQ ID NO: 416          moltype = RNA  length = 21
FEATURE                 Location/Qualifiers
misc_feature            1..21
                        note = Modified siRNA
source                  1..21
                        mol_type = other RNA
                        organism = synthetic construct
SEQUENCE: 416
tattcgttga catactttct t                                            21

SEQ ID NO: 417          moltype = RNA  length = 19
FEATURE                 Location/Qualifiers
misc_feature            1..19
                        note = Modified siRNA
source                  1..19
                        mol_type = other RNA
                        organism = synthetic construct
```

```
SEQUENCE: 417
gaaagtatgt caacgaata                                              19

SEQ ID NO: 418         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 418
tattcgttga catactttct t                                           21

SEQ ID NO: 419         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 419
gaaagtatgt caacgaata                                              19

SEQ ID NO: 420         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 420
tattcgttga catactttct t                                           21

SEQ ID NO: 421         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 421
gaaagtatgt caacgaata                                              19

SEQ ID NO: 422         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 422
tattcgttga catactttct t                                           21

SEQ ID NO: 423         moltype = RNA  length = 19
FEATURE                Location/Qualifiers
misc_feature           1..19
                       note = Modified siRNA
source                 1..19
                       mol_type = other RNA
                       organism = synthetic construct
SEQUENCE: 423
ttctccgaac gtgtcacgt                                              19

SEQ ID NO: 424         moltype = RNA  length = 21
FEATURE                Location/Qualifiers
misc_feature           1..21
                       note = Modified siRNA
source                 1..21
                       mol_type = other RNA
                       organism = synthetic construct
SEQUENCE: 424
acgtgacacg ttcggagaat t                                           21

SEQ ID NO: 425         moltype = DNA  length = 20
FEATURE                Location/Qualifiers
misc_feature           1..20
                       note = Modified siRNA
source                 1..20
                       mol_type = other DNA
```

```
                         organism = synthetic construct
SEQUENCE: 425
ccgtctgtgc cttctcatct                                                20

SEQ ID NO: 426           moltype = DNA  length = 20
FEATURE                  Location/Qualifiers
misc_feature             1..20
                         note = Modified siRNA
source                   1..20
                         mol_type = other DNA
                         organism = synthetic construct
SEQUENCE: 426
taatctcctc ccccaactcc                                                20

SEQ ID NO: 427           moltype = DNA  length = 24
FEATURE                  Location/Qualifiers
misc_feature             1..24
                         note = Modified siRNA
source                   1..24
                         mol_type = other DNA
                         organism = synthetic construct
SEQUENCE: 427
agcttctttg cagctccttc gttg                                           24

SEQ ID NO: 428           moltype = DNA  length = 24
FEATURE                  Location/Qualifiers
misc_feature             1..24
                         note = Modified siRNA
source                   1..24
                         mol_type = other DNA
                         organism = synthetic construct
SEQUENCE: 428
ttctgaccca ttcccaccat caca                                           24

SEQ ID NO: 429           moltype = DNA  length = 21
FEATURE                  Location/Qualifiers
misc_feature             1..21
                         note = Modified siRNA
source                   1..21
                         mol_type = other DNA
                         organism = synthetic construct
SEQUENCE: 429
cgtttctcct ggctcagttt a                                              21

SEQ ID NO: 430           moltype = DNA  length = 21
FEATURE                  Location/Qualifiers
misc_feature             1..21
                         note = Modified siRNA
source                   1..21
                         mol_type = other DNA
                         organism = synthetic construct
SEQUENCE: 430
cagcggtaaa aagggactca a                                              21

SEQ ID NO: 431           moltype = DNA  length = 24
FEATURE                  Location/Qualifiers
misc_feature             1..24
                         note = Modified siRNA
source                   1..24
                         mol_type = other DNA
                         organism = synthetic construct
SEQUENCE: 431
aactttggca ttgtggaagg gctc                                           24

SEQ ID NO: 432           moltype = DNA  length = 24
FEATURE                  Location/Qualifiers
misc_feature             1..24
                         note = Modified siRNA
source                   1..24
                         mol_type = other DNA
                         organism = synthetic construct
SEQUENCE: 432
tggaagagtg ggagttgctg ttga                                           24

SEQ ID NO: 433           moltype = DNA  length = 18
FEATURE                  Location/Qualifiers
misc_feature             1..18
                         note = Modified siRNA
source                   1..18
```

```
                        mol_type = other DNA
                        organism = synthetic construct
SEQUENCE: 433
accaactata cgctacat                                                  18

SEQ ID NO: 434          moltype = DNA  length = 18
FEATURE                 Location/Qualifiers
misc_feature            1..18
                        note = Modified siRNA
source                  1..18
                        mol_type = other DNA
                        organism = synthetic construct
SEQUENCE: 434
cctcctgaat aaccctct                                                  18

SEQ ID NO: 435          moltype = DNA  length = 19
FEATURE                 Location/Qualifiers
misc_feature            1..19
                        note = Modified siRNA
source                  1..19
                        mol_type = other DNA
                        organism = synthetic construct
SEQUENCE: 435
ggtcggagtc aacggattt                                                 19

SEQ ID NO: 436          moltype = DNA  length = 19
FEATURE                 Location/Qualifiers
misc_feature            1..19
                        note = Modified siRNA
source                  1..19
                        mol_type = other DNA
                        organism = synthetic construct
SEQUENCE: 436
ccagcatcgc cccacttga                                                 19

SEQ ID NO: 437          moltype = DNA  length = 23
FEATURE                 Location/Qualifiers
misc_feature            1..23
                        note = Modified siRNA
source                  1..23
                        mol_type = other DNA
                        organism = synthetic construct
SEQUENCE: 437
gaggagcagc taaccaactt aat                                            23

SEQ ID NO: 438          moltype = DNA  length = 23
FEATURE                 Location/Qualifiers
misc_feature            1..23
                        note = Modified siRNA
source                  1..23
                        mol_type = other DNA
                        organism = synthetic construct
SEQUENCE: 438
tctgcatgtg ctgttgactt aat                                            23

SEQ ID NO: 439          moltype = DNA  length = 24
FEATURE                 Location/Qualifiers
misc_feature            1..24
                        note = Modified siRNA
source                  1..24
                        mol_type = other DNA
                        organism = synthetic construct
SEQUENCE: 439
aactttggca ttgtggaagg gctc                                           24

SEQ ID NO: 440          moltype = DNA  length = 24
FEATURE                 Location/Qualifiers
misc_feature            1..24
                        note = Modified siRNA
source                  1..24
                        mol_type = other DNA
                        organism = synthetic construct
SEQUENCE: 440
tggaagagtg ggagttgctg ttga                                           24

SEQ ID NO: 441          moltype = DNA  length = 20
FEATURE                 Location/Qualifiers
misc_feature            1..20
                        note = Modified siRNA
```

```
source                  1..20
                        mol_type = other DNA
                        organism = synthetic construct
SEQUENCE: 441
ctggtggtgg catgatgagt                                              20

SEQ ID NO: 442          moltype = DNA  length = 21
FEATURE                 Location/Qualifiers
misc_feature            1..21
                        note = Modified siRNA
source                  1..21
                        mol_type = other DNA
                        organism = synthetic construct
SEQUENCE: 442
ctcttctccg ctctggctta g                                            21

SEQ ID NO: 443          moltype = DNA  length = 20
FEATURE                 Location/Qualifiers
misc_feature            1..20
                        note = Modified siRNA
source                  1..20
                        mol_type = other DNA
                        organism = synthetic construct
SEQUENCE: 443
gggagccaaa agggtcatca                                              20

SEQ ID NO: 444          moltype = DNA  length = 20
FEATURE                 Location/Qualifiers
misc_feature            1..20
                        note = Modified siRNA
source                  1..20
                        mol_type = other DNA
                        organism = synthetic construct
SEQUENCE: 444
cgtggactgt ggtcatgagt                                              20

SEQ ID NO: 445          moltype = DNA  length = 20
FEATURE                 Location/Qualifiers
misc_feature            1..20
                        note = Modified siRNA
source                  1..20
                        mol_type = other DNA
                        organism = synthetic construct
SEQUENCE: 445
gtgaccgatg gcttcagttc                                              20

SEQ ID NO: 446          moltype = DNA  length = 20
FEATURE                 Location/Qualifiers
misc_feature            1..20
                        note = Modified siRNA
source                  1..20
                        mol_type = other DNA
                        organism = synthetic construct
SEQUENCE: 446
atggataggc aggtggactt                                              20

SEQ ID NO: 447          moltype = DNA  length = 18
FEATURE                 Location/Qualifiers
misc_feature            1..18
                        note = Modified siRNA
source                  1..18
                        mol_type = other DNA
                        organism = synthetic construct
SEQUENCE: 447
ccaaccgcga gaagatga                                                18

SEQ ID NO: 448          moltype = DNA  length = 20
FEATURE                 Location/Qualifiers
misc_feature            1..20
                        note = Modified siRNA
source                  1..20
                        mol_type = other DNA
                        organism = synthetic construct
SEQUENCE: 448
ccagaggcgt acagggatag                                              20

SEQ ID NO: 449          moltype = DNA  length = 20
FEATURE                 Location/Qualifiers
misc_feature            1..20
```

```
                        note = Modified siRNA
source                  1..20
                        mol_type = other DNA
                        organism = synthetic construct
SEQUENCE: 449
gtgaccgatg gcttcagttc                                           20

SEQ ID NO: 450          moltype = DNA  length = 20
FEATURE                 Location/Qualifiers
misc_feature            1..20
                        note = Modified siRNA
source                  1..20
                        mol_type = other DNA
                        organism = synthetic construct
SEQUENCE: 450
atggataggc aggtggactt                                           20

SEQ ID NO: 451          moltype = DNA  length = 24
FEATURE                 Location/Qualifiers
misc_feature            1..24
                        note = Modified siRNA
source                  1..24
                        mol_type = other DNA
                        organism = synthetic construct
SEQUENCE: 451
agcttctttg cagctccttc gttg                                      24

SEQ ID NO: 452          moltype = DNA  length = 24
FEATURE                 Location/Qualifiers
misc_feature            1..24
                        note = Modified siRNA
source                  1..24
                        mol_type = other DNA
                        organism = synthetic construct
SEQUENCE: 452
ttctgaccca ttcccaccat caca                                      24

SEQ ID NO: 453          moltype = DNA  length = 20
FEATURE                 Location/Qualifiers
misc_feature            1..20
                        note = Modified siRNA
source                  1..20
                        mol_type = other DNA
                        organism = synthetic construct
SEQUENCE: 453
ttgaaccctg aggccaaacc                                           20

SEQ ID NO: 454          moltype = DNA  length = 20
FEATURE                 Location/Qualifiers
misc_feature            1..20
                        note = Modified siRNA
source                  1..20
                        mol_type = other DNA
                        organism = synthetic construct
SEQUENCE: 454
cggtaggagg gcactgagaa                                           20

SEQ ID NO: 455          moltype = DNA  length = 20
FEATURE                 Location/Qualifiers
misc_feature            1..20
                        note = Modified siRNA
source                  1..20
                        mol_type = other DNA
                        organism = synthetic construct
SEQUENCE: 455
gggagccaaa agggtcatca                                           20

SEQ ID NO: 456          moltype = DNA  length = 20
FEATURE                 Location/Qualifiers
misc_feature            1..20
                        note = Modified siRNA
source                  1..20
                        mol_type = other DNA
                        organism = synthetic construct
SEQUENCE: 456
cgtggactgt ggtcatgagt                                           20
```